United States Patent
Vankayalapati et al.

(10) Patent No.: US 9,951,062 B2
(45) Date of Patent: *Apr. 24, 2018

(54) SUBSTITUTED 1 H-PYRROLO [2, 3-B] PYRIDINE AND 1 H-PYRAZOLO [3, 4-B] PYRIDINE DERIVATIVES AS SALT INDUCIBLE KINASE 2 (SIK2) INHIBITORS

(71) Applicant: Arrien Pharmaceuticals LLC, Salt Lake City, UT (US)

(72) Inventors: Hariprasad Vankayalapati, Draper, UT (US); Venkatakrishnareddy Yerramreddy, Andhra Pradesh (IN); Venu Babu Ganipisetty, Andhra Pradesh (IN); Sureshkumar Talluri, Andhra Pradesh (IN); Rajendra P Appalaneni, Saddle River, NJ (US)

(73) Assignee: ARRIEN PHARMACEUTICALS LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/958,625

(22) Filed: Dec. 3, 2015

(65) Prior Publication Data

US 2016/0090382 A1    Mar. 31, 2016

Related U.S. Application Data

(62) Division of application No. 14/101,109, filed on Dec. 9, 2013, now Pat. No. 9,260,426.

(60) Provisional application No. 61/737,618, filed on Dec. 14, 2012.

(51) Int. Cl.
| | |
|---|---|
| *C07D 471/04* | (2006.01) |
| *A61K 31/437* | (2006.01) |
| *A61K 31/444* | (2006.01) |
| *A61K 31/4545* | (2006.01) |
| *A61K 31/496* | (2006.01) |
| *A61K 31/5377* | (2006.01) |
| *A61K 31/635* | (2006.01) |

(52) U.S. Cl.
CPC .......... *C07D 471/04* (2013.01); *A61K 31/437* (2013.01); *A61K 31/444* (2013.01); *A61K 31/4545* (2013.01); *A61K 31/496* (2013.01); *A61K 31/5377* (2013.01); *A61K 31/635* (2013.01)

(58) Field of Classification Search
CPC .................................................. C07D 471/04
See application file for complete search history.

(56) References Cited

U.S. PATENT DOCUMENTS

| | | | |
|---|---|---|---|
| 7,186,716 B2 | 3/2007 | Wei | |
| 7,432,375 B2 | 10/2008 | Graczyk | |
| 7,528,146 B2 | 5/2009 | Ebenbeck | |
| 7,829,558 B2 | 11/2010 | Arnold | |
| 8,987,454 B2 | 3/2015 | Salituro | |
| 9,079,912 B2 | 7/2015 | Rodgers | |
| 2004/0092546 A1 | 5/2004 | Wei | |
| 2006/0030583 A1 | 2/2006 | Arnold | |
| 2006/0128661 A1 | 6/2006 | Ebenbeck | |
| 2006/0270646 A1 | 11/2006 | Graczyk | |
| 2009/0143352 A1 | 6/2009 | Arnold | |

(Continued)

FOREIGN PATENT DOCUMENTS

| | | |
|---|---|---|
| EP | 1671970 A1 | 6/2006 |
| JP | 2006501217 A | 1/2006 |

(Continued)

OTHER PUBLICATIONS

Arnold, et al. Document No. 149:471458, retrieved from STN; Oct. 16, 2008.*

(Continued)

*Primary Examiner* — Shawquia Jackson
(74) *Attorney, Agent, or Firm* — Timothy X. Gibson, Esq.; Gibson & Dernier LLP

(57) ABSTRACT

Compounds according to Formulas I, IA or IB:

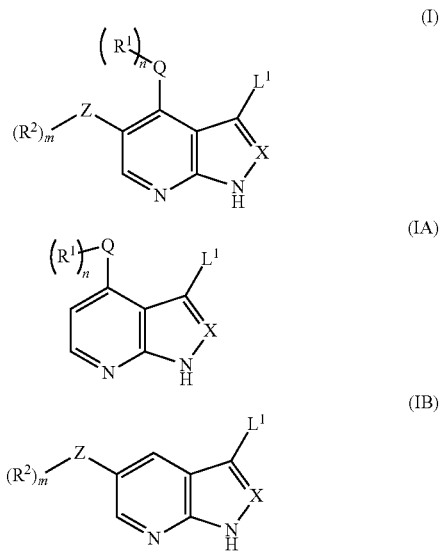

to pharmaceutically acceptable composition, salts thereof, their synthesis and their use as SIK2 inhibitors including such compounds and methods of using said compounds in the treatment of various diseases and/or disorders such as cancer, stroke, cardiovascular, obesity and type II diabetes.

4 Claims, 10 Drawing Sheets

(56) References Cited

U.S. PATENT DOCUMENTS

| | | |
|---|---|---|
| 2009/0181959 A1 | 7/2009 | Rodgers |
| 2009/0203687 A1 | 8/2009 | Arnold |
| 2011/0201599 A1 | 8/2011 | Bahceci |
| 2015/0152103 A1 | 6/2015 | Salituro |
| 2016/0272648 A1 | 9/2016 | Rodgers |

FOREIGN PATENT DOCUMENTS

| | | |
|---|---|---|
| JP | 2006521336 A | 9/2006 |
| JP | 2008508304 A | 3/2008 |
| JP | 2008156370 A | 7/2008 |
| JP | 2009519340 A | 5/2009 |
| JP | 2011526931 A | 10/2011 |
| WO | 2004078756 A2 | 9/2004 |
| WO | 2005095400 A1 | 10/2005 |
| WO | 2006069080 A2 | 6/2006 |
| WO | 2007002433 A1 | 1/2007 |
| WO | 2007084667 A2 | 7/2007 |
| WO | 2007103308 A2 | 9/2007 |
| WO | 2010003133 A2 | 1/2010 |
| WO | 2010068483 A2 | 6/2010 |
| WO | 2012135631 A1 | 10/2012 |

OTHER PUBLICATIONS

Notification of Refusal for corresponding JP Application No. 2015-547477, 5 pages, dated Sep. 27, 2016.
International Search Report for corresponding PCT Application No. PCT/US2013/074191, dated Mar. 28, 2014.
Office Action for corresponding U.S. Appl. No. 14/101,109, dated Mar. 24, 2015.
Office Action for corresponding U.S. Appl. No. 14/101,109, dated Jul. 15, 2015.
Extended European Search Report for corresponding EP Application No. EP13862263, 18 pages, dated Aug. 22, 2016.
Ayako Kumagai, et al., "A potent Inhibitor of SIK2,3,3,7-Trihydroxy-4-Methoxyflavon (4'-0-Methylfisetin), Promotes Melanogenesis in B16F10 Melanoma Cells", PLoS One, vol. 6, No. 10, e26148, pp. 1-10, Oct. 2011.
Ovarian Cancer National Alliance at http://www.ovariancancer.org/about-ovariancancer/statistics/.
Bast R. C Jr, Molecular approaches to personalizing management of ovarian cancer, Ann Oncol. 2011, 22 Suppl 8: viii5-viii15.
Bast R. C Jr., Hennessy B, Mills G. B. The biology of ovarian cancer: new opportunities for translation. Nature Rev Cancer, 2009, 9, 415-428.
Banerjee, S, Kaye, S. B.New strategies inthe treatment of ovarian cancer: current clinical perspectives and future potential. Clin Cancer Res. 2013 1, 19(5), 961-968.
Ahmed, A. A, Lu, Z, Jennings, N. B, Etemadmoghadam, D, Capalbo, L, Jacamo, R. O, Barbosa-Morais, N, Le, XF; Australian Ovarian Cancer Study Group, Vivas-Mejia, P, Lopez-Berestein, G, Grandjean, G, Bartholomeusz, G, Liao, W, Andreeff M, Bowtell, D, Glover, D. M, Sood, A. K, Bast, R. C Jr. SIK2 is a centrosome kinase required for bipolar mitotic spindle formation that provides a potential target for therapy in ovarian cancer. Cancer Cell. 2010, 9, 18(2), 109-121.
Kumagai, A, Horike, N, Satoh, Y, Uebi, T, Sasaki, T, Itoh, Y, Hirata, Y, Uchio-Yamada, K, Kitagawa, K, Uesato, S, Kawahara, H, Takemori, H, Nagaoka, Y. A potent inhibitor of SIK2, 3, 3', 7-trihydroxy-4'-methoxyflavon (4'-O-methylfisetin), promotes melanogenesis in B16F10 melanoma cells. PLoS One. 2011, 6(10), e26148.
Perez de Castro, I, de Carter, G, Montoya, G, Malumbres, M. Emerging cancer therapeutic opportunities by inhibiting mitotic kinases. Curr. Opin. Pharmacol, 2008, 8, 375-383.
Vankayalapati, H. Identification of Novel Inhibitors of SIK2 Kinase: A Novel Ser/Thr Kinase for Multiple Disease Indications presented at Emerging Targeted Oncology Partnering Forum, Feb. 19-20, 2012, San Francisco, CA.

Jia, L, Zhang S, Ye, Y, Li, X, Mercado-Uribe, I, Bast, R. C Jr, Liu, J. Paclitaxel inhibits ovarian tumor growth by inducing epithelial cancer cells to benign fibroblastlike cells. Cancer Lett. 2012, 30, 326(2), 176-182.
Horike, N, Kumagai, A, Shimono, Y, Onishi, T, Itoh, Y, Sasaki, T, Kitagawa, K, Hatano, O, Takagi, H, Susumu, T, Teraoka, H, Kusano, K, Nagaoka, Y, Kawahara, H, Takemori, H. Downregulation of SIK2 expression promotes the melanogenic program in mice. Pigment Cell Melanoma Res. 2010, 23(6), 809-819.
Clark, K, Mackenzie, K.F, Petkevicius, K, Kristariyanto, Y, Zhang, J, Choi, H. G, Peggie, M, Plater, L, Pedrioli, P. G, McIver, E, Gray, N. S, Arthur, J. S, Cohen, R. Phosphorylation of CRTC3 by the salt-inducible kinases controls the interconversion of classically activated and regulatory macrophages. Proc Natl Acad Sci U S A. 2012 16,109(42)16986-16991.
Henriksson, E, Jones, H. A, Patel, K, Peggie, M, Morrice, N, Sakamoto, K, Göransson, O. The AMPK-related kinase SIK2 is regulated by cAMP via phosphorylation at Ser358 in adipocytes. Biochem J. 2012, 15, 444(3), 503-514. Pmid: 22462548.
Sasaki, T, Takemori H, Yagita, Y, Terasaki, Y, Uebi, T, Horike, N, Takagi, H, Susumu, T, Teraoka, H, Kusano, K, Hatano, O, Oyama, N, Sugiyama, Y, Sakoda, S, Kitagawa, K. SIK2 is a key regulator for neuronal survival after ischemia via TORC1-CREB. Neuron. 2011, 13, 69(1), 106-109.
Liu, Y, Poon, V, Sanchez-Watts, G, Watts, A.G, Takemori. H, Aguilera, G. Salt inducible kinase is involved in the regulation of corticotropin-releasing hormone transcription in hypothalamic neurons in rats. Endocrinology. 2012, 153 (1), 223-233.
Gallo, E. F, Ladecola, C. Balancing life and death in the ischemic brain: SIK and TORC weigh IN. Neuron. 2011, 13, 69 (1), 3-6.
Muraoka, M, Fukushima, A, Viengchareun, S, Lombès, M, Kishi, F, Miyauchi, A, Kanematsu, M, Doi, J, Kajimura, J, Nakai, R, Uebi, T, Okamoto, M, Takemori, H. Involvement of SIK2/TORC2 signaling cascade in the regulation of insulin-induced PGC-1alpha and UCP-1 gene expression in brown adipocytes. Am J Physiol Endocrinol Metab. 2009, 296(6), E1430-1439.
Du, J, Chen, Q, Takemori, H, Xu, H. SIK2 can be activated by deprivation of nutrition and it inhibits expression of ipogenic genes in adipocytes. Obesity (Silver Spring). 2008, 16(3), 531-538.
Hashimoto, Y. K, Satoh, T, Okamoto, M, Takemori, H. Importance of autophosphorylation at Ser186 in the A-loop of salt inducible kinase 1 for its sustained kinase activity. J Cell Biochem. 2008, 1, 104(5), 1724-1739.
Ryu, D, Oh, K. J, Jo, H. Y, Hedrick, S, Kim, Y. N, Hwang, Y. J, Park, T. S, Han, J. S, Choi, C. S, Montminy, M, Koo, S. H. TORC2 regulates hepatic insulin signaling via a mammalian phosphatidic acid phosphatase, LIPIN1. Cell Metab. 2009, 9(3), 240-251.
Charoenfuprasert, S, Yang, Y. Y, Lee, Y. C, Chao, K. C, Chu, P. Y, Lai, C. R, Hsu, K. F, Chang, K. C, Chen, Y. C, Chen, L. T, Chang, J. Y, Leu, S. J, Shih, N. Y. Identification of salt-inducible kinase 3 as a novel tumor antigen associated with tumorigenesis of ovarian cancer. Oncogene. 2011, 30(33), 3570-3584.
Kitagawa, K, Sasaki, T, Terasaki, Y, Yagita, Y, Mochizuki, H. CREB activation is a key player for ischemic tolerance in the brain. Clin Neurol 2012, 52(11), 904-907. (See English abstract on page p. 907).
Imielinski, M, Berger, A. H, Hammerman, P. S, Hernandez, B, Pugh, I . J, Hodis, E, Cho, J, Suh, J, Capelletti, M, Sivachenko, A, Sougnez, C, Auclair, D, Lawrence, M. S, Stojanov, P, Cibulskis, K, Choi, K, de Waal, L, Sharifnia, T, Brooks, A, Greulich, H, Banerji, S, Zander, T, Seidel, D, Leenders, F, Ansén, S, Ludwig, C, Engel-Riedel, W, Stoelben E, Wolf J, Goparju C, Thompson K, Winckler W, Kwiatkowski D, Johnson, B. E, Janne, P. A, Miller, V. A, Pao, W, Travis, W. D, Pass, H. I, Gabriel, S. B, Lander, E. S, Thomas, R. K, Garraway, L.A, Getz, G, Meyerson, M. Mapping the Hallmarks of Lung Adenocarcinoma with Massively Parallel Sequencing. Cell. Sept. 14, 2012, 150, 1107-1120.
Copps, K. D, White, M. F. Regulation of insulin sensitivity by serineithreonine phosphorylation of insulin receptor substrate proteins IRS1 and IRS2. Diabetologia. 2012, 55(10), 2565-2582.
Wang, Y, Li, G, Goode, J, Paz, J. C, Ouyang, K, Screaton, R, Fischer, W. H, Chen, J, Tabas, I, Montminy, M. Inositol-1,4,5-

(56) References Cited

OTHER PUBLICATIONS trisphosphate receptor regulates hepatic gluconeogenesis in fasting and diabetes. Nature. 2012, 8; 485 (7396), 128-133.

Bricambert, J, Miranda, J, Benhamed, F, Girard, J, Postic, C, Dentin, R. Salt-inducible kinase 2 links transcriptional caoactivator p300 phosphorylation to the prevention of ChREBP-dependent hepatic steatosis in mice. J Clin Invest. 2010, 120(12), 4316-4331.

Salisbury, J. L. A centrosome kinase modulates antitumor drug sensitivity. Cancer Cell. 2010, 18(2), 99-100.

Wang, B, Goode, J, Best, J, Meltzer, J, Schilman, P. E, Chen, J, Garza, D, Thomas, J. B, Montminy, M. The insulin-regulated CREB coactivator TORC promotes stress resistance in *Drosophila*. Cell Metab. 2008, 7(5), 434-444.

Katoh, Y, Takemori, H, Horike, N, Doi, J, Muraoka, M, Min, L, Okamoto, M. Salt-inducible kinase (SIK) isoforms: their involvement in steroidogenesis and adipogenesis. Mol Cell Endocrinol. 2004, 217, 109-112.

Nagel, S, Leich, E, Quentmeier, H, Meyer, C, Kaufmann, M, Zaborski, M, Rosenwald, A, Drexler, H. G, Macleod, R. A. Amplification at 11q23 targets protein kinase SIK2 in diffuse large B-cell lymphoma. Leuk Lymphoma. 2010, 51(5), 881-891.

Decision of Refusal for corresponding JP Application No. 2015-547477, 6 pages, dated May 9, 2017.

European communication for corresponding EP Application No. 13862263.4, 10 pages, dated Jul. 18, 2017.

\* cited by examiner

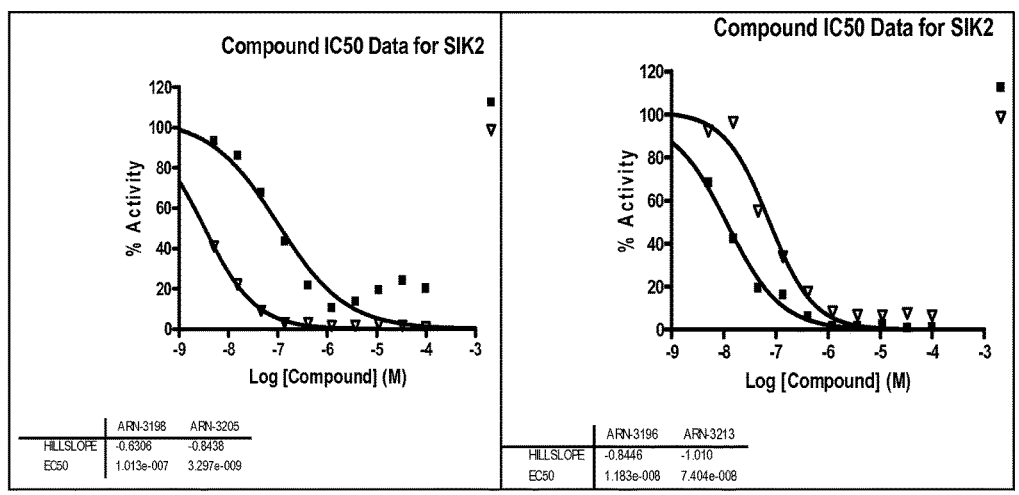
FIG. 1: SIK2 inhibitor examples: Panel A: 135 (■), 142 (△) and Palel B: 133 (■) and 168 (△).

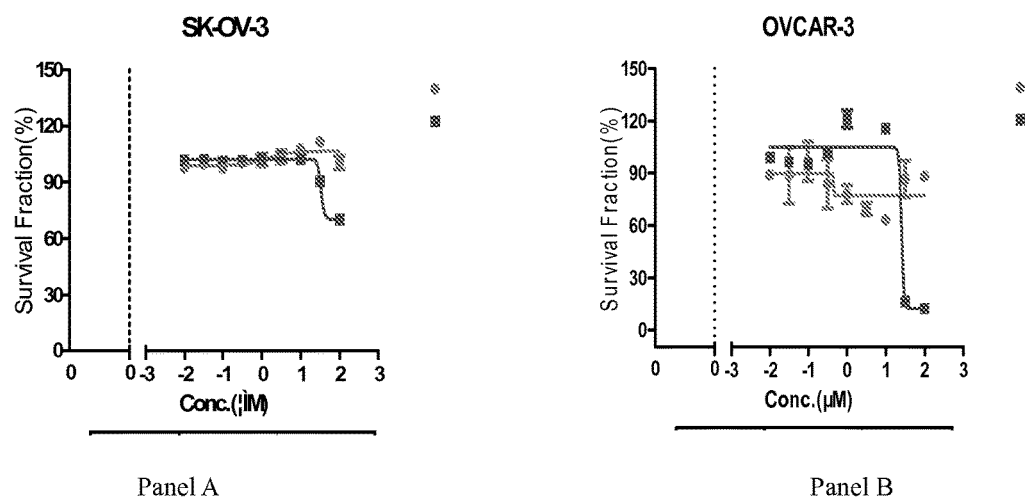
FIG. 2: SIK2 inhibitor examples tested in SK-OV-3 and OVCAR3 cell lines with Cisplatin as control.

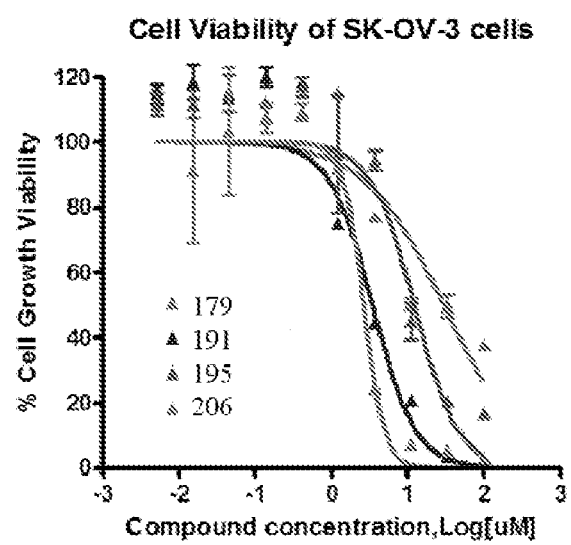
Figure 2b1

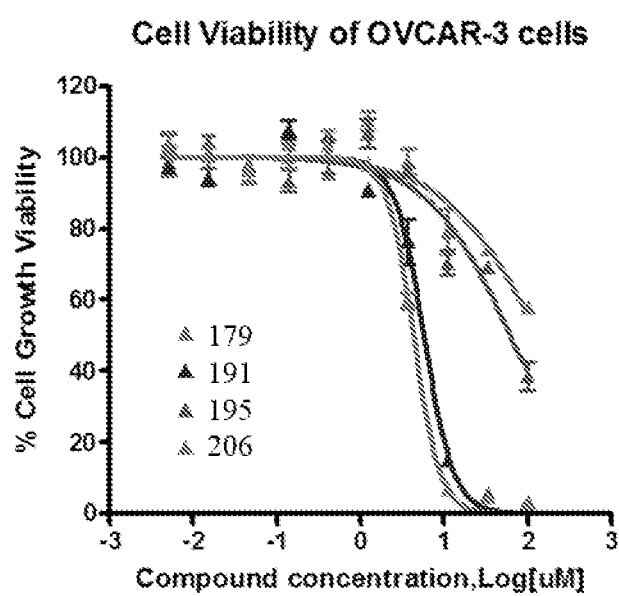
Figure 2b2

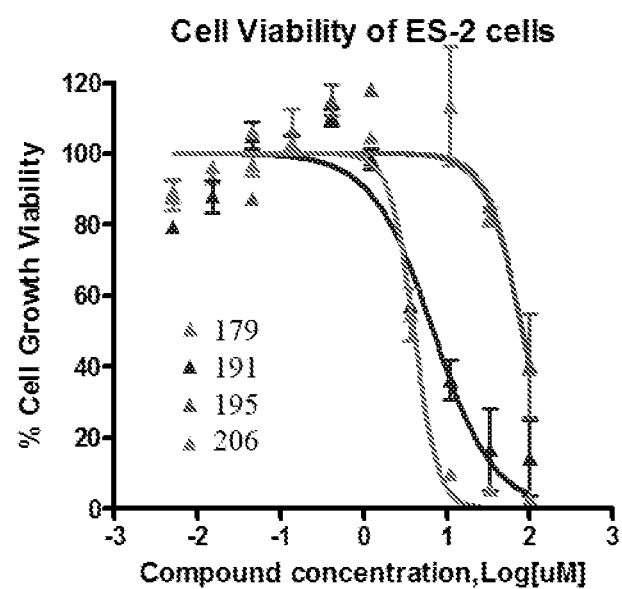
Figure 2b3

Multiple sequence alignment SIK family of kinases and its homologues

```
SIK1    1     MVIMSEFSADPAGQGQGQQKPLRVGFYDIERTLGKGNFAVVKLARHRVTKTQVAIKIIDK    60
SIK2    1     ------------QRGPVRVGFYDIEGTLGKGNFAVVKLGRHRITKTEVAIKIIDK       53
SIK3    1     -------------------MPARIGYYEIDRTIGKGNFAVVKRATHLVTKAKVAIKIIDK  41
AMPK    7     ---------------HLGRVKIGHYVLGDTLGVGTFGKVKIGEHQLTGHKVAVKILNR    49
MARK2         ----------GNSATSADEQPHIGNYRLLKTIGKGNFAKVKLARHILTGKEVAVKIIDK
                       :   *  :    *:* *.*. **    *  :*   :**;**::;

SIK1    61    TRLD-SSNLEKIYREVQLMKLLNHPHIIKLYQVMETKDMLYIV......MFDYLTSNG    119
SIK2    54    SQLD-AVNLEKIYREVQIMKMLDHPHIIKLYQVMETKSMLYLV......IFDYLANHG    112
SIK3    42    TQLD-BENLKKIFREVQIMKMLCHPHIIRLYQVMETERMIYLV......IFDHLVAHG    100
AMPK    50    QKIRSLDVVGKIKREIQNLKLFRHPHIIKLYQVISTPTDFFMV......LFDYICKHG    109
MARK2         TQLN-SSSLQKLFREVRIMKVLNHPNIVKLFEVIETEKTLYLV......VFDYLVAHG
                 ::      : *: **::  :*:: **:*::*::*:.*      :::* *:...**:**::   :*

SIK1    120   HLSENEARKKFWQILSAVEYCHDHHIVHRDLKTENLLLDGNMDIKLADFGFGNFYKSGEP 179
SIK2    113   RLNESEARRKFWQILSAVDYCHGRKIVHRDLKAENLLLDNNMNIKIADFGFGNFFKSGEL 172
SIK3    101   RMAEHEARRKFKQIVTAVYFCHCRNIVHRDLKAENLLLDANLNIKIADFGFSNLFTPGQL 160
AMPK    110   RVEEMEARRLFQQILSAVDYCHRHMVVHRDLKPENVLLDAHMNAKIADFGLSNMMSDGEF 169
MARK2         RMKEKEARAKFRQIVSAVQYCHQKFIVHRDLKAENLLLDADMNIKIADFGFSNEFTPGNK
               :: * ***   * **::**  :**  : :******.**:***   ::  *:****:.*    .*:

SIK1    180   LSTWCGSPPYAAPEVFEGKEYEGPQLDIWSLGVVLYVLVCGSLPFDGPNLPTLRQRVLEG 239
SIK2    173   LATWCGSPPYAAPEVFEGQQYEGPQLDIWSMGVVLYVLVCGALPFDGPTLPILRQRVLEG 232
SIK3    161   LKTWCGSPPYAAPELFEGKEYDGPKVDIWSLGVVLYVLVCGALPFDGSTLQNLRARVLSG 220
AMPK    170   LRDSCGSPNYAAPEVISGRLYAGPEVDIWSCGVILYALLCGTLPFDDEHVPTLFKKIRGG 229
MARK2         LDTFCGSPPYAAPELFQGKKYDGPEVDVWSLGVILYTLVSGSLPFDGQNLHELRERVLRG
               *   ****  ****:.*:  * **;:** **;**.*:.*:****.    :  *   : :

SIK1    240   RFRIPFFMSQDCESLIRRMLVVDPARRITIAQIRQHRWMRAEPCLPGPACPAFSAHSYTS 299
SIK2    233   RFRIPYFMSEDCEHLIRRMLVLDPSKRLTIAQIKEHKWMLIEVPVQRPVLYPQ.....   292
SIK3    221   KFRIPFFMSTECEHLIRHMLVLDPNKRLSMEQICKHKWMKLGDADPNFDRLIAECQQLKE 280
AMPK    230   VFYIPEYLNRSVATLLMHMLQVDPLKRATIKDIREHEWFKQDLPSYLFPE---------  279
MARK2         KYRIPFYMSTDCENLLKKFLILNPSKRGTLEQIMKDRWMNVGHEDDELKPYVAPLPDYKD
               : **  ::. .    *:  ::*  ::*   *: ::  :*   :..*:
```

FIG. 3: Structure based sequence alignment in Clustal W of the catalytic protein kinase domains of SIK1 (SNF1LK), SIK2 (SNF1LK, QIK), SIK3 (QSK), AMPK and MARK2. Amino acid residue annotation were identical residues (*), highly conserved residues (:), and similar residues (.) The active site residues highlighted in yellow and the gatekeeper residues in turquoise and the DFG residues shown in yellow.

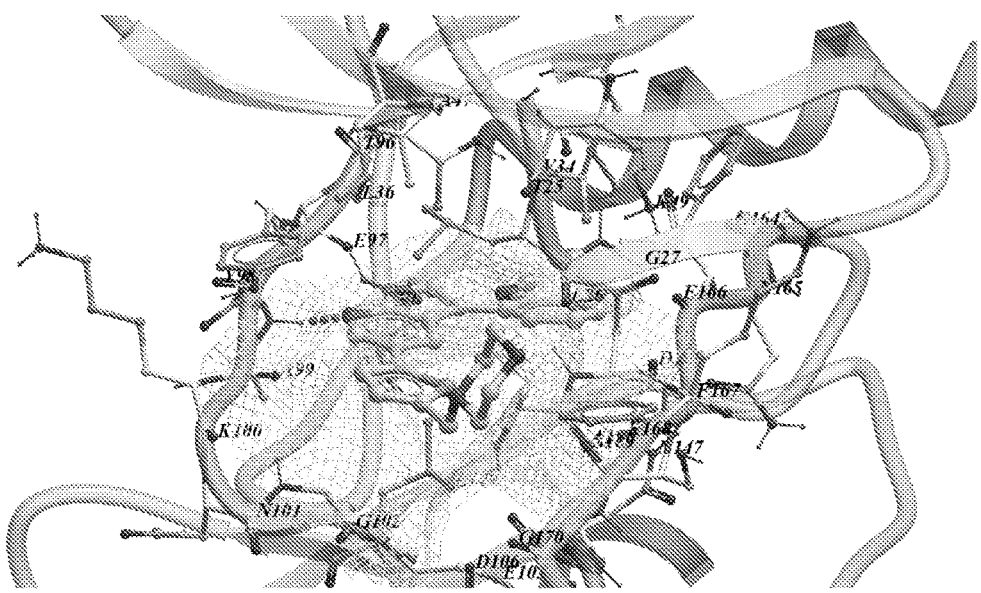
FIG. 4: Homology model of SIK2 in complex with an inhibitor. The critical active site residues shown in colour-by-atom in stick representations. The inhibitor binding site depicted in surface in complex with SIK2. Compound belongs to 1*H*-pyrrolo [2, 3-*b*] pyridine structural class of the present invention.

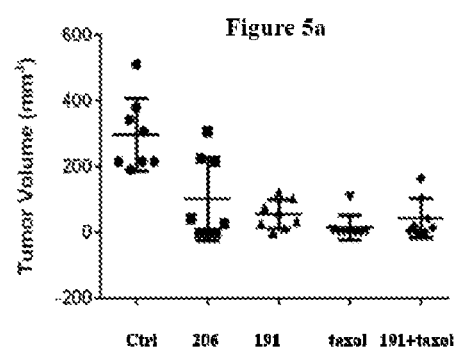

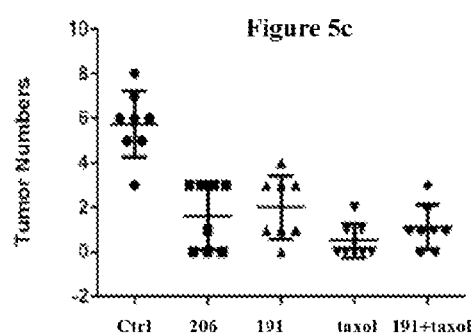

SUBSTITUTED 1 H-PYRROLO [2, 3-B] PYRIDINE AND 1 H-PYRAZOLO [3, 4-B] PYRIDINE DERIVATIVES AS SALT INDUCIBLE KINASE 2 (SIK2) INHIBITORS

CROSS-REFERENCE TO RELATED APPLICATIONS

This application is a divisional application of U.S. patent application Ser. No. 14/101,109 filed Dec. 9, 2013, the entirety of which is incorporated by reference herein, and claims the benefit of U.S. Patent Application No. 61/737,618 filed Dec. 14, 2012.

INCORPORATION BY REFERENCE

The sequence listing ("Sequence Listing") submitted in ASCII text filed in connection with this application, created Nov. 9, 2015, 231 KB, is incorporated herein by reference.

FIELD OF INVENTION

The present invention is directed to compounds, their synthesis, and their use as modulators or inhibitors of the Salt Inducible Kinase 2 ("SIK2" kinase)(SEQ ID NO: 11). The compounds of the present invention are useful for modulating (e.g. inhibiting) SIK2 (SEQ ID NO: 11) activity and for treating diseases or conditions mediated by SIK2 (SEQ ID NO: 11) such as for example, disease states associated with abnormal cell growth such as cancer, stroke, obesity and type 2 diabetes.

BACKGROUND OF THE INVENTION

Substituted 5-(pyrazin-2-yl)-1 h-pyrazolo[3,4-b]pyridine and pyrazolo[3,4-b]pyridine derivatives as protein kinase inhibitors are described in US Patent Publication No. 2013/0102586 and International Publication No. WO2012/135631.

Salt Inducible Kinase 2 (SIK2)(SEQ ID NO: 11) is a centrosome kinase required for bipolar mitotic spindle formation and is a Ser/Thr kinase. Three isoforms of SIK family have been reported; SIK1 (SNF1LK)(SEQ ID NO: 10), SIK2 (SNF1LK, QIK)(SEQ ID NO: 11) and SIK3 (QSK)(SEQ ID NO: 24). The SIK2 (SEQ ID NO: 11) is amplified in large B-cell lymphoma, ovarian, melanoma and beast cancer patients. Recent findings suggest that SIK2 (SEQ ID NO: 11) over expression enhanced cell death after ischemia and metabolic diseases as well. Inhibition of SIK2 (SEQ ID NO: 11) was reported to cause SIK2-dependent centrosome splitting in interphase while SIK2 (SEQ ID NO: 11) depletion blocked centrosome separation in mitosis, sensitizing ovarian cancers to paclitaxel in culture and in xenografts. Depletion of SIK2 (SEQ ID NO: 11) also delayed G1/S transition and reduced AKT phosphorylation. Higher expression of SIK2 (SEQ ID NO: 11) significantly correlated with poor survival in patients with high-grade serous ovarian cancers (Bast, Jr., et al., Cancer Cell., 18, 109-121, 2010) and is a plausible therapeutic target for therapy in ovarian cancers.

The Salt Inducible Kinase 2 (SIK2) (SEQ ID NO: 11) depletion in cancer cells had a significant decrease in cancer cell growth, delayed mitotic progression and G1/S transition and decreased AKT phosphorylation. Deficiency of SIK2 (SEQ ID NO: 11) significantly sensitized cancer cells to taxnae and paclitaxel in vivo xenograft models in interfering with mitotic progression. In this work we established the basis of utilizing SIK2 (SEQ ID NO: 11) as a target for therapy in cancer by evaluating its effect on taxane, paclitaxel sensitization in a panel of cell lines, confirming activity in xenografts that the SIK2 (SEQ ID NO: 11) is overexpressed in 30% of ovarian cancers and to further develop an assay to measure SIK2 (SEQ ID NO: 11) activity. Ovarian Cancer (OC) accounts 3% of cancers in women and is the fifth leading cause of cancer related death among women. Nearly 22,240 women were diagnosed in 2013 with OC in US alone with about 14,030 women estimated to die from this deadly gynecologic malignancy of American women. Ovarian cancer is one of the cancers difficult to detect prior to its advanced stage. The currently available treatments, other than surgery and radiation, are chemotheurapeutics and the few approved targeted agents.

Additionally, an advantage of SIK2 (SEQ ID NO: 11) inhibitors that block SIK2 (SEQ ID NO: 11) activity is to recruite melanogenesis. This leads to recovery of brown hair in 6 to 8 weeks.

Recent reports suggests that the over expression of SIK2 (SEQ ID NO: 11) controlled the TORC1 (Transducer of regulated CREB activity-1) from entering the nucleus and activating CREB, and this enhanced cell death after ischemia. The SIK2 (SEQ ID NO: 11) inhibitor could enhance CREB (cAMP Responsive Element-Binding) protein activity and prevent neuron death in response to ischemia. The SIK2 (SEQ ID NO: 11) deficient mice were protected from stroke suggests that SIK2 degradation after ischemia is required for neurons.

There continues to be a need for new drugs to treat multiple cancer indications, melanogenesis, stroke, cardiovascular, obesity and type II diabetes diseases where SIK2 (SEQ ID NO: 11) and its isoforms play a pivotal role in these multiple disease indications. Using the homology structure of the SIK2 (SEQ ID NO: 11) and our FFDD (Fragment Field Drug Design) or FIELDS guided lead identification, screening and SAR efforts; we have discovered the first-in-class novel H-pyrrolo[2,3-b]pyridine and 1H-pyrazolo[3,4-b]pyridine inhibitors of SIK2 (SEQ ID NO: 11) that would be useful for treating multiple disease indications, including cancer (ovarian, breast, prostate, diffuse large B-cell lymphoma and melanoma), stroke, obesity, type II diabetes. We disclose here the composition and method of use for inhibitors of SIK2 (SEQ ID NO: 11).

Accordingly, the present invention is directed to composition and method of use for novel H-pyrrolo[2,3-b]pyridine and 1H-pyrazolo[3,4-b]pyridine inhibitors of SIK2 (SEQ ID NO: 11) and SIK3 (SEQ ID NO: 24) useful for treating multiple disease indications, including cancer (ovarian, breast, prostate, diffuse large B-cell lymphoma, lung, NSCL and melanoma), autophagy function, stroke, obesity, and type II diabetes.

SUMMARY OF THE INVENTION

The present invention concerns compounds active on protein kinases, specifically SIK1 (SEQ ID NO: 10), SIK2 (SEQ ID NO: 11) and SIK3 (SEQ ID NO: 24), and in general, including but not limited to CLK1 (SEQ ID NO: 1), CLK2 (SEQ ID NO: 2), DYRK1 (SEQ ID NO: 13), DYRK1A (SEQ ID NO: 3), ITK (SEQ ID NO: 14), Janus family of kinases (JAK1 (SEQ ID NO: 4), JAK2 (SEQ ID NO: 5), JAK3 (SEQ ID NO: 6) and TYK2 (SEQ ID NO: 15)), LRRK2 (SEQ ID NO: 12), LRRK2 G2019 (SEQ ID NO: 7), MELK (SEQ ID NO: 8), MAP4K1 (SEQ ID NO: 16), MAP4K5 (SEQ ID NO: 9), NIK (SEQ ID NO: 17), PKCd (SEQ ID NO: 18), RSK4 (SEQ ID NO: 19), STK2

(SEQ ID NO: 20), STK3 (SEQ ID NO: 21), STK4 (SEQ ID NO: 22), STK10 (SEQ ID NO: 23) and TNIK1 (SEQ ID NO: 28), including any mutations of these kinases and the use thereof in treating disease and conditions associated with egulations of the activity of these kianses. More specifically the invention concerns compounds of Formula I, IA, and IB as described below. Thus the invention provides novel use of compounds for therapeutic methods involving inhibition and or modulation of protein kinases specifically SIK family of kinases; SIK1 (SNF1LK)(SEQ ID NO: 10), SIK2 (SNF1LK, QIK)(SEQ ID NO: 11) and SIK3 (QSK)(SEQ ID NO: 24), as well as novel compounds that can be used for the theurapeutic methods involving modulation of these protein kinases.

The present invention relates to compounds according to Formulas I, IA or IB:

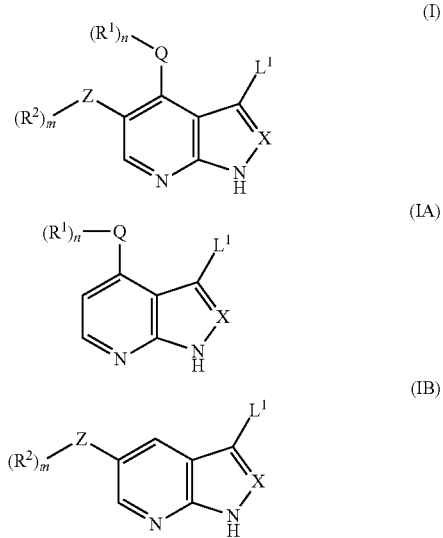

to pharmaceutically acceptable composition, salts thereof, their synthesis and their use as SIK2 inhibitors including such compounds and methods of their use in the treatment of various diseases and disorders such as cancer, stroke, obesity and type II diabetes.

BRIEF DESCRIPTION OF THE FIGURES

FIG. 1: shows two panels of SIK2 (SEQ ID NO: 11) inhibitor examples: Panel A on the left: 135 (■), 142 (Δ) and Panel B on the right: 133 (■) and 168 (Δ). The percent activity is plotted against log M.

FIG. 2: shows SIK2 inhibitor examples tested in SK-OV-3 cell lines on the left Panel A and OVCAR3 cell lines on the right Panel B with Cisplatin as control. The survival fraction is plotted against the concentration.

FIG. 2b1: Effects of four 1H-Pyrrolo[2,3-b]pyridine and 1H-Pyrazolo[3,4-b]pyridine derivatives on the SIK2-expressed SKOv3 cells.

FIG. 2b2: Effects of four 1H-Pyrrolo[2,3-b]pyridine and 1H-Pyrazolo[3,4-b]pyridine derivatives on the SIK2-expressed OVCAR3 cells.

FIG. 2b3: Effects of four 1H-Pyrrolo[2,3-b]pyridine and 1H-Pyrazolo[3,4-b]pyridine derivatives on the SIK2-expressed ES-2 cells.

FIG. 3: depicts the structure based sequence alignment in Clustal W of the catalytic protein kinase domains of SIK1 (SNF1LK)(SEQ ID NO: 10), SIK2 (SNF1LK, QIK)(SEQ ID NO: 11), SIK3 (QSK)(SEQ ID NO: 24), AMPK (SEQ ID NO: 27) and MARK2 (SEQ ID NO: 25). Amino acid residue annotation were identical residues (*), highly conserved residues (:), and similar residues (.) The active site residues highlighted in yellow and the gatekeeper residues in turquoise and the DFG residues shown in yellow.

FIG. 4: Homology model of SIK2 (SEQ ID NO: 11) in complex with one of the lead inhibitor. The critical active site residues shown in color-by-atom in stick representations. The inhibitor binding site depicted in surface in complex with SIK2 (SEQ ID NO: 11). Compound belongs to 1H-pyrrolo[2,3-b]pyridine structural class claimed.

FIG. 5a-c: Plots of tumor volume, weight, and number against a control, two 1H-Pyrrolo[2,3-b]pyridine compounds, taxol, and a combination. The data show that the compounds of the present invention and taxol have significant antitumor effects and as a single agent these series dissemination of tumor cell in vivo.

BRIEF DESCRIPTION OF THE SEQUENCES

Figure 5B:
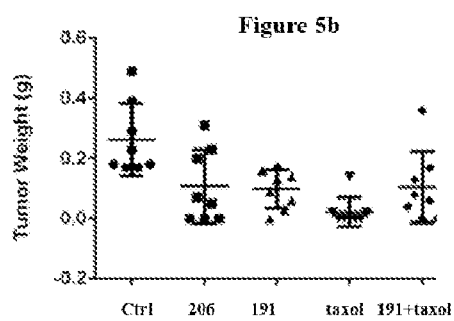

SEQ ID NO: 1 is the human CLK1 protein kinase sequence;
SEQ ID NO: 2 is the human CLK2 protein kinase sequence;
SEQ ID NO: 3 is the human DYRK1A protein kinase sequence;
SEQ ID NO: 4 is the human JAK1 protein kinase sequence;
SEQ ID NO: 5 is the human JAK2 protein kinase sequence;
SEQ ID NO: 6 is the human JAK3 protein kinase sequence;
SEQ ID NO: 7 is the human LRRK2 G2019 protein kinase sequence;
SEQ ID NO: 8 is the human MELK protein kinase sequence;
SEQ ID NO: 9 is the human MAP4K5 protein kinase sequence;
SEQ ID NO: 10 is the human SIK1 protein kinase sequence;
SEQ ID NO: 11 is the human SIK2 protein kinase sequence;
SEQ ID NO: 12 is the human LRRK2 protein kinase sequence;
SEQ ID NO: 13 is the human DYRK1 protein kinase sequence;
SEQ ID NO: 14 is the human ITK protein kinase sequence;
SEQ ID NO: 15 is the human TYK2 protein kinase sequence;
SEQ ID NO: 16 is the human MAP4K1 protein kinase sequence;
SEQ ID NO: 17 is the human NIK protein kinase sequence;
SEQ ID NO: 18 is the human PKC-delta protein kinase sequence;
SEQ ID NO: 19 is the human RSK4 protein kinase sequence
SEQ ID NO: 20 is the human NEK4 protein kinase sequence;
SEQ ID NO: 21 is the human STK3 protein kinase sequence;
SEQ ID NO: 22 is the human STK4 protein kinase sequence;

SEQ ID NO: 23 is the human STK10 protein kinase sequence;

SEQ ID NO: 24 is the human SIK3 protein kinase sequence;

SEQ ID NO: 25 is the human MARK2 protein kinase sequence;

SEQ ID NO: 26 is the human STK11 protein kinase sequence;

SEQ ID NO: 27 is the human AMPK protein kinase sequence; and

SEQ ID NO: 28 is the human TNIK protein kinase sequence.

DETAILED DESCRIPTION OF THE INVENTION

Compounds of the present invention are described by the Formulas I, IA or IB:

(I)

(IA)

(IB)

or a pharmaceutically acceptable salt thereof, wherein:
X is N or CH;
L¹ is H, F; or
L¹ is thienyl, phenyl, pyrrolyl, pyridyl,

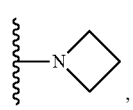

piperazinyl,

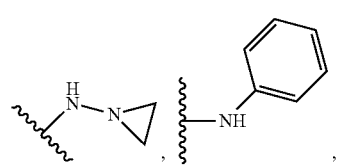

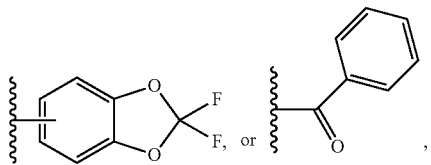

any of which is optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

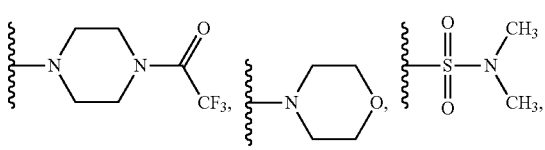

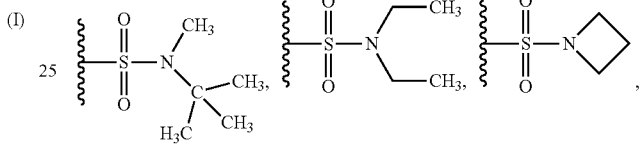

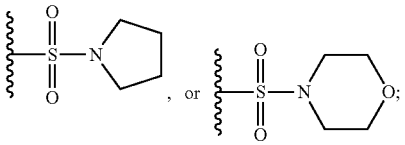

Q is a direct bond, thienyl, thiazolyl, phenyl,

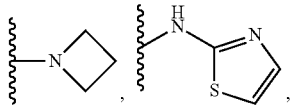

furanyl, piperazinyl, or pyrazolyl;
R¹ is each H, halo, —CN, $C_{1-4}$alkyl, $C_{1-4}$alkoxy,

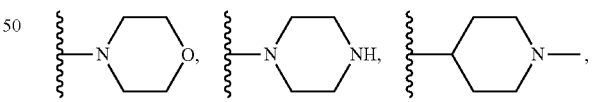

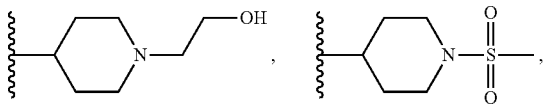

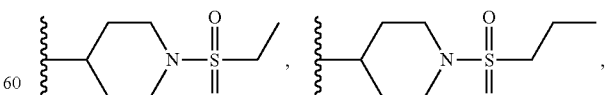

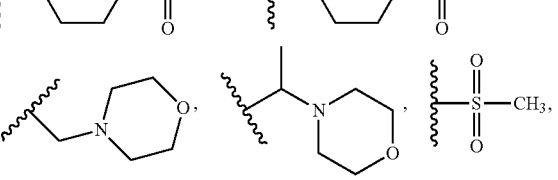

-continued
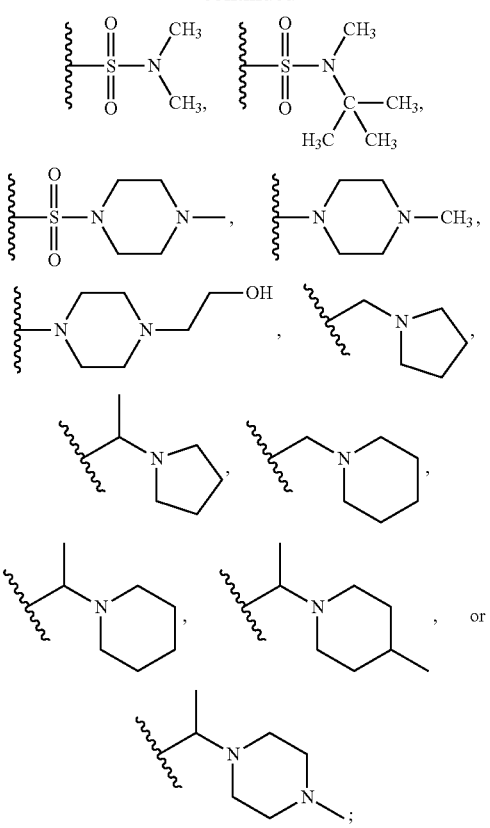
Z is a direct bond, thienyl, thiazolyl, phenyl,
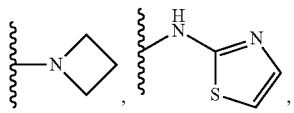
furanyl, piperazinyl, or pyrazolyl;
R² is each independently H, halo, —CN, C₁₋₄alkyl, C₁₋₄alkoxy,
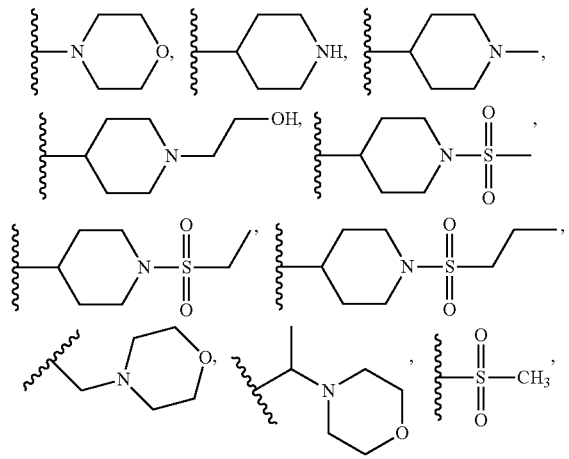
-continued
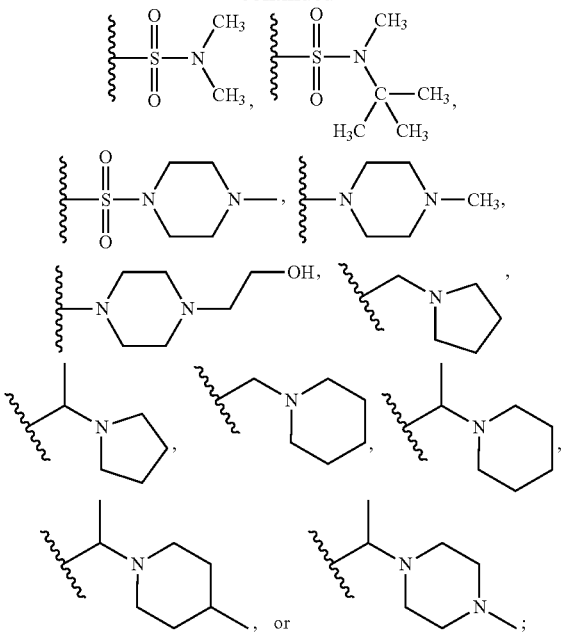
n is 0, 1, or 2; and
m is 0, 1, or 2;
provided that the compound is not a compound selected from the following list ("Exclusion List"):
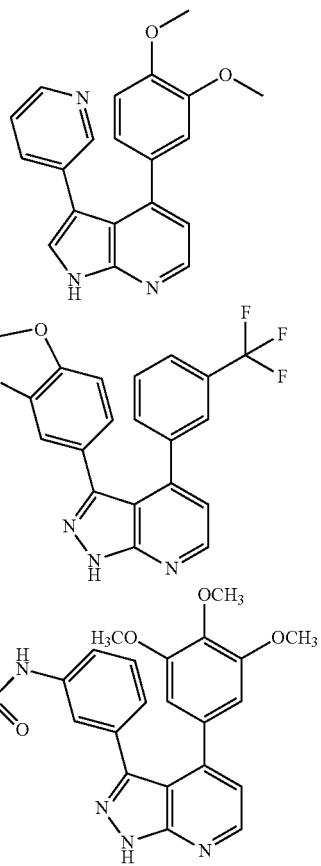

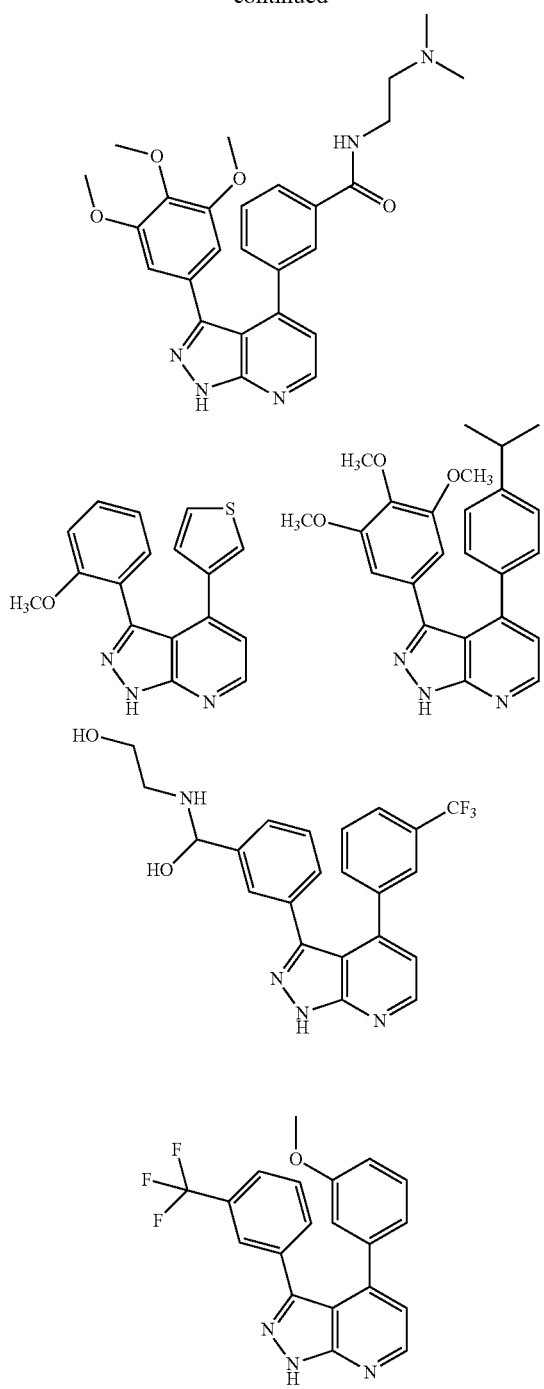

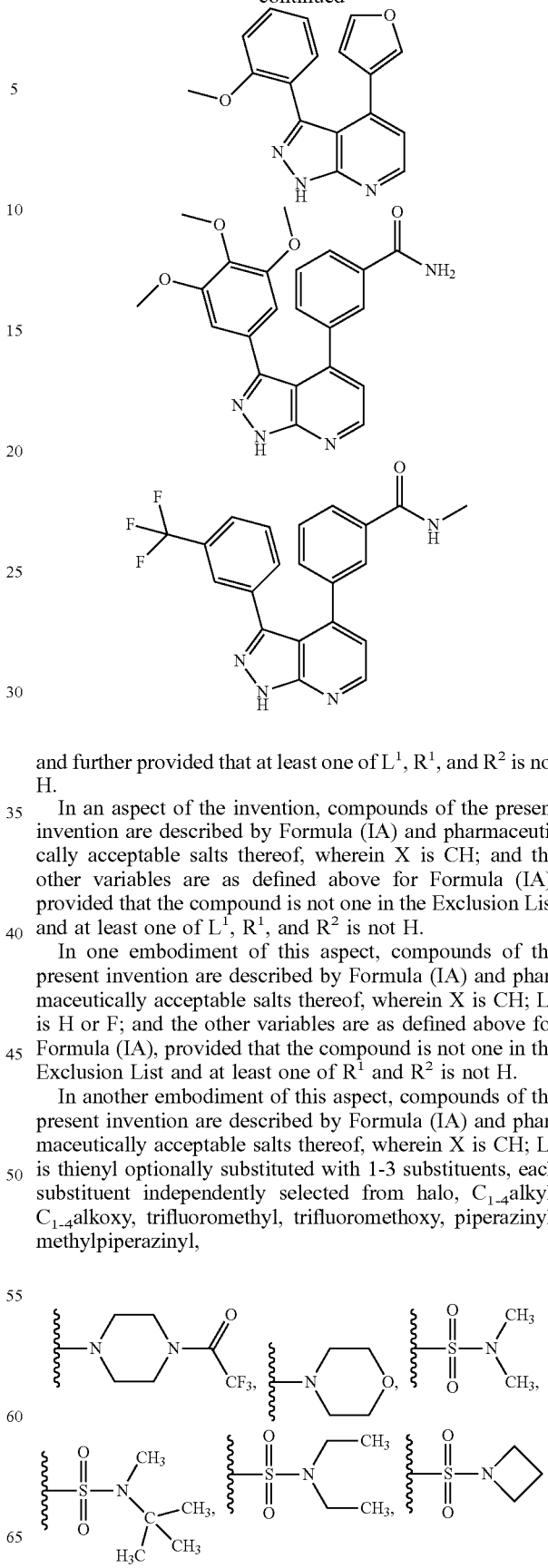

and further provided that at least one of $L^1$, $R^1$, and $R^2$ is not H.

In an aspect of the invention, compounds of the present invention are described by Formula (IA) and pharmaceutically acceptable salts thereof, wherein X is CH; and the other variables are as defined above for Formula (IA), provided that the compound is not one in the Exclusion List and at least one of $L^1$, $R^1$, and $R^2$ is not H.

In one embodiment of this aspect, compounds of the present invention are described by Formula (IA) and pharmaceutically acceptable salts thereof, wherein X is CH; $L^1$ is H or F; and the other variables are as defined above for Formula (IA), provided that the compound is not one in the Exclusion List and at least one of $R^1$ and $R^2$ is not H.

In another embodiment of this aspect, compounds of the present invention are described by Formula (IA) and pharmaceutically acceptable salts thereof, wherein X is CH; $L^1$ is thienyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

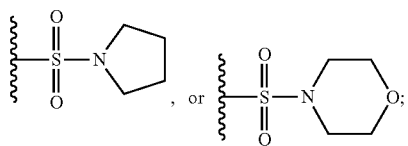

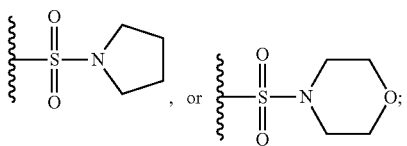

and the other variables are as defined above for Formula (IA), provided that the compound is not one in the Exclusion List.

In still another embodiment of this aspect, compounds of the present invention are described by Formula (IA) and pharmaceutically acceptable salts thereof, wherein X is CH; $L^1$ is phenyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl, and the other variables are as defined above for Formula (IA), provided that the compound is not one in the Exclusion List.

In still another embodiment of this aspect, compounds of the present invention are described by Formula (IA) and pharmaceutically acceptable salts thereof, wherein X is CH; $L^1$ is pyridyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

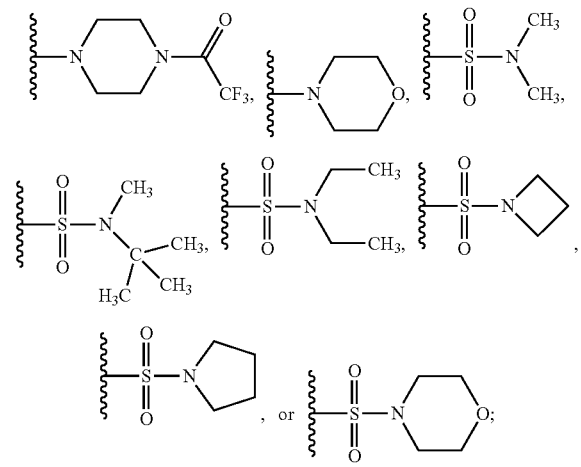

and the other variables are as defined above for Formula (IA), provided that the compound is not one in the Exclusion List.

In yet another embodiment of this aspect, compounds of the present invention are described by Formula (IA) and pharmaceutically acceptable salts thereof, wherein X is CH; $L^1$ is pyrrolyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl, and the other variables are as defined above for Formula (IA), provided that the compound is not one in the Exclusion List.

In another embodiment of this aspect, compounds of the present invention are described by Formula (IA) and pharmaceutically acceptable salts thereof, wherein X is CH; $L^1$ is

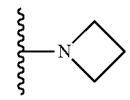

optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

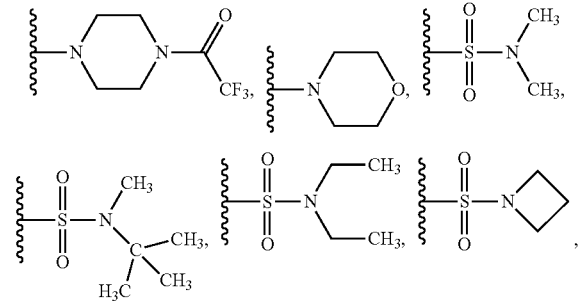

-continued

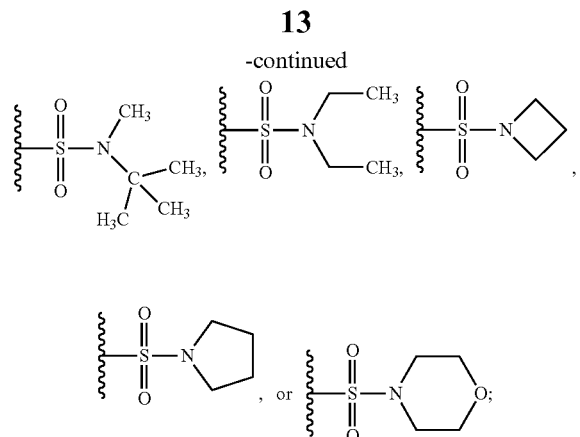

and the other variables are as defined above for Formula (IA), provided that the compound is not one in the Exclusion List.

In yet another embodiment of this aspect, compounds of the present invention are described by Formula (IA) and pharmaceutically acceptable salts thereof, wherein X is CH; $L^1$ is piperazinyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

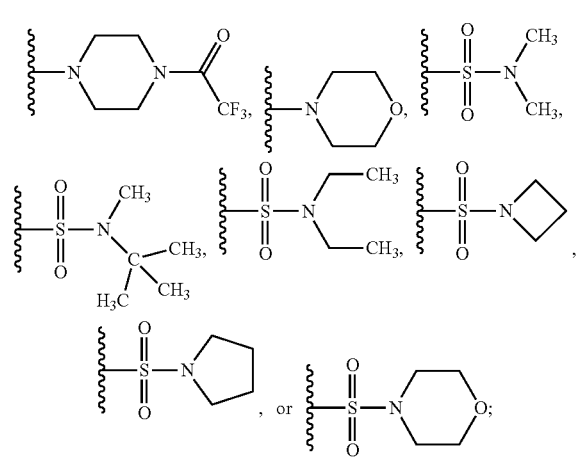

and the other variables are as defined above for Formula (IA), provided that the compound is not one in the Exclusion List.

In another embodiment of this aspect, compounds of the present invention are described by Formula (IA) and pharmaceutically acceptable salts thereof, wherein X is CH; $L^1$ is

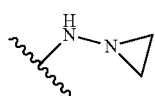 [SMILES: *NN1CC1]

optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

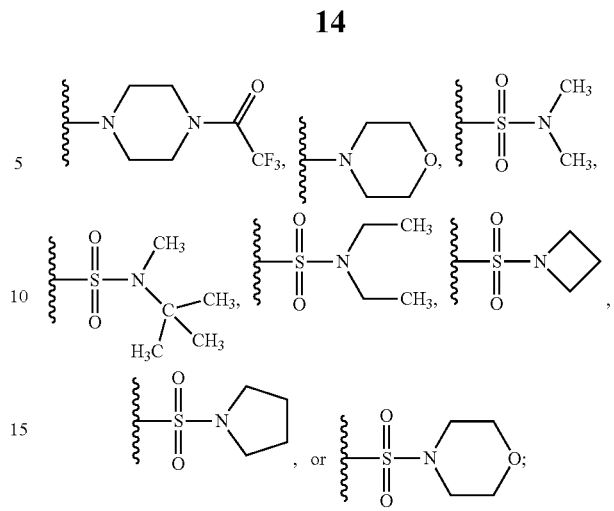

and the other variables are as defined above for Formula (IA), provided that the compound is not one in the Exclusion List.

In another embodiment of this aspect, compounds of the present invention are described by Formula (IA) and pharmaceutically acceptable salts thereof, wherein X is CH; $L^1$ is

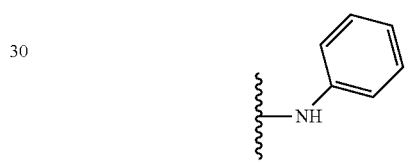

optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

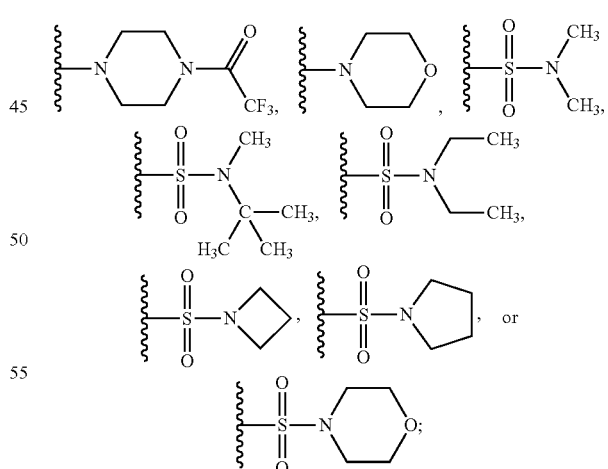

and the other variables are as defined above for Formula (IA), provided that the compound is not one in the Exclusion List.

In an aspect of the invention, compounds of the present invention are described by Formula (IA) and pharmaceutically acceptable salts thereof, wherein X is N; and the other variables are as defined above for Formula (IA), provided that the compound is not one in the Exclusion List and at least one of $L^1$, $R^1$, and $R^2$ is not H.

In one embodiment of this aspect, compounds of the present invention are described by Formula (IA) and pharmaceutically acceptable salts thereof, wherein X is N; $L^1$ is H or F; and the other variables are as defined above for Formula (IA), provided that the compound is not one in the Exclusion List and at least one of $R^1$ and $R^2$ is not H.

In another embodiment of this aspect, compounds of the present invention are described by Formula (IA) and pharmaceutically acceptable salts thereof, wherein X is N; $L^1$ is thienyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

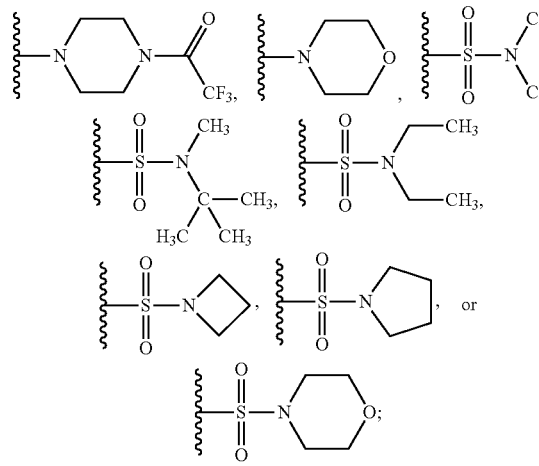

and the other variables are as defined above for Formula (IA), provided that the compound is not one in the Exclusion List.

In still another embodiment of this aspect, compounds of the present invention are described by Formula (IA) and pharmaceutically acceptable salts thereof, wherein X is N; $L^1$ is phenyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

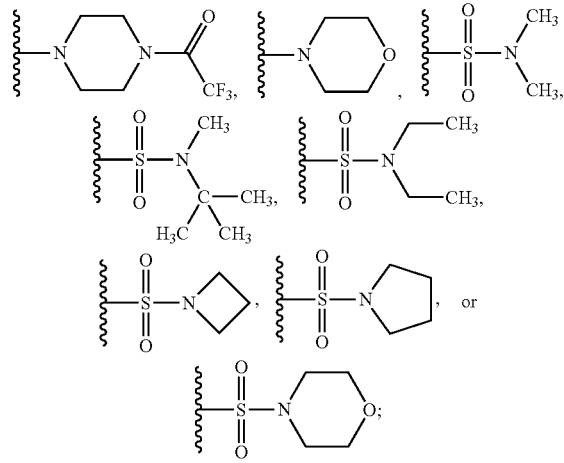

and the other variables are as defined above for Formula (IA), provided that the compound is not one in the Exclusion List.

In yet another embodiment of this aspect, compounds of the present invention are described by Formula (IA) and pharmaceutically acceptable salts thereof, wherein X is N; $L^1$ is pyrrolyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

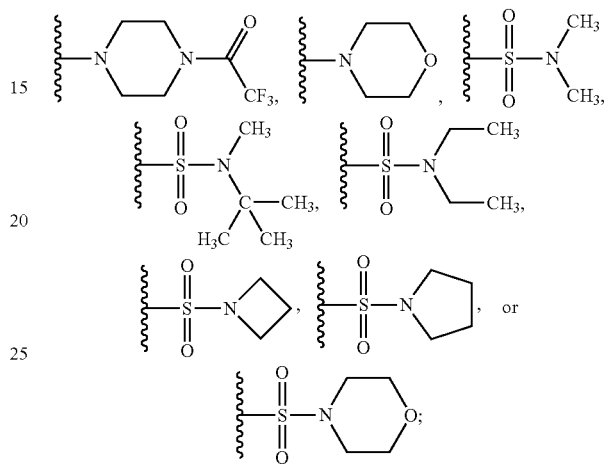

and the other variables are as defined above for Formula (IA), provided that the compound is not one in the Exclusion List.

In still another embodiment of this aspect, compounds of the present invention are described by Formula (IA) and pharmaceutically acceptable salts thereof, wherein X is N; $L^1$ is pyridyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

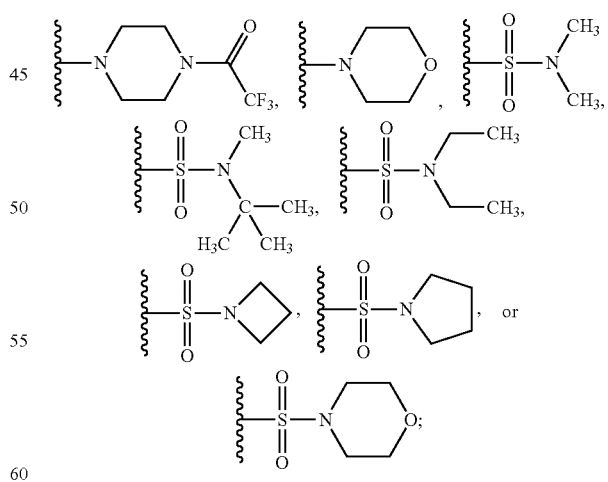

and the other variables are as defined above for Formula (IA), provided that the compound is not one in the Exclusion List.

In another embodiment of this aspect, compounds of the present invention are described by Formula (IA) and pharmaceutically acceptable salts thereof, wherein X is N; $L^1$ is

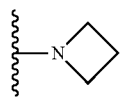 [SMILES: *N1CCC1]

optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

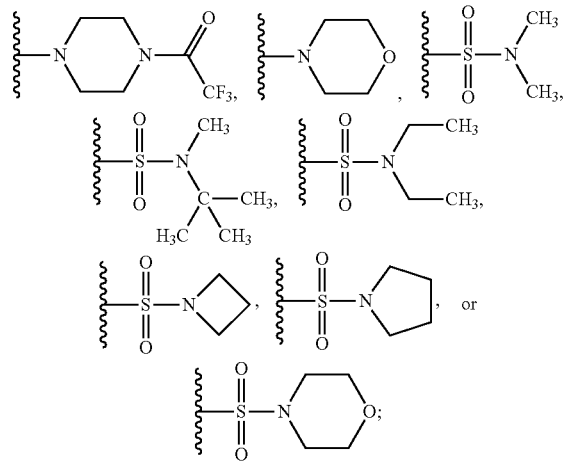

and the other variables are as defined above for Formula (IA), provided that the compound is not one in the Exclusion List.

In yet another embodiment of this aspect, compounds of the present invention are described by Formula (IA) and pharmaceutically acceptable salts thereof, wherein X is N; $L^1$ is piperazinyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

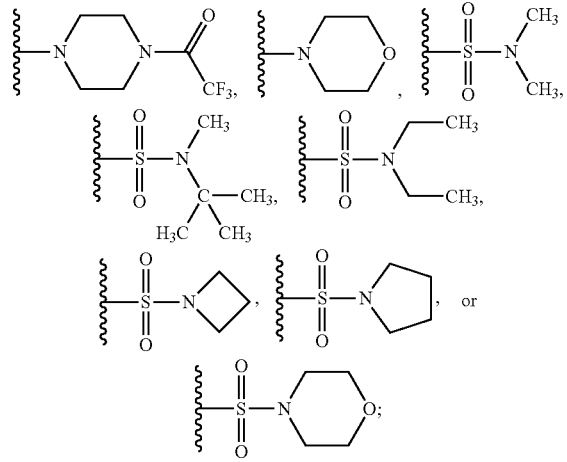

and the other variables are as defined above for Formula (IA), provided that the compound is not one in the Exclusion List.

In another embodiment of this aspect, compounds of the present invention are described by Formula (IA) and pharmaceutically acceptable salts thereof, wherein X is N; $L^1$ is

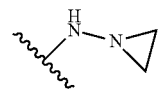

optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

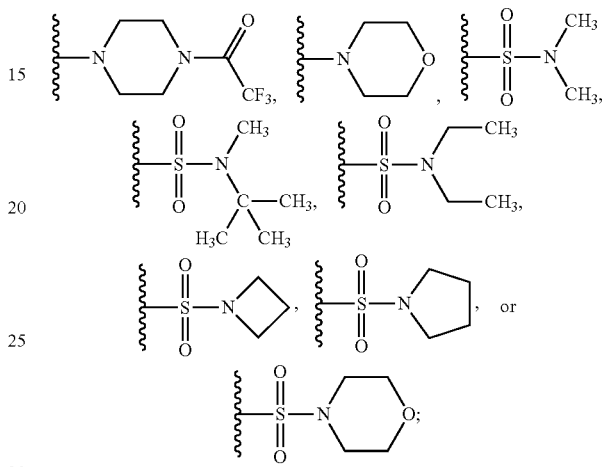

and the other variables are as defined above for Formula (IA), provided that the compound is not one in the Exclusion List.

In another embodiment of this aspect, compounds of the present invention are described by Formula (IA) and pharmaceutically acceptable salts thereof, wherein X is N; $L^1$ is

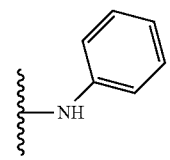 [SMILES: *Nc1ccccc1]

optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

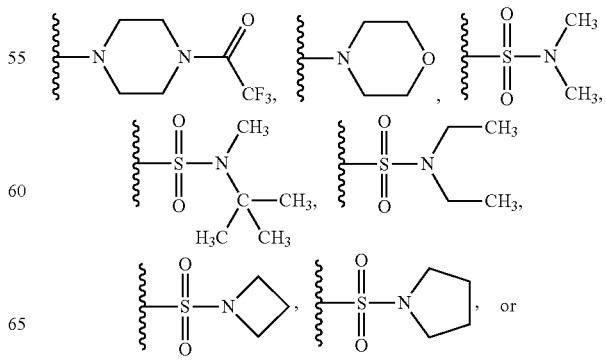

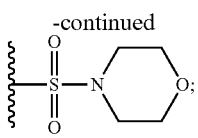

and the other variables are as defined above for Formula (IA), provided that the compound is not one in the Exclusion List.

In an aspect of the invention, compounds of the present invention are described by Formula (IB) and pharmaceutically acceptable salts thereof, wherein X is CH; and the other variables are as defined above for Formula (IB), provided that the compound is not one in the Exclusion List and at least one of $L^1$, $R^1$, and $R^2$ is not H.

In one embodiment of this aspect, compounds of the present invention are described by Formula (IB) and pharmaceutically acceptable salts thereof, wherein X is CH; $L^1$ is H or F; and the other variables are as defined above for Formula (IB), provided that the compound is not one in the Exclusion List and at least one of $R^1$ and $R^2$ is not H.

In another embodiment of this aspect, compounds of the present invention are described by Formula (IB) and pharmaceutically acceptable salts thereof, wherein X is CH; $L^1$ is thienyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

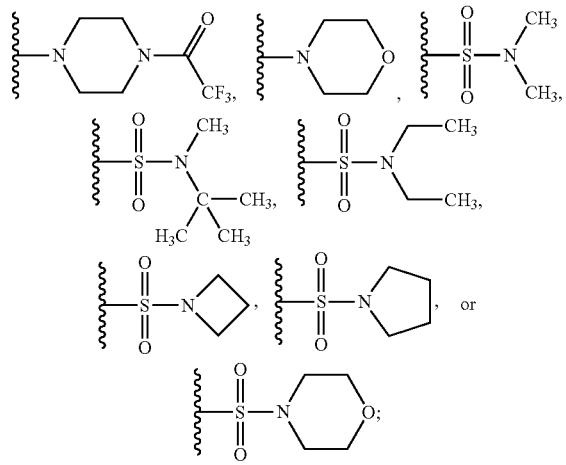

and the other variables are as defined above for Formula (IB), provided that the compound is not one in the Exclusion List.

In still another embodiment of this aspect, compounds of the present invention are described by Formula (IB) and pharmaceutically acceptable salts thereof, wherein X is CH; $L^1$ is phenyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

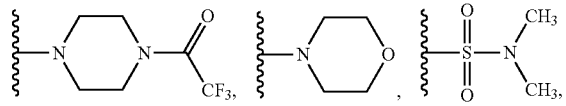

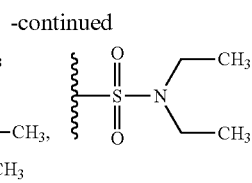

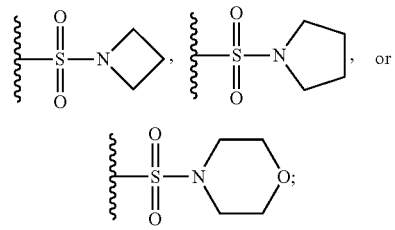

and the other variables are as defined above for Formula (IB), provided that the compound is not one in the Exclusion List.

In yet another embodiment of this aspect, compounds of the present invention are described by Formula (IB) and pharmaceutically acceptable salts thereof, wherein X is CH; $L^1$ is pyrrolyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

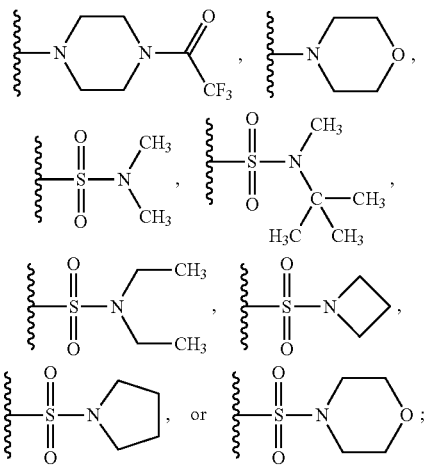

and the other variables are as defined above for Formula (IB), provided that the compound is not one in the Exclusion List.

In still another embodiment of this aspect, compounds of the present invention are described by Formula (IB) and pharmaceutically acceptable salts thereof, wherein X is CH; $L^1$ is pyridyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

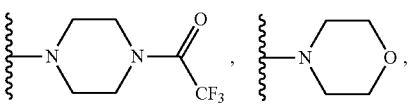

-continued

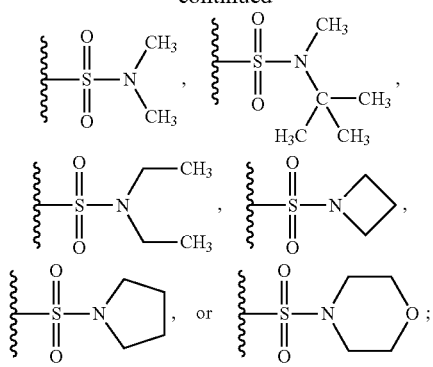

and the other variables are as defined above for Formula (IB), provided that the compound is not one in the Exclusion List.

In another embodiment of this aspect, compounds of the present invention are described by Formula (IB) and pharmaceutically acceptable salts thereof, wherein X is CH; $L^1$ is

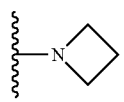 [SMILES: *N1CCC1]

optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

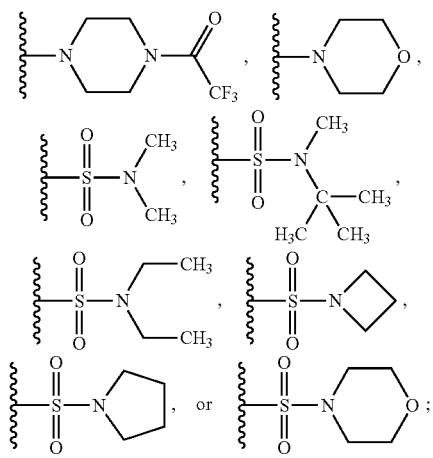

and the other variables are as defined above for Formula (IB), provided that the compound is not one in the Exclusion List.

In yet another embodiment of this aspect, compounds of the present invention are described by Formula (IB) and pharmaceutically acceptable salts thereof, wherein X is CH; $L^1$ is piperazinyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

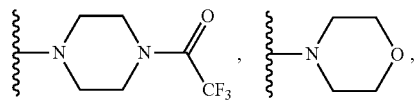

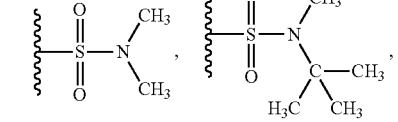

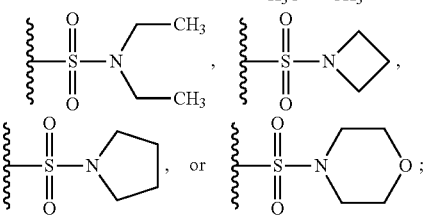

and the other variables are as defined above for Formula (IB), provided that the compound is not one in the Exclusion List.

In another embodiment of this aspect, compounds of the present invention are described by Formula (IB) and pharmaceutically acceptable salts thereof, wherein X is CH; $L^1$ is

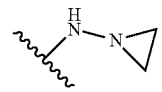 [SMILES: *NN1CC1]

optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

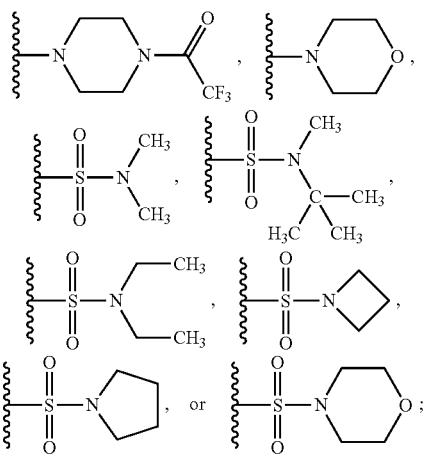

and the other variables are as defined above for Formula (IA), provided that the compound is not one in the Exclusion List.

In another embodiment of this aspect, compounds of the present invention are described by Formula (IB) and pharmaceutically acceptable salts thereof, wherein X is CH; $L^1$ is

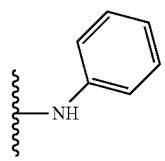
optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,
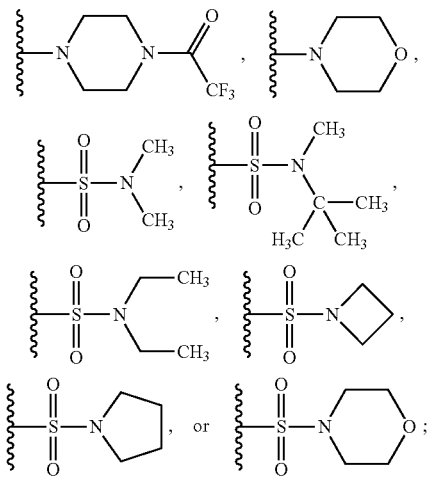
and the other variables are as defined above for Formula (IB), provided that the compound is not one in the Exclusion List.
Compounds of the present invention include:
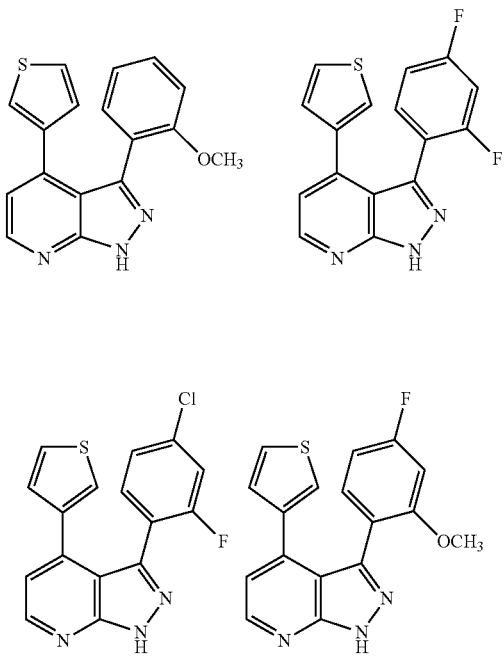
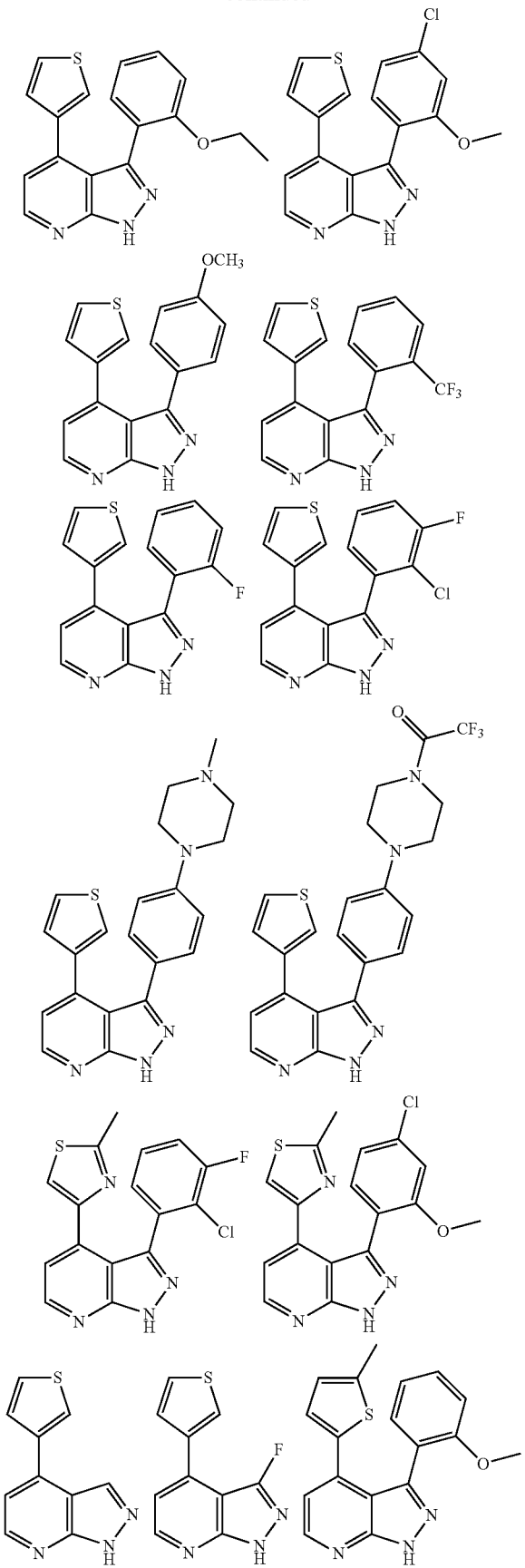

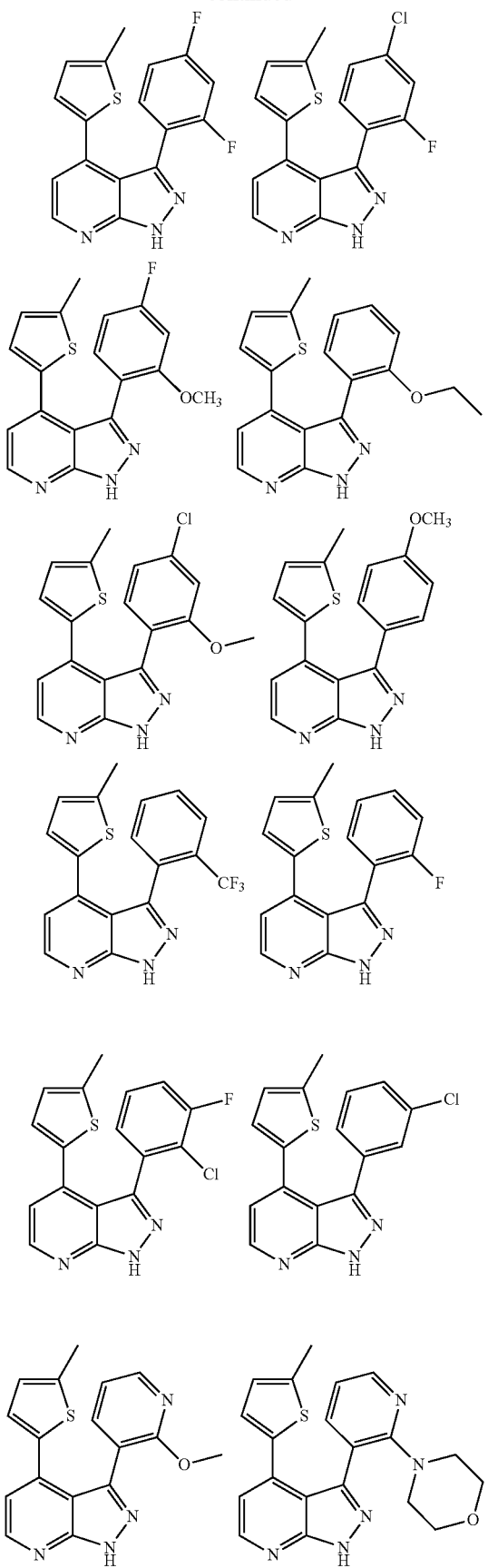
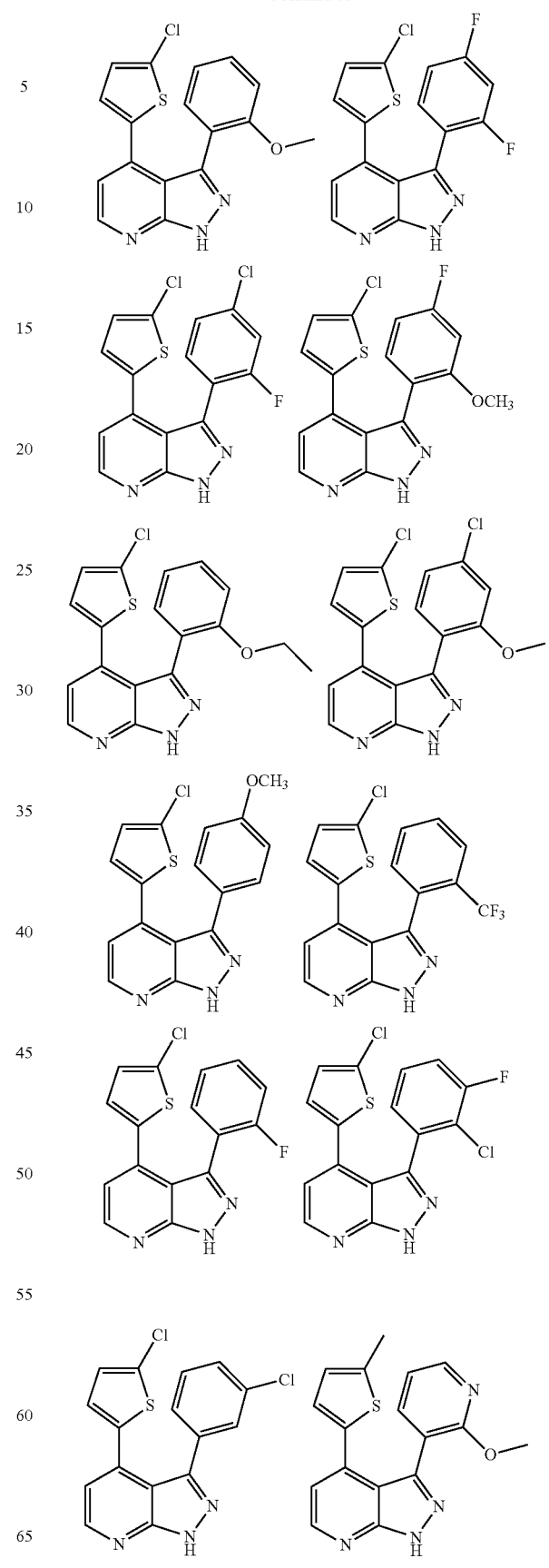

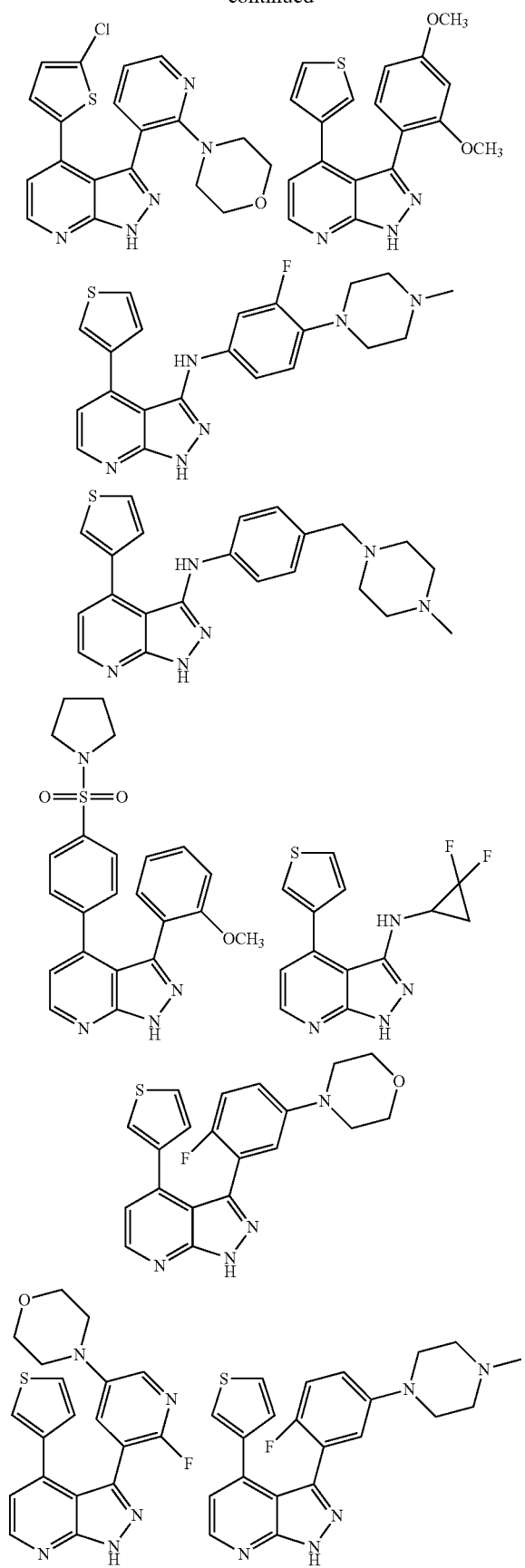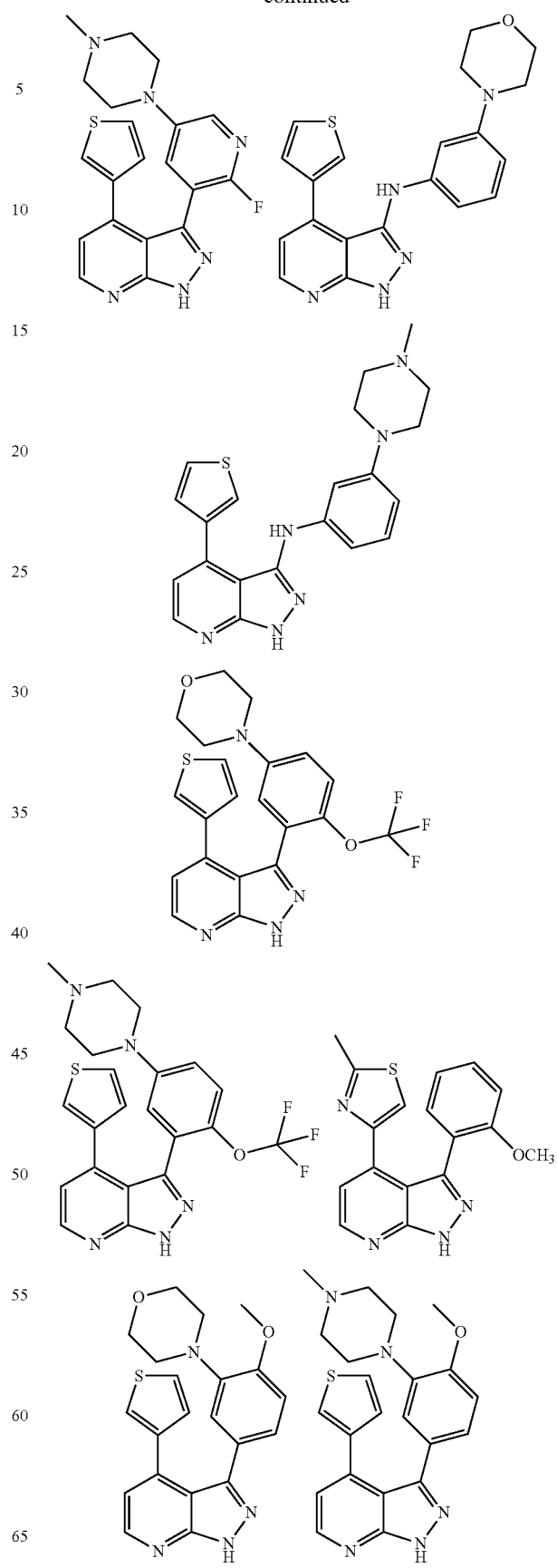

-continued
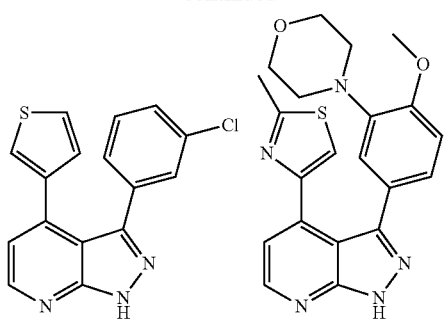
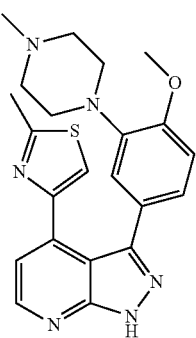
Other compounds of the present invention include:
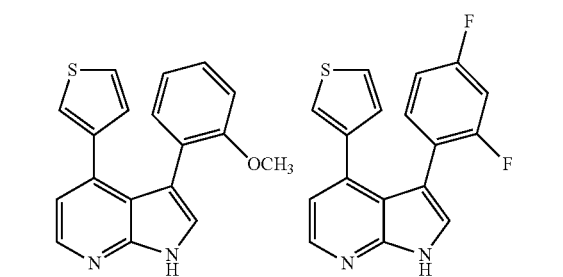
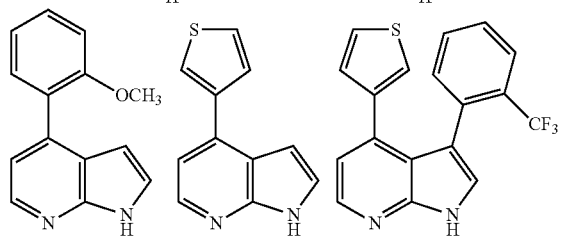
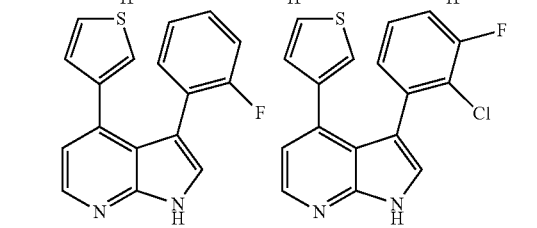
-continued
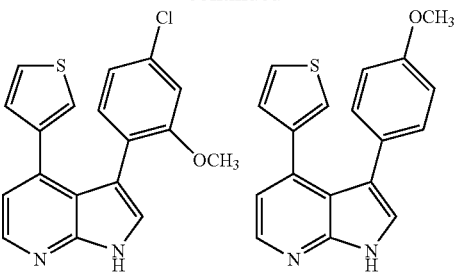
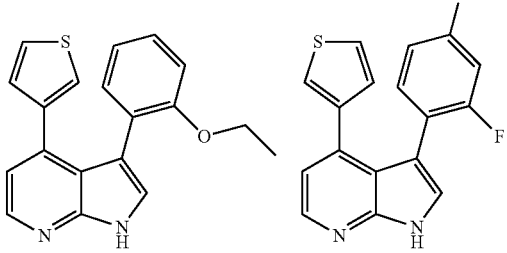
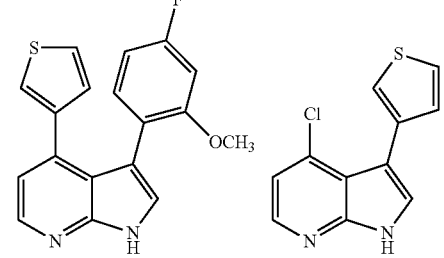
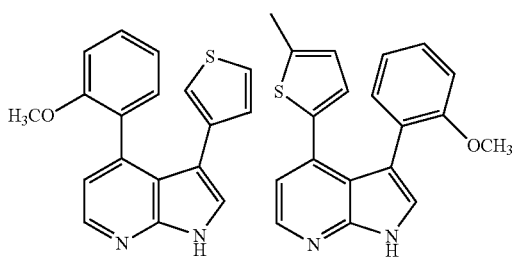
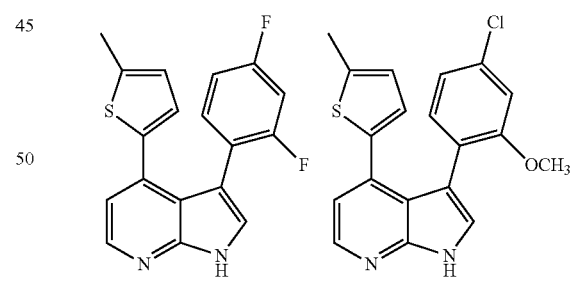
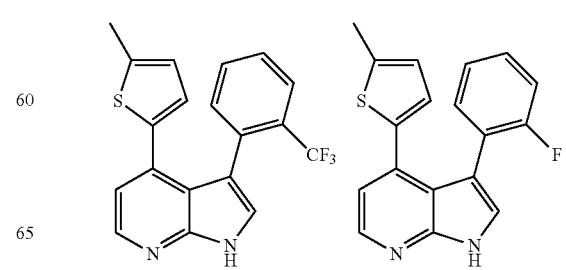

-continued
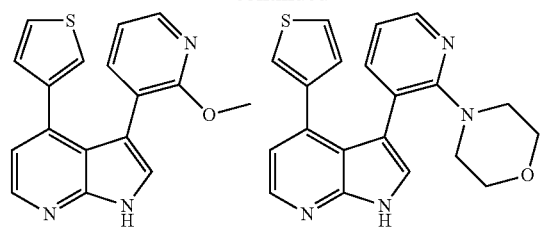
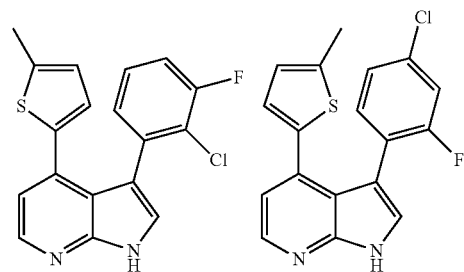
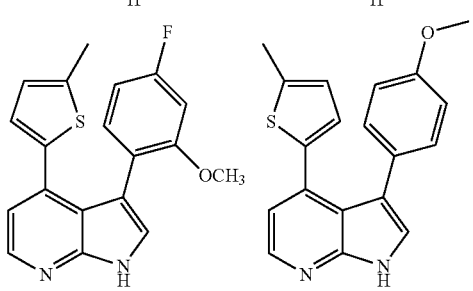
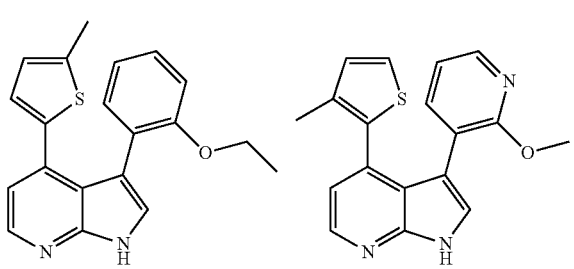
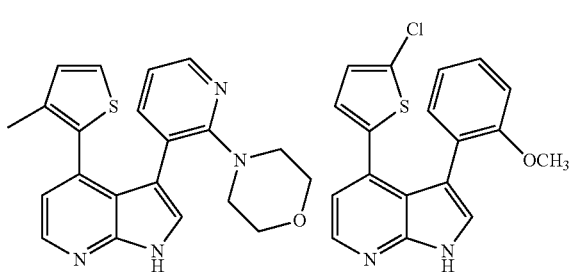
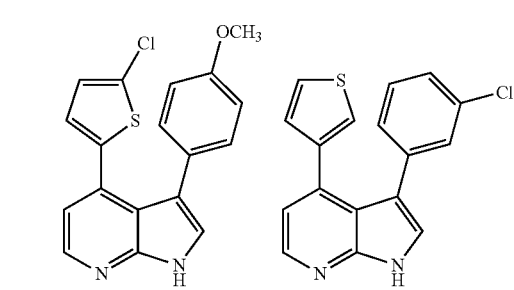
-continued
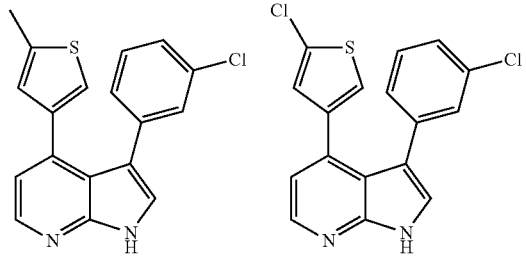
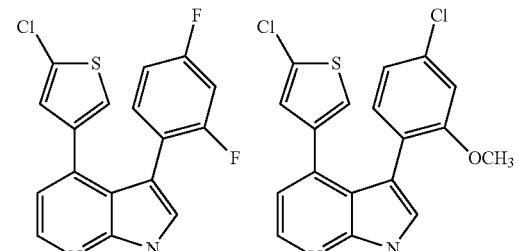
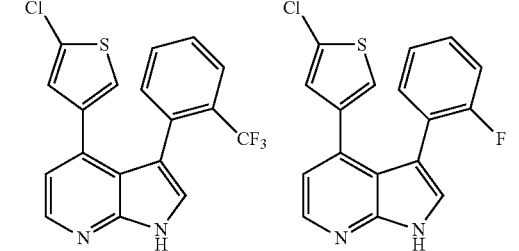
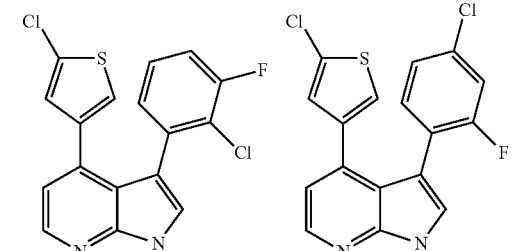
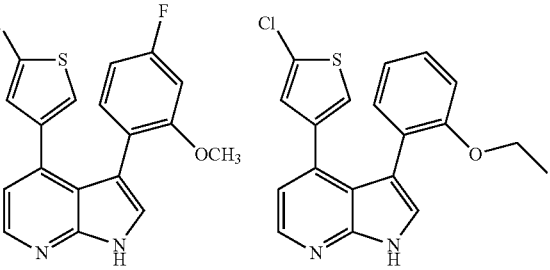
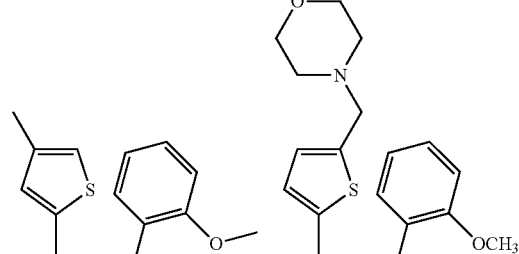

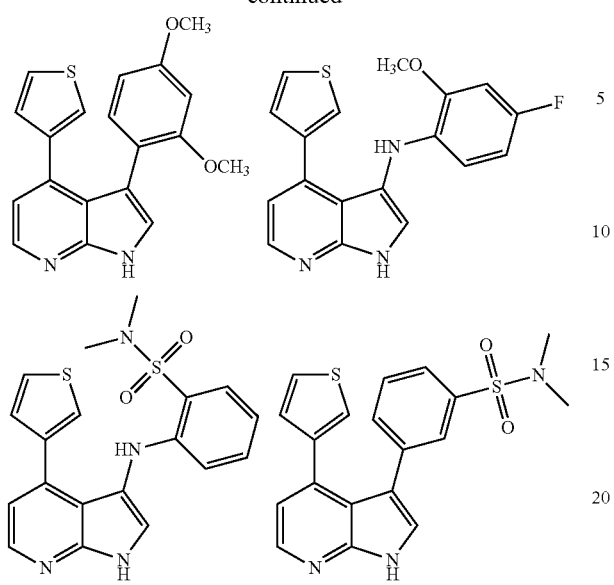
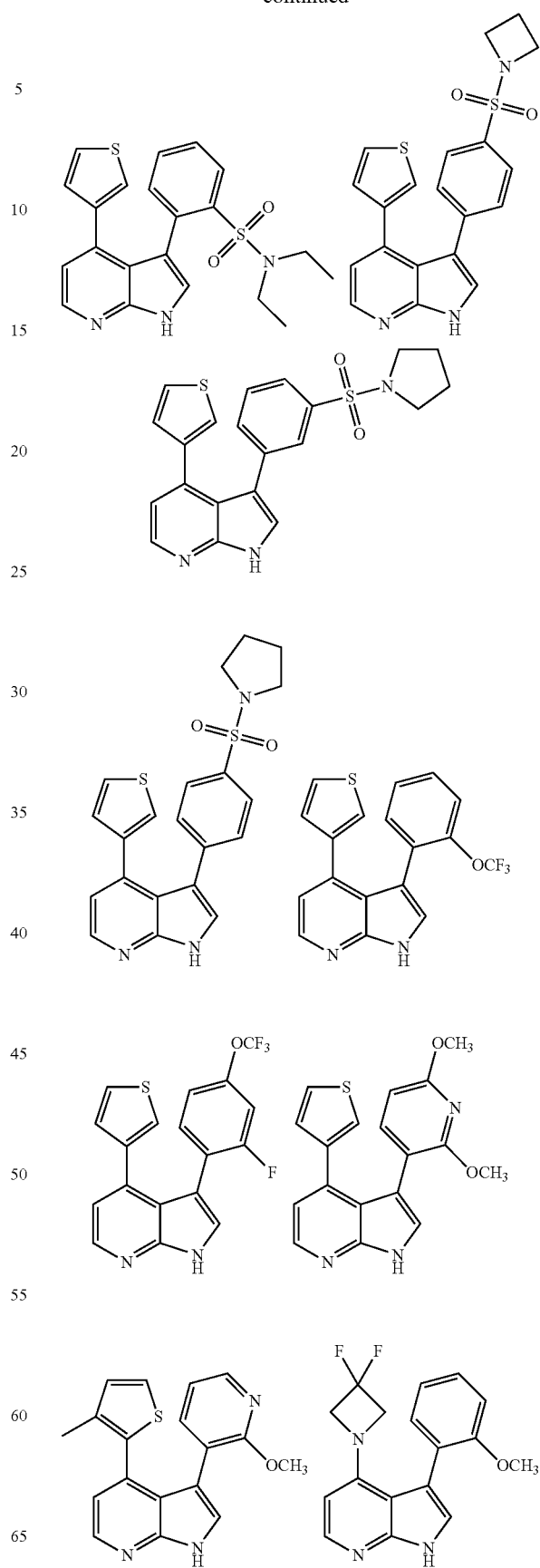

-continued
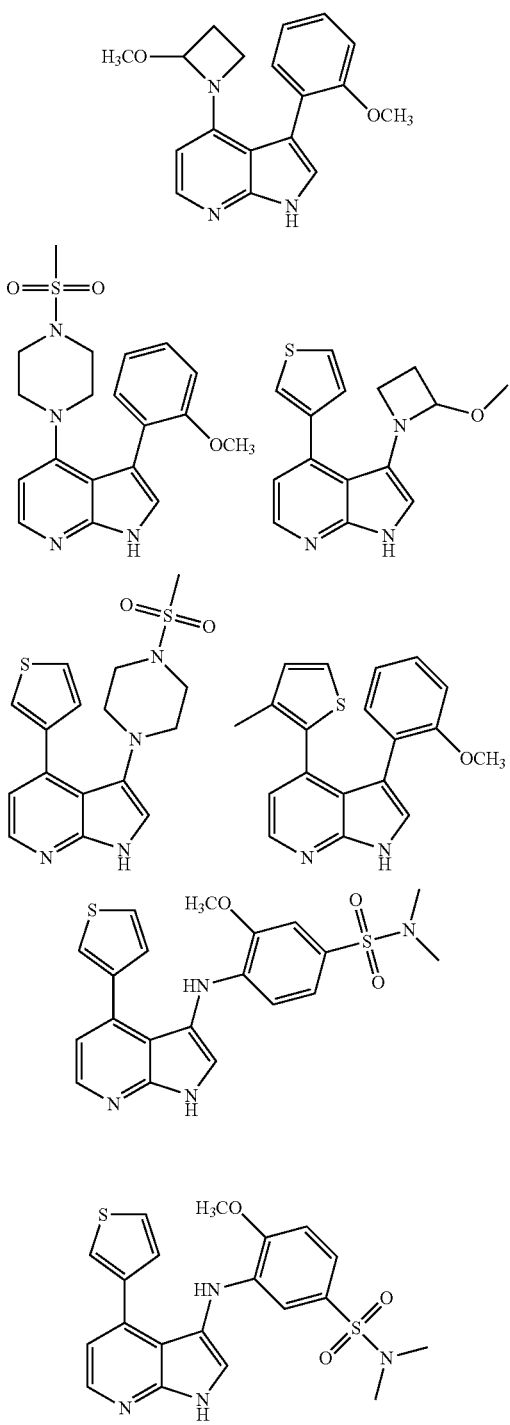
-continued
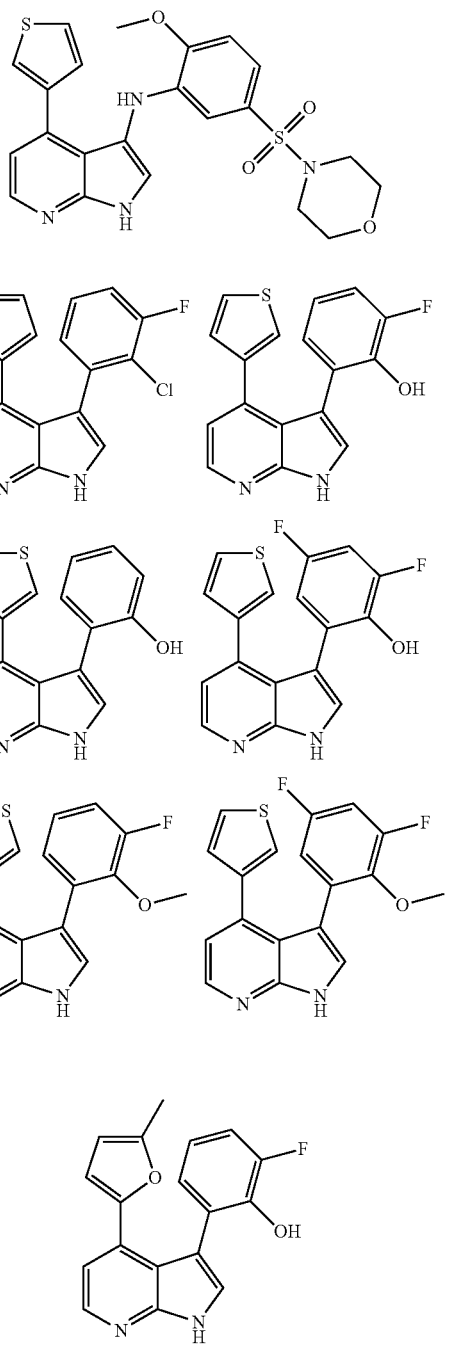
Other compounds of the present invention include:
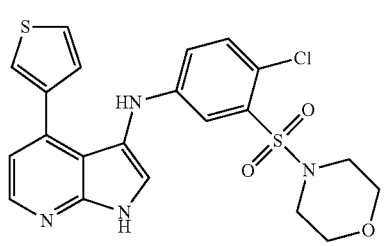

37
-continued
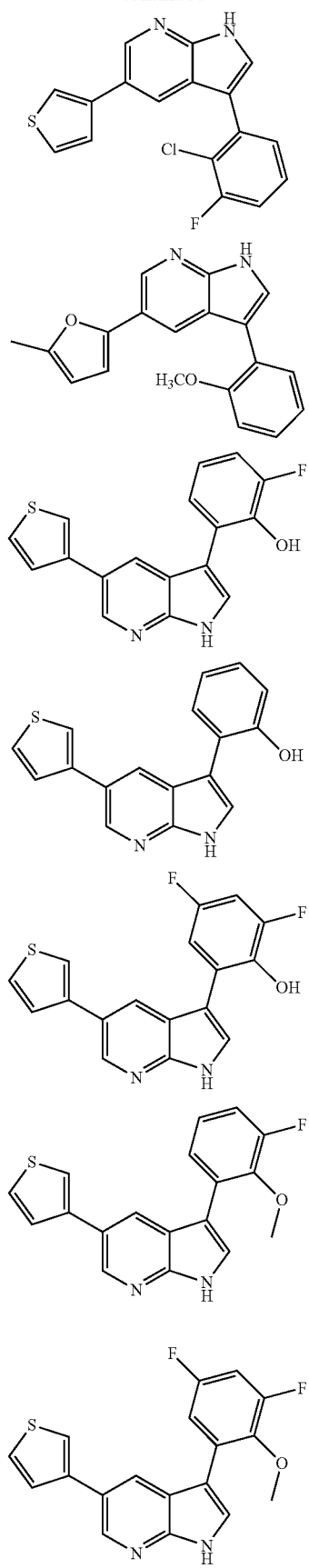
38
-continued
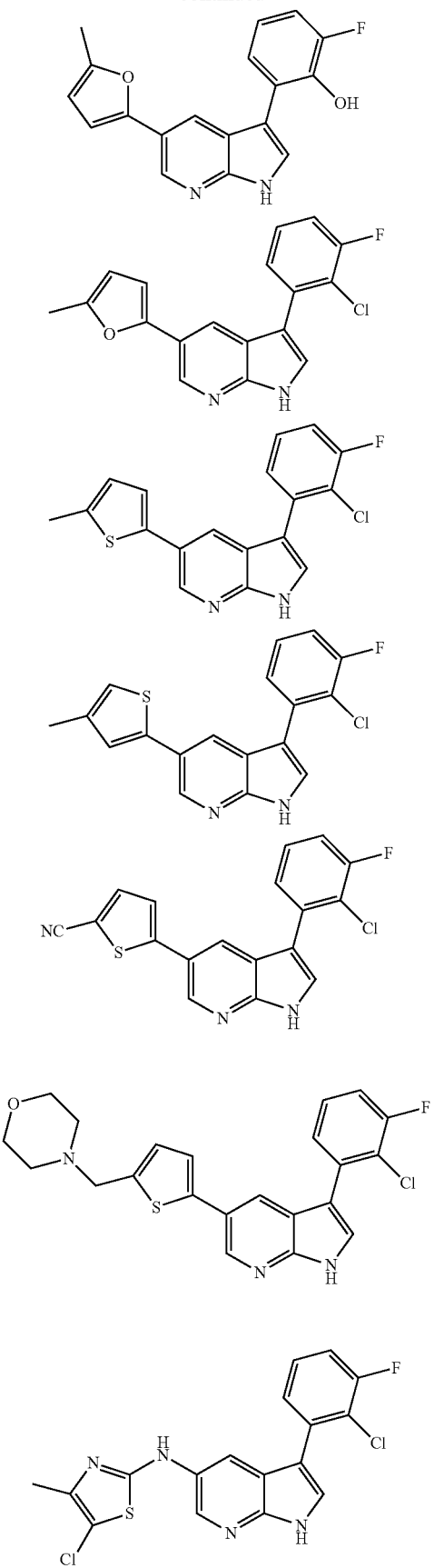

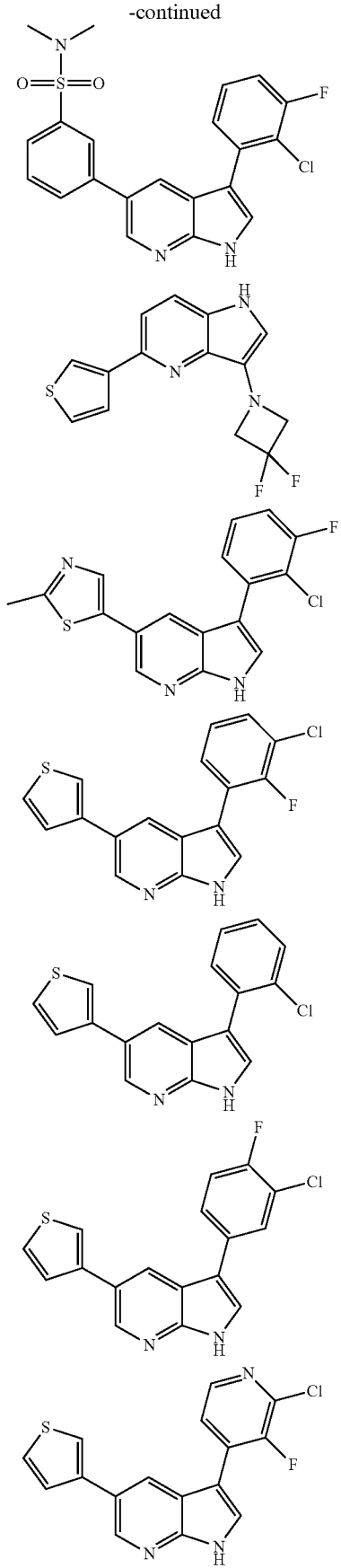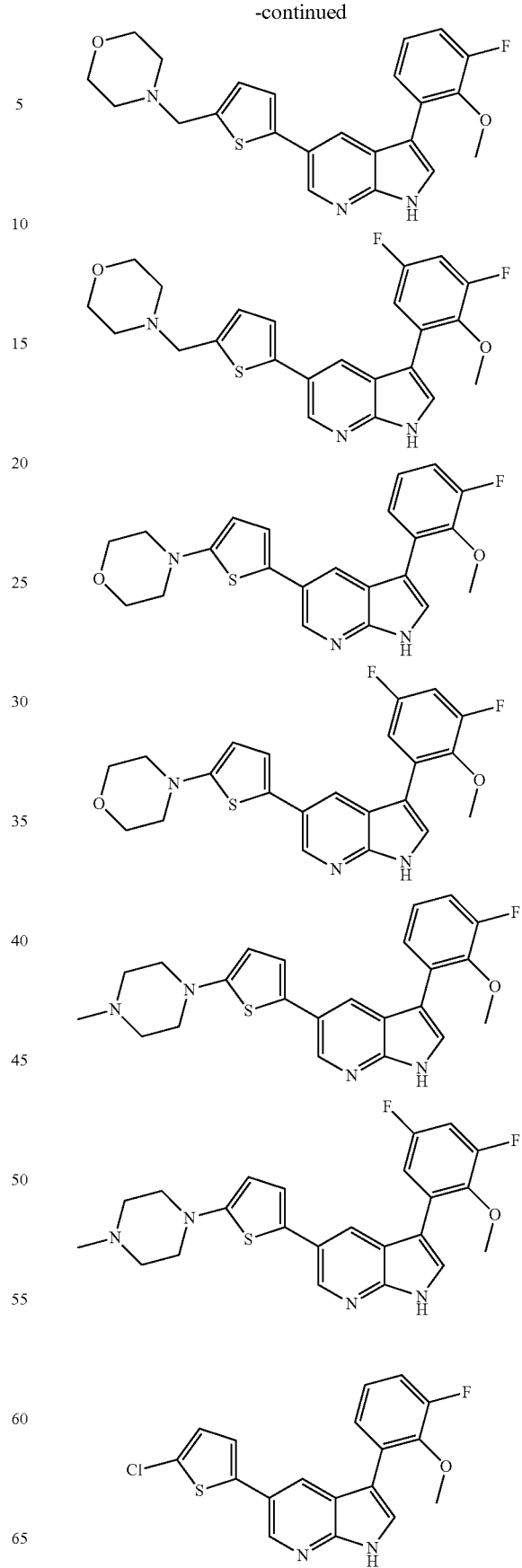

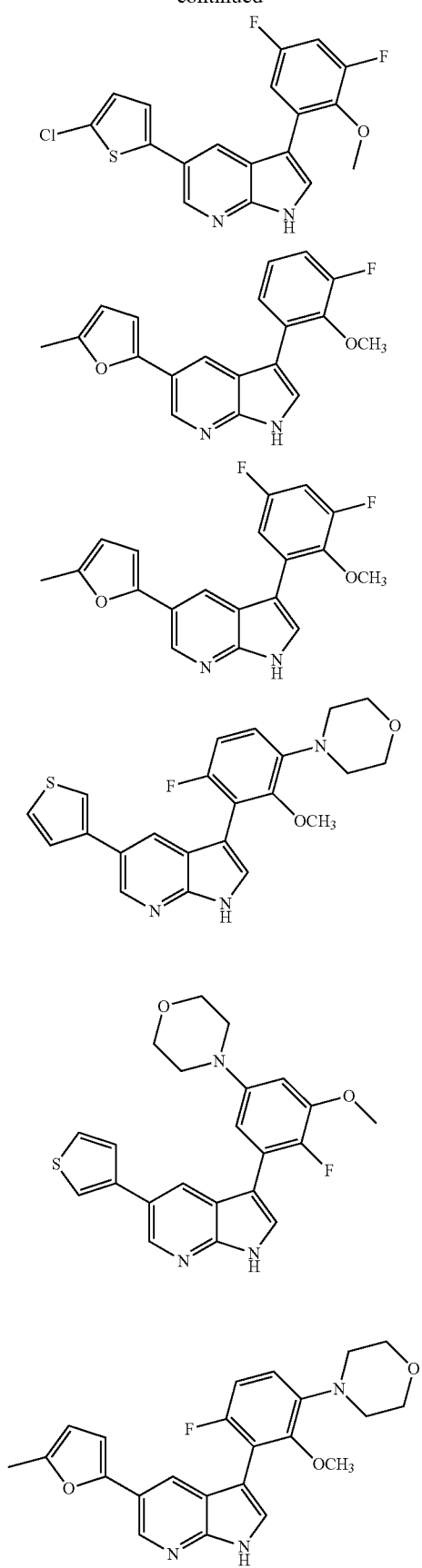
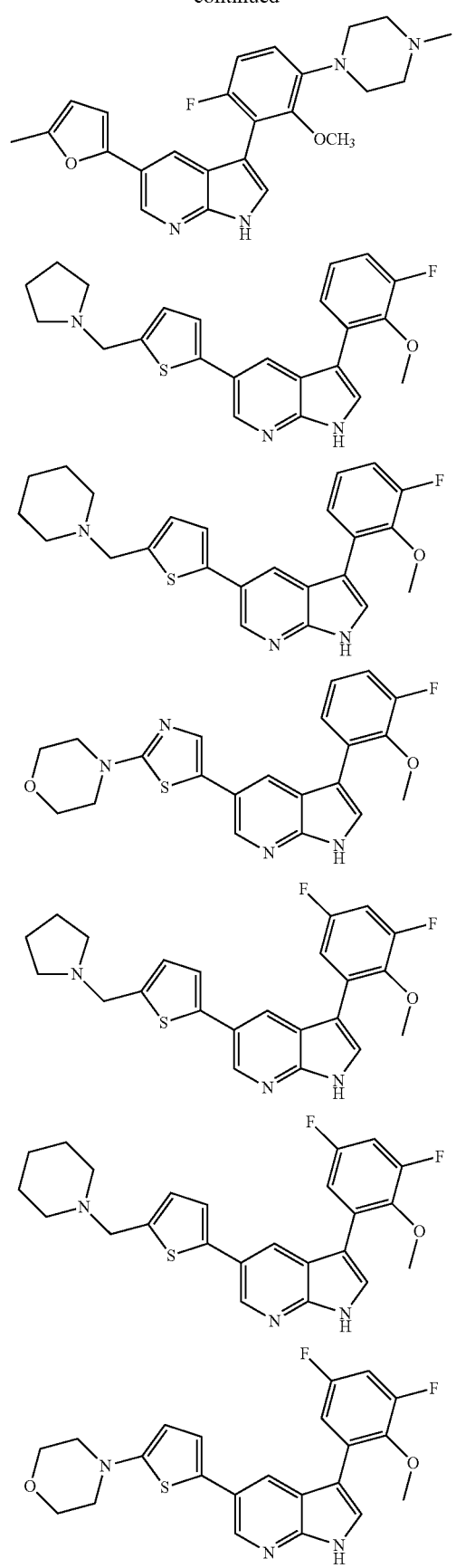

-continued
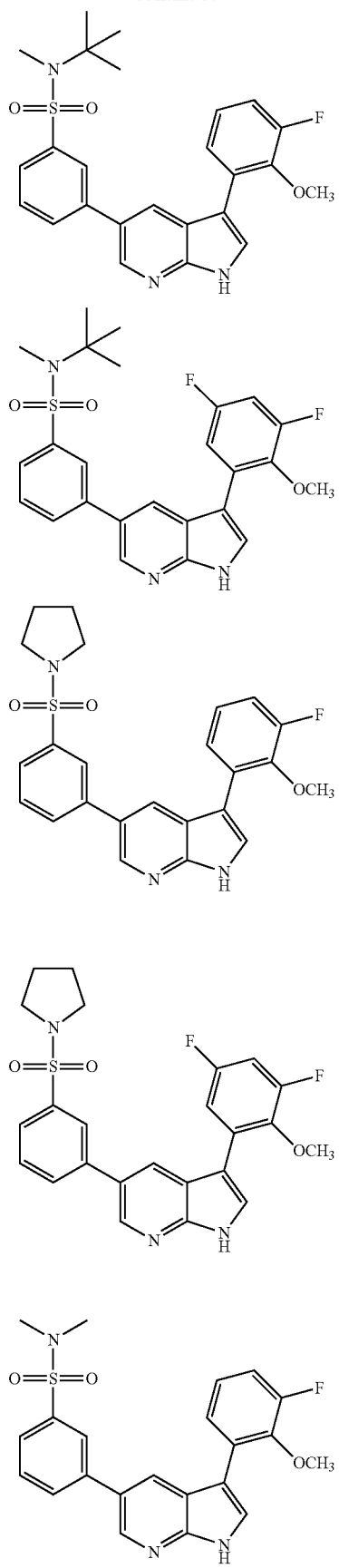
-continued
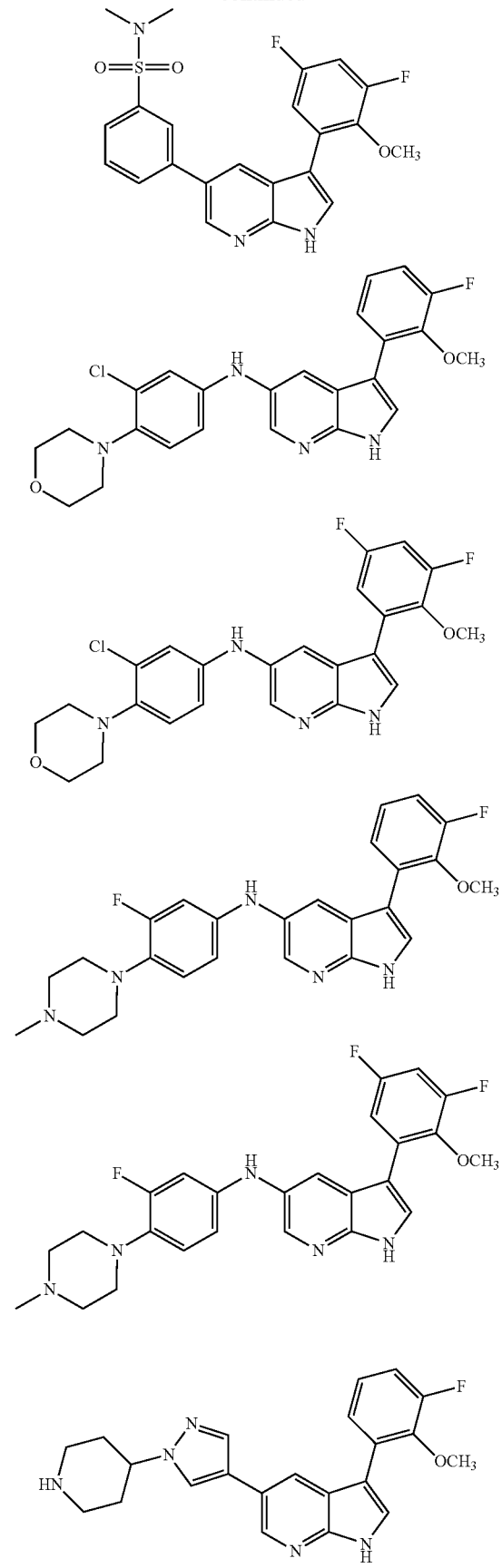

45
-continued
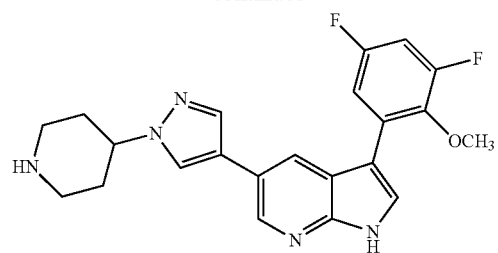
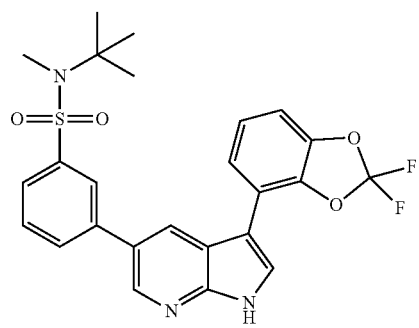
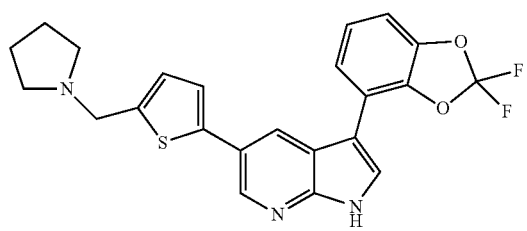
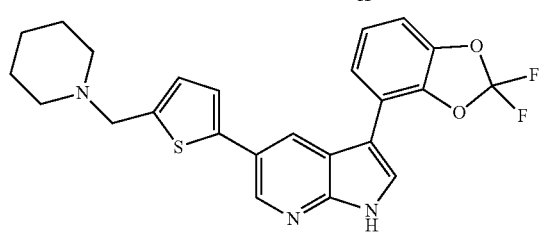
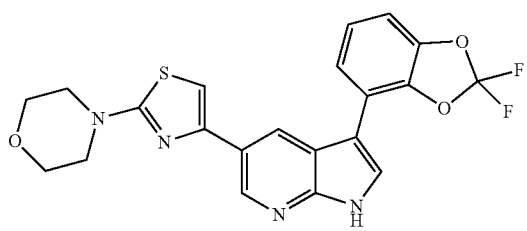
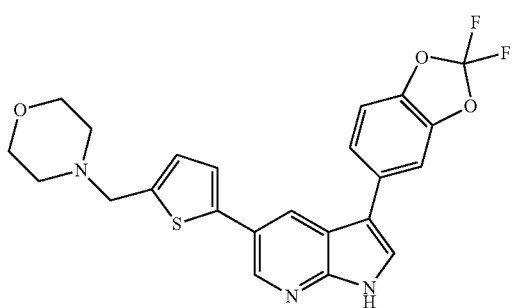
46
-continued
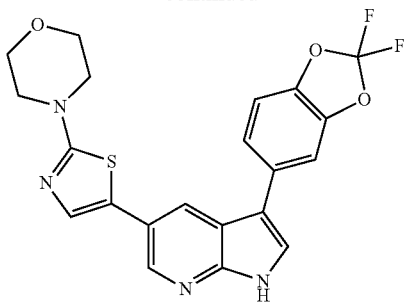
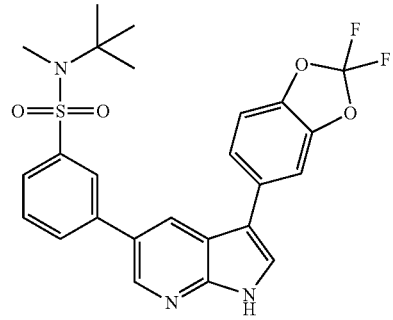
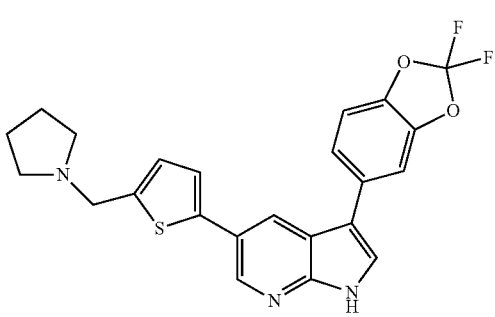
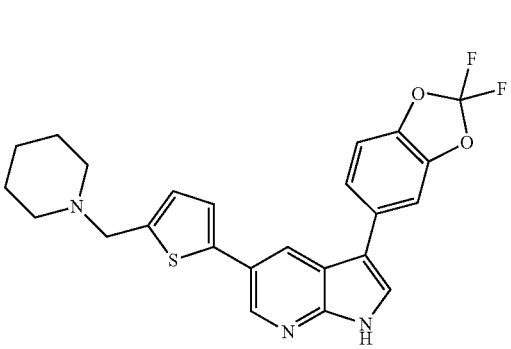
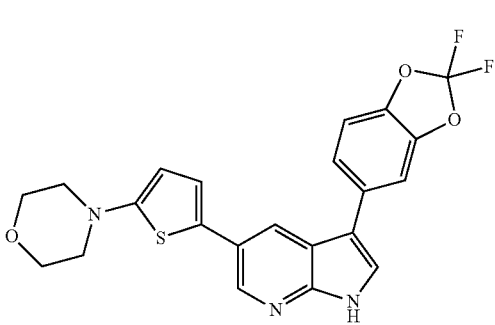

-continued
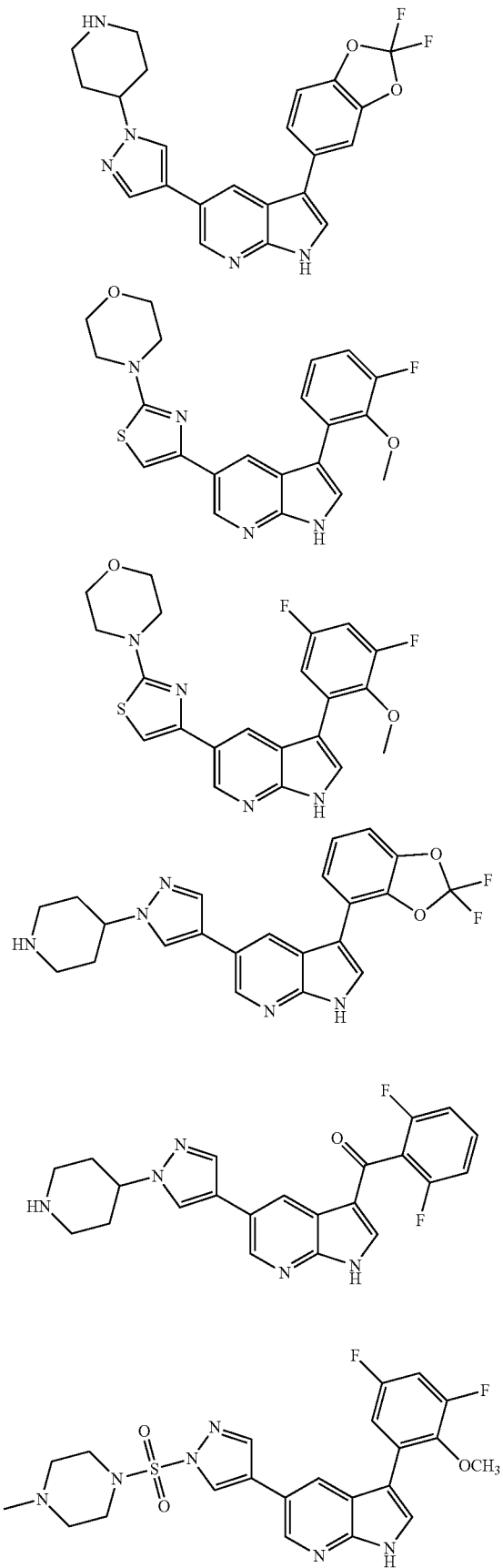
-continued
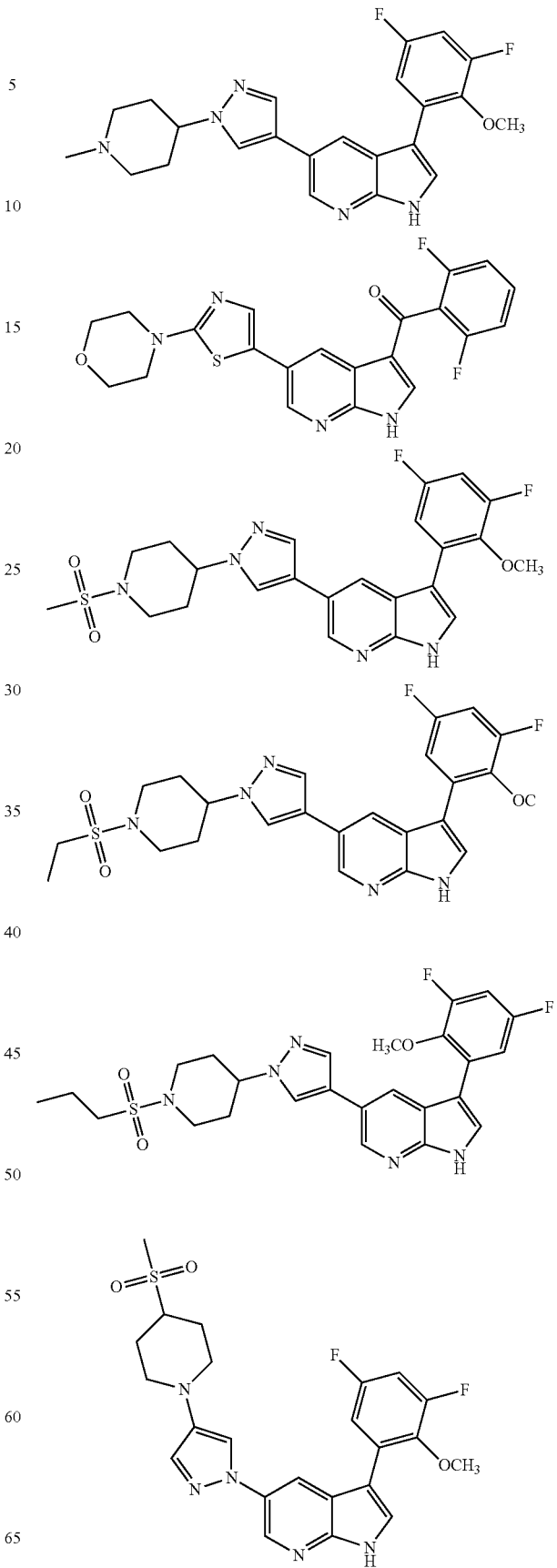

49
-continued
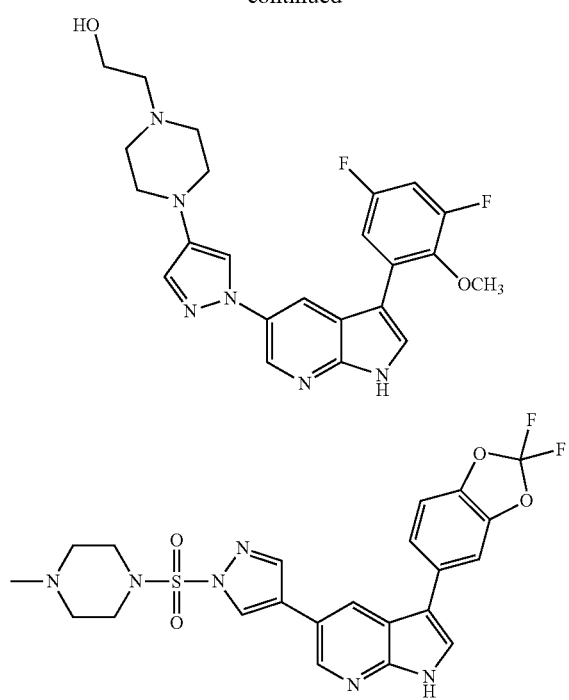
50
-continued
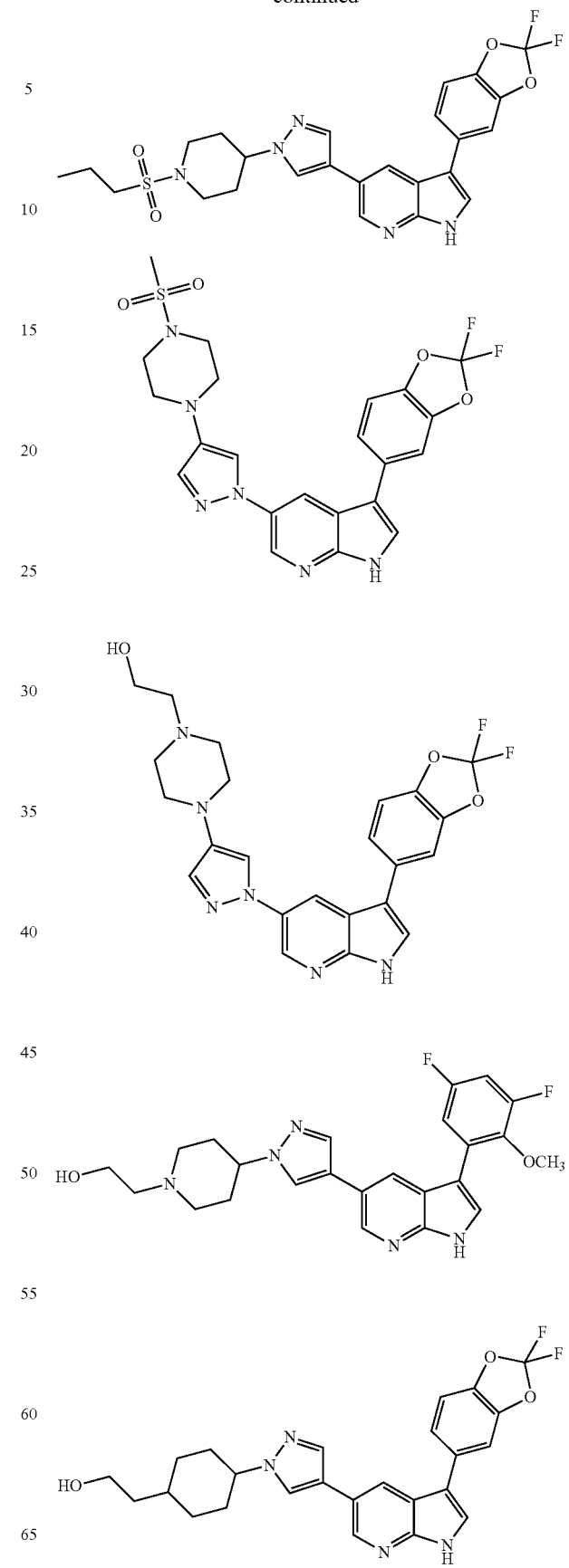

51
-continued
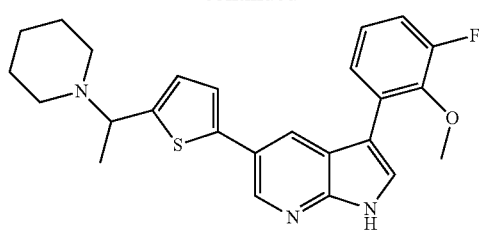
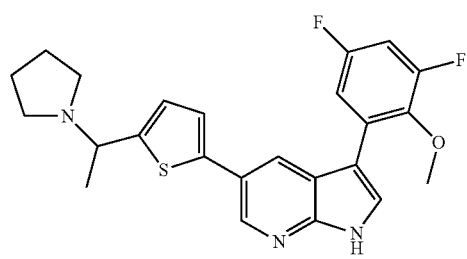
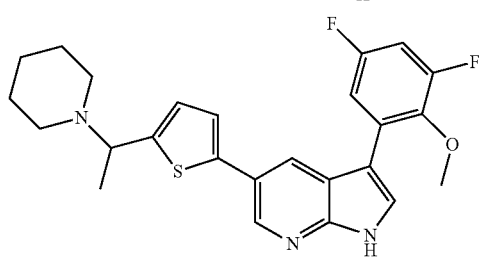
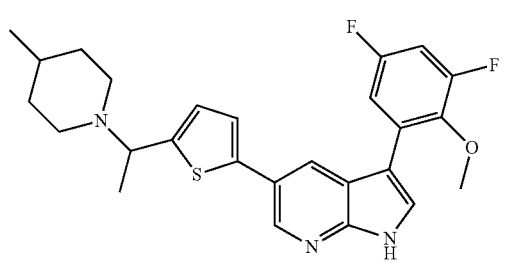
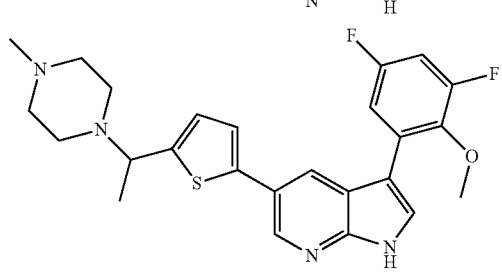
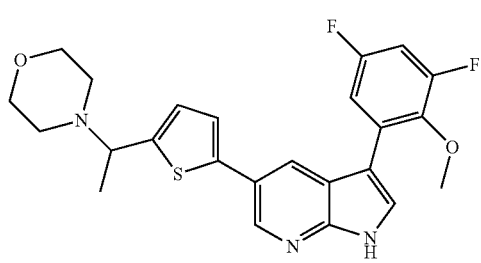
52
-continued
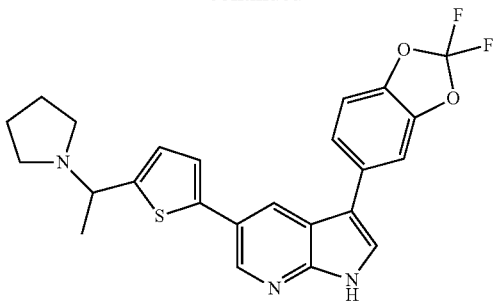
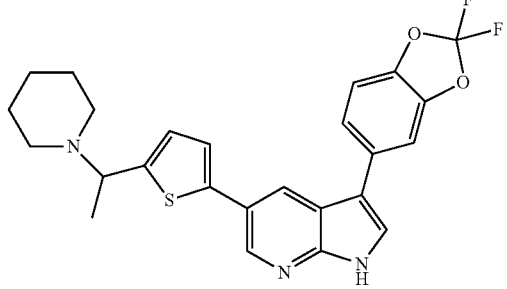
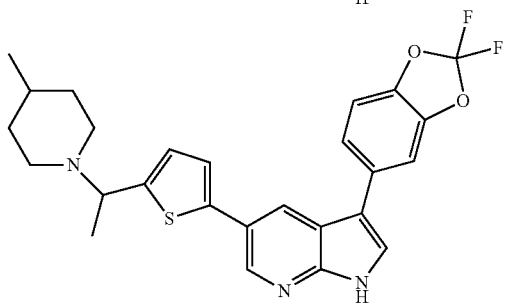
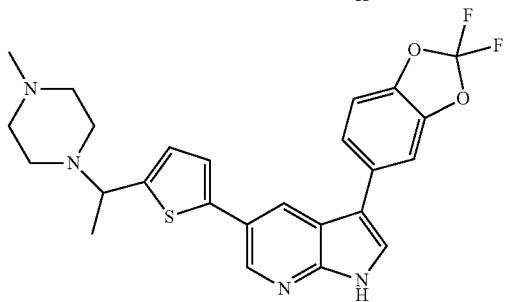
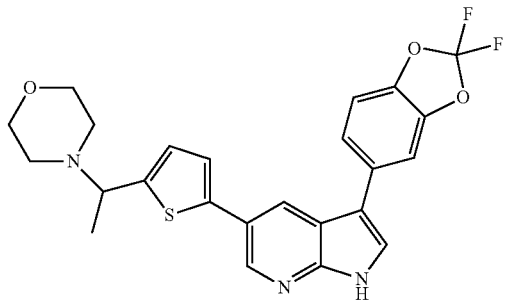
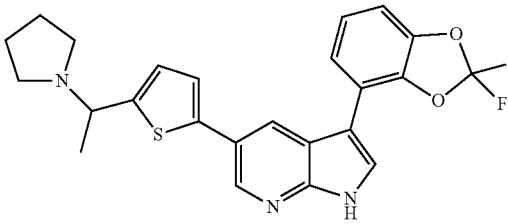

-continued

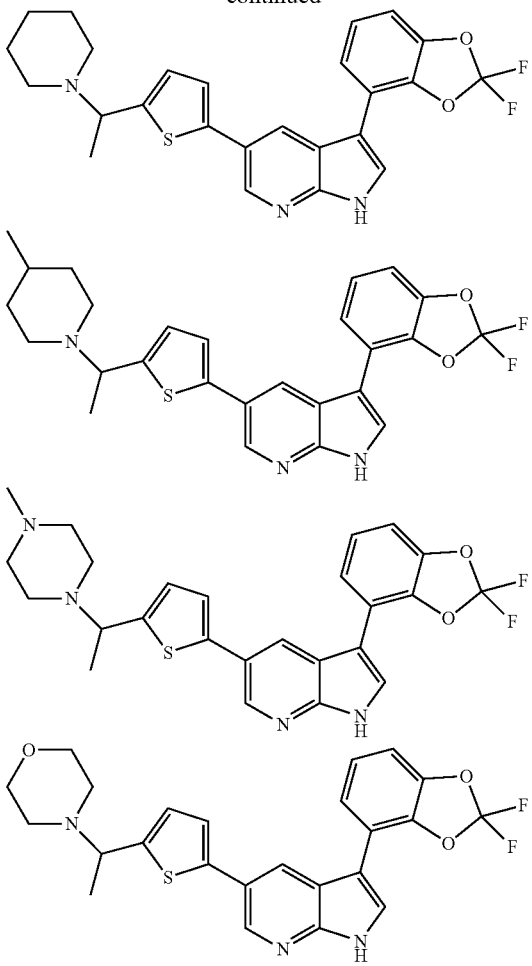

In an aspect, the present invention is a method of treating cancer or hyperproliferative disorders by administering an effective amount of a compound according to Formulas I, IA or IB:

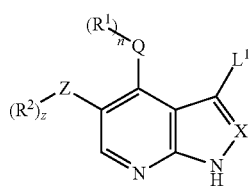
(I)

(IA)

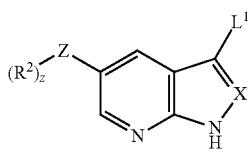
(IB)

or a pharmaceutically acceptable salt thereof, wherein:
X is N or CH;
$L^1$ is H, F; or
$L^1$ is thienyl, phenyl, pyrrolyl, pyridyl,

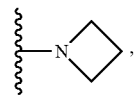 [SMILES: *N1CCC1]

piperazinyl,

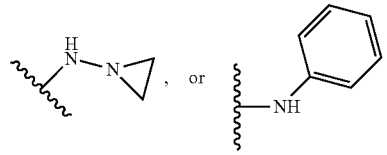 [SMILES: *NN1CC1 ; *Nc1ccccc1]

any of which is optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

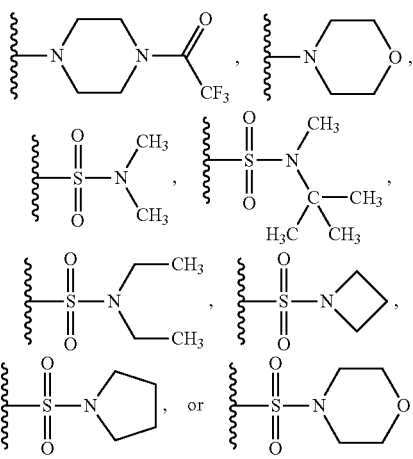

Q is a direct bond, thienyl, thiazolyl, phenyl,

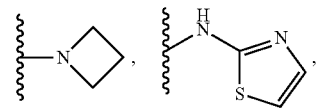

furanyl, or piperazinyl;
$R^1$ is each independently H, halo, —CN, $C_{1-4}$alkyl, $C_{1-4}$alkoxy,

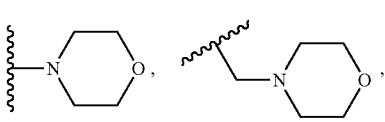

-continued

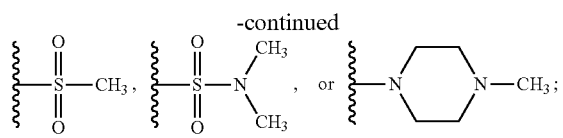

Z is a direct bond, thienyl, thiazolyl, phenyl,

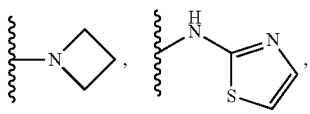

furanyl, or piperazinyl;
$R^2$ is each independently H, halo, —CN, $C_{1-4}$alkyl, $C_{1-4}$alkoxy,

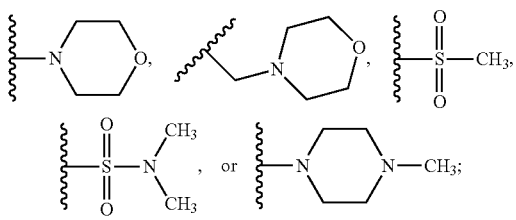

n is 0, 1, or 2; and
m is 0, 1, or 2;
provided that at least one of $L^1$, $R^1$, and $R^2$ is not H In an embodiment of the aspect, the cancer is of colon, breast, stomach, prostate, pancreas, or ovarian tissue.

In another embodiment of the aspect, the cancer or hyperproliferative disorder is lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter, renal cell carcinoma, carcinoma of the renal pelvis, pediatric malignancy, neoplasms of the central nervous system, primary CNS lymphoma, spinal axis tumors, medulloblastoma, brain stem gliomas, pituitary adenomas, Barrett's esophagus, pre-malignant syndrome, neoplastic cutaneous disease, psoriasis, mycoses fungoides, benign prostatic hypertrophy, diabetic retinopathy, retinal ischemia, and retinal neovascularization, hepatic cirrhosis, angiogenesis, cardiovascular disease, atherosclerosis, immunological disease, autoimmune disease, or renal.

These and other aspects of the invention will be apparent upon reference to the following detailed description. To that end, certain patent and other documents are cited herein to more specifically set forth various aspects of this invention. Each of these documents is hereby incorporated by reference in its entirety.

Unless otherwise stated the following terms used in the specification and claims have the meanings discussed below:

"Alkyl" refers to a saturated straight or branched hydrocarbon radical of one to six carbon atoms, preferably one to four carbon atoms, e.g., methyl, ethyl, propyl, 2-propyl, n-butyl, iso-butyl, tert-butyl, pentyl, hexyl, and the like, preferably methyl, ethyl, propyl, or 2-propyl. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Cyclic alkyls are referred to herein as a "cycloalkyl."

Unsaturated alkyls contain at least one double or triple bond between adjacent carbon atoms (referred to as an "alkenyl" or "alkynyl", respectively.) Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{0-4}$alkyl" refers to an alkyl with 0, 1, 2, 3, or 4 carbon atoms. $C_{0-4}$alkyl with 0 carbon atoms is a hydrogen atom when terminal and is a direct bond when linking.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like, preferably methylene, ethylene, or propylene.

"Cycloalkyl" refers to a saturated cyclic hydrocarbon radical of three to eight carbon atoms, e.g., cyclopropyl, cyclobutyl, cyclopentyl or cyclohexyl.

"Alkoxy" means a radical —$OR_a$ where $R_a$ is an alkyl as defined above, e.g., methoxy, ethoxy, propoxy, butoxy and the like.

"Halo" means fluoro, chloro, bromo, or iodo, preferably fluoro and chloro.

"Haloalkyl" means alkyl substituted with one or more, preferably one, two or three, same or different halo atoms, e.g., —$CH_2Cl$, —$CF_3$, —$CH_2CF_3$, —$CH_2CCl_3$, and the like.

"Haloalkoxy" means a radical —$OR_b$, where $R_b$ is an haloalkyl as defined above, e.g., trifluoromethoxy, trichloroethoxy, 2,2-dichloropropoxy, and the like.

"Acyl" means a radical —$C(O)R_c$ where $R_c$ is hydrogen, alkyl, or haloalkyl as defined herein, e.g., formyl, acetyl, trifluoroacetyl, butanoyl, and the like.

"Aryl" refers to an all-carbon monocyclic or fused-ring polycyclic (i.e., rings which share adjacent pairs of carbon atoms) groups of 6 to 12 carbon atoms having a completely conjugated pi-electron system. Examples, without limitation, of aryl groups are phenyl, naphthyl and anthracenyl. The aryl group may be substituted or unsubstituted. Unless specifically stated otherwise, "substituted aryl" refers to the aryl group being substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, phenoxy, heteroaryl, heteroaryloxy, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heteroaryl" refers to a monocyclic or fused ring (i.e., rings which share an adjacent pair of atoms) group of 5 to 12 ring atoms containing one, two, three or four ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, triazole, tetrazole, triazine, and carbazole. The heteroaryl group may be unsubstituted or substituted, such as, for example, 5-methylthiazolyl. Unless specifically stated otherwise, "substituted heteroaryl" refers to the heteroaryl group being substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Carbocycle" refers to a saturated, unsaturated or aromatic ring system having 3 to 14 ring carbon atoms. The term "carbocycle", whether saturated or partially unsaturated, also refers to rings that are optionally substituted. The term "carbocycle" includes aryl. The term "carbocycle" also includes aliphatic rings that are fused to one or more aromatic or nonaromatic rings, such as in a decahydronaphthyl or tetrahydronaphthyl, where the radical or point of attachment is on the aliphatic ring. The carbocycle group may be substituted or unsubstituted. Unless specifically stated otherwise, "substituted carbocyle" refers to the carbocycle group being substituted with one or more, more preferably one, two or three, even more preferably one or two substituents independently selected from the group consisting of alkyl (wherein the alkyl may be optionally substituted with one or two substituents), haloalkyl, halo, hydroxy, alkoxy, mercapto, alkylthio, cyano, acyl, nitro, haloalkyl, haloalkoxy, carboxy, alkoxycarbonyl, amino, alkylamino dialkylamino, aryl, heteroaryl, carbocycle or heterocycle (wherein the aryl, heteroaryl, carbocycle or heterocycle may be optionally substituted).

"Heterocycle" refers to a saturated, unsaturated or aromatic cyclic ring system having 3 to 14 ring atoms in which one, two or three ring atoms are heteroatoms selected from N, O, or $S(O)_m$, (where m is an integer from 0 to 2), the remaining ring atoms being C, where one or two C atoms may optionally be replaced by a carbonyl group. The term "heterocycle" includes heteroaryl. Unless specifically stated otherwise, "substituted heterocyclyl" refers to the heterocyclyl ring being substituted independently with one or more, preferably one, two or three substituents selected from alkyl (wherein the alkyl may be optionally substituted with one or two substituents), haloalkyl, cycloalkylamino, cycloalkylalkyl, cycloalkylaminoalkyl, cycloalkylalkylaminoalkyl, cyanoalkyl, halo, nitro, cyano, hydroxy, alkoxy, amino, alkylamino, dialkylamino, hydroxyalkyl, carboxyalkyl, aminoalkyl, alkylaminoalkyl, dialkylaminoalkyl, aralkyl, heteroaralkyl, aryl, heteroaryl, carbocycle, heterocycle (wherein the aryl, heteroaryl, carbocycle or heterocycle may be optionally substituted), aralkyl, heteroaralkyl, saturated or unsaturated heterocycloamino, saturated or unsaturated heterocycloaminoalkyl, and $-COR_d$ (where $R_d$ is alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin-3-yl, pyrrolidino, morpholino, 4-cyclopropylmethylpiperazino, thiomorpholino, thiomorpholino-1-oxide, thiomorpholino-1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof, including 2-methyl-4,5,6,7-tetrahydro-1H-pyrrolo[2,3-c]pyridinyl. In certain embodiments, the heterocycle group is optionally substituted with one or two substituents independently selected from halo, alkyl, alkyl substituted with carboxy, ester, hydroxy, alkylamino, saturated or unsaturated heterocycloamino, saturated or unsaturated heterocycloaminoalkyl, or dialkylamino.

"Optional" or "optionally" means that the subsequently described event or circumstance may but need not occur, and that the description includes instances where the event or circumstance occurs and instances in which it does not. For example, "heterocyclic group optionally substituted with an alkyl group" means that the alkyl may but need not be present, and the description includes situations where the heterocycle group is substituted with an alkyl group and situations where the heterocycle group is not substituted with the alkyl group.

Lastly, unless specifically stated otherwise, the term "substituted" as used herein means any of the above groups (e.g., alkyl, aryl, heteroaryl, carbocycle, heterocycle, etc.) wherein at least one hydrogen atom is replaced with a substituent. In the case of an oxo substituent ("=O") two hydrogen atoms are replaced. "Substituents" within the context of this invention, if not specified, include halogen, hydroxy, oxo, cyano, nitro, amino, alkylamino, dialkylamino, alkyl, alkoxy, thioalkyl, haloalkyl (e.g., $-CF_3$), hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, $-NR_eR_f$, $-NR_eC(=O)R_f$, $-NR_eC(=O)NR_eR_f$, $-NR_eC(=O)OR_f$, $-NR_eSO_2R_f$, $-OR_e$, $-C(=O)R_e$, $-C(=O)OR_e$, $-C(=O)NR_eR_f$, $-OC(=O)NR_eR_f$, $-SH$, $-SR_e$, $-SOR_e$, $-S(=O)_2R_e$, $-OS(=O)_2R_e$, $-S(=O)_2OR_e$, wherein $R_e$ and $R_f$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups; a pair of enantiomers is possible. An enantiomer can be characterized by the absolute configuration of its asymmetric center and is described by the R- and S-sequencing rules of Cahn and Prelog (Cahn, R., Ingold, C., and Prelog, V. Angew. Chem. 78:413-47, 1966; Angew. Chem. Internat. Ed. Eng. 5:385-415, 511, 1966), or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Ch. 4 of ADVANCED ORGANIC CHEMISTRY, $4^{th}$ edition, March, J., John Wiley and Sons, New York City, 1992).

The compounds of the present invention may exhibit the phenomena of tautomerism and structural isomerism. This invention encompasses any tautomeric or structural isomeric form and mixtures thereof which possess the ability to modulate SIK2 SEQ ID NO: 11) activity and is not limited to, any one tautomeric or structural isomeric form.

It is contemplated that a compound of the present invention would be metabolized by enzymes in the body of the organism such as human being to generate a metabolite that can modulate the activity of the protein kinases. Such metabolites are within the scope of the present invention.

A compound of the present invention or a pharmaceutically acceptable salt thereof can be administered as such to a human patient or can be administered in pharmaceutical compositions in which the foregoing materials are mixed with suitable carriers or excipient(s). Techniques for formulation and administration of drugs may be found, for example, in REMINGTON'S PHARMACOLOGICAL SCIENCES, Mack Publishing Co., Easton, Pa., latest edition.

A "pharmaceutical composition" refers to a mixture of one or more of the compounds described herein or pharmaceutically acceptable salts or prodrugs thereof, with other chemical components, such as pharmaceutically acceptable excipients. The purpose of a pharmaceutical composition is to facilitate administration of a compound to an organism.

"Pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Pharmaceutically acceptable salt" refers to those salts which retain the biological effectiveness and properties of the parent compound. Such salts may include: (1) acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D)- or (L)-malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The compound of the present invention may also act, or be designed to act, as a prodrug. A "prodrug" refers to an agent, which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention, which is, administered as an ester (the "prodrug"), phosphate, amide, carbamate, or urea.

"Therapeutically effective amount" refers to that amount of the compound being administered which will relieve to some extent one or more of the symptoms of the disorder being treated. In reference to the treatment of cancer, a therapeutically effective amount refers to that amount which has the effect of: (1) reducing the size of the tumor; (2) inhibiting tumor metastasis; (3) inhibiting tumor growth; and/or (4) relieving one or more symptoms associated with the cancer.

The term "disease", as used herein, means any disease or other deleterious condition in which a SIK2 (SEQ ID NO: 11) is known to play a role. The term "disease" also means those diseases or conditions that are alleviated by treatment with SIK2 (SEQ ID NO: 11) modulators. Such conditions include, without limitation, cancer and other hyperproliferative disorders as well as inflammation. In certain embodiments, the cancer is a cancer of colon, breast, stomach, prostate, pancreas, or ovarian tissue.

The term "SIK2 activity-mediated condition" or "disease", as used herein, means any disease or other deleterious condition in which SIK2 (SEQ ID NO: 11) activity is known to play a role. The term "SIK2 activity-mediated condition" also means those diseases or conditions that are alleviated by treatment with a SIK2 (SEQ ID NO: 11) inhibitor.

As used herein, "administer" or "administration" refers to the delivery of an inventive compound or of a pharmaceutically acceptable salt thereof or of a pharmaceutical composition containing an inventive compound or a pharmaceutically acceptable salt thereof of this invention to an organism for the purpose of prevention or treatment of a protein kinase-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. In certain embodiments, the preferred routes of administration are oral and intravenous. Alternatively, one may administer the compound in a local rather than systemic manner, for example, via injection of the compound directly into a solid tumor, often in a depot or sustained release formulation. Furthermore, one may administer the drug in a targeted drug delivery system, for example, in a liposome coated with tumor-specific antibody. In this way, the liposomes may be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in any conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also. Pharmaceutical compositions which may also be used include hard gelatin capsules. The capsules or pills may be packaged into brown glass or plastic bottles to protect the active compound from light. The containers containing the active compound capsule formulation are preferably stored at controlled room temperature (15-30° C.).

For administration by inhalation, the compounds for use according to the present invention may be conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD: D5W) consists of VPD diluted 1:1 with a 5% dextrose in water solution. This cosolvent system dissolves hydrophobic compounds well, and itself produces low toxicity upon systemic administration. Naturally, the proportions of such a cosolvent system may be varied considerably without destroying its solubility and toxicity characteristics. Furthermore, the identity of the cosolvent components may be varied: for example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art.

Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the SIK2-modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, malate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide ($Ca(OH)_2$), etc.).

Pharmaceutical compositions suitable for use in the present invention include compositions wherein the active ingredients are contained in an amount sufficient to achieve the intended purpose, e.g., the modulation of protein kinase activity and/or the treatment or prevention of a protein kinase-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the SIK2 (SEQ ID NO: 11), or surrogate marker activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, $9^{th}$ ed., Ed. by Hardman, J., and Limbard, L., McGraw-Hill, New York City, 1996, p. 46.)

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of SIK2 (SEQ ID NO: 11), or surrogate marker may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%.

At present, the therapeutically effective amounts of compounds of the present invention may range from approximately 2.5 $mg/m^2$ to 1500 $mg/m^2$ per day. Additional illustrative amounts range from 0.2-1000 mg/qid, 2-500 mg/qid, and 20-250 mg/qid.

In cases of local administration or selective uptake, the effective local concentration of the drug may not be related to plasma concentration, and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

As mentioned above, the compounds and compositions of the invention will find utility in a broad range of diseases and conditions mediated by protein kinases, including diseases and conditions mediated by SIK2 (SEQ ID NO: 3) activity. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (premalignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

The inventive compound can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti-androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMASIN (exemestane).

Examples of alkylating agents that the above method can be carried out in combination with include, without limitation, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that the above method can be carried out in combination with include, without limitation, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

Examples of natural product-based chemotherapeutic agents that the above method can be carried out in combination with include, without limitation, the *vinca* alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

An inventive compound can also be used with other signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, such as HERCEPTIN (Genentech, Inc., South San Francisco, Calif.). EGFR inhibitors are described in, for example in WO 95/19970, WO 98/14451, WO 98/02434, and U.S. Pat. No. 5,747,498 and such substances can be used in the present invention as described herein.

EGFR-inhibiting agents include, but are not limited to, the monoclonal antibodies C225 and anti-EGFR 22Mab (ImClone Systems, Inc., New York, N.Y.), the compounds erlotinib (OSI Pharmaceuticals, Inc., Melville, N.Y.), ZD-1839 (AstraZeneca), BIBX-1382 (Boehringer Ingelheim), MDX-447 (Medarex Inc., Annandale, N.J.), and OLX-103 (Merck & Co., Whitehouse Station, N.J.), and EGF fusion toxin (Seragen Inc., Hopkinton, Mass.).

These and other EGFR-inhibiting agents can be used in the present invention. VEGF inhibitors, for example SU-5416 and SU-6668 (Sugen Inc., South San Francisco, Calif.), can also be combined with an inventive compound. VEGF inhibitors are described in, for example, WO 01/60814 A3, WO 99/24440, PCT International Application PCT/IB99/00797, WO 95/21613, WO 99/61422, U.S. Pat. No. 5,834,504, WO 01/60814, WO 98/50356, U.S. Pat. No. 5,883,113, U.S. Pat. No. 5,886,020, U.S. Pat. No. 5,792,783, WO 99/10349, WO 97/32856, WO 97/22596, WO 98/54093, WO 98/02438, WO 99/16755, and WO 98/02437, all of which are incorporated herein in their entireties by reference. Other examples of some specific VEGF inhibitors useful in the present invention are IM862 (Cytran Inc., Kirkland, Wash.); anti-VEGF monoclonal antibody of Genentech, Inc.; and angiozyme, a synthetic ribozyme from Ribozyme (Boulder, Colo.) and Chiron (Emeryville, Calif.). These and other VEGF inhibitors can be used in the present invention as described herein. Further, pErbB2 receptor inhibitors, such as GW-282974 (Glaxo Wellcome plc), and the monoclonal antibodies AR-209 (Aronex Pharmaceuticals Inc., The Woodlands, Tex.) and 2B-1 (Chiron), can furthermore be combined with an inventive compound, for example, those indicated in WO 98/02434, WO 99/35146, WO 99/35132, WO 98/02437, WO 97/13760, WO 95/19970, U.S. Pat. No. 5,587,458 and U.S. Pat. No. 5,877,305, which are all hereby incorporated herein in their entireties by reference. ErbB2 receptor inhibitors useful in the present invention are also described in U.S. Pat. No. 6,284,764, incorporated in its entirety herein by reference.

The erbB2 receptor inhibitor compounds and substance described in the aforementioned PCT applications, U.S. patents, and U.S. provisional applications, as well as other compounds and substances that inhibit the erbB2 receptor, can be used with an inventive compound, in accordance with the present invention.

An inventive compound can also be used with other agents useful in treating cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 B1.

The above method can also be carried out in combination with radiation therapy, wherein the amount of an inventive compound in combination with the radiation therapy is effective in treating the above diseases. Techniques for administering radiation therapy are known in the art, and these techniques can be used in the combination therapy described herein. The administration of the compound of the invention in this combination therapy can be determined as described herein.

The invention will be further understood upon consideration of the following non-limiting Examples. In other aspects or embodiments are included any of the compounds in Table 1, Tables 2, 2A, 2B, and Table 3 that fall with in the scope of any of the embodiments described above of the compounds of Formula I, IA and IB, or pharmaceuticals acceptable salts thereof.

TABLE 1

List of Examples

| EX. | Structure | Chemical Name | Mol. Wt |
|---|---|---|---|
| 1 | 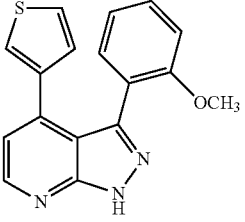 [SMILES: COc1ccccc1-c1n[nH]c2nccc(-c3ccsc3)c12] | 3-(2-methoxyphenyl)-4-(thiophen-3-yl)-1H-pyrrolo[2,3-b]pyridine | 307.2 |
| 2 | 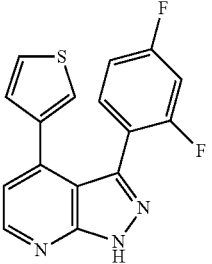 | 3-(2,4-difluorophenyl)-4-(thiophen-3-yl)-1H-pyrazolo[3,4-b]pyridine | 312.8 |
| 3 | 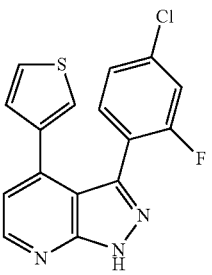 [SMILES: Fc1cc(Cl)ccc1-c1n[nH]c2nccc(-c3ccsc3)c12] | 3-(4-chloro-2-fluorophenyl)-4-(thiophen-3-yl)-1H-pyrazolo[3,4-b]pyridine | 329.78 |
| 4 | 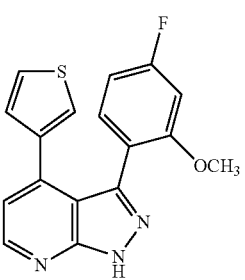 [SMILES: COc1cc(F)ccc1-c1n[nH]c2nccc(-c3ccsc3)c12] | 3-(4-fluoro-2-methoxyphenyl)-4-(thiophen-3-yl)-1H-pyrazolo[3,4-b]pyridine | 325.36 |

TABLE 1-continued

List of Examples

| EX. | Structure | Chemical Name | Mol. Wt |
|---|---|---|---|
| 5 | 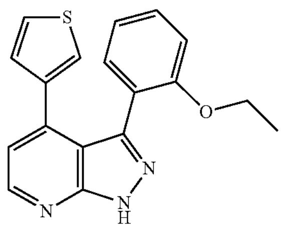 [SMILES: CCOc1ccccc1-c1n[nH]c2nccc(-c3ccsc3)c12] | 3-(2-ethoxyphenyl)-4-(thiophen-3-yl)-1H-pyrazolo[3,4-b]pyridine | 321.40 |
| 6 | 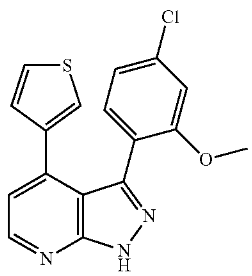 [SMILES: COc1cc(Cl)ccc1-c1n[nH]c2nccc(-c3ccsc3)c12] | 3-(4-chloro-2-methoxyphenyl)-4-(thiophen-3-yl)-1H-pyrazolo[3,4-b]pyridine | 341.81 |
| 7 | 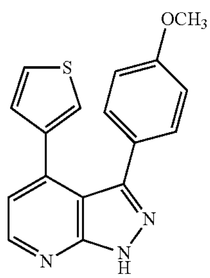 [SMILES: COc1ccc(-c2n[nH]c3nccc(-c4ccsc4)c23)cc1] | 3-(4-methoxyphenyl)-4-(thiophen-3-yl)-1H-pyrazolo[3,4-b]pyridine | 307.37 |
| 8 | 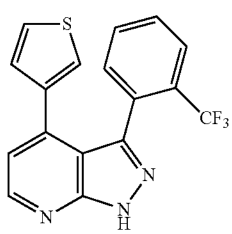 [SMILES: FC(F)(F)c1ccccc1-c1n[nH]c2nccc(-c3ccsc3)c12] | 4-(thiophen-3-yl)-3-(2-(trifluoromethyl)phenyl)-1H-pyrazolo[3,4-b]pyridine | 345.34 |
| 9 | 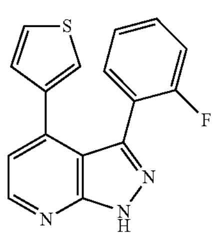 [SMILES: Fc1ccccc1-c1n[nH]c2nccc(-c3ccsc3)c12] | 3-(2-fluorophenyl)-4-(thiophen-3-yl)-1H-pyrazolo[3,4-b]pyridine | 295.33 |
| 10 | 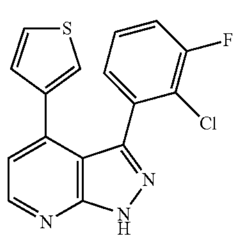 [SMILES: Fc1cccc(-c2n[nH]c3nccc(-c4ccsc4)c23)c1Cl] | 3-(2-chloro-3-fluorophenyl)-4-(thiophen-3-yl)-1H-pyrazolo[3,4-b]pyridine | 329.78 |

TABLE 1-continued

List of Examples

| EX. | Structure | Chemical Name | Mol. Wt |
|---|---|---|---|
| 11 | 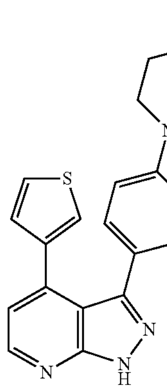 | 3-(4-(4-methylpiperazin-1-yl)phenyl)-4-(thiophen-3-yl)-1H-pyrazolo[3,4-b]pyridine | 375.49 |
| 12 | 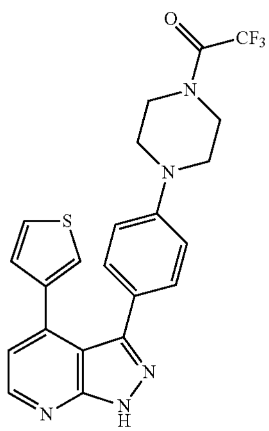 [SMILES: O=C(N1CCN(c2ccc(-c3n[nH]c4nccc(-c5ccsc5)c34)cc2)CC1)C(F)(F)F] | 2,2,2-trifluoro-1-(4-(4-(4-(thiophen-3-yl)-1H-pyrazolo[3,4-b]pyridin-3-yl)phenyl)piperazin-1-yl)ethanone | 457.47 |
| 13 | 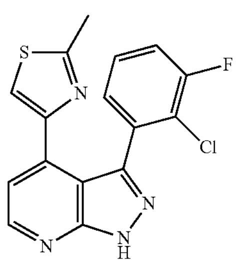 [SMILES: Cc1nc(-c2ccnc3[nH]nc(-c4cccc(F)c4Cl)c23)cs1] | 4-(3-(2-chloro-3-fluorophenyl)-1H-pyrazolo[3,4-b]pyridin-4-yl)-2-methylthiazole | 344.79 |
| 14 | 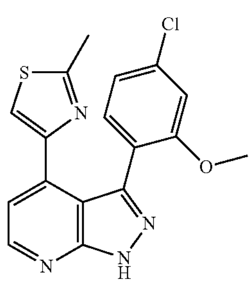 [SMILES: COc1cc(Cl)ccc1-c1n[nH]c2nccc(-c3csc(C)n3)c12] | 4-(3-(4-chloro-2-methoxyphenyl)-1H-pyrazolo[3,4-b]pyridin-4-yl)-2-methylthiazole | 356.83 |

TABLE 1-continued

| EX. | Structure | Chemical Name | Mol. Wt |
|---|---|---|---|
| 15 | 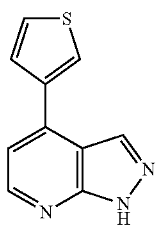 [SMILES: c1cc(-c2ccsc2)c2cn[nH]c2n1] | 4-(thiophen-3-yl)-1H-pyrazolo[3,4-b]pyridine | 201.25 |
| 16 | 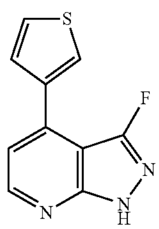 [SMILES: Fc1n[nH]c2nccc(-c3ccsc3)c12] | 3-fluoro-4-(thiophen-3-yl)-1H-pyrazolo[3,4-b]pyridine | 219.24 |
| 17 | 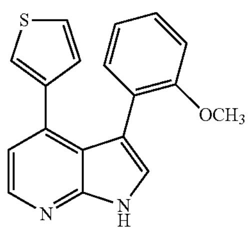 [SMILES: COc1ccccc1-c1c[nH]c2nccc(-c3ccsc3)c12] | 3-(2-methoxyphenyl)-4-(thiophen-3-yl)-1H-pyrrolo[2,3-b]pyridine | 306.382 |
| 18 | 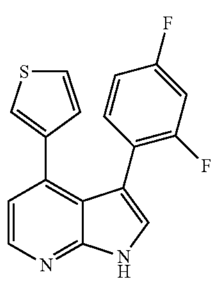 [SMILES: Fc1ccc(-c2c[nH]c3nccc(-c4ccsc4)c23)c(F)c1] | 3-(2,4-difluorophenyl)-4-(thiophen-3-yl)-1H-pyrrolo[2,3-b]pyridine | 312.337 |
| 19 | 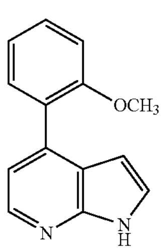 [SMILES: COc1ccccc1-c1ccnc2[nH]ccc12] | 4-(2-methoxyphenyl)-1H-pyrrolo[2,3-b]pyridine | 224.258 |
| 20 | 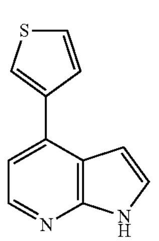 [SMILES: c1cc(-c2ccsc2)c2cc[nH]c2n1] | 4-(thiophen-3-yl)-1H-pyrrolo[2,3-b]pyridine | 200.260 |

TABLE 1-continued

List of Examples

| EX. | Structure | Chemical Name | Mol. Wt |
|---|---|---|---|
| 21 | 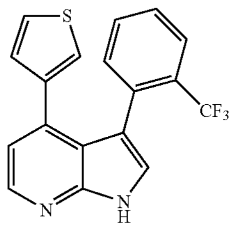 [SMILES: FC(F)(F)c1ccccc1-c1c[nH]c2nccc(-c3ccsc3)c12] | 4-(thiophen-3-yl)-3-(2-(trifluoromethyl)phenyl)-1H-pyrrolo[2,3-b]pyridine | 344.354 |
| 22 | 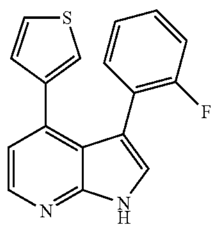 [SMILES: Fc1ccccc1-c1c[nH]c2nccc(-c3ccsc3)c12] | 3-(2-fluorophenyl)-4-(thiophen-3-yl)-1H-pyrrolo[2,3-b]pyridine | 294.346 |
| 23 | 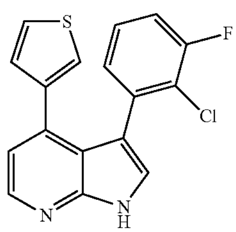 [SMILES: Fc1cccc(-c2c[nH]c3nccc(-c4ccsc4)c23)c1Cl] | 3-(2-chloro-3-fluorophenyl)-4-(thiophen-3-yl)-1H-pyrrolo[2,3-b]pyridine | 328.791 |
| 24 | 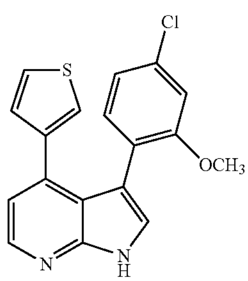 [SMILES: COc1cc(Cl)ccc1-c1c[nH]c2nccc(-c3ccsc3)c12] | 3-(4-chloro-2-methoxyphenyl)-4-(thiophen-3-yl)-1H-pyrrolo[2,3-b]pyridine | 340.827 |
| 25 | 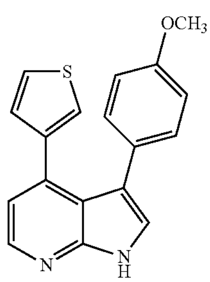 [SMILES: COc1ccc(-c2c[nH]c3nccc(-c4ccsc4)c23)cc1] | 3-(4-methoxyphenyl)-4-(thiophen-3-yl)-1H-pyrrolo[2,3-b]pyridine | 306.382 |
| 26 | 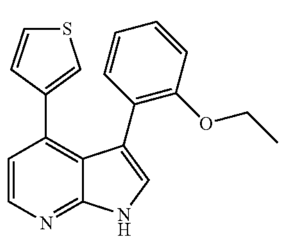 [SMILES: CCOc1ccccc1-c1c[nH]c2nccc(-c3ccsc3)c12] | 3-(2-ethoxyphenyl)-4-(thiophen-3-yl)-1H-pyrrolo[2,3-b]pyridine | 320.408 |

TABLE 1-continued

List of Examples

| EX. | Structure | Chemical Name | Mol. Wt |
|-----|-----------|---------------|---------|
| 27 | 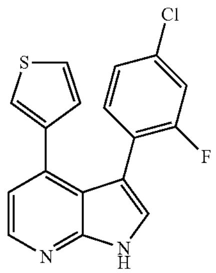 [SMILES: Fc1cc(Cl)ccc1-c1c[nH]c2nccc(-c3ccsc3)c12] | 3-(4-chloro-2-fluorophenyl)-4-(thiophen-3-yl)-1H-pyrrolo[2,3-b]pyridine | 328.791 |
| 28 | 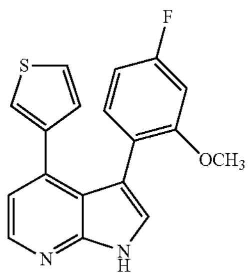 [SMILES: COc1cc(F)ccc1-c1c[nH]c2nccc(-c3ccsc3)c12] | 3-(4-fluoro-2-methoxyphenyl)-4-(thiophen-3-yl)-1H-pyrrolo[2,3-b]pyridine | 324.372 |
| 29 | 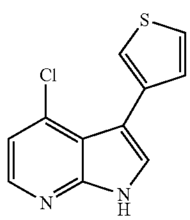 [SMILES: Clc1ccnc2[nH]cc(-c3ccsc3)c12] | 4-chloro-3-(thiophen-3-yl)-1H-pyrrolo[2,3-b]pyridine | 234.705 |
| 30 | 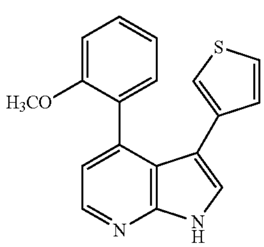 [SMILES: COc1ccccc1-c1ccnc2[nH]cc(-c3ccsc3)c12] | 4-(2-methoxyphenyl)-3-(thiophen-3-yl)-1H-pyrrolo[2,3-b]pyridine | 306.382 |
| 31 | 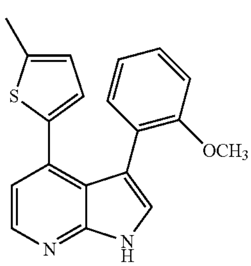 [SMILES: COc1ccccc1-c1c[nH]c2nccc(-c3ccc(C)s3)c12] | 3-(2-methoxyphenyl)-4-(5-methylthiophen-2-yl)-1H-pyrrolo[2,3-b]pyridine | 320.408 |
| 32 | 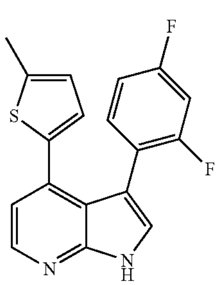 [SMILES: Cc1ccc(-c2ccnc3[nH]cc(-c4ccc(F)cc4F)c23)s1] | 3-(2,4-difluorophenyl)-4-(5-methylthiophen-2-yl)-1H-pyrrolo[2,3-b]pyridine | 326.363 |

TABLE 1-continued

List of Examples

| EX. | Structure | Chemical Name | Mol. Wt |
|---|---|---|---|
| 33 | 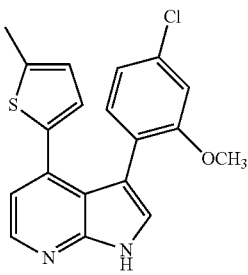 [SMILES: COc1cc(Cl)ccc1-c1c[nH]c2nccc(-c3ccc(C)s3)c12] | 3-(4-chloro-2-methoxyphenyl)-4-(5-methylthiophen-2-yl)-1H-pyrrolo[2,3-b]pyridine | 354.853 |
| 34 | 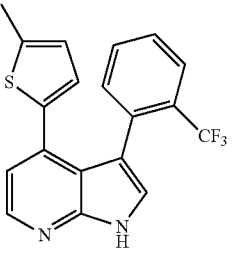 [SMILES: Cc1ccc(-c2ccnc3[nH]cc(-c4ccccc4C(F)(F)F)c23)s1] | 4-(5-methylthiophen-2-yl)-3-(2-(trfluoromethyl)phenyl)-1H-pyrrolo[2,3-b]pyridine | 358.380 |
| 35 | 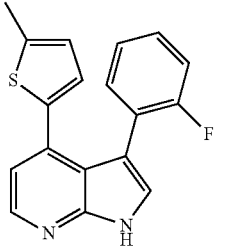 [SMILES: Cc1ccc(-c2ccnc3[nH]cc(-c4ccccc4F)c23)s1] | 3-(2-fluorophenyl)-4-(5-methylthiophen-2-yl)-1H-pyrrolo[2,3-b]pyridine | 308.373 |
| 36 | 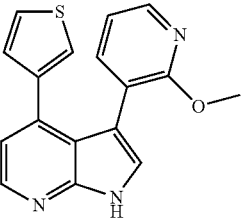 [SMILES: COc1ncccc1-c1c[nH]c2nccc(-c3ccsc3)c12] | 3-(2-methoxypyridin-3-yl)-4-(thiophen-3-yl)-1H-pyrrolo[2,3-b]pyridine | 307.370 |
| 37 | 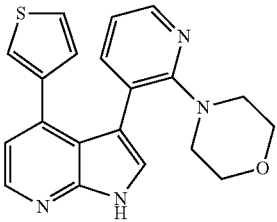 [SMILES: c1cnc(N2CCOCC2)c(-c2c[nH]c3nccc(-c4ccsc4)c23)c1] | 4-(3-(4-(thiophen-3-yl)-1H-pyrrolo[2,3-b]pyridin-3-yl)pyridin-2-yl)morpholine | 362.448 |
| 38 | 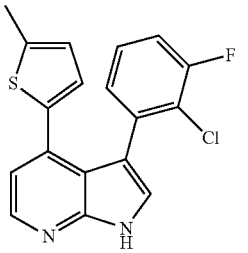 | 3-(2-chloro-3-fluorophenyl)-4-(5-methylthiophen-2-yl)-1H-pyrrolo[2,3-b]pyridine | 342.818 |

TABLE 1-continued

List of Examples

| EX. | Structure | Chemical Name | Mol. Wt |
|---|---|---|---|
| 39 | 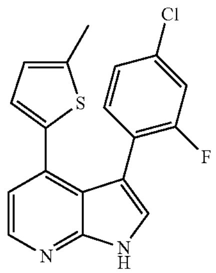 [SMILES: Cc1ccc(-c2ccnc3[nH]cc(-c4ccc(Cl)cc4F)c23)s1] | 3-(4-chloro-2-fluorophenyl)-4-(5-methylthiophen-2-yl)-1H-pyrrolo[2,3-b]pyridine | 342.818 |
| 40 | 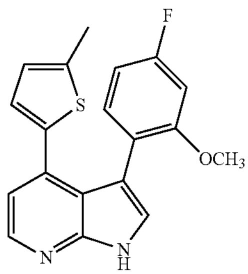 [SMILES: COc1cc(F)ccc1-c1c[nH]c2nccc(-c3ccc(C)s3)c12] | 3-(4-fluoro-2-methoxyphenyl)-4-(5-methylthiophen-2-yl)-1H-pyrrolo[2,3-b]pyridine | 338.399 |
| 41 | 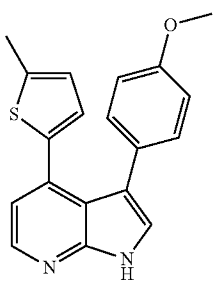 | 3-(4-methoxyphenyl)-4-(5-methylthiophen-2-yl)-1H-pyrrolo[2,3-b]pyridine | 320.408 |
| 42 | 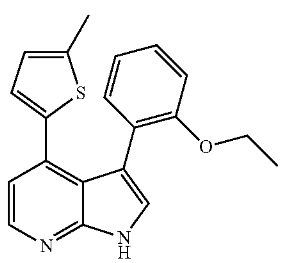 [SMILES: CCOc1ccccc1-c1c[nH]c2nccc(-c3ccc(C)s3)c12] | 3-(2-ethoxyphenyl)-4-(5-methylthiophen-2-yl)-1H-pyrrolo[2,3-b]pyridine | 334.435 |
| 43 | 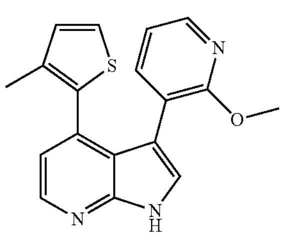 | 3-(2-methoxypyridin-3-yl)-4-(3-methylthiophen-2-yl)-1H-pyrrolo[2,3-b]pyridine | 321.396 |
| 44 | 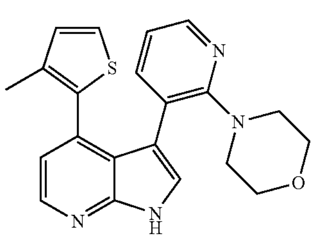 [SMILES: Cc1ccsc1-c1ccnc2[nH]cc(-c3cccnc3N3CCOCC3)c12] | 4-(3-(4-(3-methylthiophen-2-yl)-1H-pyrrolo[2,3-b]pyridin-3-yl)pyridin-2-yl)morpholine | 376.475 |

TABLE 1-continued

List of Examples

| EX. | Structure | Chemical Name | Mol. Wt |
|---|---|---|---|
| 45 | 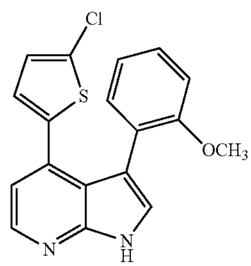 [SMILES: COc1ccccc1-c1c[nH]c2nccc(-c3ccc(Cl)s3)c12] | 4-(5-chlorothiophen-2-yl)-3-(2-methoxyphenyl)-1H-pyrrolo[2,3-b]pyridine | 340.827 |
| 46 | 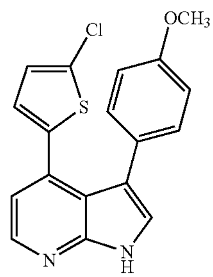 [SMILES: COc1ccc(-c2c[nH]c3nccc(-c4ccc(Cl)s4)c23)cc1] | 4-(5-chlorothiophen-2-yl)-3-(4-methoxyphenyl)-1H-pyrrolo[2,3-b]pyridine | 340.827 |
| 47 | 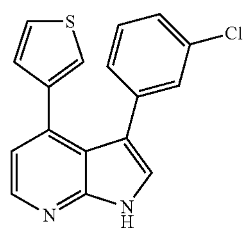 [SMILES: Clc1cccc(-c2c[nH]c3nccc(-c4ccsc4)c23)c1] | 3-(3-chlorophenyl)-4-(thiophen-3-yl)-1H-pyrrolo[2,3-b]pyridine | 310.801 |
| 48 | 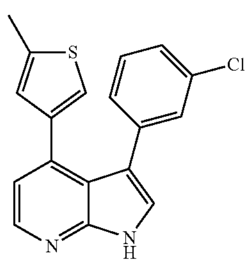 [SMILES: Cc1cc(-c2ccnc3[nH]cc(-c4cccc(Cl)c4)c23)cs1] | 3-(3-chlorophenyl)-4-(5-methylthiophen-3-yl)-1H-pyrrolo[2,3-b]pyridine | 324.827 |
| 49 | 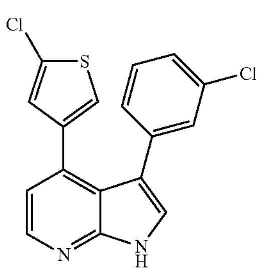 [SMILES: Clc1cccc(-c2c[nH]c3nccc(-c4csc(Cl)c4)c23)c1] | 3-(3-chlorophenyl)-4-(5-chlorothiophen-3-yl)-1H-pyrrolo[2,3-b]pyridine | 345.246 |

TABLE 1-continued

List of Examples

| EX. | Structure | Chemical Name | Mol. Wt |
|---|---|---|---|
| 50 | 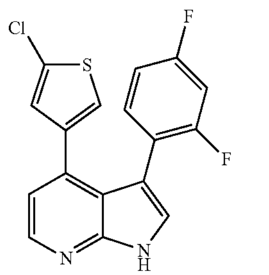 [SMILES: Fc1ccc(-c2c[nH]c3nccc(-c4csc(Cl)c4)c23)c(F)c1] | 4-(5-chlorothiophen-3-yl)-3-(2,4-difluorophenyl)-1H-pyrrolo[2,3-b]pyridine | 346.782 |
| 51 | 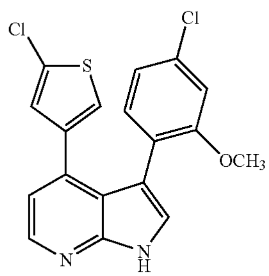 [SMILES: COc1cc(Cl)ccc1-c1c[nH]c2nccc(-c3csc(Cl)c3)c12] | 3-(4-chloro-2-methoxyphenyl)-4-(5-chlorothiophen-3-yl)-1H-pyrrolo[2,3-b]pyridine | 375.272 |
| 52 | 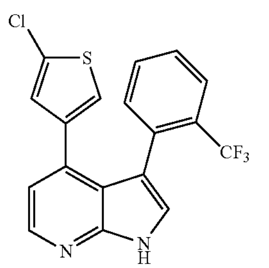 [SMILES: FC(F)(F)c1ccccc1-c1c[nH]c2nccc(-c3csc(Cl)c3)c12] | 4-(5-chlorothiophen-3-yl)-3-(2-(trifluoromethyl)phenyl)-1H-pyrrolo[2,3-b]pyridine | 378.799 |
| 53 | 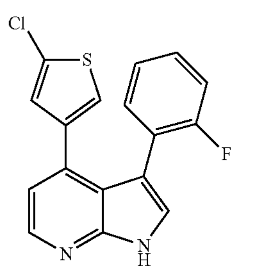 [SMILES: Fc1ccccc1-c1c[nH]c2nccc(-c3csc(Cl)c3)c12] | 4-(5-chlorothiophen-3-yl)-3-(2-fluorophenyl)-1H-pyrrolo[2,3-b]pyridine | 328.791 |
| 54 | 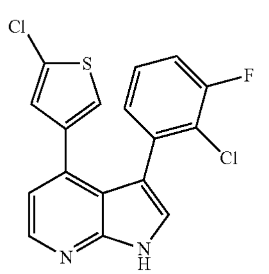 [SMILES: Fc1cccc(-c2c[nH]c3nccc(-c4csc(Cl)c4)c23)c1Cl] | 3-(2-chloro-3-fluorophenyl)-4-(5-chlorothiophen-3-yl)-1H-pyrrolo[2,3-b]pyridine | 363.236 |

TABLE 1-continued

List of Examples

| EX. | Structure | Chemical Name | Mol. Wt |
|---|---|---|---|
| 55 | 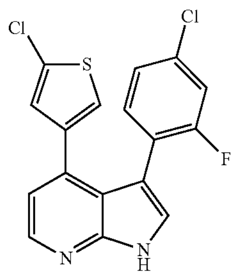 [SMILES: Fc1cc(Cl)ccc1-c1c[nH]c2nccc(-c3csc(Cl)c3)c12] | 3-(4-chloro-2-fluorophenyl)-4-(5-chlorothiophen-3-yl)-1H-pyrrolo[2,3-b]pyridine | 363.236 |
| 56 | 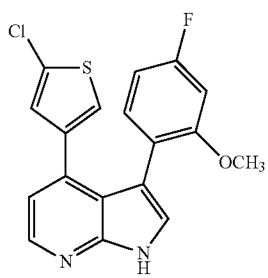 [SMILES: COc1cc(F)ccc1-c1c[nH]c2nccc(-c3csc(Cl)c3)c12] | 4-(5-chlorothiophen-3-yl)-3-(4-fluoro-2-methoxyphenyl)-1H-pyrrolo[2,3-b]pyridine | 358.817 |
| 57 | 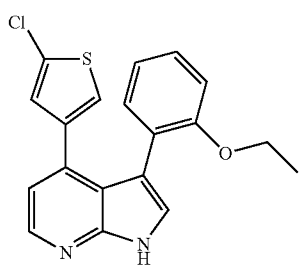 [SMILES: CCOc1ccccc1-c1c[nH]c2nccc(-c3csc(Cl)c3)c12] | 4-(5-chlorothiophen-3-yl)-3-(2-ethoxyphenyl)-1H-pyrrolo[2,3-b]pyridine | 354.853 |
| 58 | 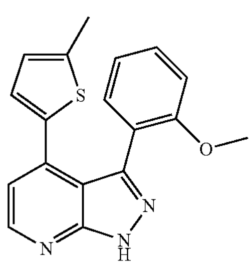 [SMILES: COc1ccccc1-c1n[nH]c2nccc(-c3ccc(C)s3)c12] | 3-(2-methoxyphenyl)-4-(5-methylthiophen-2-yl)-1H-pyrazolo[3,4-b]pyridine | 321.396 |
| 59 | 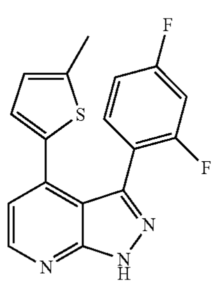 [SMILES: Cc1ccc(-c2ccnc3[nH]nc(-c4ccc(F)cc4F)c23)s1] | 3-(2,4-difluorophenyl)-4-(5-methylthiophen-2-yl)-1H-pyrazolo[3,4-b]pyridine | 327.351 |

TABLE 1-continued

| EX. | Structure | Chemical Name | Mol. Wt |
|---|---|---|---|
| 60 | 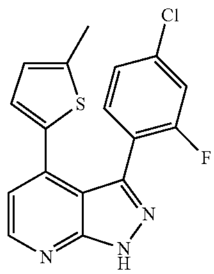 [SMILES: Cc1ccc(-c2ccnc3[nH]nc(-c4ccc(Cl)cc4F)c23)s1] | 3-(4-chloro-2-fluorophenyl)-4-(5-methylthiophen-2-yl)-1H-pyrazolo[3,4-b]pyridine | 343.806 |
| 61 | 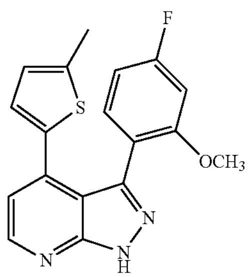 [SMILES: COc1cc(F)ccc1-c1n[nH]c2nccc(-c3ccc(C)s3)c12] | 3-(4-fluoro-2-methoxyphenyl)-4-(5-methylthiophen-2-yl)-1H-pyrazolo[3,4-b]pyridine | 339.387 |
| 62 | 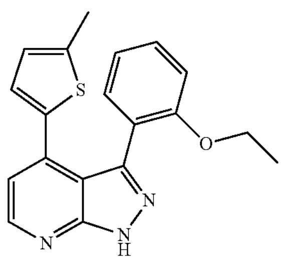 [SMILES: CCOc1ccccc1-c1n[nH]c2nccc(-c3ccc(C)s3)c12] | 3-(2-ethoxyphenyl)-4-(5-methylthiophen-2-yl)-1H-pyrazolo[3,4-b]pyridine | 335.423 |
| 63 | 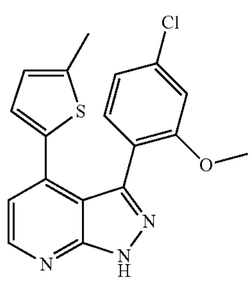 [SMILES: COc1cc(Cl)ccc1-c1n[nH]c2nccc(-c3ccc(C)s3)c12] | 3-(4-chloro-2-methoxyphenyl)-4-(5-methylthiophen-2-yl)-1H-pyrazolo[3,4-b]pyridine | 355.841 |
| 64 | 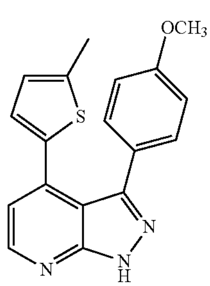 [SMILES: COc1ccc(-c2n[nH]c3nccc(-c4ccc(C)s4)c23)cc1] | 3-(4-methoxyphenyl)-4-(5-methylthiophen-2-yl)-1H-pyrazolo[3,4-b]pyridine | 321.396 |

TABLE 1-continued

List of Examples

| EX. | Structure | Chemical Name | Mol. Wt |
|---|---|---|---|
| 65 | 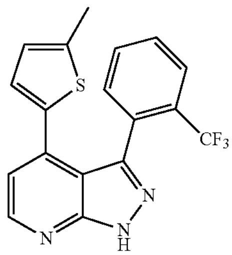 [SMILES: Cc1ccc(-c2ccnc3[nH]nc(-c4ccccc4C(F)(F)F)c23)s1] | 4-(5-methylthiophen-2-yl)-3-(2-(trifluoromethyl)phenyl)-1H-pyrazolo[3,4-b]pyridine | 359.368 |
| 66 | 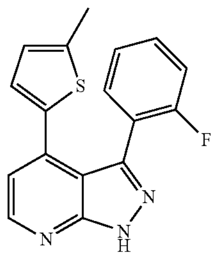 [SMILES: Cc1ccc(-c2ccnc3[nH]nc(-c4ccccc4F)c23)s1] | 3-(2-fluorophenyl)-4-(5-methylthiophen-2-yl)-1H-pyrazolo[3,4-b]pyridine | 309.361 |
| 67 | 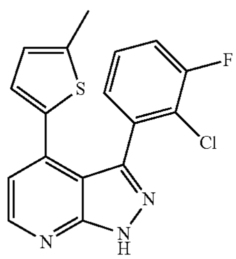 [SMILES: Cc1ccc(-c2ccnc3[nH]nc(-c4cccc(F)c4Cl)c23)s1] | 3-(2-chloro-3-fluorophenyl)-4-(5-methylthiophen-2-yl)-1H-pyrazolo[3,4-b]pyridine | 343.806 |
| 68 | 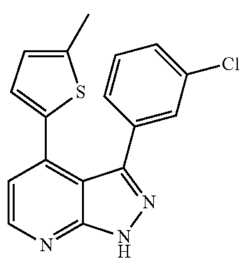 [SMILES: Cc1ccc(-c2ccnc3[nH]nc(-c4cccc(Cl)c4)c23)s1] | 3-(3-chlorophenyl)-4-(5-methylthiophen-2-yl)-1H-pyrazolo[3,4-b]pyridine | 325.815 |
| 69 | 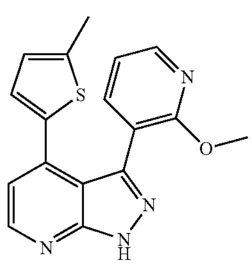 [SMILES: COc1ncccc1-c1n[nH]c2nccc(-c3ccc(C)s3)c12] | 3-(2-methoxypyridin-3-yl)-4-(5-methylthiophen-2-yl)-1H-pyrazolo[3,4-b]pyridine | 322.384 |
| 70 | 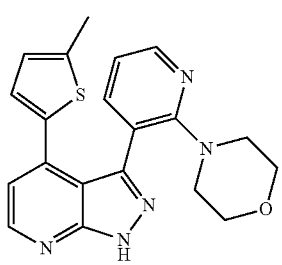 [SMILES: Cc1ccc(-c2ccnc3[nH]nc(-c4cccnc4N4CCOCC4)c23)s1] | 4-(3-(4-(5-methylthiophen-2-yl)-1H-pyrazolo[3,4-b]pyridin-3-yl)pyridin-2-yl)morpholine | 377.463 |

TABLE 1-continued

List of Examples

| EX. | Structure | Chemical Name | Mol. Wt |
|-----|-----------|---------------|---------|
| 71 | 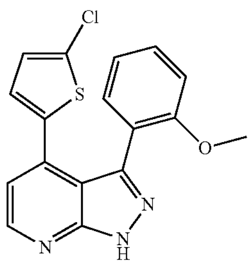 [SMILES: COc1ccccc1-c1n[nH]c2nccc(-c3ccc(Cl)s3)c12] | 4-(5-chlorothiophen-2-yl)-3-(2-methoxyphenyl)-1H-pyrazolo[3,4-b]pyridine | 341.815 |
| 72 | 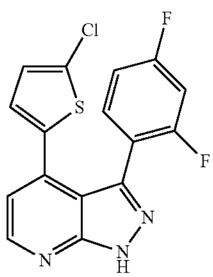 [SMILES: Fc1ccc(-c2n[nH]c3nccc(-c4ccc(Cl)s4)c23)c(F)c1] | 4-(5-chlorothiophen-2-yl)-3-(2,4-difluorophenyl)-1H-pyrazolo[3,4-b]pyridine | 347.770 |
| 73 | 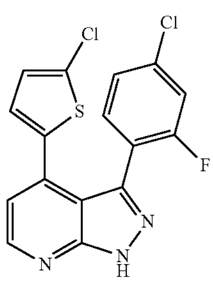 [SMILES: Fc1cc(Cl)ccc1-c1n[nH]c2nccc(-c3ccc(Cl)s3)c12] | 3-(4-chloro-2-fluorophenyl)-4-(5-chlorothiophen-2-yl)-1H-pyrazolo[3,4-b]pyridine | 364.224 |
| 74 | 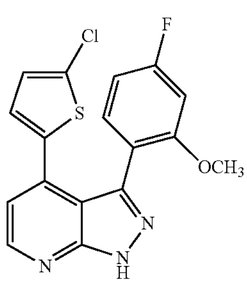 [SMILES: COc1cc(F)ccc1-c1n[nH]c2nccc(-c3ccc(Cl)s3)c12] | 4-(5-chlorothiophen-2-yl)-3-(4-fluoro-2-methoxyphenyl)-1H-pyrazolo[3,4-b]pyridine | 359.805 |
| 75 | 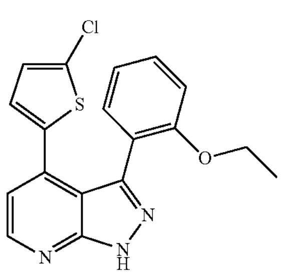 [SMILES: CCOc1ccccc1-c1n[nH]c2nccc(-c3ccc(Cl)s3)c12] | 4-(5-chlorothiophen-2-yl)-3-(2-ethoxyphenyl)-1H-pyrazolo[3,4-b]pyridine | 355.841 |

TABLE 1-continued

List of Examples

| EX. | Structure | Chemical Name | Mol. Wt |
|---|---|---|---|
| 76 | 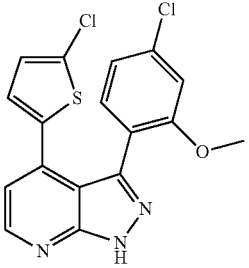 [SMILES: COc1cc(Cl)ccc1-c1n[nH]c2nccc(-c3ccc(Cl)s3)c12] | 3-(4-chloro-2-methoxyphenyl)-4-(5-chlorothiophen-2-yl)-1H-pyrazolo[3,4-b]pyridine | 376.260 |
| 77 | 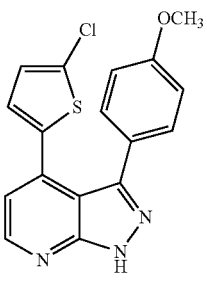 [SMILES: COc1ccc(-c2n[nH]c3nccc(-c4ccc(Cl)s4)c23)cc1] | 4-(5-chlorothiophen-2-yl)-3-(4-methoxyphenyl)-1H-pyrazolo[3,4-b]pyridine | 341.815 |
| 78 | 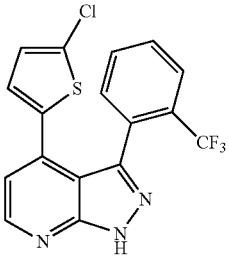 [SMILES: FC(F)(F)c1ccccc1-c1n[nH]c2nccc(-c3ccc(Cl)s3)c12] | 4-(5-chlorothiophen-2-yl)-3-(2-(trifluoromethyl)phenyl)-1H-pyrazolo[3,4-b]pyridine | 379.787 |
| 79 | 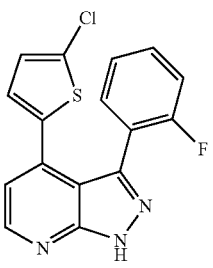 [SMILES: Fc1ccccc1-c1n[nH]c2nccc(-c3ccc(Cl)s3)c12] | 4-(5-chlorothiophen-2-yl)-3-(2-fluorophenyl)-1H-pyrazolo[3,4-b]pyridine | 329.779 |
| 80 | 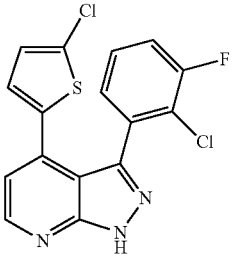 [SMILES: Fc1cccc(-c2n[nH]c3nccc(-c4ccc(Cl)s4)c23)c1Cl] | 3-(2-chloro-3-fluorophenyl)-4-(5-chlorothiophen-2-yl)-1H-pyrazolo[3,4-b]pyridine | 364.224 |

TABLE 1-continued

List of Examples

| EX. | Structure | Chemical Name | Mol. Wt |
|---|---|---|---|
| 81 | 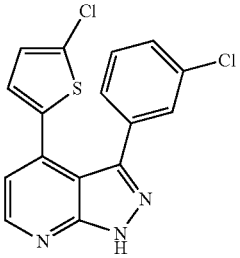 [SMILES: Clc1cccc(-c2n[nH]c3nccc(-c4ccc(Cl)s4)c23)c1] | 3-(3-chlorophenyl)-4-(5-chlorothiophen-2-yl)-1H-pyrazolo[3,4-b]pyridine | 346.234 |
| 82 | 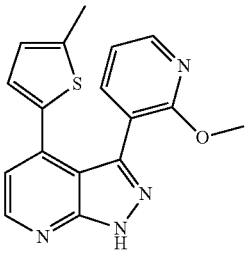 [SMILES: COc1ncccc1-c1n[nH]c2nccc(-c3ccc(C)s3)c12] | 3-(2-methoxypyridin-3-yl)-4-(5-methylthiophen-2-yl)-1H-pyrazolo[3,4-b]pyridine | 322.384 |
| 83 | 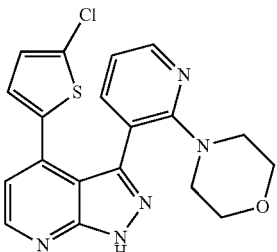 | 4-(3-(4-(5-chlorothiophen-2-yl)-1H-pyrazolo[3,4-b]pyridin-3-yl)pyridin-2-yl)morpholine | 397.881 |
| 84 | 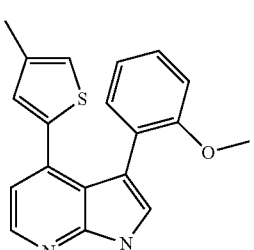 | 3-(2-methoxyphenyl)-4-(4-methylthiophen-2-yl)-1H-pyrrolo[2,3-b]pyridine | 320.408 |
| 85 | 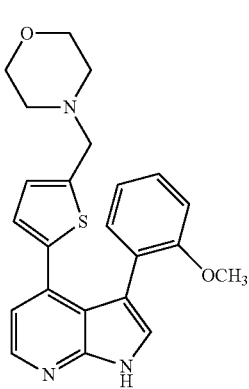 [SMILES: COc1ccccc1-c1c[nH]c2nccc(-c3ccc(CN4CCOCC4)s3)c12] | 4-((5-(3-(2-methoxyphenyl)-1H-pyrrolo[2,3-b]pyridin-4-yl)thiophen-2-yl)methyl)morpholine | 405.513 |

TABLE 1-continued

List of Examples

| EX. | Structure | Chemical Name | Mol. Wt |
|---|---|---|---|
| 86 | 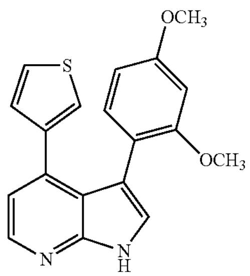 [SMILES: COc1ccc(-c2c[nH]c3nccc(-c4ccsc4)c23)c(OC)c1] | 3-(2,4-dimethoxyphenyl)-4-(thiophen-3-yl)-1H-pyrrolo[2,3-b]pyridine | 336.408 |
| 87 | 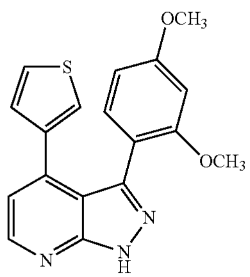 [SMILES: COc1ccc(-c2n[nH]c3nccc(-c4ccsc4)c23)c(OC)c1] | 3-(2,4-dimethoxyphenyl)-4-(thiophen-3-yl)-1H-pyrazolo[3,4-b]pyridine | 337.396 |
| 88 | 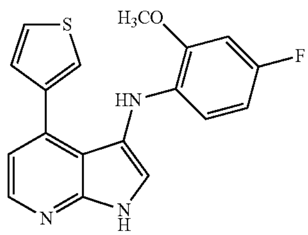 [SMILES: COc1cc(F)ccc1Nc1c[nH]c2nccc(-c3ccsc3)c12] | N-(4-fluoro-2-methoxyphenyl)-4-(thiophen-3-yl)-1H-pyrrolo[2,3-b]pyridin-3-amine | 339.387 |
| 89 | 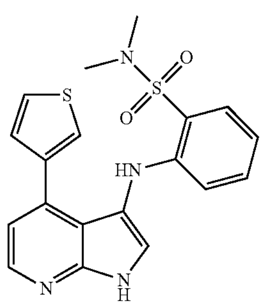 [SMILES: CN(C)S(=O)(=O)c1ccccc1Nc1c[nH]c2nccc(-c3ccsc3)c12] | N,N-dimethyl-2-((4-(thiophen-3-yl)-1H-pyrrolo[2,3-b]pyridin-3-yl)amino)benzenesulfonamide | 398.502 |
| 90 | 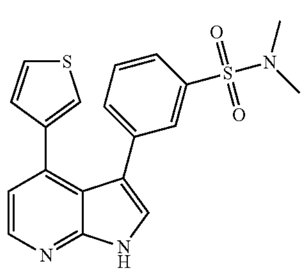 [SMILES: CN(C)S(=O)(=O)c1cccc(-c2c[nH]c3nccc(-c4ccsc4)c23)c1] | N,N-dimethyl-3-(4-(thiophen-3-yl)-1H-pyrrolo[2,3-b]pyridin-3-yl)benzenesulfonamide | 383.487 |

TABLE 1-continued

List of Examples

| EX. | Structure | Chemical Name | Mol. Wt |
|---|---|---|---|
| 91 | 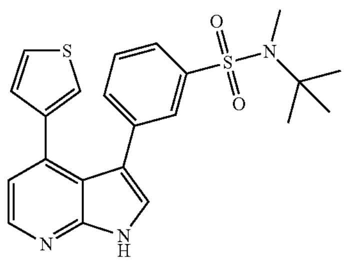 [SMILES: CN(C(C)(C)C)S(=O)(=O)c1cccc(-c2c[nH]c3nccc(-c4ccsc4)c23)c1] | N-(tert-butyl)-N-methyl-3-(4-(thiophen-3-yl)-1H-pyrrolo[2,3-b]pyridin-3-yl)benzenesulfonamide | 425.567 |
| 92 | 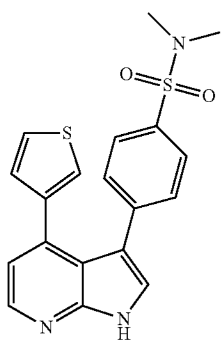 [SMILES: CN(C)S(=O)(=O)c1ccc(-c2c[nH]c3nccc(-c4ccsc4)c23)cc1] | N,N-dimethyl-4-(4-(thiophen-3-yl)-1H-pyrrolo[2,3-b]pyridin-3-yl)benzenesulfonamide | 383.487 |
| 93 | 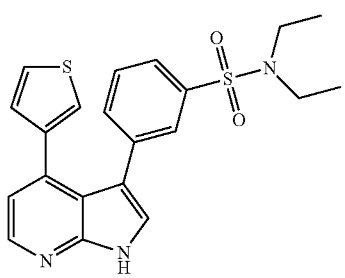 [SMILES: CCN(CC)S(=O)(=O)c1cccc(-c2c[nH]c3nccc(-c4ccsc4)c23)c1] | N,N-diethyl-3-(4-(thiophen-3-yl)-1H-pyrrolo[2,3-b]pyridin-3-yl)benzenesulfonamide | 411.540 |
| 94 | 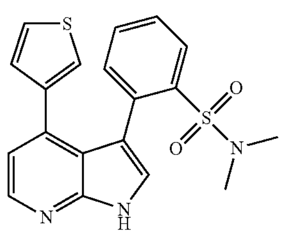 [SMILES: CN(C)S(=O)(=O)c1ccccc1-c1c[nH]c2nccc(-c3ccsc3)c12] | N,N-dimethyl-2-(4-(thiophen-3-yl)-1H-pyrrolo[2,3-b]pyridin-3-yl)benzenesulfonamide | 383.487 |
| 95 | 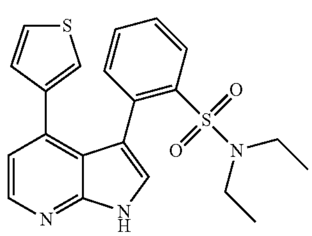 [SMILES: CCN(CC)S(=O)(=O)c1ccccc1-c1c[nH]c2nccc(-c3ccsc3)c12] | N,N-diethyl-2-(4-(thiophen-3-yl)-1H-pyrrolo[2,3-b]pyridin-3-yl)benzenesulfonamide | 411.540 |

TABLE 1-continued

List of Examples

| EX. | Structure | Chemical Name | Mol. Wt |
|---|---|---|---|
| 96 | 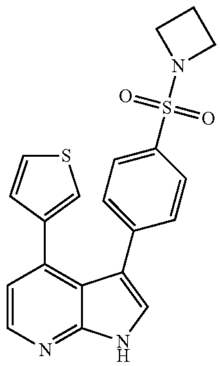 [SMILES: O=S(=O)(c1ccc(-c2c[nH]c3nccc(-c4ccsc4)c23)cc1)N1CCC1] | 3-(4-(azetidin-1-ylsulfonyl)phenyl)-4-(thiophen-3-yl)-1H-pyrrolo[2,3-b]pyridine | 395.498 |
| 97 | 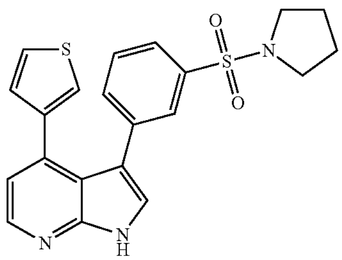 [SMILES: O=S(=O)(c1cccc(-c2c[nH]c3nccc(-c4ccsc4)c23)c1)N1CCCC1] | 3-(3-(pyrrolidin-1-ylsulfonyl)phenyl)-4-(thiophen-3-yl)-1H-pyrrolo[2,3-b]pyridine | 409.524 |
| 98 | 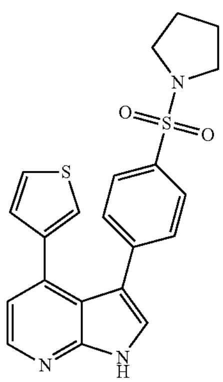 [SMILES: O=S(=O)(c1ccc(-c2c[nH]c3nccc(-c4ccsc4)c23)cc1)N1CCCC1] | 3-(4-(pyrrolidin-1-ylsulfonyl)phenyl)-4-(thiophen-3-yl)-1H-pyrrolo[2,3-b]pyridine | 409.524 |
| 99 | 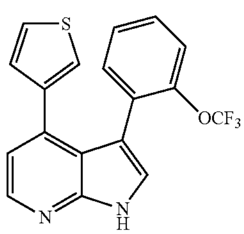 [SMILES: FC(F)(F)Oc1ccccc1-c1c[nH]c2nccc(-c3ccsc3)c12] | 4-(thiophen-3-yl)-3-(2-(trifluoromethoxy)phenyl)-1H-pyrrolo[2,3-b]pyridine | 360.353 |
| 100 | 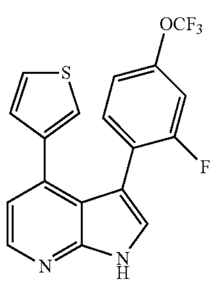 [SMILES: Fc1cc(OC(F)(F)F)ccc1-c1c[nH]c2nccc(-c3ccsc3)c12] | 3-(2-fluoro-4-(trifluoromethoxy)phenyl)-4-(thiophen-3-yl)-1H-pyrrolo[2,3-b]pyridine | 378.343 |

TABLE 1-continued

List of Examples

| EX. | Structure | Chemical Name | Mol. Wt |
|---|---|---|---|
| 101 | 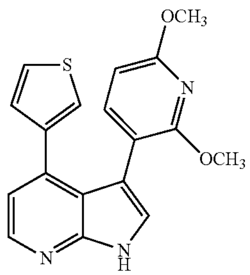 [SMILES: COc1ccc(-c2c[nH]c3nccc(-c4ccsc4)c23)c(OC)n1] | 3-(2,6-dimethoxypyridin-3-yl)-4-(thiophen-3-yl)-1H-pyrrolo[2,3-b]pyridine | 337.396 |
| 102 | 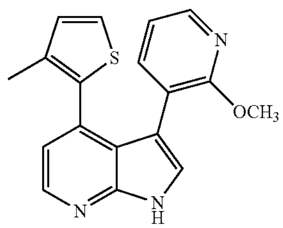 [SMILES: COc1ncccc1-c1c[nH]c2nccc(-c3sccc3C)c12] | 3-(2-methoxypyridin-3-yl)-4-(3-methylthiophen-2-yl)-1H-pyrrolo[2,3-b]pyridine | 321.396 |
| 103 | 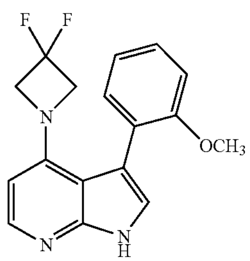 [SMILES: COc1ccccc1-c1c[nH]c2nccc(N3CC(F)(F)C3)c12] | 4-(3,3-difluoroazetidin-1-yl)-3-(2-methoxyphenyl)-1H-pyrrolo[2,3-b]pyridine | 315.317 |
| 104 | 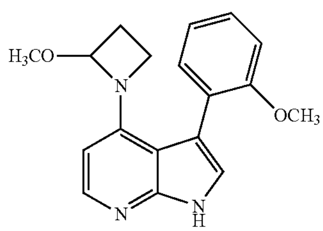 [SMILES: COc1ccccc1-c1c[nH]c2nccc(N3CCC3OC)c12] | 4-(2-methoxyazetidin-1-yl)-3-(2-methoxyphenyl)-1H-pyrrolo[2,3-b]pyridine | 309.362 |
| 105 | 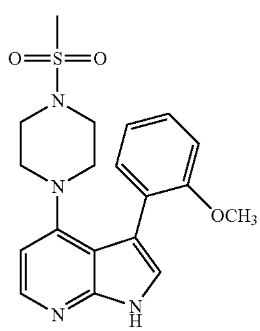 [SMILES: COc1ccccc1-c1c[nH]c2nccc(N3CCN(S(C)(=O)=O)CC3)c12] | 3-(2-methoxyphenyl)-4-(4-(methylsulfonyl)piperazin-1-yl)-1H-pyrrolo[2,3-b]pyridine | 386.468 |
| 106 | 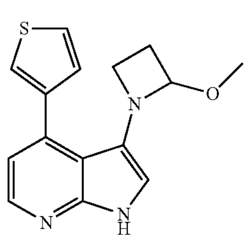 [SMILES: COC1CCN1c1c[nH]c2nccc(-c3ccsc3)c12] | 3-(2-methoxyazetidin-1-yl)-4-(thiophen-3-yl)-1H-pyrrolo[2,3-b]pyridine | 285.364 |

TABLE 1-continued

List of Examples

| EX. | Structure | Chemical Name | Mol. Wt |
|---|---|---|---|
| 107 | 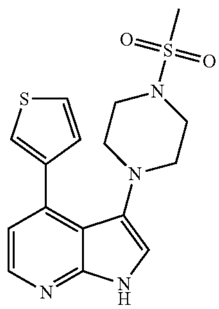 [SMILES: CS(=O)(=O)N1CCN(c2c[nH]c3nccc(-c4ccsc4)c23)CC1] | 3-(4-(methylsulfonyl)piperazin-1-yl)-4-(thiophen-3-yl)-1H-pyrrolo[2,3-b]pyridine | 362.470 |
| 108 | 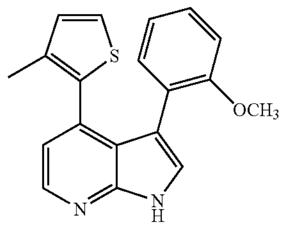 [SMILES: COc1ccccc1-c1c[nH]c2nccc(-c3sccc3C)c12] | 3-(2-methoxyphenyl)-4-(3-methylthiophen-2-yl)-1H-pyrrolo[2,3-b]pyridine | 320.408 |
| 109 | 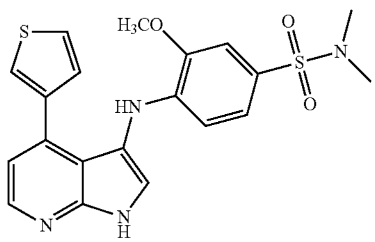 [SMILES: COc1cc(S(=O)(=O)N(C)C)ccc1Nc1c[nH]c2nccc(-c3ccsc3)c12] | 3-methoxy-N,N-dimethyl-4-((4-(thiophen-3-yl)-1H-pyrrolo[2,3-b]pyridin-3-yl)amino)benzenesulfonamide | 428.528 |
| 110 | 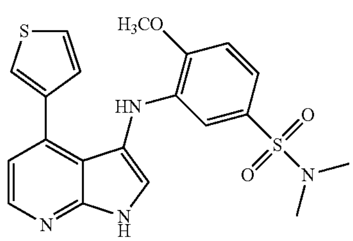 [SMILES: COc1ccc(S(=O)(=O)N(C)C)cc1Nc1c[nH]c2nccc(-c3ccsc3)c12] | 4-methoxy-N,N-dimethyl-3-((4-(thiophen-3-yl)-1H-pyrrolo[2,3-b]pyridin-3-yl)amino)benzenesulfonamide | 428.528 |
| 111 | 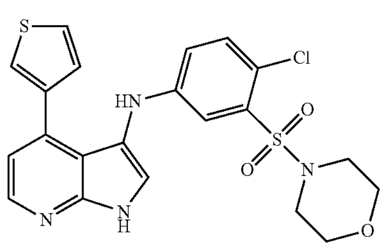 [SMILES: O=S(=O)(c1cc(Nc2c[nH]c3nccc(-c4ccsc4)c23)ccc1Cl)N1CCOCC1] | N-(4-chloro-3-(morpholinosulfonyl)phenyl)-4-(thiophen-3-yl)-1H-pyrrolo[2,3-b]pyridin-3-amine | 474.984 |
| 112 | 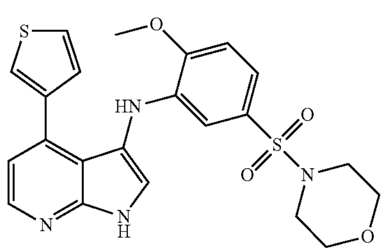 [SMILES: COc1ccc(S(=O)(=O)N2CCOCC2)cc1Nc1c[nH]c2nccc(-c3ccsc3)c12] | N-(2-methoxy-5-(morpholinosulfonyl)phenyl)-4-(thiophen-3-yl)-1H-pyrrolo[2,3-b]pyridin-3-amine | 470.564 |

TABLE 1-continued

List of Examples

| EX. | Structure | Chemical Name | Mol. Wt |
|---|---|---|---|
| 113 | 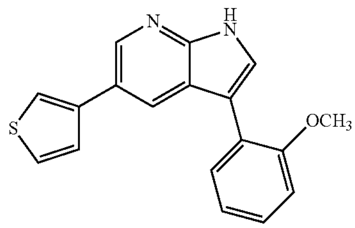 [SMILES: COc1ccccc1-c1c[nH]c2ncc(-c3ccsc3)cc12] | 3-(2-methoxyphenyl)-5-(thiophen-3-yl)-1H-pyrrolo[2,3-b]pyridine | 306.382 |
| 114 | 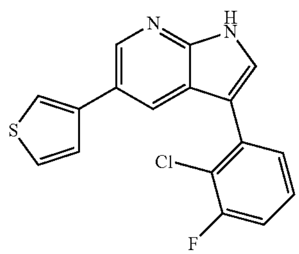 [SMILES: Fc1cccc(-c2c[nH]c3ncc(-c4ccsc4)cc23)c1Cl] | 3-(2-chloro-3-fluorophenyl)-5-(thiophen-3-yl)-1H-pyrrolo[2,3-b]pyridine | 328.791 |
| 115 | 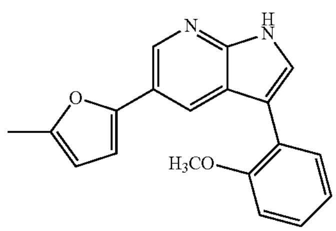 [SMILES: COc1ccccc1-c1c[nH]c2ncc(-c3ccc(C)o3)cc12] | 3-(2-methoxyphenyl)-5-(5-methylfuran-2-yl)-1H-pyrrolo[2,3-b]pyridine | 304.343 |
| 116 | 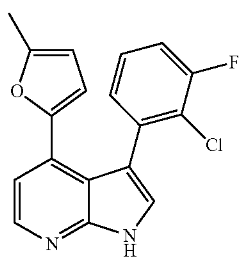 [SMILES: Cc1ccc(-c2ccnc3[nH]cc(-c4cccc(F)c4Cl)c23)o1] | 3-(2-chloro-3-fluorophenyl)-4-(5-methylfuran-2-yl)-1H-pyrrolo[2,3-b]pyridine | 326.752 |
| 117 | 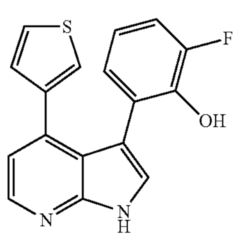 [SMILES: Oc1c(F)cccc1-c1c[nH]c2nccc(-c3ccsc3)c12] | 2-fluoro-6-(4-(thiophen-3-yl)-1H-pyrrolo[2,3-b]pyridin-3-yl)phenol | 310.345 |
| 118 | 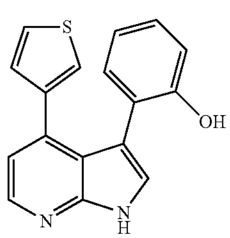 [SMILES: Oc1ccccc1-c1c[nH]c2nccc(-c3ccsc3)c12] | 2-(4-(thiophen-3-yl)-1H-pyrrolo[2,3-b]pyridin-3-yl)phenol | 292.355 |

TABLE 1-continued

List of Examples

| EX. | Structure | Chemical Name | Mol. Wt |
|---|---|---|---|
| 119 | 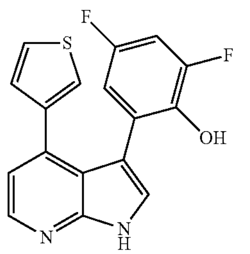 [SMILES: Oc1c(F)cc(F)cc1-c1c[nH]c2nccc(-c3ccsc3)c12] | 2,4-difluoro-6-(4-(thiophen-3-yl)-1H-pyrrolo[2,3-b]pyridin-3-yl)phenol | 328.336 |
| 120 | 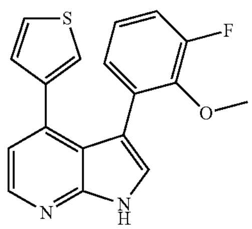 [SMILES: COc1c(F)cccc1-c1c[nH]c2nccc(-c3ccsc3)c12] | 3-(3-fluoro-2-methoxyphenyl)-4-(thiophen-3-yl)-1H-pyrrolo[2,3-b]pyridine | 324.372 |
| 121 | 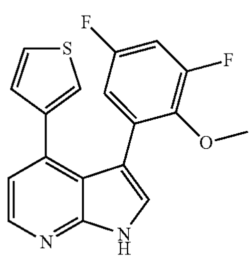 [SMILES: COc1c(F)cc(F)cc1-c1c[nH]c2nccc(-c3ccsc3)c12] | 3-(3,5-difluoro-2-methoxyphenyl)-4-(thiophen-3-yl)-1H-pyrrolo[2,3-b]pyridine | 342.362 |
| 122 | 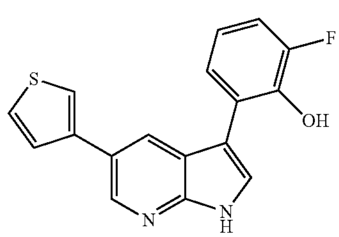 [SMILES: Oc1c(F)cccc1-c1c[nH]c2ncc(-c3ccsc3)cc12] | 2-fluoro-6-(5-(thiophen-3-yl)-1H-pyrrolo[2,3-b]pyridin-3-yl)phenol | 310.345 |
| 123 | 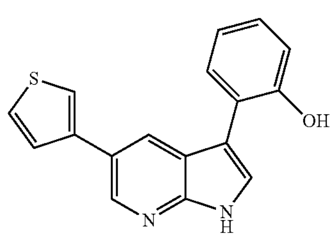 [SMILES: Oc1ccccc1-c1c[nH]c2ncc(-c3ccsc3)cc12] | 2-(5-(thiophen-3-yl)-1H-pyrrolo[2,3-b]pyridin-3-yl)phenol | 292.355 |
| 124 | 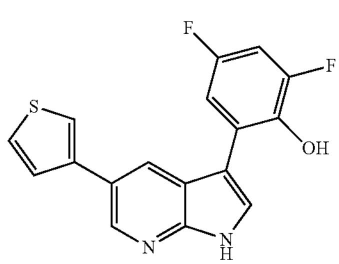 [SMILES: Oc1c(F)cc(F)cc1-c1c[nH]c2ncc(-c3ccsc3)cc12] | 2,4-difluoro-6-(5-(thiophen-3-yl)-1H-pyrrolo[2,3-b]pyridin-3-yl)phenol | 328.336 |

TABLE 1-continued

List of Examples

| EX. | Structure | Chemical Name | Mol. Wt |
|---|---|---|---|
| 125 | 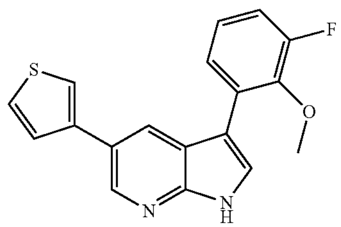 [SMILES: COc1c(F)cccc1-c1c[nH]c2ncc(-c3ccsc3)cc12] | 3-(3-fluoro-2-methoxyphenyl)-5-(thiophen-3-yl)-1H-pyrrolo[2,3-b]pyridine | 324.372 |
| 126 | 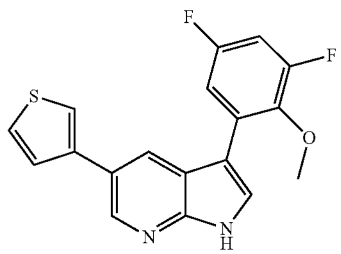 [SMILES: COc1c(F)cc(F)cc1-c1c[nH]c2ncc(-c3ccsc3)cc12] | 3-(3,5-difluoro-2-methoxyphenyl)-5-(thiophen-3-yl)-1H-pyrrolo[2,3-b]pyridine | 342.362 |
| 127 | 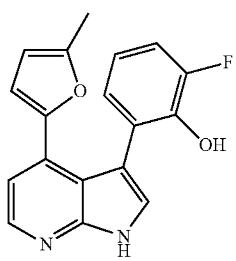 [SMILES: Cc1ccc(-c2ccnc3[nH]cc(-c4cccc(F)c4O)c23)o1] | 2-fluoro-6-(4-(5-methylfuran-2-yl)-1H-pyrrolo[2,3-b]pyridin-3-yl)phenol | 308.306 |
| 128 | 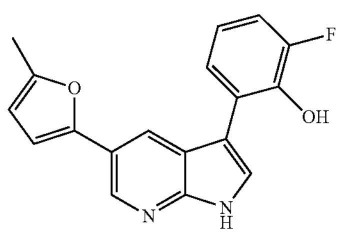 [SMILES: Cc1ccc(-c2cnc3[nH]cc(-c4cccc(F)c4O)c3c2)o1] | 2-fluoro-6-(5-(5-methylfuran-2-yl)-1H-pyrrolo[2,3-b]pyridin-3-yl)phenol | 308.306 |
| 129 | 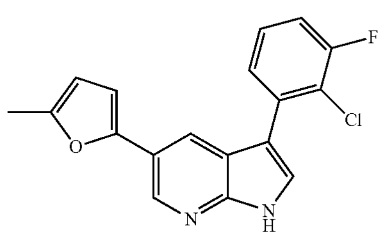 | 3-(2-chloro-3-fluorophenyl)-5-(5-methylfuran-2-yl)-1H-pyrrolo[2,3-b]pyridine | 326.752 |
| 130 | 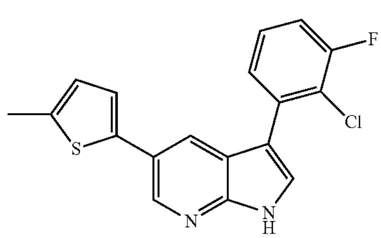 [SMILES: Cc1ccc(-c2cnc3[nH]cc(-c4cccc(F)c4Cl)c3c2)s1] | 3-(2-chloro-3-fluorophenyl)-5-(5-methylthiophen-2-yl)-1H-pyrrolo[2,3-b]pyridine | 342.818 |

TABLE 1-continued

List of Examples

| EX. | Structure | Chemical Name | Mol. Wt |
|---|---|---|---|
| 131 | 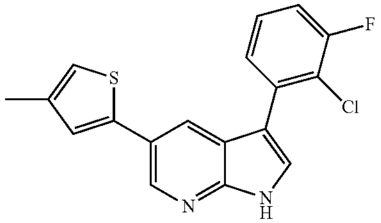 [SMILES: Cc1csc(-c2cnc3[nH]cc(-c4cccc(F)c4Cl)c3c2)c1] | 3-(2-chloro-3-fluorophenyl)-5-(4-methylthiophen-2-yl)-1H-pyrrolo[2,3-b]pyridine | 342.818 |
| 132 | 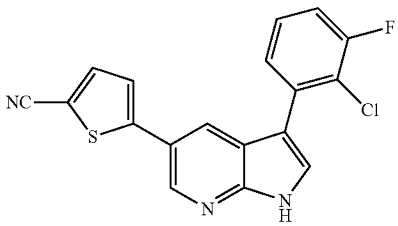 [SMILES: N#Cc1ccc(-c2cnc3[nH]cc(-c4cccc(F)c4Cl)c3c2)s1] | 5-(3-(2-chloro-3-fluorophenyl)-1H-pyrrolo[2,3-b]pyridin-5-yl)thiophene-2-carbonitrile | 353.801 |
| 133 | 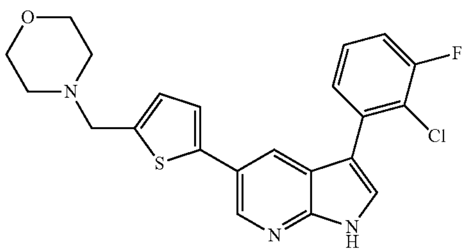 [SMILES: Fc1cccc(-c2c[nH]c3ncc(-c4ccc(CN5CCOCC5)s4)cc23)c1Cl] | 4-((5-(3-(2-chloro-3-fluorophenyl)-1H-pyrrolo[2,3-b]pyridin-5-yl)thiophen-2-yl)methyl)morpholine | 427.922 |
| 134 | 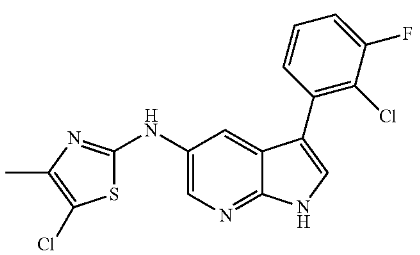 [SMILES: Cc1nc(Nc2cnc3[nH]cc(-c4cccc(F)c4Cl)c3c2)sc1Cl] | 5-chloro-N-(3-(2-chloro-3-fluorophenyl)-1H-pyrrolo[2,3-b]pyridin-5-yl)-4-methylthiazol-2-amine | 393.265 |
| 135 | 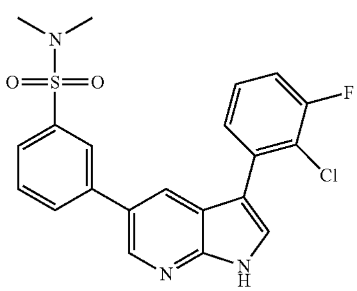 [SMILES: CN(C)S(=O)(=O)c1cccc(-c2cnc3[nH]cc(-c4cccc(F)c4Cl)c3c2)c1] | 3-(3-(2-chloro-3-fluorophenyl)-1H-pyrrolo[2,3-b]pyridin-5-yl)-N,N-dimethylbenzenesulfonamide | 429.895 |
| 136 | 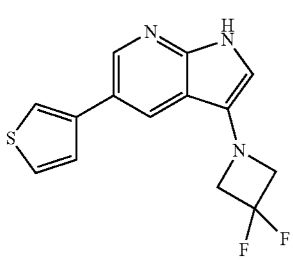 [SMILES: FC1(F)CN(c2c[nH]c3ncc(-c4ccsc4)cc23)C1] | 3-(3,3-difluoroazetidin-1-yl)-5-(thiophen-3-yl)-1H-pyrrolo[2,3-b]pyridine | 291.319 |

TABLE 1-continued

List of Examples

| EX. | Structure | Chemical Name | Mol. Wt |
|---|---|---|---|
| 137 | 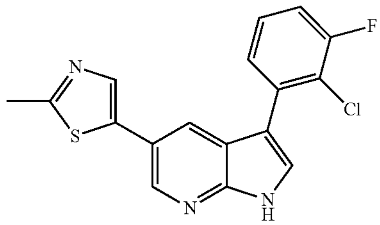 [SMILES: Cc1ncc(-c2cnc3[nH]cc(-c4cccc(F)c4Cl)c3c2)s1] | 5-(3-(2-chloro-3-fluorophenyl)-1H-pyrrolo[2,3-b]pyridin-5-yl)-2-methylthiazole | 343.806 |
| 138 | 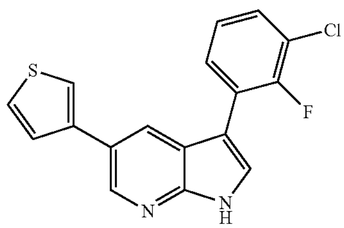 [SMILES: Fc1c(Cl)cccc1-c1c[nH]c2ncc(-c3ccsc3)cc12] | 3-(3-chloro-2-fluorophenyl)-5-(thiophen-3-yl)-1H-pyrrolo[2,3-b]pyridine | 328.791 |
| 139 | 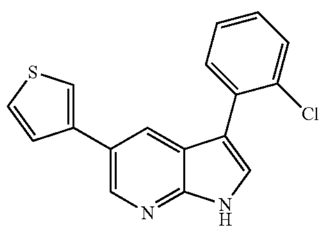 [SMILES: Clc1ccccc1-c1c[nH]c2ncc(-c3ccsc3)cc12] | 3-(2-chlorophenyl)-5-(thiophen-3-yl)-1H-pyrrolo[2,3-b]pyridine | 310.801 |
| 140 | 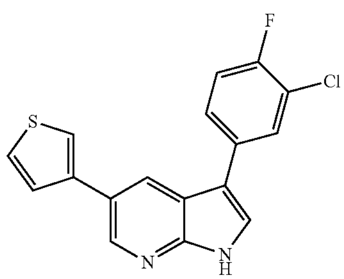 [SMILES: Fc1ccc(-c2c[nH]c3ncc(-c4ccsc4)cc23)cc1Cl] | 3-(3-chloro-4-fluorophenyl)-5-(thiophen-3-yl)-1H-pyrrolo[2,3-b]pyridine | 328.791 |
| 141 | 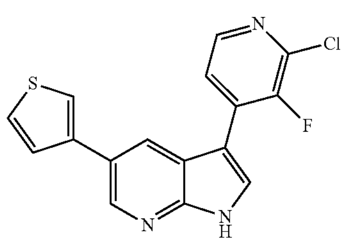 [SMILES: Fc1c(-c2c[nH]c3ncc(-c4ccsc4)cc23)ccnc1Cl] | 3-(2-chloro-3-fluoropyridin-4-yl)-5-(thiophen-3-yl)-1H-pyrrolo[2,3-b]pyridine | 329.779 |
| 142 | 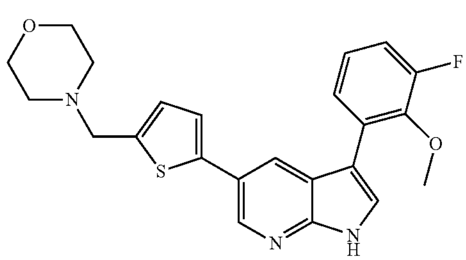 [SMILES: COc1c(F)cccc1-c1c[nH]c2ncc(-c3ccc(CN4CCOCC4)s3)cc12] | 4-((5-(3-(3-fluoro-2-methoxyphenyl)-1H-pyrrolo[2,3-b]pyridin-5-yl)thiophen-2-yl)methyl)morpholine | 423.503 |

TABLE 1-continued

List of Examples

| EX. | Structure | Chemical Name | Mol. Wt |
|---|---|---|---|
| 143 | 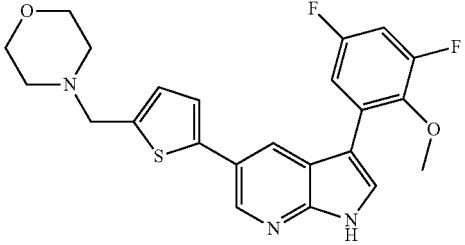 [SMILES: COc1c(F)cc(F)cc1-c1c[nH]c2ncc(-c3ccc(CN4CCOCC4)s3)cc12] | 4-((5-(3-(3,5-difluoro-2-methoxyphenyl)-1H-pyrrolo[2,3-b]pyridin-5-yl)thiophen-2-yl)methyl)morpholine | 441.494 |
| 144 | 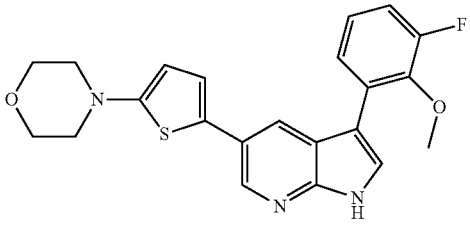 [SMILES: COc1c(F)cccc1-c1c[nH]c2ncc(-c3ccc(N4CCOCC4)s3)cc12] | 4-(5-(3-(3-fluoro-2-methoxyphenyl)-1H-pyrrolo[2,3-b]pyridin-5-yl)thiophen-2-yl)morpholine | 409.477 |
| 145 | 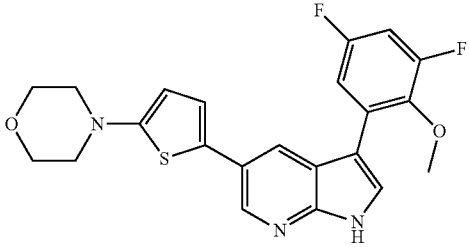 [SMILES: COc1c(F)cc(F)cc1-c1c[nH]c2ncc(-c3ccc(N4CCOCC4)s3)cc12] | 4-(5-(3-(3,5-difluoro-2-methoxyphenyl)-1H-pyrrolo[2,3-b]pyridin-5-yl)thiophen-2-yl)morpholine | 427.467 |
| 146 | 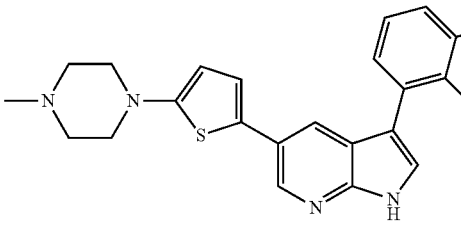 | 3-(3-fluoro-2-methoxyphenyl)-5-(5-(4-methylpiperazin-1-yl)thiophen-2-yl)-1H-pyrrolo[2,3-b]pyridine | 422.518 |
| 147 | 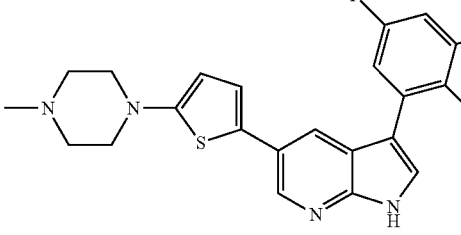 | 3-(3,5-difluoro-2-methoxyphenyl)-5-(5-(4-methylpiperazin-1-yl)thiophen-2-yl)-1H-pyrrolo[2,3-b]pyridine | 440.509 |
| 148 | 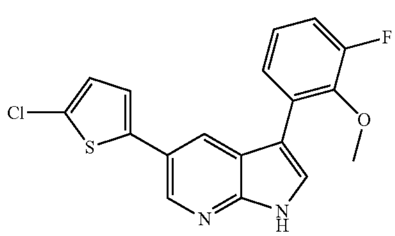 [SMILES: COc1c(F)cccc1-c1c[nH]c2ncc(-c3ccc(Cl)s3)cc12] | 5-(5-chlorothiophen-2-yl)-3-(3-fluoro-2-methoxyphenyl)-1H-pyrrolo[2,3-b]pyridine | 358.817 |

TABLE 2

List of further Examples:

| EX. | Structure | Chemical Name | Mol. Wt |
|---|---|---|---|
| 149 | 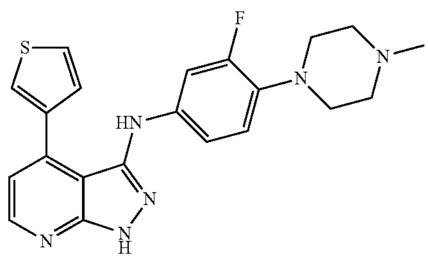 [SMILES: CN1CCN(c2ccc(Nc3n[nH]c4nccc(-c5ccsc5)c34)cc2F)CC1] | N-(3-fluoro-4-(4-methylpiperazin-1-yl)phenyl)-4-(thiophen-3-yl)-1H-pyrazolo[3,4-b]pyridin-3-amine | 408.50 |
| 150 | 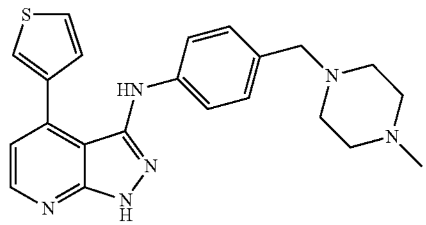 [SMILES: CN1CCN(Cc2ccc(Nc3n[nH]c4nccc(-c5ccsc5)c34)cc2)CC1] | N-(4-((4-methylpiperazin-1-yl)methyl)phenyl)-4-(thiophen-3-yl)-1H-pyrazolo[3,4-b]pyridin-3-amine | 404.53 |
| 151 | 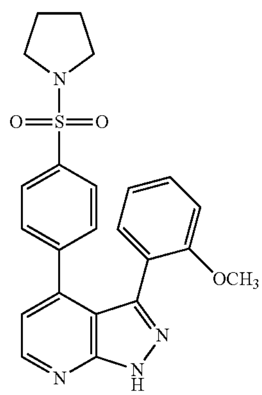 [SMILES: COc1ccccc1-c1n[nH]c2nccc(-c3ccc(S(=O)(=O)N4CCCC4)cc3)c12] | 3-(2-methoxyphenyl)-4-(4-(pyrrolidin-1-ylsulfonyl)phenyl)-1H-pyrazolo[3,4-b]pyridine | 434.52 |
| 152 | 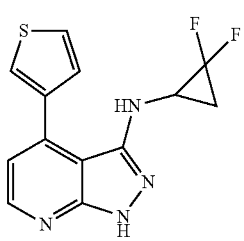 [SMILES: FC1(F)CC1Nc1n[nH]c2nccc(-c3ccsc3)c12] | N-(2,2-difluorocyclopropyl)-4-(thiophen-3-yl)-1H-pyrazolo[3,4-b]pyridin-3-amine | 292.31 |
| 153 | 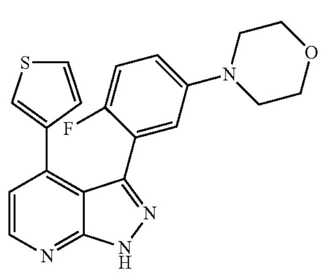 [SMILES: Fc1ccc(N2CCOCC2)cc1-c1n[nH]c2nccc(-c3ccsc3)c12] | 4-(4-fluoro-3-(4-(thiophen-3-yl)-1H-pyrazolo[3,4-b]pyridin-3-yl)phenyl)morpholine | 380.44 |

TABLE 2-continued

List of further Examples:

| EX. | Structure | Chemical Name | Mol. Wt |
|---|---|---|---|
| 154 | 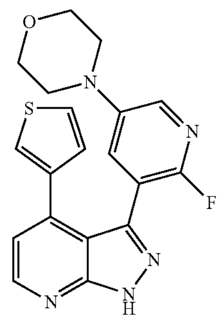 [SMILES: Fc1ncc(N2CCOCC2)cc1-c1n[nH]c2nccc(-c3ccsc3)c12] | 4-(6-fluoro-5-(4-(thiophen-3-yl)-1H-pyrazolo[3,4-b]pyridin-3-yl)pyridin-3-yl)morpholine | 381.43 |
| 155 | 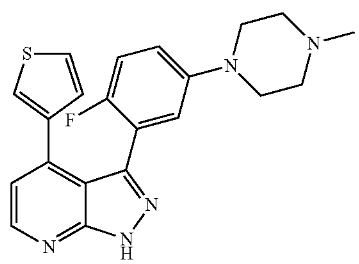 [SMILES: CN1CCN(c2ccc(F)c(-c3n[nH]c4nccc(-c5ccsc5)c34)c2)CC1] | 3-(2-fluoro-5-(4-methylpiperazin-1-yl)phenyl)-4-(thiophen-3-yl)-1H-pyrazolo[3,4-b]pyridine | 393.48 |
| 156 | 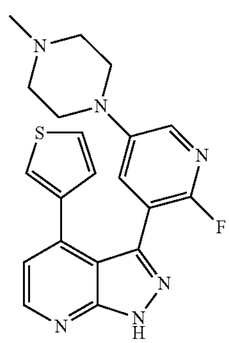 [SMILES: CN1CCN(c2cnc(F)c(-c3n[nH]c4nccc(-c5ccsc5)c34)c2)CC1] | 3-(2-fluoro-5-(4-methylpiperazin-1-yl)pyridin-3-yl)-4-(thiophen-3-yl)-1H-pyrazolo[3,4-b]pyridine | 394.47 |
| 157 | 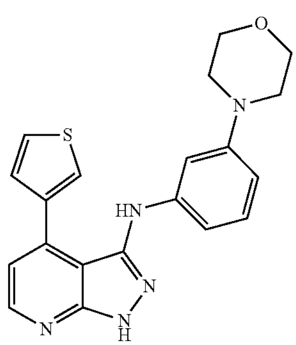 [SMILES: c1cc(Nc2n[nH]c3nccc(-c4ccsc4)c23)cc(N2CCOCC2)c1] | N-(3-morpholinophenyl)-4-(thiophen-3-yl)-1H-pyrazolo[3,4-b]pyridin-3-amine | 377.46 |

TABLE 2-continued

List of further Examples:

| EX. | Structure | Chemical Name | Mol. Wt |
|---|---|---|---|
| 158 | 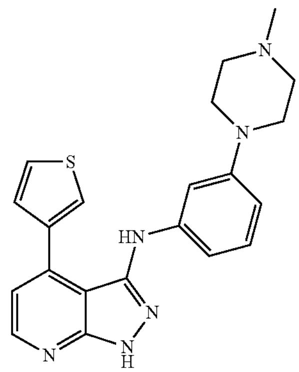 [SMILES: CN1CCN(c2cccc(Nc3n[nH]c4nccc(-c5ccsc5)c34)c2)CC1] | N-(3-(4-methylpiperazin-1-yl)phenyl)-4-(thiophen-3-yl)-1H-pyrazolo[3,4-b]pyridin-3-amine | 390.50 |
| 159 | 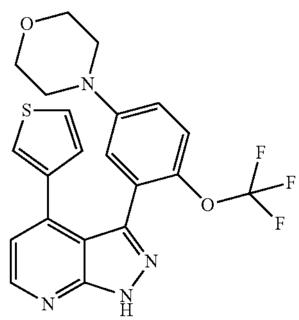 [SMILES: FC(F)(F)Oc1ccc(N2CCOCC2)cc1-c1n[nH]c2nccc(-c3ccsc3)c12] | 4-(3-(4-(thiophen-3-yl)-1H-pyrazolo[3,4-b]pyridin-3-yl)-4-(trifluoromethoxy)phenyl)morpholine | 446.45 |
| 160 | 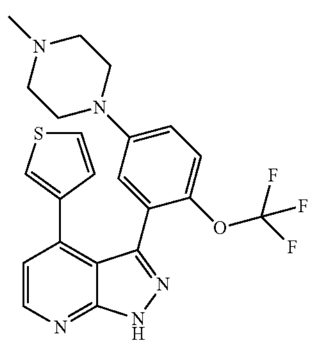 [SMILES: CN1CCN(c2ccc(OC(F)(F)F)c(-c3n[nH]c4nccc(-c5ccsc5)c34)c2)CC1] | 3-(5-(4-methylpiperazin-1-yl)-2-(trifluoromethoxy)phenyl)-4-(thiophen-3-yl)-1H-pyrazolo[3,4-b]pyridine | 459.49 |
| 161 | 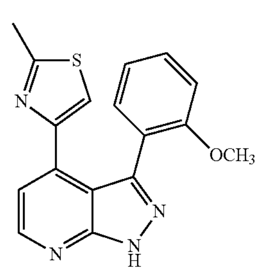 [SMILES: COc1ccccc1-c1n[nH]c2nccc(-c3csc(C)n3)c12] | 4-(3-(2-methoxyphenyl)-1H-pyrazolo[3,4-b]pyridin-4-yl)-2-methylthiazole | 322.38 |

TABLE 2-continued

List of further Examples:

| EX. | Structure | Chemical Name | Mol. Wt |
|---|---|---|---|
| 162 | 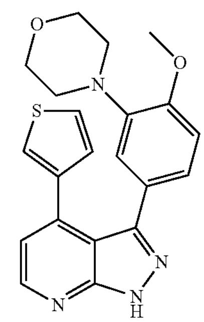 [SMILES: COc1ccc(-c2n[nH]c3nccc(-c4ccsc4)c23)cc1N1CCOCC1] | 4-(2-methoxy-5-(4-(thiophen-3-yl)-1H-pyrazolo[3,4-b]pyridin-3-yl)phenyl)morpholine | 392.47 |
| 163 | 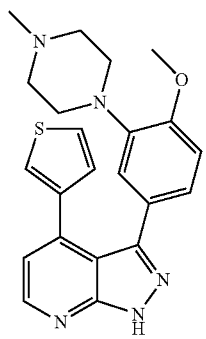 [SMILES: COc1ccc(-c2n[nH]c3nccc(-c4ccsc4)c23)cc1N1CCN(C)CC1] | 3-(4-methoxy-3-(4-methylpiperazin-1-yl)phenyl)-4-(thiophen-3-yl)-1H-pyrazolo[3,4-b]pyridine | 405.52 |
| 164 | 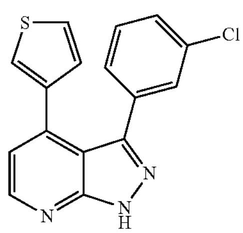 [SMILES: Clc1cccc(-c2n[nH]c3nccc(-c4ccsc4)c23)c1] | 3-(3-chlorophenyl)-4-(thiophen-3-yl)-1H-pyrazolo[3,4-b]pyridine | 311.79 |
| 165 | 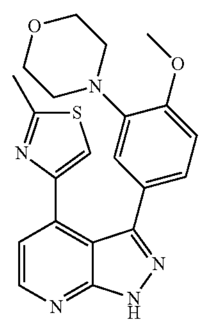 [SMILES: COc1ccc(-c2n[nH]c3nccc(-c4csc(C)n4)c23)cc1N1CCOCC1] | 4-(2-methoxy-5-(4-(2-methylthiazol-4-yl)-1H-pyrazolo[3,4-b]pyridin-3-yl)phenyl)morpholine | 407.49 |
| 166 | 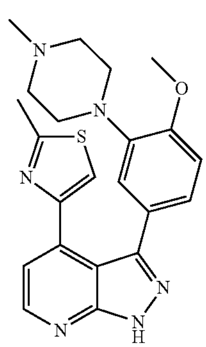 [SMILES: COc1ccc(-c2n[nH]c3nccc(-c4csc(C)n4)c23)cc1N1CCN(C)CC1] | 4-(3-(4-methoxy-3-(4-methylpiperazin-1-yl)phenyl)-1H-pyrazolo[3,4-b]pyridin-4-yl)-2-methylthiazole | 420.53 |

TABLE 2-continued

List of further Examples:

| EX. | Structure | Chemical Name | Mol. Wt |
|---|---|---|---|
| 167 | 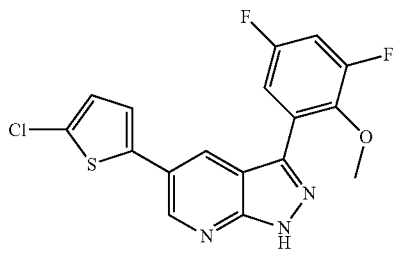 [SMILES: COc1c(F)cc(F)cc1-c1n[nH]c2ncc(-c3ccc(Cl)s3)cc12] | 5-(5-chlorothiophen-2-yl)-3-(3,5-difluoro-2-methoxyphenyl)-1H-pyrrolo[2,3-b]pyridine | 376.80 |
| 168 | 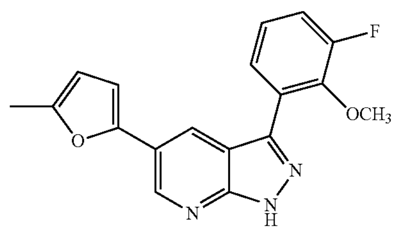 [SMILES: COc1c(F)cccc1-c1n[nH]c2ncc(-c3ccc(C)o3)cc12] | 3-(3-fluoro-2-methoxyphenyl)-5-(5-methylfuran-2-yl)-1H-pyrrolo[2,3-b]pyridine | 322.33 |
| 169 | 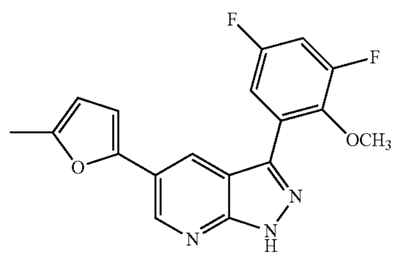 [SMILES: COc1c(F)cc(F)cc1-c1n[nH]c2ncc(-c3ccc(C)o3)cc12] | 3-(3,5-difluoro-2-methoxyphenyl)-5-(5-methylfuran-2-yl)-1H-pyrrolo[2,3-b]pyridine | 340.32 |
| 170 | 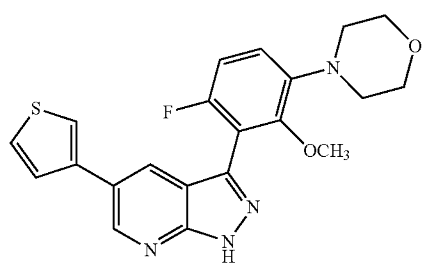 [SMILES: COc1c(N2CCOCC2)ccc(F)c1-c1n[nH]c2ncc(-c3ccsc3)cc12] | 4-(4-fluoro-2-methoxy-3-(5-(thiophen-3-yl)-1H-pyrrolo[2,3-b]pyridin-3-yl)phenyl)morpholine | 409.47 |
| 171 | 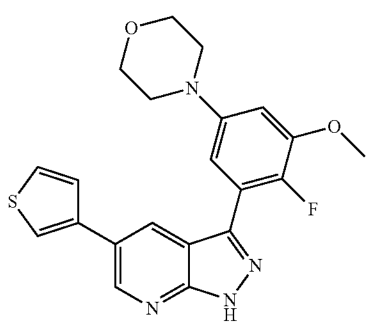 [SMILES: COc1cc(N2CCOCC2)cc(-c2n[nH]c3ncc(-c4ccsc4)cc23)c1F] | 3-(6-fluoro-2-methoxy-3-(4-methylpiperazin-1-yl)phenyl)-5-(thiophen-3-yl)-1H-pyrrolo[2,3-b]pyridine | 422.51 |

TABLE 2-continued

List of further Examples:

| EX. | Structure | Chemical Name | Mol. Wt |
|---|---|---|---|
| 172 | 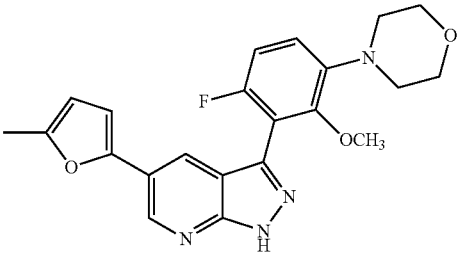 [SMILES: COc1c(N2CCOCC2)ccc(F)c1-c1n[nH]c2ncc(-c3ccc(C)o3)cc12] | 4-(4-fluoro-2-methoxy-3-(5-(5-methylfuran-2-yl)-1H-pyrrolo[2,3-b]pyridin-3-yl)phenyl)morpholine | 407.43 |
| 173 | 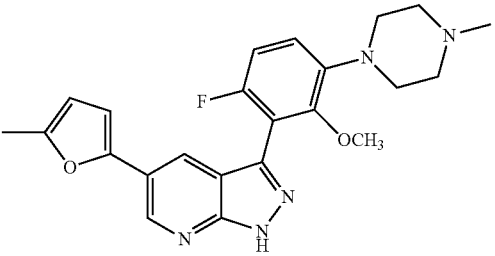 | 3-(6-fluoro-2-methoxy-3-(4-methylpiperazin-1-yl)phenyl)-5-(5-methylfuran-2-yl)-1H-pyrrolo[2,3-b]pyridine | 420.47 |
| 174 | 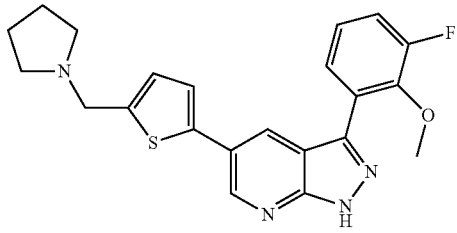 [SMILES: COc1c(F)cccc1-c1n[nH]c2ncc(-c3ccc(CN4CCCC4)s3)cc12] | 3-(3-fluoro-2-methoxyphenyl)-5-(5-(pyrrolidin-1-ylmethyl)thiophen-2-yl)-1H-pyrrolo[2,3-b]pyridine | 407.50 |
| 175 | 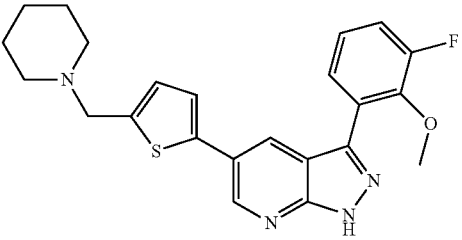 [SMILES: COc1c(F)cccc1-c1n[nH]c2ncc(-c3ccc(CN4CCCCC4)s3)cc12] | 3-(3-fluoro-2-methoxyphenyl)-5-(5-(piperidin-1-ylmethyl)thiophen-2-yl)-1H-pyrrolo[2,3-b]pyridine | 421.53 |
| 176 | 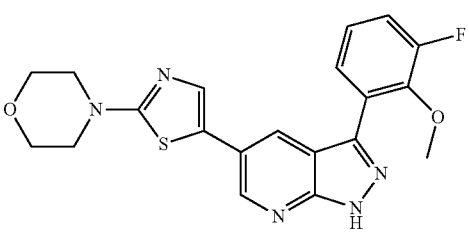 [SMILES: COc1c(F)cccc1-c1n[nH]c2ncc(-c3cnc(N4CCOCC4)s3)cc12] | 4-(5-(3-(3-fluoro-2-methoxyphenyl)-1H-pyrrolo[2,3-b]pyridin-5-yl)thiazol-2-yl)morpholine | 410.46 |
| 177 | 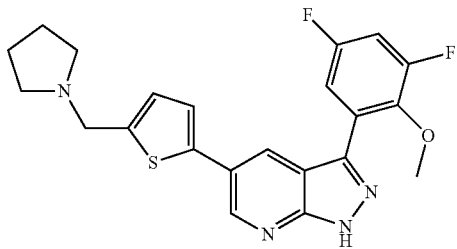 [SMILES: COc1c(F)cc(F)cc1-c1n[nH]c2ncc(-c3ccc(CN4CCCC4)s3)cc12] | 3-(3,5-difluoro-2-methoxyphenyl)-5-(5-(pyrrolidin-1-ylmethyl)thiophen-2-yl)-1H-pyrrolo[2,3-b]pyridine | 425.49 |

TABLE 2-continued

List of further Examples:

| EX. | Structure | Chemical Name | Mol. Wt |
|---|---|---|---|
| 178 | 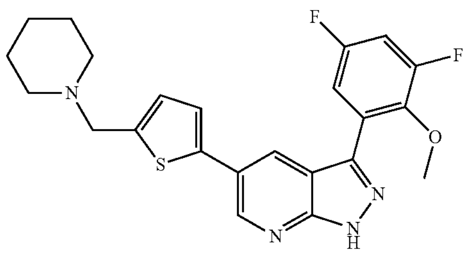 [SMILES: COc1c(F)cc(F)cc1-c1n[nH]c2ncc(-c3ccc(CN4CCCCC4)s3)cc12] | 3-(3,5-difluoro-2-methoxyphenyl)-5-(5-(piperidin-1-ylmethyl)thiophen-2-yl)-1H-pyrrolo[2,3-b]pyridine | 439.51 |
| 179 | 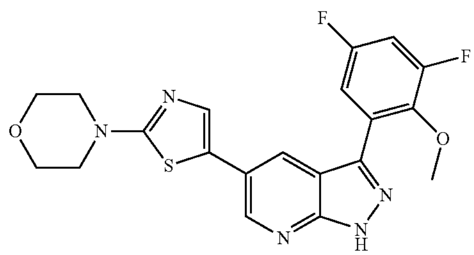 [SMILES: COc1c(F)cc(F)cc1-c1n[nH]c2ncc(-c3cnc(N4CCOCC4)s3)cc12] | 4-(5-(3-(3,5-difluoro-2-methoxyphenyl)-1H-pyrrolo[2,3-b]pyridin-5-yl)thiazol-2-yl)morpholine | 428.45 |
| 180 | 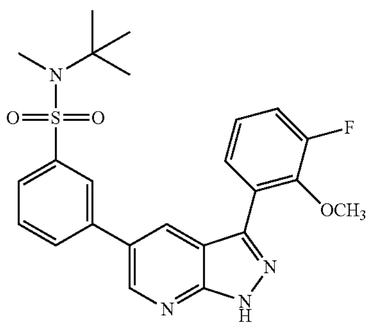 [SMILES: COc1c(F)cccc1-c1n[nH]c2ncc(-c3cccc(S(=O)(=O)N(C)C(C)(C)C)c3)cc12] | N-(tert-butyl)-3-(3-(3-fluoro-2-methoxyphenyl)-1H-pyrrolo[2,3-b]pyridin-5-yl)-N-methylbenzenesulfonamide | 467.55 |
| 181 | 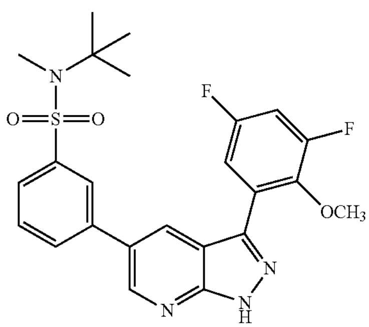 [SMILES: COc1c(F)cc(F)cc1-c1n[nH]c2ncc(-c3cccc(S(=O)(=O)N(C)C(C)(C)C)c3)cc12] | N-(tert-butyl)-3-(3-(3,5-difluoro-2-methoxyphenyl)-1H-pyrrolo[2,3-b]pyridin-5-yl)-N-methylbenzenesulfonamide | 485.54 |
| 182 | 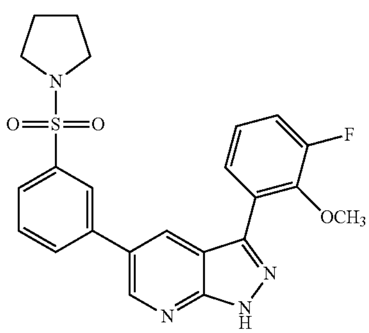 [SMILES: COc1c(F)cccc1-c1n[nH]c2ncc(-c3cccc(S(=O)(=O)N4CCCC4)c3)cc12] | 3-(3-fluoro-2-methoxyphenyl)-5-(3-(pyrrolidin-1-ylsulfonyl)phenyl)-1H-pyrrolo[2,3-b]pyridine | 451.51 |

TABLE 2-continued

List of further Examples:

| EX. | Structure | Chemical Name | Mol. Wt |
|---|---|---|---|
| 183 | 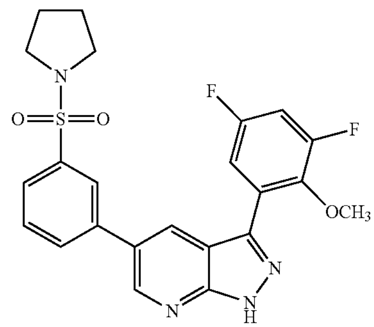 [SMILES: COc1c(F)cc(F)cc1-c1n[nH]c2ncc(-c3cccc(S(=O)(=O)N4CCCC4)c3)cc12] | 3-(3,5-difluoro-2-methoxyphenyl)-5-(3-(pyrrolidin-1-ylsulfonyl)phenyl)-1H-pyrrolo[2,3-b]pyridine | 469.50 |
| 184 | 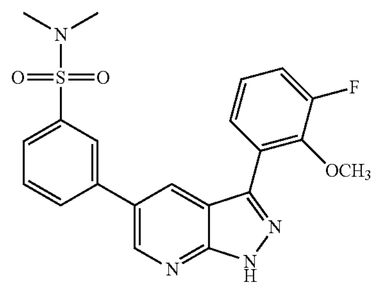 [SMILES: COc1c(F)cccc1-c1n[nH]c2ncc(-c3cccc(S(=O)(=O)N(C)C)c3)cc12] | 3-(3-(3-fluoro-2-methoxyphenyl)-1H-pyrrolo[2,3-b]pyridin-5-yl)-N,N-dimethylbenzenesulfonamide | 425.76 |
| 185 | 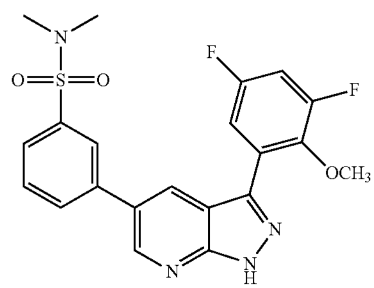 [SMILES: COc1c(F)cc(F)cc1-c1n[nH]c2ncc(-c3cccc(S(=O)(=O)N(C)C)c3)cc12] | 3-(3-(3,5-difluoro-2-methoxyphenyl)-1H-pyrrolo[2,3-b]pyridin-5-yl)-N,N-dimethylbenzenesulfonamide | 443.46 |
| 186 | 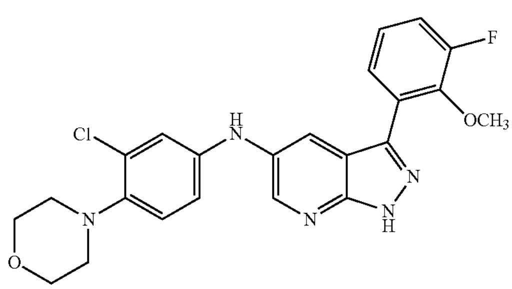 [SMILES: COc1c(F)cccc1-c1n[nH]c2ncc(Nc3ccc(N4CCOCC4)c(Cl)c3)cc12] | N-(3-chloro-4-morpholinophenyl)-3-(3-fluoro-2-methoxyphenyl)-1H-pyrrolo[2,3-b]pyridin-5-amine | 452.90 |
| 187 | 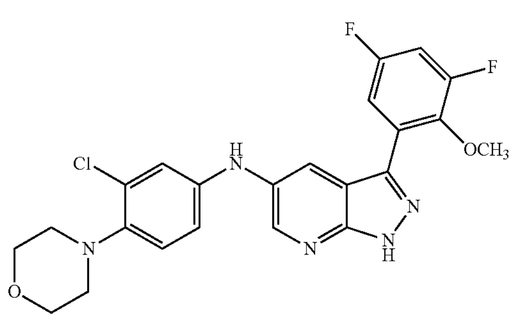 [SMILES: COc1c(F)cc(F)cc1-c1n[nH]c2ncc(Nc3ccc(N4CCOCC4)c(Cl)c3)cc12] | N-(3-chloro-4-morpholinophenyl)-3-(3,5-difluoro-2-methoxyphenyl)-1H-pyrrolo[2,3-b]pyridin-5-amine | 470.89 |

TABLE 2-continued

List of further Examples:

| EX. | Structure | Chemical Name | Mol. Wt |
|---|---|---|---|
| 188 | 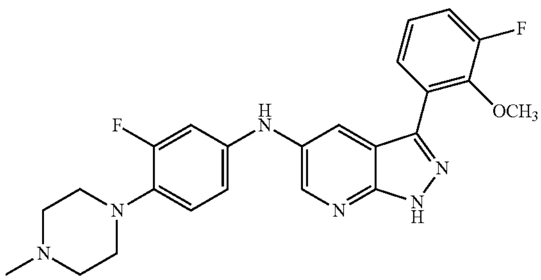 [SMILES: COc1c(F)cccc1-c1n[nH]c2ncc(Nc3ccc(N4CCN(C)CC4)c(F)c3)cc12] | 3-(3-fluoro-2-methoxyphenyl)-N-(3-fluoro-4-(4-methylpiperazin-1-yl)phenyl)-1H-pyrrolo[2,3-b]pyridin-5-amine | 449.49 |
| 189 | 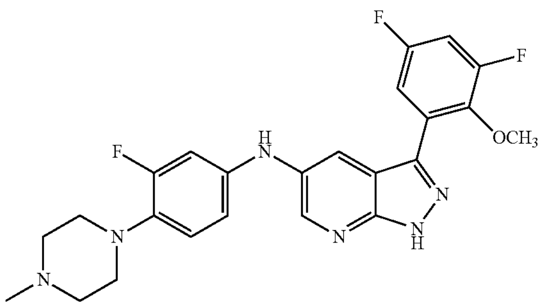 [SMILES: COc1c(F)cc(F)cc1-c1n[nH]c2ncc(Nc3ccc(N4CCN(C)CC4)c(F)c3)cc12] | 3-(3,5-difluoro-2-methoxyphenyl)-N-(3-fluoro-4-(4-methylpiperazin-1-yl)phenyl)-1H-pyrrolo[2,3-b]pyridin-5-amine | 467.48 |
| 190 | 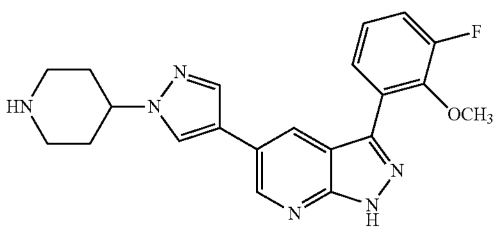 [SMILES: COc1c(F)cccc1-c1n[nH]c2ncc(-c3cnn(C4CCNCC4)c3)cc12] | 3-(3-fluoro-2-methoxyphenyl)-5-(1-(piperidin-4-yl)-1H-pyrazol-4-yl)-1H-pyrrolo[2,3-b]pyridine | 391.44 |
| 191 | 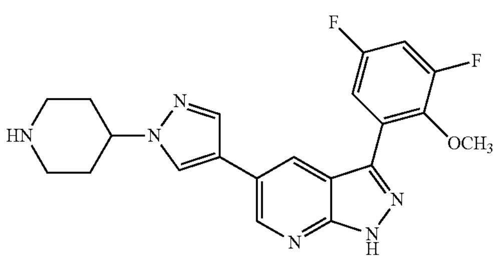 [SMILES: COc1c(F)cc(F)cc1-c1n[nH]c2ncc(-c3cnn(C4CCNCC4)c3)cc12] | 3-(3,5-difluoro-2-methoxyphenyl)-5-(1-(piperidin-4-yl)-1H-pyrazol-4-yl)-1H-pyrrolo[2,3-b]pyridine | 409.43 |
| 192 | 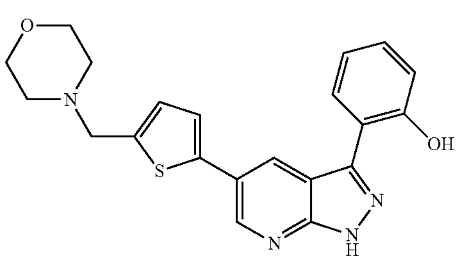 [SMILES: Oc1ccccc1-c1n[nH]c2ncc(-c3ccc(CN4CCOCC4)s3)cc12] | 2-(5-(5-(morpholinomethyl)thiophen-2-yl)-1H-pyrrolo[2,3-b]pyridin-3-yl)phenol | 391.486 |

TABLE 2-continued

List of further Examples:

| EX. | Structure | Chemical Name | Mol. Wt |
|---|---|---|---|
| 193 | 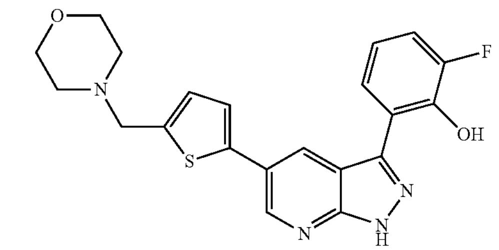 [SMILES: Oc1c(F)cccc1-c1n[nH]c2ncc(-c3ccc(CN4CCOCC4)s3)cc12] | 2-fluoro-6-(5-(5-(morpholinomethyl)thiophen-2-yl)-1H-pyrrolo[2,3-b]pyridin-3-yl)phenol | 409.477 |
| 194 | 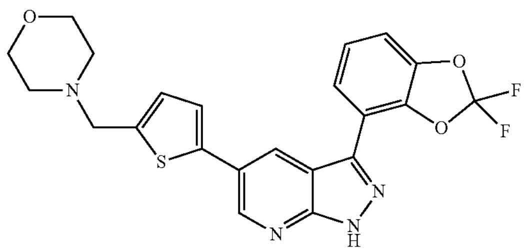 [SMILES: FC1(F)Oc2cccc(-c3n[nH]c4ncc(-c5ccc(CN6CCOCC6)s5)cc34)c2O1] | 4-((5-(3-(2,2-difluorobenzo[d][1,3]dioxol-4-yl)-1H-pyrrolo[2,3-b]pyridin-5-yl)thiophen-2-yl)methyl)morpholine | 455.457 |
| 195 | 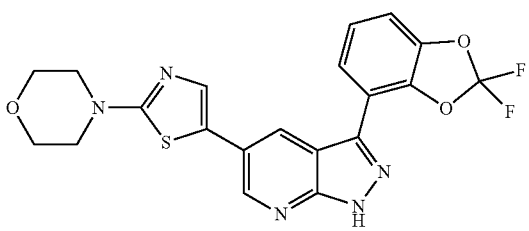 [SMILES: FC1(F)Oc2cccc(-c3n[nH]c4ncc(-c5cnc(N6CCOCC6)s5)cc34)c2O1] | 4-(5-(3-(2,2-difluorobenzo[d][1,3]dioxol-4-yl)-1H-pyrrolo[2,3-b]pyridin-5-yl)thiazol-2-yl)morpholine | 442.439 |

TABLE 2A

List of further Examples:

| EX. | Structure | Chemical Name | Mol. Wt |
|---|---|---|---|
| 196 | 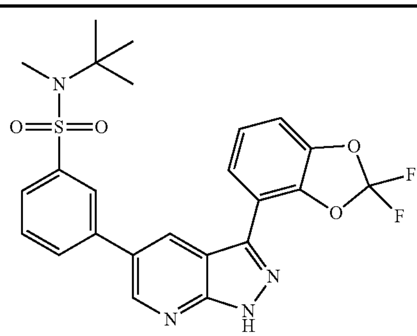 | N-(tert-butyl)-3-(3-(2,2-difluorobenzo[d][1,3]dioxol-4-yl)-1H-pyrrolo[2,3-b]pyridin-5-yl)-N-methylbenzenesulfonamide | 499.43 |
| 197 | 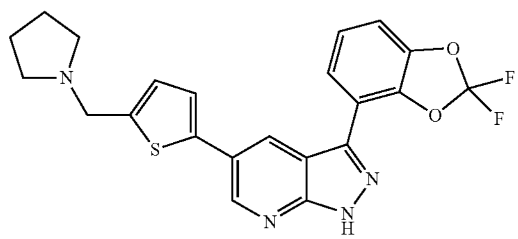 [SMILES: FC1(F)Oc2cccc(-c3n[nH]c4ncc(-c5ccc(CN6CCCC6)s5)cc34)c2O1] | 3-(2,2-difluorobenzo[d][1,3]dioxol-4-yl)-5-(5-(pyrrolidin-1-ylmethyl)thiophen-2-yl)-1H-pyrrolo[2,3-b]pyridine | 439.47 |

TABLE 2A-continued

List of further Examples:

| EX. | Structure | Chemical Name | Mol. Wt |
|---|---|---|---|
| 198 | 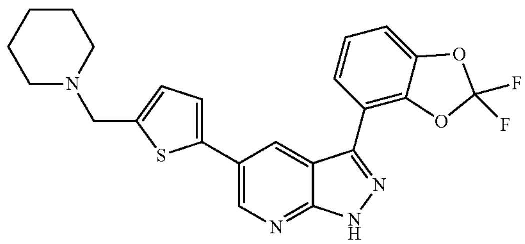 [SMILES: FC1(F)Oc2cccc(-c3n[nH]c4ncc(-c5ccc(CN6CCCCC6)s5)cc34)c2O1] | 3-(2,2-difluorobenzo[d][1,3]dioxol-4-yl)-5-(5-(piperidin-1-ylmethyl)thiophen-2-yl)-1H-pyrrolo[2,3-b]pyridine | 453.50 |
| 199 | 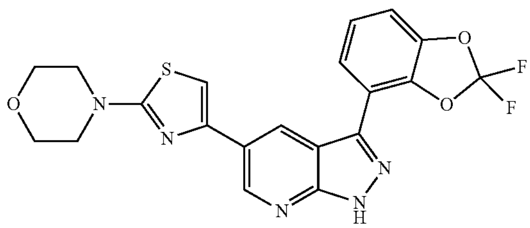 [SMILES: FC1(F)Oc2cccc(-c3n[nH]c4ncc(-c5csc(N6CCOCC6)n5)cc34)c2O1] | (4-(4-(3-(2,2-difluorobenzo[d][1,3]dioxol-4-yl)-1H-pyrrolo[2,3-b]pyridin-5-yl)thiazol-2-yl)morpholine | 442.43 |
| 200 | 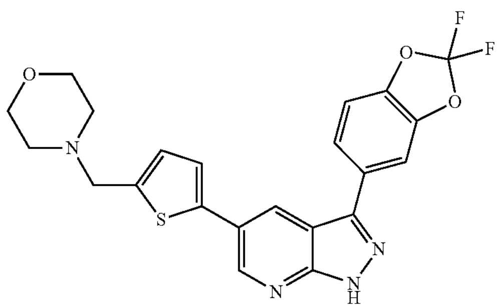 [SMILES: FC1(F)Oc2ccc(-c3n[nH]c4ncc(-c5ccc(CN6CCOCC6)s5)cc34)cc2O1] | 4-((5-(3-(2,2-difluorobenzo[d][1,3]dioxol-5-yl)-1H-pyrrolo[2,3-b]pyridin-5-yl)thiophen-2-yl)methyl)morpholine | 455.47 |
| 201 | 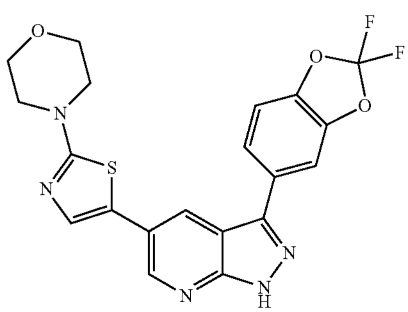 [SMILES: FC1(F)Oc2ccc(-c3n[nH]c4ncc(-c5cnc(N6CCOCC6)s5)cc34)cc2O1] | 4-(5-(3-(2,2-difluorobenzo[d][1,3]dioxol-5-yl)-1H-pyrrolo[2,3-b]pyridin-5-yl)thiazol-2-yl)morpholine | 442.43 |
| 202 | 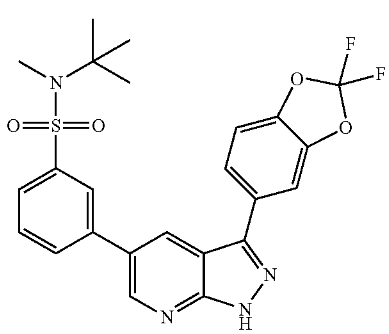 [SMILES: CN(C(C)(C)C)S(=O)(=O)c1cccc(-c2cnc3[nH]nc(-c4ccc5c(c4)OC(F)(F)O5)c3c2)c1] | N-(tert-butyl)-3-(3-(2,2-difluorobenzo[d][1,3]dioxol-5-yl)-1H-pyrrolo[2,3-b]pyridin-5-yl)-N-methylbenzenesulfonamide | 499.53 |

TABLE 2A-continued

List of further Examples:

| EX. | Structure | Chemical Name | Mol. Wt |
|---|---|---|---|
| 203 | 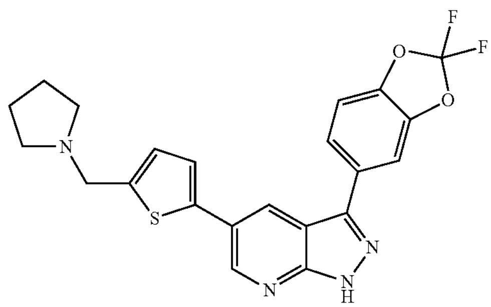 [SMILES: FC1(F)Oc2ccc(-c3n[nH]c4ncc(-c5ccc(CN6CCCC6)s5)cc34)cc2O1] | 3-(2,2-difluorobenzo[d][1,3]dioxol-5-yl)-5-(5-(pyrrolidin-1-ylmethyl)thiophen-2-yl)-1H-pyrrolo[2,3-b]pyridine | 439.47 |
| 204 | 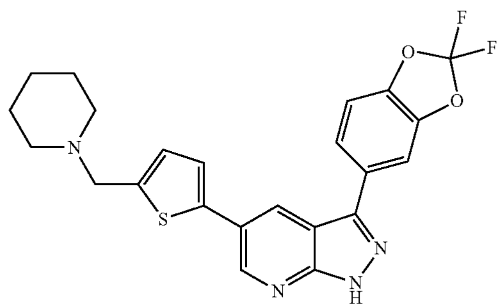 [SMILES: FC1(F)Oc2ccc(-c3n[nH]c4ncc(-c5ccc(CN6CCCCC6)s5)cc34)cc2O1] | 3(2,2-difluorobenzo[d][1,3]dioxol-5-yl)-5-(5-(piperidin-1-ylmethyl)thiophen-2-yl)-1H-pyrrolo[2,3-b]pyridine | 453.50 |
| 205 | 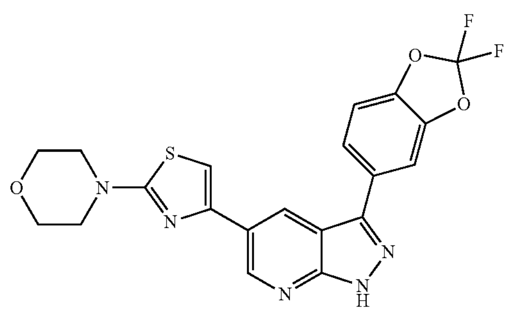 [SMILES: FC1(F)Oc2ccc(-c3n[nH]c4ncc(-c5csc(N6CCOCC6)n5)cc34)cc2O1] | 4-(4-(3-(2,2-difluorobenzo[d][1,3]dioxol-5-yl)-1H-pyrrolo[2,3-b]pyridin-5-yl)thiazol-2-yl)morpholine | 442.43 |
| 206 | 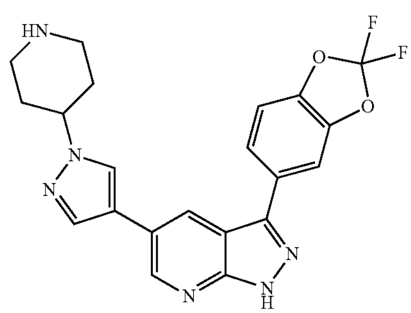 [SMILES: FC1(F)Oc2ccc(-c3n[nH]c4ncc(-c5cnn(C6CCNCC6)c5)cc34)cc2O1] | 3-(2,2-difluorobenzo[d][1,3]dioxol-5-yl)-5-(1-(piperidin-4-yl)-1H-pyrazol-4-yl)-1H-pyrrolo[2,3-b]pyridine | 423.41 |
| 207 | 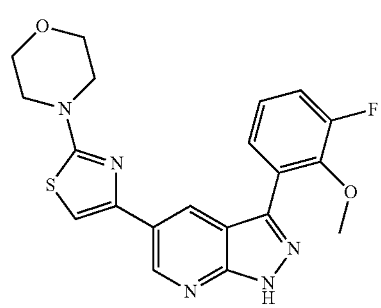 [SMILES: COc1c(F)cccc1-c1n[nH]c2ncc(-c3csc(N4CCOCC4)n3)cc12] | 4-(4-(3-(3-fluoro-2-methoxyphenyl)-1H-pyrrolo[2,3-b]pyridin-5-yl)thiazol-2-yl)morpholine | 410.46 |

TABLE 2A-continued

List of further Examples:

| EX. | Structure | Chemical Name | Mol. Wt |
|---|---|---|---|
| 208 | 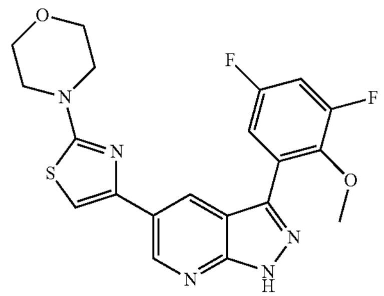 [SMILES: COc1c(F)cc(F)cc1-c1n[nH]c2ncc(-c3csc(N4CCOCC4)n3)cc12] | 4-(4-(3-(3,5-difluoro-2-methoxyphenyl)-1H-pyrrolo[2,3-b]pyridin-5-yl)thiazol-2-yl)morpholine | 428.45 |
| 209 | 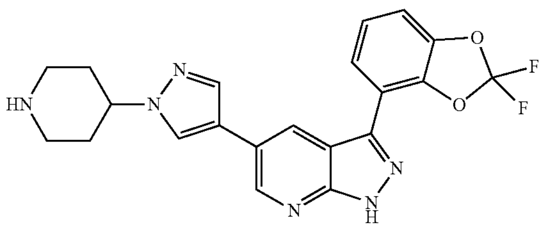 [SMILES: FC1(F)Oc2cccc(-c3n[nH]c4ncc(-c5cnn(C6CCNCC6)c5)cc34)c2O1] | 3-(2,2-difluorobenzo[d][1,3]dioxol-4-yl)-5-(1-(piperidin-4-yl)-1H-pyrazol-4-yl)-1H-pyrrolo[2,3-b]pyridine | 423.41 |
| 210 | 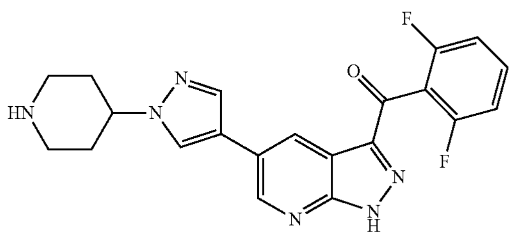 [SMILES: O=C(c1c(F)cccc1F)c1n[nH]c2ncc(-c3cnn(C4CCNCC4)c3)cc12] | (2,6-difluorophenyl)(5-(1-(piperidin-4-yl)-1H-pyrazol-4-yl)-1H-pyrrolo[2,3-b]pyridin-3-yl)methanone | 407.41 |
| 211 | 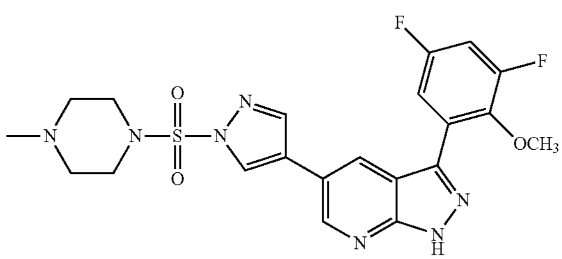 [SMILES: COc1c(F)cc(F)cc1-c1n[nH]c2ncc(-c3cnn(S(=O)(=O)N4CCN(C)CC4)c3)cc12] | 3-(3,5-difluoro-2-methoxyphenyl)-5-(1-((4-methylpiperazin-1-yl)sulfonyl)-1H-pyrazol-4-yl)-1H-pyrrolo[2,3-b]pyridine | 488.51 |
| 212 | 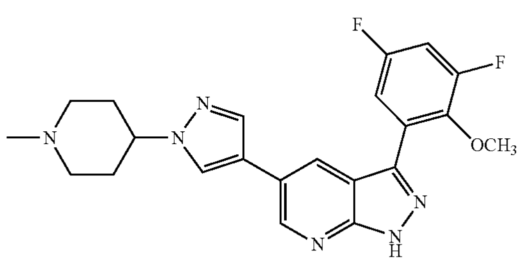 [SMILES: COc1c(F)cc(F)cc1-c1n[nH]c2ncc(-c3cnn(C4CCN(C)CC4)c3)cc12] | 3-(3,5-difluoro-2-methoxyphenyl)-5-(1-(1-methylpiperidin-4-yl)-1H-pyrazol-4-yl)-1H-pyrrolo[2,3-b]pyridine | 423.45 |
| 213 | 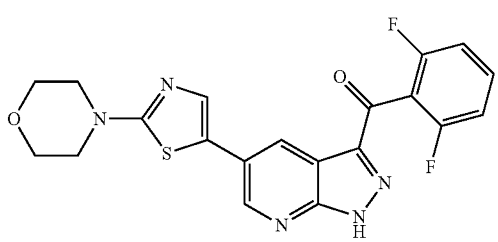 [SMILES: O=C(c1c(F)cccc1F)c1n[nH]c2ncc(-c3cnc(N4CCOCC4)s3)cc12] | (2,6-difluorophenyl)(5-(2-morpholinothiazol-5-yl)-1H-pyrrolo[2,3-b]pyridin-3-yl)methanone | 426.43 |

TABLE 2A-continued

List of further Examples:

| EX. | Structure | Chemical Name | Mol. Wt |
|---|---|---|---|
| 214 | 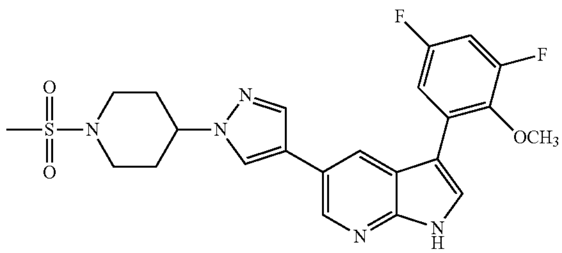 [SMILES: COc1c(F)cc(F)cc1-c1c[nH]c2ncc(-c3cnn(C4CCN(S(C)(=O)=O)CC4)c3)cc12] | 3-(3,5-difluoro-2-methoxyphenyl)-5-(1-(1-(methylsulfonyl)piperidin-4-yl)-1H-pyrazol-4-yl)-1H-pyrrolo[2,3-b]pyridine | 487.52 |
| 215 | 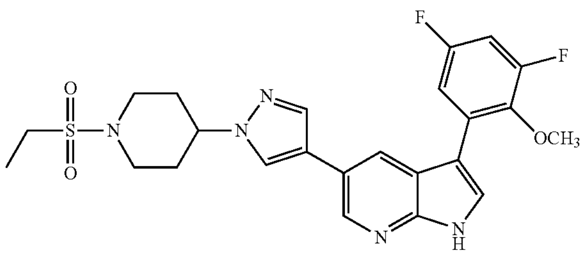 [SMILES: CCS(=O)(=O)N1CCC(n2cc(-c3cnc4[nH]cc(-c5cc(F)cc(F)c5OC)c4c3)cn2)CC1] | 3-(3,5-difluoro-2-methoxyphenyl)-5-(1-(1-(ethylsulfonyl)piperidin-4-yl)-1H-pyrazol-4-yl)-1H-pyrrolo[2,3-b]pyridine | 501.54 |
| 216 | 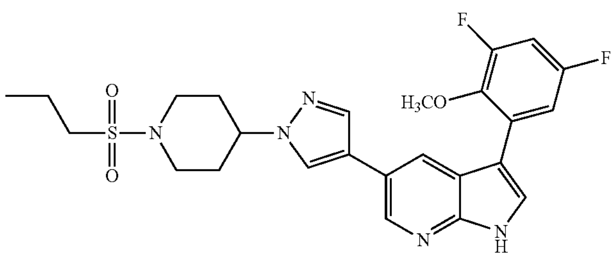 [SMILES: CCCS(=O)(=O)N1CCC(n2cc(-c3cnc4[nH]cc(-c5cc(F)cc(F)c5OC)c4c3)cn2)CC1] | 3-(3,5-difluoro-2-methoxyphenyl)-5-(1-(1-(propylsulfonyl)piperidin-4-yl)-1H-pyrazol-4-yl)-1H-pyrrolo[2,3-b]pyridine | 515.57 |
| 217 | 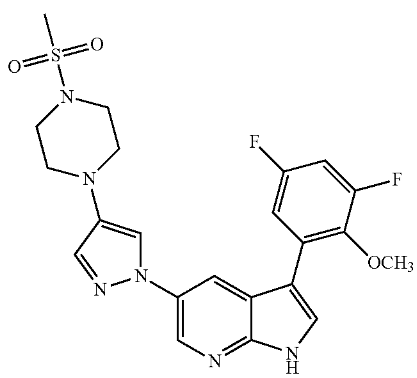 [SMILES: COc1c(F)cc(F)cc1-c1c[nH]c2ncc(-n3cc(N4CCN(S(C)(=O)=O)CC4)cn3)cc12] | 3-(3,5-difluoro-2-methoxyphenyl)-5-(4-(4-(methylsulfonyl)piperazin-1-yl)-1H-pyrazol-1-yl)-1H-pyrrolo[2,3-b]pyridine | 488.51 |
| 218 | 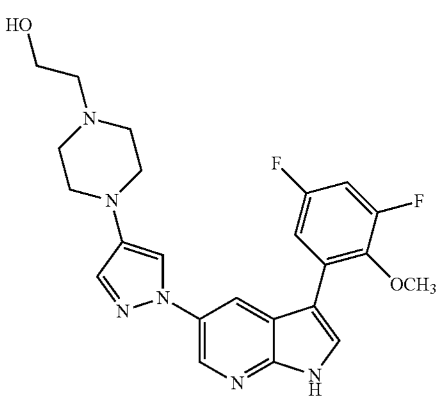 [SMILES: COc1c(F)cc(F)cc1-c1c[nH]c2ncc(-n3cc(N4CCN(CCO)CC4)cn3)cc12] | 2-(4-(1-(3-(3,5-difluoro-2-methoxyphenyl)-1H-pyrrolo[2,3-b]pyridin-5-yl)-1H-pyrazol-4-yl)piperazin-1-yl)ethanol | 454.47 |

TABLE 2A-continued

List of further Examples:

| EX. | Structure | Chemical Name | Mol. Wt |
|---|---|---|---|
| 219 | 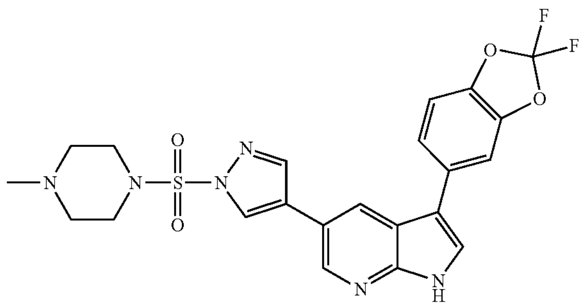 [SMILES: CN1CCN(S(=O)(=O)n2cc(-c3cnc4[nH]cc(-c5ccc6c(c5)OC(F)(F)O6)c4c3)cn2)CC1] | 3-(2,2-difluorobenzo[d][1,3]dioxol-5-yl)-5-(1-((4-methylpiperazin-1-yl)sulfonyl)-1H-pyrazol-4-yl)-1H-pyrrolo[2,3-b]pyridine | 502.49 |
| 220 | 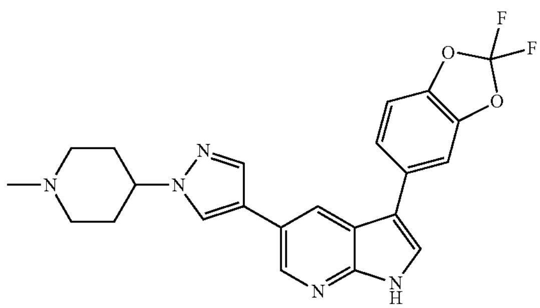 [SMILES: CN1CCC(n2cc(-c3cnc4[nH]cc(-c5ccc6c(c5)OC(F)(F)O6)c4c3)cn2)CC1] | 3-(2,2-difluorobenzo[d][1,3]dioxol-5-yl)-5-(1-(1-methylpiperidin-4-yl)-1H-pyrazol-4-yl)-1H-pyrrolo[2,3-b]pyridine | 437.44 |
| 221 | 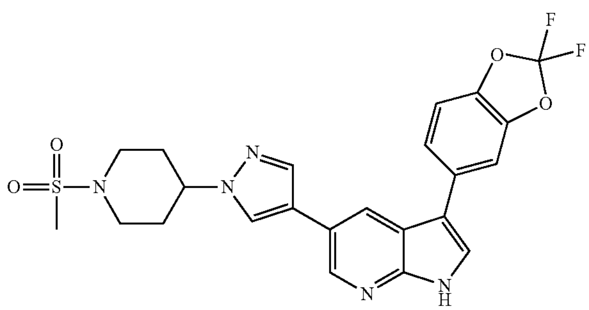 [SMILES: CS(=O)(=O)N1CCC(n2cc(-c3cnc4[nH]cc(-c5ccc6c(c5)OC(F)(F)O6)c4c3)cn2)CC1] | 3-(2,2-difluorobenzo[d][1,3]dioxol-5-yl)-5-(1-(1-(methylsulfonyl)piperidin-4-yl)-1H-pyrazol-4-yl)-1H-pyrrolo[2,3-b]pyridine | 501.50 |
| 222 | 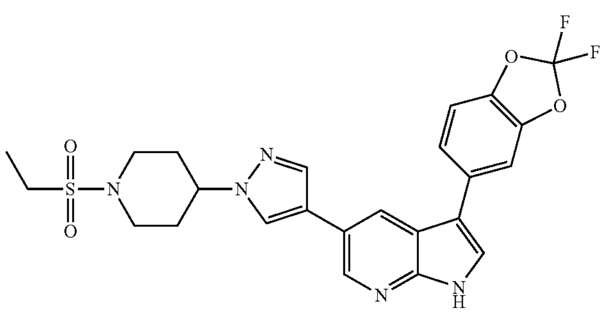 [SMILES: CCS(=O)(=O)N1CCC(n2cc(-c3cnc4[nH]cc(-c5ccc6c(c5)OC(F)(F)O6)c4c3)cn2)CC1] | 3-(2,2-difluorobenzo[d][1,3]dioxol-5-yl)-5-(1-(1-(ethylsulfonyl)piperidin-4-yl)-1H-pyrazol-4-yl)-1H-pyrrolo[2,3-b]pyridine | 515.53 |
| 223 | 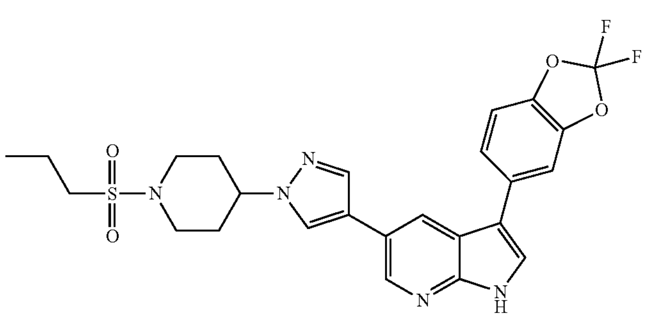 [SMILES: CCCS(=O)(=O)N1CCC(n2cc(-c3cnc4[nH]cc(-c5ccc6c(c5)OC(F)(F)O6)c4c3)cn2)CC1] | 3-(2,2-difluorobenzo[d][1,3]dioxol-5-yl)-5-(1-(1-(propylsulfonyl)piperidin-4-yl)-1H-pyrazol-4-yl)-1H-pyrrolo[2,3-b]pyridine | 529.55 |

TABLE 2A-continued

List of further Examples:

| EX. | Structure | Chemical Name | Mol. Wt |
|---|---|---|---|
| 224 | 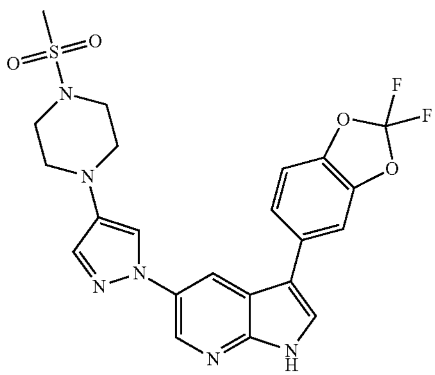 [SMILES: CS(=O)(=O)N1CCN(c2cnn(-c3cnc4[nH]cc(-c5ccc6c(c5)OC(F)(F)O6)c4c3)c2)CC1] | 3-(2,2-difluorobenzo[d][1,3]dioxol-5-yl)-5-(4-(4-(methylsulfonyl)piperazin-1-yl)-1H-pyrazol-1-yl)-1H-pyrrolo[2,3-b]pyridine | 502.49 |
| 225 | 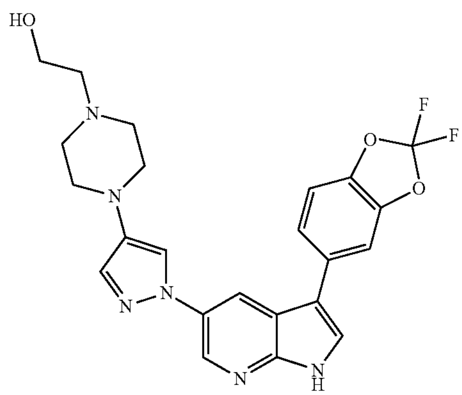 [SMILES: OCCN1CCN(c2cnn(-c3cnc4[nH]cc(-c5ccc6c(c5)OC(F)(F)O6)c4c3)c2)CC1] | 2-(4-(1-(3-(2,2-difluorobenzo[d][1,3]dioxol-5-yl)-1H-pyrrolo[2,3-b]pyridin-5-yl)-1H-pyrazol-4-yl)piperazin-1-yl)ethanol | 468.45 |
| 226 | 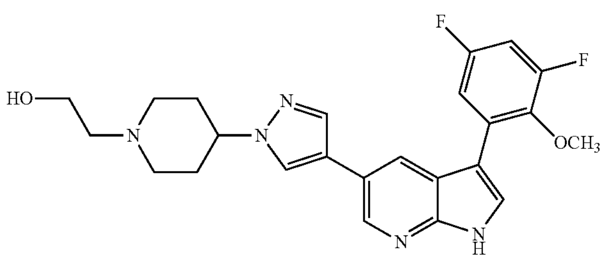 [SMILES: COc1c(F)cc(F)cc1-c1c[nH]c2ncc(-c3cnn(C4CCN(CCO)CC4)c3)cc12] | 2-(4-(4-(3-(3,5-difluoro-2-methoxyphenyl)-1H-pyrrolo[2,3-b]pyridin-5-yl)-1H-pyrazol-1-yl)piperidin-1-yl)ethanol | 453.48 |
| 227 | 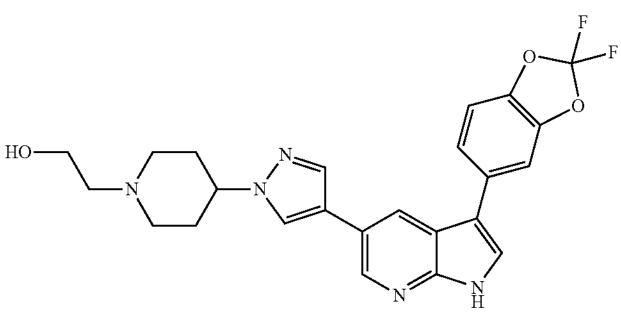 [SMILES: OCCN1CCC(n2cc(-c3cnc4[nH]cc(-c5ccc6c(c5)OC(F)(F)O6)c4c3)cn2)CC1] | 2-(4-(4-(3-(2,2-difluorobenzo[d][1,3]dioxol-5-yl)-1H-pyrrolo[2,3-b]pyridin-5-yl)-1H-pyrazol-1-yl)piperidin-1-yl)ethanol | 467.46 |
| 228 | 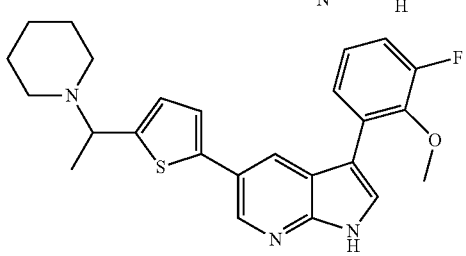 | 3-(3-fluoro-2-methoxyphenyl)-5-(5-(1-(piperidin-1-yl)ethyl)thiophen-2-yl)-1H-pyrrolo[2,3-b]pyridine | 435.55 |

TABLE 2B

List of further Examples:

| EX. | Structure | Chemical Name | Mol. Wt |
|---|---|---|---|
| 229 | 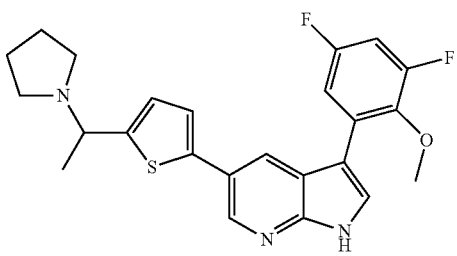 [SMILES: COc1c(F)cc(F)cc1-c1c[nH]c2ncc(-c3ccc(C(C)N4CCCC4)s3)cc12] | 3-(3,5-difluoro-2-methoxyphenyl)-5-(5-(1-(pyrrolidin-1-yl)ethyl)thiophen-2-yl)-1H-pyrrolo[2,3-b]pyridine | 439.52 |
| 230 | 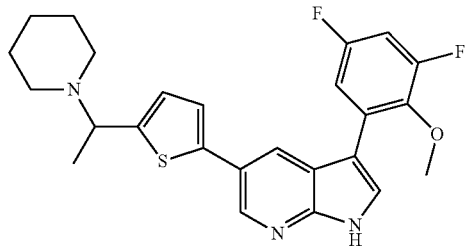 [SMILES: COc1c(F)cc(F)cc1-c1c[nH]c2ncc(-c3ccc(C(C)N4CCCCC4)s3)cc12] | 3-(3,5-difluoro-2-methoxyphenyl)-5-(5-(1-(piperidin-1-yl)ethyl)thiophen-2-yl)-1H-pyrrolo[2,3-b]pyridine | 453.55 |
| 231 | 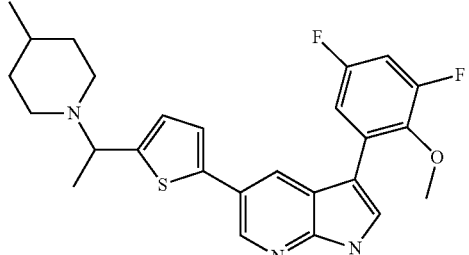 | 3-(3,5-difluoro-2-methoxyphenyl)-5-(5-(1-(4-methylpiperidin-1-yl)ethyl)thiophen-2-yl)-1H-pyrrolo[2,3-b]pyridine | 467.57 |
| 232 | 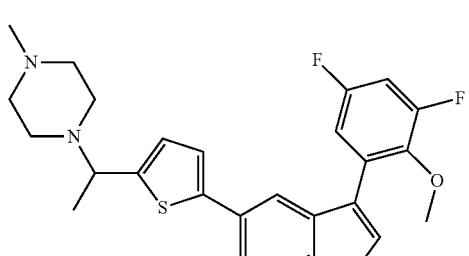 | 3-(3,5-difluoro-2-methoxyphenyl)-5-(5-(1-(4-methylpiperazin-1-yl)ethyl)thiophen-2-yl)-1H-pyrrolo[2,3-b]pyridine | 468.56 |
| 233 | 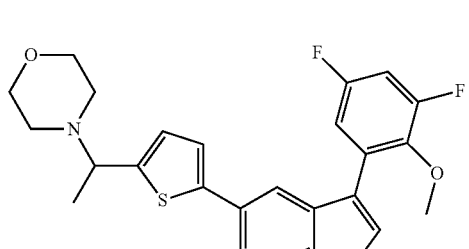 | 4-(1-(5-(3-(3,5-difluoro-2-methoxyphenyl)-1H-pyrrolo[2,3-b]pyridin-5-yl)thiophen-2-yl)ethyl)morpholine pyrrolo[2,3-b]pyridine | 455.52 |

TABLE 2B-continued

List of further Examples:

| EX. | Structure | Chemical Name | Mol. Wt |
|---|---|---|---|
| 234 | 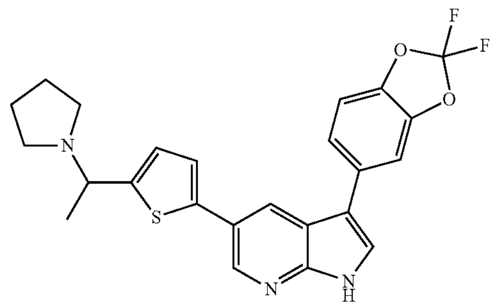 [SMILES: CC(c1ccc(-c2cnc3[nH]cc(-c4ccc5c(c4)OC(F)(F)O5)c3c2)s1)N1CCCC1] | 3-(2,2-difluorobenzo[d][1,3]dioxol-5-yl)-5-(5-(1-(pyrrolidin-1-yl)ethyl)thiophen-2-yl)-1H-pyrrolo[2,3-b]pyridine | 453.50 |
| 235 | 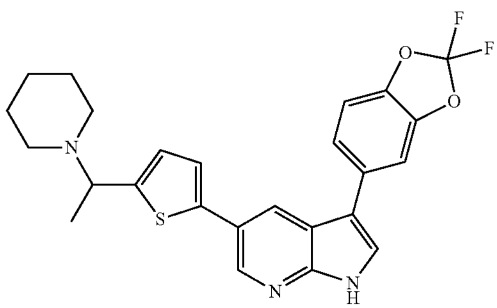 [SMILES: CC(c1ccc(-c2cnc3[nH]cc(-c4ccc5c(c4)OC(F)(F)O5)c3c2)s1)N1CCCCC1] | 3-(2,2-difluorobenzo[d][1,3]dioxol-5-yl)-5-(5-(1-(piperidin-1-yl)ethyl)thiophen-2-yl)-1H-pyrrolo[2,3-b]pyridine | 467.53 |
| 236 | 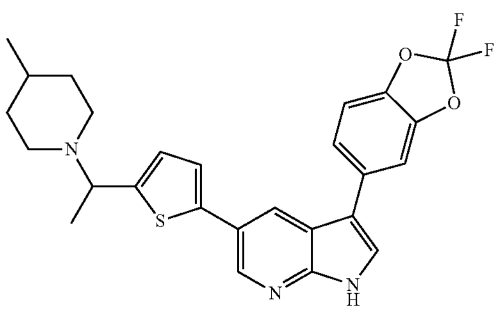 [SMILES: CC1CCN(C(C)c2ccc(-c3cnc4[nH]cc(-c5ccc6c(c5)OC(F)(F)O6)c4c3)s2)CC1] | 3-(2,2-difluorobenzo[d][1,3]dioxol-5-yl)-5-(5-(1-(4-methylpiperidin-1-yl)ethyl)thiophen-2-yl)-1H-pyrrolo[2,3-b]pyridine | 481.56 |
| 237 | 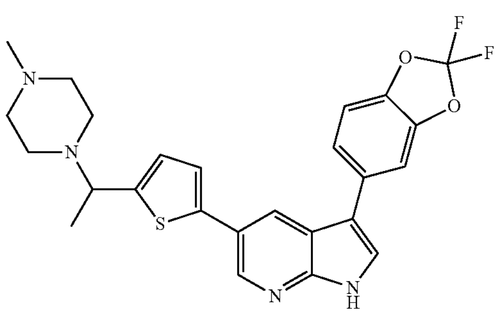 [SMILES: CC(c1ccc(-c2cnc3[nH]cc(-c4ccc5c(c4)OC(F)(F)O5)c3c2)s1)N1CCN(C)CC1] | 3-(2,2-difluorobenzo[d][1,3]dioxol-5-yl)-5-(5-(1-(4-methylpiperazin-1-yl)ethyl)thiophen-2-yl)-1H-pyrrolo[2,3-b]pyridine | 482.55 |
| 238 | 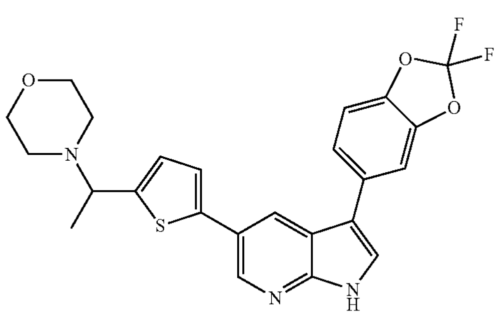 [SMILES: CC(c1ccc(-c2cnc3[nH]cc(-c4ccc5c(c4)OC(F)(F)O5)c3c2)s1)N1CCOCC1] | 4-(1-(5-(3-(2,2-difluorobenzo[d][1,3]dioxol-5-yl)-1H-pyrrolo[2,3-b]pyridin-5-yl)thiophen-2-yl)ethyl)morpholine | 469.50 |

TABLE 2B-continued

List of further Examples:

| EX. | Structure | Chemical Name | Mol. Wt |
|---|---|---|---|
| 239 | 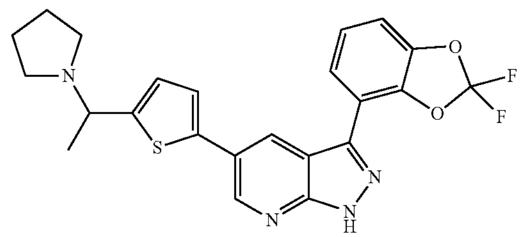 [SMILES: CC(c1ccc(-c2cnc3[nH]nc(-c4cccc5c4OC(F)(F)O5)c3c2)s1)N1CCCC1] | 3-(2,2-difluorobenzo[d][1,3]dioxol-4-yl)-5-(5-(1-(pyrrolidin-1-yl)ethyl)thiophen-2-yl)-1H-pyrrolo[2,3-b]pyridine | 453.13 |
| 240 | 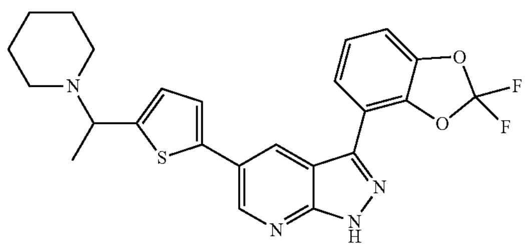 | 3-(2,2-difluorobenzo[d][1,3]dioxol-4-yl)-5-(5-(1-(piperidin-1-yl)ethyl)thiophen-2-yl)-1H-pyrrolo[2,3-b]pyridine | 467.53 |
| 241 | 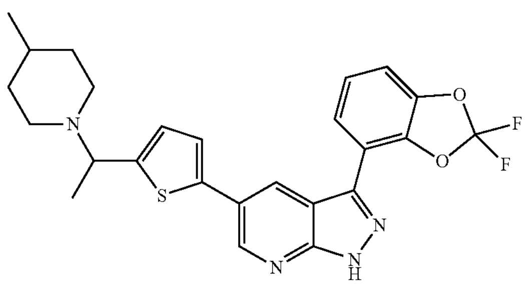 [SMILES: CC1CCN(C(C)c2ccc(-c3cnc4[nH]nc(-c5cccc6c5OC(F)(F)O6)c4c3)s2)CC1] | 3-(2,2-difluorobenzo[d][1,3]dioxol-4-yl)-5-(5-(1-(4-methylpiperidin-1-yl)ethyl)thiophen-2-yl)-1H-pyrrolo[2,3-b]pyridine | 481.56 |
| 242 | 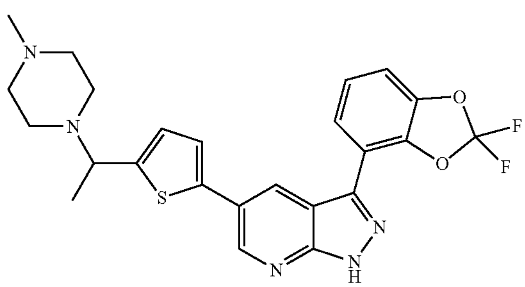 [SMILES: CC(c1ccc(-c2cnc3[nH]nc(-c4cccc5c4OC(F)(F)O5)c3c2)s1)N1CCN(C)CC1] | 3-(2,2-difluorobenzo[d][1,3]dioxol-4-yl)-5-(5-(1-(4-methylpiperazin-1-yl)ethyl)thiophen-2-yl)-1H-pyrrolo[2,3-b]pyridine | 482.55 |
| 243 | 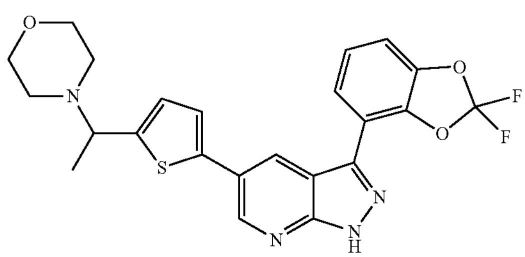 [SMILES: CC(c1ccc(-c2cnc3[nH]nc(-c4cccc5c4OC(F)(F)O5)c3c2)s1)N1CCOCC1] | 4-(1-(5-(3-(2,2-difluorobenzo[d][1,3]dioxol-4-yl)-1H-pyrrolo[2,3-b]pyridin-5-yl)thiophen-2-yl)ethyl)morpholine | 469.50 |

TABLE 3

List of Compounds purchased from vendor library

| Cmpd No | Structure | Chemical Name | Mol.Wt | SIK2 IC$_{50}$ μM |
|---|---|---|---|---|
| 1 | 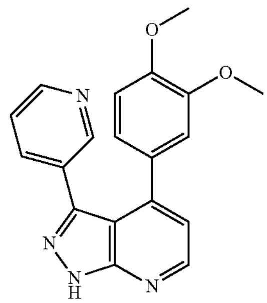 [SMILES: COc1ccc(-c2ccnc3[nH]nc(-c4cccnc4)c23)cc1OC] | 4-(3,4-dimethoxyphenyl)-3-(pyridin-3-yl)-1H-pyrazolo[3,4-b]pyridine | 332.356 | ** |
| 2 | 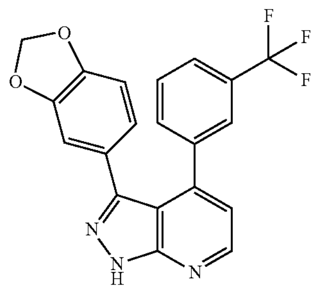 [SMILES: FC(F)(F)c1cccc(-c2ccnc3[nH]nc(-c4ccc5c(c4)OCO5)c23)c1] | 3-(benzo[d][1,3]dioxol-5-yl)-4-(3-(trifluoromethyl)phenyl)-1H-pyrazolo[3,4-b]pyridine | 383.323 | * |
| 3 | 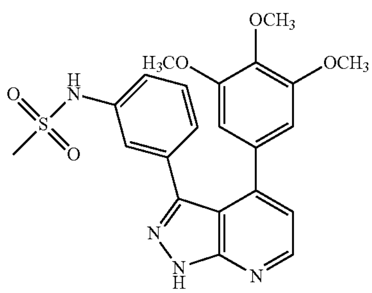 [SMILES: COc1cc(-c2ccnc3[nH]nc(-c4cccc(NS(C)(=O)=O)c4)c23)cc(OC)c1OC] | N-(3-(4-(3,4,5-trimethoxyphenyl)-1H-pyrazolo[3,4-b]pyridin-3-yl)phenyl)methanesulfonamide | 454.499 | * |
| 4 | 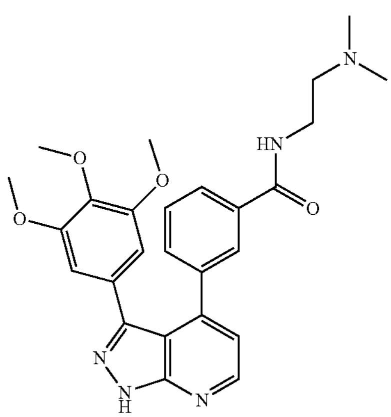 | N-(2-(dimethylamino)ethyl)-3-(3-(3,4,5-trimethoxyphenyl)-1H-pyrazolo[3,4-b]pyridin-4-yl)benzamide | 475.54 | * |
| 5 | 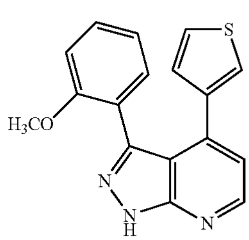 [SMILES: COc1ccccc1-c1n[nH]c2nccc(-c3ccsc3)c12] | 3-(2-methoxyphenyl)-4-(thiophen-3-yl)-1H-pyrazolo[3,4-b]pyridine | 307.370 | *** |

TABLE 3-continued

List of Compounds purchased from vendor library

| Cmpd No | Structure | Chemical Name | Mol.Wt | SIK2 IC$_{50}$ μM |
|---|---|---|---|---|
| 6 | 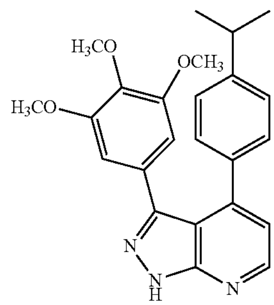 [SMILES: COc1cc(-c2n[nH]c3nccc(-c4ccc(C(C)C)cc4)c23)cc(OC)c1OC] | 4-(4-isopropylphenyl)-3-(3,4,5-trimethoxyphenyl)-1H-pyrazolo[3,4-b]pyridine | 403.474 | ** |
| 7 | 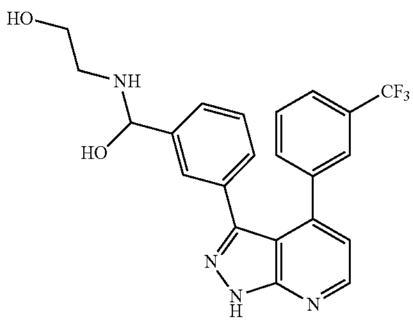 [SMILES: OCCNC(O)c1cccc(-c2n[nH]c3nccc(-c4cccc(C(F)(F)F)c4)c23)c1] | 2-((hydroxy(3-(4-(3-(trifluoromethyl)phenyl)-1H-pyrazolo[3,4-b]pyridin-3-yl)phenyl)methyl)amino)ethanol | 426.391 | * |
| 8 | 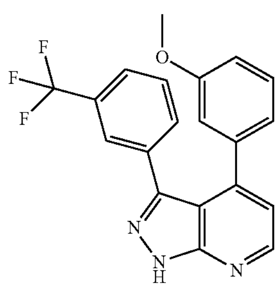 [SMILES: COc1cccc(-c2ccnc3[nH]nc(-c4cccc(C(F)(F)F)c4)c23)c1] | 4-(3-methoxyphenyl)-3-(3-(trifluoromethyl)phenyl)-1H-pyrazolo[3,4-b]pyridine | 369.34 | * |
| 9 | 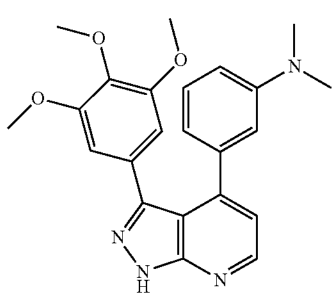 | N-N-dimethyl-3-(3-(3,4,5-trimethoxyphenyl)-1H-pyrazolo[3,4-b]pyridin-4-yl)aniline | 404.462 | * |
| 10 | 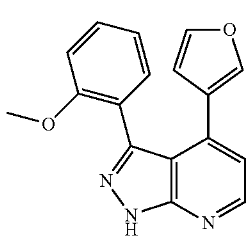 [SMILES: COc1ccccc1-c1n[nH]c2nccc(-c3ccoc3)c12] | 4-(furan-3-yl)-3-(2-methoxyphenyl)-1H-pyrazolo[3,4-b]pyridine | 292.304 | *** |

TABLE 3-continued

List of Compounds purchased from vendor library

| Cmpd No | Structure | Chemical Name | Mol.Wt | SIK2 IC$_{50}$ μM |
|---|---|---|---|---|
| 11 | 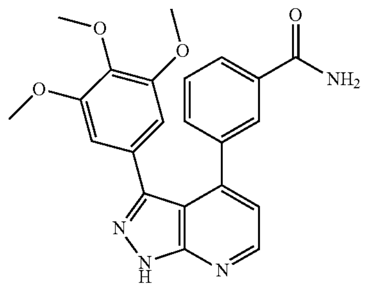 [SMILES: COc1cc(-c2n[nH]c3nccc(-c4cccc(C(N)=O)c4)c23)cc(OC)c1OC] | 3-(3-(3,4,5-trimethoxyphenyl)-1H-pyrazolo[3,4-b]pyridin-4-yl)benzamide | 404.419 | * |
| 12 | 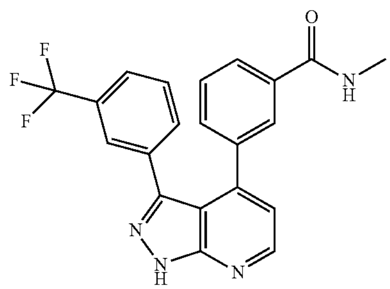 [SMILES: CNC(=O)c1cccc(-c2ccnc3[nH]nc(-c4cccc(C(F)(F)F)c4)c23)c1] | N-methyl-3-(3-(3-(trifluoromethyl)phenyl)-1H-pyrazolo[3,4-b]pyridin-4-yl)benzamide | 396.365 | * |

* Kinase Inhibition Result for Selected Compounds
*** <0.1 μM,
** >0.1 μM,
* >1 μM
ND = Not Determined

List of abbreviation and meaning used through out this application

| Abbreviation | Meaning |
|---|---|
| CHCl3 | Chloroform - CHCl$_3$ |
| CDCl3 | Chloroform deuterated solvent - CDCl$_3$ |
| DCM | Dichloromethane - CH$_2$Cl$_2$ |
| DME | 1,2-Dimethoxyethane |
| DMF | N,N-Dimethylformamide |
| DMSO | Dimethylsulfoxide |
| DMSO-d$_6$ | Dimethylsulfoxide deuterated solvent |
| Pd2(pda)3 | Tris(dibenzylideneacetone)dipalladium(0) |
| Pd(PH3)4 | Tetrakis(trifluorophosphine)palladium(0) |
| PTSA | p-Toluene Sulfonic Acid |
| THF | Tetrahydrofuran |
| ±BINAP | rac 2,2'-Bis(diphenylphosphino)-9,9-dimethylxanthene |
| Xantphos | 4,5-Bis(diphenylphosphino)-9,9-dimethylxanthene |
| Pd(dppf)Cl$_2$·CH$_2$Cl$_2$ | [1,1'-bis(diphenylphosphino)ferrocene]dichloropalladium II DCM |
| Et | Ethyl |
| Me | Methyl |
| MeOH | Methanol |
| EtOH | Ethanol |
| EtOAc | Ethylacetate |
| AcCN/MeCN | Acetonitrile |
| DIPEA | Diisopropylethylamine |
| IP | Isopropanol |
| Na$_2$CO$_3$ | Sodium Carbonate |
| K$_2$CO$_3$ | Potassium Carbonate |
| Cs$_2$CO$_3$ | Cesium Carbonate |
| TFA | Trifluoroacetic acid |
| EDC HCl | N-Ethyl-N'-(3-dimethylaminopropyl)carbodiimide HCl |
| HOBT | 1-Hydroxybenzotriazole hydrate |
| HOAc | Acetic Acid |
| Et | Ethyl |
| TMS | Trimethylsilyl |
| NBS | N-Bromosuccinamide |
| NCS | N-Chlorosuccinamide |
| PG | Protecting Group |
| g, gm | Gram(s) |
| mg | Milligram(s) |
| h, hr | Hour |
| min | Minute(s) |
| M | Molar, molarity |
| mM | Millimolar |
| μM | Micromolar |
| nM | Nanomolar |
| L, l | Liter(s) |
| mL, ml | Milliliter(s) |
| μL | Microliter(s) |
| RM | Reaction Mixture or Reaction Mass |
| SM | Starting Material |
| RT, rt | Room Temperature |
| HPLC | High-Performance Liquid Chromatography |
| LCMS | Liquid Chromatography Mass Spectrometry |
| MS or ms | Mass Spectrometry |
| NMR | Nuclear Magnetic Resonance Spectroscopy |
| TLC | Thin Layer Chromatography |
| UV | Ultra-Violet Spectrometry |
| s | Singlet |
| d, Dt, dt | Doublet, doublet of doublet |
| t, tr | Triplet |
| m | Multiplet |

Methods of Preparation of Compounds

In certain embodiments, the Examples depicted below are compounds prepared according to general procedures given in the following sections. Although the synthetic methods and Schemes depict the syntheses of certain compounds of the present invention, the methods and other methods known to one of ordinary skill in the art can be applied to all the compounds of the genus, the genus sub-class and species of each of these compounds as described herein. All aspects of this invention can be understood from the following Schemes. The following are exemplary and are not intended to limit the scope of the invention.

EXAMPLES

Experimental Details and Examples

Melting points were determined in a MP-96 digital Polmon apparatus. $^1$H NMR and $^{13}$C NMR spectra were recorded at rt in CDCl3 or DMSO-d6 at Jeol 400-MHz NMR spectrophotometer using solvent peaks for CDCl3: 7.27 and DMSO-d6 2.50 (D) as internal references. The assignment of chemical shifts is based on standard NMR experiments (1H, 13C). Mass spectra were recorded on a Shimadzu LCMS LC-210EV spectrometer with an API-ES ionization source. Jasco-FTIR-4100 was used to record the IR spectra. TLC analyses were performed on silica F254 and detection by UV light at 254 nm, or by spraying with phosphomolybdic-H$_2$SO$_4$ dyeing reagent, KMNO$_4$ or iodine. Column chromatography were performed on silica Gel 60 (230 mesh). Purifications and separations were performed on a standard silica flash chromatography system. The purity of the samples has been determined by HPLC for the % area peak corresponding to the retention of compound and elemental analysis for C, H, N and O was carried out using Perkin-Elmer 2400 elemental analyser and chloride analysis performed using calorimetric titration at the Intertek USA Inc., QTI.

General Synthesis Schemes 1-3

Scheme 1

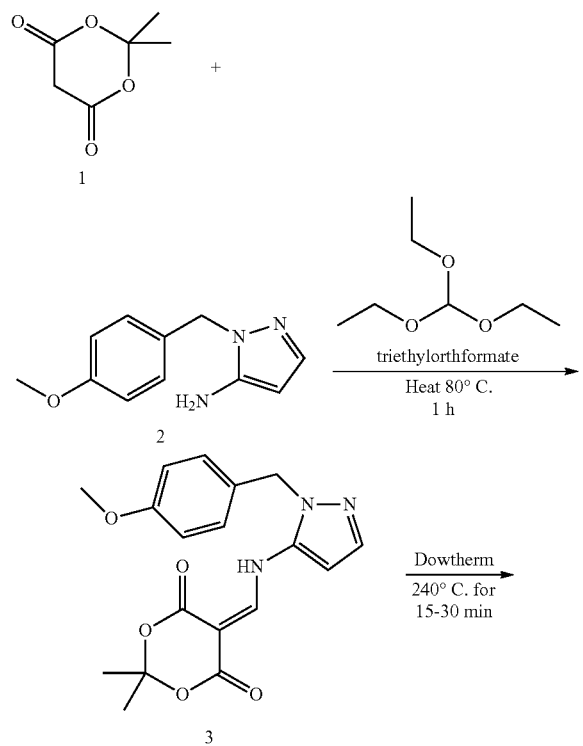

Scheme 2

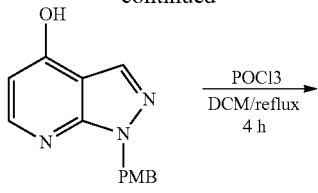

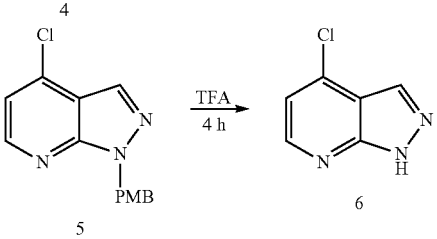

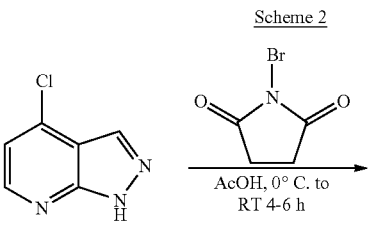

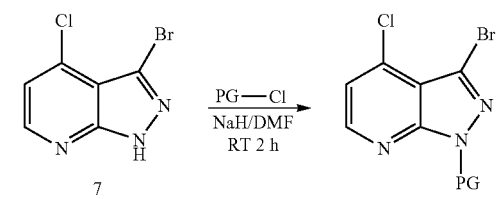

Scheme 3

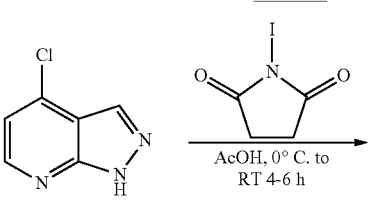

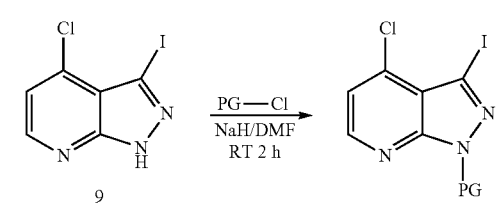

"PG" represents a protecting group, or protecting groups (PGs), and refers to a group used to protect a certain functional moiety to prevent it from participation in chemical reactions until the PG is removed. Well known to the skilled artisan, these protective groups can be removed by acid, base, and hydrogenolysis conditions in the presence or absence of organic solvents. Such PGs employed in the above synthesis schemes 1-3 include, but are not limited to, p-methoxybenzyl (PMB), 2,4-dimethoxybenzyl, benzyl (Bn), 4-toluenesulfonyl chloride (tosyl chloride or TsCl), 2-(trimethylsilyl) ethoxymethyl chloride (SEM-Cl), trityl chloride (triphenylmethyl chloride), dimethoxytrityl, tetrahydropyranyl (THP), di-tert-butyl dicarbonate (tert-Boc), fluorenylmethyloxycarbonyl chloride (FMOC-Cl), tert-butyldimethylsilyl chloride (TBDMS-Cl), and carboxybenzyl (Cbz) groups.

Intermediate 6: Preparation of 4-chloro-1H-pyrazolo[3,4-b]pyridine (6)

6

2,2-dimethyl-1,3-dioxane-4,6-dione 1 (meldrum's acid) (20 g, 139 mmol), 1-(4-methoxybenzyl)-1H-pyrazol-5-amine (2) (28.2 g, 139 mmol, 1 eq) (prepared according to the procedure described by Misra, R. N., et al. Bioorg. Med. Chem. Lett. (2003), 13, 1133-1136) in presence of triethoxymethane (30.8 g, 208 mmol, 1 eq) was heated to 85° C. for 1 hr, subsequently worked up and treated with diethyl ether, and provided the pure 5-(((1-(4-methoxybenzyl)-1H-pyrazol-5-yl)amino)methylene)-2,2-dimethyl-1,3-dioxane-4,6-dione (3) as yellow solid (39.3 g). To a stirred solution of DOWTHERM™ (80 mL) was added compound 3 (39.3 g at 200° C. under N₂ in portions over a 30 min). After completion of additions, the RM was heated at 240° C. for 1 hr. After completion of the reaction from TLC, the mixture was diluted with hexanes (300 mL) to separate the DOWTHERM™ from the crude RM. The resulting crude mixture on treatment with DCM and diethyl ether provided the off-white solid of 1-(4-methoxybenzyl)-1H-pyrazolo[3,4-b]pyridin-4-ol (4) (24.56 g). Chlorination of compound 4 (24 g, 94 mmol) on treatment with phosphoryl trichloride (43 g, 282 mmol) in dichloroethane (10 mL) at 40° C. for 4 hr yielded 19 g of 4-chloro-1-(4-methoxybenzyl)-1H-pyrazolo[3,4-b]pyridine 5.

4-Chloro-1-(4-methoxybenzyl)-1H-pyrazolo[3,4-b]pyridine (5) 19 g (69.4 mmol) in neat TFA (30 mL, 389 mmol) was stirred at 80° C. for 4 hr. The resulting RM was concentrated and MeOH was added and the obtained precipitate was filtered and washed with MeOH. The crude solid was treated with EtOAc, saturated NaHCO₃ and dried over Na₂SO₄, to yield the desired product as a half white solid. $^1$H NMR (400 MHz, CDCl₃): δ 13.23 (br s, 1H), 8.52 (d, J=5.1 Hz, 1H), 8.10 (s, 1H), 7.32 (m, 1H).

Intermediate 7: Preparation of 3-bromo-4-chloro-1H-pyrazolo[3,4-b]pyridine (7)

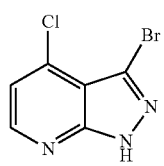

7

4-chloro-1H-pyrazolo[3,4-b]pyridine (6) 1 g (6.53 mmoles) in acetic acid (10 mL) cooled to 0° C. was added N-bromosuccinimide 2.31 g (13.06 mmol) and the resulting RM was stirred for 4 hr at rt. After completion of the SM, the RM was quenched with ice water and extracted with dichlromethane (2×10 mL). The combined organic layer was dried over sodium sulphate, and the solvent evaporated to yield compound 7 (Yield: 0.9 g, 60%). $^1$H NMR (400 MHz, CDCl₃): δ 13.19 (br s, 1H), 8.21 (s, 1H), 7.39 (m, 1H)

Intermediate 8: Preparation of 3-bromo-4-chloro-1-tosyl-1H-pyrazolo[3,4-b]pyridine (8)

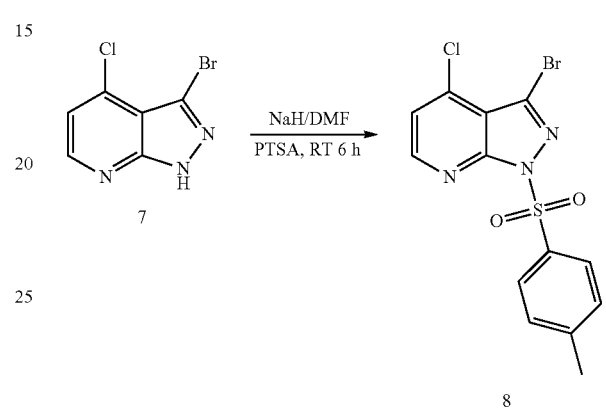

To 3-bromo-4-chloro-1H-pyrazolo[3,4-b]pyridine (7) 1 g (4.345 mmol, 1 eq) in DMF (5 mL) cooled to 0° C. was add sodium hydride 0.156 g (6.51 mmols, 1.5 eq) slowly under nitrogen atmosphere for 15 min followed by the addition of p-toluene sulfonyl chloride 0.91 g (4.77 mmol, 1.1 eq). The resulting RM was stirred for 2 hr and after completion of the SMs from TLC; the RM was quenched with ice cold water and extracted with chloroform. The combined organic layer was washed with brine solution and the organic layer was dried over sodium sulphate. The solvents were removed to get the crude product, which was passed through 100-200 mesh silica gel eluting the pure compound 8 at 6-7% ethyl acetate in hexane (Yield: 1.2 g, 72%).

Intermediate 10: Preparation of 4-chloro-3-iodo-1-tosyl-1H-pyrazolo[3,4-b]pyridine (10)

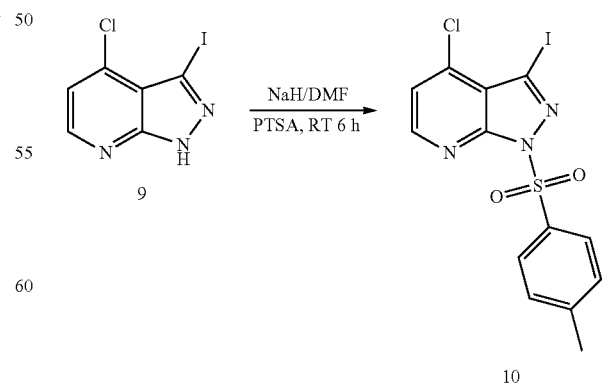

A solution of compound 9 (230 mg, 0.8273 mmol) in DMF (7 mL) was cooled to 0° C. and sodium hydride (49 mg, 1.2409 mmol) was added slowly under nitrogen atmosphere and was stirred for 20 min. The PTSA (p-toluene sulfonic acid) was added slowly to the RM and stirred for 2 hrs at RT. After completion of the reaction, the reaction was quenched with ice water and extracted with ethyl acetate twice. The organic layer was completely distilled off to get the crude material which was passed over 100-200 mesh silica gel eluting the pure compound at 5-6% ethyl acetate in hexane as eluent to get the title compound as half white colored solid 10.

General Scheme 4 Synthesis Examples:

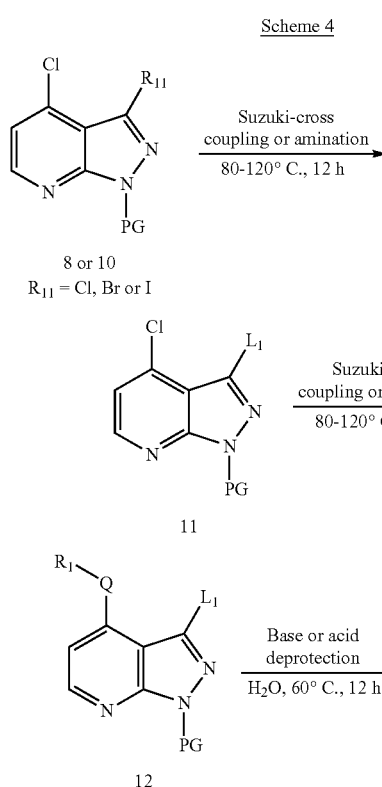

General Scheme 5 for the Synthesis of Examples:

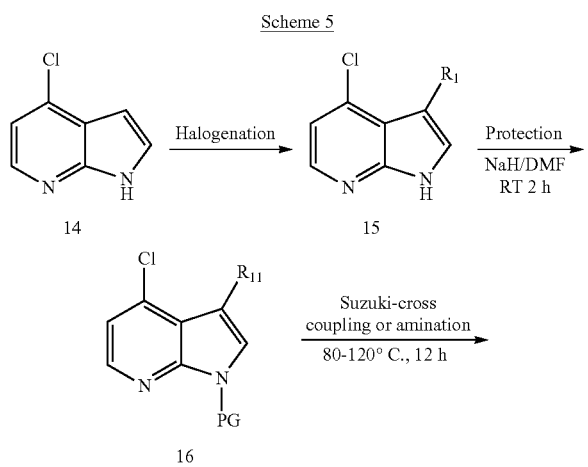

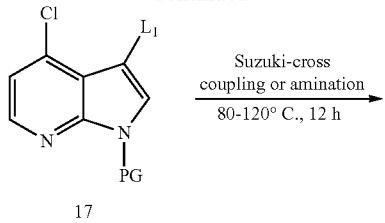

General Procedures for the Preparation Examples

The key intermediates 3-bromo-4-chloro-1H-pyrazolo[3,4-b]pyridine (7) or 4-chloro-3-iodo-1H-pyrazolo[3,4-b]pyridineprotected (9) were prepared from N-chloro- or N-bromo-succinamide, 2 eq in presence of acetic acid as solvent at rt for 4 to 6 hr, which afforded ~50-60 yields. Both the compounds 7 and 9 protected with p-toluenesulfonyl chloride (p-TsCl) (1 eq) on treatment with sodium hydride in DMF at rt for 2 hr and after completion of the SMs from TLC; the RM was quenched with ice cold water and extracted with chloroform. The combined organic layer was washed with brine solution and the organic layer was dried over sodium sulphate and the solvents were removed to get the crude product, which was passed through 100-200 mesh silica gel eluting the pure compounds 8 and 10 at 10% ethyl acetate in hexane and gave greater than 70% yields.

In subsequent step of the Suzuki-Cross coupling reactions, variously substituted aryl boronic acids and/or aryl boronic esters were reacted with either compound 8 or 10 with 1 eq. each in presence of one of the solvents: 1,4-dioxane, THF, DMF, DMSO, toluene, or acetonitrile. The resulting RM was degassed, purged with argon or $N_2$ gas a few times and was charged with $NaCO_3$, $Cs_2CO_3$, $K_2CO_3$, tBuOK, Na-tBuOK, potassium acetate or $NaHCO_3$ (1.5 to 2 eq) followed by the addition of palladium catalysts (0.01 to 0.05 eq). After the addition of catalysts the contents of the reaction were purged and degassed again and heated at 80 to 100° C. for 8 to 16 or 24 hr. After completion of the reaction monitored from TLC, the contents were cooled to rt and diluted with $CH_2Cl_2$, $CHCl_3$ or EtOAc. The organic layers were passed through a Celite pad then the solvent was completely distilled off to get the crude product, which was subjected to flash to column chromatography purification to get the variously substituted title compounds 11 and 12.

Preparation of Example 1: 3-(2-methoxyphenyl)-4-(thiophen-3-yl)-1H-pyrazolo[3,4-b]pyridine (24)

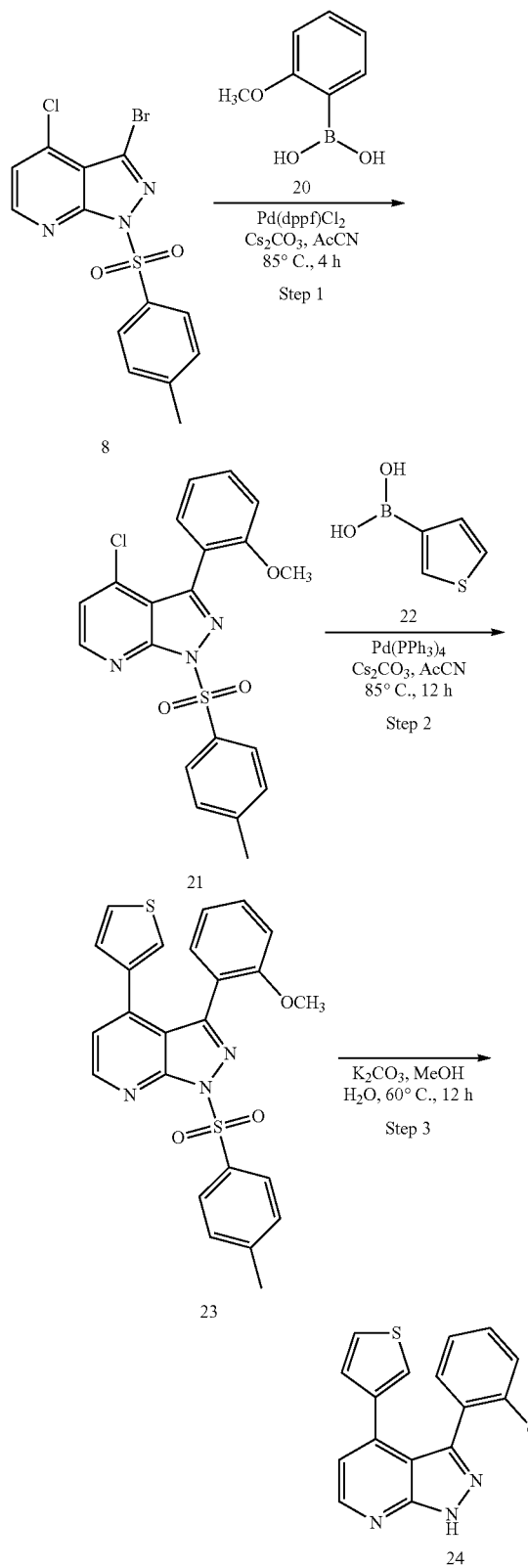

Step 1:
A stirred solution of (8) (0.150 g 0.387 mmol) and (2-methoxyphenyl) boronic acid (20) (58 mg 0.387 mmol) in acetonitrile (10 mL) was degassed and purged with nitrogen for 10 min. Then cesium carbonate (250 mg, 0.774 mmol) and Pd(dppf)Cl$_2$ (15 mg, 0.019 mmol) was added, then again degassed and purged with nitrogen for 15 min and the RM heated to 85° C. for 4 hr in a sealed tube. After completion of the reaction, the RM was cooled to rt and diluted with chloroform and filtered through celite bed. The organic layer was completely distilled off to get the crude product, which was passed through 100-200 mesh silica gel eluting the pure compound at 7-8% ethyl acetate in hexane as an off white colored compound 21.

Step 2:
To a stirred solution of 4-chloro-3-(2-methoxyphenyl)-1-tosyl-1H-pyrazolo[3,4-b]pyridine (21) (100 mg, 0.242 mmol) and thiophen-3-ylboronic acid (22) (30 mg, 0.242 mmol) in acetonitrile (7 mL), degassed and purged with nitrogen for 10 min, was added cesium carbonate (158 mg, 0.484 mmol) and Pd(PPh$_3$)$_4$ (13.9 mg, 0.0121 mmol) and again degassed and purged with nitrogen for 15 min. Then the RM was heated to 85° C. overnight in a sealed tube. After completion of the SM the RM was cooled to rt and diluted with chloroform. The organic layer was passed through a celite bed. The organic layer was completely distilled off the solvent to get the crude product, which was passed through 100-200 mesh silica gel eluting the pure compound at 10-11% ethyl acetate in hexane as off white solid 3-(2-methoxyphenyl)-4-(thiophen-3-yl)-1-tosyl-1H-pyrazolo[3,4-b]pyridine (23).

Step 3:
To a stirred solution of (23) (50 mg, 0.108 mmol) in methanol (5 mL) and water (5 mL) was added potassium carbonate (29 mg, 0.216 mmol). The RM was heated to 60° C. overnight. After completion of the SM, the solvents were completely distilled off and diluted with water and extracted with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid (24). $^1$H NMR (CDCl3) δ: 11.05 (1H), 8.57 (d, J=4.75 1H), 7.50 (m, J=5.85 1H), 7.48 (m, J=5.73 1H), 7.16 (m, J=4.87 1H), 7.12 (m, J=3.17 1H), 6.98 (m, J=4.87 3H), 6.61 (d, J=8.17 1H), 3.21 (3H) and MS m/z=308.1.

Preparation of Example 4: 3-(4-fluoro-2-methoxyphenyl)-4-(thiophen-3-yl)-1H-pyrazolo[3,4-b]pyridine (28)

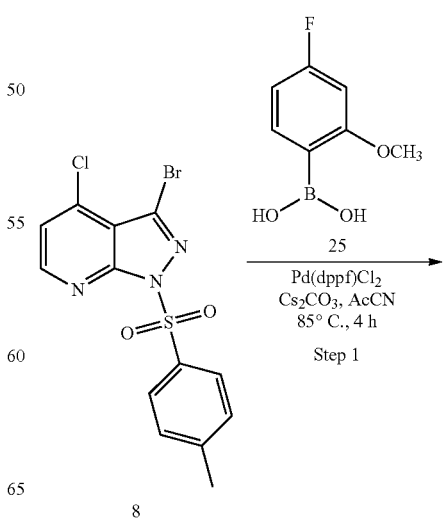

Step 1

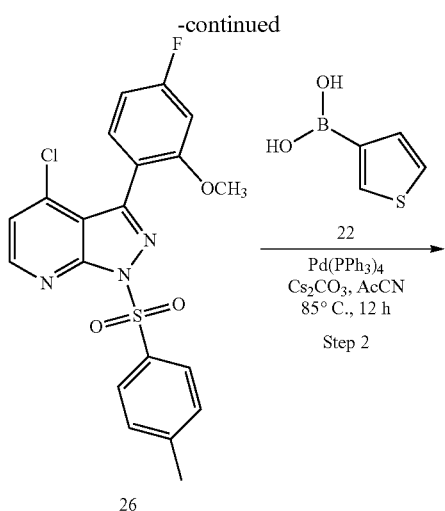

26

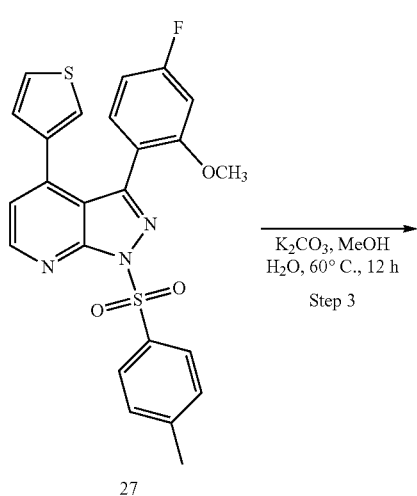

27

Step 1:

To a stirred solution of 3-bromo-4-chloro-1-tosyl-1H-pyrazolo[3,4-b]pyridine 8 (150 mg 0.387 mmol) and (4-fluoro-2-methoxyphenyl)boronic acid 25 (65 mg, 0.387 mmol) in acetonitrile (5 mL), degassed and purged with nitrogen for 10 min, cesium carbonate (252 mg 0.775 mmol) and Pd(dppf)Cl$_2$ (15 mg, 0.0193 mmol) were added. The resulting RM degassed and purged again with nitrogen for 15 min. The RM was heated to 85° C. for 4 hr in a sealed tube. After completion of the reaction, it was cooled to rt and diluted with chloroform and filtered through celite bed. The organic layer was completely distilled off to get the crude compound 26. The crude material was passed through 100-200 mesh silica gel and eluting the pure compound at 7-8% ethyl aceate in hexane obtained off white colored solid 26.

Step 2:

To a stirred solution of compound 26 (100 mg, 0.231 mmol) and compound 22 (33 mg, 0.254 mmol) in acetonitrile (5 mL), degassed and purged with nitrogen for 10 min, was added cesium carbonate (150 mg, 0.463 mmol) and Pd(PPh$_3$)$_4$ (13 mg, 0.0115 mmol) and degassed and purged again with nitrogen for 15 min. Then the RM was heated to 85° C. overnight in a sealed tube. After completion of the SM, the RM was cooled to rt and diluted with chloroform and the organic layer was passed through celite bed. The organic layer was completely distilled off to get the crude product, which was passed through 100-200 mesh silica gel eluting the pure compound 27 at 10-11% ethyl acetate in hexane as off white solid.

Step 3:

To a stirred solution of 3-(4-fluoro-2-methoxyphenyl)-4-(thiophen-3-yl)-1-tosyl-1H-pyrazolo[3,4-b]pyridine 27 (50 mg 0.102 mmol) in methanol (10 mL) and water (5 mL) was added potassium carbonate (0.204 mmol) and the RM was heated to 60° C. overnight. After completion of the SM the solvents was completely distilled off, diluted with water and extracted with chloroform twice. The organic layer was dried over sodium sulphate. The crude product was passed through 100-200 mesh silica gel eluting the pre compound at 28-30% ethyl acetate in hexane as eluent to get the pale yellow colored solid of compound 3-(4-fluoro-2-methoxyphenyl)-4-(thiophen-3-yl)-1H-pyrazolo[3,4-b]pyridine 28. $^1$H NMR (CDCl3) δ: 8.56 (d, 1H), 7.44 (m, 1H), 7.23 (m, 1H), 7.16 (m, 1H), 7.02 (m, 1H), 6.95 (m, 1H), 6.73 (m, 1H), 6.34 (m, 1H) and MS m/z=325.8.

Preparation of Example 5: 3-(2-ethoxyphenyl)-4-(thiophen-3-yl)-1H-pyrazolo[3,4-b]pyridine (32)

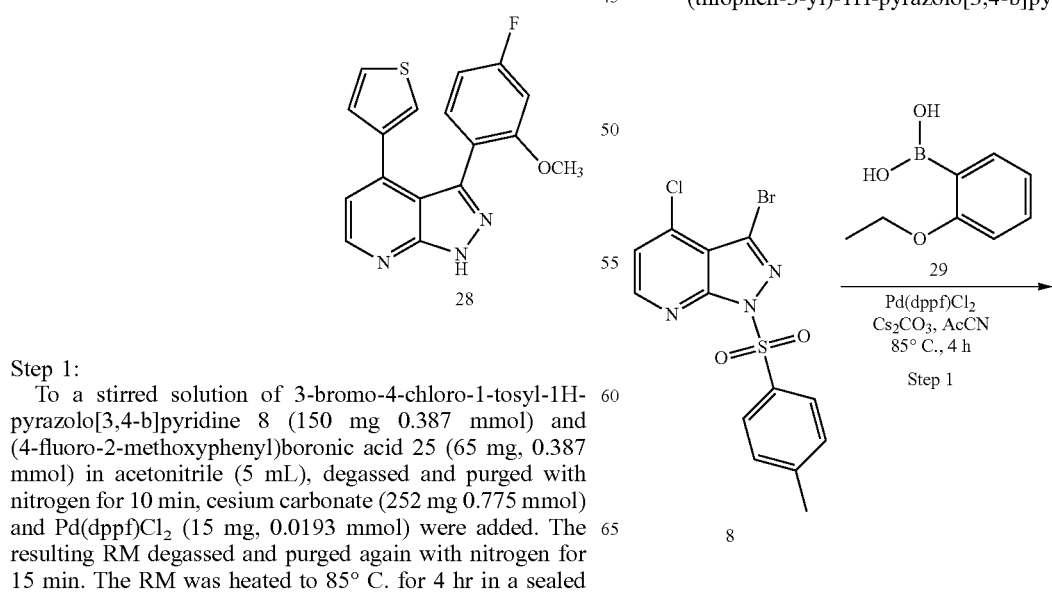

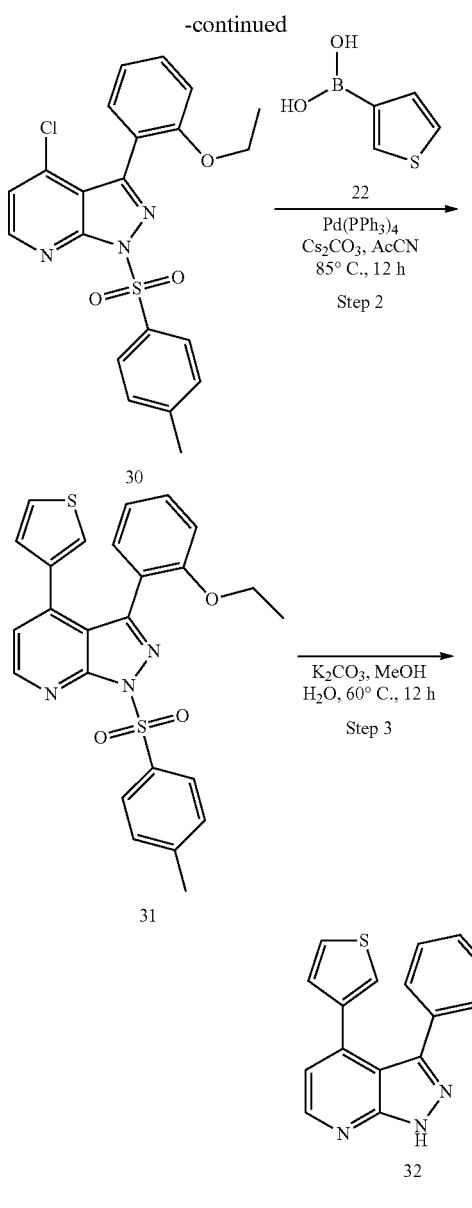

and diluted with chloroform and the organic layer was passed through celite bed. The organic layer was completely distilled off the solvent to get the crude product, which was passed through 100-200 mesh silica gel eluting the pure compound at 10-11% ethyl acetate in hexane as off white solid compound 31.

Step 3:

To a stirred solution of 31 (50 mg, 0.105 mmol) in methanol (40 mL) and water (5 mL) was added potassium carbonate (30 mg, 0.210 mmol) and the RM heated to 60° C. overnight. After completion of the SM, the solvents were completely distilled off, diluted with water and extracted with chloroform twice. The organic layer was dried over sodium sulphate. The crude was passed through 100-200 mesh silica gel eluting the pre compound at 28-30% ethyl acetate in hexane as eluent to get the pale yellow colored solid of compound 32. $^1$H NMR (CDCl3) δ: 11.28 (s, 1H), 8.57 (d, 1H), 7.52 (m, 1H), 7.32 (m, 1H), 7.17 (d, 1H), 7.00 (m, 2H) 6.95 (m, 1H), 6.57 (m, 1H); and MS m/z=321.9

Preparation of Example 6: 36

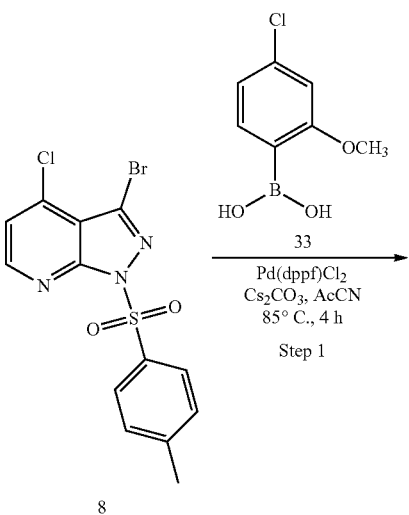

Step 1:

To a stirred solution of compound 8 (150 mg, 0.387 mmol) and 29 (65 mg, 0.387 mmol) in acetonitrile (5 mL), degassed and purged with nitrogen for 10 min, was add cesium carbonate (252 mg, 0.775 mmol) and Pd(dppf)Cl$_2$ (15 mg, 0.0193 mmol), again degassed and purged with nitrogen for 15 min and the RM was heated to 85° C. for 4 hr in a sealed tube. After completion of the reaction, the RM was cooled to rt and diluted with chloroform and filtered through celite bed. The organic layer was completely distilled off to get the crude product, which was passed through 100-200 mesh silica gel eluting the pure compound at 7-8% ethyl acetate in hexane as off white colored solid 30.

Step 2:

To a stirred solution of 30 (79 mg, 0.163 mmol) and 22 (23 mg, 0.179 mmol) in acetonitrile (5 mL), degassed and purged with nitrogen for 10 min, was added cesium carbonate (107 mg, 0.497 mmol) and Pd(PPh3)$_4$ (9 mg, 0.00817 mmol) and again degassed and purged with nitrogen for 15 min. The RM was heated to 85° C. overnight in a sealed tube. After completion of the SM, the RM was cooled to rt

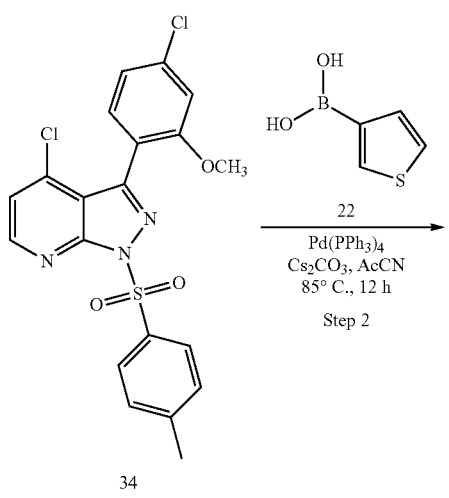

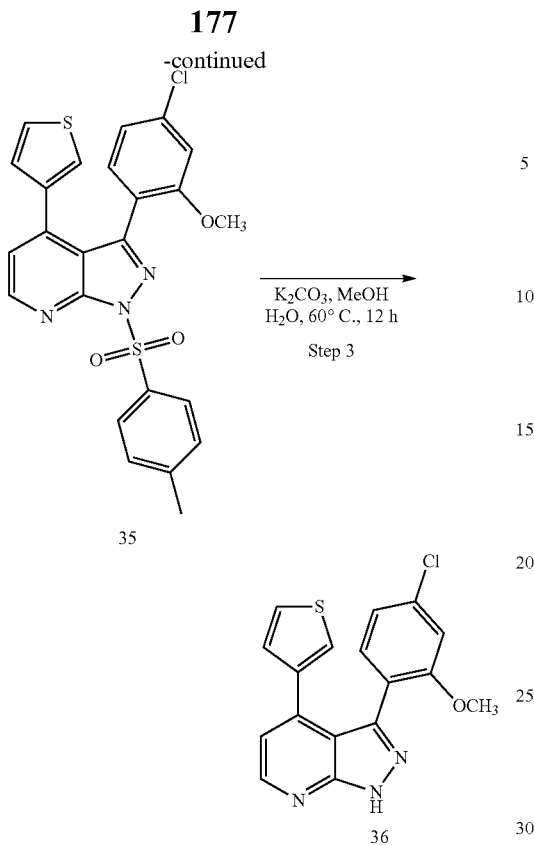

mesh silica gel, eluting the compound at 28-30% ethyl acetate in hexane as eluent to get the pale yellow colored solid of compound 36. $^1$H NMR (CDCl3) δ: 10.84 (s, 1H), 8.56 (d, 1H), 7.41 (d, 1H), 7.17 (m, 2H), 7.03 (m, 2H), 6.97 (d, 1H), 6.61 (d, 1H), 3.21 (s, 3H); and MS m/z=341.8

Preparation of Example 7: 3-(4-methoxyphenyl)-4-(thiophen-3-yl)-1H-pyrazolo[3,4-b]pyridine (40)

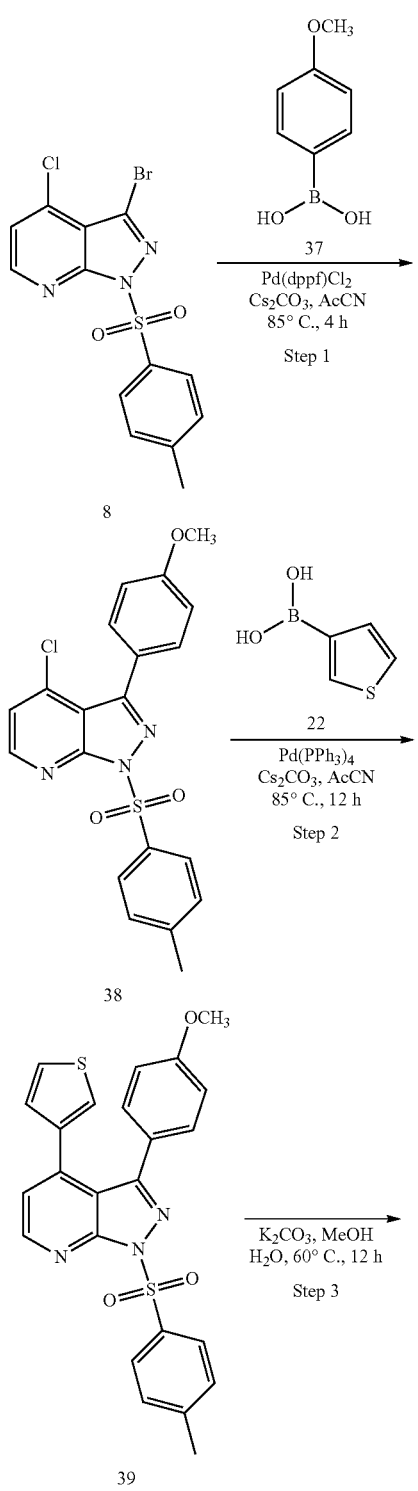

Step 1:
To a stirred solution of compound 8 (150 mg, 0.387 mmol) and 33 (72 mg, 0.387 mmol) in acetonitrile (5 mL), degassed and purged with nitrogen for 10 min, was added Cs$_2$CO$_3$ (253 mg, 0.775 mmol) and Pd(dppf)Cl$_2$ (16 mg, 0.0193 mmol). The resulting RM was degassed, purged with nitrogen again for 15 min and was heated to 85° C. for 4 hr in a sealed tube. After completion of the reaction was cooled to rt and diluted with chloroform and filtered through celite bed. The organic layer was completely distilled off to get the crude compound 34. The crude was passed through 100-200 mesh silica gel eluting the pure compound at 7-8% ethyl aceate in hexane as off white colored solid 34.

Step 2:
To a stirred solution of 34 (65 mg, 0.149 mmol) and compound 22 (21 mg, 0.159 mmol) in acetonitrile (5 mL), degassed and purged with nitrogen for 10 min, was added Cs$_2$CO$_3$ (95 mg, 0.289 mmol) and Pd(PPh3)$_4$ (8 mg, 0.00724 mmol) and continued degassing and purging with nitrogen for another 15 min. The resulting RM was heated to 85° C. overnight for 12 hrs in a sealed tube. After completion of the SM monitored from TLC, the RM was cooled to rt, diluted with chloroform and the organic layer was passed through celite bed. The organic layer was completely distilled off to get the crude product 35. The crude product was passed through 100-200 mesh silica gel eluting the pure compound 35 at 10-11% ethyl acetate in hexane as off white solid compound.

Step 3:
To a stirred solution of compound 35 (60 mg, 0.120 mmol) in methanol (10 mL) and water (5 mL) was added K$_2$CO$_3$ (33 mg, 0.241 mmol) and the RM heated to 60° C. for 12 hr. After completion of the SM, the solvents were removed, diluted with water and extracted with chloroform in two volumes. The organic layer was dried over sodium sulphate. The crude material was passed through 100-200

-continued

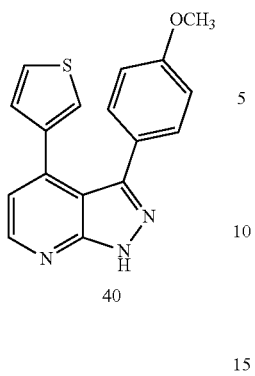

40

Preparation of Example 9: 3-(2-fluorophenyl)-4-(thiophen-3-yl)-1H-pyrazolo[3,4-b]pyridine (44)

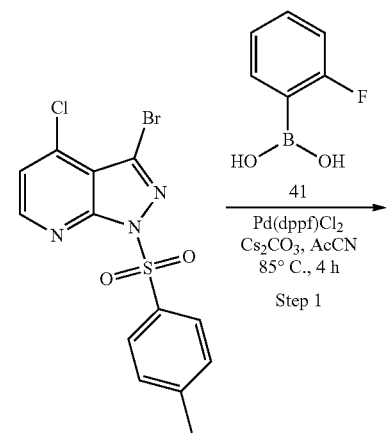

8

Step 1:

A stirred solution of 3-bromo-4-chloro-1-tosyl-1H-pyrazolo[3,4-b]pyridine 8 (150 mg, 0.387 mmol) and (4-methoxyphenyl)boronic acid 37 (59 mg, 0.387 mmol) in acetonitrile (5 mL) was degassed and purged with nitrogen for 10 min. Cesium carbonate (252 mg, 0.774 mmol) and Pd(dppf)Cl$_2$ (15 mg, 0.0193 mmol) was added to the RM and degassed and purged with nitrogen again for 15 min. The resulting RM was heated to 85° C. for 4 hr in a sealed tube. After completion of the reaction the crude RM was cooled to rt and diluted with chloroform and filtered through celite bed. The organic layer was completely distilled off. The obtained crude was passed through 100-200 mesh silica gel eluting the pure compound at 7-8% ethyl aceate in hexane to provide off white colored solid of compound 38.

Step 2:

To a stirred solution of 3-(4-methoxyphenyl)-4-(thiophen-3-yl)-1-tosyl-1H-pyrazolo[3,4-b]pyridine 38 (75 mg, 0.181 mmol) and thiophen-3-ylboronic acid 22 (25 mg, 0.199 mmol) in acetonitrile (5 mL), degassed and purged with nitrogen for 10 min, was added cesium carbonate (0.118 g 0.363 mmol) and Pd(PPh3)$_4$ (10 mg, 0.0090 mmol) and again degassed and purged with nitrogen for 15 min. Then the RM was heated to 85° C. overnight in a sealed tube. After completion of the SM, the RM was cooled to rt and diluted with chloroform and the organic layer was passed through celite bed. The organic layer was completely distilled off to get the crude product, which was passed through 100-200 mesh silica gel eluting the pure compound at 10-11% ethyl acetate in hexane giving an off white solid of 3-(4-methoxyphenyl)-4-(thiophen-3-yl)-1-tosyl-1H-pyrazolo[3,4-b]pyridine 39.

Step 3:

To a stirred solution of compound 39 (35 mg, 00758 mmol) in methanol (10 mL) and water (5 mL) was added potassium carbonate (20 mg, 0.151 mmol) and the RM heated to 60° C. overnight. After completion of the SM, the RM was completely distilled off, diluted with water and extracted with chloroform twice. The organic layer was dried over sodium sulphate and the solvent was completely distilled off to get the crude product, which was passed through 100-200 mesh silica gel eluting the compound at 28-30% ethyl acetate in hexane as eluent to get the pale yellow colored solid of compound 40. $^1$H NMR (CDCl$_3$) δ: 10.71 (s, 1H), 8.57 (d, 1H), 7.18 (m, 4H), 7.09 (m, 1H), 6.92 (m, 1H), 6.74 (m, 1H), 3.81 (s, 3H) and MS m/z=307.9.

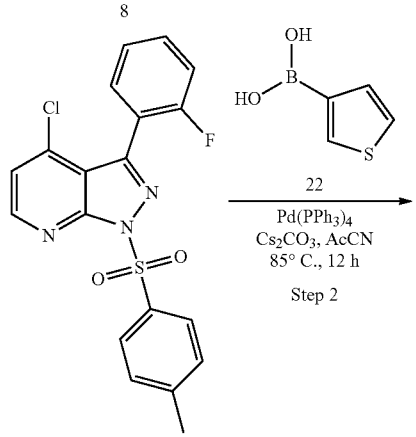

42

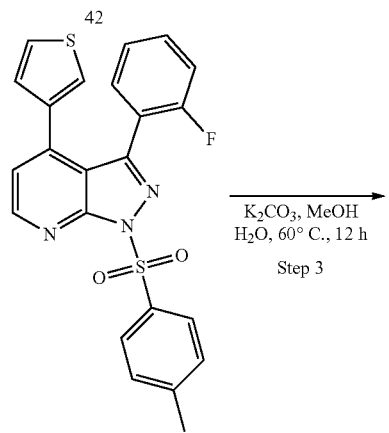

43

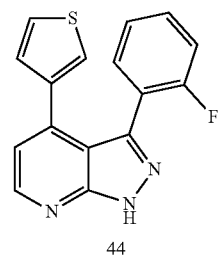

44

Step 1:

To a stirred solution of compound 8 (150 mg, 0.387 mmol) and 41 (54 mg, 0.387 mmol) in acetonitrile (5 mL), degassed and purged with nitrogen for 10 min, was added $Cs_2CO_3$ (253 mg 0.775 mmol) and $Pd(dppf)Cl_2$ (15 mg 0.0193 mmol). The resulting RM was degassed, purged with nitrogen again for 15 min again and heated to 85° C. for 4 hr in a sealed tube. After completion of the reaction, it was cooled to rt and diluted with chloroform and filtered through celite bed. The organic layer was completely distilled off to get the crude compound 38. The crude was passed through 100-200 mesh silica gel eluting the pure compound at 7-8% ethyl aceate in hexane as off white colored solid 42.

Step 2:

To a stirred solution of 42 (100 mg, 0.248 mmol) and compound 22 (35 mg, 0.273 mmol) in acetonitrile (5 mL), degassed and purged with nitrogen for 10 min, was added $Cs_2CO_3$ (162 mg 0.497 mmol) and $Pd(PPh3)_4$ (14 mg, 0.0124 mmol) and continued degassing and purging with nitrogen for another 15 min. The resulting RM was heated to 85° C. overnight or 12 hrs in a sealed tube. After completion of the SM monitored from TLC, the RM was cooled to rt and diluted with chloroform and the organic layer was passed through celite bed. The organic layer was completely distilled off to get the crude product 43. The crude product was passed through 100-200 mesh silica gel, eluting the pure compound 43 at 10-11% ethyl acetate in hexane as off white solid compound.

Step 3:

To a stirred solution of compound 43 (60 mg, 0.1334 mmol) in methanol (40 mL) and water (5 mL) was added $K_2CO_3$ (36.9 mg, 0.266 mmol) and the RM heated to 60° C. for 12 hr. After completion of the SM, the solvents were removed, diluted with water and extracted with chloroform in two volumes. The organic layer was dried over sodium sulphate. The crude material was passed through 100-200 mesh silica gel eluting the compound at 28-30% ethyl acetate in hexane as eluent to get the pale yellow colored solid of compound 44. $^1$H NMR (CDCl3) δ: 8.66 (d, 1H), 7.31 (m, 1H), 7.20 (m, 1H), 7.19 (m, 2H), 7.02 (m, 1H), 6.93 (m, 2H), 6.71 (m, 2H) and MS m/z=295.8.

Preparation of Intermediate 16

4-chloro-3-iodo-1-tosyl-1H-pyrrolo[2,3-b]pyridine (16)

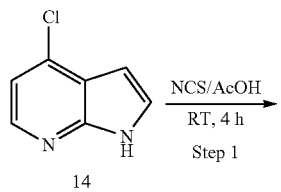

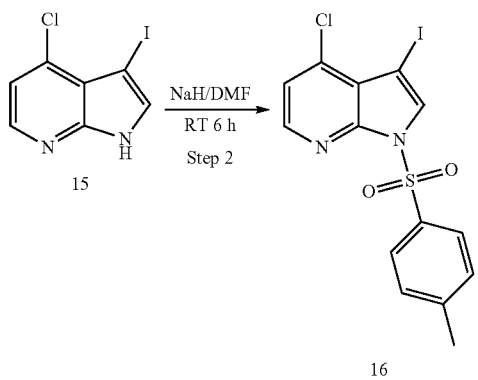

Step 1:

4-chloro-1H-pyrrolo[2,3-b]pyridine (14) 1 g (6.55 mmol) in acetic acid (10 mL) cooled to 0° C. and was added N-chlorosuccinimide (0.875 g, 6.55 mmol). The resulting RM was stirred for 4 hr at rt. After completion of the SM, the RM was quenched with ice water and extracted with dichloromethane (2×10 mL). The combined organic layer was dried over sodium sulphate, and the solvent evaporated to yield compound 4-chloro-3-iodo-1H-pyrrolo[2,3-b]pyridine 15.

Step 2:

To compound 15 (0.8 g, 2.87 mmol) in DMF (5 mL) cooled to 0° C. was add sodium hydride (0.138 g, 5.75 mmol, 2 eq) slowly under nitrogen atmosphere for 15 min followed by the addition of p-toluene sulfonyl chloride (0.820 g, 4.31 mmol, 1.5 eq). The resulting RM was stirred for 6 hr and after completion of the SMs from TLC; the RM was quenched with ice cold water and extracted with chloroform. The combined organic layer was washed with brine solution and the organic layer was dried over sodium sulphate. The solvents were removed to get the crude product, which was passed through 100-200 mesh silica gel eluting the pure compound 16 at 6-7% ethyl acetate in hexane.

Preparation of Example 17: 3-(2-methoxyphenyl)-4-(thiophen-3-yl)-1H-pyrrolo[2,3-b]pyridine (52)

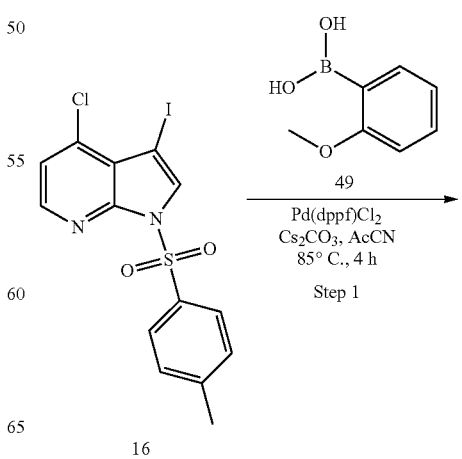

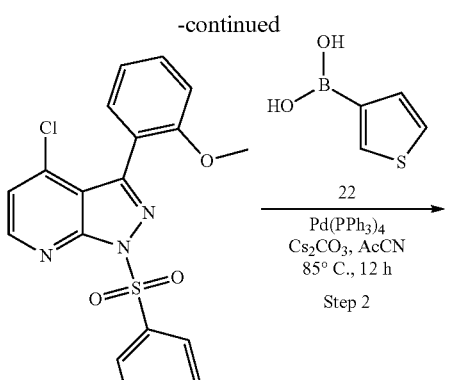

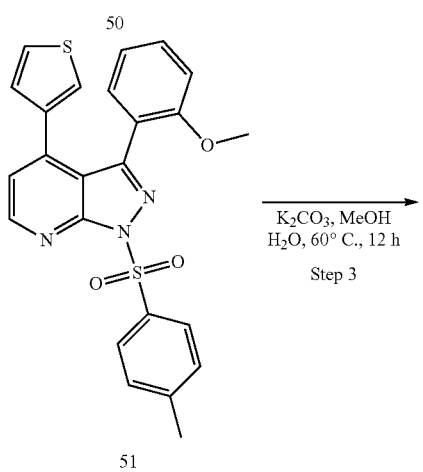

51

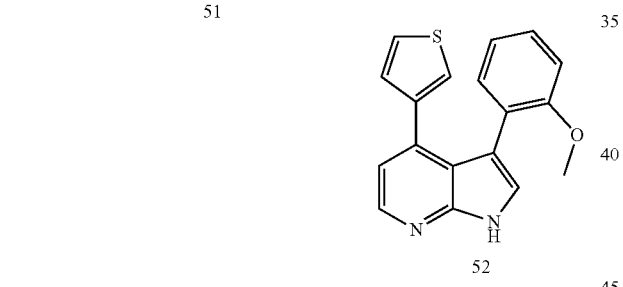

52

Step 1:

A stirred solution of compound 16 (150 mg, 0.347 mmol) and 49 (52.7 mg, 0.347 mmol) in acetonitrile (5 mL) was degassed, purged with nitrogen for 10 min and to which was added Cs$_2$CO$_3$ (151.1 mg, 0.485 mmol) and Pd(dppf)Cl (14.1 mg, 0.017 mmol). The resulting RM was degassed, purged with nitrogen again for 15 min and was heated to 85° C. for 4 hr in a sealed tube. After completion, the reaction was cooled to rt, diluted with chloroform, and filtered through celite bed. The organic layer was completely distilled off to get the crude compound 50. The crude was passed through 100-200 mesh silica gel eluting the pure compound at 5% ethyl aceate in hexane as off white colored solid 50.

Step 2:

To a stirred solution of 50 (100 mg, 0.242 mmol) and compound 22 (34.1 mg, 0.266 mmol) in acetonitrile (5 mL), degassed and purged with nitrogen for 10 min, was added Cs$_2$CO$_3$ (151.1 mg, 0.485 mmol) and Pd(PPh$_3$)$_4$ (14 mg, 0.0121 mmol) and continued degassing and purging with nitrogen for another 15 min. The resulting RM was heated to 85° C. overnight or 12 hrs in a sealed tube. After completion of the SM monitored from TLC, the RM was cooled to rt and diluted with chloroform and the organic layer was passed through celite bed. The organic layer was completely distilled off to get the crude product 51. The crude product was passed through 100-200 mesh silica gel eluting the pure compound 51 at 4-5% ethyl acetate in hexane as off white solid compound.

Step 3:

To a stirred solution of compound 51 (50 mg, 0.108 mmol) in methanol (10 mL) and water (5 mL) was added K$_2$CO$_3$ (29.9 mg, 0.217 mmol) and the RM heated to 60° C. for 12 hr. After completion of the SM, the solvents were removed, diluted with water and extracted with chloroform in two volumes. The organic layer was dried over sodium sulphate. The crude material was passed through 100-200 mesh silica gel eluting the compound at 28-30% ethyl acetate in hexane as eluent to get the pale yellow colored solid of compound 48. $^1$H NMR (CDCl3) δ: 9.00 (1-H), 8.33 (d, J=4.87 1-H), 7.35 (m, J=2.31 1-H), 7.23 (m, J=4.14 3-H), 7.11 (m, J=5.00 1-H), 7.04 (m, J=3.04 1-H), 6.90 (m, J=7.56 1-H), 6.56 (d, J=7.92 1-H), 3.27 (3-H); and MS m/z=307.2.

Preparation of Example 18: 3-(2,4-difluorophenyl)-4-(thiophen-3-yl)-1H-pyrrolo[2,3-b]pyridine (56)

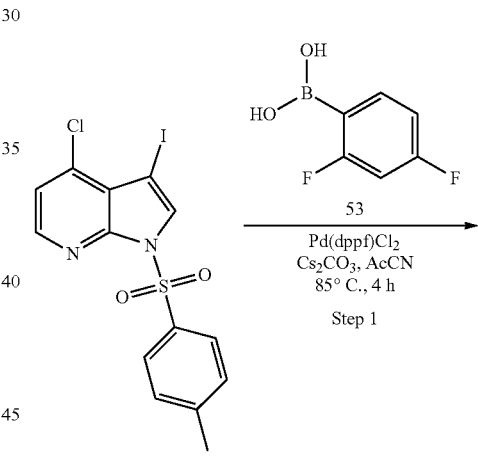

16

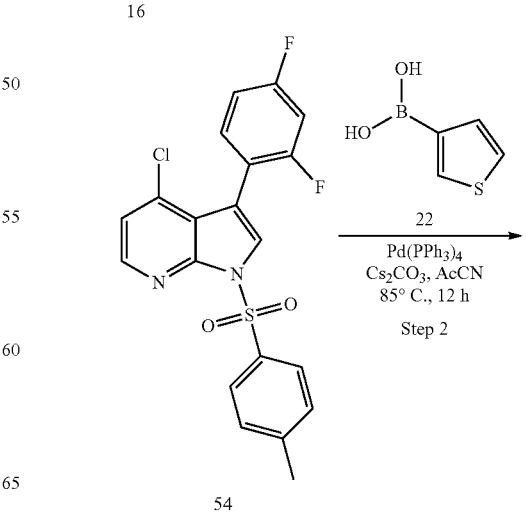

54

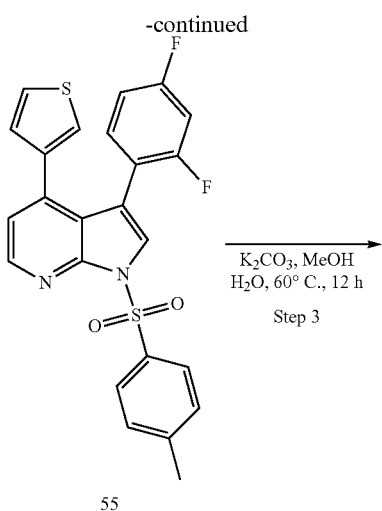

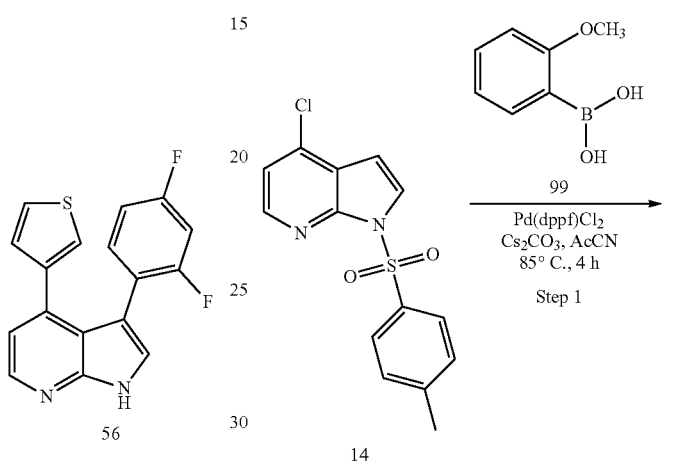

Step 1:

To a stirred solution of compound 16 (150 mg, 0.346 mmol) and 53 (54 mg, 0.346 mmol) in acetonitrile (5 mL), degassed and purged with nitrogen for 10 min, was added Cs$_2$CO$_3$ (282 mg, 0.866 mmol) and Pd(dppf)Cl (11 mg, 0.013 mmol). The resulting RM was degassed, purged with nitrogen again for 15 min and was heated to 85° C. for 4 hr in a sealed tube. After completion, the reaction was cooled to rt and diluted with chloroform 50 mL and filtered through celite bed. The organic layer was completely distilled off to get the crude compound 54. The crude was passed through 100-200 mesh silica gel eluting the pure compound at 6% ethyl aceate in hexane as off white colored solid 54.

Step 2:

To a stirred solution of 54 (100 mg, 0.239 mmol) and compound 22 (30 mg, 0.239 mmol) in acetonitrile (5 mL), degassed and purged with nitrogen for 10 min, was added Cs$_2$CO$_3$ (194 mg, 0.597 mmol) and Pd(PPh3)$_4$ (11 mg, 0.00956 mmol) and continued degassing and purging with nitrogen for another 15 min. The resulting RM was heated to 85° C. overnight or 12 hr in a sealed tube. After completion of the SM monitored from TLC, the RM was cooled to rt and diluted with chloroform and the organic layer was passed through celite bed. The organic layer was completely distilled off to get the crude product 55. The crude product was passed through 100-200 mesh silica gel eluting the pure compound 55 at 10% ethyl acetate in hexane as off white solid compound.

Step 3:

To a stirred solution of compound 55 (50 mg, 0.107 mmol) in methanol (10 mL) and water (5 mL) was added K2CO3 (37 mg, 0.268 mmol) and the RM heated to 60° C. for 12 hr. After completion of the SM, the solvents were removed, diluted with water and extracted with chloroform in two volumes. The organic layer was dried over sodium sulphate. The crude material was passed through 100-200 mesh silica gel eluting the compound at 28-30% ethyl acetate in hexane as eluent to get the pale yellow colored solid of compound 56. 1H NMR (CDCl3) δ: 9.43 (1-H), 8.37 (d, J=5.00 1-H), 7.40 (s, 1-H), 7.13 (m, J=4.87 1-H), 7.00 (m, J=6.58 2-H) 6.96 (m, J=5.12 2-H) 6.87 (d, J=3.78 1-H) 6.60 (m, J=6.95 2-H); and MS m/z=312.8

Preparation of Example 19: 4-(2-methoxyphenyl)-1H-pyrrolo[2,3-b]pyridine (101)

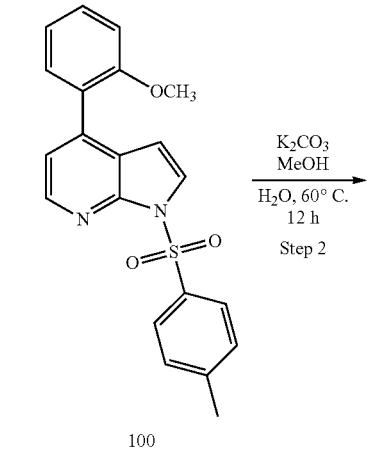

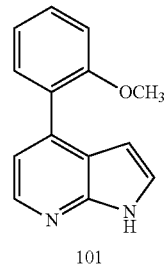

Step 1:

To a stirred solution of tosylated 14 (100 mg, 0.326 mmol) and 99 (49.6 mg, 0.326 mmol) in acetonitrile (6 mL), degassed and purged with nitrogen for 10 min, was added cesium carbonate (214 mg, 0.653 mmol) and Pd(dppf)Cl$_2$ (18.8 mg, 0.0163 mmol), again degassed and purged with nitrogen for 15 min, and the RM heated to 85° C. overnight in a sealed tube. After completion of the SM, the RM was cooled to rt and diluted with chloroform and the organic layer was passed through celite bed. The organic layer was completely distilled off the solvent to get the crude product which was passed through 100-200 mesh silica gel eluting the pure compound at 10-11% ethyl acetate in hexane as off white solid compound 100.

Step 2:

To a stirred solution of 100 (45 mg, 0.119 mmol) in methanol (10 mL) and water (5 mL) was added potassium carbonate (33 mg, 0.238 mmol) and the RM heated to 60° C. overnight. After completion of the SM, methanol was completely distilled off and the RM diluted with water and extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 101. 1H NMR (CDCl3) δ: 9.43 (1-H), 8.31 (d, J=5.12 1-H), 7.46 (m, J=5.85 2-H), 7.30 (d, J=3.53 1-H), 7.19 (d, J=5.00 1-H), 7.08 (m, J=7.43 2-H), 6.42 (d, J=3.53 1-H), 3.81 (s, 3-H).

Preparation of Example 20: 4-(thiophen-3-yl)-1H-pyrrolo[2,3-b]pyridine (66)

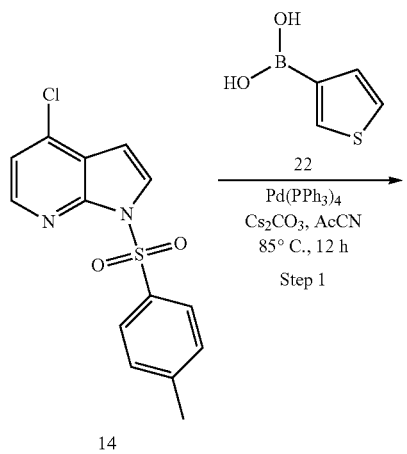

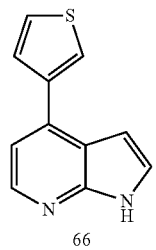

Step 1:

To a stirred solution of 14 (100 mg, 0.326 mmol) and 22 (50 mg 0.392 mmol) in DME (5 mL) and water (1 mL), degassed and purged with nitrogen for 10 min, was added cesium carbonate (214 mg, 0.653 mmol) and Pd(pph3)4 (18.8 mg, 0.0163 mmol) and again degassed and purged with nitrogen for 15 min. Then the RM was heated to 85° C. overnight in a sealed tube. After completion of the SM, the RM was cooled to rt and diluted with chloroform and the organic layer passed through celite bed. The organic layer was completely distilled off the solvent to get the crude product which was passed through 100-200 mesh silica gel, eluting the pure compound 65 at 5% ethyl acetate in hexane as off white solid.

Step 2:

To a stirred solution of 65 (30 mg, 0.0847 mmol) in methanol (5 mL) and water (1 mL) was added potassium carbonate (23.2 mg, 0.169 mmol) and heated to 60° C. overnight. After completion of the SM, methanol was completely distilled off and the RM diluted with water then extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid 66. $^1$H NMR (CDCl3) δ: 9.14 (1-H), 8.33 (M, J=5.00 1-H), 7.75 (m, J=1.58 1-H), 7.56 (m, J=3.78 1-H) 7.49 (m, J=2.92 1-H), 7.38 (m, J=3.41 1-H), 7.22 (m, J=2.56 1-H), 6.78 (m, J=1.95 1-H) and MS m/z=201.2.

Preparation of Example 21: 4-(thiophen-3-yl)-3-(2-(trifluoromethyl)phenyl)-1H-pyrrolo[2,3-b]pyridine (90)

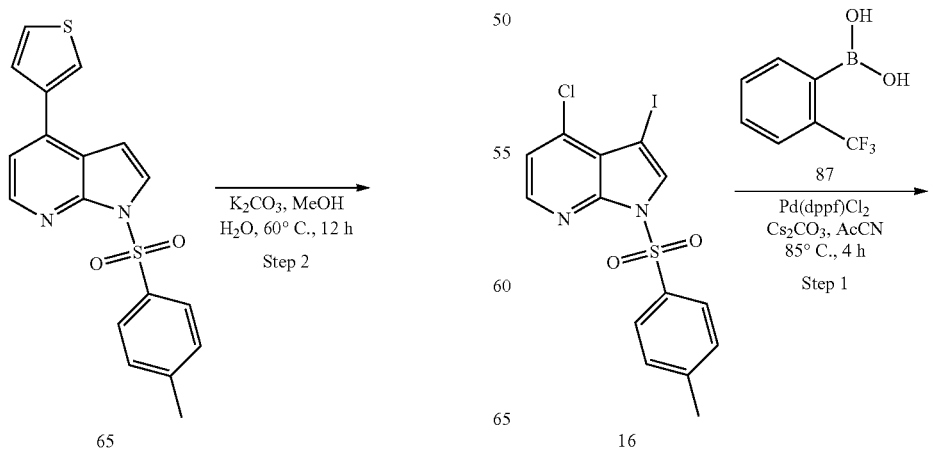

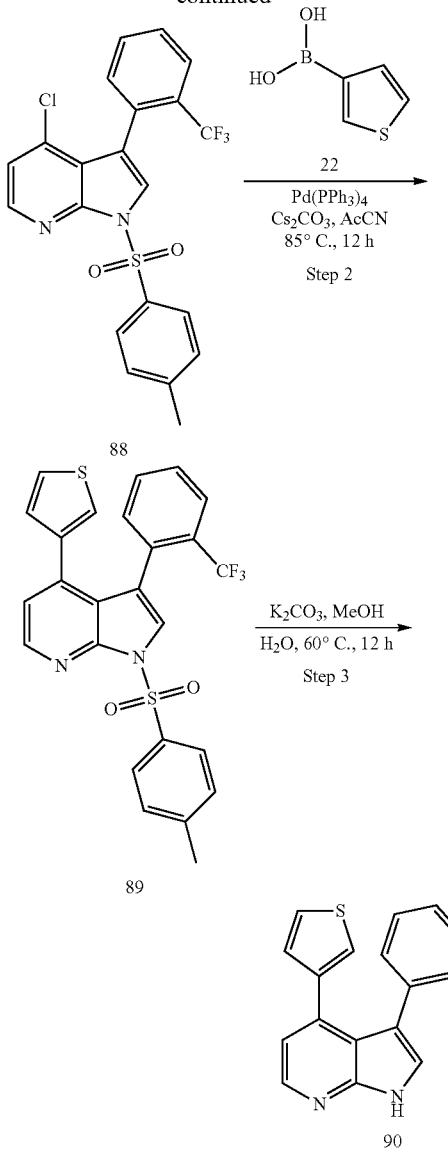

Step 1:

To a stirred solution of 16 (150 mg, 0.346 mmol) and 87 (65.8 mg, 0.346 mmol) in acetonitrile (8 mL), degassed and purged with nitrogen for 10 min, was added cesium carbonate (225.9 mg, 0.693 mmol) and Pd(dppf)Cl$_2$ (14.1 mg, 0.0173 mmol), again degassed and purged with nitrogen again for 15 min, and the RM heated to 85° C. for 4 hr in a sealed tube. After completion of the reaction the RM was cooled to rt and diluted with chloroform and filtered through celite bed. The organic layer was completely distilled off to get the crude which was passed through 100-200 mesh silica gel eluting the pure compound at 7-8% ethyl aceate in hexane as off white colored solid compound 88.

Step 2:

To a stirred solution of 88 (80 mg, 0.177 mmol) and 22 (22 mg, 0.177 mmol) in acetonitrile (6 mL), degassed and purged with nitrogen for 10 min, was added cesium carbonate (115 mg, 0.354 momL) and Pd(PPh$_3$)$_4$ (10 mg, 0.0088 mmol), again degassed and purged with nitrogen for 15 min, and the RM heated to 85° C. overnight in a sealed tube. After completion of the SM, the RM was cooled to rt and diluted with chloroform and the organic layer was passed through celite bed. The organic layer was completely distilled off the solvent to get the crude product which was passed through 100-200 mesh silica gel eluting the pure compound at 10-11% ethyl acetate in hexane as off white solid compound 89.

Step 3:

To a stirred solution of 89 (40 mg, 0.0803 mmol) in methanol (15 mL) and water (5 mL) was added potassium carbonate (22 mg, 0.160 mmol) and the RM heated to 60° C. overnight. After completion of the SM, methanol was completely distilled off and the RM diluted with water and extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 90. $^1$H NMR (CDCl3) δ: 9.21 (1-H), 8.35 (d, J=4.51 1-H), 7.64 (d, J=7.8 1-H), 7.52 (s, J=9.39 1-H), 7.09 (m, J=4.26 2-H), 6.88 (m, J=12.19 3-H), 6.73 (d, J=4.63 1-H); and MS m/z=344.8.

Preparation of Example 22: 3-(2-fluorophenyl)-4-(thiophen-3-yl)-1H-pyrrolo[2,3-b]pyridine (60)

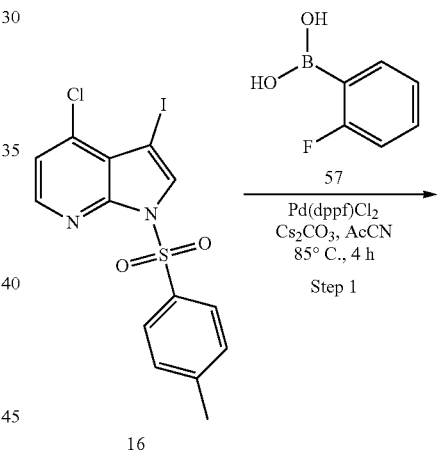

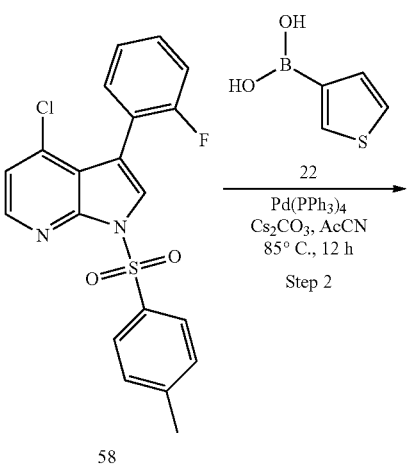

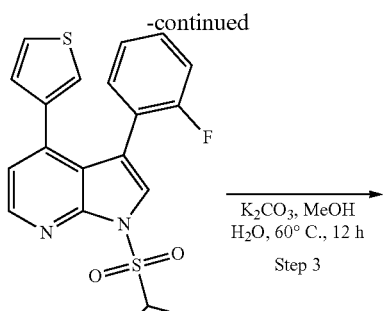

59

K₂CO₃, MeOH
H₂O, 60° C., 12 h
Step 3

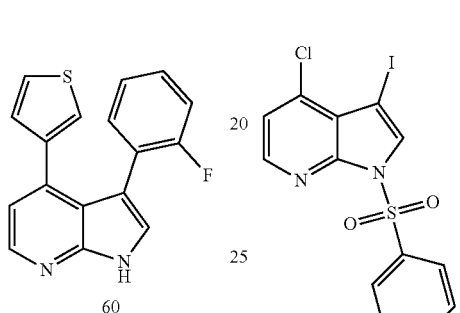

60

Step 1:
To a stirred solution of 16 (150 mg, 0.346 mmol) and 57 (48 mg, 0.346 mmol) in acetonitrile (8 mL), degassed and purged with nitrogen for 10 min, was add cesium carbonate (282 mg, 0.866 mmol) and Pd(dppf)Cl₂ (11 mg, 0.0138 mmol), then degassed and purged with nitrogen again for 15 min and the RM was heated to 85° C. for 4 hr in a sealed tube. After completion of the reaction the RM was cooled to rt and diluted with chloroform (50 mL) and filtered through celite bed. The organic layer was completely distilled off to get the crude the crude was passed through 100-200 mesh silica gel eluting the pure compound 58 at 5% ethyl aceate in hexane as off white colored solid.

Step 2:
To a stirred solution of 58 (100 mg, 0.249 m mol) and 22 (31 mg, 0.249 mmol) in acetonitrile (7 mL), degassed and purged with nitrogen for 10 min, was added cesium carbonate (203 mg, 0.623 m mol) and Pd(PPh₃)₄ (11 mg, 0.0997 mmol), and again degassed and purged with nitrogen for 15 min. Then the RM was heated to 85° C. overnight in a sealed tube. After completion of the SM the RM was cooled to rt and diluted with chloroform (50 mL) and the organic layer passed through celite bed. The organic layer was completely distilled off the solvent to get the crude product, which was passed through 100-200 mesh silica gel eluting the pure compound 59 at 10-11% ethyl acetate in hexane as off white solid.

Step 3:
To a stirred solution of 59 (50 mg, 0.111 mmol) in methanol (7 mL) and water (3 mL) was added potassium carbonate (38 mg, 0.278 m mol) and heated to 60° C. overnight. After completion of the SM, the RM was completely distilled off, diluted with water and extracted with chloroform (50 mL) twice. The organic layer was dried over sodium sulphate and completely distilled off to get the crude product, which was passed through 100-200 mesh silica gel eluting the pre compound 60 at 17% ethyl acetate in hexane as eluent to get the pale yellow colored solid. 1H NMR (CDCl3) δ: 9.08 (1-H), 8.36 (d, J=4.87 1-H), 7.42 (d, J=2.31 1-H), 7.28 (m, J=52.6 2-H), 7.17 (m, J=5.24 2-H) 7.13 (m, J=4.84 2-H) 7.05 (m, J=5.00 2-H) 6.94 (m, J=7.19 1-H), MS m/z=294.9.

Preparation of Example 23: 3-(2-chloro-3-fluoro-phenyl)-4-(thiophen-3-yl)-1H-pyrrolo[2,3-b]pyridine (98)

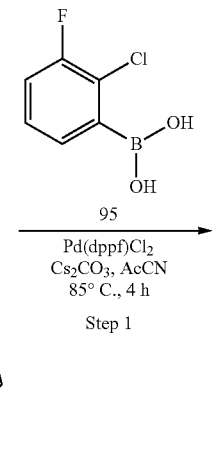

16

95

Pd(dppf)Cl₂
Cs₂CO₃, AcCN
85° C., 4 h

Step 1

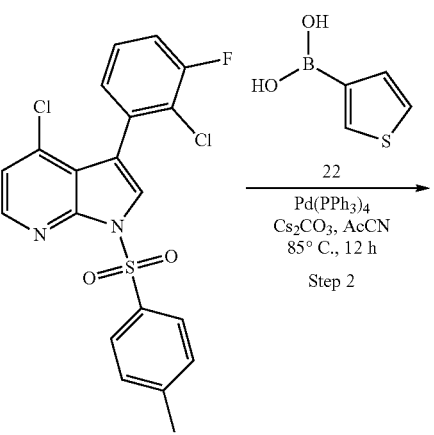

96

22

Pd(PPh₃)₄
Cs₂CO₃, AcCN
85° C., 12 h

Step 2

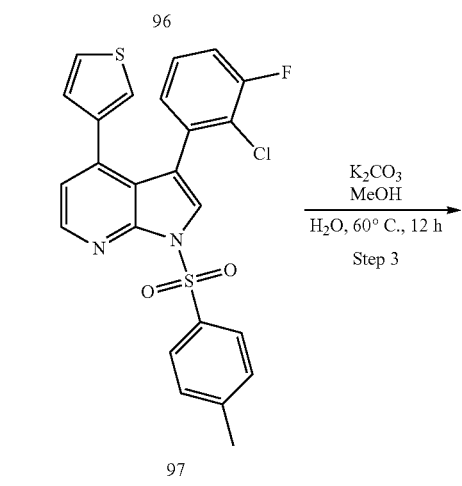

97

K₂CO₃
MeOH
H₂O, 60° C., 12 h

Step 3

-continued

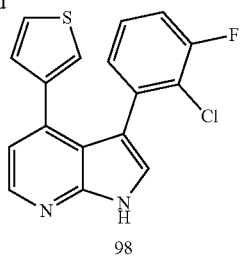

98

Step 1:

To a stirred solution of 16 (150 mg, 0.346 mmol) and 95 (60 mg, 0.346 mmol) in acetonitrile (8 mL), degassed and purged with nitrogen for 10 min, was added cesium carbonate (282 mg, 0.866 mmol) and Pd(dppf)Cl$_2$ (11 mg, 0.0138 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude which was passed through 100-200 mesh silica gel eluting the pure compound at 7-8% ethyl aceate in hexane as off white colored solid 96.

Step 2:

To a stirred solution of 96 (0.229 mmol) and 22 (0.229 mmol) in acetonitrile (6 mL), degassed and purged with nitrogen for 10 min, was added cesium carbonate (0.574 mmol) and Pd(PPh$_3$)$_4$ (0.00968 mmol), again degassed and purged with nitrogen for 15 min, and the RM heated to 85° C. overnight in a sealed tube. After completion of the SM, the RM was cooled to rt and diluted with chloroform and the organic layer was passed through celite bed. The organic layer was completely distilled off the solvent to get the crude product which was passed through 100-200 mesh silica gel eluting the pure compound at 10-11% ethyl acetate in hexane as off white solid 97.

Step 3:

To a stirred solution of 97 (30 mg, 0.0621 mmol) in methanol (10 mL) and water (5 mL) was added potassium carbonate (17 mg, 0.124 mmol) and the RM heated to 60° C. overnight. After completion of the SM, methanol was completely distilled off and the RM diluted with water then extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 98. 1H NMR (CDCl3) δ: 9.19 (1-H), 8.38 (d, J=4.75 1-H), 7.40 (d, J=2.56 1-H), 7.13 (d, J=4.87 1-H), 7.01 (m, J=4.26 3-H) 6.85 (m, J=8.53 3-H); and MS m/z=328.8

Preparation of Example 24: 3-(4-chloro-2-methoxy-phenyl)-4-(thiophen-3-yl)-1H-pyrrolo[2,3-b]pyridine (82)

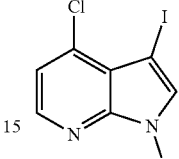 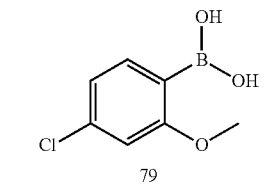

79
Pd(dppf)Cl$_2$
Cs$_2$CO$_3$, AcCN
85° C., 4 h

Step 1

16

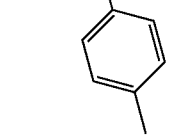

22
Pd(PPh$_3$)$_4$
Cs$_2$CO$_3$, AcCN
85° C., 12 h

Step 2

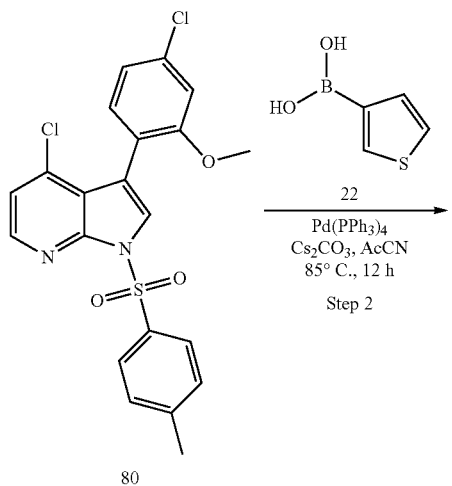

80

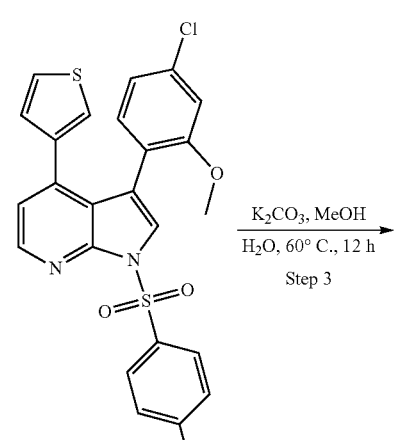

K$_2$CO$_3$, MeOH
H$_2$O, 60° C., 12 h

Step 3

81

-continued

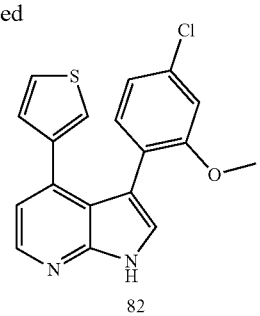

82

Preparation of Example 25: 3-(4-methoxyphenyl)-4-(thiophen-3-yl)-1H-pyrrolo[2,3-b]pyridine (64)

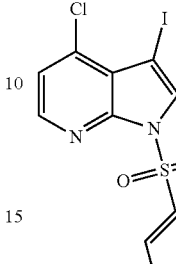

16

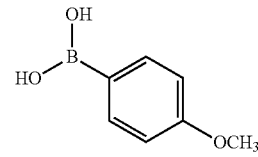

61

Pd(dppf)Cl$_2$
Cs$_2$CO$_3$, AcCN
85° C., 4 h
Step 1

Step 1:

To a stirred solution of 16 (150 mg, 0.347 mmol) and 79 (64.3 mg, 0.347 mmol) in acetonitrile (7 mL), degassed and purged with nitrogen for 10 min, was added cesium carbonate (228 mg, 0.694 mmol) and Pd(dppf)Cl$_2$ (14.1 mg, 0.0173 mmol), again degassed and purged with nitrogen again for 15 min and the RM was heated to 85° C. for 4 hr in a sealed tube. After completion of the reaction the RM was cooled to rt and diluted with chloroform and filtered through celite bed. The organic layer was completely distilled off to get the crude, which was passed through 100-200 mesh silica gel eluting the pure compound at 7-8% ethyl aceate in hexane as off white colored solid compound 80.

Step 2:

To a stirred solution of 80 (100 mg, 0.224 mmol) and 22 (31.5 mg, 0.224 mmol) in acetonitrile (7 mL), degassed and purged with nitrogen for 10 min, was added cesium carbonate (147 mg, 0.448 mmol) and Pd(PPh$_3$)$_4$ (12.9 mg, 0.011 mmol), again degassed and purged with nitrogen for 15 min, and the RM heated to 85° C. overnight in a sealed tube. After completion of the SM, the RM was cooled to rt and diluted with chloroform and the organic layer passed through celite bed. The organic layer was completely distilled off the solvent to get the crude product which was passed through 100-200 mesh silica gel eluting the pure compound at 10-11% ethyl acetate in hexane as off white solid compound 81.

Step 3:

To a stirred solution of 81 (60 mg, 0.121 mmol) in methanol (10 mL) and water (5 mL) was added potassium carbonate (33 mg, 0.2424 mmol) and heated to 60° C. overnight. After completion of the SM, methanol was completely distilled off and the RM diluted with water then extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 82. $^1$H NMR (CDCl3) δ: 9.13 (1-H), 8.34 (d, J=4.87 1-H), 7.33 (d, J=2.31 1-H), 7.09 (m, J=5.00 1-H), 6.88 (m, J=5.97 3-H), 6.55 (d, J=1.95 1-H) 3.28 (s, 3-H) and MS m/z=341.3.

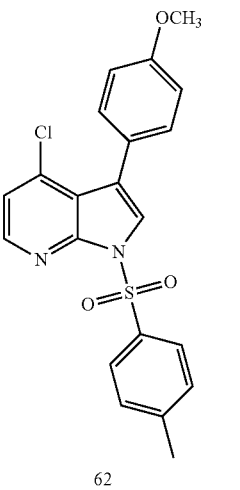

62

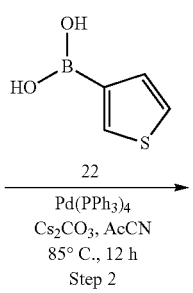

22

Pd(PPh$_3$)$_4$
Cs$_2$CO$_3$, AcCN
85° C., 12 h
Step 2

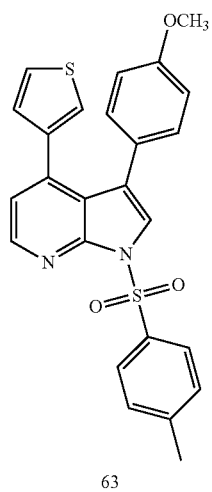

63

K$_2$CO$_3$, MeOH
H$_2$O, 60° C., 12 h
Step 3

197
-continued

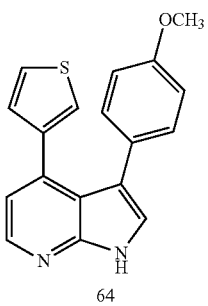

64

Step 1:

To a stirred solution of 16 (150 mg, 0.346 mmol) and 61 (52 mg, 0.346 mmol) in acetonitrile (7 mL), degassed and purged with nitrogen for 10 min, was added cesium carbonate (282 mg 0.865 mmol) and Pd(dppf)Cl$_2$ (11 mg, 0.013 mmol), again degassed and purged with nitrogen for 15 min and the RM heated to 85° C. for 4 hr in a sealed tube. After completion of the reaction the RM was cooled to rt and diluted with chloroform (50 mL) and filtered through celite bed. The organic layer was completely distilled off to get the crude, which was passed through 100-200 mesh silica gel eluting the pure compound 62 at 7-8% ethyl aceate in hexane as off white colored solid.

Step 2:

To a stirred solution of 62 (100 mg, 0.242 mmol) and 22 (31 mg, 0.242 mmol) in acetonitrile (6 mL), degassed and purged with nitrogen for 10 min, was added cesium carbonate (197 mg, 0.605 mmol) and Pd(PPh$_3$)$_4$ (11 mg 0.00908 mmol), and again degassed and purged with nitrogen for 15 min and heated to 85° C. overnight in a sealed tube. After completion of the SM the RM was cooled to rt and diluted with chloroform (50 mL) and the organic layer was passed through celite bed. The organic layer was completely distilled off the solvent to get the crude product which was passed through 100-200 mesh silica gel eluting the pure compound at 10-11% ethyl acetate in hexane as off white solid compound 63.

Step 3:

To a stirred solution of 63 (40 mg 0.086 mmol) in methanol (7 mL) and water (3 mL) was added potassium carbonate 30 mg (0.215 mmol) and heated to 60° C. overnight. After completion of the SM, the RM was completely distilled off, diluted with water and extracted with chloroform twice. The organic layer was dried over sodium sulphate and completely distilled off to get the crude product which was passed through 100-200 mesh silica gel eluting the pre compound at 20% ethyl acetate in hexane as eluent to get the pale yellow colored solid. $^1$H NMR (CDCl3) δ: 9.26 (1H), 8.35 (d, J=4.87 1H), 7.33 (d, J=2.43 1H), 7.12 (d, J=4.87 1-H), 7.07 (m, J=3.04 1-H) 6.95 (m, J=5.48 2-H) 6.93 (m, J=4.63 2-H) 6.87 (m, J=3.65 1-H), 6.67 (m, J=4.51 2-H), 3.79 (s 3-H); and MS m/z=307.2.

198

Preparation of Example 26: 3-(2-ethoxyphenyl)-4-(thiophen-3-yl)-1H-pyrrolo[2,3-b]pyridine (78)

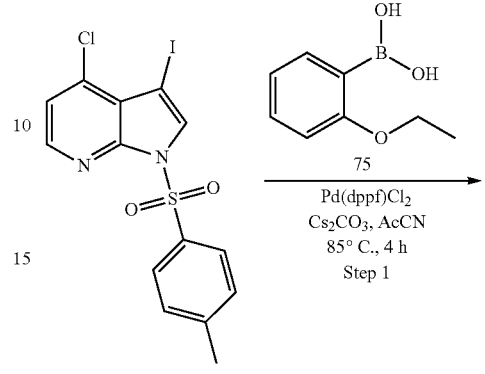

16

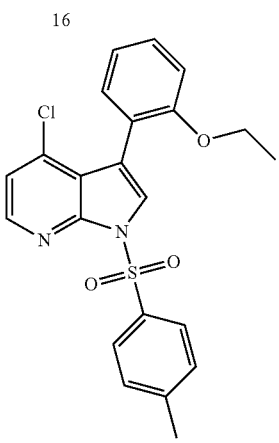

76

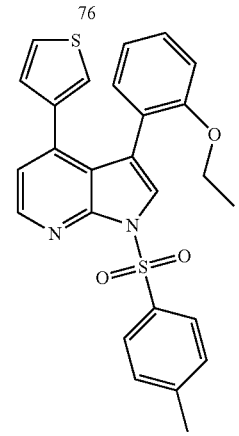

77

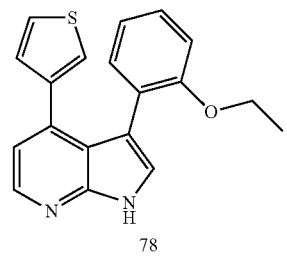

78

Step 1:

To a stirred solution of 16 (150 mg, 0.347 mmol) and 75 (57.6 mg, 0.347 mmol) in acetonitrile (7 mL), degassed and purged with nitrogen for 10 min, was added cesium carbonate (228.1 mg, 0.694 mmol) and Pd(dppf)Cl₂ (11 mg, 0.0138 mmol), again degassed and purged with nitrogen again for 15 min and the RM heated to 85° C. for 4 hr in a sealed tube. After completion of the reaction the RM was cooled to rt and diluted with chloroform (50 mL) and filtered through celite bed. The organic layer was completely distilled off to get the crude which was passed through 100-200 mesh silica gel eluting the pure compound at 7-8% ethyl aceate in hexane as off white colored solid 76.

Step 2:

To a stirred solution of 76 (100 mg, 0.234 mmol) and 22 (30 mg, 0.234 mmol) in acetonitrile (7 mL), degassed and purged with nitrogen for 10 min, was added cesium carbonate (153 mg, 0.469 mmol) and Pd(PPh3)4 (11 mg, 0.0093 mmol), again degassed and purged with nitrogen for 15 min and the RM heated to 85° C. overnight in a sealed tube. After completion of the SM, the RM was cooled to rt and diluted with chloroform (50 mL) and the organic layer was passed through celite bed. The organic layer was completely distilled off the solvent to get the crude product which was passed through 100-200 mesh silica gel eluting the pure compound at 10-11% ethyl acetate in hexane as off white solid compound 77.

Step 3:

To a stirred solution of 77 (30 mg 0.063 mmol) in methanol (5 mL) and water (1 mL) was added potassium carbonate (21.8 mg, 0.158 mmol) and the RM heated to 60° C. overnight. After completion of the SM, methanol was completely distilled off and the RM diluted with water and extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 78. ¹H NMR (CDCl3) δ: 9.10 (1-H), 8.33 (d, J=4.87 1-H), 7.36 (d, J=2.31 1-H), 7.20 (m, J=5.61 2-H), 7.11 (d, J=5.00 1-H), 7.04 (m, J=2.92 1-H), 6.98 (m, J=6.70 1-H), 6.87 (m, J=7.31 2-H), 6.55 (d, J=8.17 1-H), 3.47 (q, J=6.95 2-H), 1.04 (t, J=6.95 3-H); and MS m/z=321.2.

Preparation of Example 27: 3-(4-chloro-2-fluorophenyl)-4-(thiophen-3-yl)-1H-pyrrolo[2,3-b]pyridine (94)

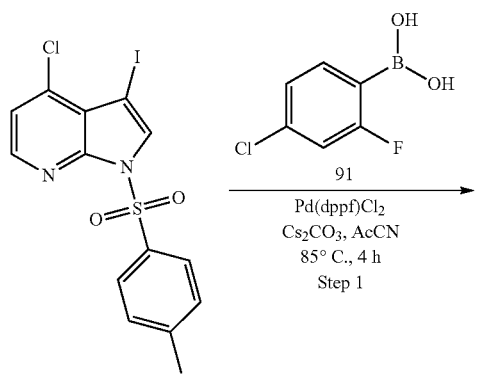

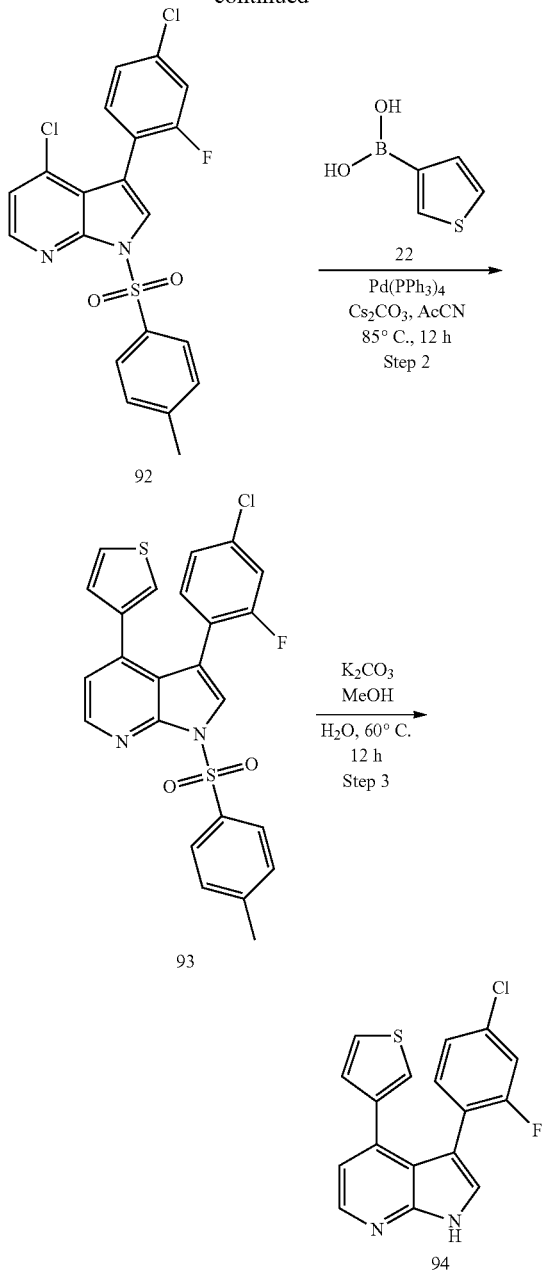

Step 1:

To a stirred solution of 16 (150 mg, 0.346 mmol) and 91 (60 mg, 0.346 mmol) in acetonitrile (8 mL), degassed and purged with nitrogen for 10 min, was added cesium carbonate (282 mg, 0.865 mmol) and Pd(dppf)Cl₂ (11 mg, 0.0138 mmol), again degassed and purged with nitrogen again for 15 min, and the RM heated to 85° C. for 4 hr in a sealed tube. After completion of the reaction the RM was cooled to rt and diluted with chloroform and filtered through celite bed. The organic layer was completely distilled off to get the crude which was passed through 100-200 mesh silica gel eluting the pure compound at 7-8% ethyl aceate in hexane as off white colored solid compound 92.

Step 2:

To a stirred solution of 92 (100 mg, 0.229 mmol) and 2 (29 mg, 0.229 mmol) in acetonitrile (6 mL), degassed and purged with nitrogen for 10 min, was added cesium carbonate (186 mg, 0.574 mmol) and Pd(PPh$_3$)$_4$ (10 mg, 0.0091 mmol), again degassed and purged with nitrogen for 15 min, and the RM heated to 85° C. overnight in a sealed tube. After completion of the SM, the RM was cooled to rt and diluted with chloroform and the organic layer was passed through celite bed. The organic layer was completely distilled off the solvent to get the crude product which was passed through 100-200 mesh silica gel eluting the pure compound at 10-11% ethyl acetate in hexane as off white solid compound 93.

Step 3:

To a stirred solution of 93 (30 mg, 0.0621 mmol) in methanol (10 mL) and water (5 mL) was added potassium carbonate (17 mg, 0.124 mmol) and the RM heated to 60° C. overnight. After completion of the SM, methanol was completely distilled off and the RM diluted with water and extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 94. $^1$H NMR (CDCl3) δ: 9.51 (1-H), 8.37 (d, J=4.75 1-H), 7.43 (s, 1-H) 7.11 (m, J=8.29 2-H), 6.91 (m, J=8.29 5-H), and MS m/z=327.6.

Preparation of Example 28: 3-(4-fluoro-2-methoxyphenyl)-4-(thiophen-3-yl)-1H-pyrrolo[2,3-b]pyridine (86)

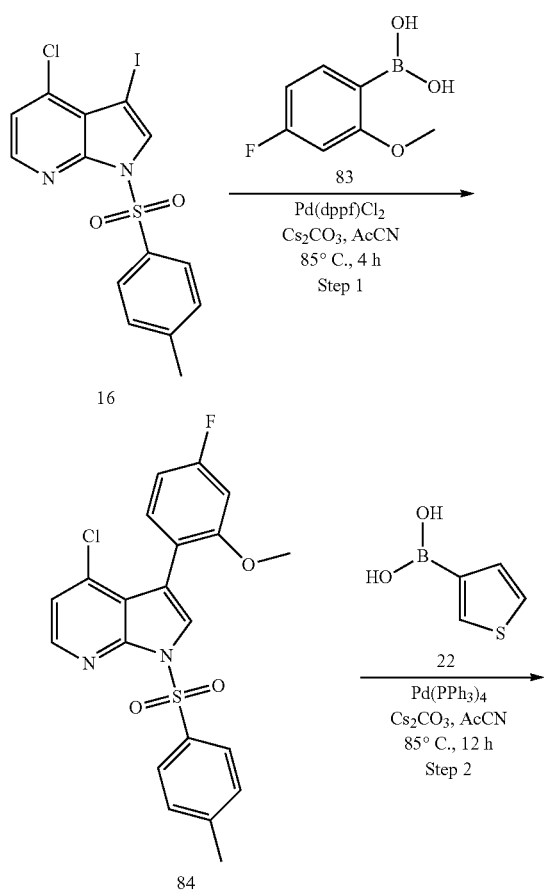

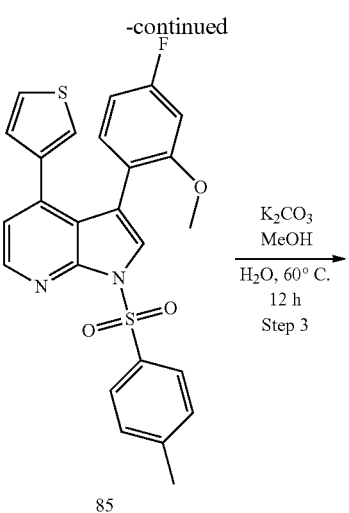

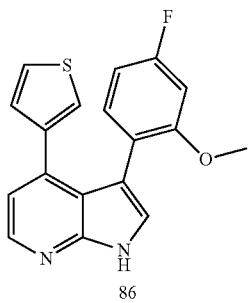

Step 1:

To a stirred solution of 16 (150 mg, 0.347 mmol) and 83 (59 mg, 0.347 mmol) in acetonitrile (7 mL), degassed and purged with nitrogen for 10 min, was added cesium carbonate (285 mg, 0.868 mmol) and Pd(dppf)Cl$_2$ (11 mg, 0.0138 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude which was passed through 100-200 mesh silica gel eluting the pure compound at 7-8% ethyl aceate in hexane as off white colored solid compound 84.

Step 2:

To a stirred solution of 84 (110 mg, 0.255 mmol) and 22 (32 mg, 0.255 mmol) in acetonitrile (7 mL), degassed and purged with nitrogen for 10 min, was added cesium carbonate (209 mg, 0.638 mmol) and Pd(PPh$_3$)$_4$ (11 mg, 0.0102 mmol), again degassed and purged with nitrogen for 15 min, and the RM heated to 85° C. overnight in a sealed tube. After completion of the SM, the RM was cooled to rt and diluted with chloroform and the organic layer was passed through celite bed. The organic layer was completely distilled off the solvent to get the crude product which was passed through 100-200 mesh silica gel eluting the pure compound at 10-11% ethyl acetate in hexane as off white solid compound 85.

Step 3:

To a stirred solution of 85 (30 mg, 0.062 mmol) in methanol (10 mL) and water (5 mL) was added potassium carbonate (17 mg, 0.125 mmol) and the RM heated to 60° C. overnight. After completion of the SM, methanol was completely distilled off and the RM diluted with water then extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 86. $^1$H NMR (CDCl3) δ: 9.11 (1-H), 8.33 (d, J=311 1-H), 7.32 (s, 2-H), 7.11 (m, J=13.17 3-H), 6.90 (d, J=4.50 2-H), 6.61 (t, J=6.09 1-H), 6.30 (d, J=9.14 1-H) 3.20 (s, 3-H) and MS m/z=324.8

Preparation of Example 29: 4-chloro-3-(thiophen-3-yl)-1H-pyrrolo[2,3-b]pyridine (103)

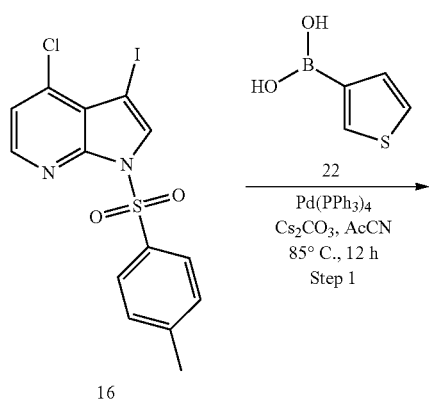

completion of the reaction the RM was cooled to rt and diluted with chloroform and filtered through celite bed. The organic layer was completely distilled off to get the crude which was passed through 100-200 mesh silica gel eluting the pure compound at 7-8% ethyl aceate in hexane as off white colored solid compound 102.

Step 2:

To a stirred solution of 102 (70 mg, 0.180 mmol) in methanol (15 mL) and water (5 mL) was added potassium carbonate (49 mg, 0.360 mmol) and the RM heated to 60° C. overnight. After completion of the SM, methanol was completely distilled and the RM diluted with water then extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 103. $^1$H NMR (CDCl3) δ: 9.78 (1-H), 8.21 (d, J=5.12 1H), 7.39 (d, J=2.31 1-H), 7.35 (m, J=3.04 2-H), 7.29 (m, J=2.92 1-H), 7.13 (d, J=5.12 1-H); and MS m/z=234.8.

Preparation of Example 30: 4-(2-methoxyphenyl)-3-(thiophen-3-yl)-1H-pyrrolo[2,3-b]pyridine (106)

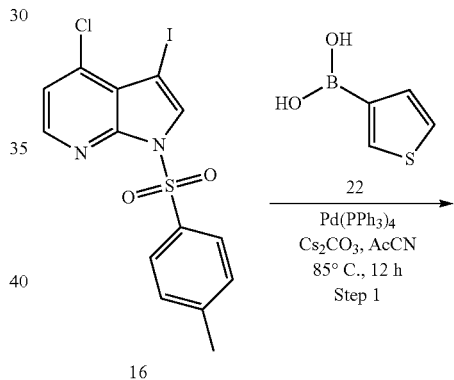

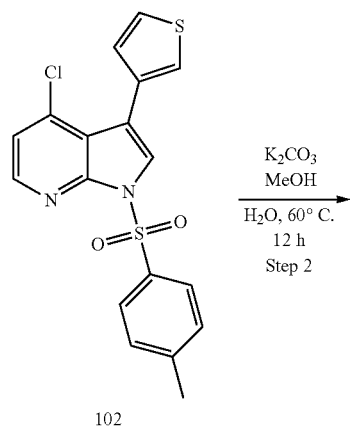

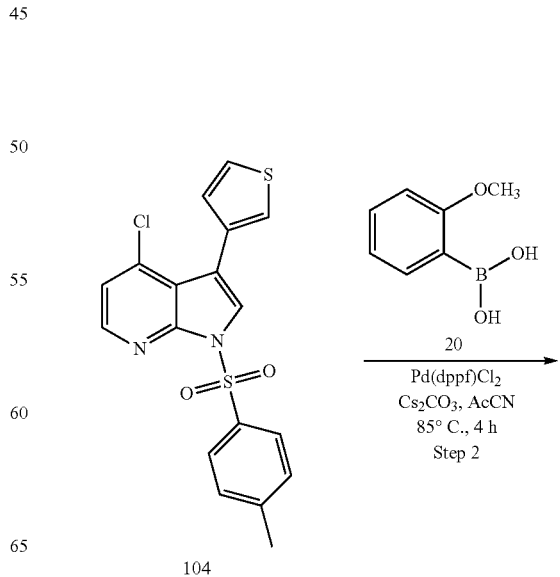

Step 1:

To a stirred solution of 16 (150 mg, 0.347 mmol) and 22 (44 mg, 0.347 mmol) in acetonitrile (7 mL), degassed and purged with nitrogen for 10 min, was added cesium carbonate (226 mg, 0.866 mmol) and Pd(dppf)Cl$_2$ (14 mg, 0.0173 mmol), again degassed and purged with nitrogen for 15 min and the RM heated to 85° C. for 4 hr in a sealed tube. After

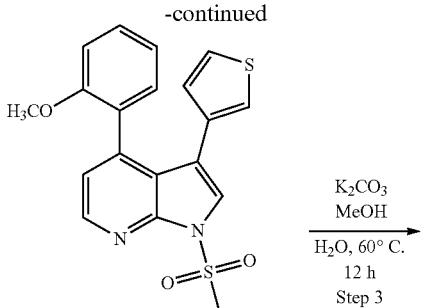

105

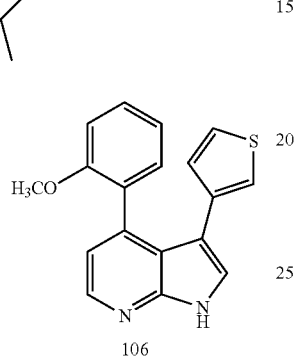

106

Step 1:
To a stirred solution of 16 (150 mg, 0.347 mmol) and 22 (44 mg, 0.347 mmol) in acetonitrile (7 mL), degassed and purged with nitrogen for 10 min, was added cesium carbonate (226 mg, 0.866 mmol) and Pd(dppf)Cl₂ (14 mg, 0.0173 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude which was passed through 100-200 mesh silica gel eluting the pure compound at 7-8% ethyl aceate in hexane as off white colored solid compound 104.

Step 2:
To a stirred solution of 104 (100 mg, 0.257 mmol) and 20 (39.1 mg, 0.257 mmol) in acetonitrile (6 mL), degassed and purged with nitrogen for 10 min, was added cesium carbonate (167.4 mg, 0.513 mmol) and Pd(PPh₃) (14.8 mg, 0.0128 mmol), again degassed and purged with nitrogen for 15 min, and the RM heated to 85° C. overnight in a sealed tube. After completion of the SM, the RM was cooled to rt and diluted with chloroform and the organic layer was passed through celite bed. The organic layer was completely distilled off the solvent to get the crude product which was passed through 100-200 mesh silica gel eluting the pure compound at 10-11% ethyl acetate in hexane as off white solid compound 105.

Step 3:
To a stirred solution of 105 (45 mg, 0.0978 mmol) in methanol (15 mL) and water (5 mL) was added potassium carbonate (26.9 mg, 0.1949 mmol) and the RM heated to 60° C. overnight. After completion of the SM, methanol was completely distilled off and the RM diluted with water and extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 106. 1H NMR (CDCl3) δ: 8.95 (s, 1H), 8.38 (d, 1H), 7.34 (d, 1H), 7.30 (m, 1H), 7.23 (d, 1H), 7.06 (d, 1H), 6.96 (m, 2H), 6.62 (m, 2H), 6.51 (m, 1H) 3.29 (s, 3H); and MS m/z=306.8.

Preparation of Example 36: 3-(2-methoxypyridin-3-yl)-4-(thiophen-3-yl)-1H-pyrrolo[2,3-b]pyridine (70, ARN-3088)

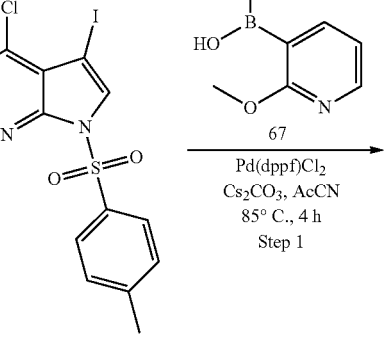

16      67

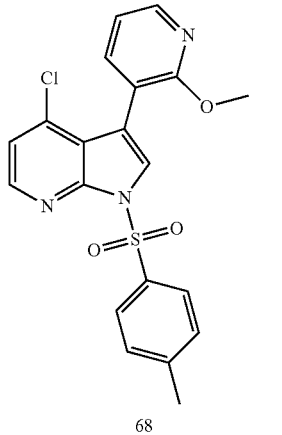

68

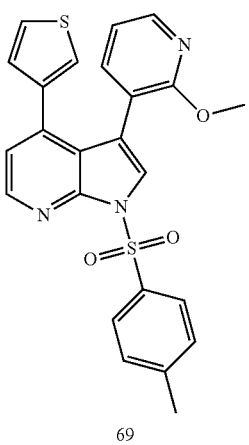

69

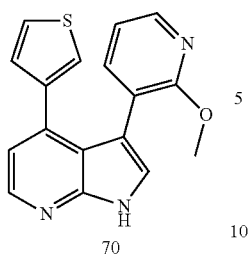

70

Step 1:

To a stirred solution of 16 (150 mg, 0.346 mmol) and 67 (53 mg 0.346 mmol) in acetonitrile (6 mL), degassed and purged with nitrogen for 10 min, was added cesium carbonate 225 mg, (0.693 mmol) and Pd(dppf)Cl₂ (14 mg 0.0173 mmol), again degassed and purged with nitrogen again for 15 min and the RM was heated to 85° C. for 4 hr in a sealed tube. After completion of the reaction the RM was cooled to rt and diluted with chloroform (50 mL) and filtered through celite bed. The organic layer was completely distilled off to get the crude which was passed through 100-200 mesh silica gel eluting the pure compound 68 at 7-8% ethyl aceate in hexane as off white colored solid.

Step 2:

To a stirred solution of 68 (130 mg, 0.314 mmol) and 22 (45 mg 0.345 mmol) in acetonitrile (7 mL), degassed and purged with nitrogen for 10 min, was added cesium carbonate (205 mg, 0.628 mmol) and Pd(pph3)4 (18 mg, 0.0157 mmol), again degassed and purged with nitrogen for 15 min, and heated to 85° C. overnight in a sealed tube. After completion of the SM, the RM was cooled to rt and diluted with chloroform (50 mL) and the organic layer was passed through celite bed. The organic layer was completely distilled off the solvent to get the crude product which was passed through 100-200 mesh silica gel eluting the pure compound 69 at 10-11% ethyl acetate in hexane as off white solid.

Step 3:

To a stirred solution of 69 (50 mg, 0.108 mmol) in methanol (10 mL) and water (5 mL) was added potassium carbonate (30 mg, 0.216 m mol) and heated to 60° C. overnight. After completion of the SM, methanol was completely distilled off and the RM diluted with water and extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 70. 1H NMR (CDCl3) δ: 9.05 (1-H), 8.35 (d, J=4.87 1-H), 8.04 (m, j=3.04 1-H), 7.41 (m, J=1.95 2-H), 7.12 (d, J=4.87 1-H), 7.07 (m, J=3.04 1-H), 6.90 (m, J=5.36 2-H), 6.79 (m, J=5.12 1-H), 3.49 (s, 1-H), and MS m/z=307.9.

Preparation of Example 37: 4-(3-(4-(thiophen-3-yl)-1H-pyrrolo[2,3-b]pyridin-3-yl)pyridin-2-yl)morpholine (74)

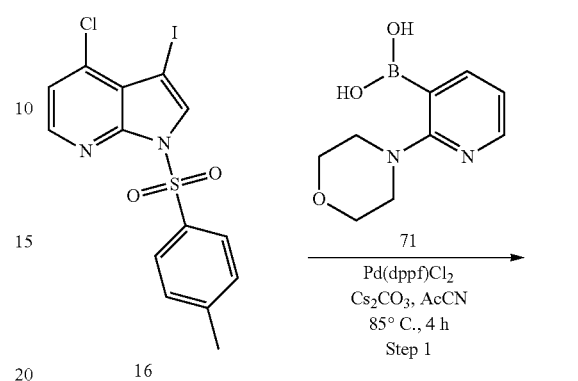

16     71

Pd(dppf)Cl₂
Cs₂CO₃, AcCN
85° C., 4 h
Step 1

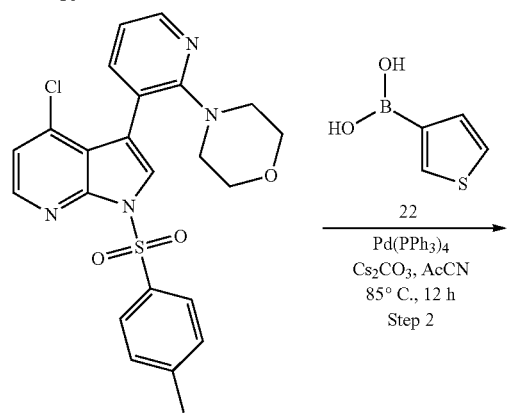

72     22

Pd(PPh₃)₄
Cs₂CO₃, AcCN
85° C., 12 h
Step 2

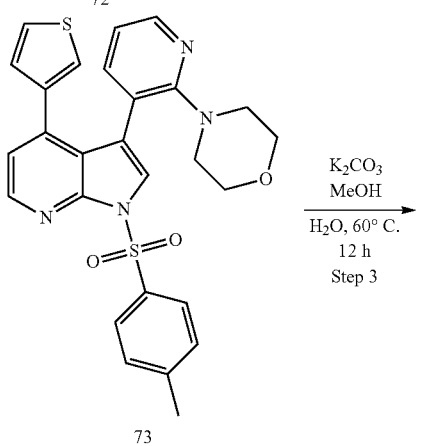

73

K₂CO₃
MeOH
H₂O, 60° C.
12 h
Step 3

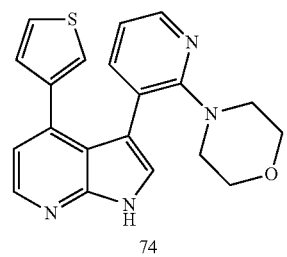

74

Step 1:

To a stirred solution of 16 (150 mg, 0.346 mmol) and 71 (72 mg, 0.346 mmol) in acetonitrile (6 mL), degassed and purged with nitrogen for 10 min, was added cesium carbonate (225 mg, 0.693 mmol) and Pd(dppf)Cl$_2$ (14 mg, 0.0173 mmol), again degassed and purged with nitrogen again for 15 min and heated to 85° C. for 4 hr in a sealed tube. After completion of the reaction, the RM was cooled to rt and diluted with chloroform (50 mL) and filtered through celite bed. The organic layer was completely distilled off to get the crude which was passed through 100-200 mesh silica gel eluting the pure compound at 7-8% ethyl aceate in hexane as off white colored solid compound 72.

Step 2:

To a stirred solution of 72 (100 mg, 0.213 mmol) and 22 (30 mg 0.345 mmol) in acetonitrile (7 mL), degassed and purged with nitrogen for 10 min, was added cesium carbonate (139 mg, 0.426 mmol) and Pd(PPh$_3$)$_4$ (12 mg, 0.0106 mmol), again degassed and purged with nitrogen for 15 min, and heated to 85° C. overnight in a sealed tube. After completion of the SM, the RM was cooled to rt and diluted with chloroform (50 mL) and the organic layer was passed through celite bed. The organic layer was completely distilled off the solvent to get the crude product which was passed through 100-200 mesh silica gel eluting the pure compound at 10-11% ethyl acetate in hexane as off white solid compound 73.

Step 3:

To a stirred solution of 73 (40 mg, 0.0774 mmol) in methanol (10 mL) and water (5 mL) was added potassium carbonate (22 mg, 0.154 mmol), then heated to 60° C. overnight. After completion of the SM, methanol was completely distilled off and the RM diluted with water then extracted with chloroform twice. The organic layer was dried over sodium sulphate and completely distilled off to get the crude product which was passed through 100-200 mesh silica gel eluting the pre compound at 25-20% ethyl acetate in hexane as eluent to get the pale yellow colored solid compound 74. 1H NMR (CDCl3) δ: 11.98 (1-H), 8.28 (d, J=4.87 1-H), 8.08 (M, J=2.92 1-H), 7.61 (d, J=2.56 1-H), 7.55 (m, J=5.48 1-H), 7.24 (m, J=2.92 1-H) 7.14 (d, J=4.87 1-H), 6.94 (m, J=4.87 3-H), 3.33 (s, 4-H), 3.07 (s, 4-H) and MS m/z=362.9.

Preparation of Example 47: 3-(3-chlorophenyl)-4-(thiophen-3-yl)-1H-pyrrolo[2,3-b]pyridine (110, ARN-3111)

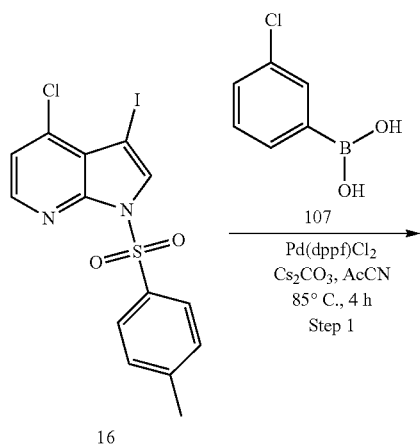

Step 1:

To a stirred solution of 16 (150 mg, 0.343 mmol) and 107 (88 mg, 0.343 mmol) in acetonitrile (7 mL), degassed and purged with nitrogen for 10 min, was added cesium carbonate (223 mg, 0.686 mmol) and Pd(dppf)Cl$_2$ (14 mg, 0.0171 mmol), again degassed and purged with nitrogen for 15 min, and the RM heated to 85° C. for 4 hr in a sealed tube. After completion of the reaction the RM was cooled to rt, diluted with chloroform and filtered through celite bed. The organic layer was completely distilled off to get the crude which was passed through 100-200 mesh silica gel eluting the pure compound at 7-8% ethyl aceate in hexane as off white colored solid compound 108.

Step 2:

To a stirred solution of 108 (100 mg, 0.239 mmol) and 22 (31 mg, 0.240 mmol) in acetonitrile (7 mL), degassed and purged with nitrogen for 10 min, was added cesium carbonate (155 mg, 0.475 mmol) and Pd(PPh$_3$)$_4$ (10 mg, 0.019 mmol), again degassed and purged with nitrogen for 15 min, and the RM heated to 85° C. overnight in a sealed tube. After completion of the SM, the RM was cooled to rt, diluted with chloroform and the organic layer passed through celite bed. The organic layer was completely distilled off the solvent to get the crude product which was passed through 100-200 mesh silica gel eluting the pure compound 109 at 10-11% ethyl acetate in hexane as off white solid.

Step 3:

To a stirred solution of 109 (45 mg, 0.097 mmol) in methanol (10 mL) and water (10 mL) was added potassium carbonate (40 mg, 0.29 mmol) and the RM heated to 60° C. overnight. After completion of the SM, methanol was completely distilled off and the RM diluted with water, then extracted with chloroform twice. The organic layer was dried over sodium sulphate and completely distilled off to get the crude product, which was passed through 100-200 mesh silica gel eluting the pre compound at 25-20% ethyl acetate in hexane as eluent to get the pale yellow colored solid compound 110. $^1$H NMR (CDCl3) δ: 9.18 (s, 1H), 8.41 (m, 1H), 7.39 (m, 1H), 7.13 (m, 6H), 6.89 (m, 2H), and MS m/z=310.8.

Preparation of Example 86: 3-(2,4-dimethoxyphenyl)-4-(thiophen-3-yl)-1H-pyrrolo[2,3-b]pyridine (114)

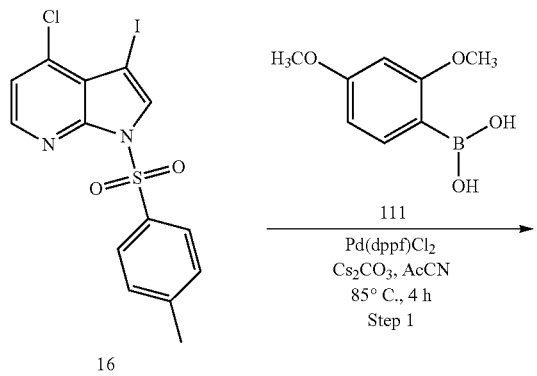

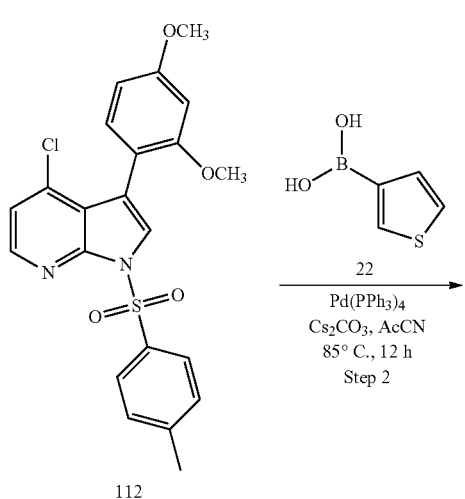

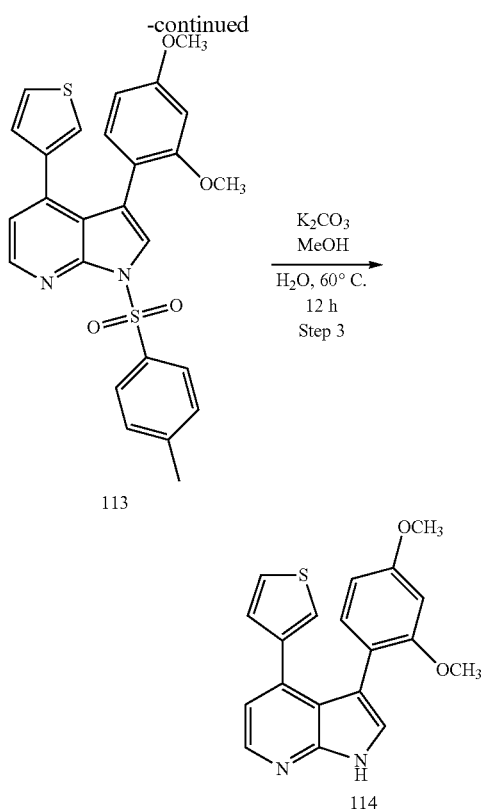

Step 1:

To a stirred solution of 16 (150 mg, 0.347 mmol) and 111 (59 mg, 0.347 mmol) in acetonitrile (7 mL), degassed and purged with nitrogen for 10 min, was added cesium carbonate (228 mg, 0.694 mmol) and Pd(dppf)Cl$_2$ (14 mg, 0.0173 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 10-11% ethyl aceate in hexane as off white colored solid compound 112.

Step 2:

To a stirred solution of 112 (100 mg, 0.339 mmol) and 22 (44 mg, 0.339 mmol) in acetonitrile (7 mL), degassed and purged with nitrogen for 10 min, was added cesium carbonate (229 mg, 0.678 mmol) and Pd(PPh$_3$)$_4$ (20 mg, 0.017 mmol), and again degassed and purged with nitrogen for 15 min. Then the RM was heated to 85° C. overnight in a sealed tube. After completion of the SM, the RM was cooled to rt and diluted with chloroform and the organic layer was passed through celite bed. The organic layer was completely distilled off to get the crude product, which was passed through 100-200 mesh silica gel eluting the pure compound in 11-13% ethyl acetate and hexane as off white solid compound 113.

Step 3:

To a stirred solution of 113 (40 mg, 0.0816 mmol) in methanol (10 mL) and water (10 mL) was added potassium carbonate (28 mg, 0.204 mmol). The RM was heated to 60° C. overnight. After completion of the SMs, the solvent methanol was completely distilled off and diluted with water extracted with chloroform twice. The organic layer was dried over sodium sulphate and the solvents removed to get the crude product, which was passed through 100-200 mesh silica gel eluting the compound at 25-20% ethyl acetate in hexane as eluent to get the pale yellow colored solid compound 114. $^1$H NMR (CDCl$_3$) δ: 9.06 (s, 1H), 8.32 (d, 1H), 7.30 (d, 1H), 7.12 (m, 2H), 7.07 (m, 1H), 6.94 (m, 1H), 6.90 (m, 1H), 6.44 (m, 1H), 6.16 (d, 1H), 3.82 (s, 3H), 3.24 (s, 3H). MS/Mz: 337.2.

Preparation of Example 87: 3-(2,4-difluorophenyl)-4-(thiophen-3-yl)-1H-pyrazolo[3,4-b]pyridine (48)

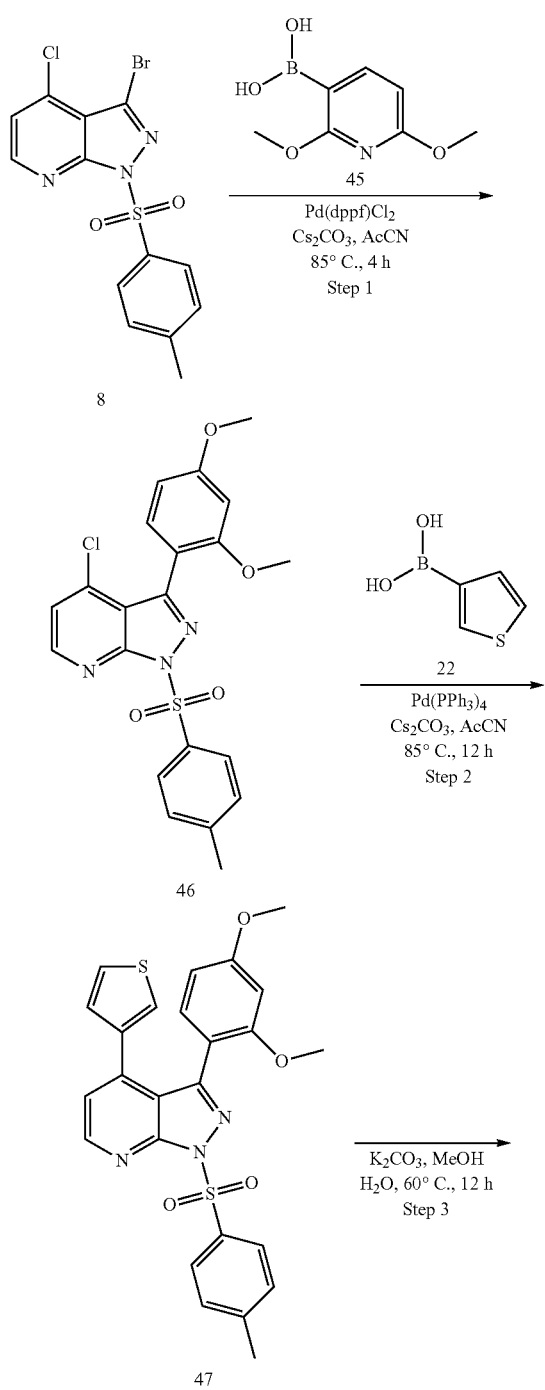

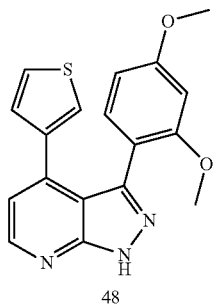

Step 1:

To a stirred solution of compound 8 (150 mg, 0.387 mmol) and 45 (66 mg, 0.387 mmol) in acetonitrile (5 mL), degassed and purged with nitrogen for 10 min, was added Cs$_2$CO$_3$ (253 mg 0.775 mmol) and Pd(dppf)Cl$_2$ (15 mg 0.0193 mmol). The resulting RM was degassed, purged with nitrogen again for 15 min and heated to 85° C. for 4 hr in a sealed tube. After completion of the reaction, it was cooled to rt and diluted with chloroform and filtered through celite bed. The organic layer was completely distilled off to get the crude compound 46. The crude was passed through 100-200 mesh silica gel, eluting the pure compound at 7-8% ethyl acetate in hexane as off white colored solid 46.

Step 2:

To a stirred solution of 46 (60 mg, 0.2135 mmol) and compound 22 (20 mg, 0.148 mmol) in acetonitrile (5 mL), degassed and purged with nitrogen for 10 min, was added Cs$_2$CO$_3$ (88 mg, 0.79 mmol) and Pd(PPh3)$_4$ (8 mg, 0.00675 mmol) and continued degassing and purging with nitrogen for another 15 min. The resulting RM was heated to 85° C. overnight or 12 hrs in a sealed tube. After completion of the SM monitored from TLC, the RM was cooled to rt and diluted with chloroform and the organic layer was passed through celite bed. The organic layer was completely distilled off to get the crude product 47. The crude product was passed through 100-200 mesh silica gel eluting the pure compound 47 at 10-11% ethyl acetate in hexane as off white solid compound.

Step 3:

To a stirred solution of compound 47 (40 mg, 0.0813 mmol) in methanol (10 mL) and water (5 mL) was added K$_2$CO$_3$ (22 mg, 0.162 mmol) and heated to 60° C. for 12 hr. After completion of the SM, the solvents were removed, diluted with water and extracted with chloroform in two volumes. The organic layer was dried over sodium sulphate. The crude material was passed through 100-200 mesh silica gel eluting the compound at 28-30% ethyl acetate in hexane as eluent to get the pale yellow colored solid of compound 48. $^1$H NMR (CDCl3) δ: 10.65 (s, 1H), 8.54 (d, 1H), 7.52 (s, 1H), 7.39 (m, 2H), 7.13 (m, 2H), 6.55 (m, 1H), 6.19 (d, 1H), 3.85 (s, 3H), 3.18 (s, 3H) and MS m/z=338.3

215

Preparation of Example 90: N,N-dimethyl-3-(4-(thiophen-3-yl)-1H-pyrrolo[2,3-b]pyridin-3-yl)benzenesulfonamide (177)

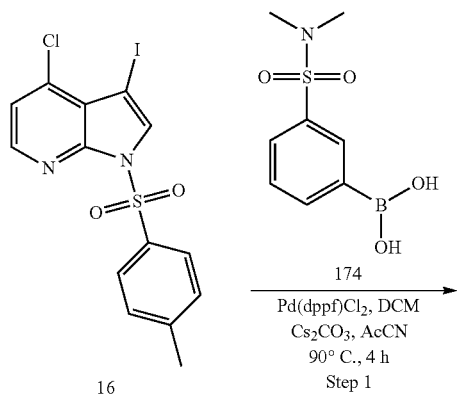

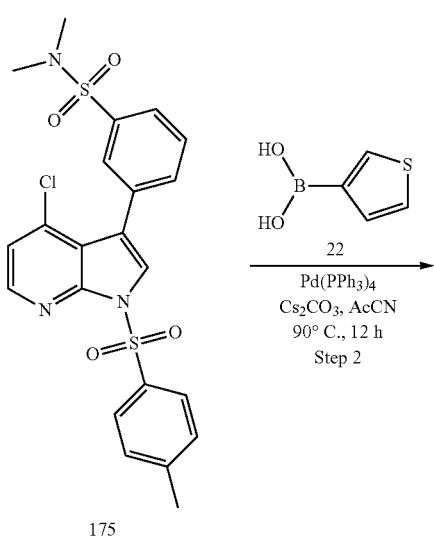

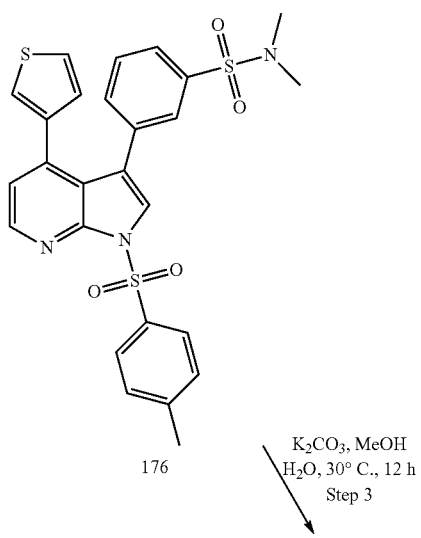

216

-continued

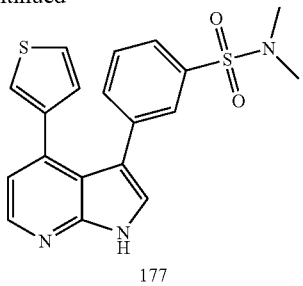

177

Step 1

To a stirred solution of 115 (150 mg, 0.347 mmol) and 174 (79 mg, 0.347 mmol) in acetonitrile (10 mL), degassed and purged with nitrogen for 10 min, was added cesium carbonate (226 mg 0.694 mmol) and Pd(dppf)Cl$_2$ (14 mg, 0.017 mmol), again degassed and purged with nitrogen for 15 min and the RM heated to 85° C. for 4 hr in a sealed tube. After completion of the reaction, the RM was cooled to rt and diluted with chloroform and filtered through celite bed. The organic layer was completely distilled off to get the crude, which was passed through 100-200 mesh silica gel eluting the pure compound at 5% ethyl aceate in hexane as off white colored solid compound 175.

Step 2

To a stirred solution of 175 (100 mg, 0.204 mmol) and 22 (26 mg, 0.204 mmol) in acetonitrile (10 mL), degassed and purged with nitrogen for 10 min, was added cesium carbonate (133 mg, 0.408 mmol) and Pd(dppf)Cl$_2$ (8 mg, 0.0102 mmol), again degassed and purged with nitrogen for 15 min and the RM heated to 85° C. for 4 hr in a sealed tube. After completion of the reaction, the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 176.

Step 3

To a stirred solution of 177 (45 mg, 0.0773 mmol) in methanol (15 mL) was added water (10 mL) and potassium carbonate (26 mg 0.193 mmol) and the RM heated to 60° C. overnight after completion of the SM, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 177.
$^1$H NMR (CDCl$_3$) δ: 9.09 (1-H), 8.39 (d, J=4.75 1H), 7.55 (m, J=6.9 3-H), 7.52 (m, J=14.39 1-H), 7.20 (d, J=7.80 2-H), 7.16 (m, J=4.87 2-H), 7.07 (m, J=11.58 1-H), 6.84 (d, J=4.87 1-H), 2.67 (6-H) and MS m/z=383.2 (M+H)$^+$.

Preparation of Example 91: N-(tert-butyl)-N-methyl-3-(4-(thiophen-3-yl)-1H-pyrrolo[2,3-b]pyridin-3-yl)benzenesulfonamide (181)

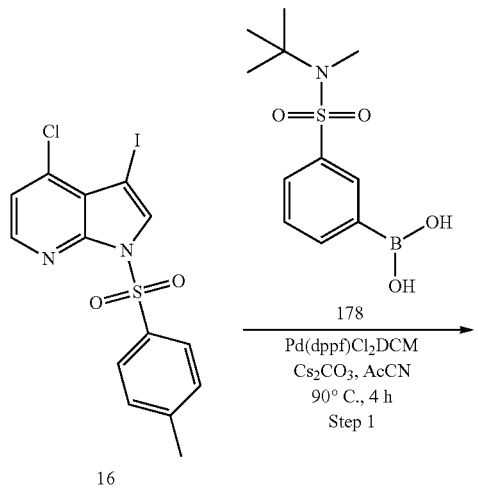

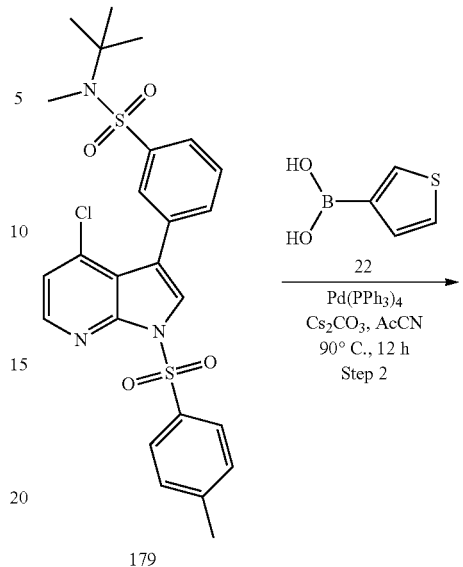

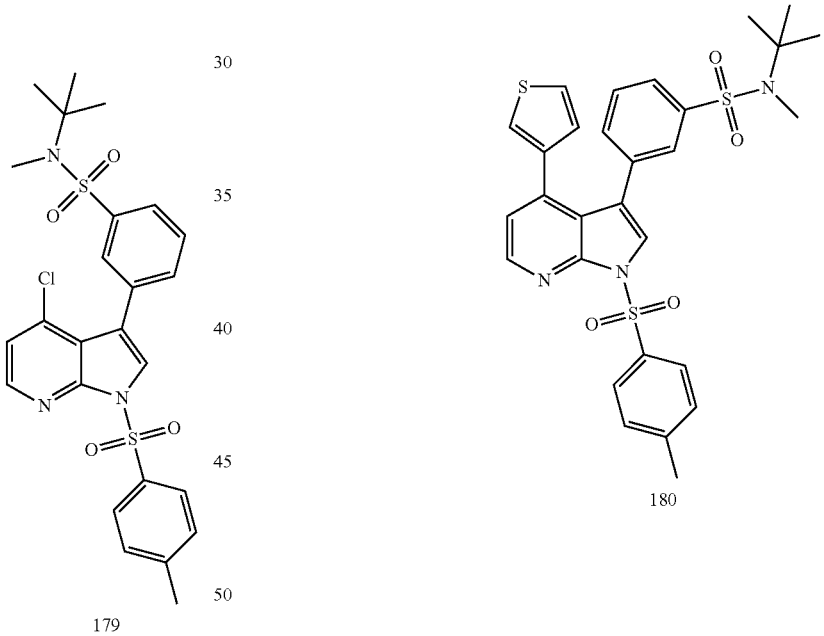

Step 1:

To a stirred solution of 16 (150 mg, 0.347 mmol) and 178 (94 mg, 0.347 mmol) in acetonitrile (5 mL), degassed and purged with nitrogen for 10 min, was added cesium carbonate (228 mg, 0.694 mmol) and Pd(dppf)Cl$_2$ (14.1 mg, 0.0173 mmol), again degassed and purged with nitrogen for 15 min and the RM heated to 85° C. for 4 hr in a sealed tube. After completion of the reaction, the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 179.

Step 2:

To a stirred solution of 179 (80 mg, 0.150 mmol) and 22 (21 mg, 0.165 mmol) in acetonitrile (5 mL), degassed and purged with nitrogen for 10 min, was added cesium carbonate and Pd(dppf)Cl$_2$, again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude, which was passed through 100-200 mesh silica gel eluting the pure compound at 5% ethyl aceate in hexane as off white colored solid compound 180.

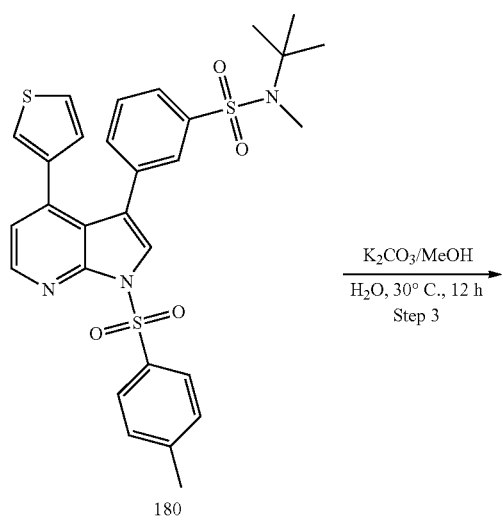

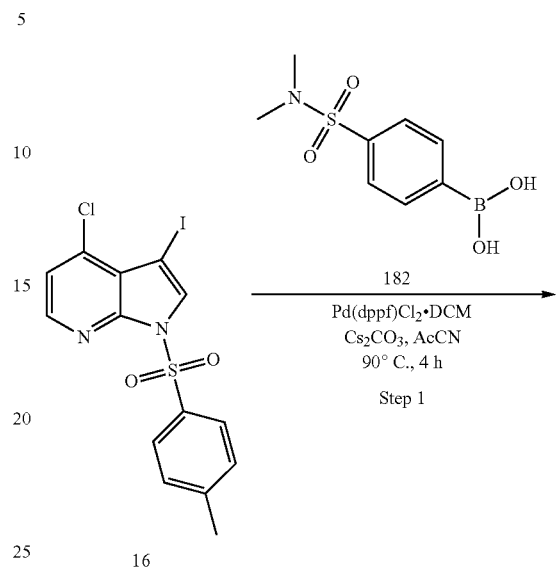

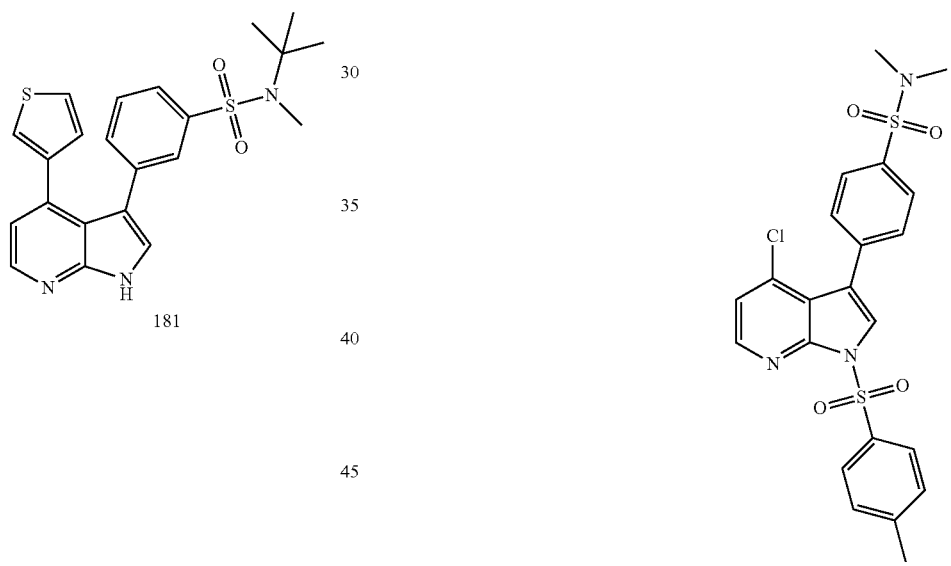

Preparation of Example 92: N,N-dimethyl-4-(4-(thiophen-3-yl)-1H-pyrrolo[2,3-b]pyridin-3-yl)benzenesulfonamide (185)

Step 3:

To a stirred solution of 180 (80 mg, 0.138 mmol) in methanol (15 mL) was added water (10 mL) and potassium carbonate (47 mg 0.345 mmol) and the RM heated to 60° C. overnight. After completion of the SM, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 181. $^1$H NMR (CDCl$_3$) δ: 12.17 (1H), 8.31 (d, J=4.26 1H), 7.72 (s, 1-H), 7.52 (m, J=8.04 2-H), 6.95 (m, J=7.56, 6H), 2.85 (s, 3H), 1.25 (s, 9H), MS m/z=426.3 (M+H)$^+$.

Step 1:

To a stirred solution of 16 (150 mg, 0.347 mmol) and 182 (79.5 mg, 0.347 mmol) in acetonitrile (5 mL), degassed and purged with nitrogen for 10 min, was added cesium carbonate (226 mg, 0.695 mmol) and Pd(dppf)Cl$_2$ (14 mg, 0.0173 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 183.

221 222

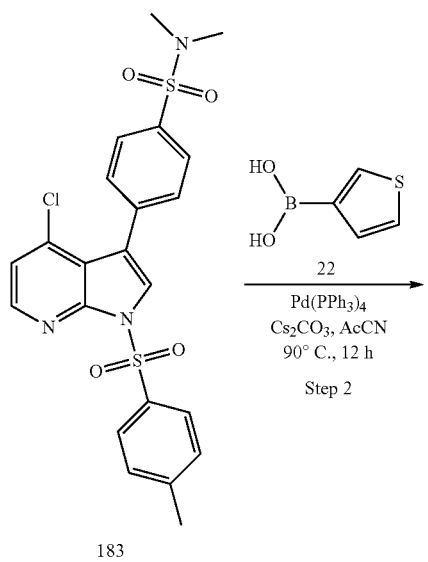

183

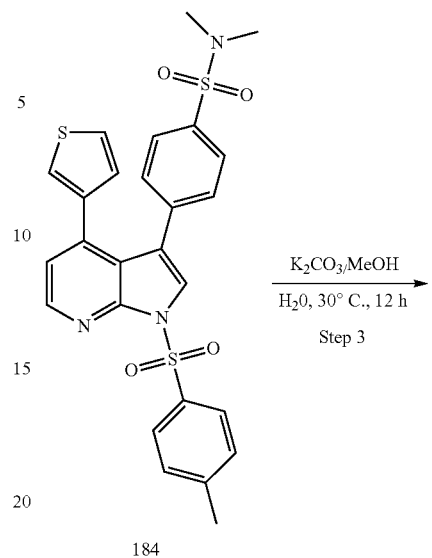

184

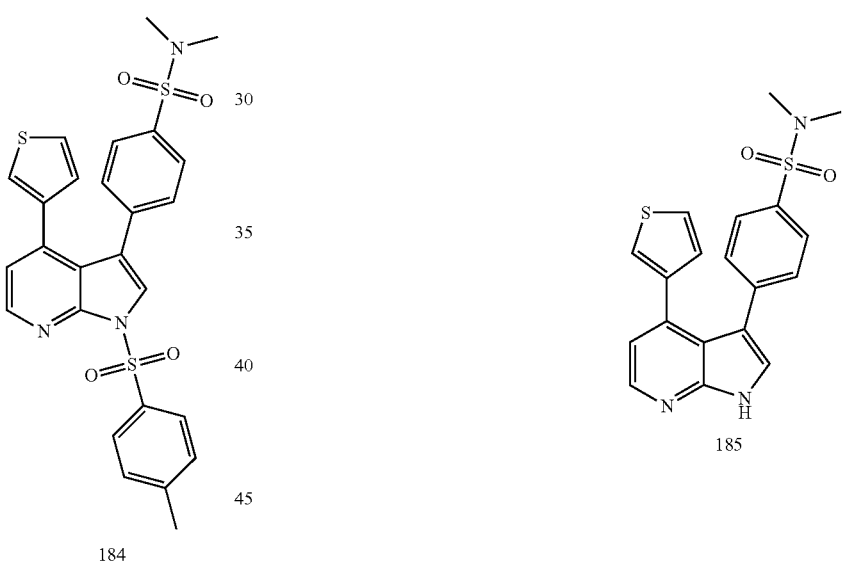

184 185

Step 2:

To a stirred solution of 183 (120 mg, 0.255 mmol) and 22 (49 mg, 0.384 mmol) in acetonitrile (5 mL), degassed and purged with nitrogen for 10 min, was added cesium carbonate (166 mg, 0.512 mmol) and Pd(dppf)Cl$_2$ (10 mg, 0.0127 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 184.

Step 3:

To a stirred solution of 184 (40 mg, 0.0744 mmol) in methanol (15 mL) was added water (10 mL) and potassium carbonate (25 mg, 0.186 mmol) and the RM heated to 60° C. overnight. After completion of the SM, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 185.
$^1$H NMR (CDCl$_3$) δ: 9.25 (1-H), 8.41 (d, J=4.87 1-H), 7.51 (m, J=8.4 2-H), 7.45 (d, J=2.56 1-H), 7.17 (m, J=5.00 3-H), 7.10 (m, J=3.04 1-H), 6.98 (m, J=4.14 1-H), 6.88 (m, J=4.87 1-H), 2.72 (S, 6-H) and MS m/z=383.9 (M+H)$^+$.

Preparation of Example 93: N,N-diethyl-3-(4-(thiophen-3-yl)-1H-pyrrolo[2,3-b]pyridin-3-yl)benzenesulfonamide (189)

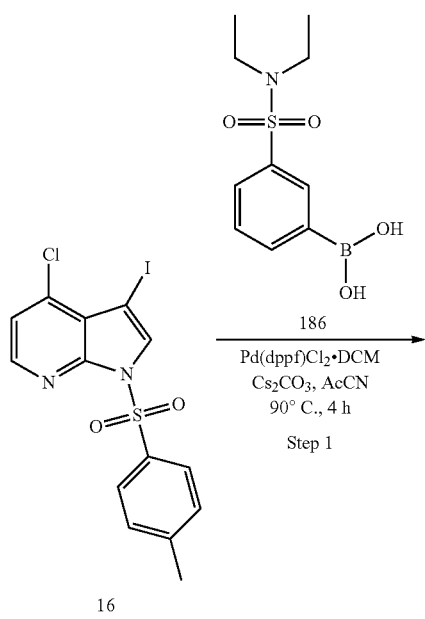

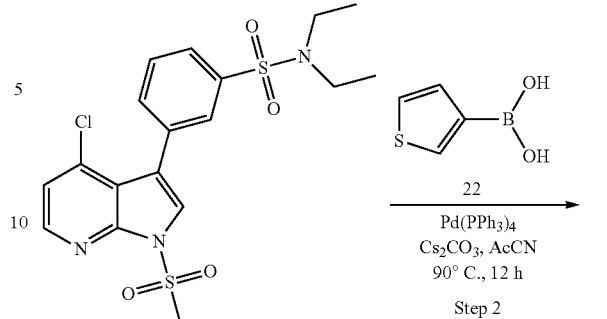

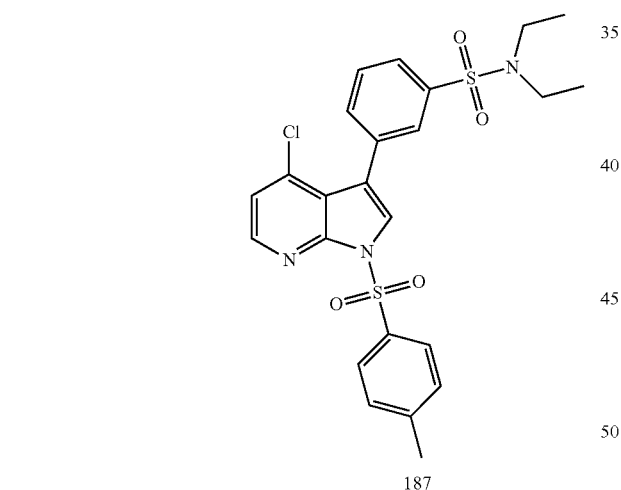

Step 1:
To a stirred solution of 16 (150 mg, 0.347 mmol) and 186 (89 mg, 0.347 mmol) in acetonitrile (5 mL), degassed and purged with nitrogen for 10 min, was added cesium carbonate (226 mg, 0.694 mmol) and Pd(dppf)Cl₂ (14 mg, 0.0173 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 187.

Step 2:
To a stirred solution of 187 (100 mg, 0.198 mmol) and 22 (64 mg, 0.198 mmol) in acetonitrile (5 mL), degassed and purged with nitrogen for 10 min, was added cesium carbonate (129 mg, 0.396 mmol) and Pd(dppf)Cl₂ (6 mg, 0.0079 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 188.

225

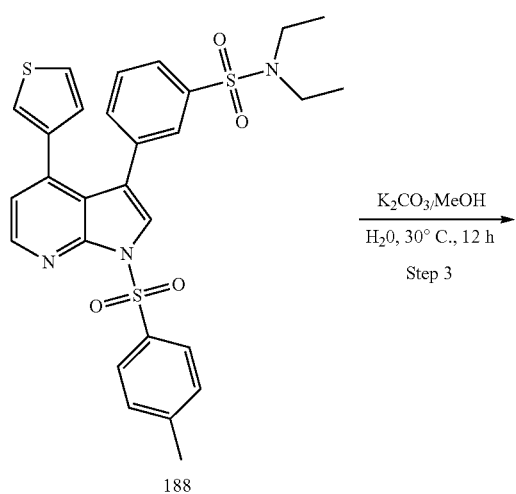

188

K₂CO₃/MeOH
────────────→
H₂O, 30° C., 12 h
Step 3

189

Step 3:

To a stirred solution of 188 (60 mg, 0.1087 mmol) in methanol (10 mL) was added water (5 mL) and potassium carbonate (45 mg, 0.326 mmol) and the RM heated to 60° C. overnight. After completion of the SM, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 189. ¹H NMR (CDCl₃) δ: 9.45 (1-H), 8.40 (S, 1-H), 7.68 (S, 1-H), 7.57 (d, J=43.1, 1-H), 7.43 (S, 1-H), 7.17 (m, J=42.56, 2-H), 6.98 (m, J=18.41, 3-H), 6.85 (d, J=52.1, 1-H), 3.21 (m, J=6.95, 4-H), 1.13 (S, 6-H) and MS m/z=412.3 (M+H)⁺.

226

Preparation of Example 94: N,N-dimethyl-2-(4-(thiophen-3-yl)-1H-pyrrolo[2,3-b]pyridin-3-yl)benzenesulfonamide (193)

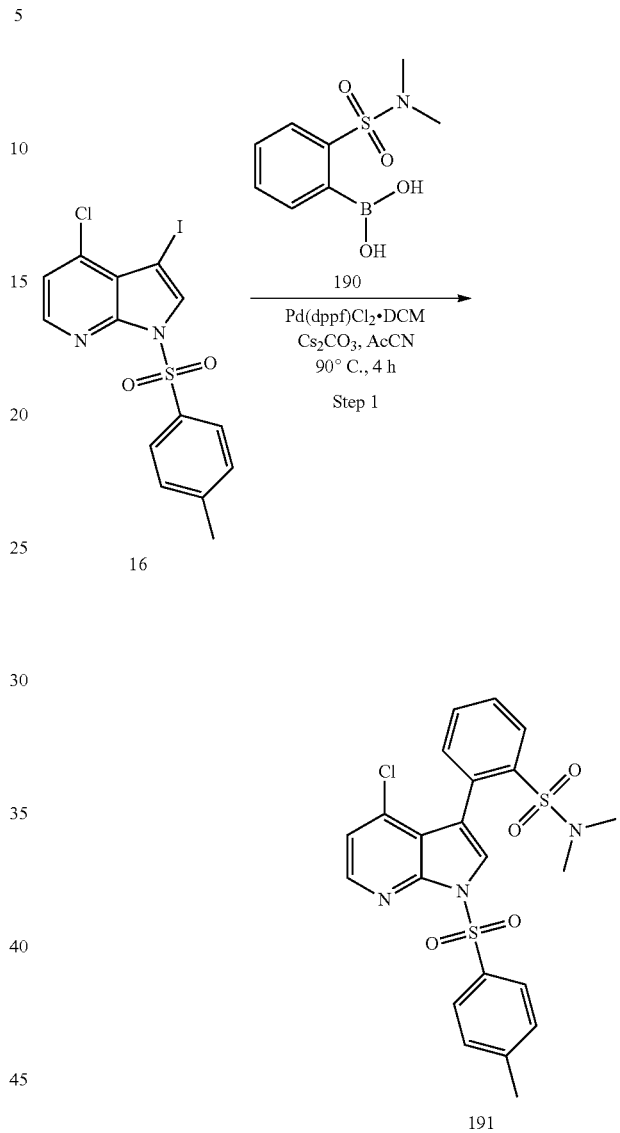

Step 1:

To a stirred solution of 16 (150 mg, 0.347 mmol) and 190 (79 mg, 0.347 mmol) in acetonitrile (5 mL), degassed and purged with nitrogen for 10 min, was added cesium carbonate (226 mg, 0.694 mmol) and Pd(dppf)Cl₂ (14 mg, 0.0173 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude, which was passed through 100-200 mesh silica gel eluting the pure compound at 5% ethyl aceate in hexane as off white colored solid compound 190.

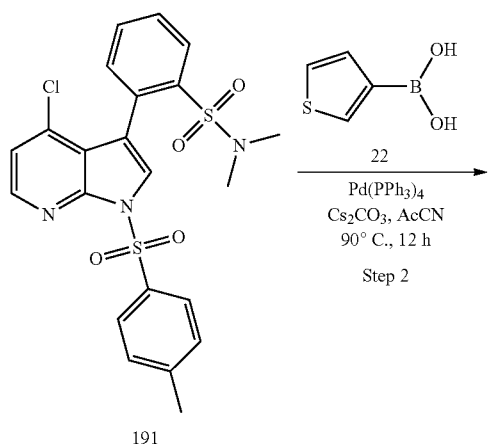

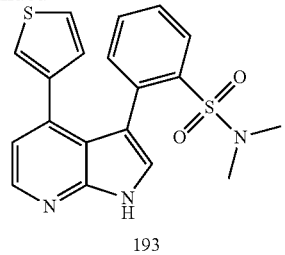

Step 2:

To a stirred solution of 191 (100 mg, 0.204 mmol) and 22 (26 mg, 0.204 mmol) in acetonitrile (5 mL), degassed and purged with nitrogen for 10 min, was added cesium carbonate (134 mg, 0.408 mmol) and Pd(dppf)Cl₂ (8 mg, 0.0101 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude, which was passed through 100-200 mesh silica gel eluting the pure compound at 5% ethyl aceate in hexane as off white colored solid compound 192.

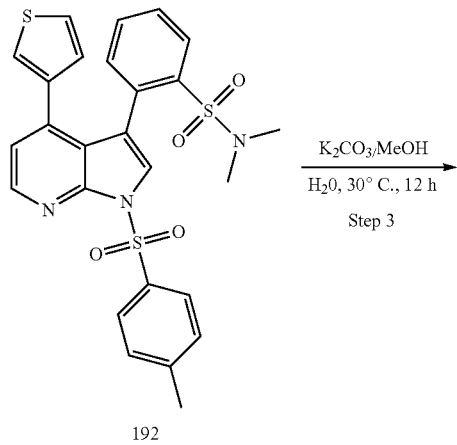

Step 3:

To a stirred solution of 192 (50 mg, 0.0931 mmol) in methanol (15 mL) was added water (10 mL) and potassium carbonate (32 mg, 0.232 mmol) and the RM heated to 60° C. overnight. After completion of the SM, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 193. ¹H NMR (CDCl3) δ: 9.41 (S, 1-H), 8.36 (d, J=5, 1-H), 7.85 (dd, J=6.7, 1-H), 7.6 (d, J=2.56, 1-H), 7.28 (m, J=6.21, 1-H), 7.12 (m, J=6.34, 2-H), 6.94 (m, J=2.92, 2-H), 6.89 (dd, J=6.34, 1-H), 6.81 (m, J=2.43, 1-H, 2.66 (S, 6-H) and MS m/z=384.2 (M+H)⁺.

Preparation of Example 95: N,N-diethyl-2-(4-(thiophen-3-yl)-1H-pyrrolo[2,3-b]pyridin-3-yl)benzenesulfonamide (197)

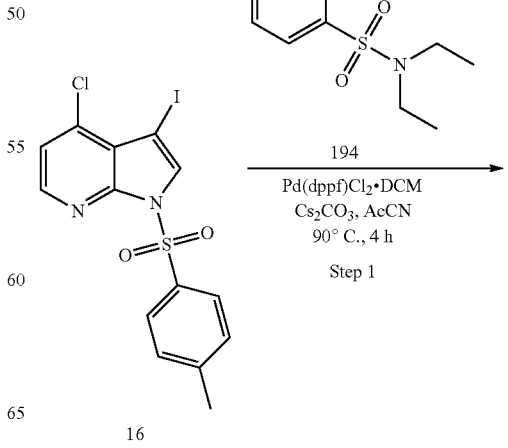

-continued

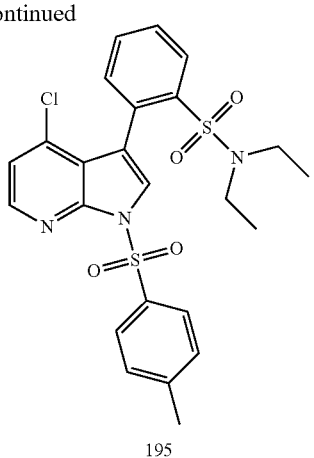

195

Step 1:

To a stirred solution of 16 (150 mg, 0.347 mmol) and 194 (89 mg, 0.347 mmol) in acetonitrile (5 mL), degassed and purged with nitrogen for 10 min, was added cesium carbonate (226 mg, 0.694 mmol) and Pd(dppf)Cl$_2$ (14 mg, 0.0173 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 195.

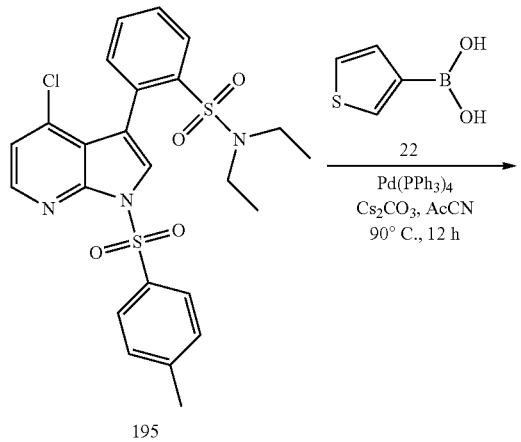

196

Step 2:

To a stirred solution of 195 (100 mg, 0.198 mmol) and 22 (64 mg, 0.198 mmol) in acetonitrile (5 mL), degassed and purged with nitrogen for 10 min, was added cesium carbonate (129 mg, 0.396 mmol) and Pd(dppf)Cl$_2$ (6 mg, 0.0079 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 196.

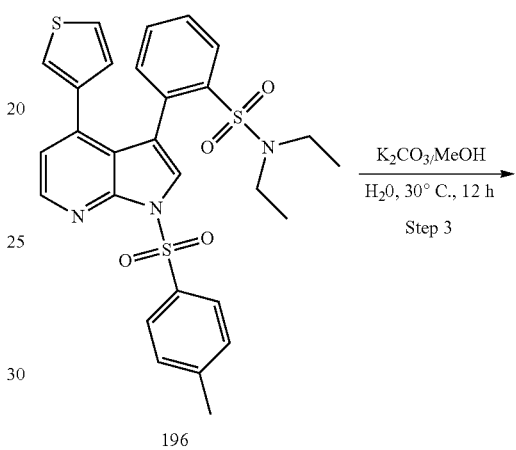

196

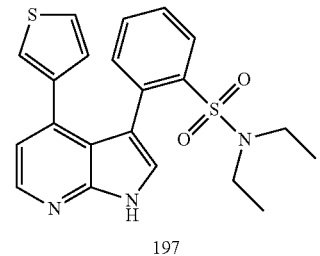

197

Step 3:

To a stirred solution of 196 (60 mg, 0.108 mmol) in methanol (10 mL) was added water (5 mL) and potassium carbonate (45 mg, 0.326 mmol) and the RM heated to 60° C. overnight. After completion of the SM, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 197. $^1$H NMR (CDCl3) δ: 9.00 (1H), 8.36 (d, J=5.0, 1-H), 7.78 (dd, J=7.92, 1H), 7.63 (d, J=63.04, 1H), 7.23 (m, J=7.92, 1-H), 7.07 (m, J=8.04 2H), 6.96 (m, J=1.7, 1H), 6.92 (m, J=2.92 1H), 6.83 (m, J=6.46, 2H), 3.2 (m, J=7.07, 4H), 1.11 (m, J=7.07, 6-H) and MS m/z=412.7 (M+H)$^+$.

Preparation of Example 96: 3-(4-(azetidin-1-ylsulfonyl)phenyl)-4-(thiophen-3-yl)-1H-pyrrolo[2,3-b]pyridine (201)

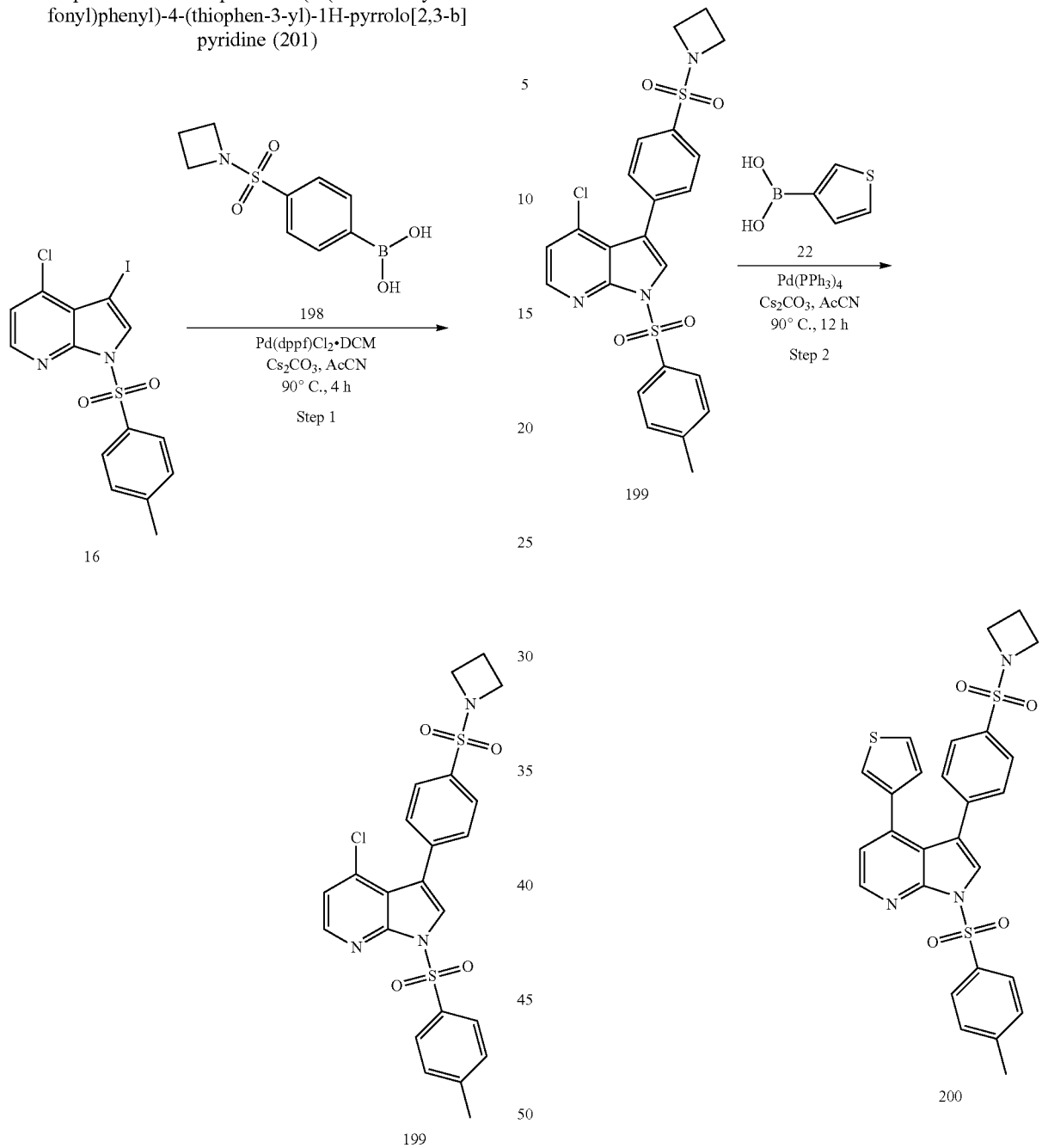

Step 1:

To a stirred solution of 16 (150 mg, 0.347 mmol) and 198 (83 mg, 0.347 mmol) in acetonitrile (5 mL), degassed and purged with nitrogen for 10 min, was added cesium carbonate (226 mg) and Pd(dppf)Cl₂ (14 mg, 0.0176 mmol), again degassed and purged with nitrogen for 15 min and the RM heated to 85° C. for 4 hr in a sealed tube. After completion of the reaction the RM was cooled to rt and diluted with chloroform and filtered through celite bed the organic layer was completely distilled off to get the crude product, which was passed through 100-200 mesh silica gel eluting the pure compound at 5% ethyl aceate in hexane as off white colored solid compound 199.

Step 2:

To a stirred solution of 199 (100 mg, 0.204 mmol) and 22 (26 mg, 0.204 mmol) in acetonitrile (5 mL) degassed and purged with nitrogen for 10 min, was added cesium carbonate (133 mg, 0.409 mmol) and Pd(dppf)Cl₂ (6 mg, 0.00819 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 200.

233 234

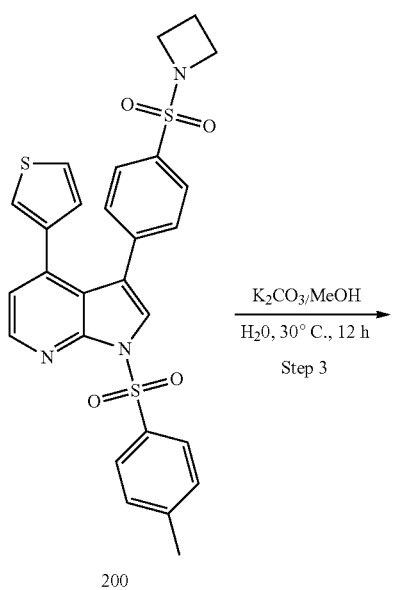

Preparation of Example 97: 3-(3-(pyrrolidin-1-yl-sulfonyl)phenyl)-4-(thiophen-3-yl)-1H-pyrrolo[2,3-b]pyridine (205)

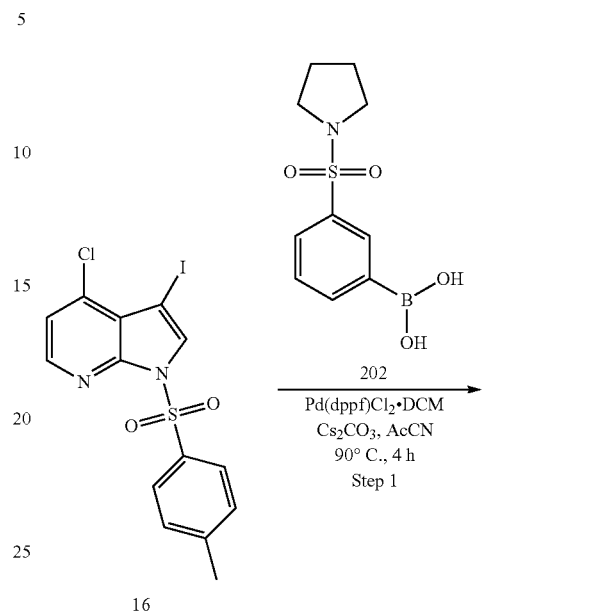

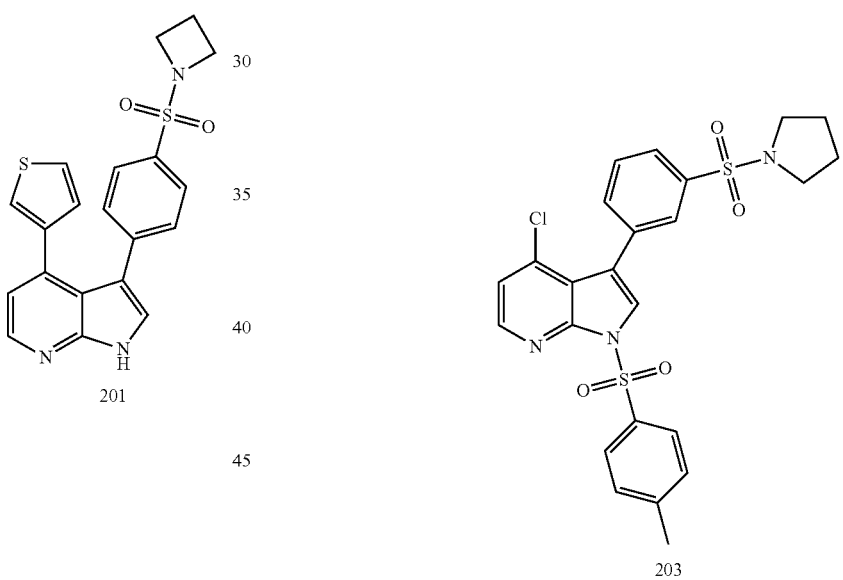

Step 3:

To a stirred solution of 200 (60 mg, 0.112 mmol) in methanol (10 mL) was added water (5 mL) and potassium carbonate (46 mg, 0.336 mmol) and the RM heated to 60° C. overnight. After completion of the reaction, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 201.
$^1$H NMR (CDCl3) δ: 9.30 (S, 1-H), 8.42 (d, J=353.77, 1-H), 7.58 (m, J=8.29 2-H), 7.2 (d, J=8.29, 1-H), 7.13 (m, J=21.21, 3-H), 7.11 (m, J=3.04, 1-H), 6.93 (m, J=4.74, 2-H) 3.79 (t, J=7.43, 4-H), 2.13 (m, J=7.56, 2-H) and MS m/z=396.3 (M+H)$^+$.

Step 1:

To a stirred solution of 16 (150 mg, 0.347 mmol) and 202 (88 mg, 0.347 mmol) in acetonitrile (5 mL), degassed and purged with nitrogen for 10 min, was added cesium carbonate (226 mg, 0.694 mmol) and Pd(dppf)Cl$_2$ (14 mg, 0.0176 mmol), again degassed and purged with nitrogen for 15 min and the RM heated to 85° C. for 4 hr in a sealed tube. After completion of the reaction the RM was cooled to rt and diluted with chloroform and filtered through celite bed the organic layer was completely distilled off to get the crude product, which was passed through 100-200 mesh silica gel eluting the pure compound at 5% ethyl aceate in hexane as off white colored solid compound 203.

235

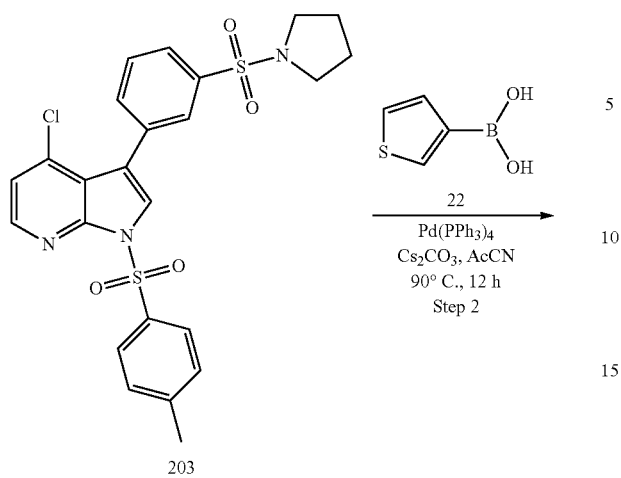

203

Step 2:

To a stirred solution of 203 (100 mg, 0.193 mmol) and 22 (24 mg, 0.193 mmol) in acetonitrile (5 mL), degassed and purged with nitrogen for 10 min, was added cesium carbonate (126 mg, 0.387 mmol) and Pd(dppf)Cl₂ (8 mg, 0.00968 mmol), again degassed and purged with nitrogen for 15 min and the RM was heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 204.

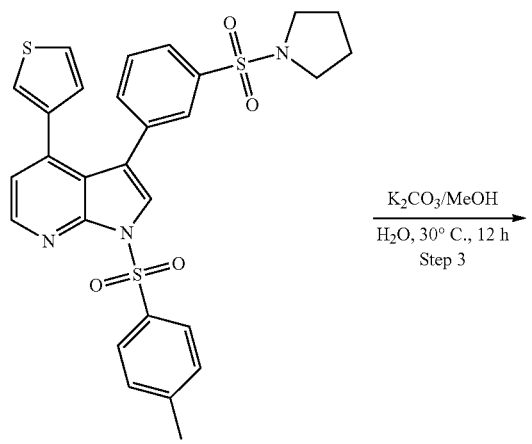

236

-continued

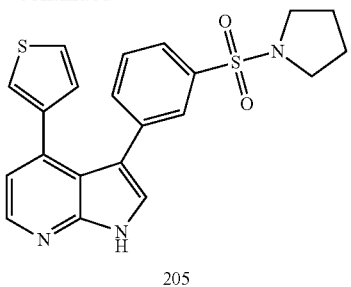

205

Step 3:

To a stirred solution of 204 (60 mg, 0.106 mmol) in methanol (10 mL) was added water (5 mL) and potassium carbonate (44 mg, 0.319 mmol) and heat the RM to 60° C. overnight. After completion of the SM, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 205. $^{1H}$ NMR (CDCl3) δ: 9.31 (1H), 8.40 (d, J=4.75 1H), 7.69 (s, 1H), 7.60 (m, J=7.56 1H), 7.43 (d, J=2.56 1H), 7.17 (m, J=6.95 2H), 7.07 (m, J=3.17 2H), 6.97 (m, J=2.19 1H), 6.84 (m, J=4.87 1H), 3.22 (m, J=6.70 4H), 1.77 (m, J=2.92 4H) and MS m/z=410.3 (M+H)⁺.

Preparation of Example 98: 3-(4-(pyrrolidin-1-yl-sulfonyl)phenyl)-4-(thiophen-3-yl)-1H-pyrrolo[2,3-b]pyridine (209)

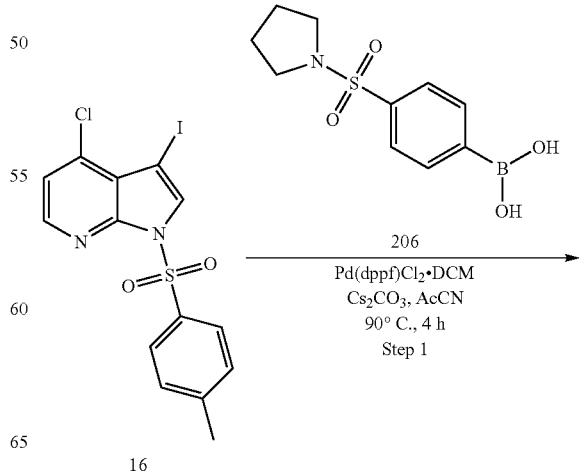

16

-continued

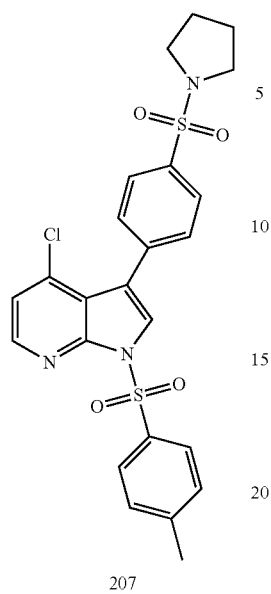

207

-continued

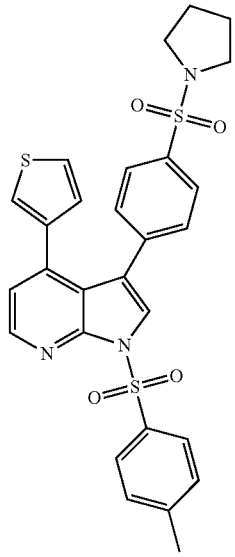

208

Step 1:

To a stirred solution of 16 (150 mg, 0.347 mmol) and 206 (88 mg, 0.347 mmol) in acetonitrile (5 mL) was degassed and purged with nitrogen for 10 min, was added cesium carbonate (226 mg, 0.694 mmol) and Pd(dppf)Cl$_2$ (14 mg, 0.0173 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 207.

Step 2:

To a stirred solution of 207 (100 mg, 0.193 mmol) and 22 (24 mg, 0.193 mmol) in acetonitrile (5 mL), degassed and purged with nitrogen for 10 min, was added cesium carbonate (126 mg, 0.387 mmol) and Pd(dppf)Cl$_2$ (8 mg, 0.00968 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 208.

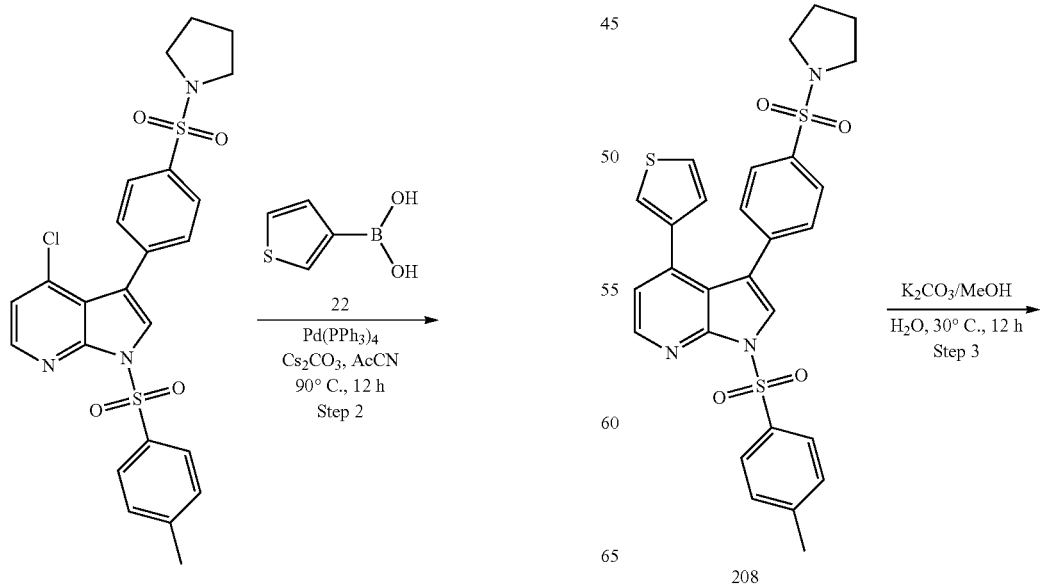

208

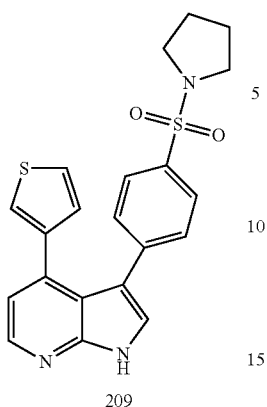

209

Step 3:

To a stirred solution of 208 (50 mg, 0.0886 mmol) in methanol (10 mL) was added water (5 mL) and potassium carbonate (36.8 mg, 0.265 mmol) and the RM heated to 60° C. overnight. After completion of the SM, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 209. $^1$H NMR (CDCl3) δ: 9.18 (s, 1H), 8.40 (d, J=5.00 1H), 7.56 (m, J=8.29 2-H), 7.45 (d, J=43.93 1-H), 7.16 (m, J=6.46 3H), 7.08 (m, J=3.04 1-H), 6.91 (m, J=4.63 2-H), 3.25 (m J=6.70 4-H) 1.82 (m J=6.58 4-H) and MS m/z=409.9 (M+H)$^+$.

Preparation of Example 99: 4-(thiophen-3-yl)-3-(2-(trifluoromethoxy)phenyl)-1H-pyrrolo[2,3-b]pyridine (213)

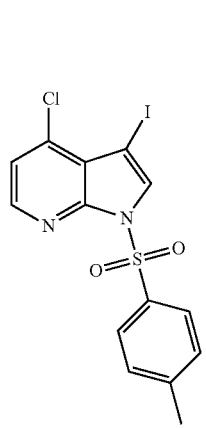

16

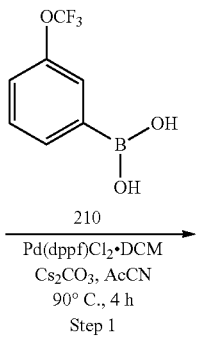

210

Pd(dppf)Cl$_2$·DCM
Cs$_2$CO$_3$, AcCN
90° C., 4 h
Step 1

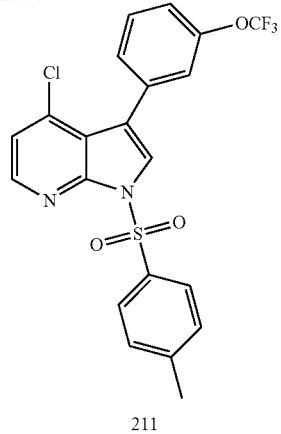

211

Step 1:

To a stirred solution of 16 (150 mg, 0.347 mmol) and 210 (48 mg, 0.347 mmol) in acetonitrile (5 mL), degassed and purged with nitrogen for 10 min, was added cesium carbonate (226 mg, 0.694 mmol) and Pd(dppf)Cl$_2$ (14 mg, 0.0173 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 211.

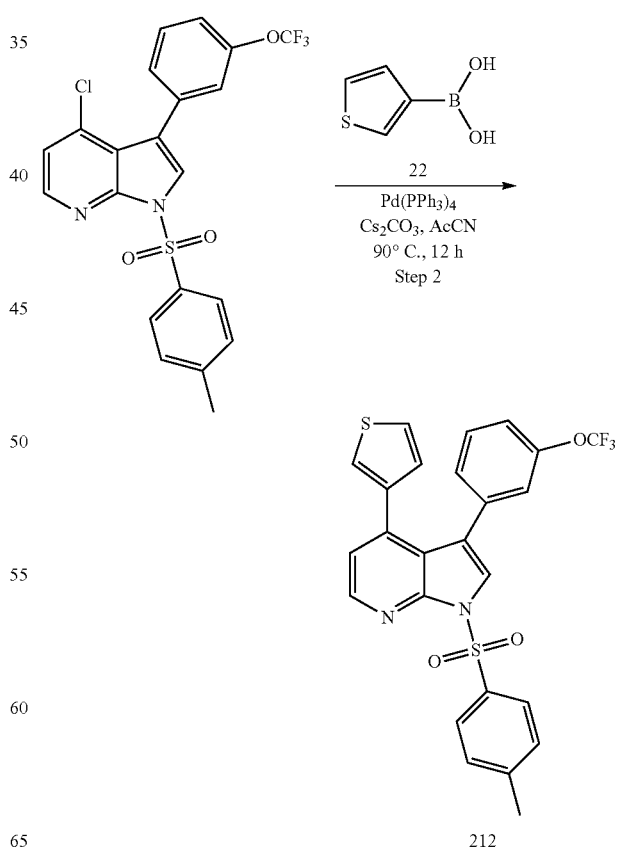

212

241

Step 2:

To a stirred solution of 211 (100 mg, 0.214 mmol) and 22 (27.3 mg, 0.214 mmol) in acetonitrile (5 mL), degassed and purged with nitrogen for 10 min, was added cesium carbonate (174 mg, 0.535 mmol) and Pd(dppf)Cl$_2$ (7 mg, 0.0107 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid 212.

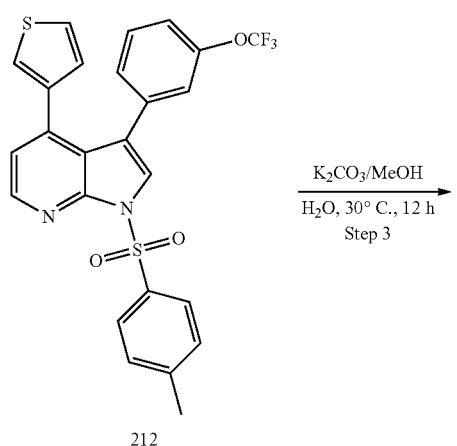

242

Preparation of Example 100: 3-(2-fluoro-4-(trifluoromethoxy)phenyl)-4-(thiophen-3-yl)-1H-pyrrolo[2,3-b]pyridine (217)

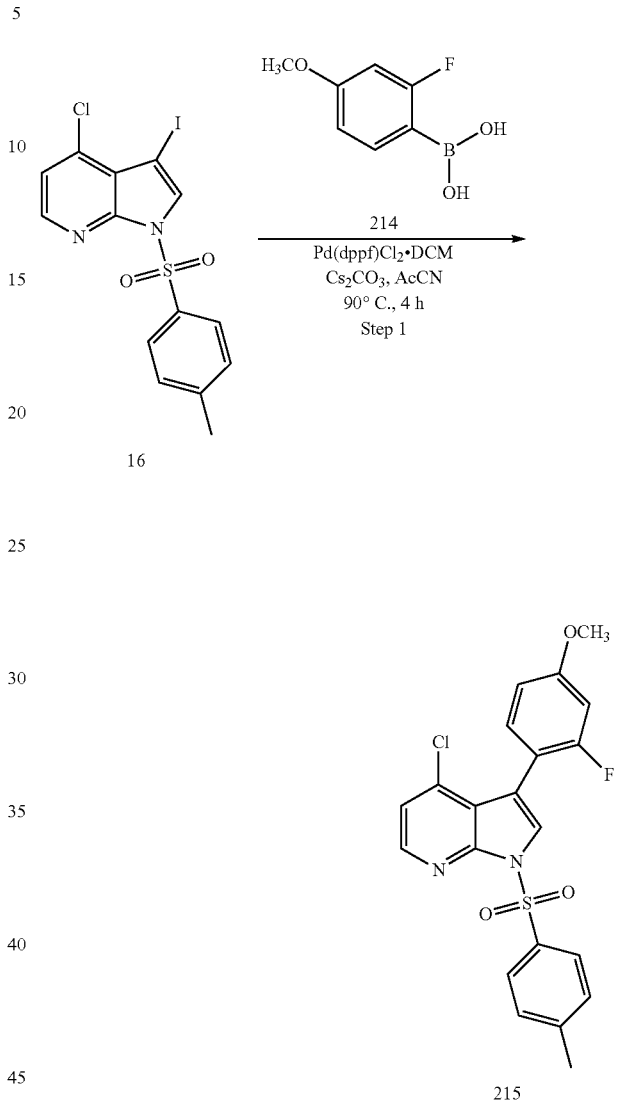

Step 3:

To a stirred solution of 212 (50 mg, 0.097 mmol) in methanol (10 mL) was added water (5 mL) and potassium carbonate (40 mg, 0.291 mmol) and the RM heated to 60° C. overnight. After completion of the sm the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 213. $^1$H NMR (CDCl3) δ: 9.52 (S, 1-H), 8.37 (d, J=5.00 1-H), 7.44 (S, 1-H), 7.20 (m, J=8.29 1-H), 7.18 (m, J=3.78 2-H), 7.02 (m J=5.00 3-H), 6.89 (m, J=2.92 1-H), 6.85 (m, J=4.87 1-H) and MS m/z=361.2 (M+H)$^+$.

Step 1:

To a stirred solution of 16 (150 mg, 0.347 mmol) and 214 (77 mg, 0.347 mmol) in acetonitrile (5 mL), degassed and purged with nitrogen for 10 min, was added cesium carbonate (226 mg, 0.694 mmol) and Pd(dppf)Cl$_2$ (14 mg, 0.0176 mmol), again degassed and purged with nitrogen for 15 min and the RM was heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 215.

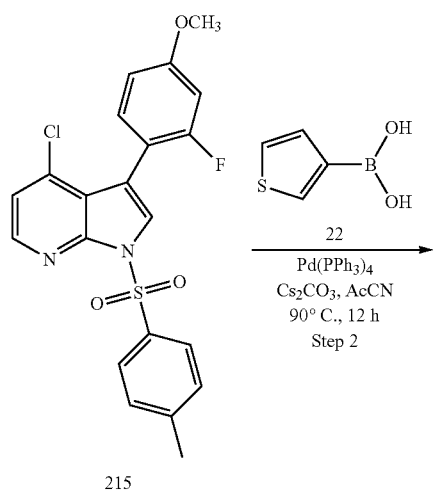

215

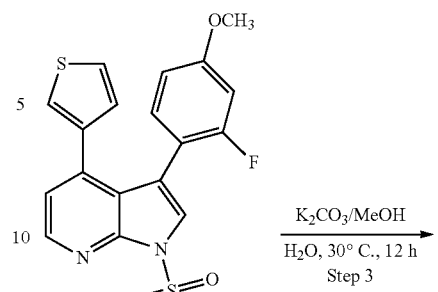

216

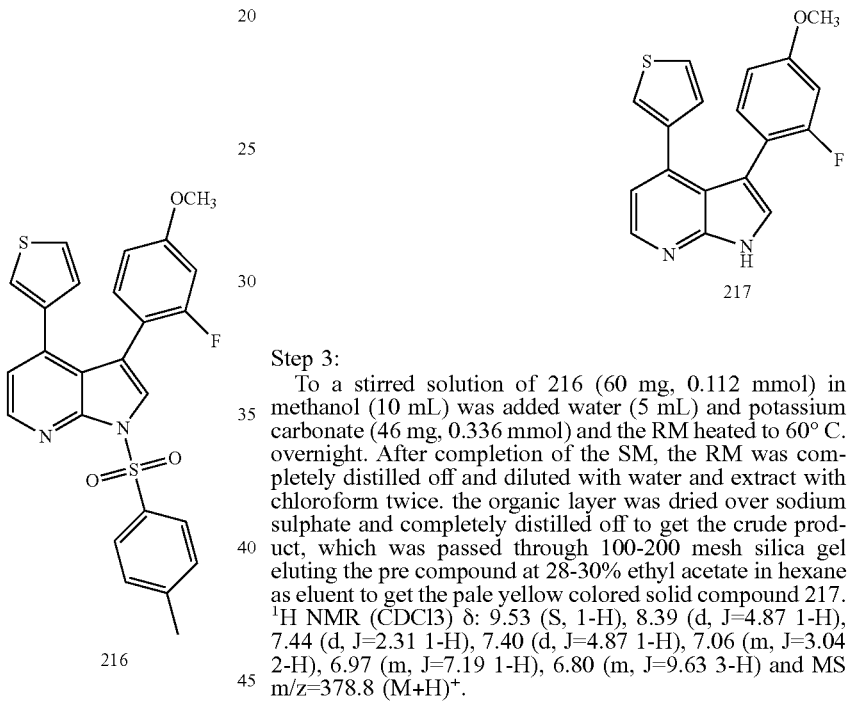

Step 2:

To a stirred solution of 215 (100 mg, 0.206 mmol) and 22 (26.4 mg, 0.206 mmol) in acetonitrile (5 mL), degassed and purged with nitrogen for 10 min, was added cesium carbonate (134 mg, 0.412 mmol) and Pd(dppf)Cl₂ (6.7 mg, 0.0082 mmol), again degassed and purged with nitrogen for 15 min and the RM was heated to 85° C. for 4 hr in a sealed tube. After completion of the reaction the RM was cooled to rt and diluted with chloroform and filtered through celite bed. The organic layer was completely distilled off to get the crude the crude was passed through 100-200 mesh silica gel eluting the pure compound at 5% ethyl aceate in hexane as off white colored solid compound 216.

Step 3:

To a stirred solution of 216 (60 mg, 0.112 mmol) in methanol (10 mL) was added water (5 mL) and potassium carbonate (46 mg, 0.336 mmol) and the RM heated to 60° C. overnight. After completion of the SM, the RM was completely distilled off and diluted with water and extract with chloroform twice. the organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 217. ¹H NMR (CDCl3) δ: 9.53 (S, 1-H), 8.39 (d, J=4.87 1-H), 7.44 (d, J=2.31 1-H), 7.40 (d, J=4.87 1-H), 7.06 (m, J=3.04 2-H), 6.97 (m, J=7.19 1-H), 6.80 (m, J=9.63 3-H) and MS m/z=378.8 (M+H)⁺.

Preparation of Example 101: 3-(2,6-dimethoxypyridin-3-yl)-4-(thiophen-3-yl)-1H-pyrrolo[2,3-b]pyridine (221)

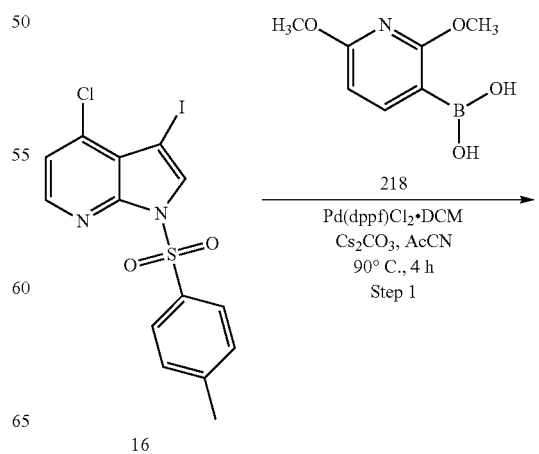

16

-continued

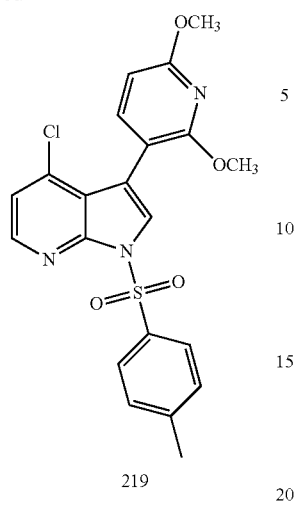

219

Step 1:

To a stirred solution of 16 (150 mg, 0.347 mmol) and 218 (63.5 mg, 0.347 mmol) in acetonitrile (5 mL), degassed and purged with nitrogen for 10 min, was added cesium carbonate (226 mg, 0.694 mmol) and Pd(dppf)Cl₂ (14 mg, 0.0173 mmol), again degassed and purged with nitrogen for 15 min and the RM heated to 85° C. for 4 hr in a sealed tube. After completion of the reaction the RM was cooled to rt and diluted with chloroform and filtered through celite bed the organic layer was completely distilled off to get the crude product, which was passed through 100-200 mesh silica gel eluting the pure compound at 5% ethyl aceate in hexane as off white colored solid compound 219.

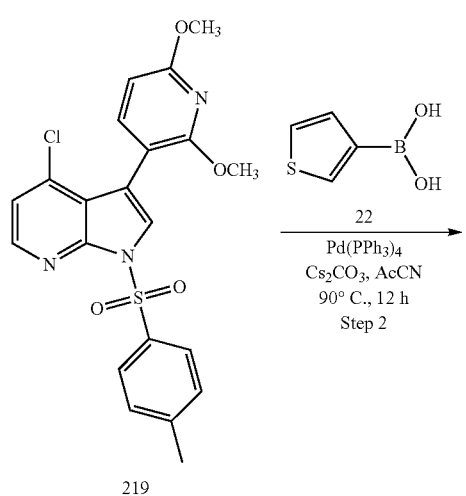

219

-continued

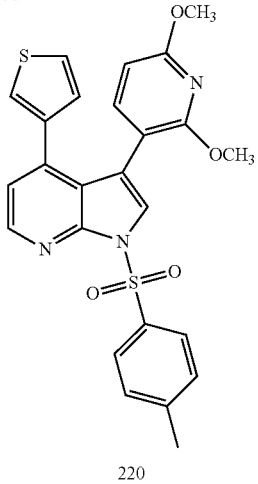

220

Step 2:

To a stirred solution of 219 (100 mg, 0.225 mmol) and 22 (29 mg, 0.225 mmol) in acetonitrile (5 mL), degassed and purged with nitrogen for 10 min, was added cesium carbonate (183 mg, 0.563 mmol) and Pd(dppf)Cl₂ (7.3 mg, 0.00112 mmol), again degassed and purged with nitrogen for 15 min and the RM heated to 85° C. for 4 hr in a sealed tube. After completion of the reaction the RM was cooled to rt and diluted with chloroform and filtered through celite bed. The organic layer was completely distilled off to get the crude product, which was passed through 100-200 mesh silica gel eluting the pure compound at 5% ethyl aceate in hexane as off white colored solid compound 220.

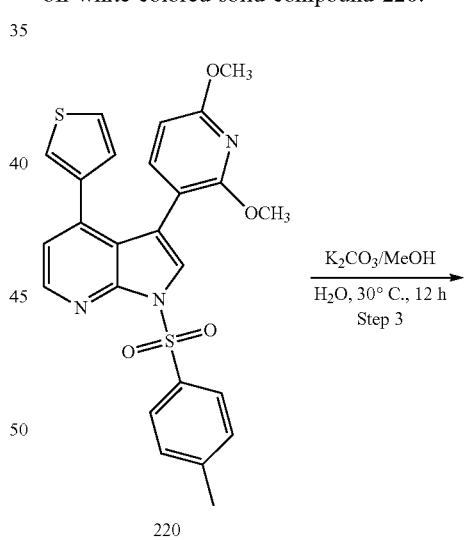

220

221

Step 3:

To a stirred solution of 220 (50 mg, 0.101 mmol) in methanol (10 mL) was added water (5 mL) and potassium carbonate (42 mg, 0.305 mmol) and the RM heated to 60° C. overnight. After completion of the SM, the RM was completely distilled off and diluted with water and extract with chloroform twice. The organic layer was dried over sodium sulphate and completely distilled off to get the crude product, which was passed through 100-200 mesh silica gel eluting the pre compound at 28-30% ethyl acetate in hexane as eluent to get the pale yellow colored solid compound 221. ¹HNMR (400 MHz, CDCl₃) δ: 9.26 (S, 1-H), 8.34 (d, J=4.75 1-H), 7.33 (m, J=6.21 2-H), 7.10 (m, J=5.00 2-H), 6.91 (m, J=5.48 2-H), 6.22 (d, J=7.92 1-H), 3.88 (S, 3-H), 3.47 (S, 3-H) and MS m/z=337.8 (M+H)⁺.

Preparation of Example 113: 3-(2-methoxyphenyl)-5-(thiophen-3-yl)-1H-pyrrolo[2,3-b]pyridine (224)

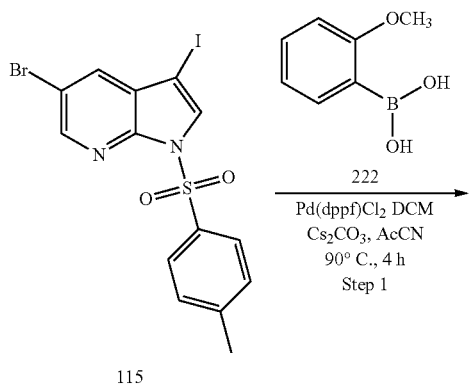

115

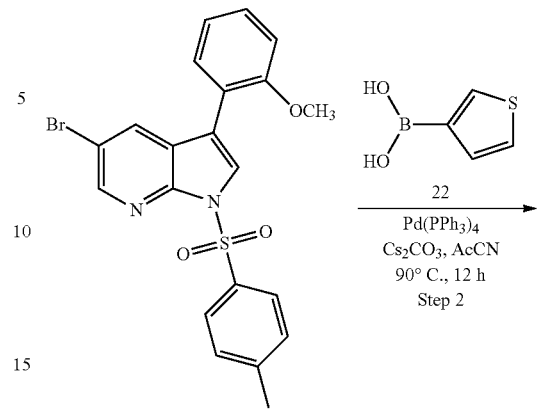

223

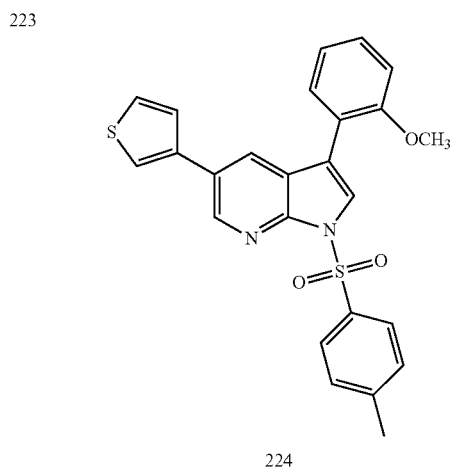

224

Step 2:

A solution of 223 (0.1 g, 0.219 mmol) and 22 (26 mg, 0.219 mmol) in acetonitrile (7 mL) in a sealed tube was added Cs₂CO₃ (143 mg, 0.438 mmol) and degassed for 15 min. To the RM was Pd(PPh₃)₄ (12.6 mg, 0.0109 mmol) and degassed again for 15 min. RM stirred for 3 hr at 90° C. After completion of the reaction, the RM was allowed to cool to rt and diluted with DCM (50 mL) and filtered through celite. The resulting crude material was purified through silica gel chromatography using a gradient of 6% ethyl acetate: hexane to afford the compound 224.

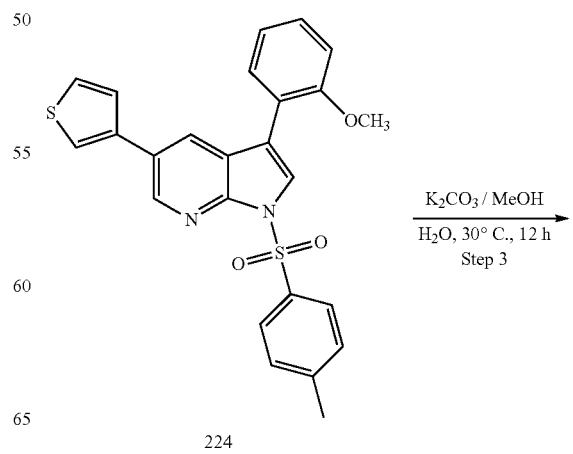

224

Step 1:

A solution of 115 (0.150 g, 0.315 mmol) and 222 (0.048 g, 0.315 mmol) in acetonitrile (7 mL) in a sealed tube was added Cs₂CO₃ (0.204 gm, 0.628 mmol) and degassed for 15 min. To the resulting RM was added Pd(dppf)Cl₂ DCM (0.012 gm, 0.0157 mmol) and degassed again for another 15 min and the contents were stirred for 3 hr at 90° C. After TLC monitoring, the RM allowed to cool to rt and diluted with DCM (50 mL) and filtered through celite and evaporated. The resulting crude material was purified thorough silica gel chromatography using a gradient of 6% ethyl acetate: hexane to afford the pure compound 223.

-continued

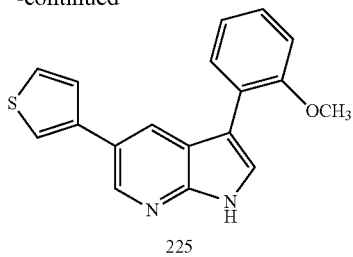
225

Step 3:

A solution of 224 (0.060 g, 0.1247 mmol) in MeOH (5 mL), water (5 mL) and K₂CO₃ (0.051 g, 0.3742 mmol) was stirred overnight at 70° C. After the termination of rection was allowed to cool and the solvents were removed and diluted with DCM (50 mL), extracted and the organic layer washed with water and dried over Na₂SO₄ and evaporated. The resulting crude material was purified through silica gel chromatography using a gradient of 25% ethyl acetate: hexane to afford title compound 225. ¹HNMR (400 MHz, CDCl₃) δ: 8.87 (s, 1H), 8.59 (d, 1H), 8.24 (d, 1H), 7.60 (m, 2H), 7.43 (m, 3H), 7.31 (m, 1H), 7.07 (m, 2H), 3.88 (s, 3H), MS m/z=306.8 (M+H)⁺.

Preparation of Example 114: 3-(2-chloro-3-fluoro-phenyl)-5-(thiophen-3-yl)-1H-pyrrolo[2,3-b]pyridine (229)

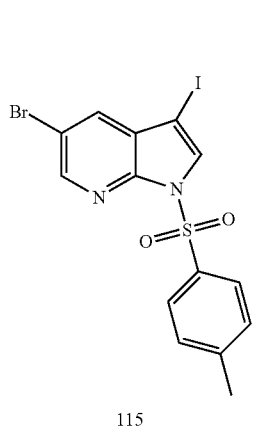
115

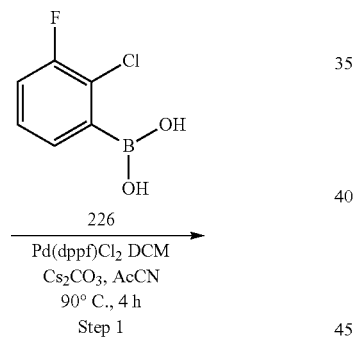
226
Pd(dppf)Cl₂ DCM
Cs₂CO₃, AcCN
90° C., 4 h
Step 1

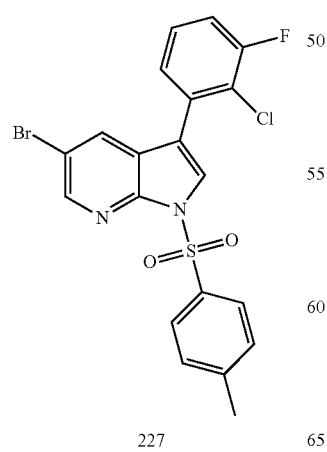
227

Step 1:

A solution of 115 (0.150 g, 0.315 mmol) and 226 (0.54.8 mg, 0.315 mmol) in acetonitrile (7 mL) in a sealed tube was added Cs₂CO₃ (0.206 g, 0.628 mmol) and degassed for 15 min. To the resulting RM was added Pd(dppf)Cl₂ DCM (0.012 g, 0.0157 mmol) and degassed again for another 15 min and the contents were stirred for 3 hr at 90° C. After TLC monitoring, the RM allowed to cool to rt and diluted with DCM (50 mL) and filtered through celite and evaporated. The resulting crude material was purified thorough silica gel chromatography using a gradient of 6% ethyl acetate: hexane to afford the pure compound 227.

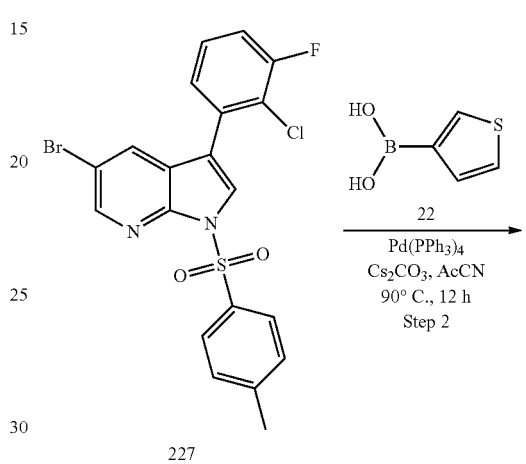
227
22
Pd(PPh₃)₄
Cs₂CO₃, AcCN
90° C., 12 h
Step 2

228

Step 2:

A solution of 227 (0.1 g, 0.219 mmol) and 22 (26.7 mg, 0.209 mmol) in acetonitrile (7 mL) in a sealed tube was added Cs₂CO₃ (137 mg, 0.418 mmol) and degassed for 15 min. To the RM was Pd(PPh₃)₄ (12 mg, 0.0104 mmol) and degassed again for 1 min. RM stirred for 3 hr at 90° C. After completion of the reaction was allowed to cool to rt and diluted with DCM (50 mL) and filtered through celite. The resulting crude material was purified trhough silica gel chromatography using a gradient of 6% ethyl acetate: hexane to afford the compound 228.

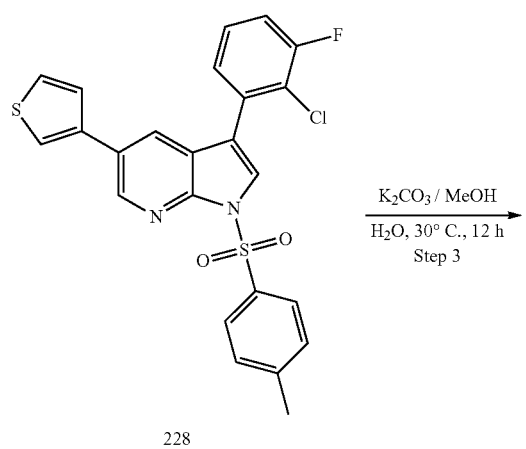

228

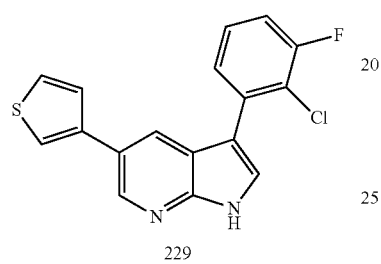

229

Step 3:

A solution of 228 (0.060 g, 0.1247 mmol) in MeOH (5 mL), water (5 mL) and $K_2CO_3$ (0.051 g, 0.3742 mmol) was stirred overnight at 70° C. After the termination of reaction was allowed to cool and the solvents were removed and diluted with DCM (50 mL) extracted and the organic layer washed with water and dried over $Na_2SO_4$ and evaporated. The resulting crude material was purified through silica gel chromatography using a gradient of 25% ethyl acetate: hexane to afford title compound 229. $^1$HNMR (400 MHz, $CDCl_3$) δ: $^1$HNMR (400 MHz, $CDCl_3$): 9.41 (s, 1H), 8.65 (s, 1H), 8.11 (s, 1H), 7.60 (d, 1H), 7.44 (m, 3H), 7.34 (m, 2H), 7.18 (m, 1H), MS m/z=328.8 (M+H)$^+$.

Preparation of Example 115: 3-(2-methoxyphenyl)-5-(5-methylfuran-2-yl)-1H-pyrrolo[2,3-b]pyridine (119)

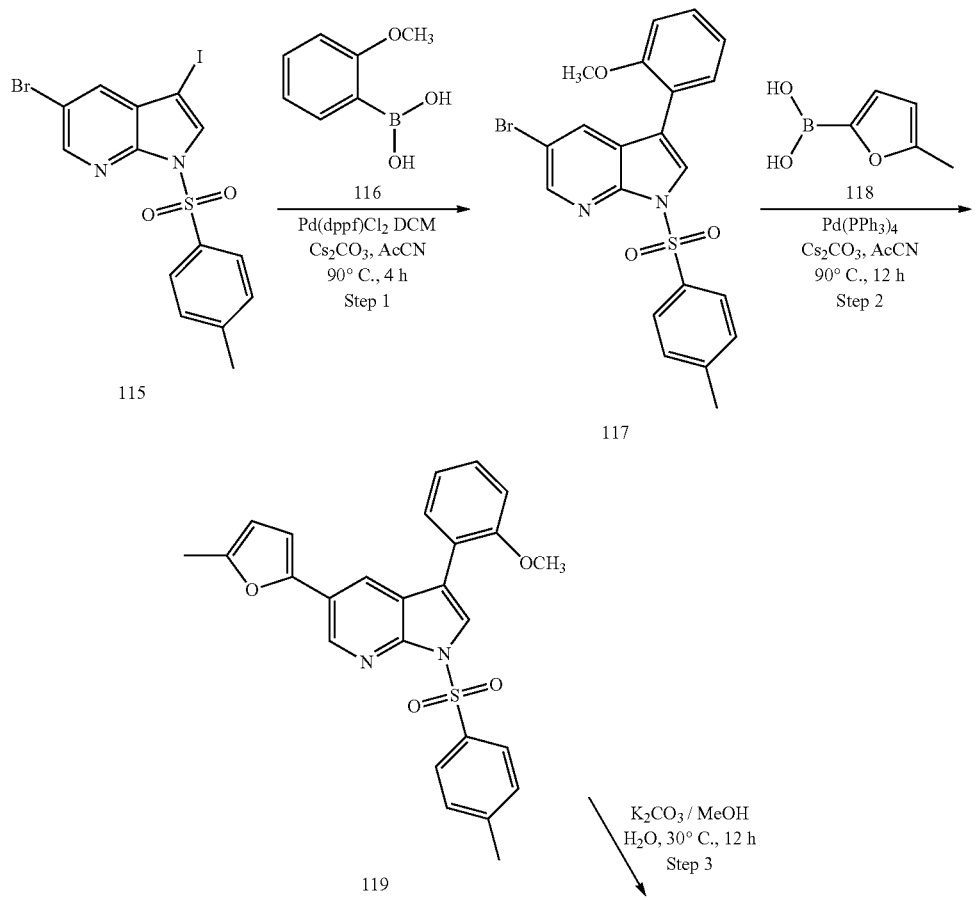

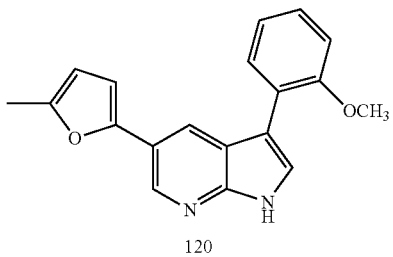

120

Step 1:
A solution of 115 (150 mg, 0.314 mmol) and 116 (47 mg, 0.314 mmol) in acetonitrile (7 mL) was taken into a sealed tube, Cs$_2$CO$_3$ (204 mg, 0.628 mmol) added, and degassed for 15 min. To the RM was added Pd(dppf)Cl$_2$ DCM (0.012 g, 0.01572 mmol) and degassed again for 15 min, and stirred for 4 hr at 90° C. After 2 hr, the TLC confirmed the reaction and the RM allowed to cool to rt. The crude material was taken in to DCM (100 mL) and filtered through celite. The resulting crude material was purified via silica gel chromatography using a gradient of 5% ethyl acetate: hexane to afford compound 117.

Step 2:
A solution of 117 (0.075 g, 0.164 mmol.) and 118 (0.034 g, 0.1641 mmol) in 5 mL acetonitrile in a sealed tube was added Cs$_2$CO$_3$ (0.04 g, 0.628 mmol), and degassed for 15 min in presence of Pd(PPh$_3$)$_4$. The resulting RM was stirred overnight at 90° C., allowed to cool to rt and taken in to DCM (100 mL) and filtered through celite. The resulting oil was purified via silica gel chromatography using a gradient of 10% ethyl acetate: hexane to afford compound 119.

Step 3:
To a solution of 119 (0.070 g, 0.1528 mmol) in MeOH (5 mL) and H$_2$O (5 mL) was added K$_2$CO$_3$ and the RM stirred overnight at 70° C. The resulting RM was allowed to cool and evaporated completely and extracted in to DCM (50 mL) followed by water wash for two times. Organic layer was dried with Na$_2$SO$_4$ and evaporated. The crude product was purified by silica gel chromatography using a gradient of 25% ethyl acetate: hexane to afford compound 120. $^1$H NMR (400 MHz, CDCl$_3$) δ: 8.95 (s, 1H), 8.64 (s, 1H), 8.28 (d, 1H), 7.61 (m, 2H), 7.33 (m, 1H), 7.12 (m, 2H), 6.53 (d, 1H), 6.06 (d, 1H), 3.88 (s, 3H), 2.38 (s, 3H). MS m/z 304.91 [M+H]$^+$.

Preparation of Example 118: 2-(4-(thiophen-3-yl)-1H-pyrrolo[2,3-b]pyridin-3-yl)phenol (161)

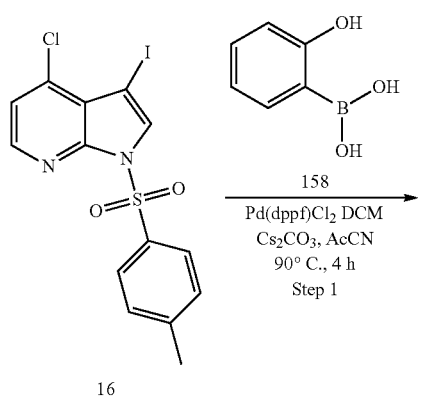

16

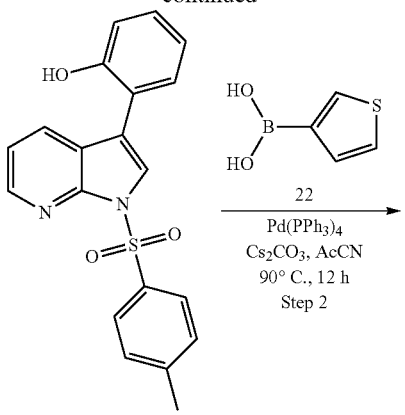

159

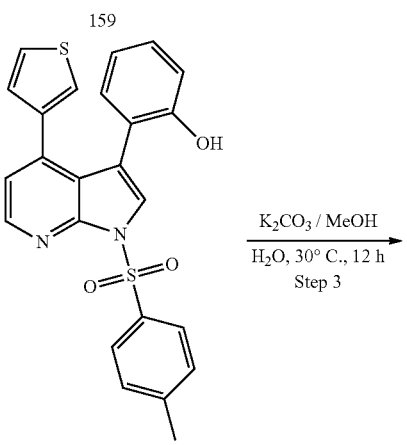

160

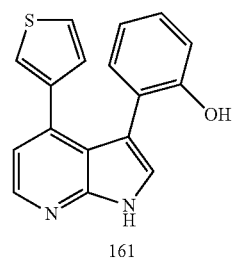

Compound 161

$^1$HNMR (400 MHz, CDCl$_3$) δ: 9.41 (bs, 1H), 8.26 (bs, 1H), 7.67 (m, 2H), 7.52 (m, 4H), 7.32 (m, 2H), 7.01 (m, 1H), 6.96 (m, 2H), MS m/z ESI: 278.8 (M+H)$^+$.

Preparation of Example 120: 3-(3-fluoro-2-methoxyphenyl)-4-(thiophen-3-yl)-1H-pyrrolo[2,3-b]pyridine (145)
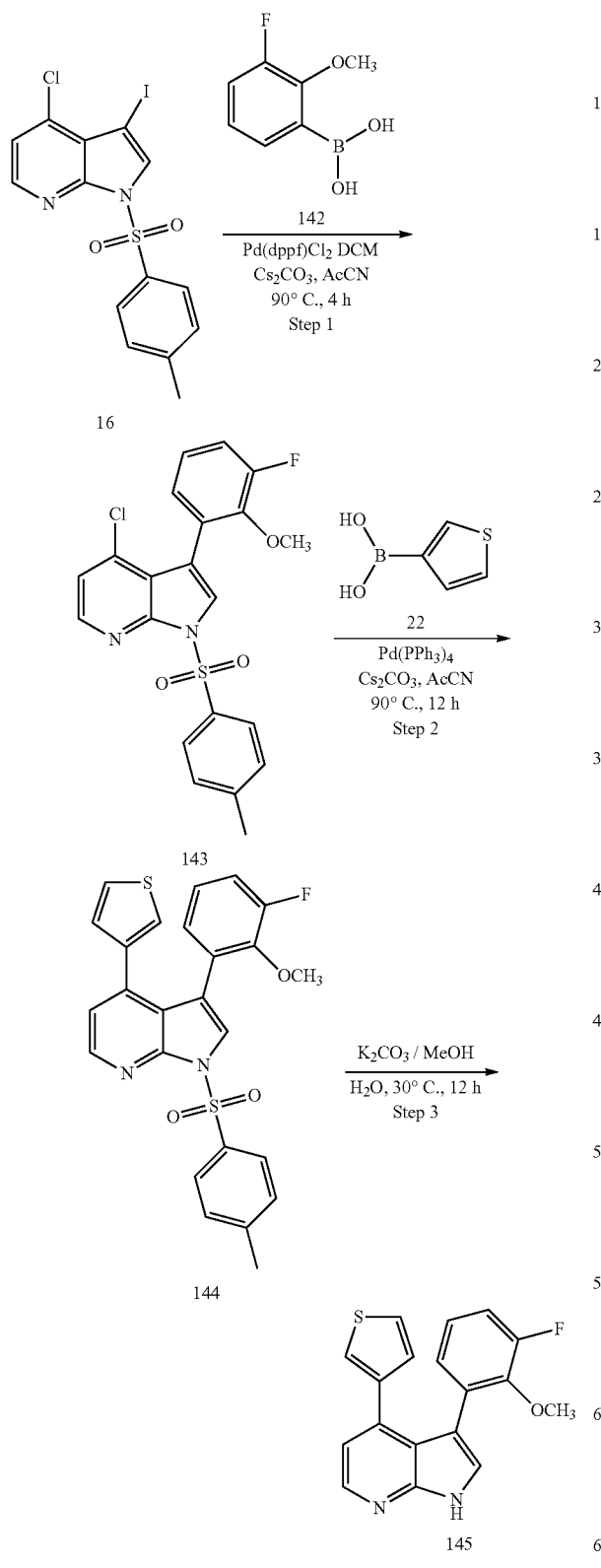
Compound 145
$^1$HNMR (400 MHz, CDCl$_3$) δ: 9.43 (1s, 1H) 8.37 (d, 1H), 8.36 (m, 1H), 7.15 (d, 1H), 7.14 (m, 1H), 6.94 (m, 3H), 6.93 (m, 2H), 3.53 (s, 3H), MS m/z: 324.0 (M+H)$^+$.
Preparation of Example 121: 3-(3,5-difluoro-2-methoxyphenyl)-4-(thiophen-3-yl)-1H-pyrrolo[2,3-b]pyridine (149)
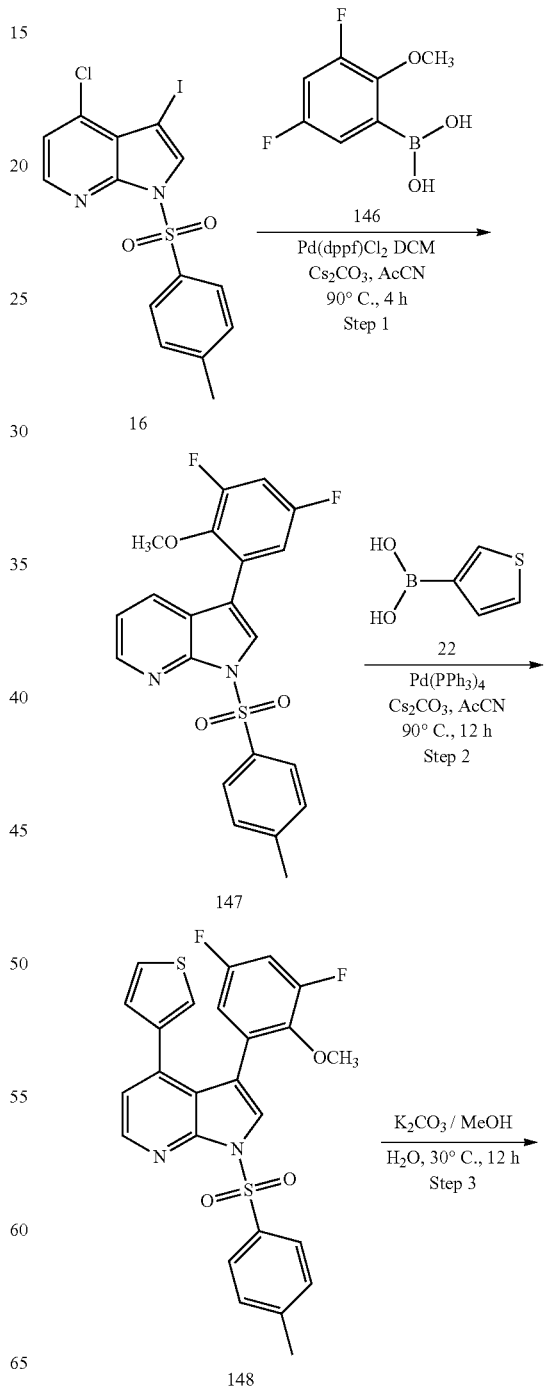

-continued
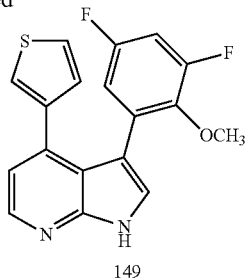
149
Compound 149
$^1$HNMR (400 MHz, CDCl$_3$) δ: 9.8 (b, 1H), 8.39 (d, 1H), 7.48 (s, 1H) 7.15 (m, 2H) 7.0 (m, 1H), 6.7 (m, 1H), 6.7 (m, 1H), 6.43 (m, 1H), 3.52 (m, 3H), MS m/z ESI: +342.9 (M+H)$^+$.
Preparation of Example 122: 2-fluoro-6-(5-(thiophen-3-yl)-1H-pyrrolo[2,3-b]pyridin-3-yl)phenol (128)
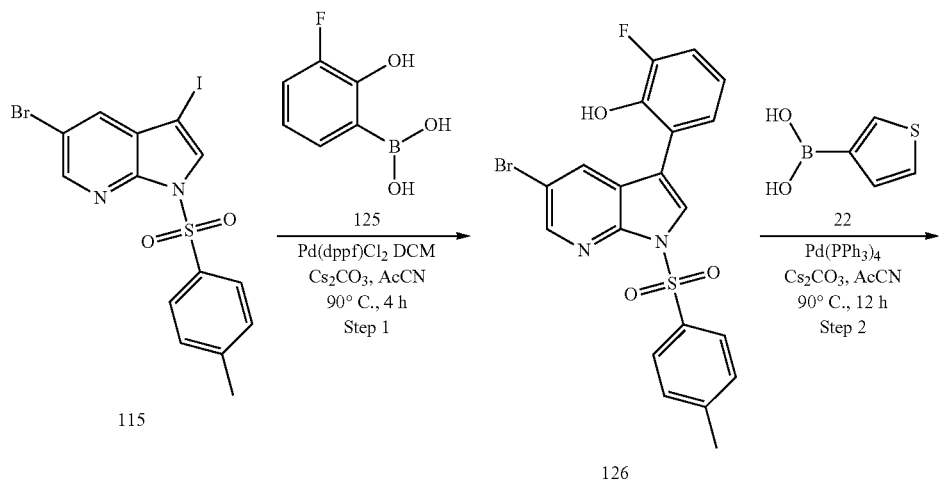
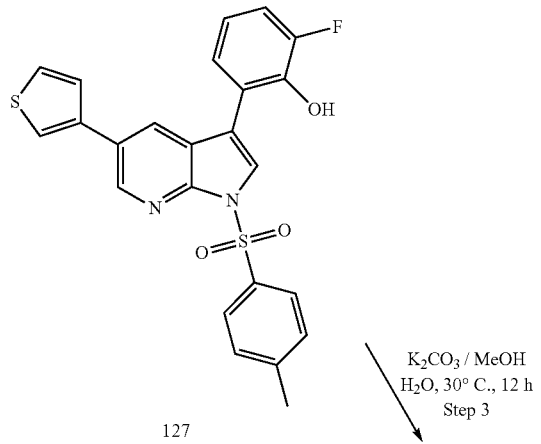
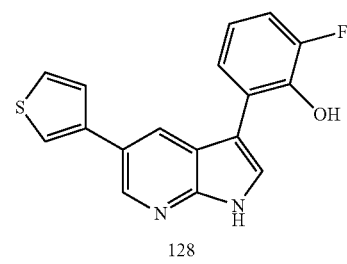

Step 1:

A solution of 115 (150 mg, 0.314 mmol.) and 121 (49 mg, 0.3144 mmol) was dissolved in acetonitrile (10 mL) in a sealed tube and was charged with Cs$_2$CO$_3$ (204 mg, 0.628 mmol). The resulting RM was degassed for 15 min. To this RM was added Pd(dppf)Cl$_2$ DCM (12 mg, 0.0157 mmol) and degassed again for 15 min. RM was stirred for 4 hr at 90° C. After 4 hr and TLC monitoring confirms the consumption of SM, the RM was cooled to rt and diluted with DCM (100 mL) and filtered through celite. The resulting crude material was purified through silica gel chromatography using a gradient of 5% ethyl acetate in hexane afforded the compound 122.

Step 2:

A solution of 122 (125 mg, 0.271 mmol) and 22 (34 mg, 0.27 mmol) was dissolved in acetonitrile (5 mL) in a sealed tube. To this RM was added Cs$_2$CO$_3$ (176 mg, 0.542 mmol) and subjected to degassing for 15 min. The catalyst Pd(PPh$_3$)$_4$ (15 mg, 0.0135 mmol) was added and degassed again for 15 min. The resulting RM was stirred overnight at 90° C. After TLC with the Rf changes from the SM confirmed the completion of the reaction, the contents were cooled to rt and diluted with DCM (100 mL) and filtered through celite. The resulting crude material was purified from silica gel chromatography using a gradient of 10% ethyl acetate: hexane to afford compound 123.

Step 3:

Compound 123 (50 mg, 0.105 mmol) in MeOH (10 mL) and H$_2$O (5 mL) was added K$_2$CO$_3$ (36 mg, 0.262 mmol) and the RM was stirred overnight at 70° C. After completion of the reaction from TLC, the solvent MeOH was evaporated completely and the crude material was diluted with DCM (50 mL) followed by water wash for two times and the organic layer was dried with Na$_2$SO$_4$ and evaporated. The resulting crude compound was purified from silica gel chromatography using a gradient of 25% ethyl acetate: hexane to afford the compound 128. 1HNMR (400 MHz, CDCl3) □: 10.24 (s, 1H), 8.55 (s, 1H), 8.33 (d, 1H), 7.67 (s, 1H), 7.43 (m, 3H), 7.1 (d, 1H), 7.09 (m, 1H), 6.96 (m, 1H), 5.34 (s, 1H), MS m/z: 310.8 (M+H)+.

Preparation of Example 123: 2-(5-(thiophen-3-yl-1H-pyrrolo[2,3-b]pyridin-3-yl)phenol (132)

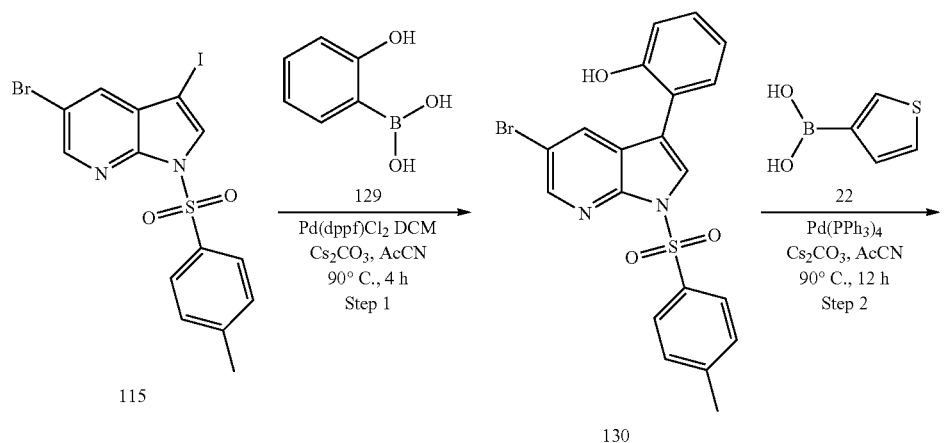

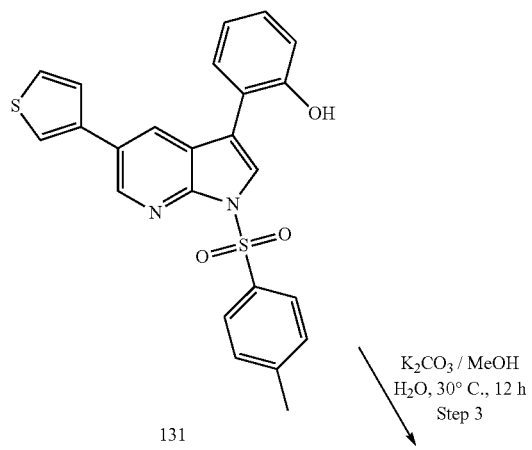

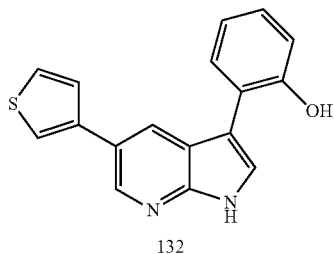

132

Step 1:
A solution of 115 (150 mg, 0.314 mmol.) and 129 (43 mg, 0.314 mmol) was dissolved in acetonitrile (10 mL) in a sealed tube and charged with Cs$_2$CO$_3$ (204 mg, 0.628 mmol). The resulting RM was degassed for 15 min. To this RM was added Pd(dppf)Cl$_2$ DCM (12 mg, 0.0157 mmol) and degassed again for 15 min. RM was stirred for 4 hr at 90° C. After 4 hr and TLC monitoring confirmed the consumption of SM, the contents of reaction was cooled to rt and diluted with DCM (100 mL) and filtered through celite. The resulting crude material was purified through silica gel chromatography using a gradient of 5% ethyl acetate in hexane to afford the compound 130.

Step 2:
A solution of 130 (100 mg, 0.25 mmol) and 22 (34 mg, 0.27 mmol) was dissolved in acetonitrile (5 mL) in a sealed tube. To this RM was added Cs$_2$CO$_3$ (147 mg, 0.542 mmol) and degassed for 15 min. The catalyst Pd(PPh$_3$)$_4$ (13 mg, 0.0122 mmol) was added and degassed again for 15 min. The resulting RM was stirred overnight at 90° C. After TLC with the Rf changes from the SM confirmed the completion of the reaction, the contents were cooled to rt and diluted with DCM (100 mL) and filtered through celite. The resulting crude material was purified from silica gel chromatography using a gradient of 10% ethyl acetate: hexane to afford compound 131.

Step 3:
Compound 131 (60 mg, 0.131 mmol) in MeOH (10 mL) and H$_2$O (5 mL) was added K$_2$CO$_3$ (45 mg, 0.38 mmol) and the RM was stirred overnight at 70° C. After completion of the reaction from TLC, the solvent MeOH was evaporated completely and the crude material was diluted with DCM (50 mL) followed by water wash for two times and the organic layer was dried with Na$_2$SO$_4$ and evaporated. The resulting crude compound was purified from silica gel chromatography using a gradient of 25% ethyl acetate: hexane to afford the compound 132. $^1$HNMR (400 MHz, CDCl$_3$) δ: 11.80 (s, 1H), 9.53 (s, 1H), 8.62 (d, 1H), 8.30 (d, 1H), 7.87 (m, 1H), 7.74 (d, 2H), 7.6 (m, 3H), 7.13 (m, 1H), 6.93 (m, 2H). MS m/z: 292.7 (M+H)$^+$.

Preparation of Example 124: 2,4-difluoro-6-(5-(thiophen-3-yl-1H-pyrrolo[2,3-b]pyridin-3-yl)phenol (153)

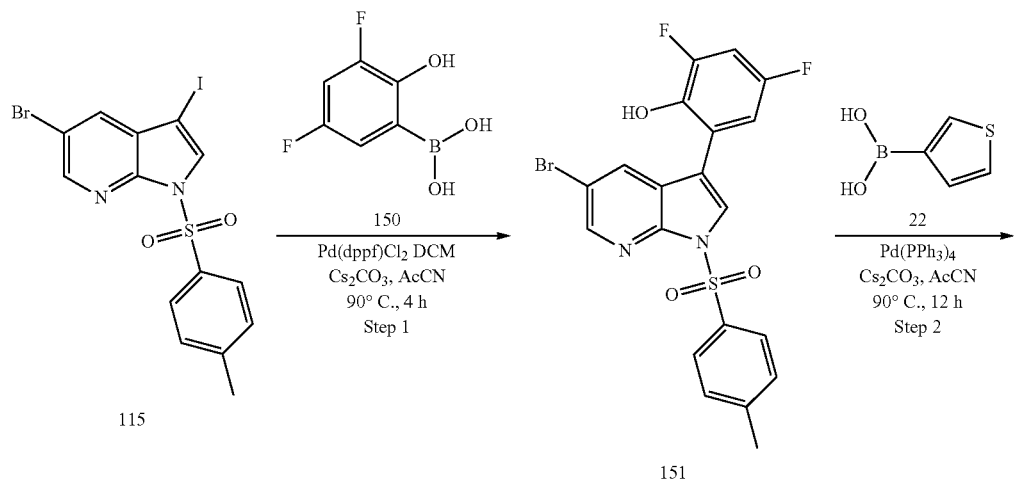

-continued
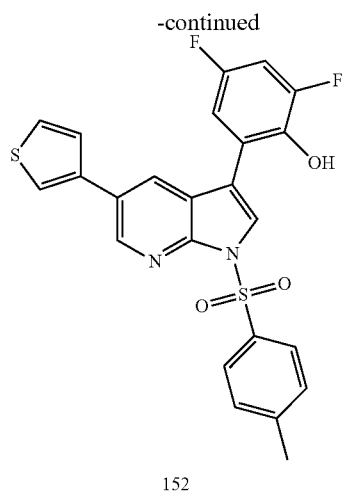
152
K₂CO₃ / MeOH
H₂O, 30° C., 12 h
Step 3
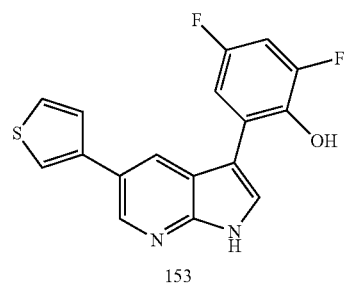
153
Compound 153
¹HNMR (400 MHz, CDCl₃) δ: 12.0 (s, 1H), 8.64 (d, 1H), 8.31 (d, 1H), 7.90 (m, 1H), 7.84 (s, 1H), 7.65 (m, 2H), 7.22 (m, 1H), 7.1 (m, 1H), MS m/z ESI: 328.8. (M+H)⁺.
Preparation of Example 125: 3-(3-fluoro-2-methoxyphenyl)-5-(thiophen-3-yl)-1H-pyrrolo[2,3-b]pyridine (124)
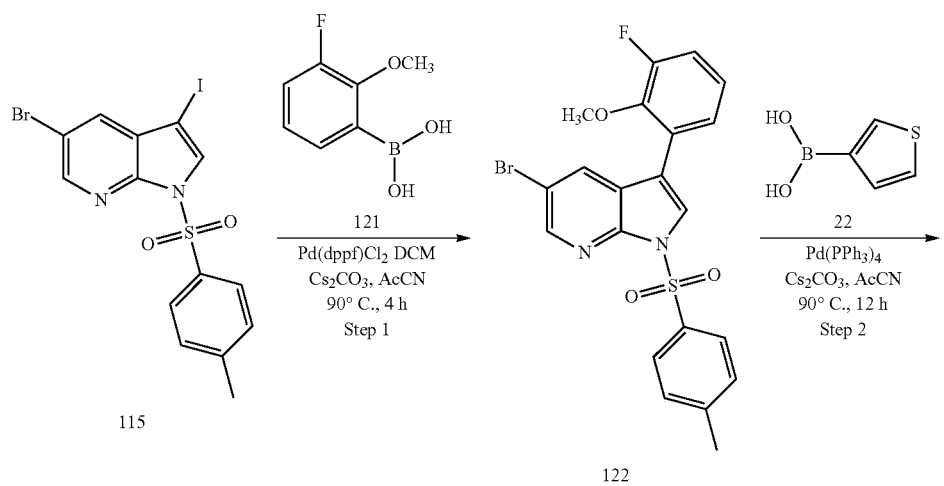

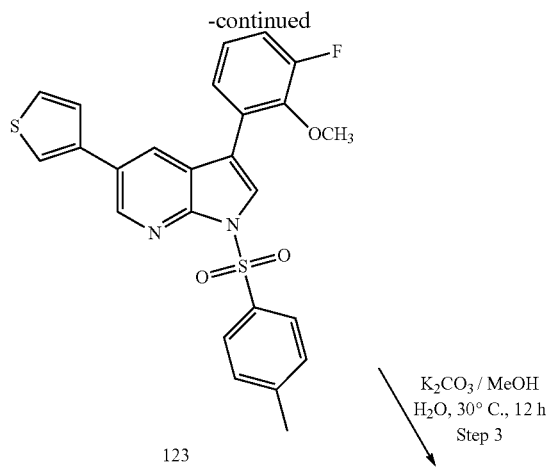

123

K$_2$CO$_3$ / MeOH
H$_2$O, 30° C., 12 h
Step 3

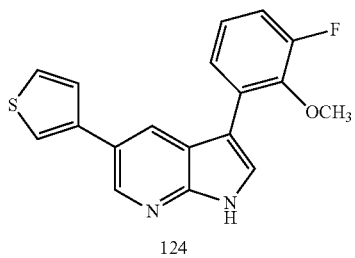

124

Step 1:

To a solution of 115 (0.150 g, 0.314 mmol.) and 121 (0.049 g, 0.314 mmol) in a sealed tube was dissolved acetonitrile (7 mL) and then Cs$_2$CO$_3$ (0.204 g, 0.628 mmol) was charged. The resulting RM was degassed for 15 min. To this RM was added Pd(dppf)Cl$_2$ DCM (0.012 g, 0.0157 mmol) and degassed again for 15 min. The resulting RM was stirred for 2 hr at 90° C. After 4 hr, TLC monitoring confirmed the consumption of SMs and the RM was cooled to rt and diluted with DCM (100 mL) and filtered through celite. The resulting crude material was purified via silica gel chromatography using a gradient of 5% ethyl acetate in hexane to afford compound 122.

Step 2:

A solution of 122 (0.100 g, 0.210 mmol) and 22 (0.027 g, 0.210 mmol) was dissolved in acetonitrile (5 mL) in a sealed tube. To this RM, Cs$_2$CO$_3$ (0.137 g, 0.421 mmol) was added and degassed for 15 min. The catalyst Pd(PPh$_3$)$_4$ (0.012 g, 0.010 mmol) was added and degassed again for 15 min. The resulting RM was stirred overnight at 90° C. After TLC showed completion of changes from the SM, the RM was allowed to cool to rt. DCM (100 mL) was added and filtered through celite. The resulting oil was purified via silica gel chromatography at a gradient of 10% ethyl acetate: hexane to afford compound 123.

Step 3:

To Compound 123 (0.050 g, 0.104 mmol) in MeOH (10 mL) and H$_2$O (5 mL) was added K$_2$CO$_3$ (0.035 g, 0.260 mmol) and the RM stirred overnight at 70° C. After completion of the reaction from TLC, the resulting contents were evaporated of methanol completely and diluted with DCM (50 mL) followed by water wash for two times and the organic layer was dried with Na$_2$SO$_4$ and evaporated. The resulting crude was purified via silica gel chromatography using a gradient of 25% ethyl acetate: hexane to afford compound 124. $^1$HNMR (400 MHz, CDCl3): 9.26 (s, 1H), 8.63 (s, 1H), 8.31 (d, 1H), 7.69 (d, 1H), 7.48 (d, 1H), 7.44 d, 2H), 7.38 (m, 1H), 7.11 (m, 2H), 3.75 (s, 3H). MS m/z: 324.8 (M+H)+.

Preparation of Example 126: 3-(3,5-difluoro-2-methoxyphenyl)-5-(thiophen-3-yl)-1H-pyrrolo[2,3-b]pyridine (157)
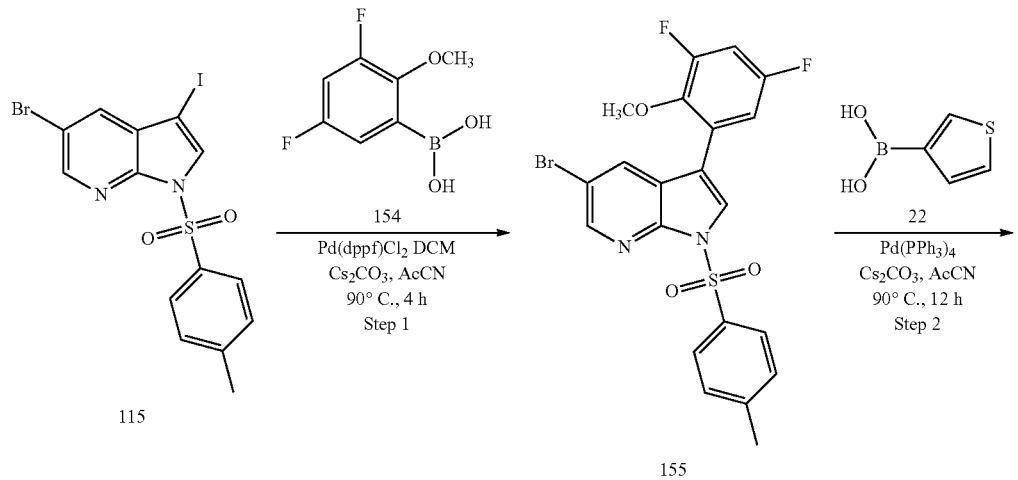
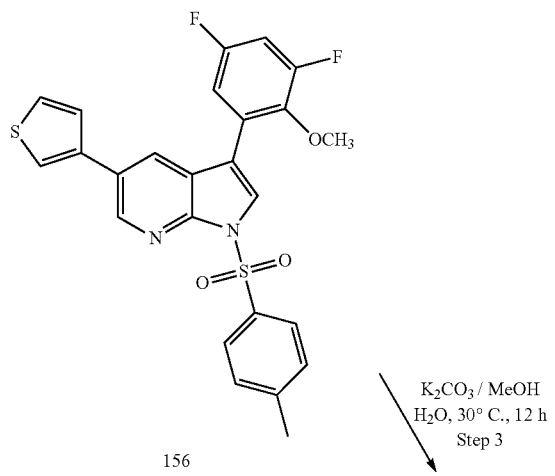
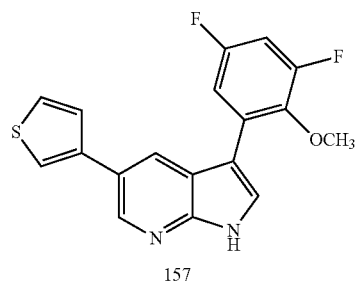

Compound 157
¹HNMR (400 MHz, CDCl₃) δ: 12.14, (t, 1H), 6.8 (m, 1H), 8.32 (m, 1H), 7.87 (m, 2H), 7.65 (m, 2H), 7.31 (m, 2H), 3.61 (m, 3H), MS m/z ESI: 342.8 (M+H)⁺.
Preparation of Example 128: 2-fluoro-6-(5-(5-methylfuran-2-yl)-1H-pyrrolo[2,3-b]pyridin-3-yl)phenol (136)
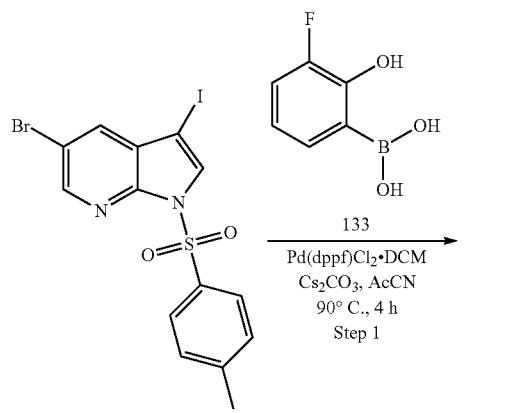
115
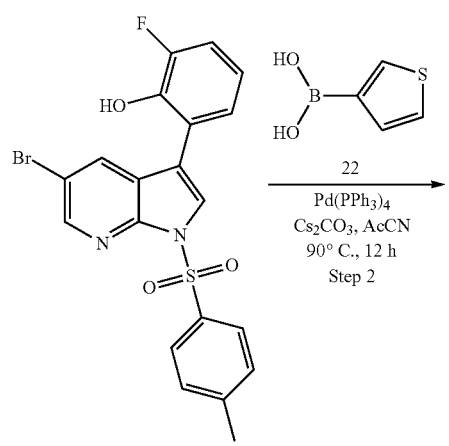
134
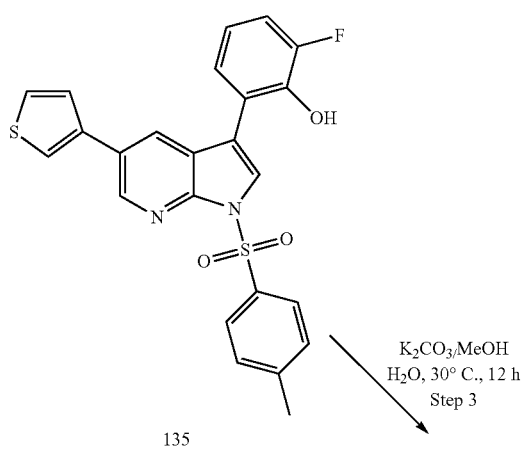
135
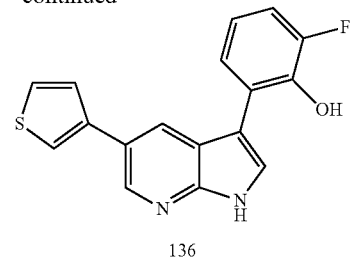
136
Compound 136
¹HNMR (400 MHz, CDCl₃) δ: 10.03 (s, 1H), 8.61 (d, 1H), 8.31 (d, 1H), 7.65 (s, 1H), 7.34 (m, 1H), 7.12 (m, 1H), 6.99 (m, 1H), 6.54 (d, 1H), 6.07 (d, 1H), 2.13 (s, 3H), MS m/z: 308.8 (M+H)⁺.
Preparation of Example 129: 3-(2-chloro-3-fluorophenyl)-5-(5-methylfuran-2-yl)-1H-pyrrolo[2,3-b]pyridine (163)
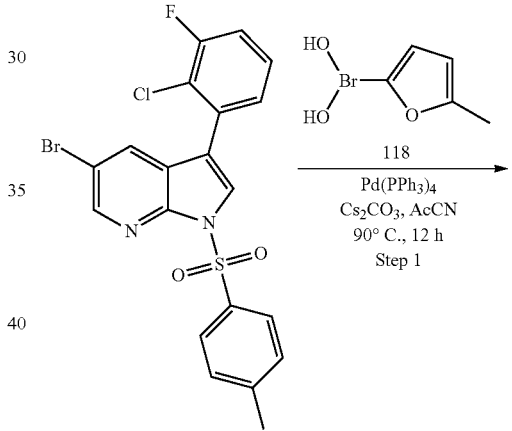
96
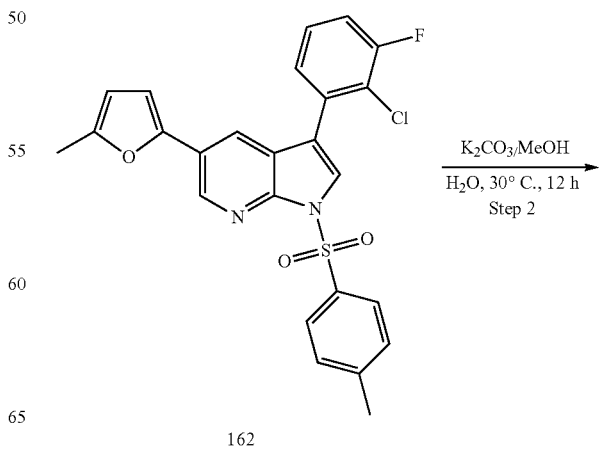
162

271
-continued
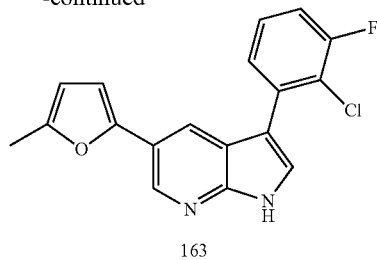
163
Compound 163
¹HNMR (400 MHz, CDCl₃) δ: 9.99 (S, 1H), 8.16 (d, 1H), 7.62 (d, 1H), 7.36 (m, 2H), 7.19 (m, 1H), 7.56 (d, 1H), 6.08 (m, 1H), MS m/z ESI: 326.9 (M+H)⁺.
Preparation of Example 131: 3-(2-chloro-3-fluoro-phenyl)-5-(4-methylthiophen-2-yl)-1H-pyrrolo[2,3-b]pyridine (141)
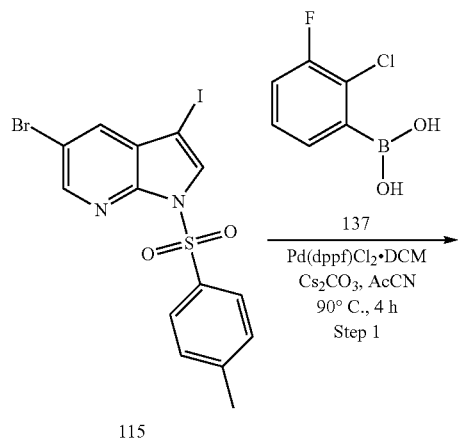
272
-continued
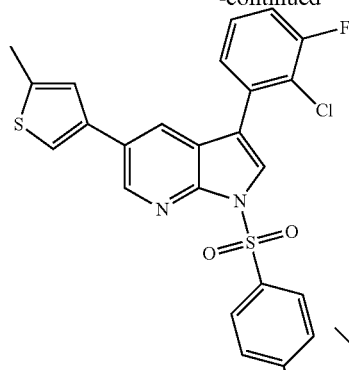
140
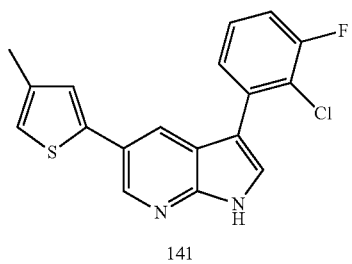
141
Compound 141
¹HNMR (400 MHz, CDCl₃) δ: 9.08 (s, 1H), 8.62 (s, 1H), 8.09 (s, 1H), 7.59 (d, 1H), 7.34 (m, 2H), 7.32 (m, 1H), 7.12 (s, 1H), 6.88 (t, 1H) 2.30 (s, 3H), MS m/z: 342.7 (M+H)⁺.
Preparation of Example 133: 4-((5-(3-(2-chloro-3-fluorophenyl)-1H-pyrrolo[2,3-b]pyridin-5-yl)thiophen-2-yl)methyl)morpholine (263)
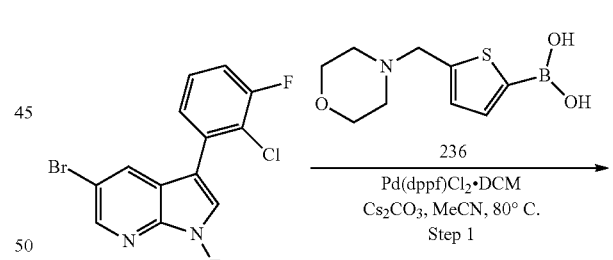
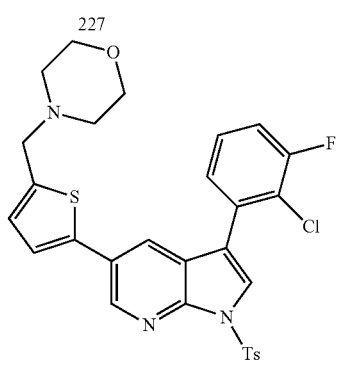
262

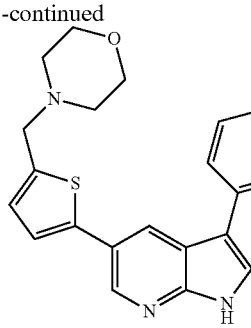

263

Step 1:
To a solution of 227 (100 mg, 0.208 mmol) and 236 (47 mg, 0.208 mmol), in acetonitrile (7 mL) was added cesium carbonate (135 mg, 0.416 mmol). The RM was degassed and purged with nitrogen for 10 min. Pd(dppf)Cl$_2$ (8 mg, 0.01042 mmol) was added to the reaction. The RM was again degassed and purged with nitrogen for another 5 min, and heated to 80° C. in a sealed tube overnight. The reaction was allowed to cool to rt and diluted with chloroform. The organic layer was concentrated to get the crude product, which was purified through flash chromatography by using 100-200 mesh silica gel. The compound was eluted at 40% ethyl acetate in hexane as half white colored solid compound 262.

Step 2:
A solution of 262 (60 mg, 0.103 mmol) in methanol (20 mL) and water (5 mL) was added potassium carbonate (42 mg, 0.3092 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude material, which was purified through flash chromatography by using 100-200 mesh silica gel. The compound was eluted at 60% ethyl acetate in hexane as pale yellow solid compound 263. $^1$HNMR (400 MHz, CDCl3): 9.42 (bs, 1H), 8.62 (d, 1H), 8.07 (d, 1H), 7.60 (d, 1H), 7.32 (m, 2H), 7.17 (m, 2H), 6.90 (d, 1H), 4.05 (m, 4H), 3.74 (m, 6H), 3.44 (m, 4H), MS-ES+ 426.01.

Preparation of Example 135: 3-(3-(2-chloro-3-fluorophenyl)-1H-pyrrolo[2,3-b]pyridin-5-yl)-N,N-dimethylbenzenesulfonamide (231)

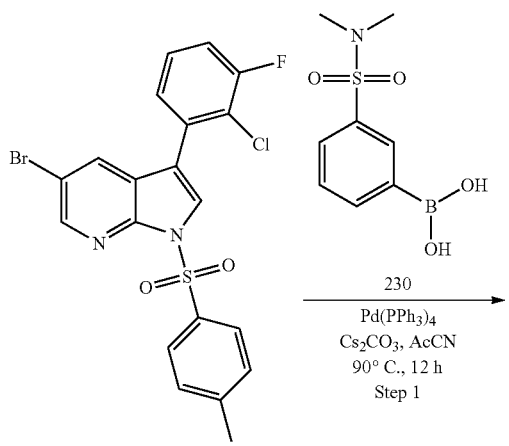

227

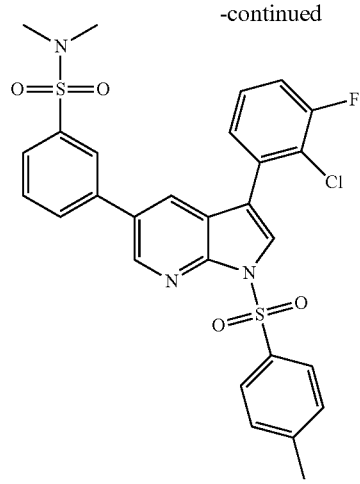

231

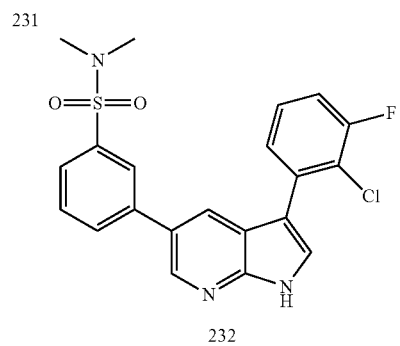

232

Compound 232

$^1$H NMR (400 MHz, CDCl$_3$) δ: 9.86 (s, 1H), 8.63 (d, 1H), 8.13 (d, 1H), 8.01 (s, 1H), 7.85 (d, 1H), 7.77 (m, 1H), 7.65 (m, 2H), 7.35 (m, 2H), 7.19 (m, 1H), 2.76 (s, 6H), MS m/z=329.9 (M+H)$^+$.

Preparation of Example 138: 3-(3-chloro-2-fluorophenyl)-5-(thiophen-3-yl)-1H-pyrrolo[2,3-b]pyridine (165)

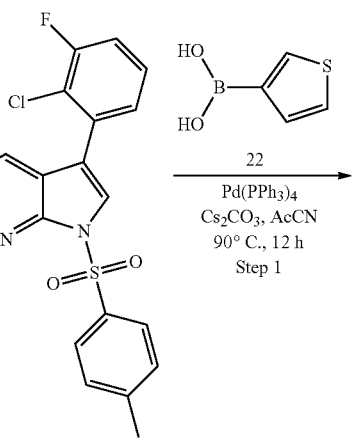

96

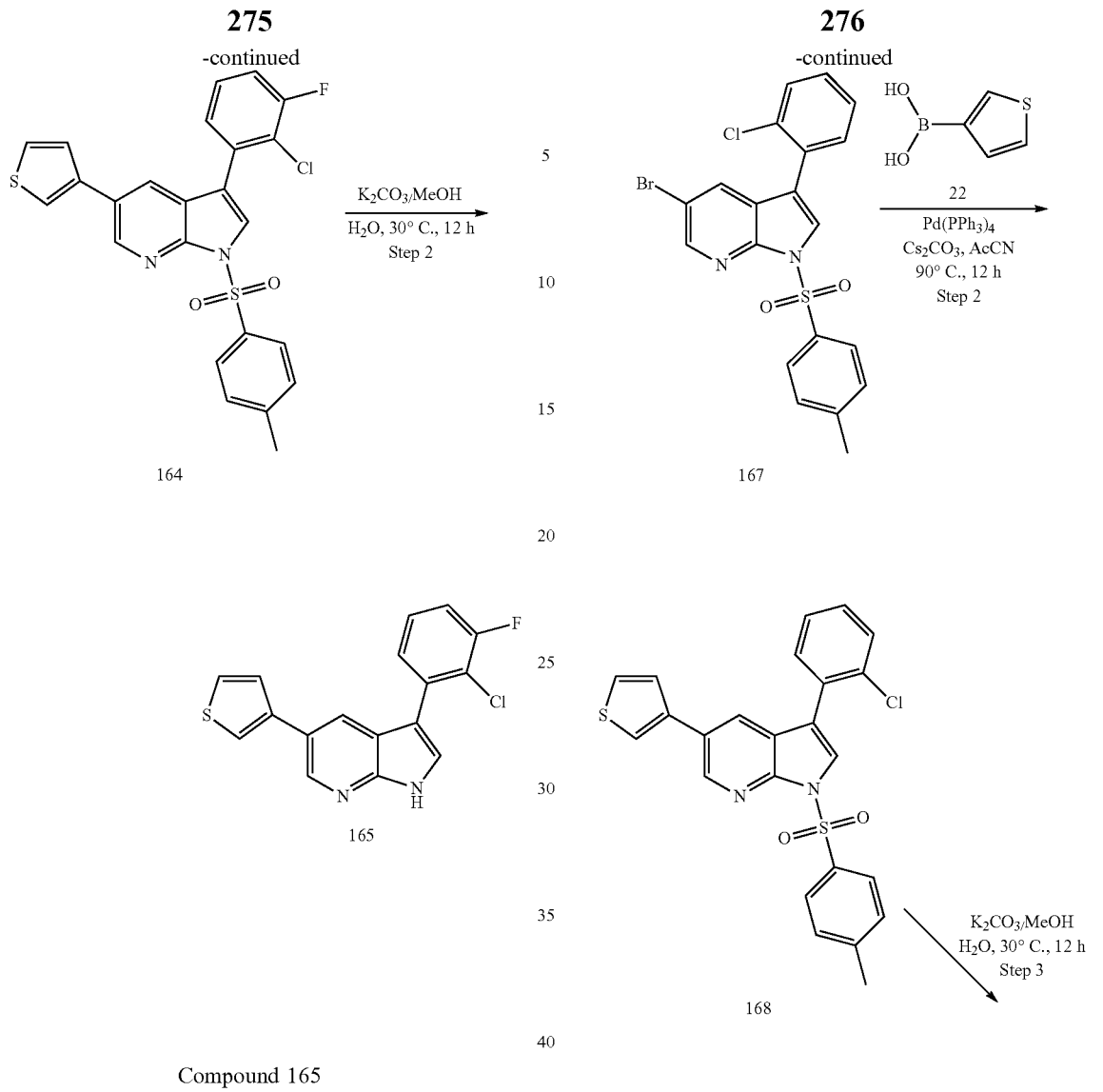
Compound 165
$^1$HNMR (400 MHz, CDCl$_3$) δ: 9.71 (m, 1H), 8.66 (d, 1H), 8.27 (s, 1H), 7.67 (s, 1H), 7.58 (m, 1H), 7.5 (m, 1H), 7.49 (m, 2H), 7.45 (m, 1H), 7.19 (t, 1H), MS m/z ESI: 328.8 (M+H)$^+$.
Preparation of Example 139: 3-(2-chlorophenyl)-5-(thiophen-3-yl)-1H-pyrrolo[2,3-b]pyridine (169)
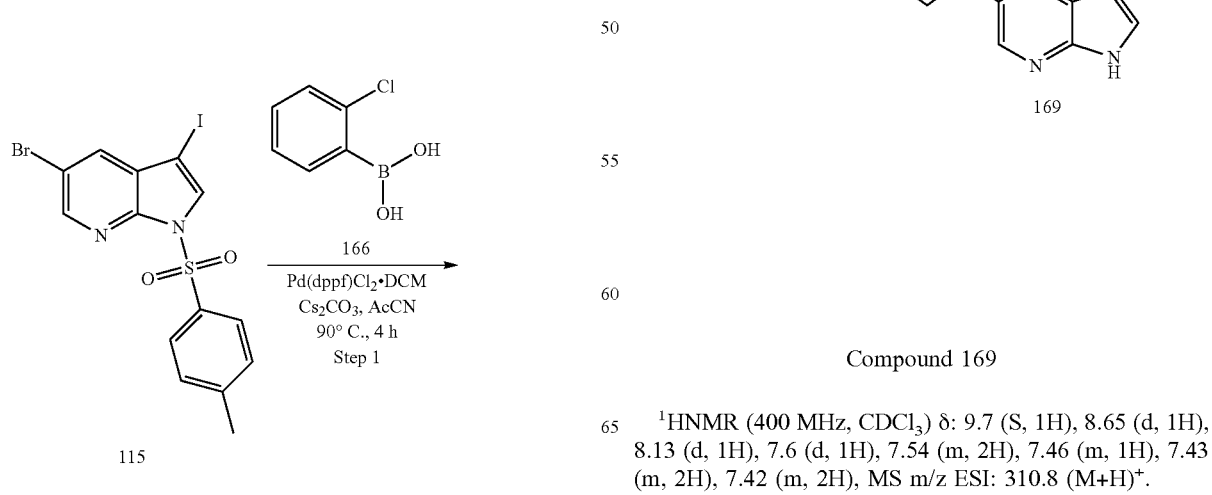
Compound 169
$^1$HNMR (400 MHz, CDCl$_3$) δ: 9.7 (S, 1H), 8.65 (d, 1H), 8.13 (d, 1H), 7.6 (d, 1H), 7.54 (m, 2H), 7.46 (m, 1H), 7.43 (m, 2H), 7.42 (m, 2H), MS m/z ESI: 310.8 (M+H)$^+$.

Preparation of Example 140: 3-(3-chloro-4-fluorophenyl)-5-(thiophen-3-yl)-1H-pyrrolo[2,3-b]pyridine (173)
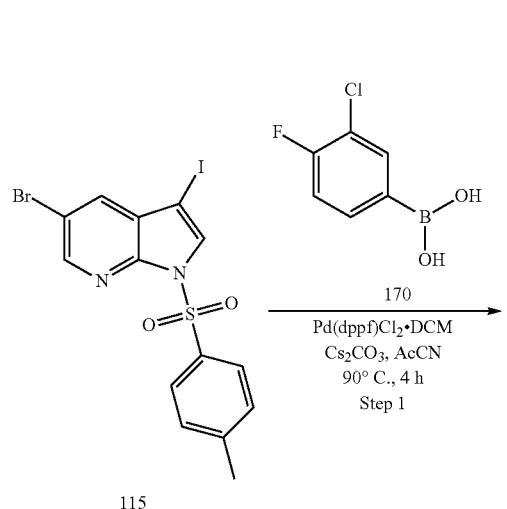
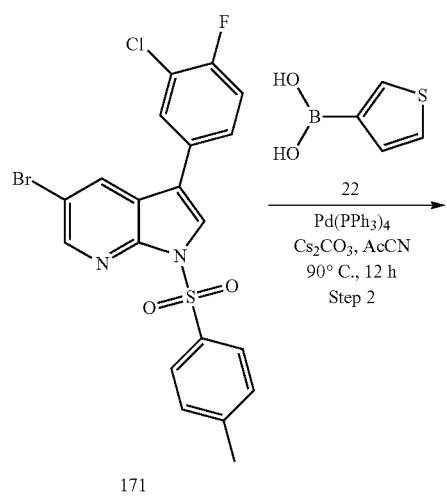
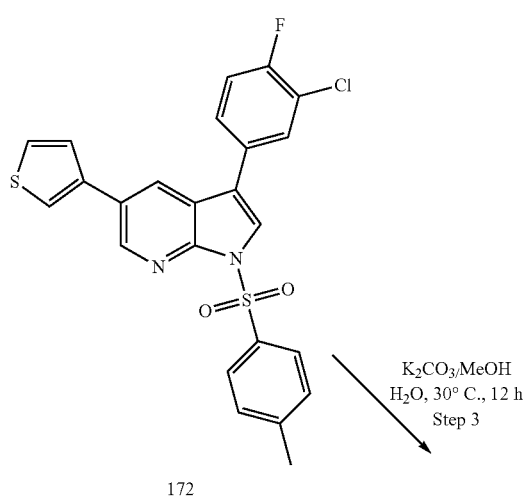
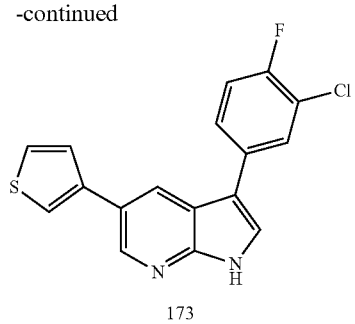
Compound 173
$^1$HNMR (400 MHz, CDCl$_3$) δ: 9.09 (b, 1H), 8.64 (m, 1H), 8.28 (S, 1H), 7.66 (d, 1H), 7.46-749 (m, 4H), MS m/z ESI: 326.8, (M+H)$^+$.
Preparation of Example 142: 4-((5-(3-(3-fluoro-2-methoxyphenyl)-1H-pyrrolo[2,3-b]pyridin-5-yl)thiophen-2-yl)methyl)morpholine (235)
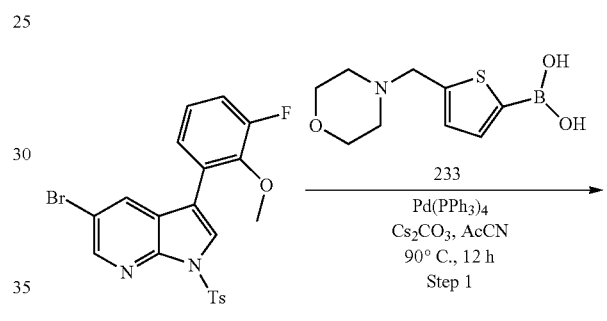
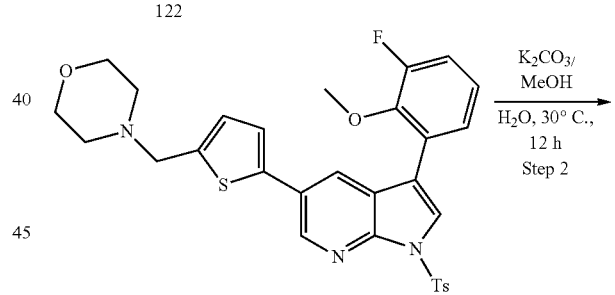
Compound 235
$^1$HNMR (400 MHz, CDCl$_3$) δ: 8.94 (s, 1H), 8.61 (d, 1H), 8.26 (d, 1H), 7.66 (d, 1H), 7.35 (m, 1H), 7.15 (m, 1H), 7.06 (m, 3H), 6.90 (d, 1H), 3.76 (m, 3H), 3.72 (s, 2H), 2.54 (m, 4H), 1.94 (m, 4H), MS m/z=422.1 (M+H)$^+$.

Preparation of Example 143: 4-((5-(3-(3,5-difluoro-2-methoxyphenyl)-1H-pyrrolo[2,3-b]pyridin-5-yl)thiophen-2-yl)methyl)morpholine (238)

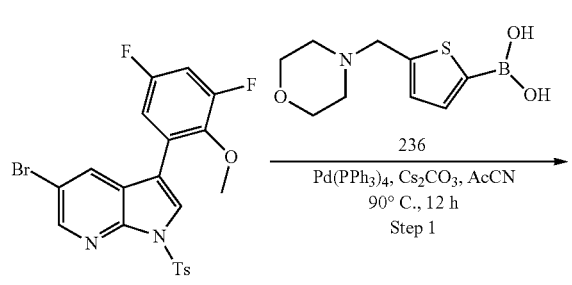

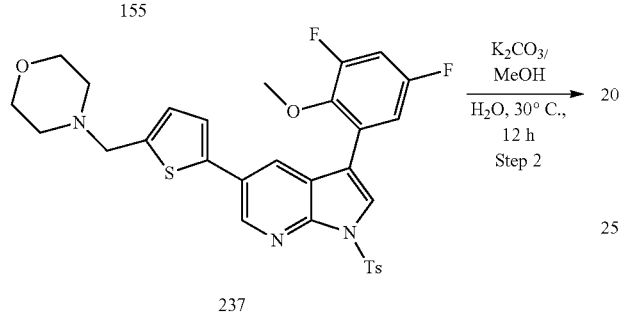

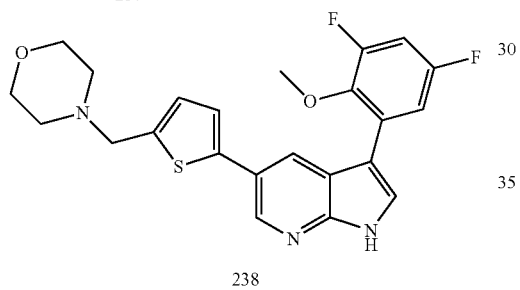

Compound 238

$^1$HNMR (400 MHz, CDCl$_3$) δ: 9.26 (bs, 1H), 8.63 (bs, 1H), 8.27 (s, 1H), 7.71 (d, 1H), 7.17 (d, 1H), 7.09 (m, 1H), 6.92 (d, 1H), 6.84 (m,), 3.75 (m, 5H), 2.55 (bs, 4H), 1.95 (m, 2H), 1.68 (m, 2H), MS m/z=440.1 (M+H)$^+$.

Preparation of Example 148: 5-(5-chlorothiophen-2-yl)-3-(3-fluoro-2-methoxyphenyl)-1H-pyrrolo[2,3-b]pyridine (254)

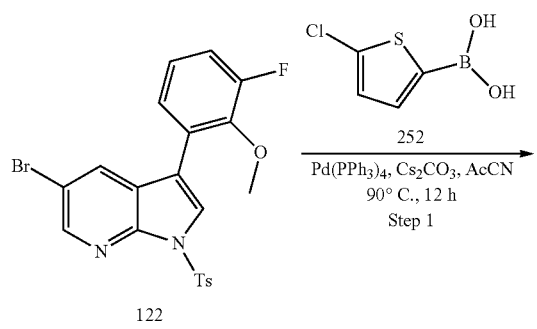

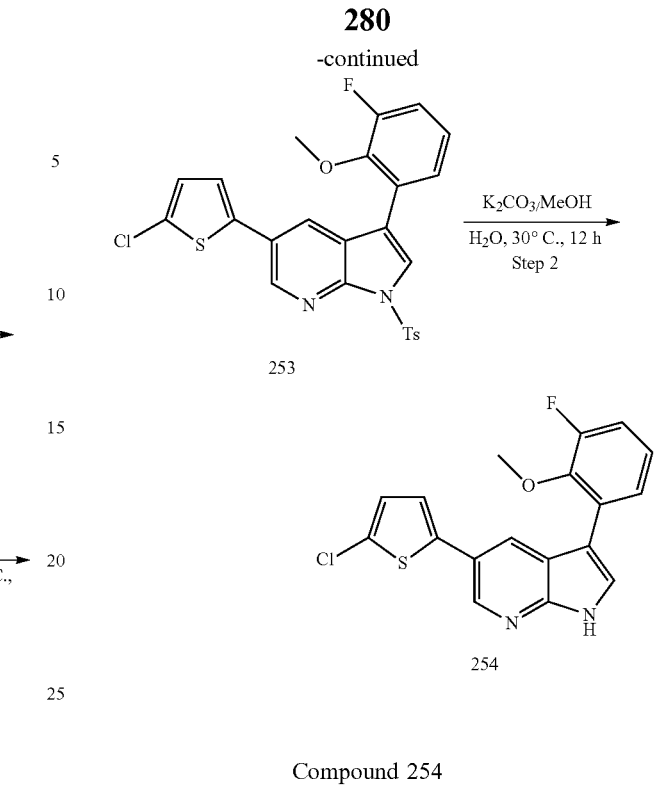

Compound 254

$^1$HNMR (400 MHz, CDCl$_3$) δ: 9.02 (s, 1H), 8.54 (s, 1H), 8.20 (d, 1H), 7.67 (d, 1H), 7.33 (m, 1H), 7.09 (m, 3H), 6.92 (d, 1H), 3.76 (s, 3H); MS m/z=358.9 (M+H).

Preparation of Example 167: 5-(5-chlorothiophen-2-yl)-3-(3,5-difluoro-2-methoxyphenyl)-1H-pyrrolo[2,3-b]pyridine (256)

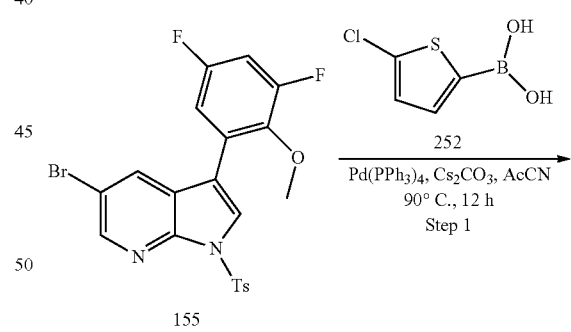

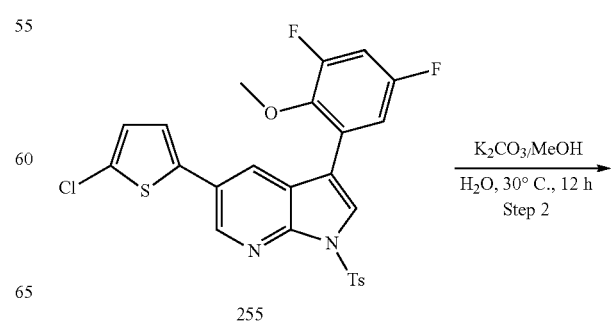

281
-continued
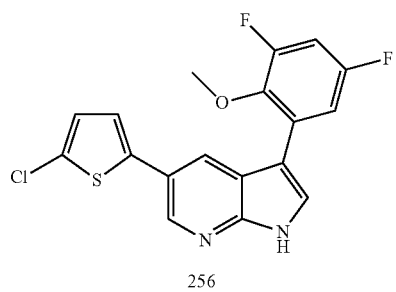
256
Compound 256
¹HNMR (400 MHz, CDCl₃) δ: 9.40 (s, H), 8.55 (d, 1H), 8.21 (d, 1H), 7.73 (s, 1H), 7.09 (m, 2H), 6.93 (d, 1H), 6.85 (m, 1H), 3.69 (s, 3H), MS m/z=376.9 (M+H).
Preparation of Example 168: 3-(3-fluoro-2-methoxyphenyl)-5-(5-methylfuran-2-yl)-1H-pyrrolo[2,3-b]pyridine (259)
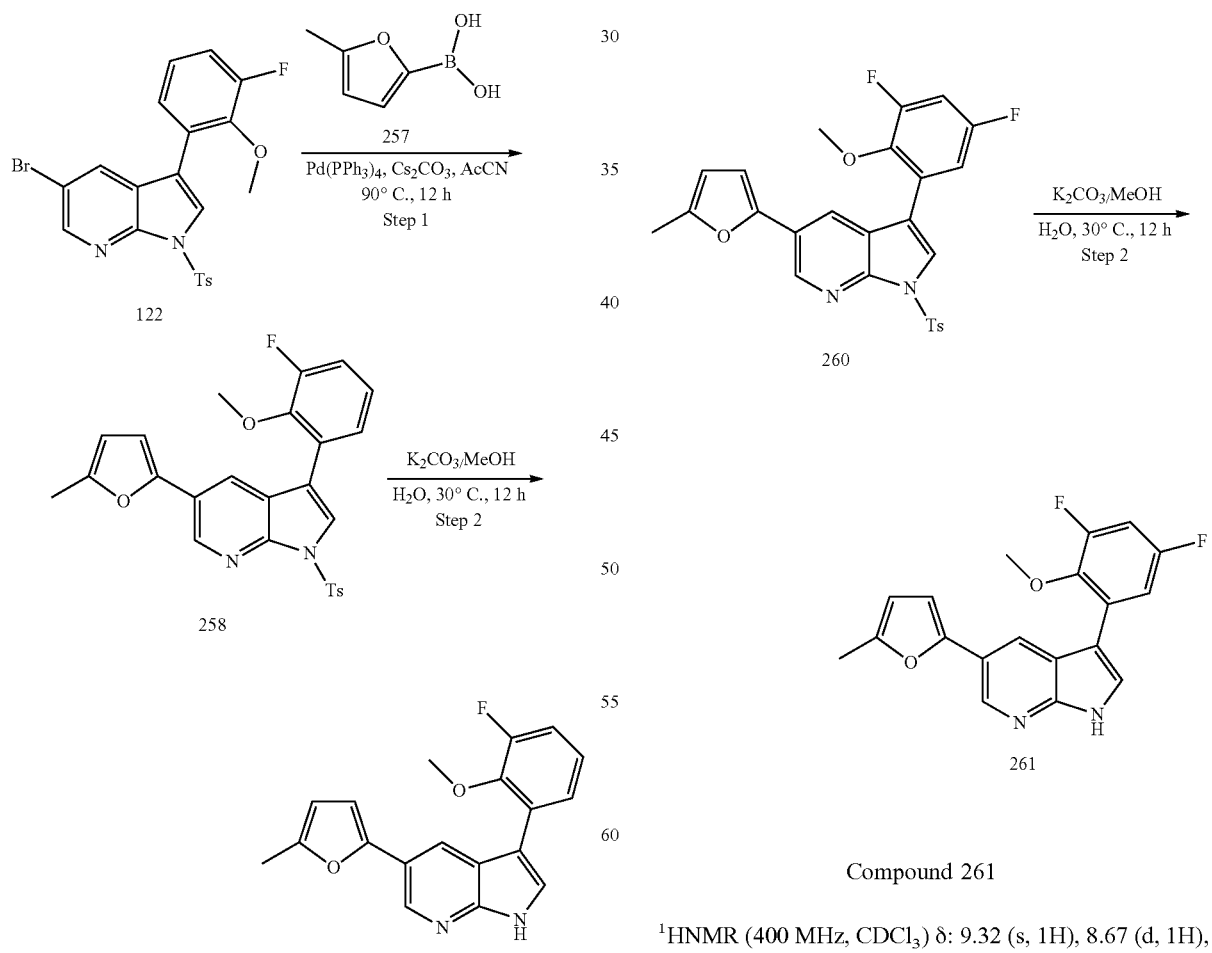
282
Compound 259
¹HNMR (400 MHz, CDCl₃) δ: 9.91 (s, 1H), 8.68 (d, 1H), 8.34 (d, 1H), 7.69 (s, 1H), 7.38 (d, 1H), 7.16 (m, 2H), 6.56 (d, 1H), 6.08 (d, 1H), 3.75 (s, 1H), 2.40 (s, 3H), MS m/z=322.9 (M+H).
Preparation of Example 169: 3-(3,5-difluoro-2-methoxyphenyl)-5-(5-methylfuran-2-yl)-1H-pyrrolo[2,3-b]pyridine (261)
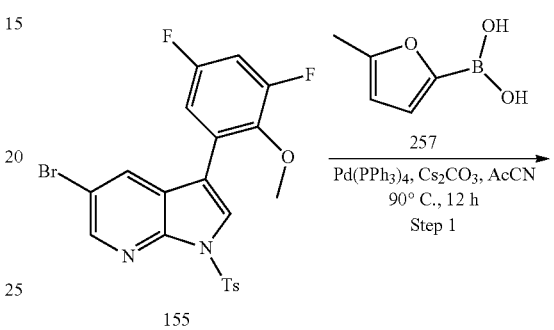
Compound 261
¹HNMR (400 MHz, CDCl₃) δ: 9.32 (s, 1H), 8.67 (d, 1H), 8.32 (d, 1H), 7.71 (s, 1H), 7.14 (m, 1H), 6.84 (m, 1H), 6.57 (m, 1H), 6.08 (m, 1H), 3.69 (s, 3H), 2.41 (s, 3H), MS m/z=339.0 (M+H).

Preparation of Example 174: 3-(3-fluoro-2-methoxyphenyl)-5-(5-(pyrrolidin-1-ylmethyl)thiophen-2-yl)-1H-pyrrolo[2,3-b]pyridine (266)

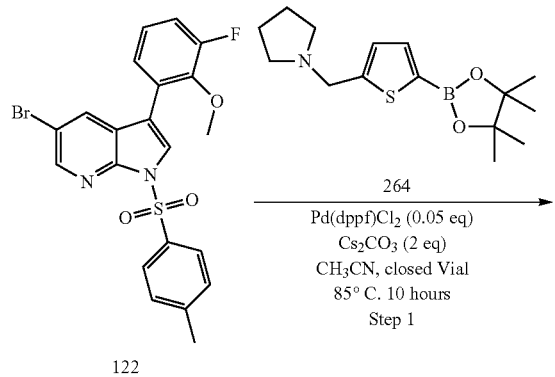

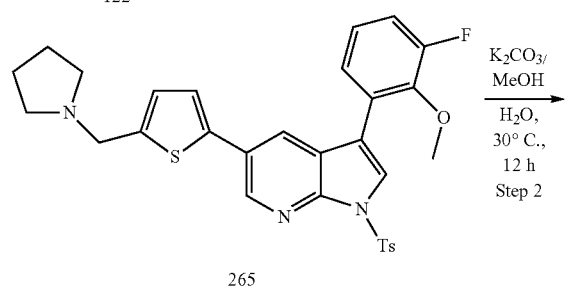

Compound 266

$^1$HNMR (400 MHz, CDCl$_3$) δ: 9.19 (bs, 1H), 8.62 (s, 1H), 8.28 (bs, 1H), 7.68 (d, 1H), 7.35 (d, 1H), 7.14 (m, 3H), 7.05 (s, 1H), 3.86 (s, 2H), 3.76 (s, 3H), 2.64 (bs, 4H), 1.84 (bs, 4H), MS-ES+ 406.1 (M+H).

Preparation of Example 175: 3-(3-fluoro-2-methoxyphenyl)-5-(5-(piperidin-1-ylmethyl)thiophen-2-yl)-1H-pyrrolo[2,3-b]pyridine (268)

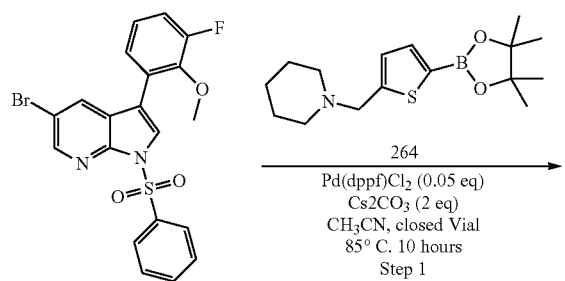

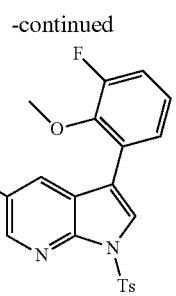

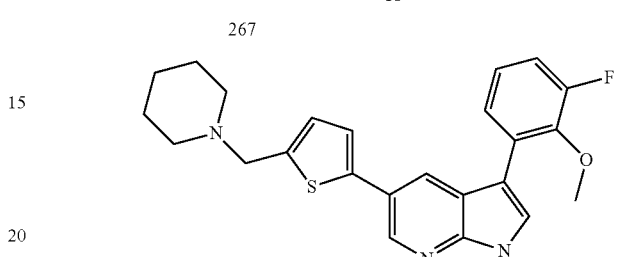

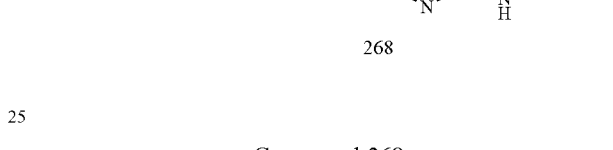

Compound 268

$^1$HNMR (400 MHz, CDCl$_3$) δ: 9.10 (bs 1H), 8.62 (d, 1H), 8.27 (d, 1H), 7.67 (d, 1H), 7.36 (m, 1H), 7.12 (m, 3H), 6.89 (bs, 1H), 3.76 (m, 3H), 3.71 (m, 2H), 2.48 (m, 4H), 1.62 (m, 4H), 1.45 (m, 2H), MS-ES+ 422.1 (M+H).

Preparation of Example 176: 4-(5-(3-(3-fluoro-2-methoxyphenyl)-1H-pyrrolo[2,3-b]pyridin-5-yl)thiazol-2-yl)morpholine (271)

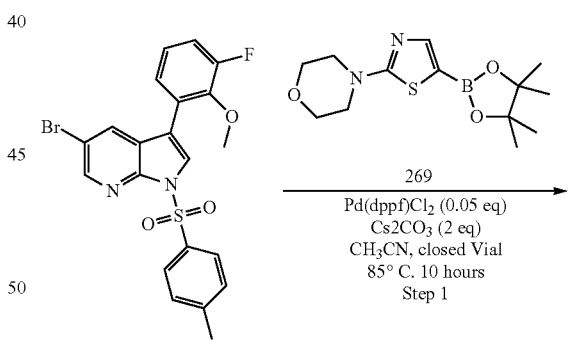

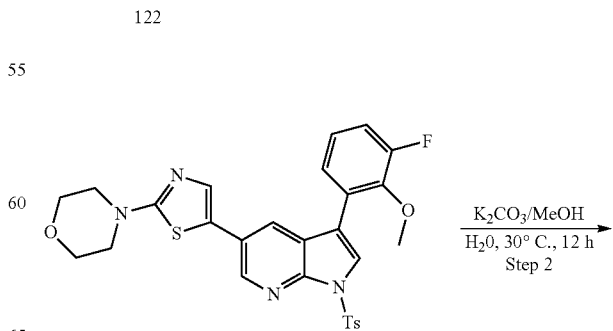

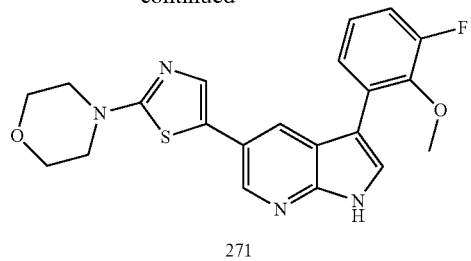

271

Compound 271

¹HNMR (400 MHz, CDCl₃) δ: 9.64 (s, 1H), 8.49 (s, 1H), 8.12 (d, 1H), 7.68 (d, 1H), 7.33 (d, 1H), 7.14 (m, 1H), 7.08 (m, 2H), 3.85 (m, 4H), 3.75 (s, 3H), 3.52 (m, 4H), MS-ES+ 411.0 (M+H).

Preparation of Example 177: 3-(3,5-difluoro-2-methoxyphenyl)-5-(5-(pyrrolidin-1-ylmethyl)thiophen-2-yl)-1H-pyrrolo[2,3-b]pyridine (273)

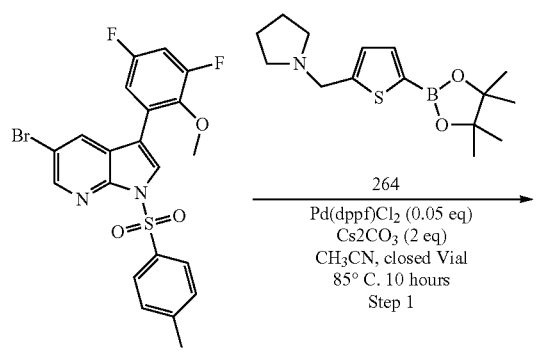

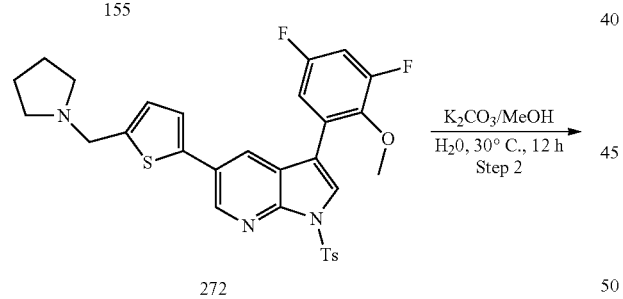

272

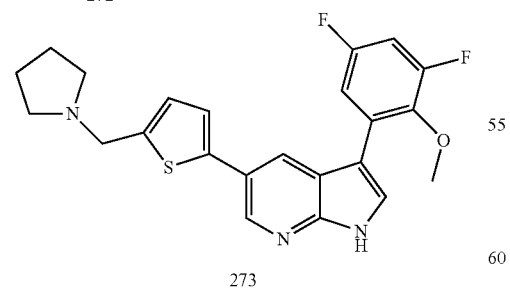

273

Compound 273

¹HNMR (400 MHz, CDCl₃) δ: 9.62 (s, 1H), 8.63 (d, 1H), 8.28 (d, 1H), 7.73 (d, 1H), 7.17 (d, 1H), 7.09 (m, 1H), 6.92 (d, 1H), 6.84 (m, 1H), 3.86 (s, 2H), 3.70 (s, 3H), 2.63 (bs, 4H), 1.83 (bs, 4H), MS-ES+ 426.0 (M+H).

Preparation of Example 178: 3-(3,5-difluoro-2-methoxyphenyl)-5-(5-(piperidin-1-ylmethyl)thiophen-2-yl)-1H-pyrrolo[2,3-b]pyridine (275)

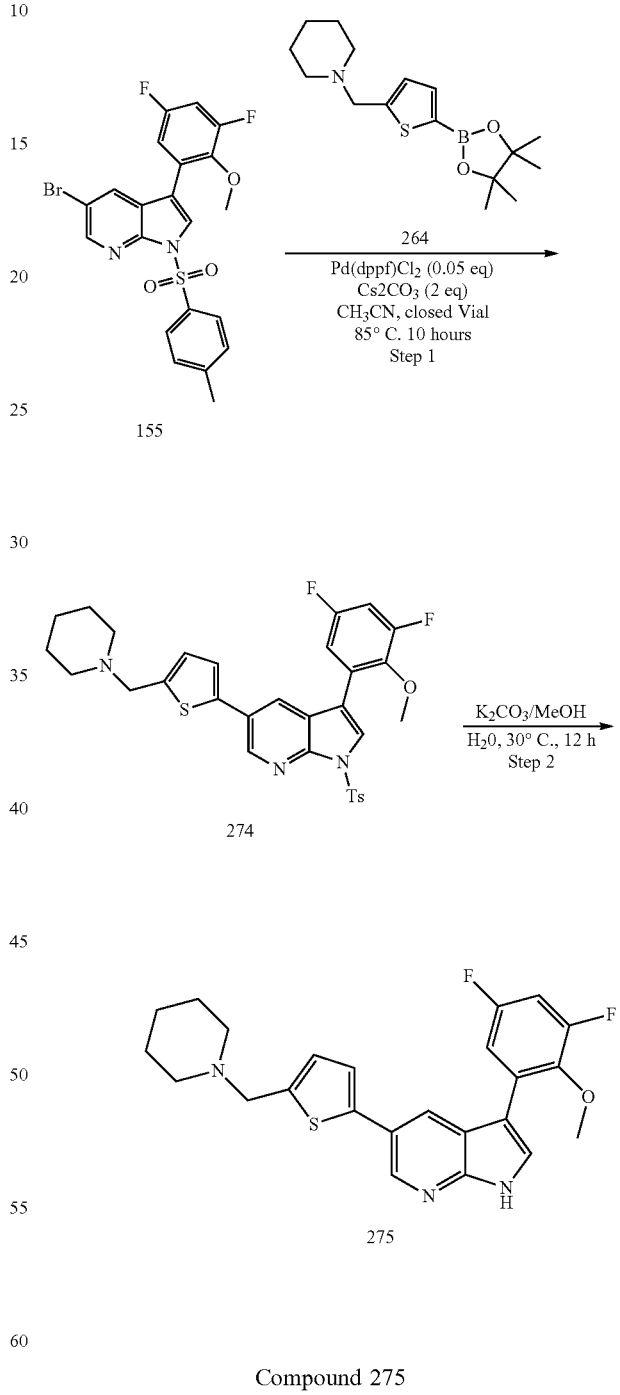

Compound 275

¹HNMR (400 MHz, CDCl₃) δ: 9.49 (bs, 1H), 8.63 (s, 1H), 8.27 (d, 1H), 7.73 (bs, 1H), 7.17 (d, 1H), 7.10 (m, 1H), 6.84 (m, 1H), 6.81 (m, 1H), 4.05 (m, 2H), 3.70 (m, 5H), 3.48 (m, 2H), 2.48 (bs, 4H), 1.92 (m, 2H), MS-ES+ 440.0 (M+H).

287
Preparation of Example 179: 4-(5-(3-(3,5-difluoro-2-methoxyphenyl)-1H-pyrrolo[2,3-b]pyridin-5-yl)thiazol-2-yl)morpholine (277)
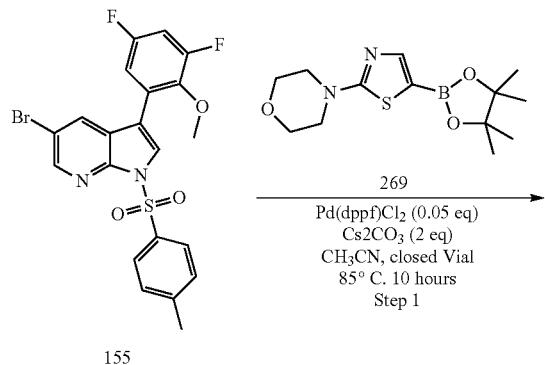
155
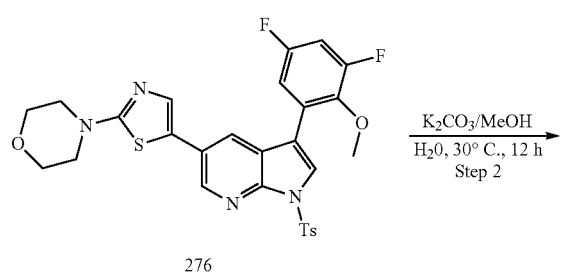
276
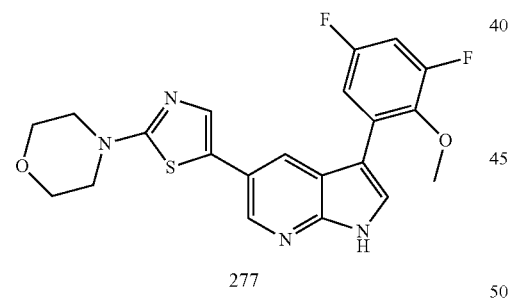
277
Compound 277
$^1$HNMR (400 MHz, CDCl$_3$) δ: 9.43 (s, 1H), 8.51 (d, 1H), 8.12 (d, 1H), 7.72 (d, 1H), 7.42 (s, 1H), 7.08 (m, 1H), 6.84 (m, 1H), 3.84 (m, 4H), 3.69 (s, 3H), 3.53 (m, 4H), MS-ES+ 429.0 (M+H).
288
Preparation of Example 180: N-(4-((4-methylpiperazin-1-yl)methyl)phenyl)-4-(thiophen-3-yl)-1H-pyrazolo[3,4-b]pyridin-3-amine (240)
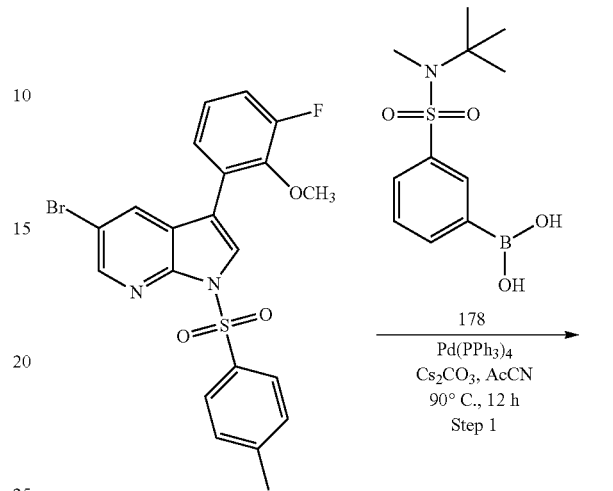
122
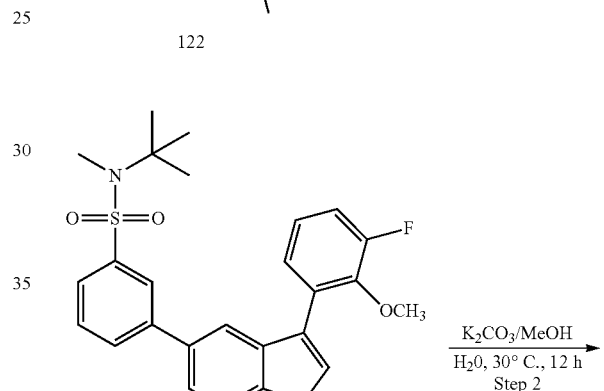
239
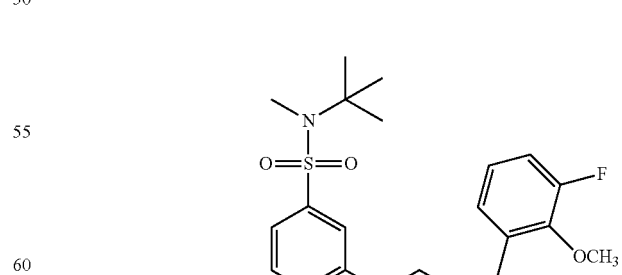
240

289
Compound 240
$^1$HNMR (400 MHz, CDCl$_3$) δ: 8.61 (s, 1H), 8.32 (s, 1H), 8.09 (s, 1H), 7.80 (m, 3H), 7.60 (m, 1H), 7.36 (d, 1H), 7.15 (m, 2H), 3.77 (s, 3H), 3.01 (s, 3H), 1.39 (s, 9H): MS m/z=468.1 (M+H).
Preparation of Example 181: N-(tert-butyl)-3-(3-(3,5-difluoro-2-methoxyphenyl)-1H-pyrrolo[2,3-b]pyridin-5-yl)-N-methylbenzenesulfonamide (242)
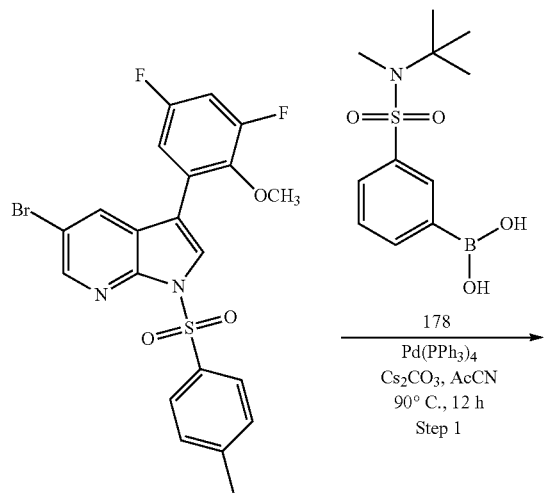
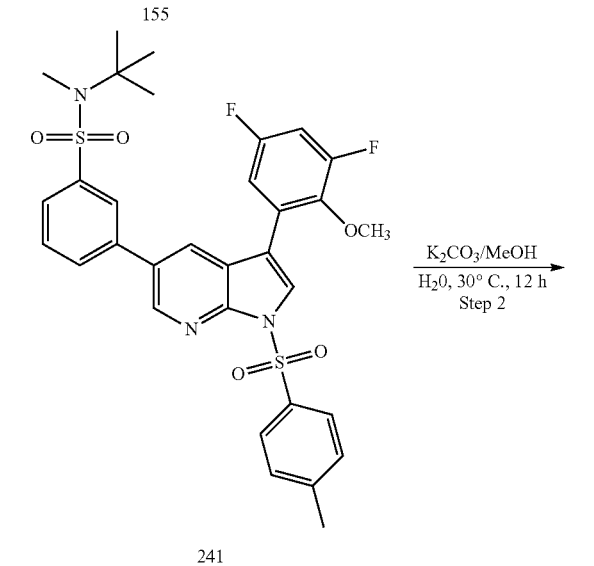
290
Compound 242
$^1$HNMR (400 MHz, CDCl$_3$) δ: 9.55 (s, 1H), 8.62 (s, 1H), 8.31 (s, 1H), 8.08 (s, 1H), 7.79 (m, 3H), 7.60 (t, 1H), 7.10 (m, 1H), 6.85 (m, 1H), 3.70 (s, 3H), 3.02 (s, 3H), 1.39 (s, 9H), MS m/z=486.1 (M+H).
Preparation of Example 182: 3-(3-fluoro-2-methoxyphenyl)-5-(3-(pyrrolidin-1-ylsulfonyl)phenyl)-1H-pyrrolo[2,3-b]pyridine (245)
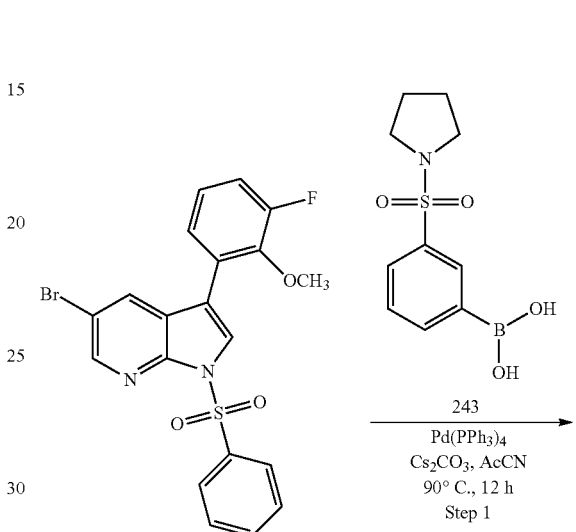
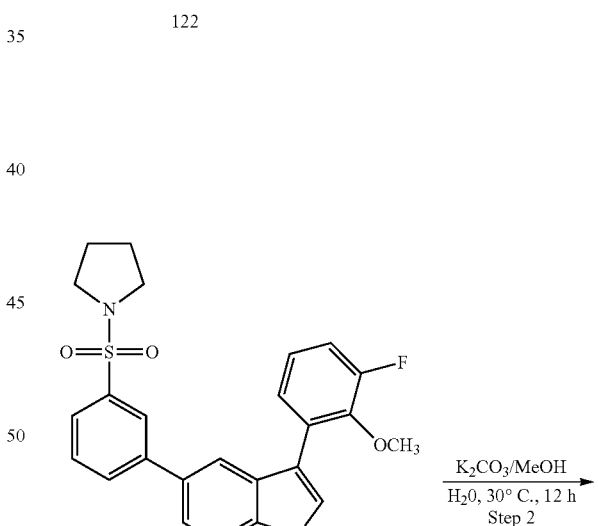

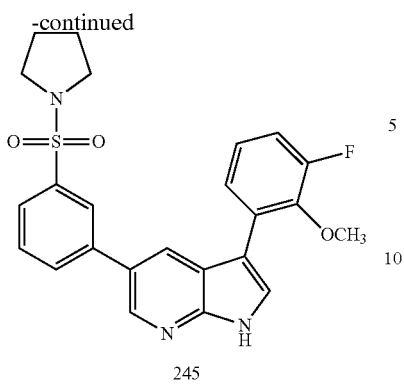
245
Compound 245
¹HNMR (400 MHz, CDCl₃) δ: 9.25 (s, 1H), 8.61 (s, 1H), 8.31 (d, 1H), 8.08 (d, 1H), 7.82 (m, 2H), 7.72 (d, 1H), 7.63 (t, 1H), 7.36 (m, 1H), 7.11 (m, 2H), 3.76 (s, 3H), 3.30 (m, 4H), 1.79 (m, 4H), MS m/z=452.0 (M+H).
Preparation of Example 183: 3-(3,5-difluoro-2-methoxyphenyl)-5-(3-(pyrrolidin-1-ylsulfonyl)phenyl)-1H-pyrrolo[2,3-b]pyridine (247)
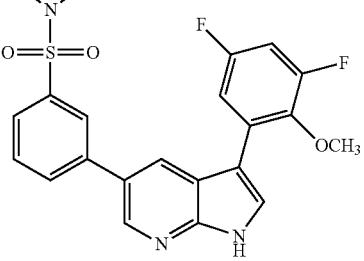
247
Compound 247
¹HNMR (400 MHz, CDCl₃) δ: 9.63 (s, 1H), 8.63 (s, 1H), 8.31 (s, 1H), 8.09 (s, 1H), 7.85 (m, 2H), 7.67 (m, 1H), 7.63 (m, 1H), 7.09 (m, 1H), 6.86 (m, 1H), 3.70 (s, 3H), 3.31 (m, 4H), 1.80 (m, 4H), MS m/z=470.1 (M+H).
Preparation of Example 184: 3-(3-(3-fluoro-2-methoxyphenyl)-1H-pyrrolo[2,3-b]pyridin-5-yl)-N,N-dimethylbenzenesulfonamide (249)
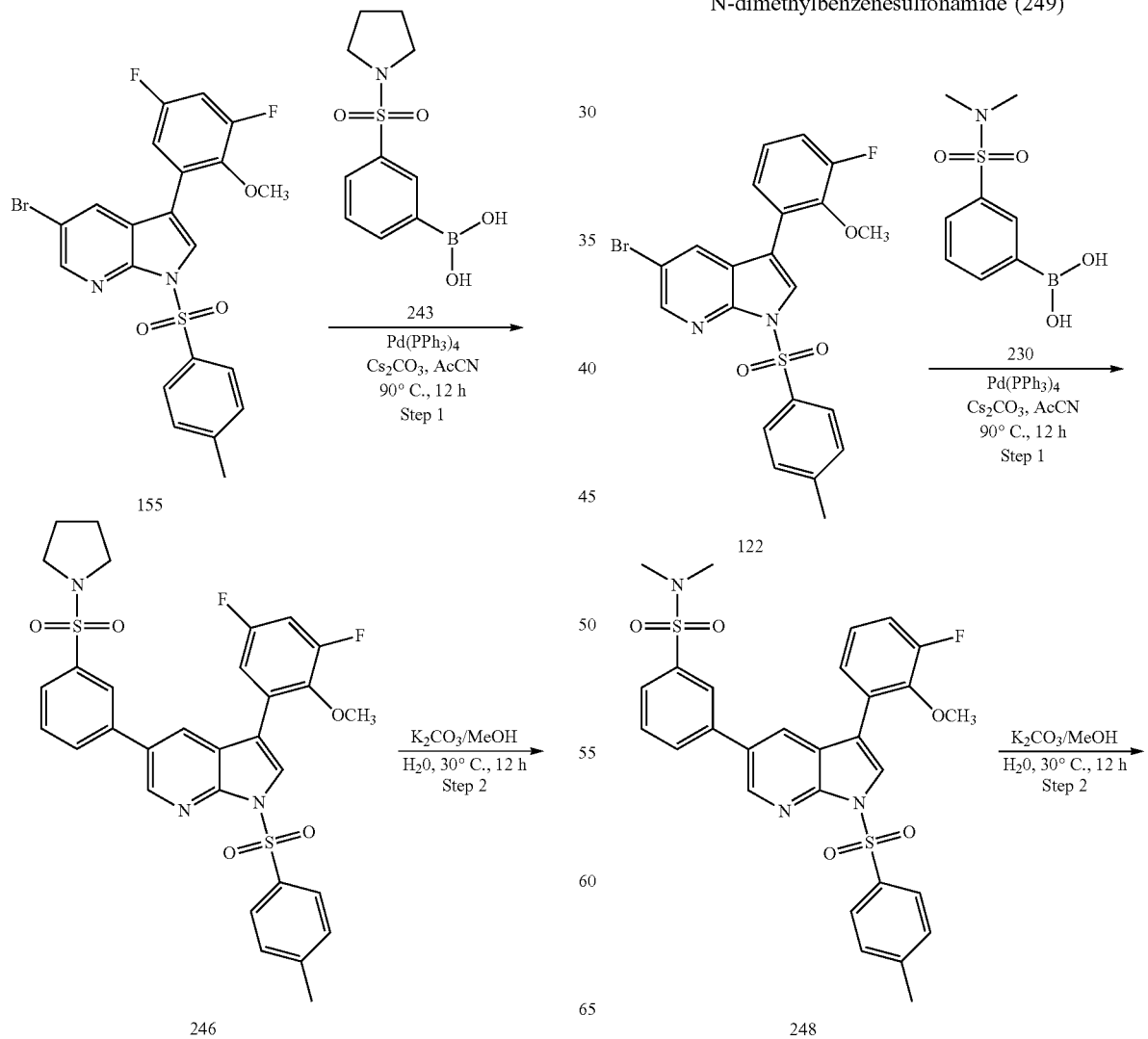

293
-continued

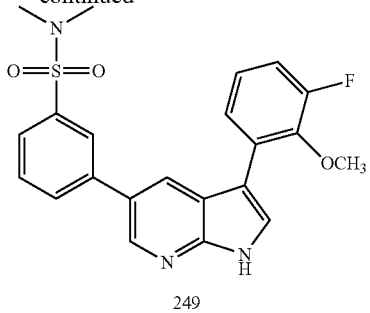

249

Compound 249

¹HNMR (400 MHz, CDCl₃) δ: 9.63 (s, 1H), 8.63 (s, 1H), 8.31 (s, 1H), 8.09 (s, 1H), 7.85 (m, 2H), 7.67 (m, 1H), 7.63 (m, 1H), 7.09 (m, 1H), 6.86 (m, 1H), 3.70 (s, 3H), 3.31 (m, 4H), 1.80 (m, 4H), MS m/z=470.1 (M+H).

Preparation of Example 185: 3-(3-(3,5-difluoro-2-methoxyphenyl)-1H-pyrrolo[2,3-b]pyridin-5-yl)-N,N-dimethylbenzenesulfonamide (251)

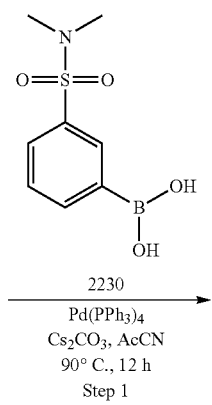

155

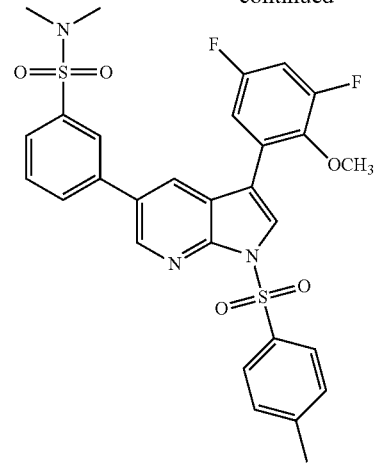

2230
———————→
Pd(PPh₃)₄
Cs₂CO₃, AcCN
90° C., 12 h
Step 1

294
-continued

K₂CO₃/MeOH
————————→
H₂O, 30° C., 12 h
Step 2

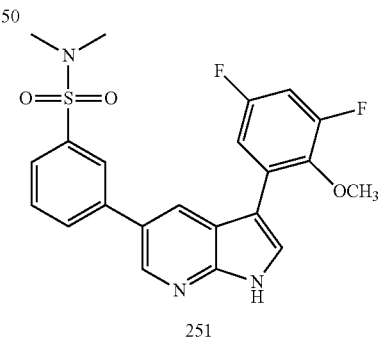

250

251

Compound 251

¹HNMR (400 MHz, CDCl₃) δ: 9.77 (s, 1H), 8.61 (s, 1H), 8.31 (s, 1H), 8.03 (s, 1H), 7.86 (d, 1H), 7.78 (m, 2H), 7.65 (m, 1H), 7.09 (m, 1H), 6.86 (m, 1H), 3.70 (s, 3H), 2.77 (s, 6H), MS m/z=446.13 (M+H).

Preparation of Example 190: 3-(3-fluoro-2-methoxyphenyl)-5-(1-(piperidin-4-yl)-1H-pyrazol-4-yl)-1H-pyrrolo[2,3-b]pyridine (280)

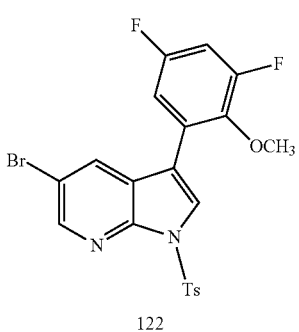

122

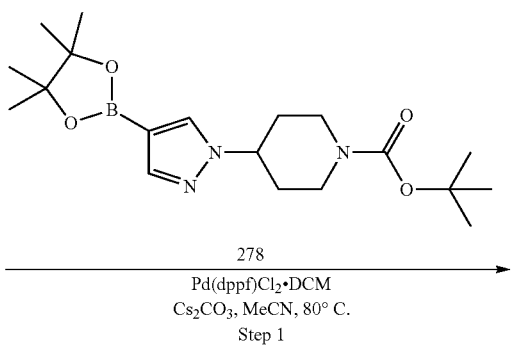

278
————————→
Pd(dppf)Cl₂·DCM
Cs₂CO₃, MeCN, 80° C.
Step 1

-continued
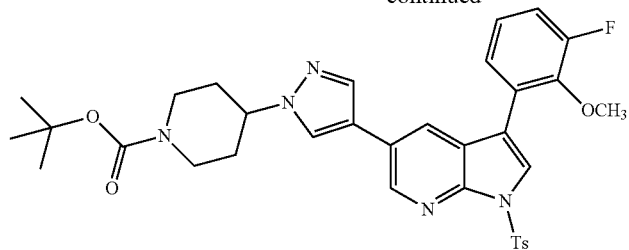
279
K₂CO₃/MeOH
H₂O, 30° C., 12 h
TFA/DCM, 4 h
TFA/DCM, 4 h
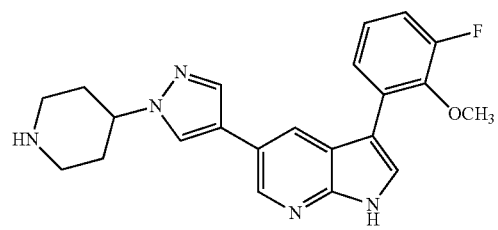
280
Compound 280
¹HNMR (400 MHz, CDCl₃) δ: 9.36 (s, 1H), 8.50 (s, 1H), 8.17 (d, 1H), 7.76 (m, 2H), 7.65 (s, 1H), 7.35 (s, 1H), 7.08 (m, 2H), 4.29 (m, 1H), 4.05 (m, 4H), 3.73 (s, 3H), 3.28 (m, 2H), 2.81 (m, 2H), MS-ES+ 392.1 (M+H).
Preparation of Example 191: 3-(3,5-difluoro-2-methoxyphenyl)-5-(1-(piperidin-4-yl)-1H-pyrazol-4-yl)-1H-pyrrolo[2,3-b]pyridine (282)
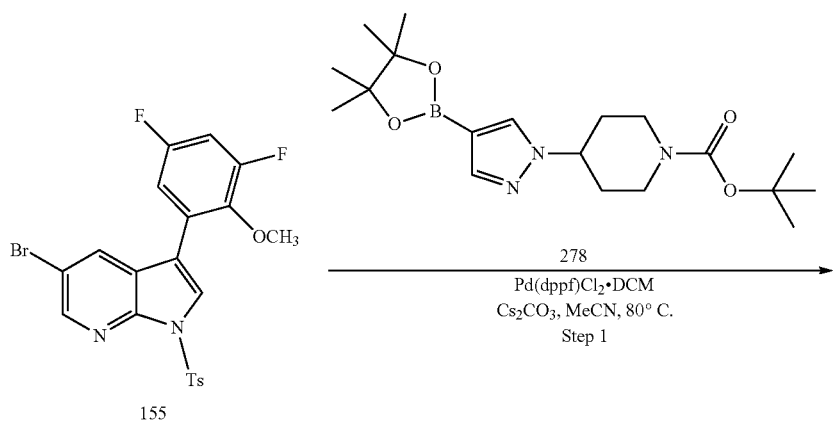
155
278
Pd(dppf)Cl₂•DCM
Cs₂CO₃, MeCN, 80° C.
Step 1

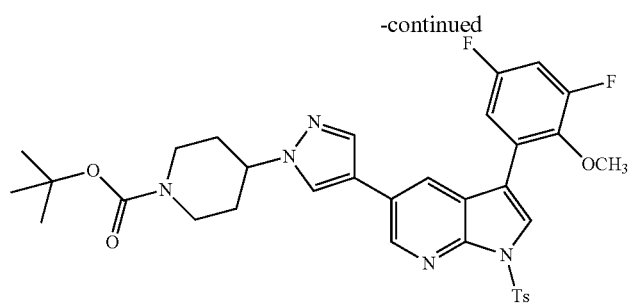
281
K₂CO₃/MeOH
H₂O, 30° C., 12 h      Step 2
TFA/DCM, 4 h
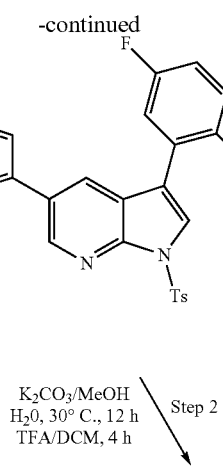
282
Compound 282
¹HNMR (400 MHz, CDCl₃) δ: 12.06 (s, 1H), 8.65 (s, 1H), 8.57 (s, 1H), 8.40 (d, 1H), 8.30 (d, 1H), 8.20 (s, 1H), 7.82 (d, 1H), 7.25 (m, 2H), 4.50 (m, 1H), 3.60 (s, 3H), 3.09 (m, 2H), 2.23 (m, 4H), MS-ES+ 410.1 (M+H).
Preparation of Example 192: 2-(5-(5-(morpholinomethyl)thiophen-2-yl)-1H-pyrrolo[2,3-b]pyridin-3-yl)phenol (286)
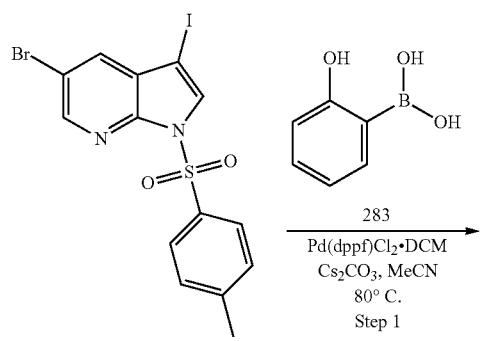
283
Pd(dppf)Cl₂·DCM
Cs₂CO₃, MeCN
80° C.
Step 1
155

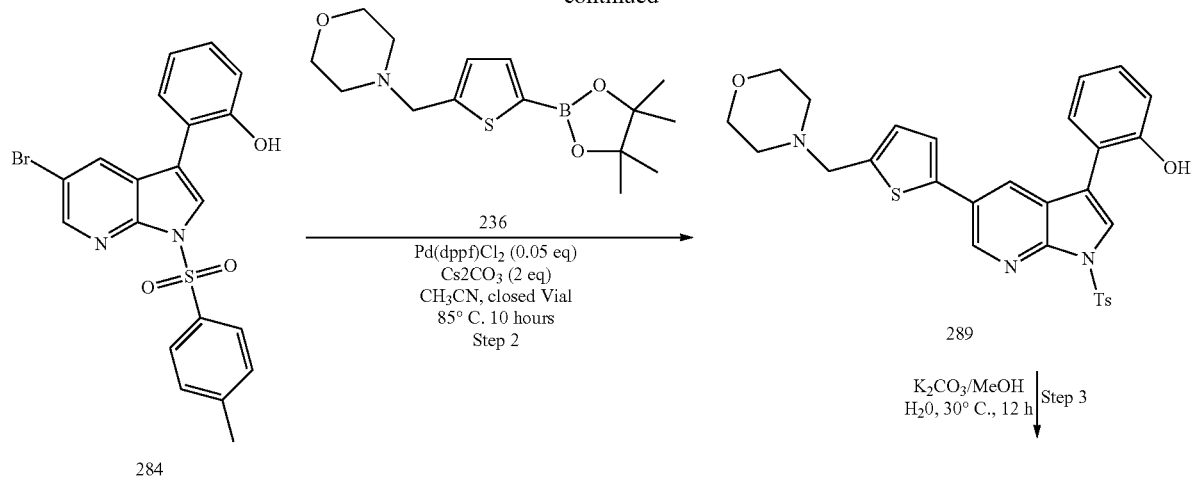

Step 1:

To a solution of 115 (150 mg, 0.314 mmol) and (2-hydroxyphenyl) boronic acid 283 (43 mg, 0.314 mmol) in acetonitrile (5 mL) was added cesium carbonate (204 mg, 0.628 mmol). The resulting reaction was degassed and purged with nitrogen for 10 min. Pd (dppf) Cl$_2$ (12 mg, 0.0157 mmol) was added to the reaction and the reaction was again degassed and purged with nitrogen for another 5 min. The reaction was heated to 80° C. in a sealed tube overnight. After completion, the reaction was allowed to cool to rt and diluted with chloroform. The organic layer was concentrated to get the crude, which was purified through flash chromatography by using 100-200 mesh silica gel. The compound was eluted at 30% ethyl acetate in hexane as half white coloured solid compound 2-(5-bromo-1-tosyl-1H-pyrrolo[2,3-b]pyridin-3-yl)phenol 284.

Step 2:

To a solution of compound 284 (100 mg, 0.225 mmol) and 236 (51 mg, 0.225 mmol) in acetonitrile (5 mL) was added cesium carbonate (146 mg, 0.4451 mmol). The reaction was degassed and purged with nitrogen for 10 min. Pd (dppf) Cl$_2$ (9 mg, 0.01127 mmol) was added to the reaction, which was again degassed and purged with nitrogen for another 5 min. The reaction was heated to 80° C. in a sealed tube overnight. The reaction was allowed to cool to rt and diluted with chloroform. The organic layer was concentrated to get the crude, which was purified through flash chromatography by using 100-200 mesh silica gel. The compound was eluted at 60% ethyl acetate in hexane as half-white coloured solid compound 285.

Step 3:

To a solution of 285 (50 mg, 0.0916 mmol) in methanol (20 mL) and water (5 mL) was added potassium carbonate (37 mg, 0.274 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered, and concentrated to get the crude, which was purified through flash chromatography by using neutral alumina. The compound was eluted at 0.5% methanol in dichloromethane as pale yellow solid compound 2-(5-(5-(morpholinomethyl) thiophen-2-yl)-1H-pyrrolo[2,3-b]pyridin-3-yl) phenol 286. $^1$H NMR (CDCl$_3$) δ: 9.33 (bs, 1H), 8.63 (bs, 1H), 8.11 (d, 1H), 7.52 (d, 1H), 7.41 (m, 2H), 7.30 (m, 1H), 7.12 (m, 1H), 7.07 (m, 2H), 6.90 (d, 1H), 3.76 (m, 6H), 2.53 (m, 4H) and MS m/z=392 (M+H).

Preparation of Example 193: 2-fluoro-6-(5-(5-(morpholinomethyl)thiophen-2-yl)-1H-pyrrolo[2,3-b]pyridin-3-yl)phenol (290)

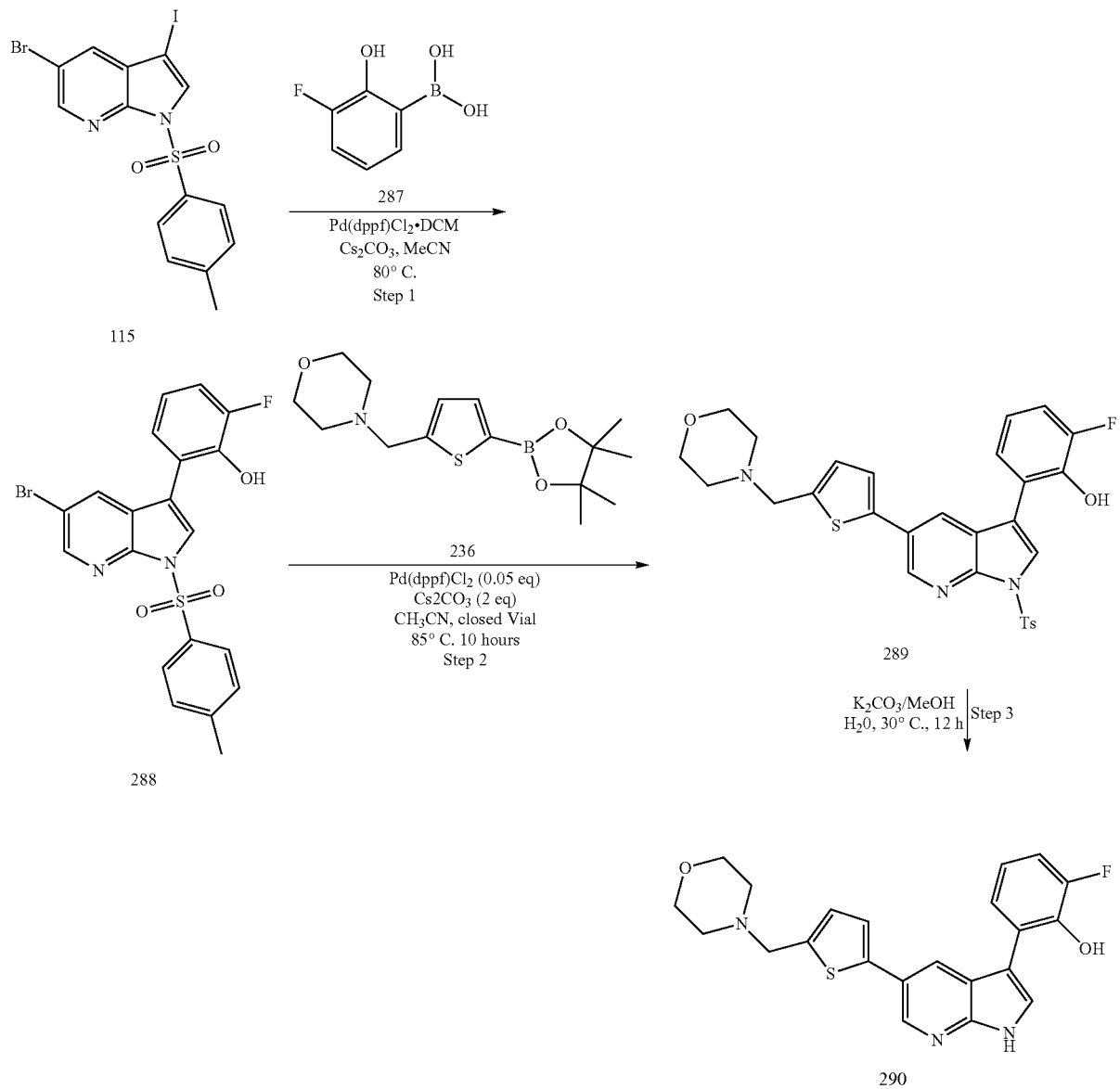

Step 1:

To a solution of 288 (100 mg, 0.216 mmol) and 236 (49 mg, 0.216 mmol) in acetonitrile (7 mL) was added cesium carbonate (141 mg, 0.433 mmol). The reaction was degassed and purged with nitrogen for 10 min. Pd(dppf)Cl$_2$. (8 mg, 0.108 mmol) was added to the RM, which was again degassed and purged with nitrogen for another 5 min. The RM was heated to 80° C. in a sealed tube overnight. The reaction was allowed to cool to rt and diluted with chloroform. The organic layer was concentrated to get the crude product, which was purified through flash chromatography by using 100-200 mesh silica gel. The compound was eluted at 42% ethyl acetate in hexane as half white colored solid compound 289.

Step 2:

To a solution of 289 (50 mg, 0.0887 mmol) in methanol (15 mL) and water (5 mL) was added potassium carbonate (36 mg, 0.266 mmol). The RM was heated to 60° C. overnight. The solvent was completely distilled and the RM diluted with water (25 mL) and extracted with chloroform twice (2×25 mL). The combined organic layer was dried over sodium sulphate, filtered and concentrated to get the crude compound, which was purified through flash chromatography by using 100-200 mesh silica gel. The compound was eluted at 65% ethyl acetate in hexane as pale yellow solid compound 290. $^1$HNMR (400 MHz, CDCl3): 12.00 (bs, 1H), 9.62 (bs, 1H), 8.55 (d, 1H), 8.17 (d, 1H), 7.77 (d, 1H), 7.35 (m, 2H), 7.12 (m, 1H), 6.97 (d, 1H), 6.89 (m, 1H), 3.67 (bs, 2H), 3.57 (m, 4H), 2.43 (m, 4H); MS-ES+ 408.8

Preparation of Example 194: 4-((5-(3-(2,2-difluorobenzo[d][1,3]dioxol-4-yl)-1H-pyrrolo[2,3-b]pyridin-5-yl)thiophen-2-yl)methyl)morpholine (294)
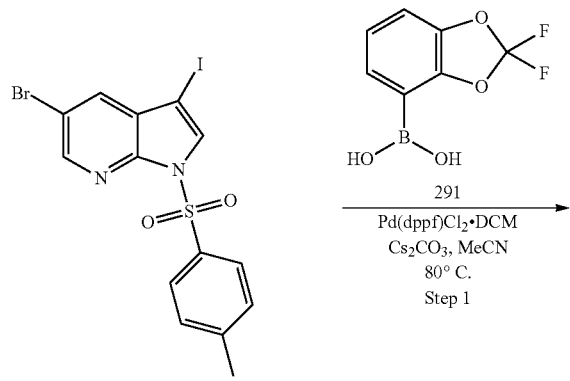
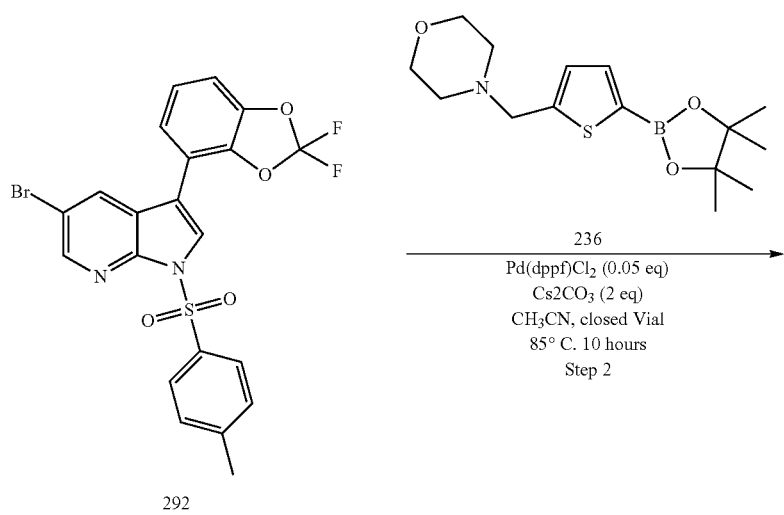

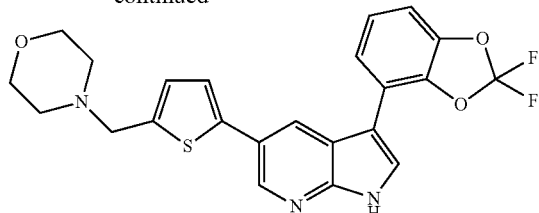

294

Step 1:

To a solution of 115 (150 mg, 0.314 mmol) and 291 (63 mg, 0.314 mmol) in acetonitrile (5 mL) was added cesium carbonate (204 mg, 0.628 mmol). The RM was degassed and purged with nitrogen for 10 min. Pd(dppf)Cl$_2$ (12 mg, 0.0157 mmol) was added and the RM was again degassed and purged with nitrogen for another 5 min. The RM was heated to 80° C. in a sealed tube overnight and then allowed to cool to rt and diluted with chloroform. The organic layer was concentrated to get the crude product, which was purified through flash chromatography by using 100-200 mesh silica gel. The compound was eluted at 6% ethyl acetate in hexane as half white colored solid compound 292.

Step 2:

To a solution of 292 (100 mg, 0.197 mmol) and 236 (44 mg, 0.197 mmol) in acetonitrile (7 mL) was added cesium carbonate (128 mg, 0.394 mmol). The RM was degassed and purged with nitrogen for 10 min. Pd(dppf)Cl$_2$ (8 mg, 0.00985 mmol) was added, and the RM was again degassed and purged with nitrogen for another 5 min, then heated to 80° C. in a sealed tube overnight. The RM was allowed to cool to rt and diluted with chloroform. The organic layer was concentrated to get the crude product, which was purified through flash chromatography by using 100-200 mesh silica gel. The compound was eluted at 40% ethyl acetate in hexane as half white colored solid compound 293.

Step 3:

To a solution of 293 (60 mg, 0.9836 mmol) in methanol (20 mL) and water (8 mL) was added potassium carbonate (40 mg, 0.295 mmol). The RM was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude compound, which was purified through flash chromatography by using 100-200 mesh silica gel. The compound was eluted at 60% ethyl acetate in hexane as pale yellow solid compound 294. $^1$HNMR (400 MHz, CDCl$_3$): 9.75 (s, 1H), 8.66 (d, 1H), 8.39 (d, 1H), 7.81 (d, 1H), 7.49 (d, 1H), 7.20 (m, 2H), 7.00 (d, 1H), 6.93 (d, 1H), 3.74 (m, 6H), 2.55 (m, 4H) MS-ES+ 456.1

Preparation of Example 195: 4-(5-(3-(2,2-difluorobenzo[d][1,3]dioxol-4-yl)-1H-pyrrolo[2,3-b]pyridin-5-yl)thiazol-2-yl)morpholine (296)

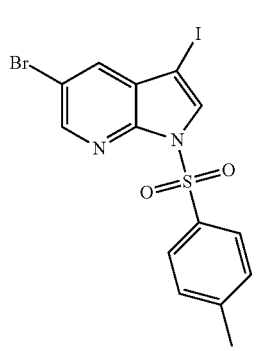

115

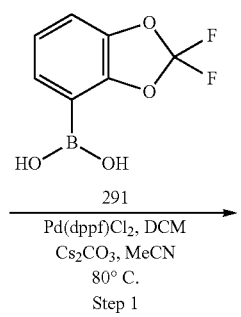

291

Pd(dppf)Cl$_2$, DCM
Cs$_2$CO$_3$, MeCN
80° C.
Step 1

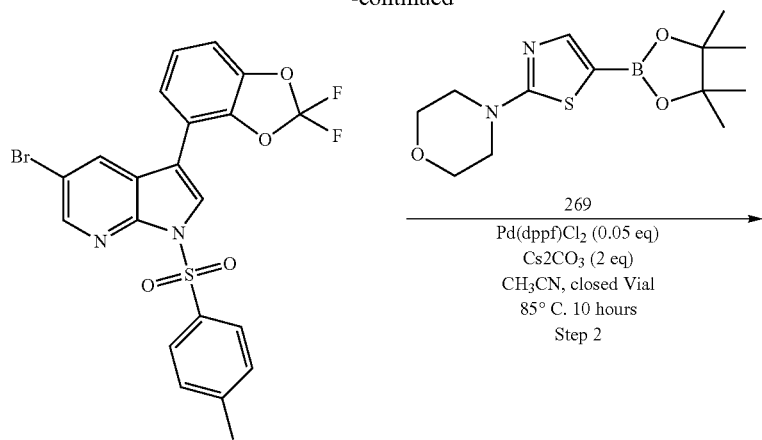

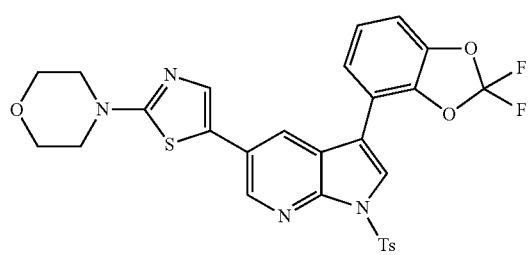

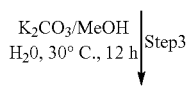

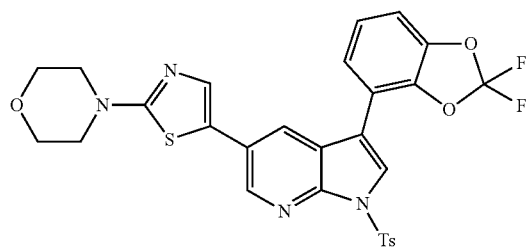

Step 1:

To a solution of 292 (100 mg, 0.197 mmol) and 269 (42 mg, 0.197 mmol) in acetonitrile (5 mL) was added cesium carbonate (128 mg, 0.394 mmol). The RM was degassed and purged with nitrogen for 10 min. Pd(dppf)Cl$_2$ (8 mg, 0.00985 mmol) was added and the RM was again degassed and purged with nitrogen for another 5 min. The RM was heated to 80° C. in a sealed tube overnight, then allowed to cool to rt and diluted with chloroform. The organic layer was concentrated to get the crude product, which was purified through flash chromatography by using 100-200 mesh silica gel. The compound was eluted at 40% ethyl acetate in hexane as half white colored solid compound 295.

Step 2:

To a solution of 295 (60 mg, 0.1005 mmol) in methanol (20 mL) and water (5 mL) was added potassium carbonate (41 mg, 0.3016 mmol). The RM was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude compound. The crude was purified through flash chromatography by using 100-200 mesh silica gel. The compound was eluted at 70% ethyl acetate in hexane as pale yellow solid compound 296. $^1$HNMR (400 MHz, CDCl$_3$): 9.51 (bs, 1H), 8.52 (d, 1H), 8.23 (d, 1H), 7.77 (d, 1H), 7.44 (m, 2H), 7.20 (t, 1H), 7.00 (d, 1H), 3.84 (m, 4H), 3.53 (m, 4H). MS-ES+ 443.09

Preparation of Example 196: N-(tertbutyl)-3-(3-(2,2-difluorobenzo[d][1,3]dioxol-4-yl)-1H-pyrrolo[2,3-b]pyridin-5-yl)-N-methylbenzene-sulfonamide (298)

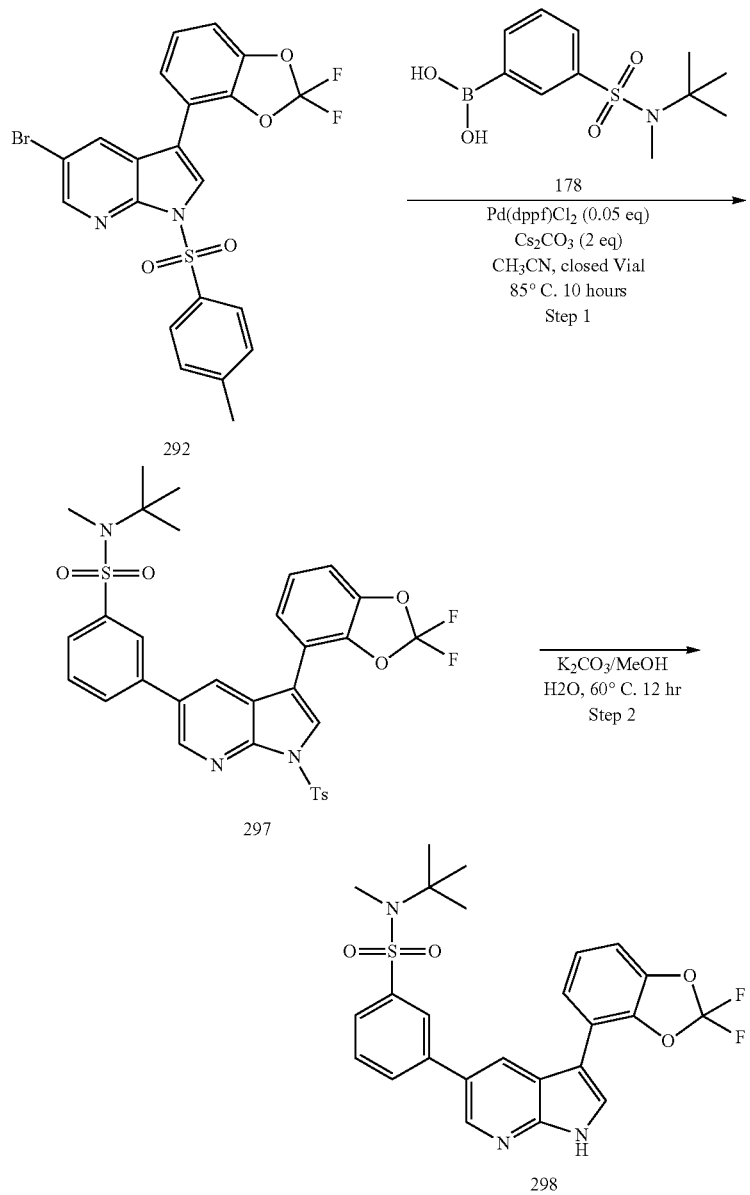

Step 1:

To a solution of compound 292 (100 mg, 0.1971 mmol) and 178 (0.53 mg, 0.197 mol) in acetonitrile (5 mL) was added cesium carbonate (128 mg, 0.3942 mmol). The reaction was degassed and purged with nitrogen for 10 min and charged with Pd(dppf)Cl$_2$ (8 mg, 0.009856 mmol). The reaction was again degassed and purged with nitrogen for another 5 min. The reaction was heated to 80° C. in a sealed tube overnight, allowed to cool to rt, and diluted with chloroform. The organic layer was concentrated to get the crude. The crude was purified through flash chromatography by using 100-200 mesh silica gel. The compound was eluted at 35% ethyl acetate in hexane as half white coloured solid compound 297.

Step 2:

To a solution of 297 (70 mg, 0.10707 mmol) in methanol (20 mL) and water (5 mL) was added potassium carbonate (44 mg, 0.3212 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using neutral alumina. The compound was eluted at 2% methanol in chloroform as half white solid 298. $^1$H NMR (CDCl$_3$) δ: 9.66 (bs, 1H), 8.64 (bs, 1H), 8.41 (d, 1H), 8.10 (m, 1H), 7.83 (m, 3H), 7.59 (m, 1H), 7.49 (m, 1H), 7.21 (m, 1H), 7.01 (m, 1H), 3.02 (s, 3H), 1.39 (s, 9H) and MS m/z=500.1 (M+H).

Preparation of Example 197: 3-(2,2-difluorobenzo[d][1,3]dioxol-4-yl)-5-(5-(pyrrolidin-1-ylmethyl)thiophen-2-yl)-1H-pyrrolo[2,3-b]pyridine (300)

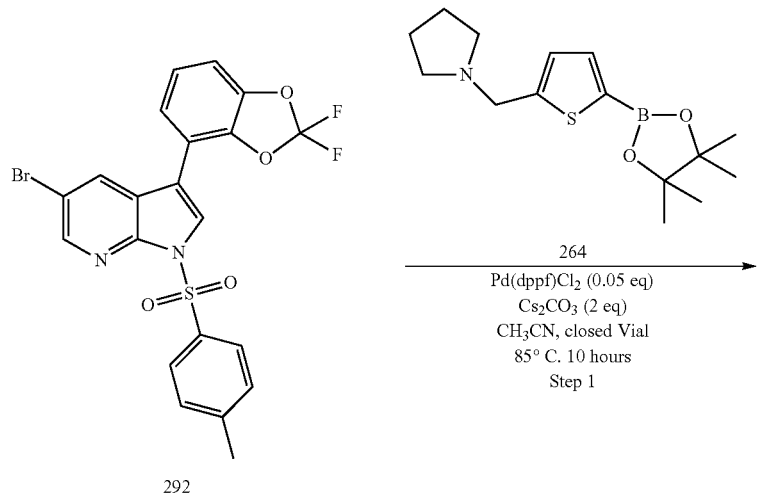

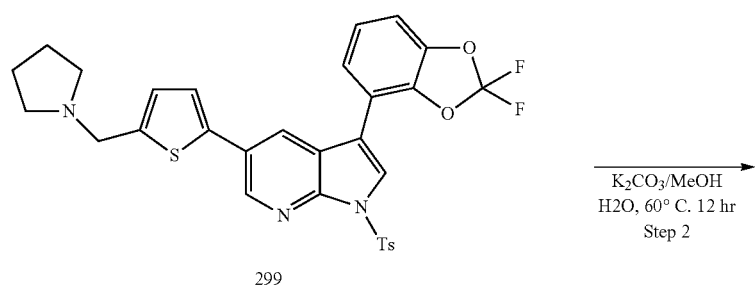

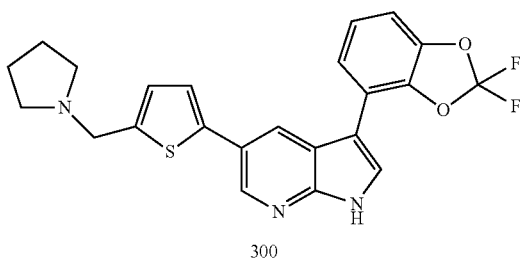

Step 1:

To a solution of compound 292 (100 mg, 0.1971 mmol) and 264 (57 mg, 0.1971 mmol) in acetonitrile (5 mL) was added cesium carbonate (128 mg, 0.3942 mmol). The reaction was degassed and purged with nitrogen for 10 min. Pd(dppf) Cl$_2$ (8 mg, 0.00985 mmol) was added to the reaction, which was again degassed and purged with nitrogen for another 5 min. The reaction was heated to 80° C. in a sealed tube overnight, allowed to cool to rt and diluted with chloroform. The organic layer was concentrated to get the crude, which was purified through flash chromatography by using 100-200 mesh silica gel. Eluting at 40% ethyl acetate in hexane gave a half white coloured solid 299.

Step 2:

To a solution of 299 (60 mg, 0.101 mmol) in methanol (20 mL) and water (5 mL) was added potassium carbonate (41 mg, 0,303 mmol). The reaction was heated to 60° C. overnight. The solvent was completely distilled off and the remainder diluted with water (25 mL), and extracted with chloroform twice (2×25 mL). The combined organic layer was dried over sodium sulphate, filtered, and concentrated to get the crude, which was purified through flash chromatography by using neutral alumina. The compound was eluted at 0.5% methanol in chloroform as pale brown solid compound 300. $^1$HNMR (CDCl$_3$) δ: 9.50 (bs, 1H), 8.65 (d, 1H), 8.39 (d, 1H), 7.79 (d, 1H), 7.49 (dd, 1H), 7.20 (m, 2H), 6.99 (dd, 1H), 6.92 (d, 1H), 3.86 (s, 2H), 2.63 (m, 4H), 1.83 (m, 4H) and MS m/z=440.0 (M+H).

Preparation of Example 198: 3-(2,2-difluorobenzo[d][1,3]dioxol-4-yl)-5-(5-(piperidin-1-ylmethyl)thiophen-2-yl)-1H-pyrrolo[2,3-b]pyridine (302)

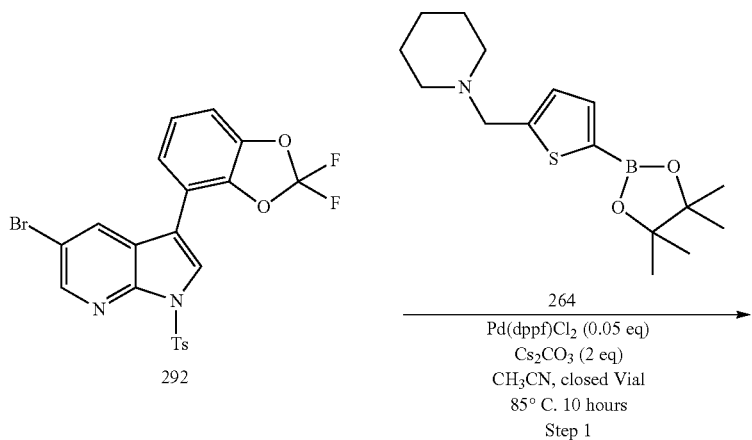

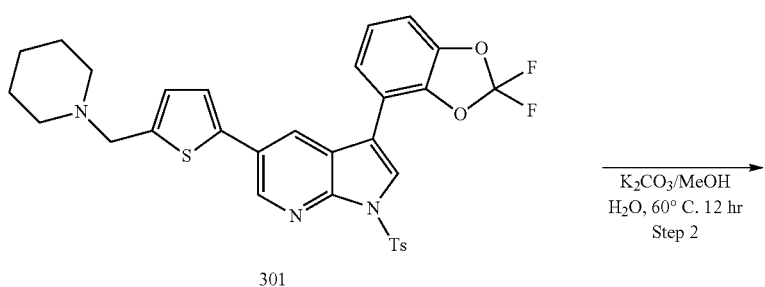

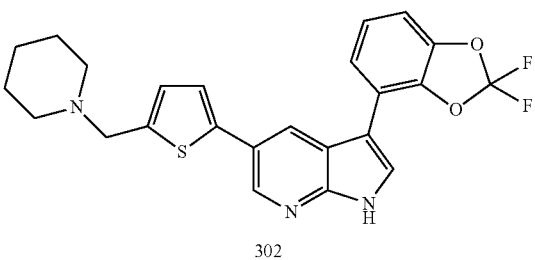

Step 1:

To a solution of compound 292 (100 mg, 0.1971 mmol) and 264 (0.53 mg, 0.197 mmol) in acetonitrile (5 mL) was added cesium carbonate (128 mg, 0.3942 mmol). The reaction was degassed and purged with nitrogen for 10 min and Pd (dppf) Cl$_2$ (8 mg, 0.009856 mmol) was added to the reaction, which was again degassed and purged with nitrogen for another 5 min. The reaction was heated to 80° C. in a sealed tube overnight. The reaction was allowed to cool to rt and diluted with chloroform. The organic layer was concentrated to get the crude, which was purified through flash chromatography by using 100-200 mesh silica gel. The compound was eluted at 40% ethyl acetate in hexane as half white coloured solid 301.

Step 2:

To a solution of 301 (60 mg, 0.0987 mmol) in methanol (20 mL) and water (5 mL) was added potassium carbonate (40 mg, 0.2963 mmol). The reaction was heated to 60° C. overnight. The solvent was completely distilled off, the remainder diluted with water (25 mL), and extracted with chloroform twice (2×25 mL). The combined organic layer was dried over sodium sulphate filtered and concentrated to get the crude, which was purified through flash chromatography by using neutral alumina. The compound was eluted at 1.5% methanol in chloroform as pale yellow solid 302. $^1$H NMR (CDCl$_3$) δ: 9.53 (bs, 1H), 8.66 (d, 1H), 8.39 (d, 1H), 7.79 (d, 1H), 7.49 (d, 1H), 7.20 (m, 2H), 7.00 (d, 1H), 6.90 (d, 1H), 3.71 (s, 2H), 2.48 (bs, 4H), 1.63 (m, 4H), 1.45 (m, 2H) and MS m/z=454.1 (M+H).

Preparation of Example 199: 4-(4-(3-(2,2-difluorobenzo[d][1,3]dioxol-4-yl)-1H-pyrrolo[2,3-b]pyridin-5-yl)thiazol-2-yl)morpholine (306)

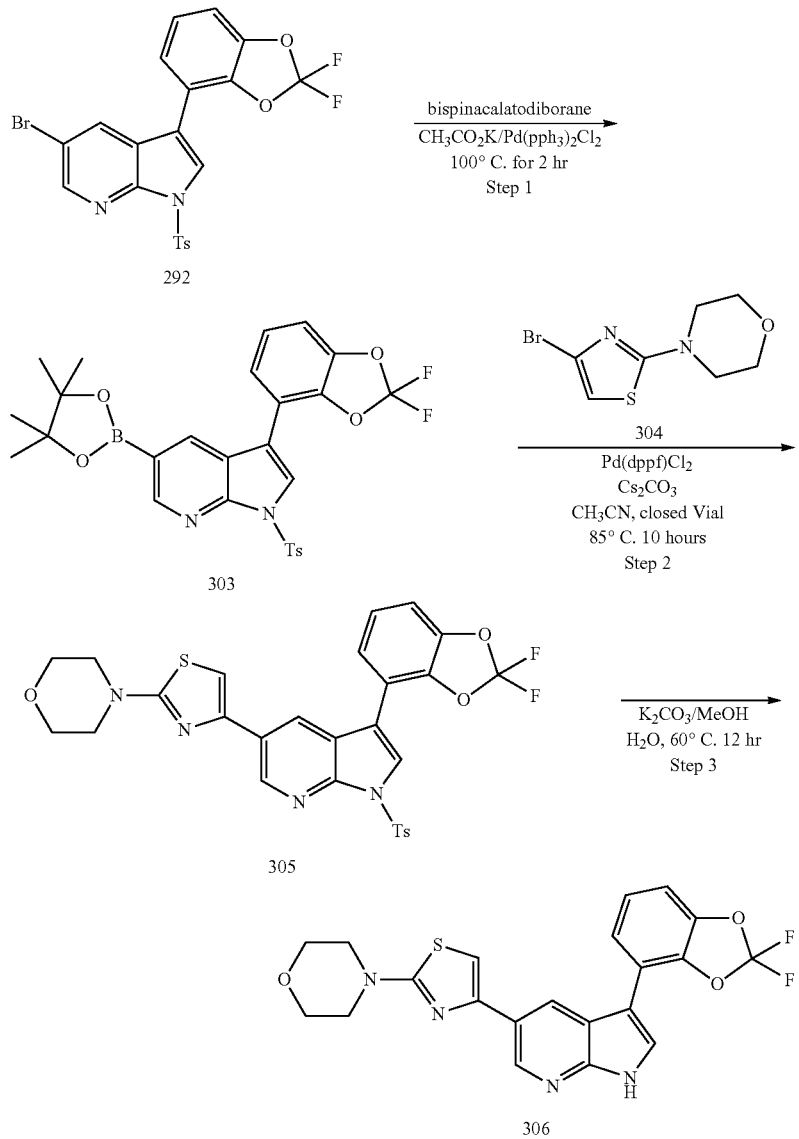

Step 1:

To a solution of 292 (400 mg, 0.788 mmol) in DMF was added potassium acetate (154 mg, 1.576 mmol) and bispinacalatodiborane (400 mg, 1.576 mmol). The reaction mixture was degassed and purged with nitrogen for 10 min. Pd $(pph3)_2Cl_2$ (27 mg, 0.03942 mmol) was added and again degassed and purged with nitrogen for 10 min. The reaction was heated to 100° C. for 2 h. After completion of the reaction, the RM was diluted with chloroform and washed with cold water followed by Brine solution. The organic layer was dried over sodium sulphate and evaporated to get the crude, which was triturated with Hexane to afford a brown solid 3-(2,2-difluorobenzo[d][1,3]dioxol-4-yl)-5-(4,4,5,5-tetramethyl-1,3,2-dioxaborolan-2-yl)-1-tosyl-1H-pyrrolo[2,3-b]pyridine 303 taken up for next step without further purification.

Step 2:

To a solution of 303 (438 mg, 0.786 mmol) and 304 (196 mg, 0.786 mmol) in acetonitrile (10 mL) was added cesium carbonate (512 mg, 0.157 mmol). The reaction was degassed and purged with nitrogen for 10 min. Pd (dppf) $Cl_2$ (32 mg, 0.0393 mmol) was added to the reaction, which was again degassed and purged with nitrogen for another 5 min. The reaction was heated to 80° C. in a sealed tube overnight. The reaction was allowed to cool to rt and diluted with chloroform. The organic layer was concentrated to get the crude, which was purified through flash chromatography by using 100-200 mesh silica gel. The compound was eluted at 40% ethyl acetate in hexane as half white coloured solid 305.

Step 3:

To a solution of 305 (200 mg, 0.335 mmol) in methanol (20 mL) and water (5 mL) was added potassium carbonate (138 mg, 1.01005 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using 100-200 mesh silica gel. The compound was eluted at 5% methanol in chloroform as pale yellow solid 4-(4-(3-(2,2-difluorobenzo[d][1,3]dioxol-4-yl)-1H-pyrrolo[2,3-b]pyridin-5-yl)thiazol-2-yl)morpholine 306. $^1$H NMR (CDCl$_3$) δ: 12.30 (s, 1H), 8.87 (d, 1H), 8.67 (d, 1H), 7.95 (d, 1H), 7.61 (m, 1H), 7.41 (s, 1H), 7.31 (m, 2H), 3.73 (m, 4H), 3.45 (m, 4H) and MS m/z=443.0 (M+H).

Preparation of Example 200: (4-((5-(3-(2,2-difluorobenzo[d][1,3]dioxol-5-yl)-1H-pyrrolo[2,3-b]pyridin-5-yl)thiophen-2-yl)methyl)morpholine (309)

again degassed and purged with nitrogen for another 5 min. The reaction was heated to 80° C. in a sealed tube overnight, allowed to cool to rt, and diluted with chloroform. The organic layer was concentrated to get the crude, which was purified through flash chromatography by using 100-200 mesh silica gel. The compound was eluted at 50% ethyl acetate in hexane as half white coloured solid 308.

Step 2:
To a solution of 308 (70 mg, 0.1148 mmol) in methanol (20 mL) and water (5 mL) was added potassium carbonate (47 mg, 0.344 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using neutral alumina. The compound was eluted at 2% methanol in dichloromethane as pale yellow solid

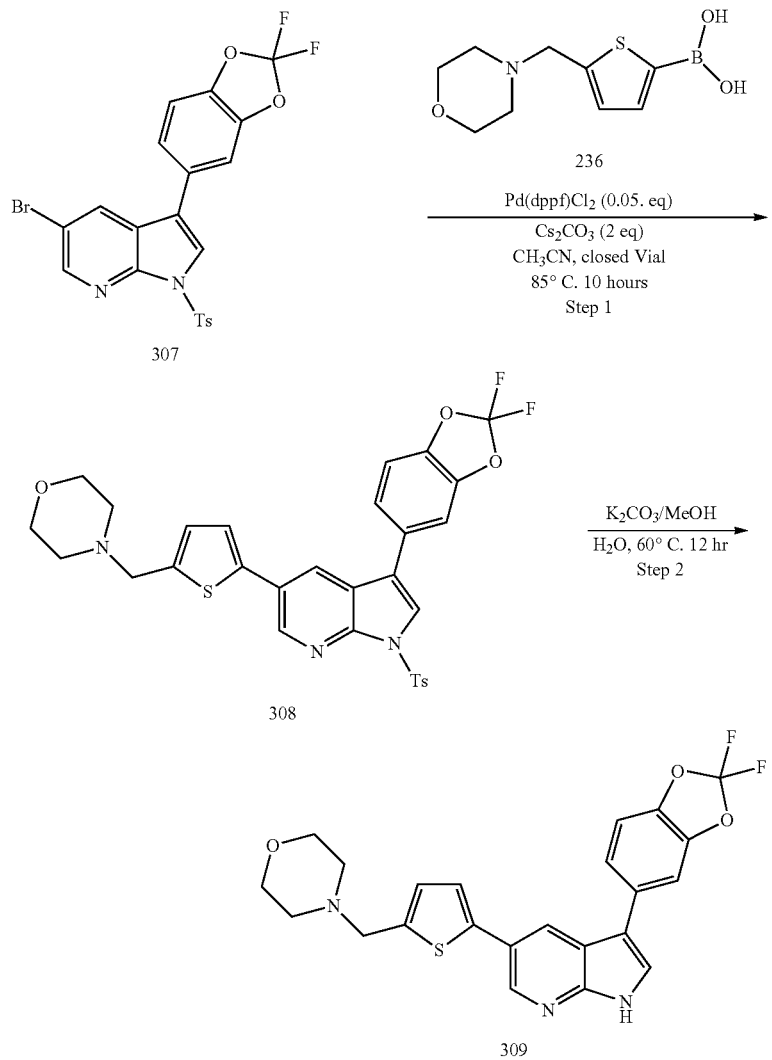

Step 1:
To a solution of 307 (100 mg, and 0.197 mmol) and 236 (60 mg, 0.197 mmol) in acetonitrile (5 mL) was added cesium carbonate (128 mg, 0.3942 mmol). The reaction was degassed and purged with nitrogen for 10 min. Pd (dppf) Cl$_2$ (8 mg, 0.00985 mmol) was added to the reaction, which was 4-((5-(3-(2,2-difluorobenzo[d][1,3]dioxol-5-yl)-1H-pyrrolo[2,3-b]pyridin-5-yl)thiophen-2-yl)methyl)morpholine 309. $^1$H NMR (CDCl$_3$) δ: 9.13 (s, 1H), 8.63 (d, 1H), 8.25 (d, 1H), 7.45 (d, 1H), 7.32 (m, 2H), 7.15 (m, 2H), 6.92 (d, 1H), 3.75 (m, 4H), 3.73 (m, 2H), 2.55 (m, 4H) and MS m/z=454.1 (M+H).

Preparation of Example 201: 4-(5-(3-(2,2-difluorobenzo[d][1,3]dioxol-5-yl)-1H-pyrrolo[2,3-b]pyridin-5-yl)thiazol-2-yl)morpholine (311)

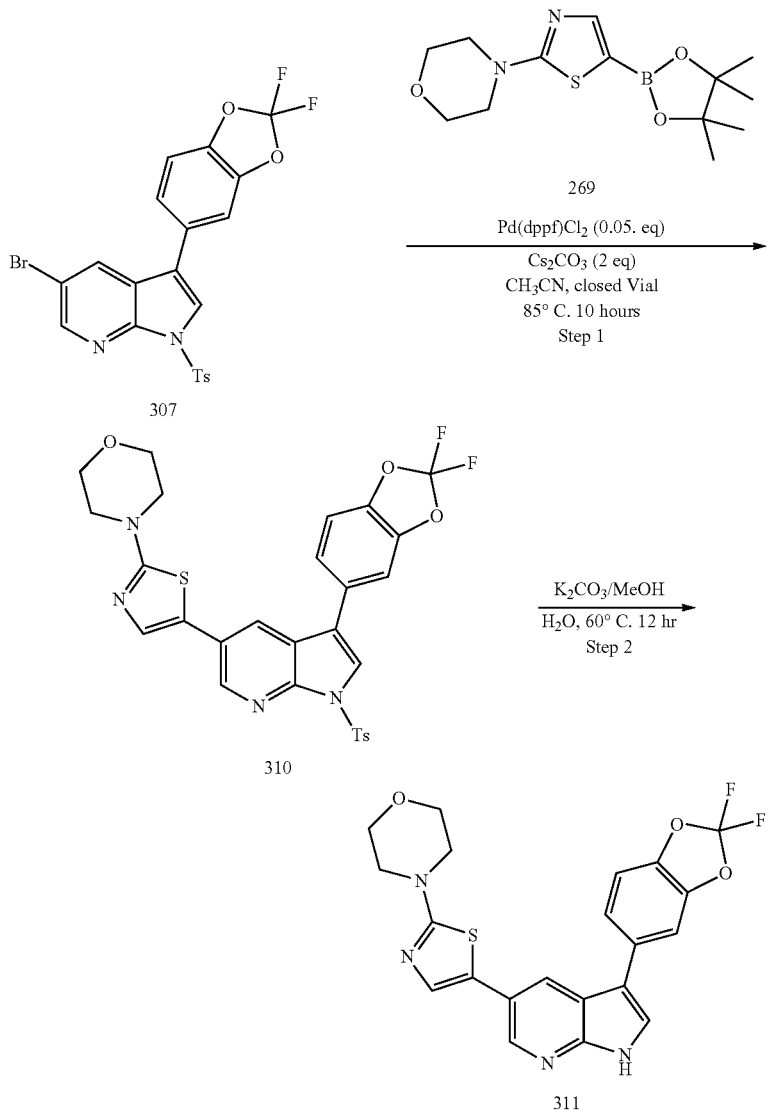

Step 1:

A solution of 307 (100 mg, 0.1971 mmol) and 269 (58 mg, 0.01971 mmol) in acetonitrile (5 mL) was added cesium carbonate (128 mg, 0.3942 mmol). The reaction was degassed and purged with nitrogen for 10 min. Pd (dppf) Cl$_2$ (8 mg, 0.009856 mmol) was added to the reaction, which was again degassed and purged with nitrogen for another 5 min. The reaction was heated to 80° C. in a sealed tube overnight, allowed to cool to rt and diluted with chloroform. The organic layer was concentrated to get the crude, which was purified through flash chromatography by using 100-200 mesh silica gel. The compound was eluted at 30% ethyl acetate in hexane as half white coloured solid 310.

Step 2:

To a solution of 310 (60 mg, 0.1005 mmol) in methanol (20 mL) and water (5 mL) was added potassium carbonate (41 mg, 0.30169 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using neutral alumina. The compound was eluted at 70% ethyl acetate in hexane as a half white solid 4-(5-(3-(2,2-difluorobenzo[d][1,3]dioxol-5-yl)-1H-pyrrolo[2,3-b]pyridin-5-yl)thiazol-2-yl)morpholine 311. $^1$H NMR (CDCl$_3$) δ: 9.19 (s, 1H), 8.51 (s, 1H), 8.09 (d, 1H), 7.45 (m, 2H), 7.30 (m, 2H), 7.15 (d, 1H), 3.84 (m, 4H), 3.53 (m, 4H) and MS m/z=443.0 (M+H).

Preparation of Example 202: N-(tert-butyl)-3-(3-(2,2-difluorobenzo[d][1,3]dioxol-5-yl) 1H-pyrrolo[2,3-b]pyridin-5-yl)-N-methylbenzenesulfonamide (313)

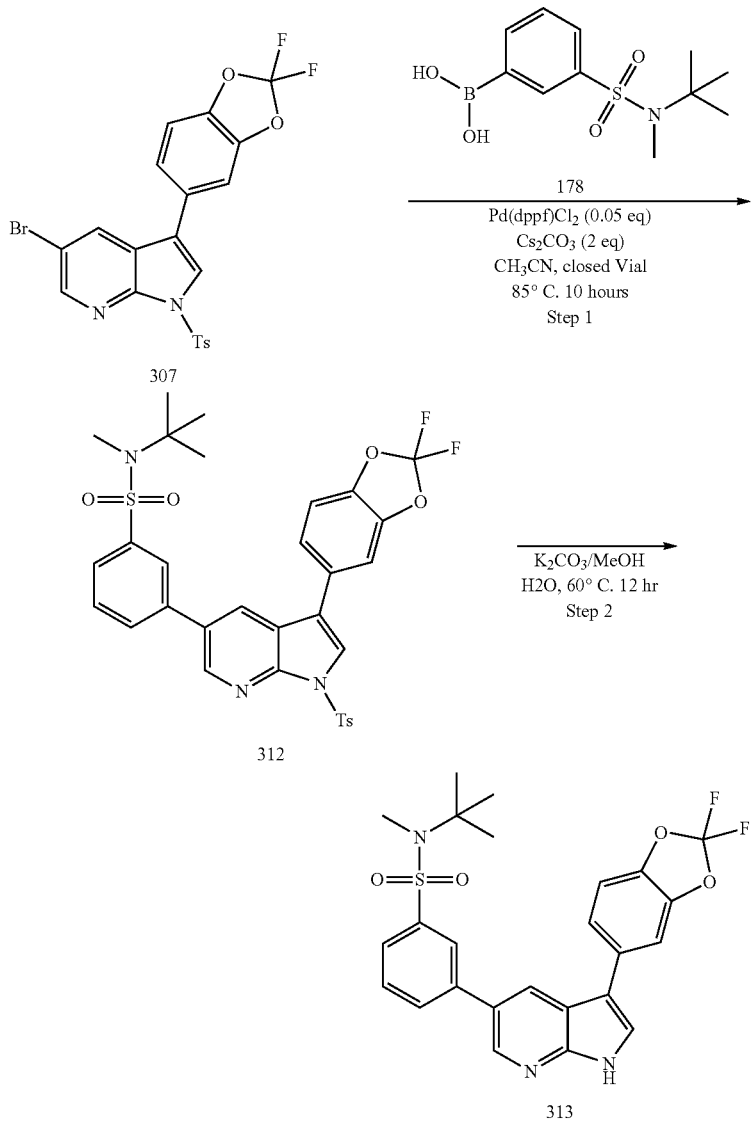

Step 1:
To a solution of 307 (100 mg, 0.1971 mmol) and 178 (53 mg, 0.1971 mmol) in acetonitrile (5 mL) was added cesium carbonate (128 mg, 0.3942 mmol). The reaction was degassed and purged with nitrogen for 10 min. Pd (dppf) Cl$_2$ (8 mg, 0.009856 mmol) was added to the reaction, which was again degassed and purged with nitrogen for another 5 min. The reaction was heated to 80° C. in a sealed tube overnight, allowed to cool to rt and diluted with chloroform. The organic layer was concentrated to get the crude, which was purified through flash chromatography by using 100-200 mesh silica gel. The compound was eluted at 46% ethyl acetate in hexane as half white coloured solid 313.

Step 2:
To a solution of 313 (70 mg, 0.10708 mmol) in methanol (20 mL) and water (5 mL) was added potassium carbonate (44 mg, 0.3212 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using 100-200 mesh silica gel. The compound was eluted at 1.5% methanol in chloroform as pale yellow solid N-(tert-butyl)-3-(3-(2,2-difluorobenzo[d][1,3]dioxol-5-yl)-1H-pyrrolo[2,3-b]pyridin-5-yl)-N methylbenzene-sulphonamide 313. $^1$H NMR (CDCl$_3$) δ: 9.44 (s, 1H), 8.61 (d, 1H), 8.29 (d, 1H), 8.08 (d, 1H), 7.81 (m, 2H), 7.60 (t, 1H), 7.52 (m, 1H), 7.34 (m, 2H), 7.16 (d, 1H), 3.01 (s, 3H), 1.39 (s, 9H) and MS ES+500.1.

Preparation of Example 203: 3-(2,2-difluorobenzo[d][1,3]dioxol-5-yl)-5-(5-(pyrrolidin-1-ylmethyl)thiophen-2-yl)-1H-pyrrolo[2,3-b]pyridine (315)

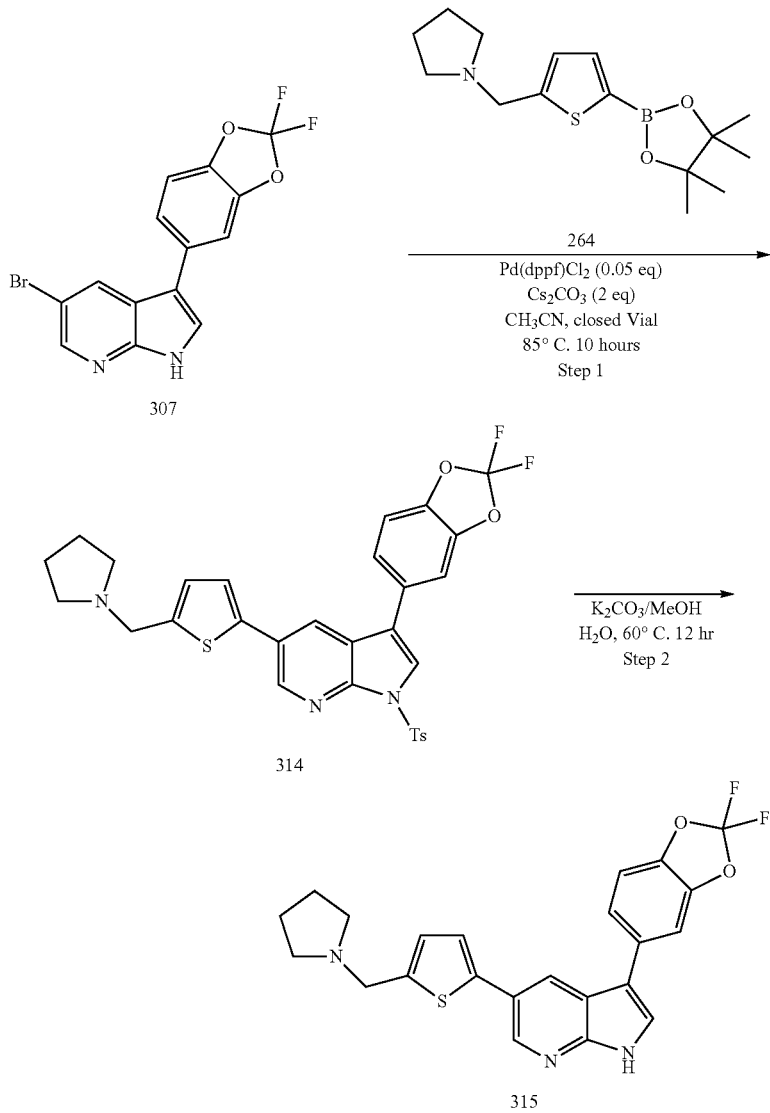

Step 1:
To a solution of 292 (100 mg, 0.0001971 mmol) and 264 (58 mg, 0.1971 mmol) in acetonitrile (5 mL) was added cesium carbonate (128 mg, 0.3942 mmol). The reaction was degassed and purged with nitrogen for 10 min and Pd (dppf) Cl$_2$ DCM (8 mg, 0.00985 mmol) was added to the reaction, which was again degassed and purged with nitrogen for another 5 min. The reaction was heated to 80° C. in a sealed tube overnight, allowed to cool to rt and diluted with chloroform. The organic layer was concentrated to get the crude, which was purified through flash chromatography by using 100-200 mesh silica gel. The compound was eluted at 36% ethyl acetate in hexane as half white coloured solid compound 314.

Step 2:
To a solution of 314 (60 mg, 0.101 mml) in methanol (20 mL) and water (5 mL) was added potassium carbonate (41 mg, 0.303 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using 100-200 mesh silica gel. The compound was eluted at 3% Methanol in chloroform as half white solid 3-(2,2-difluorobenzo[d][1,3]dioxol-5-yl)-5-(5-(pyrrolidin-1-ylmethyl)thiophen-2-yl)-1H-pyrrolo[2,3-b]pyridine 315. $^1$H NMR (CDCl$_3$) δ: 9.27 (s, 1H), 8.63 (d, 1H), 8.26 (d, 1H) 7.45 (d, 1H), 7.34 (m, 2H), 7.16 (m, 2H), 6.91 (d, 1H), 3.85 (s, 2H), 2.62 (bs, 4H), 1.83 (bs, 4H) MS ES+ 440.0.

Preparation of Example 204: 3-(2,2-difluorobenzo[d][1,3]dioxol-5-yl)-5-(5-(piperidin-1-ylmethyl)thiophen-2-yl)-1H-pyrrolo[2,3-b]pyridine (318)

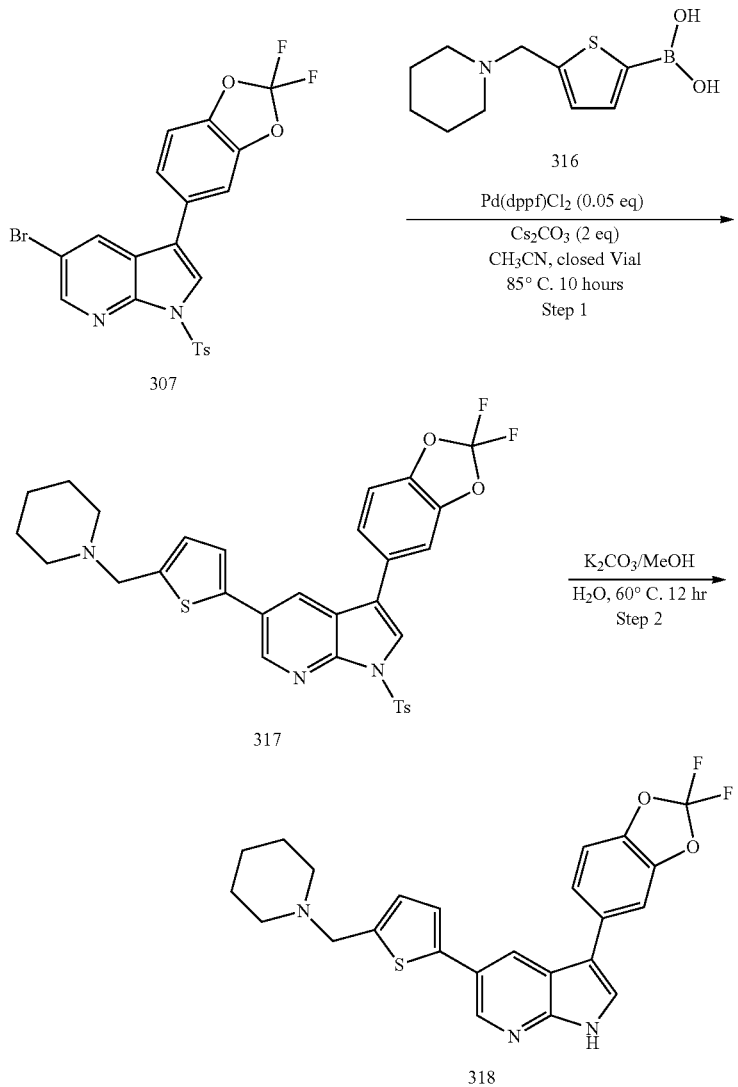

Step 1:

To a solution of 307 (100 mg, 0.1971 mmol) and 316 (60 mg, 0.1971 mmol) in acetonitrile (5 mL) was added cesium carbonate (128 mg, 0.3942 mmol). The reaction was degassed and purged with nitrogen for 10 min. Pd (dppf)Cl$_2$ (8 mg, 0.00985 mmol) was added to the reaction, which was again degassed and purged with nitrogen for another 5 min. The reaction was heated to 80° C. in a sealed tube overnight, allowed to cool to rt and diluted with chloroform. The organic layer was concentrated to get the crude, which was purified through flash chromatography by using 100-200 mesh silica gel. The compound was eluted at 45% ethyl acetate in hexane as half white coloured solid 317.

Step 2:

To a solution of 317 (60 mg, 0.0987 mmol) in methanol (20 mL) and water (5 mL) was added potassium carbonate (40 mg, 0.2962 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude. The crude was purified through flash chromatography by using neutral alumina. The compound was eluted at 0.5% methanol in dichloromethane as pale yellow solid 3-(2,2-difluorobenzo[d][1,3]dioxol-5-yl)-5-(5-(piperidin-1-ylmethyl)thiophen-2-yl)-1H-pyrrolo[2,3-b]pyridine 318. $^1$H NMR (CDCl$_3$) δ: 9.29 (s, 1H), 8.63 (d, 1H), 8.26 (d, 1H), 7.45 (d, 1H), 7.32 (m, 2H), 7.15 (m, 2H), 6.89 (d, 1H), 3.70 (s, 2H), 2.47 (s, 4H), 1.61 (m, 4H), 1.25 (m, 2H) and MS ES+ 454.1.

Preparation of Example 205: 4-(4-(3-(2,2-difluorobenzo[d][1,3]dioxol-5-yl)-1H-pyrrolo[2,3-b]pyridin-5-yl)thiazol-2-yl)morpholine (321)

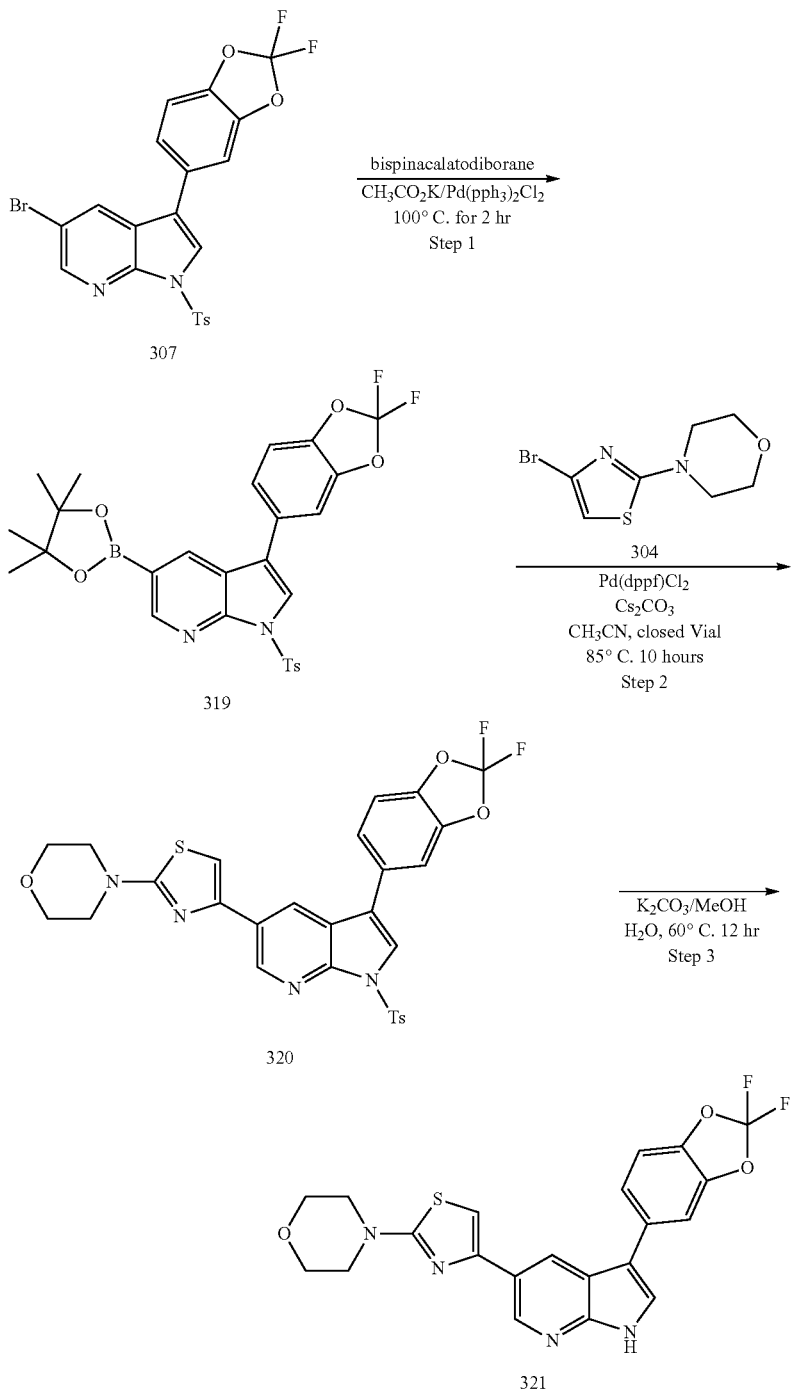

Step 1:
To a solution of 307 (400 mg, 0.788 mmol) in DMF was added potassium acetate (154 mg, 1.576 mmol) and bispinacalatodiborane (400 mg, 1.576 mmol). The reaction mixture was degassed and purged with nitrogen for 10 min. Pd(pph3)$_2$ Cl$_2$ (27 mg, 0.03942 mmol) was added and again degassed and purged with nitrogen for 10 min. The reaction was heated to 100° C. for 2 h. After completion of the reaction the RM was diluted with chloroform and washed with cold water followed by Brine solution. The organic layer was dried over sodium sulphate and evaporated to get the crude, which was triturated with Hexane to afford brown solid 319. The solid itself proceeded for next step without further purification.

Step 2:

To a solution of 319 (438 mg, 0.786 mmol) and 304 (196 mg, 0.786 mmol) in acetonitrile (10 mL) was added cesium carbonate (512 mg, 0.157 mmol). The reaction was degassed and purged with nitrogen for 10 min. Pd (dppf) Cl$_2$ (32 mg, 0.0393 mmol) was added to the reaction, which was again degassed and purged with nitrogen for another 5 min. The reaction was heated to 80° C. in a sealed tube overnight, allowed to cool to rt and diluted with chloroform. The organic layer was concentrated to get the crude, which was purified through flash chromatography by using 100-200 mesh silica gel. The compound was eluted at 40% ethyl acetate in hexane as half white coloured solid 320.

Step 3:

To a solution of 320 (200 mg, 0.335 mmol) in methanol (20 mL) and water (5 mL) was added potassium carbonate (138 mg, 1.01005 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using 100-200 mesh silica gel. The compound was eluted at 5% methanol in chloroform as pale yellow solid 4-(4-(3-(2,2-difluorobenzo[d][1,3]dioxol-5-yl)-1H-pyrrolo[2,3-b]pyridin-5-yl)thiazol-2-yl)morpholine 321. $^1$H NMR (CDCl$_3$) δ: 10.05 (s, 1H), 8.84 (s, 1H), 8.53 (s, 1H), 7.44 (d, 1H), 7.34 (d, 3H), 7.14 (d, 1H), 6.83 (s, 1H), 3.85 (t, 4H), 3.55 (t, 4H) and MS ES+ 443.00.

Preparation of Example 206: 3-(2,2-difluorobenzo[d][1,3]dioxol-5-yl)-5-(1-(piperidin-4-yl)-1H-pyrazol-4-yl)-1H-pyrrolo[2,3-b]pyridine (324)

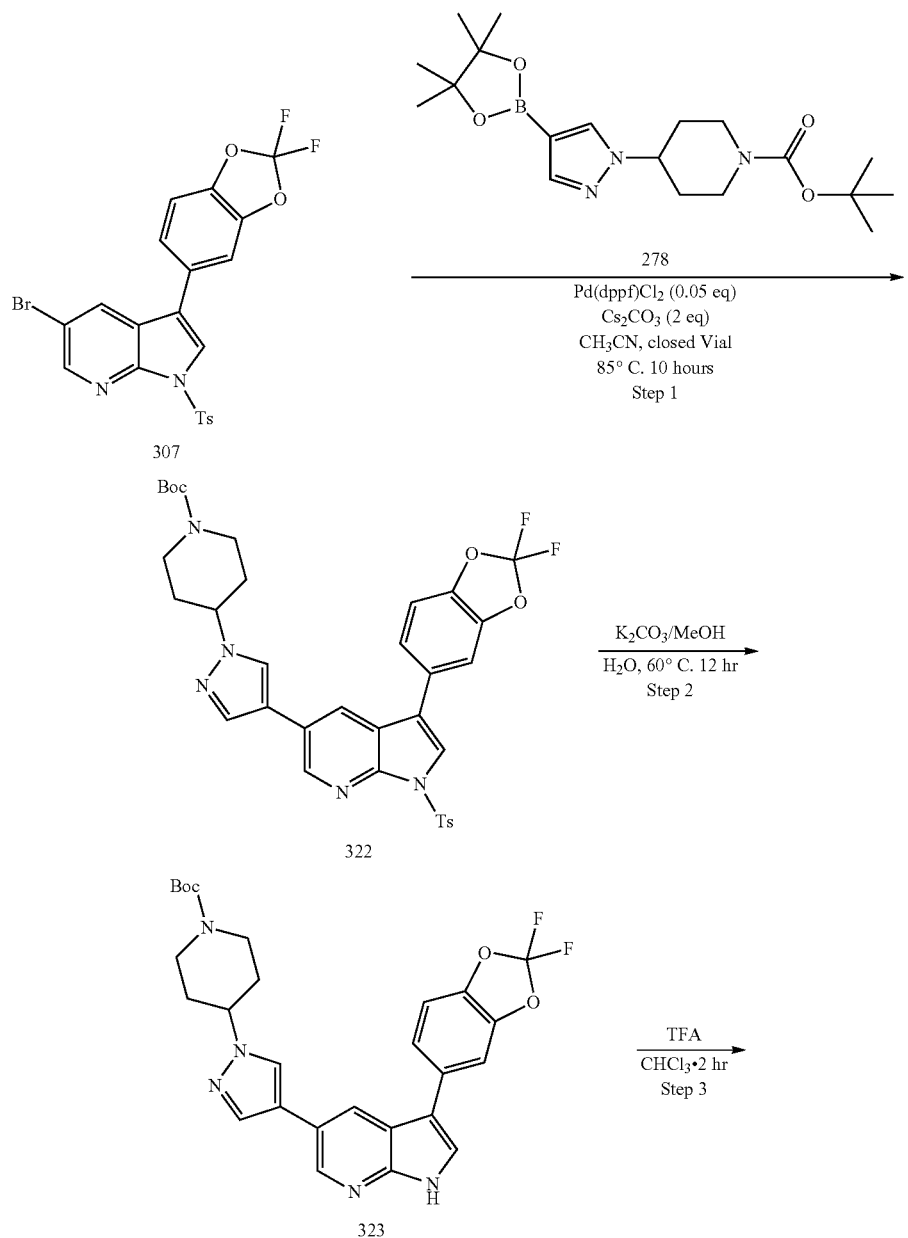

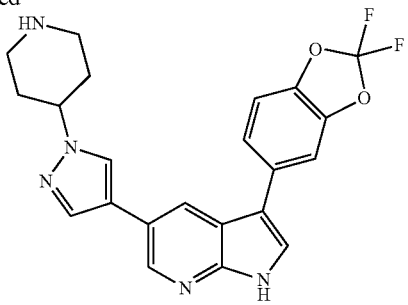

324

Step 1:

To a solution of 307 (100 mg, 0.1971 mmol) and 278 (74 mg, 0.1971 mmol) in acetonitrile (5 mL) was added cesium carbonate (128 mg, 0.3942 mmol). The reaction was degassed and purged with nitrogen for 10 min and Pd (dppf)Cl$_2$ (8 mg, 0.00985 mmol) was added to the reaction, which was again degassed and purged with nitrogen for another 5 min. The reaction was heated to 80° C. in a sealed tube overnight, allowed to cool to rt and diluted with chloroform. The organic layer was concentrated to get the crude, which was purified through flash chromatography by using 100-200 mesh silica gel. The compound was eluted at 40% ethyl acetate in hexane as half white coloured solid 322.

Step 2:

To a solution of 322 (70 mg, 0.1033 mmol) in methanol (20 mL) and water (5 mL) was added potassium carbonate (42 mg, 0.31009 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using 100-200 mesh silica gel. The compound was eluted at 70% ethyl acetate in Hexane as pale yellow solid 323.

Step 3:

A solution of 323 (0.050 mg, 0.0955 mmol) in CHCl$_3$ (20 mL) was taken and added TFA (5 mL) at rt. The reaction mixture was stirred for 2 h at rt. After confirmation of TLC, the reaction mixture evaporated TFA completely then taken in CHCl$_3$ and washed with Na$_2$CO$_3$ solution followed by water wash. Organic layer was dried with Na$_2$SO$_4$ and evaporated. The resulting crude was purified via silica gel chromatography using a gradient of 3% methanol in chloroform to afford pale brown solid 3-(2,2-difluorobenzo[d][1,3]dioxol-5-yl)-5-(1-(piperidin-4-yl)-1H-pyrazol-4-yl)-1H-pyrrolo[2,3-b]pyridine 324. $^1$H NMR (CDCl$_3$) δ: 11.94 (s, 1H), 8.55 (d, 1H), 8.40 (s, 1H), 8.34 (s, 1H), 7.99 (s, 1H), 7.89 (s, 1H), 7.79 (s, 1H), 7.59 (d, 1H), 7.44 (d, 1H), 4.17 (m, 1H), 3.04 (m, 2H), 2.57 (m, 2H), 1.98 (m, 2H), 1.81 (m, 2H) and MS ES+ 424.0.

Preparation of Example 207: 4-(4-(3-(3-fluoro-2-methoxyphenyl)-1H-pyrrolo[2,3-b]pyridin-5-yl)thiazol-2-yl)morpholine (327)

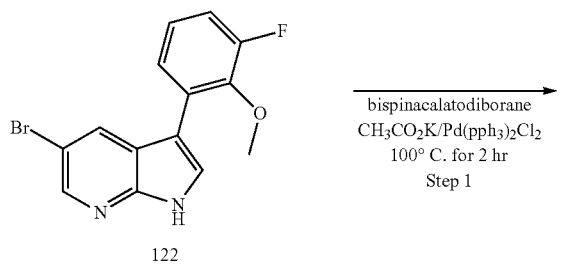

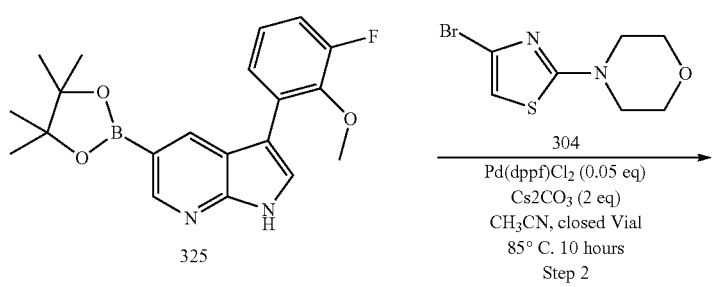

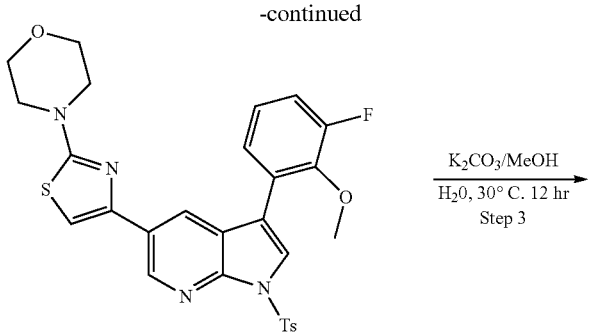

326

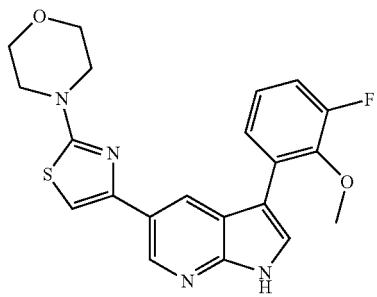

327

Step 1:

To a solution of 122 (400 mg, 0.8415 mmol) in DMF was added potassium acetate (165 mg, 1.683 mmol) and bispinacalatodiborane (427 mg, 1.683 mmol). The reaction mixture was degassed and purged with nitrogen for 10 min and Pd(pph3)$_2$Cl$_2$ (29 mg, 0.0427 mmol) was added, again degassed and purged with nitrogen for 10 min. The reaction was heated to 100° C. for 2 h. After completion of the reaction, the RM was diluted with chloroform and washed with cold water followed by brine solution. The organic layer was dried over sodium sulphate and evaporated to get the crude, which was triturated with hexane to afford brown solid. The solid itself was used in the next step without further purification.

Step 2:

To a solution of 325 (441 mg, 0.841 mmol) and 304 (209 mg, 0.841 mmol) in acetonitrile (10 mL) was added cesium carbonate (547 mg, 1.681 mmol). The reaction was degassed and purged with nitrogen for 10 min. Pd(dppf)Cl$_2$ DCM (34 mg, 0.04203 mmol) was added to the reaction, which was again degassed and purged with nitrogen for another 5 min. The reaction was heated to 80° C. in a sealed tube overnight, allowed to cool to rt, and diluted with chloroform. The organic layer was concentrated to get the crude, which was purified through flash chromatography by using 100-200 mesh silica gel. The compound was eluted at 40% ethyl acetate in hexane as half white coloured solid 326.

Step 3:

To a solution of 326 (200 mg, 0.335 mmol) in methanol (20 mL) and water (5 mL) was added potassium carbonate (138 mg, 1.0056 mml). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using 100-200 mesh silica gel. The compound was eluted at 5% methanol in chloroform as pale yellow solid 4-(4-(3-(3-fluoro-2-methoxyphenyl)-1H-pyrrolo[2,3-b]pyridin-5-yl)thiazol-2-yl)morpholine 327. $^1$H NMR (400 MHz, CDCl3) δ: 9.52 (s, 1H), 8.86 (s, 1H), 8.54 (s, 1H), 7.68 (s, 1H), 7.38 (d, 1H), 7.07 (m, 2H), 6.82 (s, 1H), 3.85 (t, 4H), 3.75 (s, 3H), 3.55 (t, 4H) and MS ES+ 411.0.

Preparation of Example 208: 4-(4-(3-(3,5-difluoro-2-methoxyphenyl)-1H-pyrrolo[2,3-b]pyridin-5-yl)thiazol-2-yl)morpholine (329)

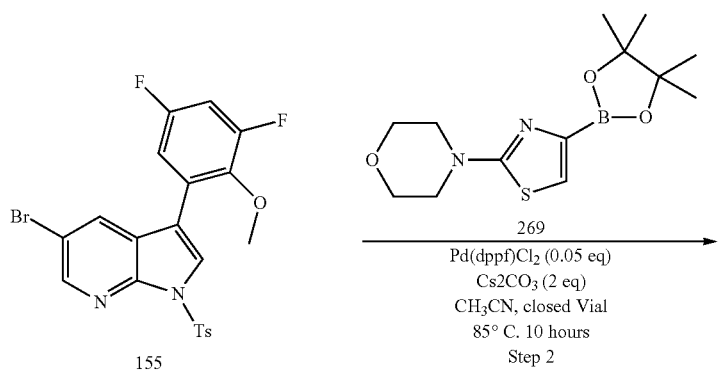

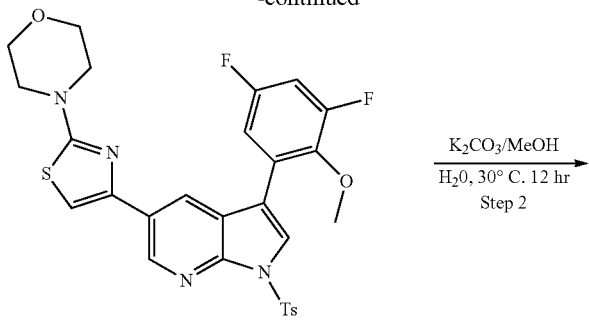

328

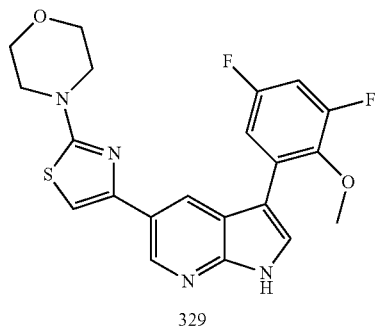

329

Step 1:

To a solution of 155 (40 mg, 0.08108 mmol) and 269 (24 mg, 0.08108 mmol) in acetonitrile (5 mL) was added cesium carbonate (52 mg, 0.161 mmol). The reaction was degassed and purged with nitrogen for 10 min. Pd(dppf)Cl$_2$ (3 mg, 0.04054 mmol) was added to the reaction, which was again degassed and purged with nitrogen for another 5 min. The reaction was heated to 80° C. in a sealed tube overnight, allowed to cool to rt, and diluted with chloroform. The organic layer was concentrated to get the crude, which was purified through flash chromatography by using 100-200 mesh silica gel. The compound was eluted at 40% ethyl acetate in hexane as half white coloured solid 328.

Step 2:

To a solution of 328 (25 mg, 0.0429 mmol) in methanol (20 mL) and water (5 mL) was added potassium carbonate (17 mg, 0.107 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using neutral alumina. The compound was eluted at 1.5% methanol in chloroform as pale yellow solid 4-(4-(3-(3,5-difluoro-2-methoxyphenyl)-1H-pyrrolo[2,3-b]pyridin-5-yl)thiazol-2-yl)morpholine 329. $^1$H NMR (400 MHz, CDCl$_3$) δ: 9.46 (s, 1H), 8.87 (s, 1H), 8.54 (s, 1H), 7.73 (s, 1H), 7.14 (s, 1H), 6.84 (m, 2H), 3.85 (m, 4H), 3.69 (s, 3H), 3.57 (m, 4H) and MS ES+ 429.0.

Preparation of Example 209: 3-(2,2-difluorobenzo[d][1,3]dioxol-4-yl)-5-(1-(piperidin-4-yl)-1H-pyrazol-4-yl)-1H-pyrrolo[2,3-b]pyridine (332)

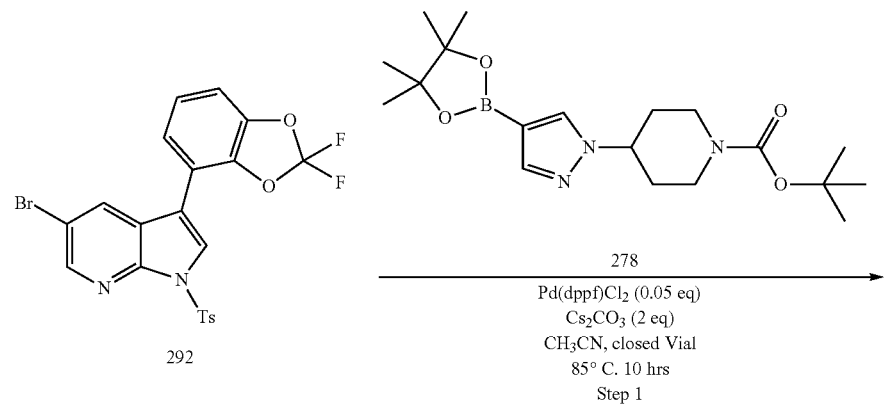

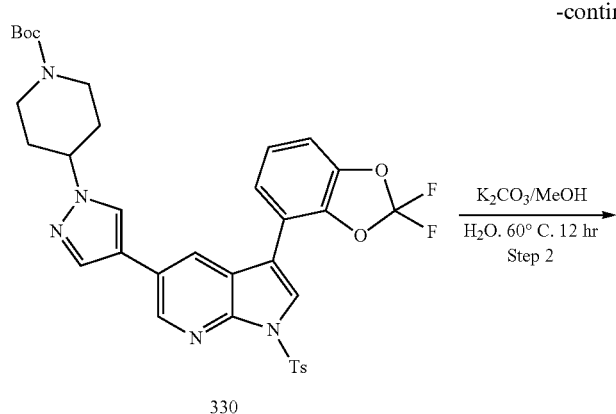

330

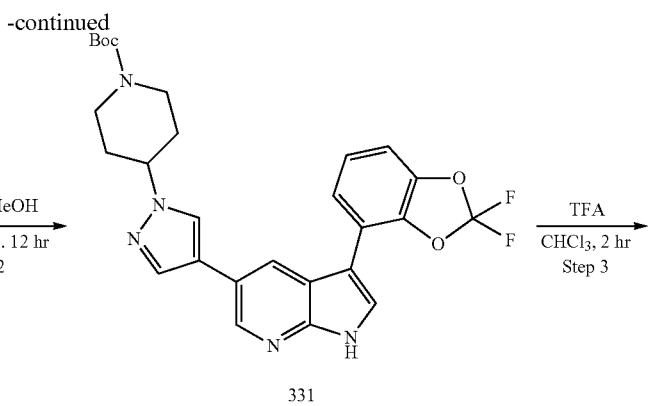

331

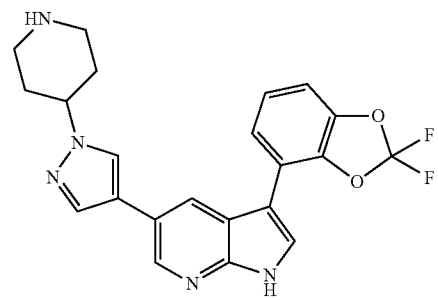

332

Step 1:

To a solution of 292 (100 mg, 0.1971 mmol) and 278 (74 mg, 0.1971 mmol) in acetonitrile (5 mL) was added cesium carbonate (128 mg, 0.3942 mmol). The reaction was degassed and purged with nitrogen for 10 min. Pd(dppf)Cl$_2$ (8 mg, 0.00985 mmol) was added to the reaction, which was again degassed and purged with nitrogen for another 5 min. The reaction was heated to 80° C. in a sealed tube overnight, allowed to cool to rt, and diluted with chloroform. The organic layer was concentrated to get the crude, which was purified through flash chromatography by using 100-200 mesh silica gel. The compound was eluted at 40% ethyl acetate in hexane as half white coloured solid 330.

Step 2:

To a solution of 330 (70 mg, 0.1033 mmol) in methanol (20 mL) and water (5 mL) was added potassium carbonate (42 mg, 0.31009 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using 100-200 mesh silica gel. The compound was eluted at 70% ethyl acetate in hexane as pale yellow solid 331.

Step 3:

A solution of 331 (0.050 gm, 0.0955 mmol) in CHCl$_3$ (20 mL) was taken and added TFA (5 mL) at rt. The reaction mixture was stirred for 2 hr at rt. After TLC confirmation, the RM was evaporated TFA completely then taken in CHCl$_3$ and washed with Na$_2$CO$_3$ solution followed by water wash. Organic layer was dried with Na$_2$SO$_4$ and evaporated. The resulting crude was purified via silica gel chromatography using a gradient of 3% methanol in chloroform to afford pale brown solid 3-(2,2-difluorobenzo[d][1,3]dioxol-4-yl)-5-(1-(piperidin-4-yl)-1H-pyrazol-4-yl)-1H-pyrrolo[2,3-b]pyridine 332. $^1$H NMR (400 MHz, CDCl3) δ: 9.90 (s, 1H), 8.59 (d, 1H), 8.29 (d, 1H), 7.89 (s, 1H), 7.84 (d, 1H), 7.77 (d, 1H), 7.49 (dd, 1H), 7.18 (t, 1H), 7.00 (dd, 1H), 4.29 (m, 1H), 3.29 (d, 2H), 2.80 (m, 2H), 2.21 (m, 2H), 2.03 (m, 2H) and MS ES+ 424.0.

Preparation of Example 212: 3-(3,5-difluoro-2-methoxyphenyl)-5-(1-(1-methylpiperidin-4-yl)-1H-pyrazol-4-yl)-1H-pyrrolo[2,3-b]pyridine (334)

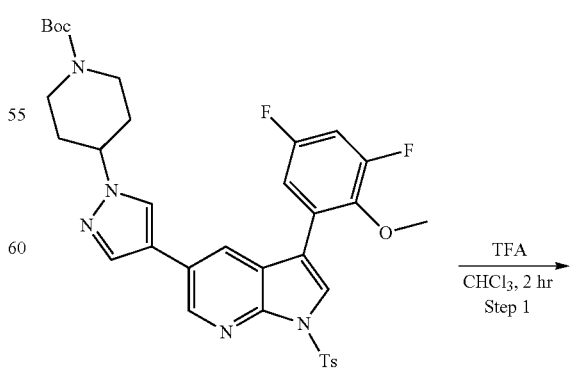

281

-continued

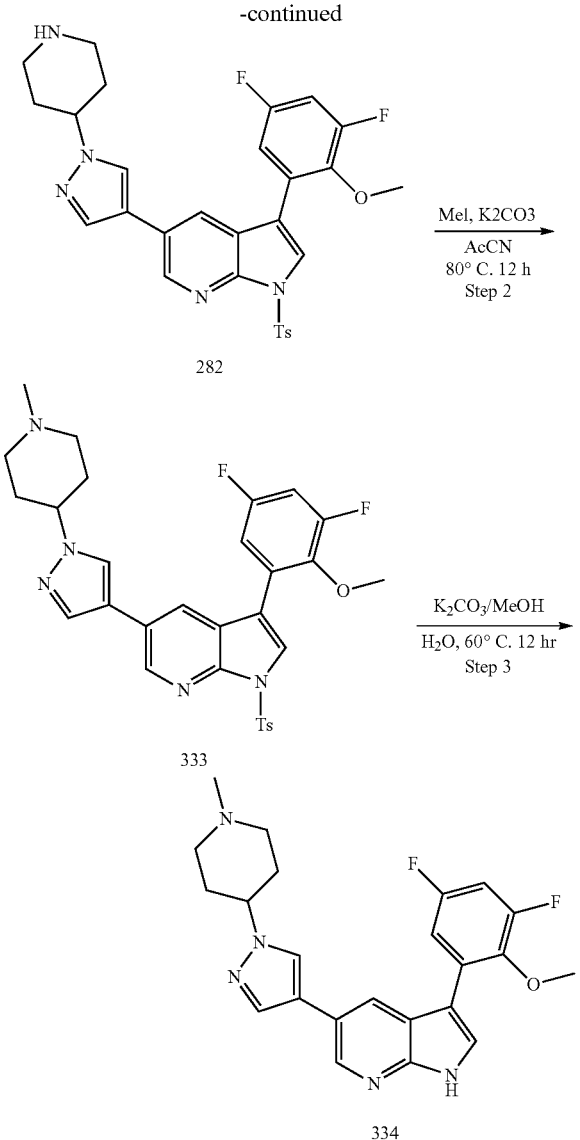

Step 1:
A solution of 281 (300 mg, 0.451 mmol) in CHCl₃ (20 mL) was taken and added TFA (5 mL) at rt. The reaction mixture was stirred for 2 h at rt. After TLC confirmation, RM evaporated TFA completely, then taken in CHCl₃ and washed with Na₂CO₃ solution followed by water wash. Organic layer was dried with Na₂SO₄ and evaporated. The resulting crude was purified via silica gel chromatography using a gradient of 3% methanol in chloroform to afford pale brown solid 282.

Step 2:
A solution of 282 (150 mg, 0.266 mmol) in acetonitrile was taken and add potassium carbonate (73 mg, 0.5322 mmol) and methyl iodide (56 mg, 0.399 mmol). The RM was stirred at 80° C. overnight. After completion of the reaction the RM was diluted with chloroform and filtered off the solids. The organic layer was evaporated to dryness. The resulting crude was purified via silica gel chromatography using 4% methanol in chloroform to afford off white solid 333.

Step 3:
To a solution of 333 (0.1731 mmol) in methanol (20 mL) and water (5 mL) was added potassium carbonate (71 mg, 0.5193 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using 100-200 mesh silica gel. The compound was eluted at 5% methanol in chloroform as pale yellow solid 3-(3,5-difluoro-2-methoxyphenyl)-5-(1-(1-methylpiperidin-4-yl)-1H-pyrazol-4-yl)-1H-pyrrolo[2,3-b]pyridine 334. ¹H NMR (400 MHz, DMSO) δ: 12.08 (s, 1H), 8.57 (d, 1H), 8.43 (s, 1H), 8.18 (d, 1H), 8.02 (s, 1H), 7.82 (d, 1H), 7.23 (m, 2H), 4.46 (m, 1H), 3.55 (m, 7H), 3.17 (d, 6H), 2.32 (m, 4H) and MS ES+ 424.10.

Preparation of Example 214: 3-(3,5-difluoro-2-methoxyphenyl)-5-(1-(1-(methylsulfonyl)piperidin-4-yl)-1H-pyrazol-4-yl)-1H-pyrrolo[2,3-b]pyridine (336)

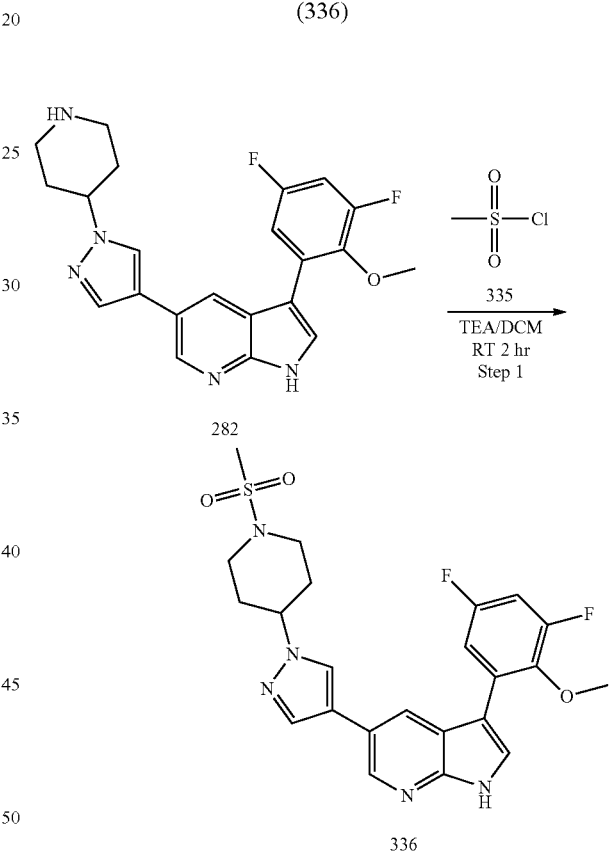

Step 1:
To a solution of 282 (100 mg, 0.244 mmol) in DCM was added triethylamine (49 mg, 0.4887 mmol). Methanesulfonyl chloride 335 (41 mg, 0.3665 mmol) was added to the reaction and stirred for 2 h at rt. The reaction mixture was diluted with dichloromethane and washed with water twice. The organic layer was dried over sodium sulphate and concentrated to get the crude, which was purified by flash column using 100-200 mesh silica gel. The compound was eluted at 2% methanol in chloroform as off white coloured solid 3-(3,5-difluoro-2-methoxyphenyl)-5-(1-(1-(methylsulfonyl)piperidin-4-yl)-1H-pyrazol-4-yl)-1H pyrrolo[2,3-b]pyridine 336. ¹H NMR (400 MHz, DMSO) δ: 12.05 (s, 1H), 8.55 (d, 1H), 8.30 (s, 1H), 8.19 (d, 1H), 7.97 (s, 1H), 7.82

(d, 1H), 7.24 (m, 2H), 4.33 (m, 1H), 3.65 (d, 2H), 3.60 (s, 3H), 2.94, (m, 2H), 2.92 (s, 3H), 2.03 (m, 2H), 1.98 (m, 2H) and MS ES+ 488.0.

Preparation of Example 215: 3-(3,5-difluoro-2-methoxyphenyl)-5-(1-(1-(ethylsulfonyl)piperidin-4-yl)-1H-pyrazol-4-yl)-1H-pyrrolo[2,3-b]pyridine (338)

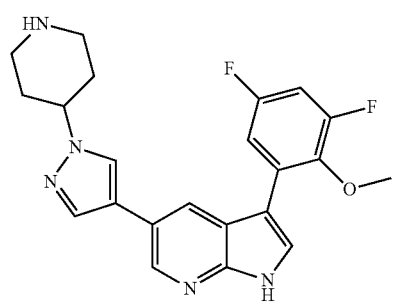

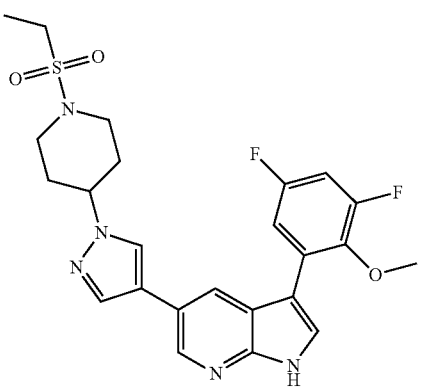

Preparation of Example 216: 3-(3,5-difluoro-2-methoxyphenyl)-5-(1-(1-(propylsulfonyl)piperidin-4-yl)-1H-pyrazol-4-yl)-1H-pyrrolo[2,3-b]pyridine (340)

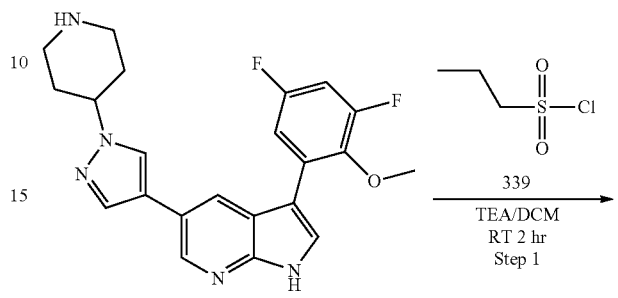

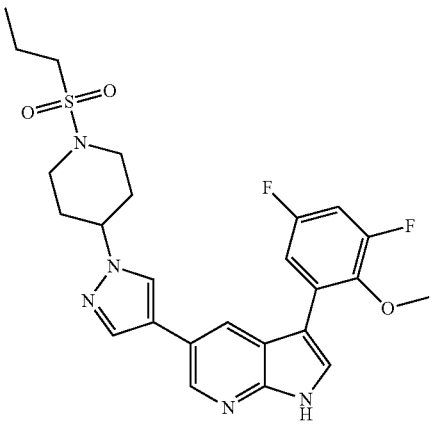

Step 1:
To a solution of 282 (100 mg, 0.244 mmol) in DCM was added triethylamine (49 mg, 0.4887 mmol). Ethane sulfonyl chloride 337 (47 mg, 0.3665 mmol) was added to the reaction and stirred it for 2 h at rt. The reaction mixture was diluted with dichloromethane and washed with water twice. The organic layer was dried over sodium sulphate and concentrated to get the crude, which was purified by flash column using 100-200 mesh silica gel. The compound was eluted at 2% methanol in chloroform as off white coloured solid 3-(3,5-difluoro-2-methoxyphenyl)-5-(1-(1-(ethylsulfonyl)piperidin-4-yl)-1H-pyrazol-4-yl)-1H-pyrrolo[2,3-b]pyridine 338. $^1$H NMR (400 MHz, CDCl3) δ: 9.58 (s, 1H), 8.52 (d, 1H), 8.17 (d, 1H), 7.84 (s, 1H), 7.72 (m, 2H), 7.09 (m, 1H), 6.82 (m, 1H), 4.31 (m, 1H), 3.96 (m, 2H), 3.68 (s, 3H), 3.06 (m, 2H), 3.00 (m, 3H), 2.29 (m, 2H), 2.14 (m, 2H), 1.40 (m, 5H), 1.25 (m, 5H) and MS ES+ 502.1.

Step 1:
To a solution of 282 (100 mg, 0.244 mmol) in DCM was added triethylamine (49 mg, 0.4887 mmol). Propane sulfonyl chloride 339 (52 mg, 0.366 mmol) was added to the reaction and stirred for 2 h at rt. The reaction mixture was diluted with dichloromethane and washed with water twice. The organic layer was dried over sodium sulphate and concentrated to get the crude, which was purified by flash column using 100-200 mesh silica gel. The compound was eluted at 2% methanol in chloroform as off white coloured solid 3-(3,5-difluoro-2-methoxyphenyl)-5-(1-(1-(propylsulfonyl)piperidin-4-yl)-1H-pyrazol-4-yl)-1H-pyrrolo[2,3-b]pyridine 340. $^1$H NMR (400 MHz, CDCl3) δ: 9.68 (s, 1H), 8.53 (d, 1H), 8.17 (d, 1H), 7.84 (s, 1H), 7.73 (m, 2H), 7.09 (m, 1H), 6.82 (m, 1H), 4.31 (m, 1H), 3.95 (m, 2H), 3.68 (d, 3H), 3.01 (m, 2H), 2.94 (m, 2H), 2.36 (m, 2H), 2.14 (m, 2H), 1.86 (m, 2H), 1.06 (m, 3H) and MS ES+ 516.1.

343

Preparation of Example 220: 3-(2,2-difluorobenzo[d][1,3]dioxol-5-yl)-5-(1-(1-methylpiperidin-4-yl)-1H-pyrazol-4-yl)-1H-pyrrolo[2,3-b]pyridine (341)

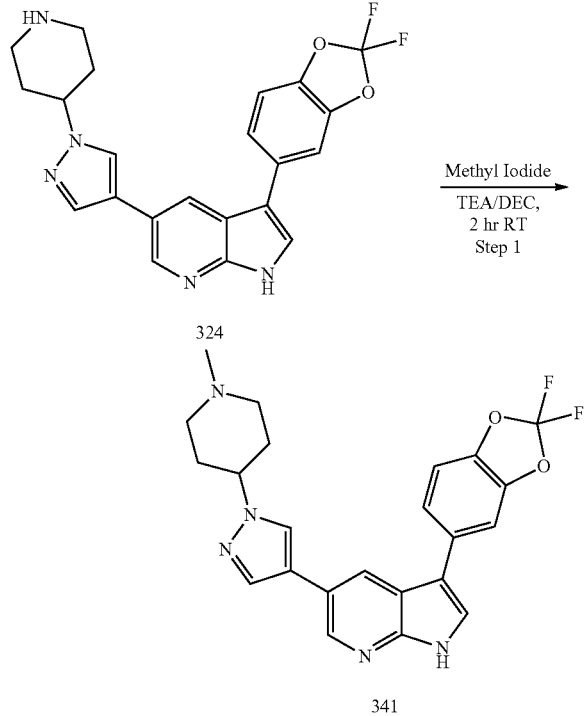

To a solution of 324 (50 mg, 0.1182 mmol) in DCM was added triethylamine (17.9 mg, 0.236 mmol). Methyl iodide (18.3 mg, 0.130 mmol) was added to the reaction and stirred for 2 h at rt. The reaction mixture was diluted with dichloromethane and washed with water twice. The organic layer was dried over sodium sulphate and concentrated to get the crude, which was purified by flash column using 100-200 mesh silica gel. The compound was eluted at 2% methanol in chloroform as off white coloured solid 3-(2,2-difluorobenzo[d][1,3]dioxol-5-yl)-5-(1-(1-methylpiperidin-4-yl)-1H-pyrazol-4-yl)-1H-pyrrolo[2,3-b]pyridine 341.

Preparation of Example 221: 3-(2,2-difluorobenzo[d][1,3]dioxol-5-yl)-5-(1-(1-(methylsulfonyl)piperidin-4-yl)-1H-pyrazol-4-yl)-1H-pyrrolo[2,3-b]pyridine (343)

344

-continued

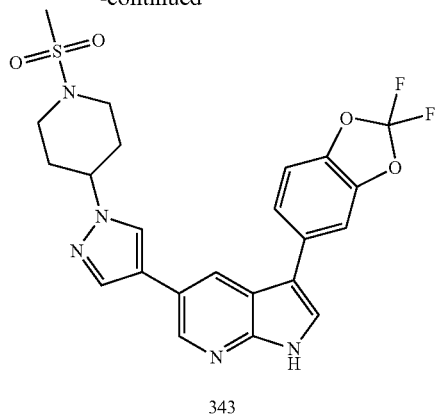

Step 1:

To a solution of 324 (50 mg, 0.1182 mmol) in DCM was added triethylamine (17.9 mg, 0.1773 mmol). Methane sulfonyl chloride 342 (13.5 mg, 0.1182 mmol) was added to the reaction and stirred for 2 h at rt. The reaction mixture was diluted with dichloromethane and washed with water twice. The organic layer was dried over sodium sulphate and concentrated to get the crude, which was purified by flash column using 100-200 mesh silica gel. The compound was eluted at 2% methanol in chloroform as off white coloured solid 3-(2,2-difluorobenzo[d][1,3]dioxol-5-yl)-5-(1-(1-(methylsulfonyl)piperidin-4-yl)-1H-pyrazol-4-yl)-1H-pyrrolo[2,3-b]pyridine 343. $^1$H NMR (400 MHz, DMSO) δ: 11.94 (s, 1H), 8.55 (d, 1H), 8.39 (m, 2H), 8.03 (s, 1H), 7.88 (d, 1H), 7.78 (d, 1H), 7.58 (m, 1H), 7.44 (d, 1H), 4.31 (m, 1H), 3.66 (m, 2H), 2.95 (s, 3H), 2.16 (m, 2H), 2.01 (m, 2H) and MS ES+ 502.1.

Preparation of Example 222: 3-(2,2-difluorobenzo[d][1,3]dioxol-5-yl)-5-(1-(1-(ethylsulfonyl)piperidin-4-yl)-1H-pyrazol-4-yl)-1H-pyrrolo[2,3-b]pyridine (344)

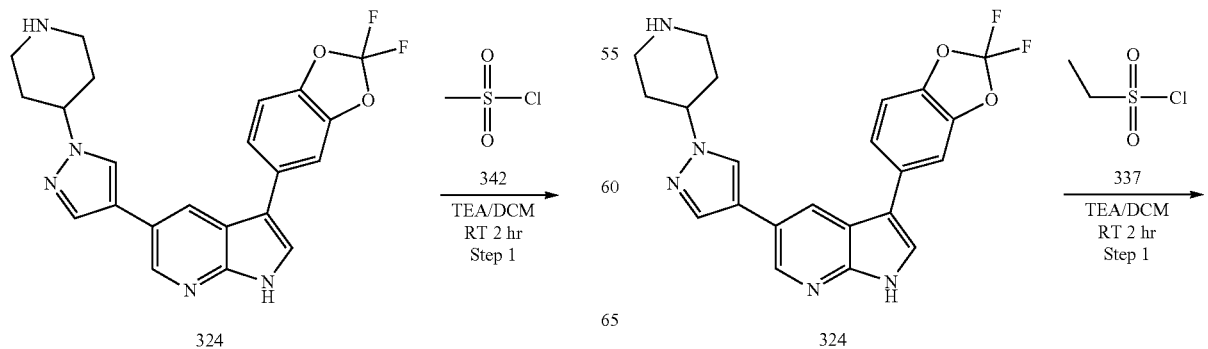

345

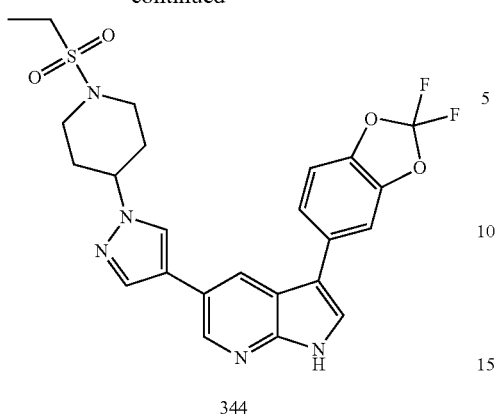

344

Step 1:

To a solution of 324 (50 mg, 0.1182 mmol) in DCM was added triethylamine (17.9 mg, 0.1771 mmol). Ethane sulfonyl chloride 337 (15 mg, 0.1182 mmol) was added to the reaction and stirred for 2 h at rt. The reaction mixture was diluted with dichloromethane and washed with water twice. The organic layer was dried over sodium sulphate and concentrated to get the crude, which was purified by flash column using 100-200 mesh silica gel. The compound was eluted at 2% methanol in chloroform to give off white coloured solid 3-(2,2-difluorobenzo[d][1,3]dioxol-5-yl)-5-(1-(1-(ethylsulfonyl)piperidin-4-yl)-1H-pyrazol-4-yl)-1H-pyrrolo[2,3-b]pyridine 344. $^1$HNMR (400 MHz, DMSO) δ: 11.95 (s, 1H), 8.55 (d, 1H), 8.39 (m, 2H), 8.02 (s, 1H), 7.88 (d, 1H), 7.78 (d, 1H), 7.58 (m, 1H, 7.44 (d, 1H), 4.33 (m, 1H), 3.71 (m, 2H), 3.04 (m, 4H), 2.14 (m, 2H), 1.97 (m, 2H), 1.21 (m, 4H) and Ms ES+516.1.

Preparation of Example 223: 3-(2,2-difluorobenzo[d][1,3]dioxol-5-yl)-5-(1-(1-(propylsulfonyl)piperidin-4-yl)-1H-pyrazol-4-yl)-1H-pyrrolo[2,3-b]pyridine (345)

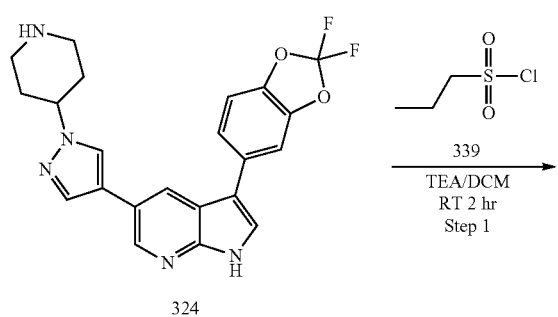

346

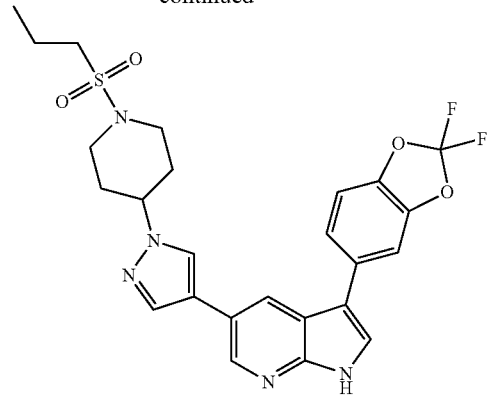

345

Step 1:

To a solution of 324 (50 mg, 0.1182 mmol) in DCM was added triethylamine (17.9 mg, 0.1773 mmol) and propane sulfonyl chloride 339 (16.7 mg, 0.1182 mmol) and stirred for 2 h at rt. The RM was diluted with dichloromethane and washed with water twice. The organic layer was dried over sodium sulphate and concentrated to get the crude, which was purified by flash column using 100-200 mesh silica gel. The compound was eluted at 2% Methanol in chloroform as off white coloured solid 345. $^1$HNMR (400 MHz, DMSO) δ: 11.95 (s, 1H), 8.55 (d, 1H), 8.39 (m, 2H), 8.03 (s, 1H), 7.88 (d, 1H), 7.78 (d, 1H), 7.58 (m, 1H), 7.44 (d, 1H), 4.35 (m, 1H), 3.69 (m, 2H), 3.03 (m, 4H), 2.14 (m, 2H), 1.97 (m, 2H), 1.70 (m, 2H), 1.00 (m, 3H) and MS ES+ 530.1.

Preparation of Example 226: 2-(4-(4-(3-(3,5-difluoro-2-methoxyphenyl)-1H-pyrrolo[2,3-b]pyridin-5-yl)-1H-pyrazol-1-yl)piperidin-1-yl)ethanol (347)

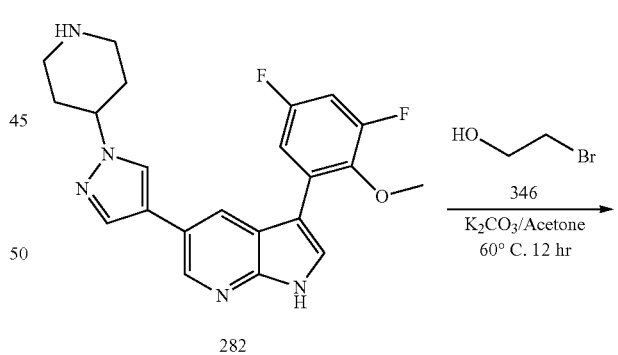

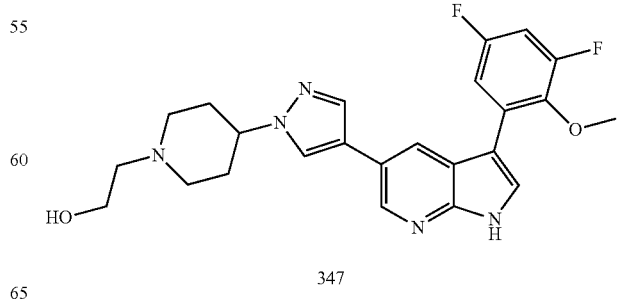

347

Step 1:

To a solution of 282 (50 mg, 0.122 mmol) in acetone was added potassium carbonate (25 mg, 0.244 mmol) and 2-bromo ethanol (18.3 mg, 0.146 mmol) and stirred for 12 h at 60° C. The reaction was filtered through celite bed and washed with ethyl acetate. The organic layer was concentrated to get the crude, which was purified by neutral alumina and the compound was eluted at 2% methanol in chloroform as half white coloured solid 2-(4-(4-(3-(3,5-difluoro-2-methoxyphenyl)-1H-pyrrolo[2,3-b]pyridin-5-yl)-1H-pyrazol-1-yl)piperidin-1-yl)ethanol 347. $^1$HNMR (400 MHz, DMSO) δ: 12.04 (s, 1H), 8.54 (d, 1H), 8.31 (s, 1H), 8.18 (d, 1H), 7.93 (s, 1H), 7.81 (d, 1H), 7.22 (m, 2H), 4.39 (m, 1H), 4.10 (m, 1H), 4.00 (m, 1H), 3.60 (s, 3H), 3.50 (m, 2H), 2.96 (d, 2H), 2.42 (m, 2H), 2.13 (m, 2H), 1.99 (m, 3H), 1.16 (t, 1H) and MS ES+ 454.0.

Preparation of Example 227: 2-(4-(4-(3-(2,2-difluorobenzo[d][1,3]dioxol-5-yl)-1H-pyrrolo[2,3-b]pyridin-5-yl)-1H-pyrazol-1-yl)piperidin-1-yl)ethanol (348)

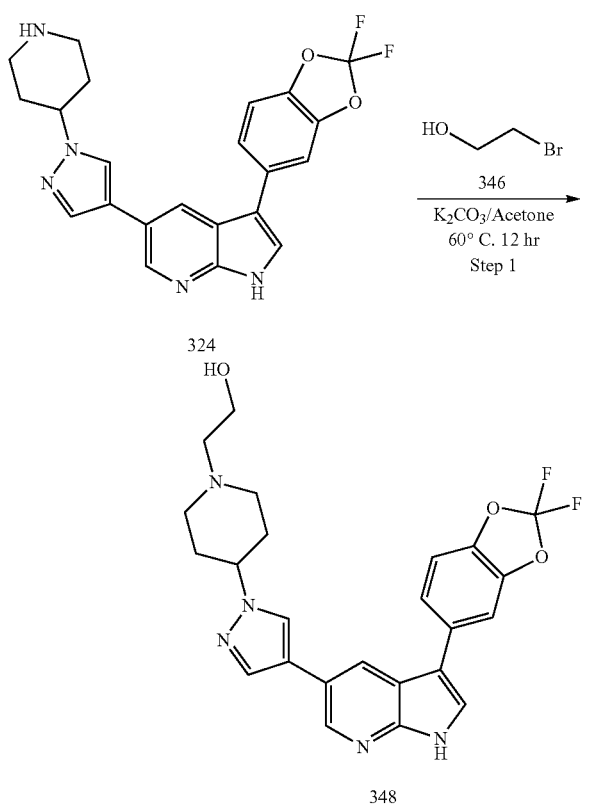

Step 1:

To a solution of 324 (50 mg, 0.118 mmol) in acetone was added potassium carbonate (32 mg, 0.236 mmol) and 2-bromo ethanol (17.7 mg, 0.141 mmol), and stirred for 12 h at 60° C. The reaction was filtered through celite bed and washed with ethyl acetate. The organic layer was concentrated to get the crude, which was purified by neutral alumina and the compound was eluted at 2% methanol in chloroform as half white coloured solid 2-(4-(4-(3-(2,2-difluorobenzo[d][1,3]dioxol-5-yl)-1H-pyrrolo[2,3-b]pyridin-5-yl)-1H-pyrazol-1-yl)piperidin-1-yl)ethanol 348.

348

$^1$HNMR (400 MHz, DMSO) δ: 11.93 (s, 1H), 8.54 (d, 1H), 8.38 (m, 2H), 7.99 (s, 1H), 7.88 (d, 1H), 7.78 (d, 1H), 7.58 (m, 1H), 7.43 (d, 1H), 4.39 (m, 1H), 4.11 (m, 1H, 3.50 (m, 2H), 2.97 (d, 2H), 2.43 (m, 2H), 2.14 (m, 2H), 1.96 (m, 4H) and MS ES+ 468.0.

Preparation of Example 228: 3-(3-fluoro-2-methoxyphenyl)-5-(5-(1-(piperidin-1-yl)ethyl)thiophen-2-yl)-1H-pyrrolo[2,3-b]pyridine (349)

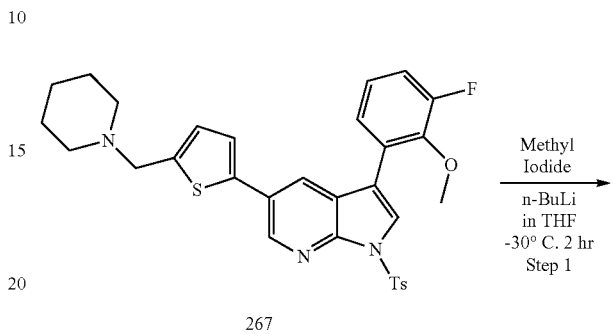

Step 1:

To a solution of 267 (50 mg, 0.386 mmol) in THF was added n-butyl lithium (11 mg, 0.173 mmol). Methyl iodide (18.3 mg, 0.129 mmol) was added to the reaction and stirred for 2 h at −30° C. The RM was quenched with ammonium chloride solution and stirred for 15 min. The aqueous phase was extracted twice with ethyl acetate. The resulting organic layer was dried over sodium sulphate and concentrated to get the crude, which was purified by flash column using 100-200 mesh silica gel. The compound was eluted at 2% methanol in chloroform as off white coloured solid 268.

Step 2:

To a solution of 368 (30 mg, 0.0508 mmol) in methanol (20 mL) and water (5 mL) was added potassium carbonate (21 mg, 0.152 mmol). The reaction was heated to 60° C. overnight. The solvent was completely distilled off and the remainder diluted with water (25 mL) and extracted with chloroform twice (2×25 mL). The combined organic layer was dried over sodium sulphate, filtered and concentrated to get the crude, which was purified through flash chromatography by using neutral alumina. The compound was eluted at 5% methanol in chloroform as pale yellow solid (10 mg) compound 3-(3-fluoro-2-methoxyphenyl)-5-(5-(1-(piperidin-1-yl)ethyl)thiophen-2-yl)-1H-pyrrolo[2,3-b]pyridine 349.

Pharmaceutical Salts

Hydrochloric acid salts of the foregoing compounds were prepared by solubilizing the compound in a minimum of ethanol and a solution of ethanolic HCl 20% was added drop wise and the mixture stirred for 1 hour followed by addition of diethyl ether. A precipitated off-white solid hydrochloride was separated by filtration, washer with diethyl ether and dried. In certain embodiments, the invention contemplates the treatment of diseases or patients using a compound, or a prodrug, tautomeric, an isomeric, pharmaceutically acceptable salt, N-oxide, or stereoisomeric form thereof, having a structure of Formula I, IA and IB. Pharmaceutically acceptable salts are derivatives of the claimed compounds wherein the parent compound is modified by making acid or base salts thereof. Examples of pharmaceutically acceptable salts include, but are not limited to organic acid salts of basic residues such as amines; alkali or organic salts of acidic residues such as carboxylic acids. The pharmaceutically acceptable salts include the standard non-toxic salts or the quaternary ammonium salts of the parent compound formed, for example, from non-toxic inorganic or organic acids. For example, such non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic and isethionic salts. The pharmaceutically acceptable salts of the present invention can be synthesized from the parent compound which contains a basic or acidic moiety by established chemical methods. Such salts can be prepared by reacting free acid or base forms of these compounds with a stoichiometric amount of the appropriate base or acid in water or in an organic solvent, or in a mixture of the two; generally, nonaqueous media like ether, EtOAc, ethanol, isopropanol, or acetonitrile are preferred. Lists of suitable salts are found in Remington's Pharmaceutical Sciences. 18$^{th}$ ed., Mack Publishing Company, Easton, Pa., 1990, p. 1445.

Additional Examples

Usage Method

The subject matter disclosed herein relates to the substituted 1H-Pyrrolo[2,3-b]pyridine and 1H-Pyrazolo[3,4-b]pyridine derivatives as inhibitors of SIK1 (SNF1LK)(SEQ ID NO: 10, SIK2 (SNF1LK, QIK)(SEQ ID NO: 11) and SIK3 (QSK)(SEQ ID NO: 24). Pharmaceutical compositions containing the Formula I, IA and IB compounds and methods of using the compounds or compositions to treat various types of diseases or conditions mediated by SIK family isoform (SIK1 (SEQ ID NO: 10), SIK2 (SEQ ID NO: 11) and SIK3 (SEQ ID NO: 24)) such as for example, disease states associated with abnormal cell growth such as cancer, stroke, obesity and type II diabetes. Additionally these compounds and compositions containing the compounds are employed to treat ovarian and breast cancers. In addition, these compounds are important future therapeutic agents for the treatment of lung, prostate and testicular tumours cancers. Methods of making the compounds and pharmaceutical salts thereof are also described herein.

The in vivo efficacy of 1H-Pyrrolo[2,3-b]pyridine and 1H-Pyrazolo[3,4-b]pyridine derivatives in an established human ovarian xenograft growth inhibition experiments conducted is described and in combination with taxane and paclitaxel drugs. The potent and selective two SIK2 (SEQ ID NO: 11) inhibitors were administered orally in dose escalation in vivo experiments starting from 20, 40, 60 and 80 mg/Kg after 2 weeks of sub-cutaneous SKOV3 ovarian cancer cells injection into 32 female nu/nu mice.

In Vitro Inhibition Assay

SIK2 Kinase Assay

Procedure: Enzyme was incubated with substrate peptide in reaction buffer in the presence and absence of test compounds or Staurosporine. All additions were done on ice, followed by the addition of ATP mix. Wells were uniformly mixed using an Eppendorff plate shaker and incubated at 30° C. for 20 min, and stopped by the addition of 54 of 3% phosphoric acid. Volume was increased to 1000 μL by adding 0.8% phosphoric acid which was then transferred to PC filter mats (Millipore), pre-equilibrated with 70% ethanol and water. Plates were washed thrice with 100 μL 0.8% phosphoric acid and dried for an hour at 60° C. 100 μL scintillation fluid was added into each well and reading taken in Perkin Elmer TOPCOUNT beta counter. The data analysis was performed by averaging the duplicate top count readings for each standard, negative, positive control (enzyme control) and samples and subtracting the average negative control from each reading which results in corrected values. A validation $EC_{50}$ curve was generated by plotting CPM for each Staurosporine concentration on y-axis against the Log concentration of Staurosporine (nM) on the x-axis followed by a best fit curve through the points.

% Inhibition=((Enzyme Control−Compound Treated)/Enzyme Control)×100

Coefficient of Variance (% CV) between replicates: The % CV values between the replicates were mostly within the acceptable limits of a radiometric experiment. Z' factor evaluation: The value of Z' factor was found to be 0.8 for SIK2 (SEQ ID NO: 11) and 0.9 was derived for others.

All the compounds were tested in 10-dose $IC_{50}$ mode with 3 fold serial dilution starting at 100 μM. The control compound Staurosporine was tested in 10 dose $IC_{50}$ with 3 fold serial dilution starting at 20 μM. The reactions were carried out at 10 μM ATP for SIK2 (SEQ ID NO: 11) and the results shown in FIG. 1. Referring to FIG. 1, SIK2 (SEQ ID NO: 11) inhibitor examples: Panel A: 135 (■), 142 (Δ) and Palel B: 133 (■) and 168 (Δ).

General Protein Kinase Assay Methodology Employed for Selected Kinases

In vitro profiling of the 337 member kinase panel was performed at Reaction Biology Corporation using the "HotSpot" assay platform. Briefly, specific kinase/substrate pairs along with required cofactors were prepared in reaction buffer; 20 mM Hepes (pH 7.5), 10 mMmgCl2, 1 mM EGTA, 0.02% Brij35, 0.02 mg/ml BSA, 0.1 mM Na3VO4, 2 mM DTT, 1% DMSO. Compounds were delivered into the reaction, followed ~20 min later by addition of a mixture of ATP (Sigma) and 33P ATP (PerkinElmer) to a final concentration of 10 μM. Reactions were carried out at 25° C. for 120 min, followed by spotting of the reactions onto P81 ion exchange filter paper (Whatman). Unbound phosphate was removed by extensive washing of filters in 0.75% phosphoric acid. After subtraction of background derived from control reactions containing inactive enzyme, kinase activity data were expressed as the percent remaining kinase activity in test samples compared to vehicle (dimethyl sulfoxide) reactions. $IC_{50}$ values and curve fits were obtained using Prism (GraphPad Software). Kinome tree representations were prepared using Kinome Mapper (http://www.reactionbiology.com/apps/kinome/mapper/LaunchKinome.htm).

TABLE 4

List of Compounds and Corresponding three isoforms of SIK family*

| EX. | SIK2 (QIK) (SEQ ID NO: 11) | SIK1 (SEQ ID NO: 10) | SIK3 (QSK) (SEQ ID NO: 24) |
|---|---|---|---|
| 1 | ** | * | * |
| 2 | ** | * | * |
| 5 | ** | * | *** |
| 6 | ** | ** | * |
| 7 | ** | ND | ND |
| 17 | ** | ** | ** |
| 20 | * | ND | ND |
| 22 | * | ND | ND |
| 23 | ** | ND | ND |
| 24 | ** | ND | ND |
| 25 | * | ND | ND |
| 26 | ** | ND | ND |
| 28 | ** | ND | ND |
| 29 | ** | ND | ND |
| 30 | * | ND | ND |
| 36 | ** | ** | ND |
| 37 | ** | ** | ND |
| 47 | ** | ND | ND |
| 87 | ** | * | ND |
| 94 | * | ND | ND |
| 95 | * | * | * |
| 96 | * | * | * |
| 97 | * | * | * |
| 98 | * | * | * |
| 99 | * | ND | ND |
| 100 | * | ND | ND |
| 101 | ** | ND | ND |
| 113 | ** | ND | ND |
| 114 | *** | ** | * |
| 115 | *** | ** | * |
| 116 | ** | * | * |
| 120 | *** | ** | ** |
| 123 | ** | ** | ** |
| 124 | ** | ** | ** |
| 125 | *** | * | ND |
| 126 | * | ND | ND |
| 128 | *** | ** | ** |
| 132 | ** | ND | ND |
| 133 | *** | * | ** |
| 134 | ** | ** | * |
| 135 | *** | ** | ** |
| 136 | *** | ** | ** |
| 137 | ** | ND | ND |
| 138 | *** | ** | ** |
| 139 | * | ND | ND |
| 140 | * | ND | ND |
| 141 | *** | * | ** |
| 142 | *** | * | *** |
| 168 | *** | * | * |
| 174 | *** | * | ** |
| 175 | *** | * | ** |
| 176 | *** | * | ** |
| 177 | *** | * | ** |
| 178 | *** | * | ** |
| 179 | *** | * | ** |
| 180 | *** | * | ** |
| 181 | *** | * | ** |
| 182 | *** | * | ** |
| 183 | *** | * | ** |
| 184 | *** | * | ** |
| 185 | *** | * | ** |
| 191 | *** | ** | ** |
| 192 | *** | ** | ** |
| 193 | *** | ** | ** |
| 196 | *** | ** | *** |
| 197 | *** | ** | *** |
| 198 | *** | ** | *** |
| 199 | *** | ** | ** |
| 200 | *** | ** | *** |
| 201 | * | * | * |
| 202 | *** | ** | *** |
| 203 | *** | * | * |
| 204 | *** | ** | *** |
| 205 | *** | ** | *** |
| 206 | *** | ** | *** |
| 207 | *** | ** | *** |
| 208 | *** | ** | *** |
| 209 | *** | *** | *** |
| 210 | *** | ** | *** |
| 211 | *** | ** | *** |
| 212 | *** | ** | *** |
| 213 | *** | ** | *** |
| 214 | ** | * | ** |
| 215 | ** | * | ** |
| 216 | ** | * | ** |
| 217 | *** | ** | *** |
| 218 | *** | ** | *** |
| 219 | *** | ** | *** |
| 220 | ** | * | * |
| 221 | * | * | * |
| 222 | * | * | * |
| 223 | * | * | * |
| 224 | *** | ** | *** |
| 225 | *** | ** | *** |
| 226 | *** | ** | *** |
| 227 | *** | ** | *** |
| 228 | ND | ND | ND |

*Kinase Inhibition Result for Selected Compounds
*** <0.1 μM,
** >0.1 μM,
* >1 μM
ND = Not Determined Protein Kinase Selectivity Profiler Selected compounds were tested against 299 protein kinases+17 additional preview kinases in single dose duplicate mode at a concentration of 1 μM. A control compound was tested in 10-dose $IC_{50}$ mode with 3-fold serial dilution starting at 20 μM. Reactions were carried out at 10 μM ATP. Data pages include raw data, % Enzyme activity (relative to DMSO controls), and curve fits.

Cell Culture Models of Cancer

Determining 50% Inhibition Concentration ($IC_{50}$) of 3 Compounds on 2 Human Tumor Cell Lines CellTiter-Glo (CTG)

(Product No.: G7572, Promega. Store CellTiter-Glo buffer and CellTiter-Glo substrate at −20° C.), the following protocol is recommended for the preparation of CTG reagent. Thaw the CellTiter-Glo Buffer, and equilibrate to rt prior to use. For convenience the CellTiter-Glo buffer may be thawed and stored at rt for up to 48 hr prior to use. Equilibrate the lyophilized CellTiter-Glo substrate to rt prior to use. Transfer 100 mL of CellTiter-Glo buffer into the amber bottle containing CellTiter-Glo substrate to reconstitute the lyophilized enzyme/substrate mixture. This forms the CellTiter-Glo reagent. Mix by gently vortexing, swirling or inverting the contents to obtain a homogeneous solution. The CellTiter-Glo substrate should go into solution easily in less than 1 minute. Aliquot and store the CTG reagent at −20° C. freezer for long term storage.

Cytotoxicity and $IC_{50}$ Determination

Day 1: The cells will be harvested during the logarithmic growth period and counted with hemocytometer. The cell viability should be over 98% by trypan blue exclusion. Adjust cell solution to the appropriate concentration with respective medium according the seeding density. Add 90 μl cell suspensions to 96-well plates; the final cell seeding density is $5 \times 10^3$ cells/90 μl/well for OVCAR-3, $5 \times 10^3$ cells/90 μl/well for SK-OV-3. Incubate the assay plate for 24 hours at 37° C. in a humidified, 5% $CO_2$ atmosphere. Day 2: Prepare serial solution of test articles with DMSO then dilute with PBS to prepare 10× injection solution. Prepare 10× positive drug injection solution with PBS (see appendix 1). Dispense 104 drug injection solution in each well. The plates will be cultured for another 72 h, and then measured by means of MTS assay or CTG assay. Day 5: Thaw the MTS Solution and the PMS Solution, just before addition to the culture plate containing cells, mix PMS Solution with MTS Solution at 1:20 ratio immediately, the final volume was based on the actual requirement. Gently swirl the tube to ensure complete mixing of the combined MTS/PMS solution. Pipet 204, of the combined MTS/PMS solution into the assay wells in one 96 well plate. Incubate the plate for 1-4 h at 37° C. in a humidified, 5% $CO_2$ atmosphere, record the absorbance at 490 nm using SpectraMax. Thaw CTG reagent and equilibrate to rt, pipet 254, to the assay wells in another 96 well plate, shake for 2 min with the plate shaker, and incubate for 10 min at dark place, then record luminescence reading using Envision.

Data Analysis

The data will be displayed graphically using GraphPad Prism 5.0 software. In order to calculate $IC_{50}$, a dose-responsive curve will be fitted using nonlinear regression model with a sigmoidal dose response. The $IC_{50}$ will be automatically produced by GraphPad Prism 5.0. FIG. 2 displays two such plots of SIK2 (SEQ ID NO: 11) inhibitor (191, 206) examples tested in SK-OV-3 and OVCAR3 cell lines with Cisplatin as control. The SK-OV-3 is on the left and the OVCAR3 is on the right.

Survival rate is calculated with the formula of
$Value_{sample}/Value_{vehicle\ control}*100\%$ for CTG
assay, and calculated with the formula
of $(Value_{sample}-Value_{blank\ control})/$
$(Value_{vehicle\ control}-Value_{blank\ control})*100\%$ Effects of the Test Compounds on the SIK2-Expressed SKOv3, OVCAR3, ES-2 and HEY Cells Test compound at various concentrations are added in duplicate and the cells were incubated for 72 h. After incubation, CellTiter-Glo® Reagent are added to each test well and mixed for 2 min on an orbital shaker. The plates are shortly centrifuged and incubated at rt for additional 10 min to stabilize the luminescent signal and the luminescence signals are recorded on Pherastar Plus. The cell viability after 72 h compound treatment was assayed. 1H-Pyrrolo[2, 3-b] pyridine and 1H-Pyrazolo[3,4-b]pyridine series of compounds and its analogues were tested on panel of ovarian cancer cell lines where 1H-Pyrazolo[3,4-b]pyridine series inhibited SKOv3 (1.2 µM), OVCAR-3 (0.7 µM), HEY 0.07 µM), ES-2 (1.2 µM) (FIGS. 2b1-3) and COV434, COV504, EFO-27, HO-8910, OV56, OV90, OVCAR-4, OVISE, OVSAHO, OVTOKO, SW626, TOV-112D and TOV-21G cells inhibited by 1H-Pyrazolo[3,4-b]pyridine series with an $IC_{50}$ between 0.5 to 3.0 µM.

Functional Kinase Assay and the Onset of SIK2 Inhibition:

The functional assays was conducted in order to examine the phosphorylation of SIK2 (SEQ ID NO: 11) at Thr175 that is required for kinase activity and downstream targets on treatment with 1H-Pyrrolo[2,3-b]pyridine and 1H-Pyrazolo [3,4-b]pyridine derivatives. In SKOv3, OVCAR-3, HEY cells the inhibition of phosphorylation of SIK2 (SEQ ID NO: 11) at Thr175 and Ser186 monitored after the 1 h treatment with 1H-Pyrrolo[2,3-b]pyridine and 1H-Pyrazolo [3,4-b]pyridine derivatives. The treatment with 1H-Pyrrolo [2,3-b]pyridine and 1H-Pyrazolo[3,4-b]pyridine derivatives results in inhibition of SIK2 (SEQ ID NO: 11) kinase activity will examined from ovarian cancer cell lines by western blot. Levels of phospho-SIK2 relative to total-SIK2 upon exposure to 1H-Pyrrolo[2,3-b]pyridine and 1H-Pyrazolo[3,4-b]pyridine derivatives was determined. The experimental details involves 10 thousand SKOV3ip ovarian carcinoma cells plated in 6 cm plates and will be allowed to adhere overnight. All plates treated with demecolcine for 6 h, cells were collected released in to new media containing 1H-Pyrrolo[2,3-b]pyridine and 1H-Pyrazolo[3,4-b]pyridine derivatives at 1 h at rt. The cell lysates will be used in Western blot analysis.

Effects of 1H-Pyrrolo[2,3-b]pyridine and 1H-Pyrazolo[3, 4-b]pyridine Derivatives on Ovarian Carcinoma Proliferation and Apoptosis:

As a part of cellular efficacy and possible mechanisms causing the tumor growth inhibition evidenced in the 1H-Pyrrolo[2,3-b]pyridine and 1H-Pyrazolo[3,4-b]pyridine derivatives experiments, we further examined the effects on tumor cell proliferation by calculating the proliferative index after immunohistochemistry on tumors collected at necropsy from all efficacy experiments. In the SKOv3 model, the proliferation index for animals treated with vehicle, 1H-Pyrrolo[2,3-b]pyridine and 1H-Pyrazolo[3,4-b]pyridine derivatives alone and in combination with paclitaxel and monitor the proliferative indices. Further to gain additional insight into downstream effects of 1H-Pyrrolo[2,3-b]pyridine and 1H-Pyrazolo[3,4-b]pyridine derivatives, we will conduct the expression profile studies on SKOv3, OVCAR-3, HEY tumors harvested from either vehicle- or 1H-Pyrrolo[2,3-b] pyridine and 1H-Pyrazolo[3,4-b]pyridine derivatives treated animals.

In Vivo Models of SIK2 (SEQ ID NO: 11)

SKOV3 ovarian cancer cells injected sub-cutaneous into 32 female nu/nu mice of approximately and four groups of 8 mice observed with twice weekly measurements and weekly weights. Treatment with SIK2 (SEQ ID NO: 11) inhibitors when progressive growth is observed at 7-14 days. In separate experiments, each of two SIK2 (SEQ ID NO: 11) inhibitors 1H-Pyrrolo[2,3-b]pyridine derivatives delivered daily by gavage in 3 different concentrations (20, 40 and 80 mg/kg) in a volume of 2 mL. Vehicle will be administered for 4th group by gavage. When the control xenografts have grown to 1.5 cm in diameter, all mice will be sacrificed, tumors weighed and tumor tissue cryopreserved and fixed for routine and EM studies and the duration of time required ~4 to 6 weeks. The 1H-Pyrrolo[2,3-b]pyridine compounds had significant antitumor effects as a single agent over combination with taxol.

Efficacy of 1H-Pyrrolo[2,3-b]Pyridine Derivatives in Nu/Nu SKOv3 Xenograft Mice:

We examined the growth-inhibitory effect of 1H-Pyrrolo [2,3-b]pyridine derivatives in-vivo employing an i.p. xenograft model in which nu/nu mice were inoculated i.p. with sensitive cell line SKOv3 cells. One week after inoculation, mice were randomized into six treatment groups receiving vehicle, 1H-Pyrrolo[2,3-b]pyridine derivatives 30, 60 mg/kg, taxol 10 mg/kg and 1H-Pyrrolo[2,3-b]pyridine plus taxol. Drug treatment was well tolerated except i.p. treatment second group, with no apparent toxicity throughout the study. At the end of an experiment, all mice were sacrificed for tumor volume, weight and each mouse examined and recorded at autopsy. The two 1H-Pyrrolo[2,3-b]pyridine compounds and taxol groups all inhibited the abdominal tumor growth and tumor cell dissemination (reduced tumor numbers) (FIG. 5a-c). Taken together, these findings indicates that two 1H-Pyrrolo[2,3-b]pyridine compounds, taxol had significant antitumor effects and compound as a single agent with the ability not only to inhibit ovarian tumor growth, but also inhibits dissemination of tumor cells in vivo.

The Effect of 1H-Pyrrolo[2,3-b]Pyridine Compounds on SKOv3 Induced Orthotopic Murine Model:

Dose-finding experiments initiated by injecting SKOV3ip1 (SKOV3ip1 cells were collected from cultures using either 0.25% trypsin-EDTA (Life Technologies) on the cell line) tumor cells i.p. ($2.5 \times 10^5$) into athymic female mice. 19 days after tumor cell orthotopic inoculation and when i.p. tumors were palpable, then the mice randomized into 6 dosage groups: 0 mg (vehicle alone, group 1), 20 and 40 mg/kg (groups 2, 3) received 1H-Pyrrolo[2,3-b]pyridine compound i.p QD for 3 days (M/W/F), 60 and 80 mg/kg (groups 4, 5) received 1H-Pyrrolo[2,3-b]pyridine compound p.o BID for 3 days (M/W/F) and 100 mg/kg group received 1H-Pyrrolo[2,3-b]pyridine compound+Taxol p.o BID for 3 days (M/W/F). BID (twice daily doses) of inhibitor or vehicle were administered by p.o 12 h apart and the treatment continued until the vehicle-treated animals showed significant tumor burden (for a total of 4 to 6 weeks) and terminate the study at the end of 4 or $6^{th}$ week and sacrifice animals (mice were sacrificed at 24, 48, and 72 h after the final i.p/p.o) and tumors were harvested for tumor growth inhibition percent and immunohistochemistry to see the effect of each animal in the group and all tumor nodules were collected, counted, and weighed at necropsy. In order to establish the optimal dose and frequency of dosing to effectively inhibit SIK2 (SEQ ID NO: 11) in-vivo, these dose-finding experimental samples from orthotopic murine models and using functional assay we at first investigated the SIK2 (SEQ ID NO: 11) expression profiling in control group mice and inhibition of phosphorylation of SIK2 by 1H-Pyrrolo[2,3-b]pyridine compound and Taxol. Additionally, we performed quantitative RT-PCR, Western blot, and immunocytology experiments to identify overexpression of SIK2 in control groups against treatment groups along with SIK2 inhibition of transcription factor CREB via phosphorylation of its cofactor TORC2/CRTC2 as a biological indicator of SIK2 kinase activity. Further characterized the effects of SIK2 kinase inhibition on tumor growth inhibition, examined the tumor nodule formation. 1H-Pyrrolo[2,3-b]pyridine compound, taxol had significant antitumor effects and compound as a single agent, with the ability not only to inhibit ovarian tumor growth, but also inhibits dissemination of tumor cells in vivo.

The Effect of 1H-Pyrrolo[2,3-b]Pyridine Compound on OVCAR-3 Induced Orthotopic Murine Model:

Dose-finding experiments initiated by injecting OVCAR-3 (OVCAR-3 cells were collected from cultures using either 0.1% EDTA (Life Technologies) on the cell line) tumor cells i.p. ($2.5 \times 10^5$) into athymic female mice. Similar study design protocols and analysis performed as described under SKOv3 orthotopic murine experiments.

Pharmacokinetics/ADME/Tox:

The objective of this study was to investigate the bioavailability and pharmacokinetics of a 1H-Pyrrolo[2,3-b]pyridine compound in male Sprague Dawley rats. A total of 6 male rats were used in the study. The study was performed using parallel design (n=3) with serial sampling, as summarized in the Table 5:

TABLE 5

| Route | Group # | No. of rats | Dose (mg/kg) | Dose volume (mL/kg) | Strength (mg/mL) |
|---|---|---|---|---|---|
| IV[a] | 1 | 3 | 5 | 2.5 | 2 |
| PO[b] | 2 | 3 | 20 | 10 | 2 |

[a]Ethyl alcohol (5% v/v), Polyethylene glycol-300 (50% v/v), Propylene glycol (20% v/v) and water for injection q.s.
[b]Ethyl alcohol (5% v/v), Polyethylene glycol-300 (50% v/v), Propylene glycol (20% v/v) and Milli-Q ® water q.s.
1H-Pyrrolo [2,3-b] pyridine compound is orally bioavailable with % F is >20, $T_{max}$ (h) is 6 and $T_{1/2}$ (h) is 5.

1H-Pyrrolo[2,3-b]pyridine compound had solubility at pH 3 is 380 µg/mL, in SGF/SIF its stability is over 120 min (half-life), P-gp substrate classification is negative. It has no hERG inhibition ($IC_{50}$>10 µM) and the P450 $IC_{50}$ for 1A2, 2C19, 2C9, 2D6>10 µM. 1H-Pyrrolo[2,3-b]pyridine compound hepatocytes clearance is 9.12 ($CL_{int}$ mL/min/g liver) and in microsomes is 8 ($CL_{int}$ mL/min/g liver).

Dose formulations were prepared on the day of doing. Blood samples were collected at 0.083 (only IV), 0.25, 0.5, 1, 2, 4, 8 and 24 h post-dose. At each time point, approximately 0.2 mL of blood was withdrawn from each cannulated rat through jugular vein and transferred to a pre-labeled microfuge tube containing 20 µL of 200 mM $K_2$EDTA permL of blood. Following collection of blood sample, equal volume of heparinized saline was flushed into jugular vein of rat. The blood samples were centrifuged at 5000 g for 5 minutes at 4±2° C. The plasma was separated within 30 min of scheduled time and stored below −60° C. until bioanalysis. The plasma samples were analyzed for 114 using a fit-for purpose liquid chromatographic tandem mass spectrometric detection (LC-MS/MS) method with a lower limit of quantification of 2.21 ng/mL. The pharmacokinetic parameters for compound 114 were calculated using the non-compartmental analysis tool of validated WinNonlin® software (Version 5.2).

TABLE 6

Table 6: Rat PK: The pharmacokinetic profiles of test compound 114 following intravenous bolus administration and oral gavage in male Sprague Dawley rats.

| Route (Dose) | $T_{max}$ (h) | $C_{max}$ (ng/mL) | $AUC_{last}$ (ng · h/mL) | $AUC_{inf}$ (ng · h/mL) | CL (mL/min/kg) | $V_{ss}$ (L/kg) | $T_{1/2}$ (h) | F [a] (%) |
|---|---|---|---|---|---|---|---|---|
| IV (5 mg/kg) | NA | 3849.91 [b] ± 710.44 | 2599.10 ± 636.93 | 2617.38 ± 647.47 | 33.42 ± 9.57 | 1.61 ± 0.28 | 0.54 ± 0.05 | — |
| PO (20 mg/kg) | 0.25 [c] (0.25-0.5) | 852.56 ± 83.61 | 1583.84 ± 179.45 | 1599.77 ± 182.86 | NA | NA | NA | 15 |

[a] $AUC_{inf}$ and nominal doses were used for bioavailability (% F) calculation;
[b] concentration at time zero;
[c] $T_{max}$ is represented as median (range)

Structural Homology Modeling—Salt Inducible Kinase 2 (SIK2)

The compounds of Formula I, IA and IB provided in Tables 1-3 were designed using a structural homology model of SIK2 and its mutant form of SIK2. The homology model of structural model of the kinase domain of SIK2 was constructed using Salt Inducible Kinase 2 (SIK2) domain region sequence (11-336) from the full length protein sequence NP_9056006 (FIG. 3).

Referring to FIG. 3, Structure based sequence alignment in Clustal W of the catalytic protein kinase domains of SIK1 (SNF1LK), SIK2 (SNF1LK, QIK), SIK3 (QSK), AMPK and MARK2. Amino acid residue annotation were identical residues (*), highly conserved residues (:), and similar residues (.) The active site residues highlighted in yellow and the gatekeeper residues in turquoise and the DFG residues shown in yellow.

Sequence search with in the RCSB provided the 2 homologues X-ray crystal structure templates with ~52% sequence identity and ~65% sequence similarities was considered as starting point for multiple sequence alignment using Clustal W alignment (FIG. 4) and homology modeling. The Swiss-Model was applied in sequence alignment, model building, loop prediction and refinement. With the application of FFDD™ (Fragment-Field Drug Design) workflow design strategy, the final models of SIK2 shown in FIG. 4 were utilized and served as template for designing claimed compounds. Based on the 3-D profile scoring the structural template chosen from PDB database and were both MARK2 and AMP-activated protein kianse (AMPK) crystal structures (PDB ID: 2ROI and 3AQV). Several models were built and refined to check the 3D profile and are shown in FIG. 4.

Referring to FIG. 4, the homology model of SIK2 in complex with one of the lead inhibitor is shown. The critical active site residues shown in color-by-atom in stick representations. The inhibitor binding site depicted in surface in complex with SIK2. Compound belongs to 1H-pyrrolo[2,3-b]pyridine structural class claimed.

REFERENCES

1. Ovarian Cancer National Alliance at http://www.ovariancancer.org/about-ovarian-cancer/statistics/.
2. Bast R. C Jr, Molecular approaches to personalizing management of ovarian cancer, Ann Oncol. 2011, 22 Suppl 8:viii5-viii15.
3. Bast R. C Jr., Hennessy B, Mills G B. The biology of ovarian cancer: new opportunities for translation. Nature Rev Cancer, 2009, 9, 415-428.
4. Banerjee, S, Kaye, S. B. New strategies in the treatment of ovarian cancer: current clinical perspectives and future potential. Clin Cancer Res. 2013 1, 19(5), 961-968.
5. Ahmed, A. A, Lu, Z, Jennings, N. B, Etemadmoghadam, D, Capalbo, L, Jacamo, R. O, Barbosa-Morais, N, Le, X F; Australian Ovarian Cancer Study Group, Vivas-Mejia, P, Lopez-Berestein, Grandjean, G, Bartholomeusz, G; Liao, W, Andreeff M, Bowtell, D, Glover, D. M, Sood, A. K, Bast, R. C Jr. SIK2 is a centrosome kinase required for bipolar mitotic spindle formation that provides a potential target for therapy in ovarian cancer. Cancer Cell. 2010, 9, 18(2), 109-121.
6. Kumagai, A, Horike, N, Satoh, Y, Uebi, T, Sasaki, T, Itoh, Y, Hirata, Y, Uchio-Yamada, K, Kitagawa, K, Uesato, S, Kawahara, H, Takemori, H, Nagaoka, Y. A potent inhibitor of SIK2, 3,3',7-trihydroxy-4'-methoxyflavon (4'-O-methylfisetin), promotes melanogenesis in B16F10 melanoma cells. PLoS One. 2011, 6(10), e26148.
7. Perez de Castro, I, de Carcer, G; Montoya, G, Malumbres, M. Emerging cancer therapeutic opportunities by inhibiting mitotic kinases. Curr. Opin. Pharmacol, 2008, 8, 375-383.
8. Nagel, S, Leich, E, Quentmeier, H, Meyer, C, Kaufmann, M, Zaborski, M, Rosenwald, A, Drexler, H. G; Macleod, R. A. Amplification at 11q23 targets protein kinase SIK2 in diffuse large B-cell lymphoma. Leuk Lymphoma. 2010, 51(5), 881-891.
9. Vankayalapati, H. Identification of Novel Inhibitors of SIK2 Kinase: A Novel Ser/Thr Kinase for Multiple Disease Indications presented at Emerging Targeted Oncology Partnering Forum, Feb. 19-20, 2012, San Francisco, Calif.
10. Jia, L, Zhang S, Ye, Y, Li, X, Mercado-Uribe, I, Bast, R. C Jr, Liu, J. Paclitaxel inhibits ovarian tumor growth by inducing epithelial cancer cells to benign fibroblast-like cells. Cancer Lett. 2012, 30, 326(2), 176-182.
11. Horike, N, Kumagai, A, Shimono, Y, Onishi, T, Itoh, Y, Sasaki, T, Kitagawa, K, Hatano, O, Takagi, H, Susumu, T, Teraoka, H, Kusano, K, Nagaoka, Y, Kawahara, H, Takemori, H. Downregulation of SIK2 expression promotes the melanogenic program in mice. Pigment Cell Melanoma Res. 2010, 23(6), 809-819.
12. Clark, K, Mackenzie, K. F, Petkevicius, K, Kristariyanto, Y, Zhang, J, Choi, H. G, Peggie, M, Plater, L, Pedrioli, P. G, McIver, E, Gray, N. S, Arthur, J. S, Cohen, P. Phosphorylation of CRTC3 by the salt-inducible kinases controls the interconversion of classically activated and regulatory macrophages. Proc Natl Acad Sci USA. 2012 16, 109(42)16986-16991.
13. Henriksson, E, Jones, H. A, Patel, K, Peggie, M, Morrice, N, Sakamoto, K, Göransson, O. The AMPK-related kinase SIK2 is regulated by cAMP via phosphorylation at Ser358 in adipocytes. Biochem J. 2012, 15, 444(3), 503-514. Pmid: 22462548.
14. Sasaki, T, Takemori H, Yagita, Y, Terasaki, Y, Uebi, T, Horike, N, Takagi, H, Susumu, T, Teraoka, H, Kusano, K, Hatano, O, Oyama, N, Sugiyama, Y, Sakoda, S, Kitagawa, K. SIK2 is a key regulator for neuronal survival after ischemia via TORC1-CREB. Neuron. 2011, 13, 69(1), 106-109.
15. Liu, Y, Poon, V, Sanchez-Watts, G, Watts, A. G, Takemori. H, Aguilera, G Salt-inducible kinase is involved in the regulation of corticotropin-releasing hormone transcription in hypothalamic neurons in rats. Endocrinology. 2012, 153(1), 223-233.
16. Gallo, E. F, Ladecola, C. Balancing life and death in the ischemic brain: SIK and TORC weigh IN. Neuron. 2011, 13, 69(1), 3-6.
17. Muraoka, M, Fukushima, A, Viengchareun, S, Lombès, M, Kishi, F, Miyauchi, A, Kanematsu, M, Doi, J, Kajimura, J, Nakai, R, Uebi, T, Okamoto, M, Takemori, H. Involvement of SIK2/TORC2 signaling cascade in the regulation of insulin-induced PGC-1 alpha and UCP-1 gene expression in brown adipocytes. Am J Physiol Endocrinol Metab. 2009, 296(6), E1430-439.
18. Du, J, Chen, Q, Takemori, H, Xu, H. SIK2 can be activated by deprivation of nutrition and it inhibits expression of lipogenic genes in adipocytes. Obesity (Silver Spring). 2008, 6(3), 531-538.
19. Hashimoto, Y. K, Satoh, T, Okamoto, M, Takemori, H. Importance of autophosphorylation at Ser186 in the A-loop of salt inducible kinase 1 for its sustained kinase activity. *J Cell Biochem.* 2008, 1, 104(5), 1724-3179.
20. Ryu, D, Oh, K. J, Jo, H. Y, Hedrick, S, Kim, Y. N, Hwang, Y. J, Park, T. S, Han, J. S, Choi, C. S, Montminy, M, Koo, S. H. TORC2 regulates hepatic insulin signaling via a mammalian phosphatidic acid phosphatase, LIPIN1. *Cell Metab.* 2009, 9(3), 240-251.
21. Charoenfuprasert, S, Yang, Y. Y, Lee, Y. C, Chao, K. C, Chu, P. Y, Lai, C. R, Hsu, K. F, Chang, K. C, Chen, Y. C, Chen, L. T, Chang, J. Y, Leu, S. J, Shih, N. Y. Identification of salt-inducible kinase 3 as a novel tumor antigen associated with tumorigenesis of ovarian cancer. *Oncogene.* 2011, 18, 30(33), 3570-3584.
22. Kitagawa, K, Sasaki, T, Terasaki, Y, Yagita, Y, Mochizuki, H. CREB activation is a key player for ischemic tolerance in the brain. *Rinsho Shinkeigaku.* 2012, 52(11), 904-907.
23. Imielinski, M, Berger, A. H, Hammerman, P. S, Hernandez, B, Pugh, T. J, Hodis, E, Cho, J, Suh, J, Capelletti, M, Sivachenko, A, Sougnez, C, Auclair, D, Lawrence, M. S, Stojanov, P, Cibulskis, K, Choi, K, de Waal, L, Sharifnia, T, Brooks, A, Greulich, H, Banerji, S, Zander, T, Seidel, D, Leenders, F, Ansén, S, Ludwig, C, Engel-Riedel, W, Stoelben E, Wolf J, Goparju C, Thompson K, Winckler W, Kwiatkowski D, Johnson, B. E, Jänne, P. A, Miller, V. A, Pao, W, Travis, W. D, Pass, H. I, Gabriel, S. B, Lander, E. S, Thomas, R. K, Garraway, L. A, Getz, G, Meyerson, M. Mapping the hallmarks of lung adenocarcinoma with massively parallel sequencing. *Cell.* 2012, 4, 150(6), 1107-1120.
24. Copps, K. D, White, M. F. Regulation of insulin sensitivity by serine/threonine phosphorylation of insulin receptor substrate proteins IRS1 and IRS2. *Diabetologia.* 2012, 55(10), 2565-2582.
25. Wang, Y, Li, G, Goode, J, Paz, J. C, Ouyang, K, Screaton, R, Fischer, W. H, Chen, J, Tabas, I, Montminy, M. Inositol-1,4,5-trisphosphate receptor regulates hepatic gluconeogenesis in fasting and diabetes. *Nature.* 2012, 8; 485(7396), 128-132.
26. Bricambert, J, Miranda, J, Benhamed, F, Girard, J, Postic, C, Dentin, R. Salt-inducible kinase 2 links transcriptional coactivator p300 phosphorylation to the prevention of ChREBP-dependent hepatic steatosis in mice. *J Clin Invest.* 2010, 120(12), 4316-4331.
27. Salisbury, J. L. A centrosome kinase modulates antitumor drug sensitivity. *Cancer Cell.* 2010, 9, 18(2), 99-100.
28. Wang, B, Goode, J, Best, J, Meltzer, J, Schilman, P. E, Chen, J, Garza, D, Thomas, J. B, Montminy, M. The insulin-regulated CREB coactivator TORC promotes stress resistance in *Drosophila*. *Cell Metab.* 2008, 7(5), 434-44.
29. Katoh, Y, Takemori, H, Horike, N, Doi, J, Muraoka, M, Min, L, Okamoto, M. Salt-inducible kinase (SIK) isoforms: their involvement in steroidogenesis and adipogenesis. *Mol Cell Endocrinol.* 2004, 31; 217(1-2), 109-112.

What is claimed is:

1. A compound of Formula IB:

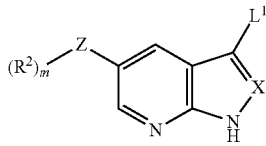

(IB)

or a pharmaceutically acceptable salt thereof, wherein:

X is CH;

L¹ is phenyl optionally substituted with 1-3 substituents, each substituent independently selected from halo, $C_{1-4}$alkyl, $C_{1-4}$alkoxy, trifluoromethyl, trifluoromethoxy, piperazinyl, methylpiperazinyl,

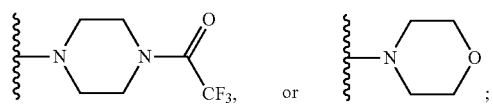

Z is a direct bond, thiazolyl,

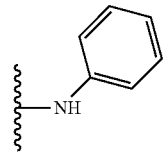 [SMILES: *Nc1ccccc1]

wherein the phenyl group is optionally halo substituted,

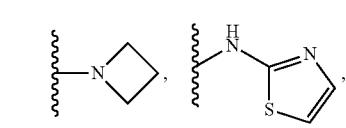

piperazinyl, or pyrazolyl;

R² is each independently H, halo, —CN, $C_{1-4}$alkyl, $C_{1-4}$alkoxy,

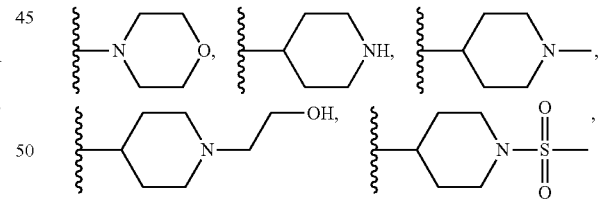

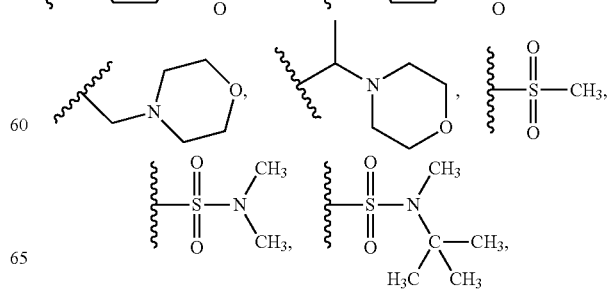

-continued
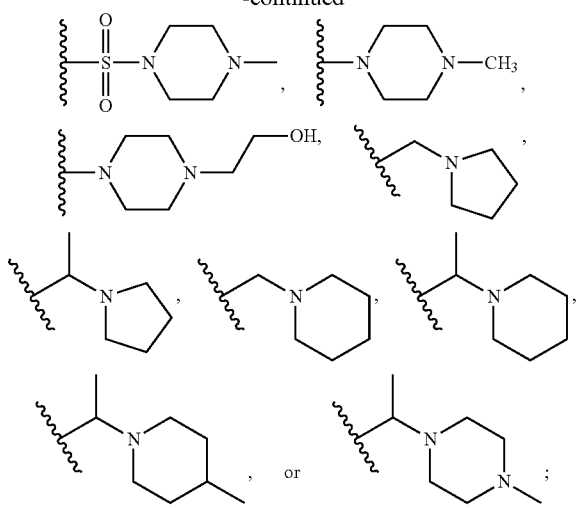
and
m is 1 or 2.
2. A compound selected from
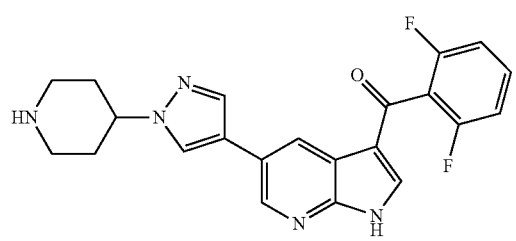
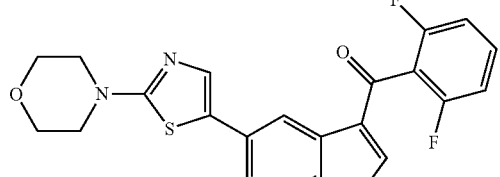
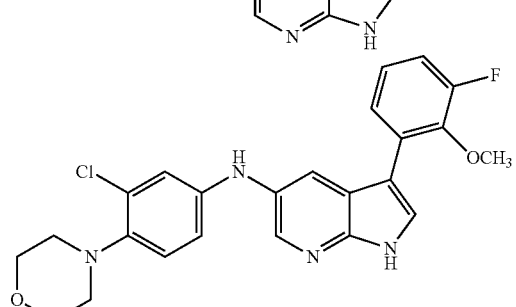
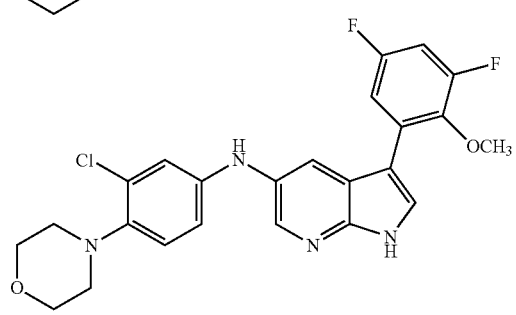
-continued
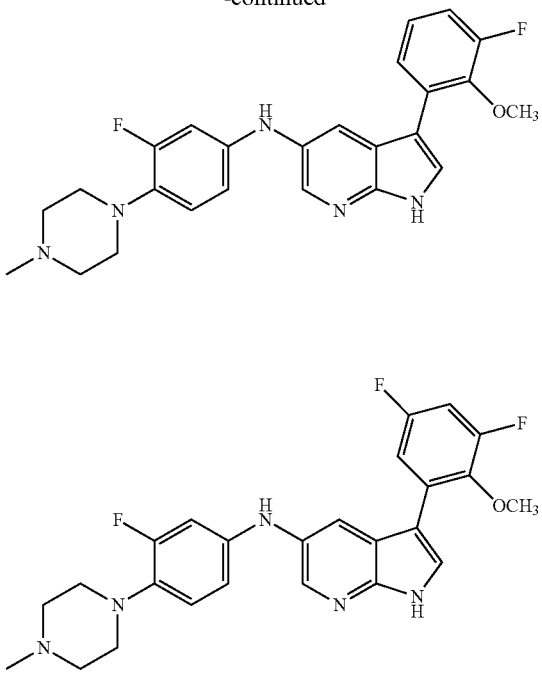
or a pharmaceutically acceptable salt thereof.
3. A method of inhibiting Salt Inducible Kinase (SIK) activity in a mammal comprising administering to said mammal an effective amount of a compound according to claim 1.
4. The method of claim 3 wherein the compound is selected from
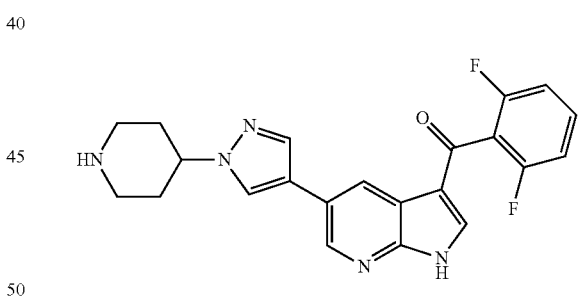
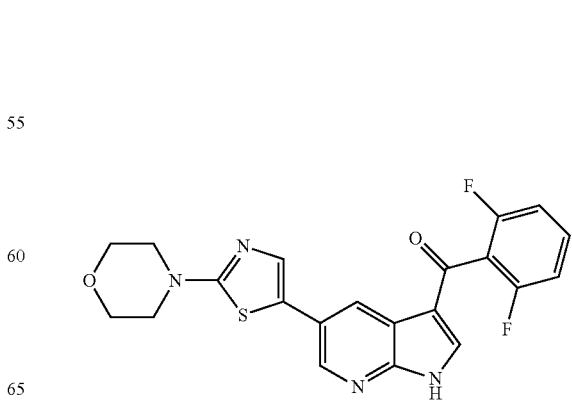

505
-continued
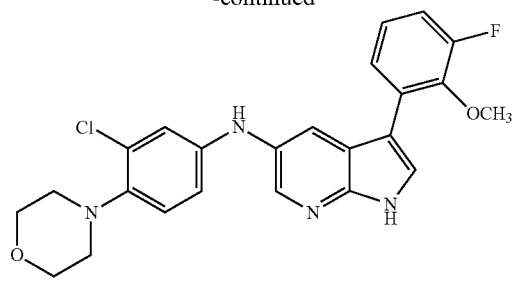
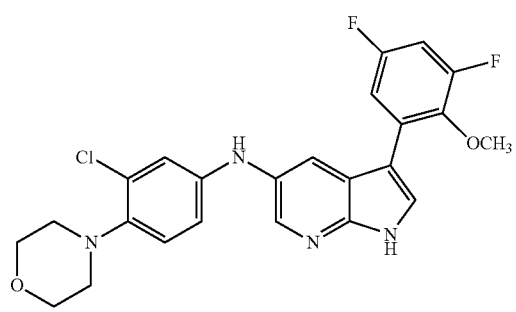
506
-continued
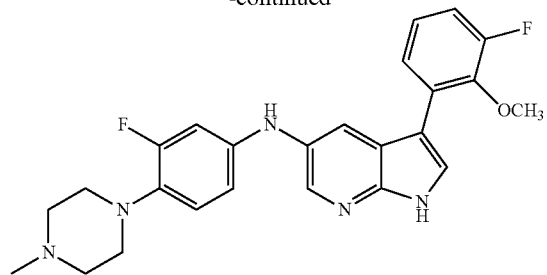
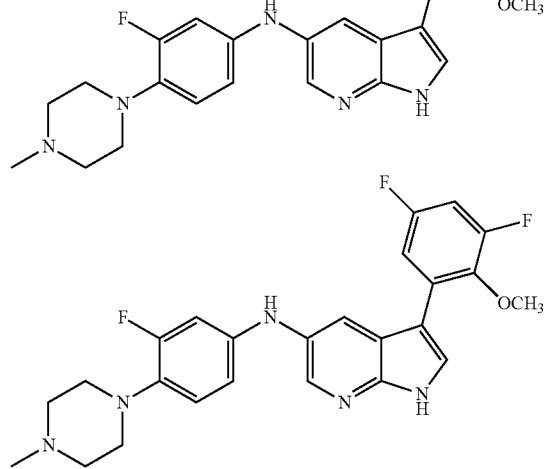
or a pharmaceutically acceptable salt thereof.
* * * * *

SEQUENCE LISTING

<160> NUMBER OF SEQ ID NOS: 28

<210> SEQ ID NO 1
<211> LENGTH: 484
<212> TYPE: PRT
<213> ORGANISM: HUMAN
<300> PUBLICATION INFORMATION:
<301> AUTHORS: Colwill,K., Pawson,T., Andrews,B., Prasad,J.,
    Manley,J.L.,
<302> TITLE: The Clk/Sty protein kinase phosphorylates SR splicing
    factors and
<303> JOURNAL: EMBO J.
<304> VOLUME: 15
<305> ISSUE: 2
<306> PAGES: 265-275
<307> DATE: 1996-01-15
<308> DATABASE ACCESSION NUMBER: NP_004062
<309> DATABASE ENTRY DATE: 2012-04-29
<313> RELEVANT RESIDUES IN SEQ ID NO: (1)..(484)

<400> SEQUENCE: 1

Met Arg His Ser Lys Arg Thr Tyr Cys Pro Asp Trp Asp Asp Lys Asp
1               5                   10                  15

Trp Asp Tyr Gly Lys Trp Arg Ser Ser Ser His Lys Arg Arg Lys
            20                  25                  30

Arg Ser His Ser Ser Ala Gln Glu Asn Lys Arg Cys Lys Tyr Asn His
        35                  40                  45

Ser Lys Met Cys Asp Ser His Tyr Leu Glu Ser Arg Ser Ile Asn Glu
    50                  55                  60

Lys Asp Tyr His Ser Arg Arg Tyr Ile Asp Glu Tyr Arg Asn Asp Tyr
65                  70                  75                  80

Thr Gln Gly Cys Glu Pro Gly His Arg Gln Arg Asp His Glu Ser Arg
                85                  90                  95

Tyr Gln Asn His Ser Ser Lys Ser Ser Gly Arg Ser Gly Arg Ser Ser
            100                 105                 110

Tyr Lys Ser Lys His Arg Ile His His Ser Thr Ser His Arg Arg Ser
            115                 120                 125

His Gly Lys Ser His Arg Arg Lys Arg Thr Arg Ser Val Glu Asp Asp
            130                 135                 140

Glu Glu Gly His Leu Ile Cys Gln Ser Gly Asp Val Leu Ser Ala Arg
145                 150                 155                 160

Tyr Glu Ile Val Asp Thr Leu Gly Glu Gly Ala Phe Gly Lys Val Val
                165                 170                 175

Glu Cys Ile Asp His Lys Ala Gly Gly Arg His Val Ala Val Lys Ile
                180                 185                 190

Val Lys Asn Val Asp Arg Tyr Cys Glu Ala Ala Arg Ser Glu Ile Gln
            195                 200                 205

Val Leu Glu His Leu Asn Thr Thr Asp Pro Asn Ser Thr Phe Arg Cys
            210                 215                 220

Val Gln Met Leu Glu Trp Phe Glu His His Gly His Ile Cys Ile Val
225                 230                 235                 240

Phe Glu Leu Leu Gly Leu Ser Thr Tyr Asp Phe Ile Lys Glu Asn Gly
                245                 250                 255

Phe Leu Pro Phe Arg Leu Asp His Ile Arg Lys Met Ala Tyr Gln Ile
                260                 265                 270

Cys Lys Ser Val Asn Phe Leu His Ser Asn Lys Leu Thr His Thr Asp
            275                 280                 285

Leu Lys Pro Glu Asn Ile Leu Phe Val Gln Ser Asp Tyr Thr Glu Ala
            290                 295                 300

Tyr Asn Pro Lys Ile Lys Arg Asp Glu Arg Thr Leu Ile Asn Pro Asp
305                 310                 315                 320

Ile Lys Val Val Asp Phe Gly Ser Ala Thr Tyr Asp Asp Glu His His
                325                 330                 335

Ser Thr Leu Val Ser Thr Arg His Tyr Arg Ala Pro Glu Val Ile Leu
                340                 345                 350

Ala Leu Gly Trp Ser Gln Pro Cys Asp Val Trp Ser Ile Gly Cys Ile
            355                 360                 365

Leu Ile Glu Tyr Tyr Leu Gly Phe Thr Val Phe Pro Thr His Asp Ser
            370                 375                 380

Lys Glu His Leu Ala Met Met Glu Arg Ile Leu Gly Pro Leu Pro Lys
385                 390                 395                 400

His Met Ile Gln Lys Thr Arg Lys Arg Lys Tyr Phe His His Asp Arg
                405                 410                 415

Leu Asp Trp Asp Glu His Ser Ser Ala Gly Arg Tyr Val Ser Arg Arg
                420                 425                 430

Cys Lys Pro Leu Lys Glu Phe Met Leu Ser Gln Asp Val Glu His Glu
            435                 440                 445

Arg Leu Phe Asp Leu Ile Gln Lys Met Leu Glu Tyr Asp Pro Ala Lys
            450                 455                 460

Arg Ile Thr Leu Arg Glu Ala Leu Lys His Pro Phe Phe Asp Leu Leu
465                 470                 475                 480

Lys Lys Ser Ile

<210> SEQ ID NO 2
<211> LENGTH: 498
<212> TYPE: PRT
<213> ORGANISM: HUMAN
<300> PUBLICATION INFORMATION:
<301> AUTHORS: Nam,S.Y., Seo,H.H., Park,H.S., An,S., Kim,J.Y.,

```
        Yang,K.H.,
<302>   TITLE: Phosphorylation of CLK2 at serine 34 and threonine 127 by
        AKT
<303>   JOURNAL: 31157-31163
<304>   VOLUME: 285
<305>   ISSUE: 41
<306>   PAGES: 31157-31163
<307>   DATE: 2010-08-01
<308>   DATABASE ACCESSION NUMBER: NP_003984
<309>   DATABASE ENTRY DATE: 2012-04-21
<313>   RELEVANT RESIDUES IN SEQ ID NO: (1)..(498)

<400>   SEQUENCE: 2

Met Pro His Pro Arg Arg Tyr His Ser Ser Glu Arg Gly Ser Arg Gly
1               5                   10                  15

Ser Tyr Arg Glu His Tyr Arg Ser Arg Lys His Lys Arg Arg Arg Ser
            20                  25                  30

Arg Ser Trp Ser Ser Ser Asp Arg Thr Arg Arg Arg Arg Arg Arg Glu
        35                  40                  45

Asp Ser Tyr His Val Arg Ser Arg Ser Tyr Asp Asp Arg Ser Ser
    50                  55                  60

Asp Arg Arg Val Tyr Asp Arg Arg Tyr Cys Gly Ser Tyr Arg Arg Asn
65                  70                  75                  80

Asp Tyr Ser Arg Asp Arg Gly Asp Ala Tyr Tyr Asp Thr Asp Tyr Arg
            85                  90                  95

His Ser Tyr Glu Tyr Gln Arg Glu Asn Ser Ser Tyr Arg Ser Gln Arg
            100                 105                 110

Ser Ser Arg Arg Lys His Arg Arg Arg Arg Ser Arg Thr Phe
            115                 120                 125

Ser Arg Ser Ser Ser His Ser Ser Arg Arg Ala Lys Ser Val Glu Asp
    130                 135                 140

Asp Ala Glu Gly His Leu Ile Tyr His Val Gly Asp Trp Leu Gln Glu
145                 150                 155                 160

Arg Tyr Glu Ile Val Ser Thr Leu Gly Glu Gly Thr Phe Gly Arg Val
            165                 170                 175

Val Gln Cys Val Asp His Arg Arg Gly Gly Ala Arg Val Ala Leu Lys
            180                 185                 190

Ile Ile Lys Asn Val Glu Lys Tyr Lys Glu Ala Ala Arg Leu Glu Ile
            195                 200                 205

Asn Val Leu Glu Lys Ile Asn Glu Lys Asp Pro Asp Asn Lys Asn Leu
    210                 215                 220

Cys Val Gln Met Phe Asp Trp Phe Asp Tyr His Gly His Met Cys Ile
225                 230                 235                 240

Ser Phe Glu Leu Leu Gly Leu Ser Thr Phe Asp Phe Leu Lys Asp Asn
            245                 250                 255

Asn Tyr Leu Pro Tyr Pro Ile His Gln Val Arg His Met Ala Phe Gln
            260                 265                 270

Leu Cys Gln Ala Val Lys Phe Leu His Asp Asn Lys Leu Thr His Thr
            275                 280                 285

Asp Leu Lys Pro Glu Asn Ile Leu Phe Val Asn Ser Asp Tyr Glu Leu
    290                 295                 300

Thr Tyr Asn Leu Glu Lys Lys Arg Asp Glu Arg Ser Val Lys Ser Thr
305                 310                 315                 320

Ala Val Arg Val Val Asp Phe Gly Ser Ala Thr Phe Asp His Glu His
            325                 330                 335

His Ser Thr Ile Val Ser Thr Arg His Tyr Arg Ala Pro Glu Val Ile
            340                 345                 350
```

```
Leu Glu Leu Gly Trp Ser Gln Pro Cys Asp Val Trp Ser Ile Gly Cys
        355                 360                 365

Ile Ile Phe Glu Tyr Tyr Val Gly Phe Thr Leu Phe Gln Thr His Asp
        370                 375                 380

Asn Arg Glu His Leu Ala Met Met Glu Arg Ile Leu Gly Pro Ile Pro
385                 390                 395                 400

Ser Arg Met Ile Arg Lys Thr Arg Lys Gln Lys Tyr Phe Tyr Arg Gly
                405                 410                 415

Arg Leu Asp Trp Asp Glu Asn Thr Ser Ala Gly Arg Tyr Val Arg Glu
                420                 425                 430

Asn Cys Lys Pro Leu Arg Arg Tyr Leu Thr Ser Glu Ala Glu Glu His
                435                 440                 445

His Gln Leu Phe Asp Leu Ile Glu Ser Met Leu Glu Tyr Glu Pro Ala
        450                 455                 460

Lys Arg Leu Thr Leu Gly Glu Ala Leu Gln His Pro Phe Phe Ala Arg
465                 470                 475                 480

Leu Arg Ala Glu Pro Pro Asn Lys Leu Trp Asp Ser Ser Arg Asp Ile
                485                 490                 495

Ser Arg

<210> SEQ ID NO 3
<211> LENGTH: 763
<212> TYPE: PRT
<213> ORGANISM: HUMAN
<300> PUBLICATION INFORMATION:
<301> AUTHORS: Malinge,S., Bliss-Moreau,M., Kirsammer,G., Diebold,L.,
      Chlon,T.,
<302> TITLE: Increased dosage of the chromosome 21 ortholog Dyrk1a
      promotes
<303> JOURNAL: J. Clin. Invest.
<304> VOLUME: 122
<305> ISSUE: 3
<306> PAGES: 958-962
<307> DATE: 2012-03-01
<308> DATABASE ACCESSION NUMBER: NP_001387
<309> DATABASE ENTRY DATE: 2012-05-06
<313> RELEVANT RESIDUES IN SEQ ID NO: (1)..(763)

<400> SEQUENCE: 3

Met His Thr Gly Gly Glu Thr Ser Ala Cys Lys Pro Ser Ser Val Arg
1               5                   10                  15

Leu Ala Pro Ser Phe Ser Phe His Ala Ala Gly Leu Gln Met Ala Gly
            20                  25                  30

Gln Met Pro His Ser His Gln Tyr Ser Asp Arg Arg Gln Pro Asn Ile
        35                  40                  45

Ser Asp Gln Gln Val Ser Ala Leu Ser Tyr Ser Asp Gln Ile Gln Gln
    50                  55                  60

Pro Leu Thr Asn Gln Val Met Pro Asp Ile Val Met Leu Gln Arg Arg
65                  70                  75                  80

Met Pro Gln Thr Phe Arg Asp Pro Ala Thr Ala Pro Leu Arg Lys Leu
                85                  90                  95

Ser Val Asp Leu Ile Lys Thr Tyr Lys His Ile Asn Glu Val Tyr Tyr
            100                 105                 110

Ala Lys Lys Lys Arg Arg His Gln Gln Gly Gln Gly Asp Asp Ser Ser
        115                 120                 125

His Lys Lys Glu Arg Lys Val Tyr Asn Asp Gly Tyr Asp Asp Asp Asn
    130                 135                 140

Tyr Asp Tyr Ile Val Lys Asn Gly Glu Lys Trp Met Asp Arg Tyr Glu
```

-continued

```
                145                 150                 155                 160
Ile Asp Ser Leu Ile Gly Lys Gly Ser Phe Gly Gln Val Val Lys Ala
                    165                 170                 175
Tyr Asp Arg Val Glu Gln Glu Trp Val Ala Ile Lys Ile Ile Lys Asn
                180                 185                 190
Lys Lys Ala Phe Leu Asn Gln Ala Gln Ile Glu Val Arg Leu Leu Glu
            195                 200                 205
Leu Met Asn Lys His Asp Thr Glu Met Lys Tyr Tyr Ile Val His Leu
210                 215                 220
Lys Arg His Phe Met Phe Arg Asn His Leu Cys Leu Val Phe Glu Met
225                 230                 235                 240
Leu Ser Tyr Asn Leu Tyr Asp Leu Leu Arg Asn Thr Asn Phe Arg Gly
                245                 250                 255
Val Ser Leu Asn Leu Thr Arg Lys Phe Ala Gln Gln Met Cys Thr Ala
                260                 265                 270
Leu Leu Phe Leu Ala Thr Pro Glu Leu Ser Ile Ile His Cys Asp Leu
            275                 280                 285
Lys Pro Glu Asn Ile Leu Leu Cys Asn Pro Lys Arg Ser Ala Ile Lys
        290                 295                 300
Ile Val Asp Phe Gly Ser Ser Cys Gln Leu Gly Gln Arg Ile Tyr Gln
305                 310                 315                 320
Tyr Ile Gln Ser Arg Phe Tyr Arg Ser Pro Glu Val Leu Leu Gly Met
                325                 330                 335
Pro Tyr Asp Leu Ala Ile Asp Met Trp Ser Leu Gly Cys Ile Leu Val
                340                 345                 350
Glu Met His Thr Gly Glu Pro Leu Phe Ser Gly Ala Asn Glu Val Asp
            355                 360                 365
Gln Met Asn Lys Ile Val Glu Val Leu Gly Ile Pro Pro Ala His Ile
        370                 375                 380
Leu Asp Gln Ala Pro Lys Ala Arg Lys Phe Phe Glu Lys Leu Pro Asp
385                 390                 395                 400
Gly Thr Trp Asn Leu Lys Lys Thr Lys Asp Gly Lys Arg Glu Tyr Lys
                405                 410                 415
Pro Pro Gly Thr Arg Lys Leu His Asn Ile Leu Gly Val Glu Thr Gly
                420                 425                 430
Gly Pro Gly Gly Arg Arg Ala Gly Glu Ser Gly His Thr Val Ala Asp
            435                 440                 445
Tyr Leu Lys Phe Lys Asp Leu Ile Leu Arg Met Leu Asp Tyr Asp Pro
        450                 455                 460
Lys Thr Arg Ile Gln Pro Tyr Tyr Ala Leu Gln His Ser Phe Phe Lys
465                 470                 475                 480
Lys Thr Ala Asp Glu Gly Thr Asn Thr Ser Asn Ser Val Ser Thr Ser
                485                 490                 495
Pro Ala Met Glu Gln Ser Gln Ser Ser Gly Thr Thr Ser Ser Thr Ser
                500                 505                 510
Ser Ser Ser Gly Gly Ser Ser Gly Thr Ser Asn Ser Gly Arg Ala Arg
            515                 520                 525
Ser Asp Pro Thr His Gln His Arg His Ser Gly Gly His Phe Thr Ala
        530                 535                 540
Ala Val Gln Ala Met Asp Cys Glu Thr His Ser Pro Gln Val Arg Gln
545                 550                 555                 560
Gln Phe Pro Ala Pro Leu Gly Trp Ser Gly Thr Glu Ala Pro Thr Gln
                565                 570                 575
```

-continued

```
Val Thr Val Glu Thr His Pro Val Gln Glu Thr Thr Phe His Val Ala
            580                 585                 590

Pro Gln Gln Asn Ala Leu His His His Gly Asn Ser Ser His His
        595                 600                 605

His His His His His His His His His Gly Gln Gln Ala Leu
    610                 615                 620

Gly Asn Arg Thr Arg Pro Arg Val Tyr Asn Ser Pro Thr Asn Ser Ser
625                 630                 635                 640

Ser Thr Gln Asp Ser Met Glu Val Gly His Ser His His Ser Met Thr
                645                 650                 655

Ser Leu Ser Ser Ser Thr Thr Ser Ser Thr Ser Ser Ser Ser Thr
            660                 665                 670

Gly Asn Gln Gly Asn Gln Ala Tyr Gln Asn Arg Pro Val Ala Ala Asn
675                 680                 685

Thr Leu Asp Phe Gly Gln Asn Gly Ala Met Asp Val Asn Leu Thr Val
            690                 695                 700

Tyr Ser Asn Pro Arg Gln Glu Thr Gly Ile Ala Gly His Pro Thr Tyr
705                 710                 715                 720

Gln Phe Ser Ala Asn Thr Gly Pro Ala His Tyr Met Thr Glu Gly His
                725                 730                 735

Leu Thr Met Arg Gln Gly Ala Asp Arg Glu Glu Ser Pro Met Thr Gly
            740                 745                 750

Val Cys Val Gln Gln Ser Pro Val Ala Ser Ser
            755                 760

<210> SEQ ID NO 4
<211> LENGTH: 1154
<212> TYPE: PRT
<213> ORGANISM: HUMAN
<300> PUBLICATION INFORMATION:
<301> AUTHORS: Simoncic,P.D., Lee-Loy,A., Barber,D.L., Tremblay,M.L. and
<302> TITLE: The T cell protein tyrosine phosphatase is a negative
      regulator of
<303> JOURNAL: Curr. Biol.
<304> VOLUME: 12
<305> ISSUE: 6
<306> PAGES: 446-453
<307> DATE: 2002-03-19
<308> DATABASE ACCESSION NUMBER: NP_002218
<309> DATABASE ENTRY DATE: 2012-05-13
<313> RELEVANT RESIDUES IN SEQ ID NO: (1)..(1154)

<400> SEQUENCE: 4

Met Gln Tyr Leu Asn Ile Lys Glu Asp Cys Asn Ala Met Ala Phe Cys
1               5                   10                  15

Ala Lys Met Arg Ser Ser Lys Lys Thr Glu Val Asn Leu Glu Ala Pro
            20                  25                  30

Glu Pro Gly Val Glu Val Ile Phe Tyr Leu Ser Asp Arg Glu Pro Leu
        35                  40                  45

Arg Leu Gly Ser Gly Glu Tyr Thr Ala Glu Glu Leu Cys Ile Arg Ala
    50                  55                  60

Ala Gln Ala Cys Arg Ile Ser Pro Leu Cys His Asn Leu Phe Ala Leu
65                  70                  75                  80

Tyr Asp Glu Asn Thr Lys Leu Trp Tyr Ala Pro Asn Arg Thr Ile Thr
                85                  90                  95

Val Asp Asp Lys Met Ser Leu Arg Leu His Tyr Arg Met Arg Phe Tyr
            100                 105                 110

Phe Thr Asn Trp His Gly Thr Asn Asp Asn Glu Gln Ser Val Trp Arg
```

```
            115                 120                 125
His Ser Pro Lys Lys Gln Lys Asn Gly Tyr Glu Lys Lys Ile Pro
    130                 135                 140

Asp Ala Thr Pro Leu Leu Asp Ala Ser Ser Leu Glu Tyr Leu Phe Ala
145                 150                 155                 160

Gln Gly Gln Tyr Asp Leu Val Lys Cys Leu Ala Pro Ile Arg Asp Pro
                165                 170                 175

Lys Thr Glu Gln Asp Gly His Asp Ile Glu Asn Glu Cys Leu Gly Met
            180                 185                 190

Ala Val Leu Ala Ile Ser His Tyr Ala Met Met Lys Lys Met Gln Leu
        195                 200                 205

Pro Glu Leu Pro Lys Asp Ile Ser Tyr Lys Arg Tyr Ile Pro Glu Thr
    210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
            260                 265                 270

Thr Leu Glu Thr Leu Thr Lys His Tyr Gly Ala Glu Ile Phe Glu Thr
        275                 280                 285

Ser Met Leu Leu Ile Ser Ser Glu Asn Glu Met Asn Trp Phe His Ser
    290                 295                 300

Asn Asp Gly Gly Asn Val Leu Tyr Tyr Glu Val Met Val Thr Gly Asn
305                 310                 315                 320

Leu Gly Ile Gln Trp Arg His Lys Pro Asn Val Val Ser Val Glu Lys
                325                 330                 335

Glu Lys Asn Lys Leu Lys Arg Lys Lys Leu Glu Asn Lys His Lys Lys
            340                 345                 350

Asp Glu Glu Lys Asn Lys Ile Arg Glu Glu Trp Asn Asn Phe Ser Tyr
        355                 360                 365

Phe Pro Glu Ile Thr His Ile Val Ile Lys Glu Ser Val Val Ser Ile
    370                 375                 380

Asn Lys Gln Asp Asn Lys Lys Met Glu Leu Lys Leu Ser Ser His Glu
385                 390                 395                 400

Glu Ala Leu Ser Phe Val Ser Leu Val Asp Gly Tyr Phe Arg Leu Thr
                405                 410                 415

Ala Asp Ala His His Tyr Leu Cys Thr Asp Val Ala Pro Pro Leu Ile
            420                 425                 430

Val His Asn Ile Gln Asn Gly Cys His Gly Pro Ile Cys Thr Glu Tyr
        435                 440                 445

Ala Ile Asn Lys Leu Arg Gln Glu Gly Ser Glu Gly Met Tyr Val
    450                 455                 460

Leu Arg Trp Ser Cys Thr Asp Phe Asp Asn Ile Leu Met Thr Val Thr
465                 470                 475                 480

Cys Phe Glu Lys Ser Glu Gln Val Gln Gly Ala Gln Lys Gln Phe Lys
                485                 490                 495

Asn Phe Gln Ile Glu Val Gln Lys Gly Arg Tyr Ser Leu His Gly Ser
            500                 505                 510

Asp Arg Ser Phe Pro Ser Leu Gly Asp Leu Met Ser His Leu Lys Lys
        515                 520                 525

Gln Ile Leu Arg Thr Asp Asn Ile Ser Phe Met Leu Lys Arg Cys Cys
    530                 535                 540
```

-continued

```
Gln Pro Lys Pro Arg Glu Ile Ser Asn Leu Leu Val Ala Thr Lys Lys
545                 550                 555                 560

Ala Gln Glu Trp Gln Pro Val Tyr Pro Met Ser Gln Leu Ser Phe Asp
            565                 570                 575

Arg Ile Leu Lys Lys Asp Leu Val Gln Gly Glu His Leu Gly Arg Gly
        580                 585                 590

Thr Arg Thr His Ile Tyr Ser Gly Thr Leu Met Asp Tyr Lys Asp Asp
    595                 600                 605

Glu Gly Thr Ser Glu Glu Lys Lys Ile Lys Val Ile Leu Lys Val Leu
610                 615                 620

Asp Pro Ser His Arg Asp Ile Ser Leu Ala Phe Glu Ala Ala Ser
625                 630                 635                 640

Met Met Arg Gln Val Ser His Lys His Ile Val Tyr Leu Tyr Gly Val
                645                 650                 655

Cys Val Arg Asp Val Glu Asn Ile Met Val Glu Glu Phe Val Glu Gly
            660                 665                 670

Gly Pro Leu Asp Leu Phe Met His Arg Lys Ser Asp Val Leu Thr Thr
        675                 680                 685

Pro Trp Lys Phe Lys Val Ala Lys Gln Leu Ala Ser Ala Leu Ser Tyr
    690                 695                 700

Leu Glu Asp Lys Asp Leu Val His Gly Asn Val Cys Thr Lys Asn Leu
705                 710                 715                 720

Leu Leu Ala Arg Glu Gly Ile Asp Ser Glu Cys Gly Pro Phe Ile Lys
                725                 730                 735

Leu Ser Asp Pro Gly Ile Pro Ile Thr Val Leu Ser Arg Gln Glu Cys
            740                 745                 750

Ile Glu Arg Ile Pro Trp Ile Ala Pro Glu Cys Val Glu Asp Ser Lys
        755                 760                 765

Asn Leu Ser Val Ala Ala Asp Lys Trp Ser Phe Gly Thr Thr Leu Trp
770                 775                 780

Glu Ile Cys Tyr Asn Gly Glu Ile Pro Leu Lys Asp Lys Thr Leu Ile
785                 790                 795                 800

Glu Lys Glu Arg Phe Tyr Glu Ser Arg Cys Arg Pro Val Thr Pro Ser
                805                 810                 815

Cys Lys Glu Leu Ala Asp Leu Met Thr Arg Cys Met Asn Tyr Asp Pro
            820                 825                 830

Asn Gln Arg Pro Phe Phe Arg Ala Ile Met Arg Asp Ile Asn Lys Leu
        835                 840                 845

Glu Glu Gln Asn Pro Asp Ile Val Ser Glu Lys Lys Pro Ala Thr Glu
850                 855                 860

Val Asp Pro Thr His Phe Glu Lys Arg Phe Leu Lys Arg Ile Arg Asp
865                 870                 875                 880

Leu Gly Glu Gly His Phe Gly Lys Val Glu Leu Cys Arg Tyr Asp Pro
                885                 890                 895

Glu Gly Asp Asn Thr Gly Glu Gln Val Ala Val Lys Ser Leu Lys Pro
            900                 905                 910

Glu Ser Gly Gly Asn His Ile Ala Asp Leu Lys Lys Glu Ile Glu Ile
        915                 920                 925

Leu Arg Asn Leu Tyr His Glu Asn Ile Val Lys Tyr Lys Gly Ile Cys
930                 935                 940

Thr Glu Asp Gly Gly Asn Gly Ile Lys Leu Ile Met Glu Phe Leu Pro
945                 950                 955                 960
```

```
Ser Gly Ser Leu Lys Glu Tyr Leu Pro Lys Asn Lys Asn Lys Ile Asn
            965                 970                 975

Leu Lys Gln Gln Leu Lys Tyr Ala Val Gln Ile Cys Lys Gly Met Asp
        980                 985                 990

Tyr Leu Gly Ser Arg Gln Tyr Val His Arg Asp Leu Ala Ala Arg Asn
        995                 1000                1005

Val Leu Val Glu Ser Glu His Gln Val Lys Ile Gly Asp Phe Gly
    1010                1015                1020

Leu Thr Lys Ala Ile Glu Thr Asp Lys Glu Tyr Tyr Thr Val Lys
    1025                1030                1035

Asp Asp Arg Asp Ser Pro Val Phe Trp Tyr Ala Pro Glu Cys Leu
    1040                1045                1050

Met Gln Ser Lys Phe Tyr Ile Ala Ser Asp Val Trp Ser Phe Gly
    1055                1060                1065

Val Thr Leu His Glu Leu Leu Thr Tyr Cys Asp Ser Asp Ser Ser
    1070                1075                1080

Pro Met Ala Leu Phe Leu Lys Met Ile Gly Pro Thr His Gly Gln
    1085                1090                1095

Met Thr Val Thr Arg Leu Val Asn Thr Leu Lys Glu Gly Lys Arg
    1100                1105                1110

Leu Pro Cys Pro Pro Asn Cys Pro Asp Glu Val Tyr Gln Leu Met
    1115                1120                1125

Arg Lys Cys Trp Glu Phe Gln Pro Ser Asn Arg Thr Ser Phe Gln
    1130                1135                1140

Asn Leu Ile Glu Gly Phe Glu Ala Leu Leu Lys
    1145                1150

<210> SEQ ID NO 5
<211> LENGTH: 1132
<212> TYPE: PRT
<213> ORGANISM: HUMAN
<300> PUBLICATION INFORMATION:
<301> AUTHORS: Gupta,M., Han,J.J., Stenson,M., Maurer,M., Wellik,L.,
      Hu,G.,
<302> TITLE: Elevated serum IL-10 levels in diffuse large B-cell
      lymphoma: a
<303> JOURNAL: Blood
<304> VOLUME: 119
<305> ISSUE: 12
<306> PAGES: 2844-2853
<307> DATE: 2012-02-08
<308> DATABASE ACCESSION NUMBER: NP_004963
<309> DATABASE ENTRY DATE: 2012-05-13
<313> RELEVANT RESIDUES IN SEQ ID NO: (1)..(1132)

<400> SEQUENCE: 5

Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
```

```
                100                 105                 110
Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
        130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
        210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
        290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
        355                 360                 365

Ile Asp Gly Tyr Tyr Arg Leu Thr Ala Asp Ala His His Tyr Leu Cys
        370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
        435                 440                 445

Tyr Lys His Cys Leu Ile Thr Lys Asn Glu Asn Glu Glu Tyr Asn Leu
        450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495

Lys Cys Cys Pro Pro Lys Pro Lys Asp Lys Ser Asn Leu Leu Val Phe
            500                 505                 510

Arg Thr Asn Gly Val Ser Asp Val Pro Thr Ser Pro Thr Leu Gln Arg
        515                 520                 525
```

```
Pro Thr His Met Asn Gln Met Val Phe His Lys Ile Arg Asn Glu Asp
    530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
            580                 585                 590

Ser Phe Phe Glu Ala Ala Ser Met Met Ser Lys Leu Ser His Lys His
        595                 600                 605

Leu Val Leu Asn Tyr Gly Val Cys Val Cys Gly Asp Glu Asn Ile Leu
    610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
            660                 665                 670

Asn Val Cys Ala Lys Asn Ile Leu Leu Ile Arg Glu Glu Asp Arg Lys
        675                 680                 685

Thr Gly Asn Pro Pro Phe Ile Lys Leu Ser Asp Pro Gly Ile Ser Ile
    690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
        755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
        915                 920                 925

Met Glu Tyr Leu Pro Tyr Gly Ser Leu Arg Asp Tyr Leu Gln Lys His
    930                 935                 940
```

```
Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro
    1010            1015                1020

Glu Ser Leu Thr Glu Ser Lys Phe Ser Val Ala Ser Asp Val Trp
    1025            1030                1035

Ser Phe Gly Val Val Leu Tyr Glu Leu Phe Thr Tyr Ile Glu Lys
    1040            1045                1050

Ser Lys Ser Pro Pro Ala Glu Phe Met Arg Met Ile Gly Asn Asp
    1055            1060                1065

Lys Gln Gly Gln Met Ile Val Phe His Leu Ile Glu Leu Leu Lys
    1070            1075                1080

Asn Asn Gly Arg Leu Pro Arg Pro Asp Gly Cys Pro Asp Glu Ile
    1085            1090                1095

Tyr Met Ile Met Thr Glu Cys Trp Asn Asn Val Asn Gln Arg
    1100            1105                1110

Pro Ser Phe Arg Asp Leu Ala Leu Arg Val Asp Gln Ile Arg Asp
    1115            1120                1125

Asn Met Ala Gly
    1130

<210> SEQ ID NO 6
<211> LENGTH: 1124
<212> TYPE: PRT
<213> ORGANISM: HUMAN
<300> PUBLICATION INFORMATION:
<301> AUTHORS: Bhavsar,S.K., Gu,S., Bobbala,D. and Lang,F.
<302> TITLE: Janus kinase 3 is expressed in erythrocytes, phosphorylated
      upon
<303> JOURNAL: Cell. Physiol. Biochem.
<304> VOLUME: 27
<305> ISSUE: 5
<306> PAGES: 547-556
<307> DATE: 2011-06-15
<308> DATABASE ACCESSION NUMBER: NP_000206
<309> DATABASE ENTRY DATE: 2012-05-20
<313> RELEVANT RESIDUES IN SEQ ID NO: (1)..(1124)

<400> SEQUENCE: 6

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Phe Gly Asp His
        35                  40                  45

Leu Ala Glu Asp Leu Cys Val Gln Ala Ala Lys Ala Ser Gly Ile Leu
    50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
            100                 105                 110
```

```
Glu Lys Cys His Arg Phe Gly Leu Arg Lys Asp Leu Ala Ser Ala Ile
        115                 120                 125

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Arg Arg Arg Ile Arg Arg Thr Val Arg Arg Ala Leu Arg Arg Val
    210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Glu Thr Phe His Val
                245                 250                 255

Gly Leu Pro Gly Ala Leu Gly Gly His Asp Gly Leu Gly Leu Leu Arg
            260                 265                 270

Val Ala Gly Asp Gly Gly Ile Ala Trp Thr Gln Gly Glu Gln Glu Val
        275                 280                 285

Leu Gln Pro Phe Cys Asp Phe Pro Glu Ile Val Asp Ile Ser Ile Lys
    290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
            340                 345                 350

Thr Asp Ser Gln His Phe Phe Cys Lys Glu Val Ala Pro Pro Arg Leu
        355                 360                 365

Leu Glu Glu Val Ala Glu Gln Cys His Gly Pro Ile Thr Leu Asp Phe
    370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
            420                 425                 430

Ser Pro Thr Gly Thr Phe Leu Leu Val Gly Leu Ser Arg Pro His Ser
        435                 440                 445

Ser Leu Arg Glu Leu Leu Ala Thr Cys Trp Asp Gly Gly Leu His Val
    450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
            500                 505                 510

Phe His Lys Ile Pro Ala Asp Ser Leu Glu Trp His Glu Asn Leu Gly
        515                 520                 525
```

```
His Gly Ser Phe Thr Lys Ile Tyr Arg Gly Cys Arg His Glu Val Val
        530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
            580                 585                 590

Ala Gly Asp Ser Thr Met Val Gln Glu Phe Val His Leu Gly Ala Ile
        595                 600                 605

Asp Met Tyr Leu Arg Lys Arg Gly His Leu Val Pro Ala Ser Trp Lys
610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
        675                 680                 685

Pro Trp Val Ala Pro Glu Cys Leu Arg Glu Ala Gln Thr Leu Ser Leu
690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
                725                 730                 735

Phe Tyr Glu Asp Arg Gln Gln Leu Pro Ala Pro Lys Trp Thr Glu Leu
            740                 745                 750

Ala Leu Leu Ile Gln Gln Cys Met Ala Tyr Glu Pro Val Gln Arg Pro
        755                 760                 765

Ser Phe Arg Ala Val Ile Arg Asp Leu Asn Ser Leu Ile Ser Ser Asp
770                 775                 780

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
                805                 810                 815

Phe Glu Glu Arg His Leu Lys Tyr Ile Ser Gln Leu Gly Lys Gly Asn
            820                 825                 830

Phe Gly Ser Val Glu Leu Cys Arg Tyr Asp Pro Leu Gly Asp Asn Thr
        835                 840                 845

Gly Ala Leu Val Ala Val Lys Gln Leu Gln His Ser Gly Pro Asp Gln
850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Gln
                885                 890                 895

Ser Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
        915                 920                 925

Tyr Ser Ser Gln Ile Cys Lys Gly Met Glu Tyr Leu Gly Ser Arg Arg
930                 935                 940

Cys Val His Arg Asp Leu Ala Ala Arg Asn Ile Leu Val Glu Ser Glu
```

```
945                 950                 955                 960
Ala His Val Lys Ile Ala Asp Phe Gly Leu Ala Lys Leu Leu Pro Leu
            965                 970                 975
Asp Lys Asp Tyr Tyr Val Val Arg Glu Pro Gly Gln Ser Pro Ile Phe
            980                 985                 990
Trp Tyr Ala Pro Glu Ser Leu Ser Asp Asn Ile Phe Ser Arg Gln Ser
        995                 1000                1005
Asp Val Trp Ser Phe Gly Val Val Leu Tyr Glu Leu Phe Thr Tyr
    1010                1015                1020
Cys Asp Lys Ser Cys Ser Pro Ser Ala Glu Phe Leu Arg Met Met
    1025                1030                1035
Gly Cys Glu Arg Asp Val Pro Ala Leu Cys Arg Leu Leu Glu Leu
    1040                1045                1050
Leu Glu Glu Gly Gln Arg Leu Pro Ala Pro Pro Ala Cys Pro Ala
    1055                1060                1065
Glu Val His Glu Leu Met Lys Leu Cys Trp Ala Pro Ser Pro Gln
    1070                1075                1080
Asp Arg Pro Ser Phe Ser Ala Leu Gly Pro Gln Leu Asp Met Leu
    1085                1090                1095
Trp Ser Gly Ser Arg Gly Cys Glu Thr His Ala Phe Thr Ala His
    1100                1105                1110
Pro Glu Gly Lys His His Ser Leu Ser Phe Ser
    1115                1120
```

<210> SEQ ID NO 7
<211> LENGTH: 2527
<212> TYPE: PRT
<213> ORGANISM: HUMAN
<300> PUBLICATION INFORMATION:
<301> AUTHORS: Inzelberg,R., Cohen,O.S., Aharon-Peretz,J.,
      Schlesinger,I.,
<302> TITLE: The LRRK2 G2019S mutation is associated with Parkinson
      disease and
<303> JOURNAL: Neurology
<304> VOLUME: 78
<305> ISSUE: 11
<306> PAGES: 781-786
<307> DATE: 2012-02-08
<308> DATABASE ACCESSION NUMBER: NP_940980
<309> DATABASE ENTRY DATE: 2012-05-20
<313> RELEVANT RESIDUES IN SEQ ID NO: (1)..(2527)

<400> SEQUENCE: 7

```
Met Ala Ser Gly Ser Cys Gln Gly Cys Glu Glu Asp Glu Glu Thr Leu
1               5                   10                  15
Lys Lys Leu Ile Val Arg Leu Asn Asn Val Gln Glu Gly Lys Gln Ile
            20                  25                  30
Glu Thr Leu Val Gln Ile Leu Glu Asp Leu Leu Val Phe Thr Tyr Ser
        35                  40                  45
Glu His Ala Ser Lys Leu Phe Gln Gly Lys Asn Ile His Val Pro Leu
    50                  55                  60
Leu Ile Val Leu Asp Ser Tyr Met Arg Val Ala Ser Val Gln Gln Val
65                  70                  75                  80
Gly Trp Ser Leu Leu Cys Lys Leu Ile Glu Val Cys Pro Gly Thr Met
                85                  90                  95
Gln Ser Leu Met Gly Pro Gln Asp Val Gly Asn Asp Trp Glu Val Leu
            100                 105                 110
Gly Val His Gln Leu Ile Leu Lys Met Leu Thr Val His Asn Ala Ser
        115                 120                 125
```

```
Val Asn Leu Ser Val Ile Gly Leu Lys Thr Leu Asp Leu Leu Thr
    130                 135                 140

Ser Gly Lys Ile Thr Leu Leu Ile Leu Asp Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
                180                 185                 190

Glu Glu Gln Leu Thr Glu Phe Val Glu Asn Lys Asp Tyr Met Ile Leu
                195                 200                 205

Leu Ser Ala Leu Thr Asn Phe Lys Asp Glu Glu Ile Val Leu His
210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
                260                 265                 270

Leu Leu His Arg Leu Thr Leu Gly Asn Phe Phe Asn Ile Leu Val Leu
                275                 280                 285

Asn Glu Val His Glu Phe Val Val Lys Ala Val Gln Gln Tyr Pro Glu
290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Asp Lys Leu Phe Trp Leu Glu Ala
                340                 345                 350

Cys Tyr Lys Ala Leu Thr Trp His Arg Lys Asn Lys His Val Gln Glu
                355                 360                 365

Ala Ala Cys Trp Ala Leu Asn Asn Leu Leu Met Tyr Gln Asn Ser Leu
                370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
                405                 410                 415

Ala Ser Ala Asn Ala Leu Ser Thr Leu Leu Glu Gln Asn Val Asn Phe
                420                 425                 430

Arg Lys Ile Leu Leu Ser Lys Gly Ile His Leu Asn Val Leu Glu Leu
                435                 440                 445

Met Gln Lys His Ile His Ser Pro Glu Val Ala Glu Ser Gly Cys Lys
                450                 455                 460

Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
                500                 505                 510

Val Pro Gly Met Pro Glu Glu Ser Arg Glu Asp Thr Glu Phe His His
                515                 520                 525

Lys Leu Asn Met Val Lys Lys Gln Cys Phe Lys Asn Asp Ile His Lys
530                 535                 540
```

-continued

```
Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
            595                 600                 605

Leu Ile Gly Tyr Leu Ile Thr Lys Lys Asn Val Phe Ile Gly Thr Gly
        610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
                660                 665                 670

Leu Val Ile Phe His Gln Met Ser Ser Asn Ile Met Glu Gln Lys Asp
            675                 680                 685

Gln Gln Phe Leu Asn Leu Cys Cys Lys Cys Phe Ala Lys Val Ala Met
690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
                740                 745                 750

Ser Ser Pro Lys Leu Val Glu Leu Leu Asn Ser Gly Ser Arg Glu
                755                 760                 765

Gln Asp Val Arg Lys Ala Leu Thr Ile Ser Ile Gly Lys Gly Asp Ser
            770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
            835                 840                 845

Lys Ser Ala Val Glu Gly Thr Ala Ser Gly Ser Asp Gly Asn Phe
850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Leu Asp Ser Glu
                885                 890                 895

Gly Ser Glu Gly Ser Phe Leu Val Lys Lys Ser Asn Ser Ile Ser
                900                 905                 910

Val Gly Glu Phe Tyr Arg Asp Ala Val Leu Gln Arg Cys Ser Pro Asn
                915                 920                 925

Leu Gln Arg His Ser Asn Ser Leu Gly Pro Ile Phe Asp His Glu Asp
            930                 935                 940

Leu Leu Lys Arg Lys Arg Lys Ile Leu Ser Ser Asp Asp Ser Leu Arg
945                 950                 955                 960

Ser Ser Lys Leu Gln Ser His Met Arg His Ser Asp Ser Ile Ser Ser
```

-continued

```
                965                 970                 975
Leu Ala Ser Glu Arg Glu Tyr Ile Thr Ser Leu Asp Leu Ser Ala Asn
            980                 985                 990
Glu Leu Arg Asp Ile Asp Ala Leu  Ser Gln Lys Cys Cys Ile Ser Val
        995                1000                1005
His Leu Glu His Leu Glu Lys  Leu Glu Leu His Gln  Asn Ala Leu
       1010                1015                1020
Thr Ser Phe Pro Gln Gln Leu  Cys Glu Thr Leu Lys  Ser Leu Thr
       1025                1030                1035
His Leu Asp Leu His Ser Asn  Lys Phe Thr Ser Phe  Pro Ser Tyr
       1040                1045                1050
Leu Leu Lys Met Ser Cys Ile  Ala Asn Leu Asp Val  Ser Arg Asn
       1055                1060                1065
Asp Ile Gly Pro Ser Val Val  Leu Asp Pro Thr Val  Lys Cys Pro
       1070                1075                1080
Thr Leu Lys Gln Phe Asn Leu  Ser Tyr Asn Gln Leu  Ser Phe Val
       1085                1090                1095
Pro Glu Asn Leu Thr Asp Val  Val Glu Lys Leu Glu  Gln Leu Ile
       1100                1105                1110
Leu Glu Gly Asn Lys Ile Ser  Gly Ile Cys Ser Pro  Leu Arg Leu
       1115                1120                1125
Lys Glu Leu Lys Ile Leu Asn  Leu Ser Lys Asn His  Ile Ser Ser
       1130                1135                1140
Leu Ser Glu Asn Phe Leu Glu  Ala Cys Pro Lys Val  Glu Ser Phe
       1145                1150                1155
Ser Ala Arg Met Asn Phe Leu  Ala Ala Met Pro Phe  Leu Pro Pro
       1160                1165                1170
Ser Met Thr Ile Leu Lys Leu  Ser Gln Asn Lys Phe  Ser Cys Ile
       1175                1180                1185
Pro Glu Ala Ile Leu Asn Leu  Pro His Leu Arg Ser  Leu Asp Met
       1190                1195                1200
Ser Ser Asn Asp Ile Gln Tyr  Leu Pro Gly Pro Ala  His Trp Lys
       1205                1210                1215
Ser Leu Asn Leu Arg Glu Leu  Leu Phe Ser His Asn  Gln Ile Ser
       1220                1225                1230
Ile Leu Asp Leu Ser Glu Lys  Ala Tyr Leu Trp Ser  Arg Val Glu
       1235                1240                1245
Lys Leu His Leu Ser His Asn  Lys Leu Lys Glu Ile  Pro Pro Glu
       1250                1255                1260
Ile Gly Cys Leu Glu Asn Leu  Thr Ser Leu Asp Val  Ser Tyr Asn
       1265                1270                1275
Leu Glu Leu Arg Ser Phe Pro  Asn Glu Met Gly Lys  Leu Ser Lys
       1280                1285                1290
Ile Trp Asp Leu Pro Leu Asp  Glu Leu His Leu Asn  Phe Asp Phe
       1295                1300                1305
Lys His Ile Gly Cys Lys Ala  Lys Asp Ile Ile Arg  Phe Leu Gln
       1310                1315                1320
Gln Arg Leu Lys Lys Ala Val  Pro Tyr Asn Arg Met  Lys Leu Met
       1325                1330                1335
Ile Val Gly Asn Thr Gly Ser  Gly Lys Thr Thr Leu  Leu Gln Gln
       1340                1345                1350
Leu Met Lys Thr Lys Lys Ser  Asp Leu Gly Met Gln  Ser Ala Thr
       1355                1360                1365
```

-continued

```
Val Gly Ile Asp Val Lys Asp Trp Pro Ile Gln Ile Arg Asp Lys
    1370            1375            1380

Arg Lys Arg Asp Leu Val Leu Asn Val Trp Asp Phe Ala Gly Arg
    1385            1390            1395

Glu Glu Phe Tyr Ser Thr His Pro His Phe Met Thr Gln Arg Ala
    1400            1405            1410

Leu Tyr Leu Ala Val Tyr Asp Leu Ser Lys Gly Gln Ala Glu Val
    1415            1420            1425

Asp Ala Met Lys Pro Trp Leu Phe Asn Ile Lys Ala Arg Ala Ser
    1430            1435            1440

Ser Ser Pro Val Ile Leu Val Gly Thr His Leu Asp Val Ser Asp
    1445            1450            1455

Glu Lys Gln Arg Lys Ala Cys Met Ser Lys Ile Thr Lys Glu Leu
    1460            1465            1470

Leu Asn Lys Arg Gly Phe Pro Ala Ile Arg Asp Tyr His Phe Val
    1475            1480            1485

Asn Ala Thr Glu Glu Ser Asp Ala Leu Ala Lys Leu Arg Lys Thr
    1490            1495            1500

Ile Ile Asn Glu Ser Leu Asn Phe Lys Ile Arg Asp Gln Leu Val
    1505            1510            1515

Val Gly Gln Leu Ile Pro Asp Cys Tyr Val Glu Leu Glu Lys Ile
    1520            1525            1530

Ile Leu Ser Glu Arg Lys Asn Val Pro Ile Glu Phe Pro Val Ile
    1535            1540            1545

Asp Arg Lys Arg Leu Leu Gln Leu Val Arg Glu Asn Gln Leu Gln
    1550            1555            1560

Leu Asp Glu Asn Glu Leu Pro His Ala Val His Phe Leu Asn Glu
    1565            1570            1575

Ser Gly Val Leu Leu His Phe Gln Asp Pro Ala Leu Gln Leu Ser
    1580            1585            1590

Asp Leu Tyr Phe Val Glu Pro Lys Trp Leu Cys Lys Ile Met Ala
    1595            1600            1605

Gln Ile Leu Thr Val Lys Val Glu Gly Cys Pro Lys His Pro Lys
    1610            1615            1620

Gly Ile Ile Ser Arg Arg Asp Val Glu Lys Phe Leu Ser Lys Lys
    1625            1630            1635

Arg Lys Phe Pro Lys Asn Tyr Met Ser Gln Tyr Phe Lys Leu Leu
    1640            1645            1650

Glu Lys Phe Gln Ile Ala Leu Pro Ile Gly Glu Glu Tyr Leu Leu
    1655            1660            1665

Val Pro Ser Ser Leu Ser Asp His Arg Pro Val Ile Glu Leu Pro
    1670            1675            1680

His Cys Glu Asn Ser Glu Ile Ile Ile Arg Leu Tyr Glu Met Pro
    1685            1690            1695

Tyr Phe Pro Met Gly Phe Trp Ser Arg Leu Ile Asn Arg Leu Leu
    1700            1705            1710

Glu Ile Ser Pro Tyr Met Leu Ser Gly Arg Glu Arg Ala Leu Arg
    1715            1720            1725

Pro Asn Arg Met Tyr Trp Arg Gln Gly Ile Tyr Leu Asn Trp Ser
    1730            1735            1740

Pro Glu Ala Tyr Cys Leu Val Gly Ser Glu Val Leu Asp Asn His
    1745            1750            1755
```

```
Pro Glu Ser Phe Leu Lys Ile Thr Val Pro Ser Cys Arg Lys Gly
    1760                1765                1770

Cys Ile Leu Leu Gly Gln Val Val Asp His Ile Asp Ser Leu Met
    1775                1780                1785

Glu Glu Trp Phe Pro Gly Leu Leu Glu Ile Asp Ile Cys Gly Glu
    1790                1795                1800

Gly Glu Thr Leu Leu Lys Lys Trp Ala Leu Tyr Ser Phe Asn Asp
    1805                1810                1815

Gly Glu Glu His Gln Lys Ile Leu Leu Asp Asp Leu Met Lys Lys
    1820                1825                1830

Ala Glu Glu Gly Asp Leu Leu Val Asn Pro Asp Gln Pro Arg Leu
    1835                1840                1845

Thr Ile Pro Ile Ser Gln Ile Ala Pro Asp Leu Ile Leu Ala Asp
    1850                1855                1860

Leu Pro Arg Asn Ile Met Leu Asn Asn Asp Glu Leu Glu Phe Glu
    1865                1870                1875

Gln Ala Pro Glu Phe Leu Leu Gly Asp Gly Ser Phe Gly Ser Val
    1880                1885                1890

Tyr Arg Ala Ala Tyr Glu Gly Glu Glu Val Ala Val Lys Ile Phe
    1895                1900                1905

Asn Lys His Thr Ser Leu Arg Leu Leu Arg Gln Glu Leu Val Val
    1910                1915                1920

Leu Cys His Leu His His Pro Ser Leu Ile Ser Leu Leu Ala Ala
    1925                1930                1935

Gly Ile Arg Pro Arg Met Leu Val Met Glu Leu Ala Ser Lys Gly
    1940                1945                1950

Ser Leu Asp Arg Leu Leu Gln Gln Asp Lys Ala Ser Leu Thr Arg
    1955                1960                1965

Thr Leu Gln His Arg Ile Ala Leu His Val Ala Asp Gly Leu Arg
    1970                1975                1980

Tyr Leu His Ser Ala Met Ile Ile Tyr Arg Asp Leu Lys Pro His
    1985                1990                1995

Asn Val Leu Leu Phe Thr Leu Tyr Pro Asn Ala Ala Ile Ile Ala
    2000                2005                2010

Lys Ile Ala Asp Tyr Ser Ile Ala Gln Tyr Cys Cys Arg Met Gly
    2015                2020                2025

Ile Lys Thr Ser Glu Gly Thr Pro Gly Phe Arg Ala Pro Glu Val
    2030                2035                2040

Ala Arg Gly Asn Val Ile Tyr Asn Gln Gln Ala Asp Val Tyr Ser
    2045                2050                2055

Phe Gly Leu Leu Leu Tyr Asp Ile Leu Thr Thr Gly Gly Arg Ile
    2060                2065                2070

Val Glu Gly Leu Lys Phe Pro Asn Glu Phe Asp Glu Leu Glu Ile
    2075                2080                2085

Gln Gly Lys Leu Pro Asp Pro Val Lys Glu Tyr Gly Cys Ala Pro
    2090                2095                2100

Trp Pro Met Val Glu Lys Leu Ile Lys Gln Cys Leu Lys Glu Asn
    2105                2110                2115

Pro Gln Glu Arg Pro Thr Ser Ala Gln Val Phe Asp Ile Leu Asn
    2120                2125                2130

Ser Ala Glu Leu Val Cys Leu Thr Arg Arg Ile Leu Leu Pro Lys
    2135                2140                2145

Asn Val Ile Val Glu Cys Met Val Ala Thr His His Asn Ser Arg
```

```
                2150                2155                2160

Asn Ala Ser Ile Trp Leu Gly Cys Gly His Thr Asp Arg Gly Gln
                2165                2170                2175

Leu Ser Phe Leu Asp Leu Asn Thr Glu Gly Tyr Thr Ser Glu Glu
                2180                2185                2190

Val Ala Asp Ser Arg Ile Leu Cys Leu Ala Leu Val His Leu Pro
                2195                2200                2205

Val Glu Lys Glu Ser Trp Ile Val Ser Gly Thr Gln Ser Gly Thr
                2210                2215                2220

Leu Leu Val Ile Asn Thr Glu Asp Gly Lys Lys Arg His Thr Leu
                2225                2230                2235

Glu Lys Met Thr Asp Ser Val Thr Cys Leu Tyr Cys Asn Ser Phe
                2240                2245                2250

Ser Lys Gln Ser Lys Gln Lys Asn Phe Leu Leu Val Gly Thr Ala
                2255                2260                2265

Asp Gly Lys Leu Ala Ile Phe Glu Asp Lys Thr Val Lys Leu Lys
                2270                2275                2280

Gly Ala Ala Pro Leu Lys Ile Leu Asn Ile Gly Asn Val Ser Thr
                2285                2290                2295

Pro Leu Met Cys Leu Ser Glu Ser Thr Asn Ser Thr Glu Arg Asn
                2300                2305                2310

Val Met Trp Gly Gly Cys Gly Thr Lys Ile Phe Ser Phe Ser Asn
                2315                2320                2325

Asp Phe Thr Ile Gln Lys Leu Ile Glu Thr Arg Thr Ser Gln Leu
                2330                2335                2340

Phe Ser Tyr Ala Ala Phe Ser Asp Ser Asn Ile Thr Val Val
                2345                2350                2355

Val Asp Thr Ala Leu Tyr Ile Ala Lys Gln Asn Ser Pro Val Val
                2360                2365                2370

Glu Val Trp Asp Lys Lys Thr Glu Lys Leu Cys Gly Leu Ile Asp
                2375                2380                2385

Cys Val His Phe Leu Arg Glu Val Met Val Lys Glu Asn Lys Glu
                2390                2395                2400

Ser Lys His Lys Met Ser Tyr Ser Gly Arg Val Lys Thr Leu Cys
                2405                2410                2415

Leu Gln Lys Asn Thr Ala Leu Trp Ile Gly Thr Gly Gly Gly His
                2420                2425                2430

Ile Leu Leu Leu Asp Leu Ser Thr Arg Arg Leu Ile Arg Val Ile
                2435                2440                2445

Tyr Asn Phe Cys Asn Ser Val Arg Val Met Met Thr Ala Gln Leu
                2450                2455                2460

Gly Ser Leu Lys Asn Val Met Leu Val Leu Gly Tyr Asn Arg Lys
                2465                2470                2475

Asn Thr Glu Gly Thr Gln Lys Gln Lys Glu Ile Gln Ser Cys Leu
                2480                2485                2490

Thr Val Trp Asp Ile Asn Leu Pro His Glu Val Gln Asn Leu Glu
                2495                2500                2505

Lys His Ile Glu Val Arg Lys Glu Leu Ala Glu Lys Met Arg Arg
                2510                2515                2520

Thr Ser Val Glu
                2525

<210> SEQ ID NO 8
```

```
<211> LENGTH: 651
<212> TYPE: PRT
<213> ORGANISM: HUMAN
<300> PUBLICATION INFORMATION:
<301> AUTHORS: Choi,S. and Ku,J.L.
<302> TITLE: Resistance of colorectal cancer cells to radiation and 5-FU
       is
<303> JOURNAL: Biochem. Biophys. Res. Commun.
<304> VOLUME: 412
<305> ISSUE: 2
<306> PAGES: 207-213
<307> DATE: 2011-07-22
<308> DATABASE ACCESSION NUMBER: NP_055606
<309> DATABASE ENTRY DATE: 2012-04-30
<313> RELEVANT RESIDUES IN SEQ ID NO: (1)..(651)

<400> SEQUENCE: 8

Met Lys Asp Tyr Asp Glu Leu Leu Lys Tyr Tyr Glu Leu His Glu Thr
1               5                   10                  15

Ile Gly Thr Gly Gly Phe Ala Lys Val Lys Leu Ala Cys His Ile Leu
            20                  25                  30

Thr Gly Glu Met Val Ala Ile Lys Ile Met Asp Lys Asn Thr Leu Gly
        35                  40                  45

Ser Asp Leu Pro Arg Ile Lys Thr Glu Ile Glu Ala Leu Lys Asn Leu
50                  55                  60

Arg His Gln His Ile Cys Gln Leu Tyr His Val Leu Glu Thr Ala Asn
65                  70                  75                  80

Lys Ile Phe Met Val Leu Glu Tyr Cys Pro Gly Gly Glu Leu Phe Asp
                85                  90                  95

Tyr Ile Ile Ser Gln Asp Arg Leu Ser Glu Glu Glu Thr Arg Val Val
            100                 105                 110

Phe Arg Gln Ile Val Ser Ala Val Ala Tyr Val His Ser Gln Gly Tyr
        115                 120                 125

Ala His Arg Asp Leu Lys Pro Glu Asn Leu Leu Phe Asp Glu Tyr His
130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
                165                 170                 175

Pro Glu Leu Ile Gln Gly Lys Ser Tyr Leu Gly Ser Glu Ala Asp Val
            180                 185                 190

Trp Ser Met Gly Ile Leu Leu Tyr Val Leu Met Cys Gly Phe Leu Pro
        195                 200                 205

Phe Asp Asp Asp Asn Val Met Ala Leu Tyr Lys Lys Ile Met Arg Gly
210                 215                 220

Lys Tyr Asp Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Lys Asn
                245                 250                 255

Leu Leu Asn His Pro Trp Ile Met Gln Asp Tyr Asn Tyr Pro Val Glu
            260                 265                 270

Trp Gln Ser Lys Asn Pro Phe Ile His Leu Asp Asp Asp Cys Val Thr
        275                 280                 285

Glu Leu Ser Val His His Arg Asn Asn Arg Gln Thr Met Glu Asp Leu
290                 295                 300

Ile Ser Leu Trp Gln Tyr Asp His Leu Thr Ala Thr Tyr Leu Leu Leu
305                 310                 315                 320

Leu Ala Lys Lys Ala Arg Gly Lys Pro Val Arg Leu Arg Leu Ser Ser
```

```
                        325                 330                 335
Phe Ser Cys Gly Gln Ala Ser Ala Thr Pro Phe Thr Asp Ile Lys Ser
            340                 345                 350
Asn Asn Trp Ser Leu Glu Asp Val Thr Ala Ser Asp Lys Asn Tyr Val
        355                 360                 365
Ala Gly Leu Ile Asp Tyr Asp Trp Cys Glu Asp Leu Ser Thr Gly
    370                 375                 380
Ala Ala Thr Pro Arg Thr Ser Gln Phe Thr Lys Tyr Trp Thr Glu Ser
385                 390                 395                 400
Asn Gly Val Glu Ser Lys Ser Leu Thr Pro Ala Leu Cys Arg Thr Pro
                405                 410                 415
Ala Asn Lys Leu Lys Asn Lys Glu Asn Val Tyr Thr Pro Lys Ser Ala
            420                 425                 430
Val Lys Asn Glu Glu Tyr Phe Met Phe Pro Glu Pro Lys Thr Pro Val
        435                 440                 445
Asn Lys Asn Gln His Lys Arg Glu Ile Leu Thr Thr Pro Asn Arg Tyr
    450                 455                 460
Thr Thr Pro Ser Lys Ala Arg Asn Gln Cys Leu Lys Glu Thr Pro Ile
465                 470                 475                 480
Lys Ile Pro Val Asn Ser Thr Gly Thr Asp Lys Leu Met Thr Gly Val
                485                 490                 495
Ile Ser Pro Glu Arg Arg Cys Arg Ser Val Glu Leu Asp Leu Asn Gln
            500                 505                 510
Ala His Met Glu Glu Thr Pro Lys Arg Lys Gly Ala Lys Val Phe Gly
        515                 520                 525
Ser Leu Glu Arg Gly Leu Asp Lys Val Ile Thr Val Leu Thr Arg Ser
    530                 535                 540
Lys Arg Lys Gly Ser Ala Arg Asp Gly Pro Arg Arg Leu Lys Leu His
545                 550                 555                 560
Tyr Asn Val Thr Thr Thr Arg Leu Val Asn Pro Asp Gln Leu Leu Asn
                565                 570                 575
Glu Ile Met Ser Ile Leu Pro Lys Lys His Val Asp Phe Val Gln Lys
            580                 585                 590
Gly Tyr Thr Leu Lys Cys Gln Thr Gln Ser Asp Phe Gly Lys Val Thr
        595                 600                 605
Met Gln Phe Glu Leu Glu Val Cys Gln Leu Gln Lys Pro Asp Val Val
    610                 615                 620
Gly Ile Arg Arg Gln Arg Leu Lys Gly Asp Ala Trp Val Tyr Lys Arg
625                 630                 635                 640
Leu Val Glu Asp Ile Leu Ser Ser Cys Lys Val
                645                 650

<210> SEQ ID NO 9
<211> LENGTH: 846
<212> TYPE: PRT
<213> ORGANISM: HUMAN
<300> PUBLICATION INFORMATION:
<301> AUTHORS: Rikova,K., Guo,A., Zeng,Q., Possemato,A., Yu,J.,
      Haack,H.,
<302> TITLE: Global survey of phosphotyrosine signaling identifies
      oncogenic
<303> JOURNAL: Cell
<304> VOLUME: 131
<305> ISSUE: 6
<306> PAGES: 1190-1203
<307> DATE: 2007-12-14
<308> DATABASE ACCESSION NUMBER: NP_006566
<309> DATABASE ENTRY DATE: 2012-05-05
```

```
<313> RELEVANT RESIDUES IN SEQ ID NO: (1)..(846)

<400> SEQUENCE: 9

Met Glu Ala Pro Leu Arg Pro Ala Ala Asp Ile Leu Arg Arg Asn Pro
1               5                   10                  15

Gln Gln Asp Tyr Glu Leu Val Gln Arg Val Gly Ser Gly Thr Tyr Gly
            20                  25                  30

Asp Val Tyr Lys Ala Arg Asn Val His Thr Gly Glu Leu Ala Ala Val
        35                  40                  45

Lys Ile Ile Lys Leu Glu Pro Gly Asp Asp Phe Ser Leu Ile Gln Gln
50                  55                  60

Glu Ile Phe Met Val Lys Glu Cys Lys His Cys Asn Ile Val Ala Tyr
65                  70                  75                  80

Phe Gly Ser Tyr Leu Ser Arg Glu Lys Leu Trp Ile Cys Met Glu Tyr
                85                  90                  95

Cys Gly Gly Gly Ser Leu Gln Asp Ile Tyr His Val Thr Gly Pro Leu
            100                 105                 110

Ser Glu Leu Gln Ile Ala Tyr Val Cys Arg Glu Thr Leu Gln Gly Leu
        115                 120                 125

Ala Tyr Leu His Thr Lys Gly Lys Met His Arg Asp Ile Lys Gly Ala
130                 135                 140

Asn Ile Leu Leu Thr Asp His Gly Asp Val Lys Leu Ala Asp Phe Gly
145                 150                 155                 160

Val Ala Ala Lys Ile Thr Ala Thr Ile Ala Lys Arg Lys Ser Phe Ile
                165                 170                 175

Gly Thr Pro Tyr Trp Met Ala Pro Glu Val Ala Ala Val Glu Lys Asn
            180                 185                 190

Gly Gly Tyr Asn Gln Leu Cys Asp Ile Trp Ala Val Gly Ile Thr Ala
        195                 200                 205

Ile Glu Leu Gly Glu Leu Gln Pro Pro Met Phe Asp Leu His Pro Met
210                 215                 220

Arg Ala Leu Phe Leu Met Ser Lys Ser Asn Phe Gln Pro Pro Lys Leu
225                 230                 235                 240

Lys Asp Lys Thr Lys Trp Ser Ser Thr Phe His Asn Phe Val Lys Ile
                245                 250                 255

Ala Leu Thr Lys Asn Pro Lys Lys Arg Pro Thr Ala Glu Arg Leu Leu
            260                 265                 270

Thr His Thr Phe Val Ala Gln Pro Gly Leu Ser Arg Ala Leu Ala Val
        275                 280                 285

Glu Leu Leu Asp Lys Val Asn Asn Pro Asp Asn His Ala His Tyr Thr
290                 295                 300

Glu Ala Asp Asp Asp Phe Glu Pro His Ala Ile Ile Arg His Thr
305                 310                 315                 320

Ile Arg Ser Thr Asn Arg Asn Ala Arg Ala Glu Arg Thr Ala Ser Glu
                325                 330                 335

Ile Asn Phe Asp Lys Leu Gln Phe Glu Pro Pro Leu Arg Lys Glu Thr
            340                 345                 350

Glu Ala Arg Asp Glu Met Gly Leu Ser Ser Asp Pro Asn Phe Met Leu
        355                 360                 365

Gln Trp Asn Pro Phe Val Asp Gly Ala Asn Thr Gly Lys Ser Thr Ser
370                 375                 380

Lys Arg Ala Ile Pro Pro Leu Pro Pro Lys Pro Arg Ile Ser Ser
385                 390                 395                 400
```

-continued

```
Tyr Pro Glu Asp Asn Phe Pro Asp Glu Glu Lys Ala Ser Thr Ile Lys
                405                 410                 415

His Cys Pro Asp Ser Glu Ser Arg Ala Pro Gln Ile Leu Arg Arg Gln
            420                 425                 430

Ser Ser Pro Ser Cys Gly Pro Val Ala Glu Thr Ser Ser Ile Gly Asn
        435                 440                 445

Gly Asp Gly Ile Ser Lys Leu Met Ser Glu Asn Thr Glu Gly Ser Ala
    450                 455                 460

Gln Ala Pro Gln Leu Pro Arg Lys Lys Asp Lys Asp Phe Pro Lys
465                 470                 475                 480

Pro Ala Ile Asn Gly Leu Pro Pro Thr Pro Lys Val Leu Met Gly Ala
                485                 490                 495

Cys Phe Ser Lys Val Phe Asp Gly Cys Pro Leu Lys Ile Asn Cys Ala
            500                 505                 510

Thr Ser Trp Ile His Pro Asp Thr Lys Asp Gln Tyr Ile Ile Phe Gly
        515                 520                 525

Thr Glu Asp Gly Ile Tyr Thr Leu Asn Leu Asn Glu Leu His Glu Ala
    530                 535                 540

Thr Met Glu Gln Leu Phe Pro Arg Lys Cys Thr Trp Leu Tyr Val Ile
545                 550                 555                 560

Asn Asn Thr Leu Met Ser Leu Ser Glu Gly Lys Thr Phe Gln Leu Tyr
                565                 570                 575

Ser His Asn Leu Ile Ala Leu Phe Glu His Ala Lys Lys Pro Gly Leu
            580                 585                 590

Ala Ala His Ile Gln Thr His Arg Phe Pro Asp Arg Ile Leu Pro Arg
    595                 600                 605

Lys Phe Ala Leu Thr Thr Lys Ile Pro Asp Thr Lys Gly Cys His Lys
610                 615                 620

Cys Cys Ile Val Arg Asn Pro Tyr Thr Gly His Lys Tyr Leu Cys Gly
625                 630                 635                 640

Ala Leu Gln Ser Gly Ile Val Leu Leu Gln Trp Tyr Glu Pro Met Gln
                645                 650                 655

Lys Phe Met Leu Ile Lys His Phe Asp Phe Pro Leu Pro Ser Pro Leu
            660                 665                 670

Asn Val Phe Glu Met Leu Val Ile Pro Glu Gln Glu Tyr Pro Met Val
    675                 680                 685

Cys Val Ala Ile Ser Lys Gly Thr Glu Ser Asn Gln Val Val Gln Phe
690                 695                 700

Glu Thr Ile Asn Leu Asn Ser Ala Ser Ser Trp Phe Thr Glu Ile Gly
705                 710                 715                 720

Ala Gly Ser Gln Gln Leu Asp Ser Ile His Val Thr Gln Leu Glu Arg
                725                 730                 735

Asp Thr Val Leu Val Cys Leu Asp Lys Phe Val Lys Ile Val Asn Leu
            740                 745                 750

Gln Gly Lys Leu Lys Ser Ser Lys Lys Leu Ala Ser Glu Leu Ser Phe
    755                 760                 765

Asp Phe Arg Ile Glu Ser Val Val Cys Leu Gln Asp Ser Val Leu Ala
770                 775                 780

Phe Trp Lys His Gly Met Gln Gly Lys Ser Phe Lys Ser Asp Glu Val
785                 790                 795                 800

Thr Gln Glu Ile Ser Asp Glu Thr Arg Val Phe Arg Leu Leu Gly Ser
                805                 810                 815

Asp Arg Val Val Val Leu Glu Ser Arg Pro Thr Glu Asn Pro Thr Ala
```

His Ser Asn Leu Tyr Ile Leu Ala Gly His Glu Asn Ser Tyr
        835                 840                 845

<210> SEQ ID NO 10
<211> LENGTH: 783
<212> TYPE: PRT
<213> ORGANISM: HUMAN
<300> PUBLICATION INFORMATION:
<301> AUTHORS: Hashimoto,Y.K., Satoh,T., Okamoto,M. and Takemori,H.
<302> TITLE: Importance of autophosphorylation at Ser186 in the A-loop
       of salt
<303> JOURNAL: J. Cell. Biochem.
<304> VOLUME: 104
<305> ISSUE: 5
<306> PAGES: 1724-1739
<307> DATE: 2008-08-01
<308> DATABASE ACCESSION NUMBER: NP_775490
<309> DATABASE ENTRY DATE: 2012-04-21
<313> RELEVANT RESIDUES IN SEQ ID NO: (1)..(783)

<400> SEQUENCE: 10

Met Val Ile Met Ser Glu Phe Ser Ala Asp Pro Ala Gly Gln Gly Gln
1               5                   10                  15

Gly Gln Gln Lys Pro Leu Arg Val Gly Phe Tyr Asp Ile Glu Arg Thr
            20                  25                  30

Leu Gly Lys Gly Asn Phe Ala Val Val Lys Leu Ala Arg His Arg Val
        35                  40                  45

Thr Lys Thr Gln Val Ala Ile Lys Ile Ile Asp Lys Thr Arg Leu Asp
    50                  55                  60

Ser Ser Asn Leu Glu Lys Ile Tyr Arg Glu Val Gln Leu Met Lys Leu
65                  70                  75                  80

Leu Asn His Pro His Ile Ile Lys Leu Tyr Gln Val Met Glu Thr Lys
                85                  90                  95

Asp Met Leu Tyr Ile Val Thr Glu Phe Ala Lys Asn Gly Glu Met Phe
            100                 105                 110

Asp Tyr Leu Thr Ser Asn Gly His Leu Ser Glu Asn Glu Ala Arg Lys
        115                 120                 125

Lys Phe Trp Gln Ile Leu Ser Ala Val Glu Tyr Cys His Asp His His
    130                 135                 140

Ile Val His Arg Asp Leu Lys Thr Glu Asn Leu Leu Leu Asp Gly Asn
145                 150                 155                 160

Met Asp Ile Lys Leu Ala Asp Phe Gly Phe Gly Asn Phe Tyr Lys Ser
                165                 170                 175

Gly Glu Pro Leu Ser Thr Trp Cys Gly Ser Pro Tyr Ala Ala Pro
            180                 185                 190

Glu Val Phe Glu Gly Lys Glu Tyr Glu Gly Pro Gln Leu Asp Ile Trp
        195                 200                 205

Ser Leu Gly Val Val Leu Tyr Val Leu Val Cys Gly Ser Leu Pro Phe
    210                 215                 220

Asp Gly Pro Asn Leu Pro Thr Leu Arg Gln Arg Val Leu Glu Gly Arg
225                 230                 235                 240

Phe Arg Ile Pro Phe Phe Met Ser Gln Asp Cys Glu Ser Leu Ile Arg
                245                 250                 255

Arg Met Leu Val Val Asp Pro Ala Arg Arg Ile Thr Ile Ala Gln Ile
            260                 265                 270

Arg Gln His Arg Trp Met Arg Ala Glu Pro Cys Leu Pro Gly Pro Ala
        275                 280                 285

```
Cys Pro Ala Phe Ser Ala His Ser Tyr Thr Ser Asn Leu Gly Asp Tyr
290                 295                 300

Asp Glu Gln Ala Leu Gly Ile Met Gln Thr Leu Gly Val Asp Arg Gln
305                 310                 315                 320

Arg Thr Val Glu Ser Leu Gln Asn Ser Ser Tyr Asn His Phe Ala Ala
                325                 330                 335

Ile Tyr Tyr Leu Leu Leu Glu Arg Leu Lys Glu Tyr Arg Asn Ala Gln
                340                 345                 350

Cys Ala Arg Pro Gly Pro Ala Arg Gln Pro Arg Pro Arg Ser Ser Asp
                355                 360                 365

Leu Ser Gly Leu Glu Val Pro Gln Glu Gly Leu Ser Thr Asp Pro Phe
370                 375                 380

Arg Pro Ala Leu Leu Cys Pro Gln Pro Gln Thr Leu Val Gln Ser Val
385                 390                 395                 400

Leu Gln Ala Glu Met Asp Cys Glu Leu Gln Ser Ser Leu Gln Trp Pro
                405                 410                 415

Leu Phe Phe Pro Val Asp Ala Ser Cys Ser Gly Val Phe Arg Pro Arg
                420                 425                 430

Pro Val Ser Pro Ser Ser Leu Leu Asp Thr Ala Ile Ser Glu Glu Ala
                435                 440                 445

Arg Gln Gly Pro Gly Leu Glu Glu Glu Gln Asp Thr Gln Glu Ser Leu
450                 455                 460

Pro Ser Ser Thr Gly Arg Arg His Thr Leu Ala Glu Val Ser Thr Arg
465                 470                 475                 480

Leu Ser Pro Leu Thr Ala Pro Cys Ile Val Val Ser Pro Ser Thr Thr
                485                 490                 495

Ala Ser Pro Ala Glu Gly Thr Ser Ser Asp Ser Cys Leu Thr Phe Ser
                500                 505                 510

Ala Ser Lys Ser Pro Ala Gly Leu Ser Gly Thr Pro Ala Thr Gln Gly
                515                 520                 525

Leu Leu Gly Ala Cys Ser Pro Val Arg Leu Ala Ser Pro Phe Leu Gly
530                 535                 540

Ser Gln Ser Ala Thr Pro Val Leu Gln Ala Gln Gly Gly Leu Gly Gly
545                 550                 555                 560

Ala Val Leu Leu Pro Val Ser Phe Gln Glu Gly Arg Arg Ala Ser Asp
                565                 570                 575

Thr Ser Leu Thr Gln Gly Leu Lys Ala Phe Arg Gln Gln Leu Arg Lys
                580                 585                 590

Thr Thr Arg Thr Lys Gly Phe Leu Gly Leu Asn Lys Ile Lys Gly Leu
                595                 600                 605

Ala Arg Gln Val Cys Gln Ala Pro Ala Ser Arg Ala Ser Arg Gly Gly
610                 615                 620

Leu Ser Pro Phe His Ala Pro Ala Gln Ser Pro Gly Leu His Gly Gly
625                 630                 635                 640

Ala Ala Gly Ser Arg Glu Gly Trp Ser Leu Leu Glu Glu Val Leu Glu
                645                 650                 655

Gln Gln Arg Leu Leu Gln Leu Gln His His Pro Ala Ala Ala Pro Gly
                660                 665                 670

Cys Ser Gln Ala Pro Gln Pro Pro Ala Pro Phe Val Ile Ala Pro
                675                 680                 685

Cys Asp Gly Pro Gly Ala Ala Pro Leu Pro Ser Thr Leu Leu Thr Ser
690                 695                 700

Gly Leu Pro Leu Leu Pro Pro Leu Leu Gln Thr Gly Ala Ser Pro
```

```
                        705                 710                 715                 720
Val Ala Ser Ala Ala Gln Leu Leu Asp Thr His Leu His Ile Gly Thr
                    725                 730                 735

Gly Pro Thr Ala Leu Pro Ala Val Pro Pro Arg Leu Ala Arg Leu
                740                 745                 750

Ala Pro Gly Cys Glu Pro Leu Gly Leu Gln Gly Asp Cys Glu Met
            755                 760                 765

Glu Asp Leu Met Pro Cys Ser Leu Gly Thr Phe Val Leu Val Gln
        770                 775                 780

<210> SEQ ID NO 11
<211> LENGTH: 926
<212> TYPE: PRT
<213> ORGANISM: HUMAN
<300> PUBLICATION INFORMATION:
<301> AUTHORS: Ahmed,A.A., Lu,Z., Jennings,N.B., Etemadmoghadam,D.,
       Capalbo,L.,
<302> TITLE: SIK2 is a centrosome kinase required for bipolar mitotic
       spindle
<303> JOURNAL: Cancer Cell
<304> VOLUME: 18
<305> ISSUE: 2
<306> PAGES: 109-121
<307> DATE: 2010-08-17
<308> DATABASE ACCESSION NUMBER: NP_056006
<309> DATABASE ENTRY DATE: 2012-03-25
<313> RELEVANT RESIDUES IN SEQ ID NO: (1)..(926)

<400> SEQUENCE: 11

Met Val Met Ala Asp Gly Pro Arg His Leu Gln Arg Gly Pro Val Arg
1               5                   10                  15

Val Gly Phe Tyr Asp Ile Glu Gly Thr Leu Gly Lys Gly Asn Phe Ala
            20                  25                  30

Val Val Lys Leu Gly Arg His Arg Ile Thr Lys Thr Glu Val Ala Ile
        35                  40                  45

Lys Ile Ile Asp Lys Ser Gln Leu Asp Ala Val Asn Leu Glu Lys Ile
    50                  55                  60

Tyr Arg Glu Val Gln Ile Met Lys Met Leu Asp His Pro His Ile Ile
65                  70                  75                  80

Lys Leu Tyr Gln Val Met Glu Thr Lys Ser Met Leu Tyr Leu Val Thr
                85                  90                  95

Glu Tyr Ala Lys Asn Gly Glu Ile Phe Asp Tyr Leu Ala Asn His Gly
            100                 105                 110

Arg Leu Asn Glu Ser Glu Ala Arg Arg Lys Phe Trp Gln Ile Leu Ser
        115                 120                 125

Ala Val Asp Tyr Cys His Gly Arg Lys Ile Val His Arg Asp Leu Lys
    130                 135                 140

Ala Glu Asn Leu Leu Leu Asp Asn Asn Met Asn Ile Lys Ile Ala Asp
145                 150                 155                 160

Phe Gly Phe Gly Asn Phe Phe Lys Ser Gly Glu Leu Leu Ala Thr Trp
                165                 170                 175

Cys Gly Ser Pro Pro Tyr Ala Ala Pro Glu Val Phe Glu Gly Gln Gln
            180                 185                 190

Tyr Glu Gly Pro Gln Leu Asp Ile Trp Ser Met Gly Val Val Leu Tyr
        195                 200                 205

Val Leu Val Cys Gly Ala Leu Pro Phe Asp Gly Pro Thr Leu Pro Ile
    210                 215                 220

Leu Arg Gln Arg Val Leu Glu Gly Arg Phe Arg Ile Pro Tyr Phe Met
225                 230                 235                 240
```

```
Ser Glu Asp Cys Glu His Leu Ile Arg Arg Met Leu Val Leu Asp Pro
                245                 250                 255
Ser Lys Arg Leu Thr Ile Ala Gln Ile Lys Glu His Lys Trp Met Leu
                260                 265                 270
Ile Glu Val Pro Val Gln Arg Pro Val Leu Tyr Pro Gln Glu Gln Glu
                275                 280                 285
Asn Glu Pro Ser Ile Gly Glu Phe Asn Glu Gln Val Leu Arg Leu Met
            290                 295                 300
His Ser Leu Gly Ile Asp Gln Gln Lys Thr Ile Glu Ser Leu Gln Asn
305                 310                 315                 320
Lys Ser Tyr Asn His Phe Ala Ala Ile Tyr Phe Leu Leu Val Glu Arg
                325                 330                 335
Leu Lys Ser His Arg Ser Ser Phe Pro Val Glu Gln Arg Leu Asp Gly
                340                 345                 350
Arg Gln Arg Arg Pro Ser Thr Ile Ala Glu Gln Thr Val Ala Lys Ala
                355                 360                 365
Gln Thr Val Gly Leu Pro Val Thr Met His Ser Pro Asn Met Arg Leu
            370                 375                 380
Leu Arg Ser Ala Leu Leu Pro Gln Ala Ser Asn Val Glu Ala Phe Ser
385                 390                 395                 400
Phe Pro Ala Ser Gly Cys Gln Ala Glu Ala Ala Phe Met Glu Glu Glu
                405                 410                 415
Cys Val Asp Thr Pro Lys Val Asn Gly Cys Leu Leu Asp Pro Val Pro
                420                 425                 430
Pro Val Leu Val Arg Lys Gly Cys Gln Ser Leu Pro Ser Asn Met Met
                435                 440                 445
Glu Thr Ser Ile Asp Glu Gly Leu Glu Thr Gly Glu Ala Glu Glu
            450                 455                 460
Asp Pro Ala His Ala Phe Glu Ala Phe Gln Ser Thr Arg Ser Gly Gln
465                 470                 475                 480
Arg Arg His Thr Leu Ser Glu Val Thr Asn Gln Leu Val Val Met Pro
                485                 490                 495
Gly Ala Gly Lys Ile Phe Ser Met Asn Asp Ser Pro Ser Leu Asp Ser
                500                 505                 510
Val Asp Ser Glu Tyr Asp Met Gly Ser Val Gln Arg Asp Leu Asn Phe
            515                 520                 525
Leu Glu Asp Asn Pro Ser Leu Lys Asp Ile Met Leu Ala Asn Gln Pro
530                 535                 540
Ser Pro Arg Met Thr Ser Pro Phe Ile Ser Leu Arg Pro Thr Asn Pro
545                 550                 555                 560
Ala Met Gln Ala Leu Ser Ser Gln Lys Arg Glu Val His Asn Arg Ser
                565                 570                 575
Pro Val Ser Phe Arg Glu Gly Arg Arg Ala Ser Asp Thr Ser Leu Thr
                580                 585                 590
Gln Gly Ile Val Ala Phe Arg Gln His Leu Gln Asn Leu Ala Arg Thr
            595                 600                 605
Lys Gly Ile Leu Glu Leu Asn Lys Val Gln Leu Leu Tyr Glu Gln Ile
            610                 615                 620
Gly Pro Glu Ala Asp Pro Asn Leu Ala Pro Ala Pro Gln Leu Gln
625                 630                 635                 640
Asp Leu Ala Ser Ser Cys Pro Gln Glu Glu Val Ser Gln Gln Gln Glu
                645                 650                 655
```

```
Ser Val Ser Thr Leu Pro Ala Ser Val His Pro Gln Leu Ser Pro Arg
            660                 665                 670

Gln Ser Leu Glu Thr Gln Tyr Leu Gln His Arg Leu Gln Lys Pro Ser
        675                 680                 685

Leu Leu Ser Lys Ala Gln Asn Thr Cys Gln Leu Tyr Cys Lys Glu Pro
    690                 695                 700

Pro Arg Ser Leu Glu Gln Gln Leu Gln Glu His Arg Leu Gln Gln Lys
705                 710                 715                 720

Arg Leu Phe Leu Gln Lys Gln Ser Gln Leu Gln Ala Tyr Phe Asn Gln
                725                 730                 735

Met Gln Ile Ala Glu Ser Ser Tyr Pro Gln Pro Ser Gln Gln Leu Pro
            740                 745                 750

Leu Pro Arg Gln Glu Thr Pro Pro Ser Gln Gln Ala Pro Pro Phe
        755                 760                 765

Ser Leu Thr Gln Pro Leu Ser Pro Val Leu Glu Pro Ser Ser Glu Gln
    770                 775                 780

Met Gln Tyr Ser Pro Phe Leu Ser Gln Tyr Glu Met Gln Leu Gln
785                 790                 795                 800

Pro Leu Pro Ser Thr Ser Gly Pro Arg Ala Ala Pro Pro Leu Pro Thr
                805                 810                 815

Gln Leu Gln Gln Gln Gln Pro Pro Pro Pro Pro Pro Pro Pro Pro Pro
            820                 825                 830

Arg Gln Pro Gly Ala Ala Pro Ala Pro Leu Gln Phe Ser Tyr Gln Thr
                835                 840                 845

Cys Glu Leu Pro Ser Ala Ala Ser Pro Ala Pro Asp Tyr Pro Thr Pro
850                 855                 860

Cys Gln Tyr Pro Val Asp Gly Ala Gln Gln Ser Asp Leu Thr Gly Pro
865                 870                 875                 880

Asp Cys Pro Arg Ser Pro Gly Leu Gln Glu Ala Pro Ser Ser Tyr Asp
                885                 890                 895

Pro Leu Ala Leu Ser Glu Leu Pro Gly Leu Phe Asp Cys Glu Met Leu
                900                 905                 910

Asp Ala Val Asp Pro Gln His Asn Gly Tyr Val Leu Val Asn
        915                 920                 925
```

<210> SEQ ID NO 12
<211> LENGTH: 2527
<212> TYPE: PRT
<213> ORGANISM: HUMAN
<300> PUBLICATION INFORMATION:
<301> AUTHORS: Zimprich,A., Biskup,S., Leitner,P., Lichtner,P., Farrer,M.,
<302> TITLE: Mutations in LRRK2 cause autosomal-dominant parkinsonism with
<303> JOURNAL: Neuron
<304> VOLUME: 44
<305> ISSUE: 4
<306> PAGES: 601-607
<307> DATE: 2004-11-18
<308> DATABASE ACCESSION NUMBER: NP_940980
<309> DATABASE ENTRY DATE: 2012-05-27
<313> RELEVANT RESIDUES IN SEQ ID NO: (1)..(2527)

<400> SEQUENCE: 12

```
Met Ala Ser Gly Ser Cys Gln Gly Cys Glu Glu Asp Glu Glu Thr Leu
1               5                   10                  15

Lys Lys Leu Ile Val Arg Leu Asn Asn Val Gln Glu Gly Lys Gln Ile
            20                  25                  30

Glu Thr Leu Val Gln Ile Leu Glu Asp Leu Leu Val Phe Thr Tyr Ser
```

```
                35                  40                  45
Glu His Ala Ser Lys Leu Phe Gln Gly Lys Asn Ile His Val Pro Leu
 50                  55                  60

Leu Ile Val Leu Asp Ser Tyr Met Arg Val Ala Ser Val Gln Gln Val
 65                  70                  75                  80

Gly Trp Ser Leu Leu Cys Lys Leu Ile Glu Val Cys Pro Gly Thr Met
                 85                  90                  95

Gln Ser Leu Met Gly Pro Gln Asp Val Gly Asn Asp Trp Glu Val Leu
                100                 105                 110

Gly Val His Gln Leu Ile Leu Lys Met Leu Thr Val His Asn Ala Ser
                115                 120                 125

Val Asn Leu Ser Val Ile Gly Leu Lys Thr Leu Asp Leu Leu Leu Thr
130                 135                 140

Ser Gly Lys Ile Thr Leu Leu Ile Leu Asp Glu Glu Ser Asp Ile Phe
145                 150                 155                 160

Met Leu Ile Phe Asp Ala Met His Ser Phe Pro Ala Asn Asp Glu Val
                165                 170                 175

Gln Lys Leu Gly Cys Lys Ala Leu His Val Leu Phe Glu Arg Val Ser
                180                 185                 190

Glu Glu Gln Leu Thr Glu Phe Val Glu Asn Lys Asp Tyr Met Ile Leu
                195                 200                 205

Leu Ser Ala Leu Thr Asn Phe Lys Asp Glu Glu Ile Val Leu His
210                 215                 220

Val Leu His Cys Leu His Ser Leu Ala Ile Pro Cys Asn Asn Val Glu
225                 230                 235                 240

Val Leu Met Ser Gly Asn Val Arg Cys Tyr Asn Ile Val Val Glu Ala
                245                 250                 255

Met Lys Ala Phe Pro Met Ser Glu Arg Ile Gln Glu Val Ser Cys Cys
                260                 265                 270

Leu Leu His Arg Leu Thr Leu Gly Asn Phe Phe Asn Ile Leu Val Leu
                275                 280                 285

Asn Glu Val His Glu Phe Val Val Lys Ala Val Gln Gln Tyr Pro Glu
290                 295                 300

Asn Ala Ala Leu Gln Ile Ser Ala Leu Ser Cys Leu Ala Leu Leu Thr
305                 310                 315                 320

Glu Thr Ile Phe Leu Asn Gln Asp Leu Glu Glu Lys Asn Glu Asn Gln
                325                 330                 335

Glu Asn Asp Asp Glu Gly Glu Glu Asp Lys Leu Phe Trp Leu Glu Ala
                340                 345                 350

Cys Tyr Lys Ala Leu Thr Trp His Arg Lys Asn Lys His Val Gln Glu
                355                 360                 365

Ala Ala Cys Trp Ala Leu Asn Asn Leu Leu Met Tyr Gln Asn Ser Leu
                370                 375                 380

His Glu Lys Ile Gly Asp Glu Asp Gly His Phe Pro Ala His Arg Glu
385                 390                 395                 400

Val Met Leu Ser Met Leu Met His Ser Ser Lys Glu Val Phe Gln
                405                 410                 415

Ala Ser Ala Asn Ala Leu Ser Thr Leu Leu Glu Gln Asn Val Asn Phe
                420                 425                 430

Arg Lys Ile Leu Leu Ser Lys Gly Ile His Leu Asn Val Leu Glu Leu
                435                 440                 445

Met Gln Lys His Ile His Ser Pro Glu Val Ala Glu Ser Gly Cys Lys
                450                 455                 460
```

-continued

```
Met Leu Asn His Leu Phe Glu Gly Ser Asn Thr Ser Leu Asp Ile Met
465                 470                 475                 480

Ala Ala Val Val Pro Lys Ile Leu Thr Val Met Lys Arg His Glu Thr
                485                 490                 495

Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
        515                 520                 525

Lys Leu Asn Met Val Lys Lys Gln Cys Phe Lys Asn Asp Ile His Lys
530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Leu Asn Ser Gly Ser Arg Glu
        755                 760                 765

Gln Asp Val Arg Lys Ala Leu Thr Ile Ser Ile Gly Lys Gly Asp Ser
        770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
        850                 855                 860

Ser Glu Asp Val Leu Ser Lys Phe Asp Glu Trp Thr Phe Ile Pro Asp
865                 870                 875                 880
```

```
Ser Ser Met Asp Ser Val Phe Ala Gln Ser Asp Leu Asp Ser Glu
            885                 890                 895

Gly Ser Glu Gly Ser Phe Leu Val Lys Lys Ser Asn Ser Ile Ser
        900                 905                 910

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
        930                 935                 940

Leu Leu Lys Arg Lys Arg Lys Ile Leu Ser Ser Asp Ser Leu Arg
945                 950                 955                 960

Ser Ser Lys Leu Gln Ser His Met Arg His Ser Asp Ser Ile Ser Ser
            965                 970                 975

Leu Ala Ser Glu Arg Glu Tyr Ile Thr Ser Leu Asp Leu Ser Ala Asn
        980                 985                 990

Glu Leu Arg Asp Ile Asp Ala Leu Ser Gln Lys Cys Cys Ile Ser Val
        995                 1000                1005

His Leu Glu His Leu Glu Lys Leu Glu Leu His Gln Asn Ala Leu
    1010                1015                1020

Thr Ser Phe Pro Gln Gln Leu Cys Glu Thr Leu Lys Ser Leu Thr
    1025                1030                1035

His Leu Asp Leu His Ser Asn Lys Phe Thr Ser Phe Pro Ser Tyr
    1040                1045                1050

Leu Leu Lys Met Ser Cys Ile Ala Asn Leu Asp Val Ser Arg Asn
    1055                1060                1065

Asp Ile Gly Pro Ser Val Val Leu Asp Pro Thr Val Lys Cys Pro
    1070                1075                1080

Thr Leu Lys Gln Phe Asn Leu Ser Tyr Asn Gln Leu Ser Phe Val
    1085                1090                1095

Pro Glu Asn Leu Thr Asp Val Val Glu Lys Leu Glu Gln Leu Ile
    1100                1105                1110

Leu Glu Gly Asn Lys Ile Ser Gly Ile Cys Ser Pro Leu Arg Leu
    1115                1120                1125

Lys Glu Leu Lys Ile Leu Asn Leu Ser Lys Asn His Ile Ser Ser
    1130                1135                1140

Leu Ser Glu Asn Phe Leu Glu Ala Cys Pro Lys Val Glu Ser Phe
    1145                1150                1155

Ser Ala Arg Met Asn Phe Leu Ala Ala Met Pro Phe Leu Pro Pro
    1160                1165                1170

Ser Met Thr Ile Leu Lys Leu Ser Gln Asn Lys Phe Ser Cys Ile
    1175                1180                1185

Pro Glu Ala Ile Leu Asn Leu Pro His Leu Arg Ser Leu Asp Met
    1190                1195                1200

Ser Ser Asn Asp Ile Gln Tyr Leu Pro Gly Pro Ala His Trp Lys
    1205                1210                1215

Ser Leu Asn Leu Arg Glu Leu Leu Phe Ser His Asn Gln Ile Ser
    1220                1225                1230

Ile Leu Asp Leu Ser Glu Lys Ala Tyr Leu Trp Ser Arg Val Glu
    1235                1240                1245

Lys Leu His Leu Ser His Asn Lys Leu Lys Glu Ile Pro Pro Glu
    1250                1255                1260

Ile Gly Cys Leu Glu Asn Leu Thr Ser Leu Asp Val Ser Tyr Asn
    1265                1270                1275

Leu Glu Leu Arg Ser Phe Pro Asn Glu Met Gly Lys Leu Ser Lys
```

-continued

```
            1280                1285                1290
Ile Trp Asp Leu Pro Leu Asp Glu Leu His Leu Asn Phe Asp Phe
            1295                1300                1305
Lys His Ile Gly Cys Lys Ala Lys Asp Ile Ile Arg Phe Leu Gln
            1310                1315                1320
Gln Arg Leu Lys Lys Ala Val Pro Tyr Asn Arg Met Lys Leu Met
            1325                1330                1335
Ile Val Gly Asn Thr Gly Ser Gly Lys Thr Thr Leu Leu Gln Gln
            1340                1345                1350
Leu Met Lys Thr Lys Lys Ser Asp Leu Gly Met Gln Ser Ala Thr
            1355                1360                1365
Val Gly Ile Asp Val Lys Asp Trp Pro Ile Gln Ile Arg Asp Lys
            1370                1375                1380
Arg Lys Arg Asp Leu Val Leu Asn Val Trp Asp Phe Ala Gly Arg
            1385                1390                1395
Glu Glu Phe Tyr Ser Thr His Pro His Phe Met Thr Gln Arg Ala
            1400                1405                1410
Leu Tyr Leu Ala Val Tyr Asp Leu Ser Lys Gly Gln Ala Glu Val
            1415                1420                1425
Asp Ala Met Lys Pro Trp Leu Phe Asn Ile Lys Ala Arg Ala Ser
            1430                1435                1440
Ser Ser Pro Val Ile Leu Val Gly Thr His Leu Asp Val Ser Asp
            1445                1450                1455
Glu Lys Gln Arg Lys Ala Cys Met Ser Lys Ile Thr Lys Glu Leu
            1460                1465                1470
Leu Asn Lys Arg Gly Phe Pro Ala Ile Arg Asp Tyr His Phe Val
            1475                1480                1485
Asn Ala Thr Glu Glu Ser Asp Ala Leu Ala Lys Leu Arg Lys Thr
            1490                1495                1500
Ile Ile Asn Glu Ser Leu Asn Phe Lys Ile Arg Asp Gln Leu Val
            1505                1510                1515
Val Gly Gln Leu Ile Pro Asp Cys Tyr Val Glu Leu Glu Lys Ile
            1520                1525                1530
Ile Leu Ser Glu Arg Lys Asn Val Pro Ile Glu Phe Pro Val Ile
            1535                1540                1545
Asp Arg Lys Arg Leu Leu Gln Leu Val Arg Glu Asn Gln Leu Gln
            1550                1555                1560
Leu Asp Glu Asn Glu Leu Pro His Ala Val His Phe Leu Asn Glu
            1565                1570                1575
Ser Gly Val Leu Leu His Phe Gln Asp Pro Ala Leu Gln Leu Ser
            1580                1585                1590
Asp Leu Tyr Phe Val Glu Pro Lys Trp Leu Cys Lys Ile Met Ala
            1595                1600                1605
Gln Ile Leu Thr Val Lys Val Glu Gly Cys Pro Lys His Pro Lys
            1610                1615                1620
Gly Ile Ile Ser Arg Arg Asp Val Glu Lys Phe Leu Ser Lys Lys
            1625                1630                1635
Arg Lys Phe Pro Lys Asn Tyr Met Ser Gln Tyr Phe Lys Leu Leu
            1640                1645                1650
Glu Lys Phe Gln Ile Ala Leu Pro Ile Gly Glu Glu Tyr Leu Leu
            1655                1660                1665
Val Pro Ser Ser Leu Ser Asp His Arg Pro Val Ile Glu Leu Pro
            1670                1675                1680
```

```
His Cys Glu Asn Ser Glu Ile Ile Arg Leu Tyr Glu Met Pro
    1685                1690                1695

Tyr Phe Pro Met Gly Phe Trp Ser Arg Leu Ile Asn Arg Leu Leu
    1700                1705                1710

Glu Ile Ser Pro Tyr Met Leu Ser Gly Arg Glu Arg Ala Leu Arg
    1715                1720                1725

Pro Asn Arg Met Tyr Trp Arg Gln Gly Ile Tyr Leu Asn Trp Ser
    1730                1735                1740

Pro Glu Ala Tyr Cys Leu Val Gly Ser Glu Val Leu Asp Asn His
    1745                1750                1755

Pro Glu Ser Phe Leu Lys Ile Thr Val Pro Ser Cys Arg Lys Gly
    1760                1765                1770

Cys Ile Leu Leu Gly Gln Val Val Asp His Ile Asp Ser Leu Met
    1775                1780                1785

Glu Glu Trp Phe Pro Gly Leu Leu Glu Ile Asp Ile Cys Gly Glu
    1790                1795                1800

Gly Glu Thr Leu Leu Lys Lys Trp Ala Leu Tyr Ser Phe Asn Asp
    1805                1810                1815

Gly Glu Glu His Gln Lys Ile Leu Leu Asp Asp Leu Met Lys Lys
    1820                1825                1830

Ala Glu Glu Gly Asp Leu Leu Val Asn Pro Asp Gln Pro Arg Leu
    1835                1840                1845

Thr Ile Pro Ile Ser Gln Ile Ala Pro Asp Leu Ile Leu Ala Asp
    1850                1855                1860

Leu Pro Arg Asn Ile Met Leu Asn Asn Asp Glu Leu Glu Phe Glu
    1865                1870                1875

Gln Ala Pro Glu Phe Leu Leu Gly Asp Gly Ser Phe Gly Ser Val
    1880                1885                1890

Tyr Arg Ala Ala Tyr Glu Gly Glu Glu Val Ala Val Lys Ile Phe
    1895                1900                1905

Asn Lys His Thr Ser Leu Arg Leu Leu Arg Gln Glu Leu Val Val
    1910                1915                1920

Leu Cys His Leu His His Pro Ser Leu Ile Ser Leu Leu Ala Ala
    1925                1930                1935

Gly Ile Arg Pro Arg Met Leu Val Met Glu Leu Ala Ser Lys Gly
    1940                1945                1950

Ser Leu Asp Arg Leu Leu Gln Gln Asp Lys Ala Ser Leu Thr Arg
    1955                1960                1965

Thr Leu Gln His Arg Ile Ala Leu His Val Ala Asp Gly Leu Arg
    1970                1975                1980

Tyr Leu His Ser Ala Met Ile Ile Tyr Arg Asp Leu Lys Pro His
    1985                1990                1995

Asn Val Leu Leu Phe Thr Leu Tyr Pro Asn Ala Ala Ile Ile Ala
    2000                2005                2010

Lys Ile Ala Asp Tyr Gly Ile Ala Gln Tyr Cys Cys Arg Met Gly
    2015                2020                2025

Ile Lys Thr Ser Glu Gly Thr Pro Gly Phe Arg Ala Pro Glu Val
    2030                2035                2040

Ala Arg Gly Asn Val Ile Tyr Asn Gln Gln Ala Asp Val Tyr Ser
    2045                2050                2055

Phe Gly Leu Leu Leu Tyr Asp Ile Leu Thr Thr Gly Gly Arg Ile
    2060                2065                2070
```

```
Val Glu Gly Leu Lys Phe Pro Asn Glu Phe Asp Glu Leu Glu Ile
2075                2080                2085

Gln Gly Lys Leu Pro Asp Pro Val Lys Glu Tyr Gly Cys Ala Pro
2090                2095                2100

Trp Pro Met Val Glu Lys Leu Ile Lys Gln Cys Leu Lys Glu Asn
2105                2110                2115

Pro Gln Glu Arg Pro Thr Ser Ala Gln Val Phe Asp Ile Leu Asn
2120                2125                2130

Ser Ala Glu Leu Val Cys Leu Thr Arg Arg Ile Leu Leu Pro Lys
2135                2140                2145

Asn Val Ile Val Glu Cys Met Val Ala Thr His His Asn Ser Arg
2150                2155                2160

Asn Ala Ser Ile Trp Leu Gly Cys Gly His Thr Asp Arg Gly Gln
2165                2170                2175

Leu Ser Phe Leu Asp Leu Asn Thr Glu Gly Tyr Thr Ser Glu Glu
2180                2185                2190

Val Ala Asp Ser Arg Ile Leu Cys Leu Ala Leu Val His Leu Pro
2195                2200                2205

Val Glu Lys Glu Ser Trp Ile Val Ser Gly Thr Gln Ser Gly Thr
2210                2215                2220

Leu Leu Val Ile Asn Thr Glu Asp Gly Lys Lys Arg His Thr Leu
2225                2230                2235

Glu Lys Met Thr Asp Ser Val Thr Cys Leu Tyr Cys Asn Ser Phe
2240                2245                2250

Ser Lys Gln Ser Lys Gln Lys Asn Phe Leu Leu Val Gly Thr Ala
2255                2260                2265

Asp Gly Lys Leu Ala Ile Phe Glu Asp Lys Thr Val Lys Leu Lys
2270                2275                2280

Gly Ala Ala Pro Leu Lys Ile Leu Asn Ile Gly Asn Val Ser Thr
2285                2290                2295

Pro Leu Met Cys Leu Ser Glu Ser Thr Asn Ser Thr Glu Arg Asn
2300                2305                2310

Val Met Trp Gly Gly Cys Gly Thr Lys Ile Phe Ser Phe Ser Asn
2315                2320                2325

Asp Phe Thr Ile Gln Lys Leu Ile Glu Thr Arg Thr Ser Gln Leu
2330                2335                2340

Phe Ser Tyr Ala Ala Phe Ser Asp Ser Asn Ile Ile Thr Val Val
2345                2350                2355

Val Asp Thr Ala Leu Tyr Ile Ala Lys Gln Asn Ser Pro Val Val
2360                2365                2370

Glu Val Trp Asp Lys Lys Thr Glu Lys Leu Cys Gly Leu Ile Asp
2375                2380                2385

Cys Val His Phe Leu Arg Glu Val Met Val Lys Glu Asn Lys Glu
2390                2395                2400

Ser Lys His Lys Met Ser Tyr Ser Gly Arg Val Lys Thr Leu Cys
2405                2410                2415

Leu Gln Lys Asn Thr Ala Leu Trp Ile Gly Thr Gly Gly Gly His
2420                2425                2430

Ile Leu Leu Leu Asp Leu Ser Thr Arg Arg Leu Ile Arg Val Ile
2435                2440                2445

Tyr Asn Phe Cys Asn Ser Val Arg Val Met Met Thr Ala Gln Leu
2450                2455                2460

Gly Ser Leu Lys Asn Val Met Leu Val Leu Gly Tyr Asn Arg Lys
```

```
                    2465                2470                2475

Asn  Thr  Glu  Gly  Thr  Gln  Lys  Gln  Lys  Glu  Ile  Gln  Ser  Cys  Leu
          2480                2485                2490

Thr  Val  Trp  Asp  Ile  Asn  Leu  Pro  His  Glu  Val  Gln  Asn  Leu  Glu
          2495                2500                2505

Lys  His  Ile  Glu  Val  Arg  Lys  Glu  Leu  Ala  Glu  Lys  Met  Arg  Arg
     2510                2515                2520

Thr  Ser  Val  Glu
     2525
```

<210> SEQ ID NO 13
<211> LENGTH: 763
<212> TYPE: PRT
<213> ORGANISM: HUMAN
<300> PUBLICATION INFORMATION:
<301> AUTHORS: Chen JY, Lin JR, Tsai FC and Meyer T.
<302> TITLE: Dosage of Dyrk1a shifts cells within a p21-cyclin D1
       signaling map
<303> JOURNAL: Mol. Cell
<304> VOLUME: 52
<305> ISSUE: 1
<306> PAGES: 87-100
<307> DATE: 2013
<308> DATABASE ACCESSION NUMBER: NP_001387
<309> DATABASE ENTRY DATE: 2014-01-02
<313> RELEVANT RESIDUES IN SEQ ID NO: (1)..(763)

<400> SEQUENCE: 13

```
Met  His  Thr  Gly  Gly  Glu  Thr  Ser  Ala  Cys  Lys  Pro  Ser  Ser  Val  Arg
1                   5                   10                  15

Leu  Ala  Pro  Ser  Phe  Ser  Phe  His  Ala  Ala  Gly  Leu  Gln  Met  Ala  Gly
               20                  25                  30

Gln  Met  Pro  His  Ser  His  Gln  Tyr  Ser  Asp  Arg  Arg  Gln  Pro  Asn  Ile
          35                  40                  45

Ser  Asp  Gln  Gln  Val  Ser  Ala  Leu  Ser  Tyr  Ser  Asp  Gln  Ile  Gln  Gln
     50                  55                  60

Pro  Leu  Thr  Asn  Gln  Val  Met  Pro  Asp  Ile  Val  Met  Leu  Gln  Arg  Arg
65                  70                  75                  80

Met  Pro  Gln  Thr  Phe  Arg  Asp  Pro  Ala  Thr  Ala  Pro  Leu  Arg  Lys  Leu
               85                  90                  95

Ser  Val  Asp  Leu  Ile  Lys  Thr  Tyr  Lys  His  Ile  Asn  Glu  Val  Tyr  Tyr
               100                 105                 110

Ala  Lys  Lys  Lys  Arg  Arg  His  Gln  Gln  Gly  Gln  Gly  Asp  Asp  Ser  Ser
               115                 120                 125

His  Lys  Lys  Glu  Arg  Lys  Val  Tyr  Asn  Asp  Gly  Tyr  Asp  Asp  Asp  Asn
          130                 135                 140

Tyr  Asp  Tyr  Ile  Val  Lys  Asn  Gly  Glu  Lys  Trp  Met  Asp  Arg  Tyr  Glu
145                 150                 155                 160

Ile  Asp  Ser  Leu  Ile  Gly  Lys  Gly  Ser  Phe  Gly  Gln  Val  Val  Lys  Ala
               165                 170                 175

Tyr  Asp  Arg  Val  Glu  Gln  Glu  Trp  Val  Ala  Ile  Lys  Ile  Ile  Lys  Asn
               180                 185                 190

Lys  Lys  Ala  Phe  Leu  Asn  Gln  Ala  Gln  Ile  Glu  Val  Arg  Leu  Leu  Glu
               195                 200                 205

Leu  Met  Asn  Lys  His  Asp  Thr  Glu  Met  Lys  Tyr  Tyr  Ile  Val  His  Leu
          210                 215                 220

Lys  Arg  His  Phe  Met  Phe  Arg  Asn  His  Leu  Cys  Leu  Val  Phe  Glu  Met
225                 230                 235                 240
```

```
Leu Ser Tyr Asn Leu Tyr Asp Leu Leu Arg Asn Thr Asn Phe Arg Gly
            245                 250                 255

Val Ser Leu Asn Leu Thr Arg Lys Phe Ala Gln Gln Met Cys Thr Ala
        260                 265                 270

Leu Leu Phe Leu Ala Thr Pro Glu Leu Ser Ile Ile His Cys Asp Leu
    275                 280                 285

Lys Pro Glu Asn Ile Leu Leu Cys Asn Pro Lys Arg Ser Ala Ile Lys
290                 295                 300

Ile Val Asp Phe Gly Ser Ser Cys Gln Leu Gly Gln Arg Ile Tyr Gln
305                 310                 315                 320

Tyr Ile Gln Ser Arg Phe Tyr Arg Ser Pro Glu Val Leu Leu Gly Met
                325                 330                 335

Pro Tyr Asp Leu Ala Ile Asp Met Trp Ser Leu Gly Cys Ile Leu Val
            340                 345                 350

Glu Met His Thr Gly Glu Pro Leu Phe Ser Gly Ala Asn Glu Val Asp
        355                 360                 365

Gln Met Asn Lys Ile Val Glu Val Leu Gly Ile Pro Pro Ala His Ile
    370                 375                 380

Leu Asp Gln Ala Pro Lys Ala Arg Lys Phe Phe Glu Lys Leu Pro Asp
385                 390                 395                 400

Gly Thr Trp Asn Leu Lys Lys Thr Lys Asp Gly Lys Arg Glu Tyr Lys
                405                 410                 415

Pro Pro Gly Thr Arg Lys Leu His Asn Ile Leu Gly Val Glu Thr Gly
            420                 425                 430

Gly Pro Gly Gly Arg Arg Ala Gly Glu Ser Gly His Thr Val Ala Asp
        435                 440                 445

Tyr Leu Lys Phe Lys Asp Leu Ile Leu Arg Met Leu Asp Tyr Asp Pro
    450                 455                 460

Lys Thr Arg Ile Gln Pro Tyr Tyr Ala Leu Gln His Ser Phe Phe Lys
465                 470                 475                 480

Lys Thr Ala Asp Glu Gly Thr Asn Thr Ser Asn Ser Val Ser Thr Ser
                485                 490                 495

Pro Ala Met Glu Gln Ser Gln Ser Ser Gly Thr Thr Ser Ser Thr Ser
            500                 505                 510

Ser Ser Ser Gly Gly Ser Ser Gly Thr Ser Asn Ser Gly Arg Ala Arg
        515                 520                 525

Ser Asp Pro Thr His Gln His Arg His Ser Gly Gly His Phe Thr Ala
530                 535                 540

Ala Val Gln Ala Met Asp Cys Glu Thr His Ser Pro Gln Val Arg Gln
545                 550                 555                 560

Gln Phe Pro Ala Pro Leu Gly Trp Ser Gly Thr Glu Ala Pro Thr Gln
                565                 570                 575

Val Thr Val Glu Thr His Pro Val Gln Glu Thr Thr Phe His Val Ala
            580                 585                 590

Pro Gln Gln Asn Ala Leu His His His Gly Asn Ser Ser His His
        595                 600                 605

His His His His His His His His His Gly Gln Gln Ala Leu
    610                 615                 620

Gly Asn Arg Thr Arg Pro Arg Val Tyr Asn Ser Pro Thr Asn Ser Ser
625                 630                 635                 640

Ser Thr Gln Asp Ser Met Glu Val Gly His Ser His His Ser Met Thr
                645                 650                 655

Ser Leu Ser Ser Ser Thr Thr Ser Ser Ser Thr Ser Ser Ser Ser Thr
```

```
                        660                 665                 670
Gly Asn Gln Gly Asn Gln Ala Tyr Gln Asn Arg Pro Val Ala Ala Asn
                    675                 680                 685

Thr Leu Asp Phe Gly Gln Asn Gly Ala Met Asp Val Asn Leu Thr Val
    690                 695                 700

Tyr Ser Asn Pro Arg Gln Glu Thr Gly Ile Ala Gly His Pro Thr Tyr
705                 710                 715                 720

Gln Phe Ser Ala Asn Thr Gly Pro Ala His Tyr Met Thr Glu Gly His
                    725                 730                 735

Leu Thr Met Arg Gln Gly Ala Asp Arg Glu Glu Ser Pro Met Thr Gly
                740                 745                 750

Val Cys Val Gln Gln Ser Pro Val Ala Ser Ser
            755                 760
```

<210> SEQ ID NO 14
<211> LENGTH: 620
<212> TYPE: PRT
<213> ORGANISM: HUMAN
<300> PUBLICATION INFORMATION:
<301> AUTHORS: Gibson S, Leung B, Squire JA, Hill M, Arima N, Goss P, Hogg D and
<302> TITLE: Identification, cloning, and characterization of a novel human
<303> JOURNAL: Blood
<304> VOLUME: 324
<305> ISSUE: 1
<306> PAGES: 1561-1572
<307> DATE: 1993
<308> DATABASE ACCESSION NUMBER: NP_005537
<309> DATABASE ENTRY DATE: 2014-01-26
<313> RELEVANT RESIDUES IN SEQ ID NO: (1)..(620)

<400> SEQUENCE: 14

```
Met Asn Asn Phe Ile Leu Leu Glu Glu Gln Leu Ile Lys Lys Ser Gln
1               5                   10                  15

Gln Lys Arg Arg Thr Ser Pro Ser Asn Phe Lys Val Arg Phe Phe Val
                20                  25                  30

Leu Thr Lys Ala Ser Leu Ala Tyr Phe Glu Asp Arg His Gly Lys Lys
            35                  40                  45

Arg Thr Leu Lys Gly Ser Ile Glu Leu Ser Arg Ile Lys Cys Val Glu
        50                  55                  60

Ile Val Lys Ser Asp Ile Ser Ile Pro Cys His Tyr Lys Tyr Pro Phe
65                  70                  75                  80

Gln Val Val His Asp Asn Tyr Leu Leu Tyr Val Phe Ala Pro Asp Arg
                85                  90                  95

Glu Ser Arg Gln Arg Trp Val Leu Ala Leu Lys Glu Glu Thr Arg Asn
                100                 105                 110

Asn Asn Ser Leu Val Pro Lys Tyr His Pro Asn Phe Trp Met Asp Gly
            115                 120                 125

Lys Trp Arg Cys Cys Ser Gln Leu Glu Lys Leu Ala Thr Gly Cys Ala
        130                 135                 140

Gln Tyr Asp Pro Thr Lys Asn Ala Ser Lys Lys Pro Leu Pro Pro Thr
145                 150                 155                 160

Pro Glu Asp Asn Arg Arg Pro Leu Trp Glu Pro Glu Glu Thr Val Val
                165                 170                 175

Ile Ala Leu Tyr Asp Tyr Gln Thr Asn Asp Pro Gln Glu Leu Ala Leu
            180                 185                 190

Arg Arg Asn Glu Glu Tyr Cys Leu Leu Asp Ser Ser Glu Ile His Trp
        195                 200                 205
```

-continued

Trp Arg Val Gln Asp Arg Asn Gly His Glu Gly Tyr Val Pro Ser Ser
    210                 215                 220

Tyr Leu Val Glu Lys Ser Pro Asn Asn Leu Glu Thr Tyr Glu Trp Tyr
225                 230                 235                 240

Asn Lys Ser Ile Ser Arg Asp Lys Ala Glu Lys Leu Leu Leu Asp Thr
                245                 250                 255

Gly Lys Glu Gly Ala Phe Met Val Arg Asp Ser Arg Thr Ala Gly Thr
            260                 265                 270

Tyr Thr Val Ser Val Phe Thr Lys Ala Val Val Ser Glu Asn Asn Pro
        275                 280                 285

Cys Ile Lys His Tyr His Ile Lys Glu Thr Asn Asp Asn Pro Lys Arg
    290                 295                 300

Tyr Tyr Val Ala Glu Lys Tyr Val Phe Asp Ser Ile Pro Leu Leu Ile
305                 310                 315                 320

Asn Tyr His Gln His Asn Gly Gly Leu Val Thr Arg Leu Arg Tyr
                325                 330                 335

Pro Val Cys Phe Gly Arg Gln Lys Ala Pro Val Thr Ala Gly Leu Arg
            340                 345                 350

Tyr Gly Lys Trp Val Ile Asp Pro Ser Glu Leu Thr Phe Val Gln Glu
        355                 360                 365

Ile Gly Ser Gly Gln Phe Gly Leu Val His Leu Gly Tyr Trp Leu Asn
370                 375                 380

Lys Asp Lys Val Ala Ile Lys Thr Ile Arg Glu Gly Ala Met Ser Glu
385                 390                 395                 400

Glu Asp Phe Ile Glu Glu Ala Glu Val Met Met Lys Leu Ser His Pro
                405                 410                 415

Lys Leu Val Gln Leu Tyr Gly Val Cys Leu Glu Gln Ala Pro Ile Cys
            420                 425                 430

Leu Val Phe Glu Phe Met Glu His Gly Cys Leu Ser Asp Tyr Leu Arg
        435                 440                 445

Thr Gln Arg Gly Leu Phe Ala Ala Glu Thr Leu Leu Gly Met Cys Leu
    450                 455                 460

Asp Val Cys Glu Gly Met Ala Tyr Leu Glu Glu Ala Cys Val Ile His
465                 470                 475                 480

Arg Asp Leu Ala Ala Arg Asn Cys Leu Val Gly Glu Asn Gln Val Ile
                485                 490                 495

Lys Val Ser Asp Phe Gly Met Thr Arg Phe Val Leu Asp Asp Gln Tyr
            500                 505                 510

Thr Ser Ser Thr Gly Thr Lys Phe Pro Val Lys Trp Ala Ser Pro Glu
        515                 520                 525

Val Phe Ser Phe Ser Arg Tyr Ser Ser Lys Ser Asp Val Trp Ser Phe
    530                 535                 540

Gly Val Leu Met Trp Glu Val Phe Ser Glu Gly Lys Ile Pro Tyr Glu
545                 550                 555                 560

Asn Arg Ser Asn Ser Glu Val Val Glu Asp Ile Ser Thr Gly Phe Arg
                565                 570                 575

Leu Tyr Lys Pro Arg Leu Ala Ser Thr His Val Tyr Gln Ile Met Asn
            580                 585                 590

His Cys Trp Lys Glu Arg Pro Glu Asp Arg Pro Ala Phe Ser Arg Leu
        595                 600                 605

Leu Arg Gln Leu Ala Glu Ile Ala Glu Ser Gly Leu
    610                 615                 620

```
<210> SEQ ID NO 15
<211> LENGTH: 1187
<212> TYPE: PRT
<213> ORGANISM: HUMAN
<300> PUBLICATION INFORMATION:
<301> AUTHORS: Sohn SJ, Barrett K, Van Abbema A, Chang C, Kohli PB,
       Kanda H, Smith
<302> TITLE: A restricted role for TYK2 catalytic activity in human
       cytokine
<303> JOURNAL: J. Immunol
<304> VOLUME: 191
<305> ISSUE: 5
<306> PAGES: 2205-216
<307> DATE: 2013-06-08
<308> DATABASE ACCESSION NUMBER: NP_003322
<309> DATABASE ENTRY DATE: 2013-02-10
<313> RELEVANT RESIDUES IN SEQ ID NO: (1)..(1184)

<400> SEQUENCE: 15
```

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

Ser Ser Leu Thr Ala Glu Glu Val Cys Ile His Ile Ala His Lys Val
    50                  55                  60

Gly Ile Thr Pro Pro Cys Phe Asn Leu Phe Ala Leu Phe Asp Ala Gln
65                  70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
        115                 120                 125

Gly Thr Glu Ala Ser Ser Asp Gln Thr Ala Gln Gly Met Gln Leu Leu
    130                 135                 140

Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
        195                 200                 205

Thr Ser Phe Lys Asp Cys Ile Pro Arg Ser Phe Arg Arg His Ile Arg
    210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
            260                 265                 270

Glu Arg Val Pro Val Cys His Leu Arg Leu Leu Ala Gln Ala Glu Gly
        275                 280                 285

Glu Pro Cys Tyr Ile Arg Asp Ser Gly Val Ala Pro Thr Asp Pro Gly
    290                 295                 300

Pro Glu Ser Ala Ala Gly Pro Pro Thr His Glu Val Leu Val Thr Gly

```
305                 310                 315                 320
Thr Gly Gly Ile Gln Trp Trp Pro Val Glu Glu Val Asn Lys Glu
                325                 330                 335
Glu Gly Ser Ser Gly Ser Ser Gly Arg Asn Pro Gln Ala Ser Leu Phe
                340                 345                 350
Gly Lys Lys Ala Lys Ala His Lys Ala Val Gly Gln Pro Ala Asp Arg
                355                 360                 365
Pro Arg Glu Pro Leu Trp Ala Tyr Phe Cys Asp Phe Arg Asp Ile Thr
                370                 375                 380
His Val Val Leu Lys Glu His Cys Val Ser Ile His Arg Gln Asp Asn
385                 390                 395                 400
Lys Cys Leu Glu Leu Ser Leu Pro Ser Arg Ala Ala Ala Leu Ser Phe
                405                 410                 415
Val Ser Leu Val Asp Gly Tyr Phe Arg Leu Thr Ala Asp Ser Ser His
                420                 425                 430
Tyr Leu Cys His Glu Val Ala Pro Pro Arg Leu Val Met Ser Ile Arg
                435                 440                 445
Asp Gly Ile His Gly Pro Leu Leu Glu Pro Phe Val Gln Ala Lys Leu
450                 455                 460
Arg Pro Glu Asp Gly Leu Tyr Leu Ile His Trp Ser Thr Ser His Pro
465                 470                 475                 480
Tyr Arg Leu Ile Leu Thr Val Ala Gln Arg Ser Gln Ala Pro Asp Gly
                485                 490                 495
Met Gln Ser Leu Arg Leu Arg Lys Phe Pro Ile Glu Gln Gln Asp Gly
                500                 505                 510
Ala Phe Val Leu Glu Gly Trp Gly Arg Ser Phe Pro Ser Val Arg Glu
                515                 520                 525
Leu Gly Ala Ala Leu Gln Gly Cys Leu Leu Arg Ala Gly Asp Asp Cys
                530                 535                 540
Phe Ser Leu Arg Arg Cys Cys Leu Pro Gln Pro Gly Glu Thr Ser Asn
545                 550                 555                 560
Leu Ile Ile Met Arg Gly Ala Arg Ala Ser Pro Arg Thr Leu Asn Leu
                565                 570                 575
Ser Gln Leu Ser Phe His Arg Val Asp Gln Lys Glu Ile Thr Gln Leu
                580                 585                 590
Ser His Leu Gly Gln Gly Thr Arg Thr Asn Val Tyr Glu Gly Arg Leu
                595                 600                 605
Arg Val Glu Gly Ser Gly Asp Pro Glu Glu Gly Lys Met Asp Asp Glu
                610                 615                 620
Asp Pro Leu Val Pro Gly Arg Asp Arg Gly Gln Glu Leu Arg Val Val
625                 630                 635                 640
Leu Lys Val Leu Asp Pro Ser His His Asp Ile Ala Leu Ala Phe Tyr
                645                 650                 655
Glu Thr Ala Ser Leu Met Ser Gln Val Ser His Thr His Leu Ala Phe
                660                 665                 670
Val His Gly Val Cys Val Arg Gly Pro Glu Asn Ile Met Val Thr Glu
                675                 680                 685
Tyr Val Glu His Gly Pro Leu Asp Val Trp Leu Arg Arg Glu Arg Gly
                690                 695                 700
His Val Pro Met Ala Trp Lys Met Val Ala Gln Gln Leu Ala Ser
705                 710                 715                 720
Ala Leu Ser Tyr Leu Glu Asn Lys Asn Leu Val His Gly Asn Val Cys
                725                 730                 735
```

-continued

```
Gly Arg Asn Ile Leu Leu Ala Arg Leu Gly Leu Ala Glu Gly Thr Ser
                740                 745                 750
Pro Phe Ile Lys Leu Ser Asp Pro Gly Val Gly Leu Gly Ala Leu Ser
755                 760                 765
Arg Glu Glu Arg Val Glu Arg Ile Pro Trp Leu Ala Pro Glu Cys Leu
    770                 775                 780
Pro Gly Gly Ala Asn Ser Leu Ser Thr Ala Met Asp Lys Trp Gly Phe
785                 790                 795                 800
Gly Ala Thr Leu Leu Glu Ile Cys Phe Asp Gly Glu Ala Pro Leu Gln
                805                 810                 815
Ser Arg Ser Pro Ser Glu Lys Glu His Phe Tyr Gln Arg Gln His Arg
                820                 825                 830
Leu Pro Glu Pro Ser Cys Pro Gln Leu Ala Thr Leu Thr Ser Gln Cys
            835                 840                 845
Leu Thr Tyr Glu Pro Thr Gln Arg Pro Ser Phe Arg Thr Ile Leu Arg
850                 855                 860
Asp Leu Thr Arg Leu Gln Pro His Asn Leu Ala Asp Val Leu Thr Val
865                 870                 875                 880
Asn Pro Asp Ser Pro Ala Ser Asp Pro Thr Val Phe His Lys Arg Tyr
                885                 890                 895
Leu Lys Lys Ile Arg Asp Leu Gly Glu Gly His Phe Gly Lys Val Ser
                900                 905                 910
Leu Tyr Cys Tyr Asp Pro Thr Asn Asp Gly Thr Gly Glu Met Val Ala
            915                 920                 925
Val Lys Ala Leu Lys Ala Asp Cys Gly Pro Gln His Arg Ser Gly Trp
930                 935                 940
Lys Gln Glu Ile Asp Ile Leu Arg Thr Leu Tyr His Glu His Ile Ile
945                 950                 955                 960
Lys Tyr Lys Gly Cys Cys Glu Asp Gln Gly Glu Lys Ser Leu Gln Leu
                965                 970                 975
Val Met Glu Tyr Val Pro Leu Gly Ser Leu Arg Asp Tyr Leu Pro Arg
                980                 985                 990
His Ser Ile Gly Leu Ala Gln Leu Leu Leu Phe Ala Gln Gln Ile Cys
            995                 1000                1005
Glu Gly Met Ala Tyr Leu His Ala Gln His Tyr Ile His Arg Asp
    1010                1015                1020
Leu Ala Ala Arg Asn Val Leu Leu Asp Asn Asp Arg Leu Val Lys
    1025                1030                1035
Ile Gly Asp Phe Gly Leu Ala Lys Ala Val Pro Glu Gly His Glu
    1040                1045                1050
Tyr Tyr Arg Val Arg Glu Asp Gly Asp Ser Pro Val Phe Trp Tyr
    1055                1060                1065
Ala Pro Glu Cys Leu Lys Glu Tyr Lys Phe Tyr Tyr Ala Ser Asp
    1070                1075                1080
Val Trp Ser Phe Gly Val Thr Leu Tyr Glu Leu Leu Thr His Cys
    1085                1090                1095
Asp Ser Ser Gln Ser Pro Pro Thr Lys Phe Leu Glu Leu Ile Gly
    1100                1105                1110
Ile Ala Gln Gly Gln Met Thr Val Leu Arg Leu Thr Glu Leu Leu
    1115                1120                1125
Glu Arg Gly Glu Arg Leu Pro Arg Pro Asp Lys Cys Pro Cys Glu
    1130                1135                1140
```

```
Val Tyr His Leu Met Lys Asn Cys Trp Glu Thr Glu Ala Ser Phe
    1145                1150                1155

Arg Pro Thr Phe Glu Asn Leu Ile Pro Ile Leu Lys Thr Val His
    1160                1165                1170

Glu Lys Tyr Gln Gly Gln Ala Pro Ser Val Phe Ser Val Cys
    1175                1180                1185

<210> SEQ ID NO 16
<211> LENGTH: 821
<212> TYPE: PRT
<213> ORGANISM: HUMAN
<300> PUBLICATION INFORMATION:
<301> AUTHORS: Wang,Q., Zhang,Y. and Yang,H.S.
<302> TITLE: Pdcd4 knockdown up-regulates MAP4K1 expression and
       activation of
<303> JOURNAL: Biochim. Biophys. Acta
<304> VOLUME: 1823
<305> ISSUE: 10
<306> PAGES: 1807-1814
<307> DATE: 2012
<308> DATABASE ACCESSION NUMBER: NP_001036065
<309> DATABASE ENTRY DATE: 2014-01-11
<313> RELEVANT RESIDUES IN SEQ ID NO: (1)..(821)

<400> SEQUENCE: 16

Met Asp Val Val Asp Pro Asp Ile Phe Asn Arg Asp Pro Arg Asp His
1               5                   10                  15

Tyr Asp Leu Leu Gln Arg Leu Gly Gly Gly Thr Tyr Gly Glu Val Phe
            20                  25                  30

Lys Ala Arg Asp Lys Val Ser Gly Asp Leu Val Ala Leu Lys Met Val
        35                  40                  45

Lys Met Glu Pro Asp Asp Asp Val Ser Thr Leu Gln Lys Glu Ile Leu
    50                  55                  60

Ile Leu Lys Thr Cys Arg His Ala Asn Ile Val Ala Tyr His Gly Ser
65                  70                  75                  80

Tyr Leu Trp Leu Gln Lys Leu Trp Ile Cys Met Glu Phe Cys Gly Ala
                85                  90                  95

Gly Ser Leu Gln Asp Ile Tyr Gln Val Thr Gly Ser Leu Ser Glu Leu
            100                 105                 110

Gln Ile Ser Tyr Val Cys Arg Glu Val Leu Gln Gly Leu Ala Tyr Leu
        115                 120                 125

His Ser Gln Lys Lys Ile His Arg Asp Ile Lys Gly Ala Asn Ile Leu
    130                 135                 140

Ile Asn Asp Ala Gly Glu Val Arg Leu Ala Asp Phe Gly Ile Ser Ala
145                 150                 155                 160

Gln Ile Gly Ala Thr Leu Ala Arg Arg Leu Ser Phe Ile Gly Thr Pro
                165                 170                 175

Tyr Trp Met Ala Pro Glu Val Ala Ala Val Ala Leu Lys Gly Gly Tyr
            180                 185                 190

Asn Glu Leu Cys Asp Ile Trp Ser Leu Gly Ile Thr Ala Ile Glu Leu
        195                 200                 205

Ala Glu Leu Gln Pro Pro Leu Phe Asp Val His Pro Leu Arg Val Leu
    210                 215                 220

Phe Leu Met Thr Lys Ser Gly Tyr Gln Pro Pro Arg Leu Lys Glu Lys
225                 230                 235                 240

Gly Lys Trp Ser Ala Ala Phe His Asn Phe Ile Lys Val Thr Leu Thr
                245                 250                 255

Lys Ser Pro Lys Lys Arg Pro Ser Ala Thr Lys Met Leu Ser His Gln
            260                 265                 270
```

```
Leu Val Ser Gln Pro Gly Leu Asn Arg Gly Leu Ile Leu Asp Leu Leu
        275                 280                 285

Asp Lys Leu Lys Asn Pro Gly Lys Gly Pro Ser Ile Gly Asp Ile Glu
        290                 295                 300

Asp Glu Glu Pro Glu Leu Pro Pro Ala Ile Pro Arg Arg Ile Arg Ser
305                 310                 315                 320

Thr His Arg Ser Ser Leu Gly Ile Pro Asp Ala Asp Cys Cys Arg
                325                 330                 335

Arg His Met Glu Phe Arg Lys Leu Arg Gly Met Glu Thr Arg Pro Pro
                340                 345                 350

Ala Asn Thr Ala Arg Leu Gln Pro Pro Arg Asp Leu Arg Ser Ser Ser
                355                 360                 365

Pro Arg Lys Gln Leu Ser Glu Ser Ser Asp Asp Tyr Asp Val
        370                 375                 380

Asp Ile Pro Thr Pro Ala Glu Asp Thr Pro Pro Leu Pro Pro Lys
385                 390                 395                 400

Pro Lys Phe Arg Ser Pro Ser Asp Glu Gly Pro Gly Ser Met Gly Asp
                405                 410                 415

Asp Gly Gln Leu Ser Pro Gly Val Leu Val Arg Cys Ala Ser Gly Pro
                420                 425                 430

Pro Pro Asn Ser Pro Arg Pro Gly Pro Pro Ser Thr Ser Ser Pro
                435                 440                 445

His Leu Thr Ala His Ser Glu Pro Ser Leu Trp Asn Pro Pro Ser Arg
        450                 455                 460

Glu Leu Asp Lys Pro Pro Leu Leu Pro Pro Lys Lys Glu Lys Met Lys
465                 470                 475                 480

Arg Lys Gly Cys Ala Leu Leu Val Lys Leu Phe Asn Gly Cys Pro Leu
                485                 490                 495

Arg Ile His Ser Thr Ala Ala Trp Thr His Pro Ser Thr Lys Asp Gln
                500                 505                 510

His Leu Leu Leu Gly Ala Glu Glu Gly Ile Phe Ile Leu Asn Arg Asn
        515                 520                 525

Asp Gln Glu Ala Thr Leu Glu Met Leu Phe Pro Ser Arg Thr Thr Trp
        530                 535                 540

Val Tyr Ser Ile Asn Asn Val Leu Met Ser Leu Ser Gly Lys Thr Pro
545                 550                 555                 560

His Leu Tyr Ser His Ser Ile Leu Gly Leu Leu Glu Arg Lys Glu Thr
                565                 570                 575

Arg Ala Gly Asn Pro Ile Ala His Ile Ser Pro His Arg Leu Leu Ala
                580                 585                 590

Arg Lys Asn Met Val Ser Thr Lys Ile Gln Asp Thr Lys Gly Cys Arg
                595                 600                 605

Ala Cys Cys Val Ala Glu Gly Ala Ser Ser Gly Pro Phe Leu Cys
        610                 615                 620

Gly Ala Leu Glu Thr Ser Val Val Leu Leu Gln Trp Tyr Gln Pro Met
625                 630                 635                 640

Asn Lys Phe Leu Leu Val Arg Gln Val Leu Phe Pro Leu Pro Thr Pro
                645                 650                 655

Leu Ser Val Phe Ala Leu Leu Thr Gly Pro Gly Ser Glu Leu Pro Ala
                660                 665                 670

Val Cys Ile Gly Val Ser Pro Gly Arg Pro Gly Lys Ser Val Leu Phe
                675                 680                 685
```

```
His Thr Val Arg Phe Gly Ala Leu Ser Cys Trp Leu Gly Glu Met Ser
    690                 695                 700

Thr Glu His Arg Gly Pro Val Gln Val Thr Gln Val Glu Glu Asp Met
705                 710                 715                 720

Val Met Val Leu Met Asp Gly Ser Val Lys Leu Val Thr Pro Glu Gly
                725                 730                 735

Ser Pro Val Arg Gly Leu Arg Thr Pro Glu Ile Pro Met Thr Glu Ala
                740                 745                 750

Val Glu Ala Val Ala Met Val Gly Gly Gln Leu Gln Ala Phe Trp Lys
                755                 760                 765

His Gly Val Gln Val Trp Ala Leu Gly Ser Asp Gln Leu Leu Gln Glu
        770                 775                 780

Leu Arg Asp Pro Thr Leu Thr Phe Arg Leu Leu Gly Ser Pro Arg Pro
785                 790                 795                 800

Val Val Val Glu Thr Arg Pro Val Asp Asp Pro Thr Ala Pro Ser Asn
                805                 810                 815

Leu Tyr Ile Gln Glu
        820

<210> SEQ ID NO 17
<211> LENGTH: 947
<212> TYPE: PRT
<213> ORGANISM: HUMAN
<300> PUBLICATION INFORMATION:
<301> AUTHORS: Lin,X., Mu,Y., Cunningham,E.T. Jr., Marcu,K.B.,
      Geleziunas,R. and
<302> TITLE: Molecular determinants of NF-kappaB-inducing kinase action
<303> JOURNAL: Mol. Cell. Biol.
<304> VOLUME: 18
<305> ISSUE: 10
<306> PAGES: 5899-5907
<307> DATE: 1998
<308> DATABASE ACCESSION NUMBER: NP_003945
<309> DATABASE ENTRY DATE: 2014-02-09
<313> RELEVANT RESIDUES IN SEQ ID NO: (1)..(947)

<400> SEQUENCE: 17

Met Ala Val Met Glu Met Ala Cys Pro Gly Ala Pro Gly Ser Ala Val
1               5                   10                  15

Gly Gln Gln Lys Glu Leu Pro Lys Ala Lys Glu Lys Thr Pro Pro Leu
                20                  25                  30

Gly Lys Lys Gln Ser Ser Val Tyr Lys Leu Glu Ala Val Glu Lys Ser
            35                  40                  45

Pro Val Phe Cys Gly Lys Trp Glu Ile Leu Asn Asp Val Ile Thr Lys
50                  55                  60

Gly Thr Ala Lys Glu Gly Ser Glu Ala Gly Pro Ala Ala Ile Ser Ile
65                  70                  75                  80

Ile Ala Gln Ala Glu Cys Glu Asn Ser Gln Glu Phe Ser Pro Thr Phe
                85                  90                  95

Ser Glu Arg Ile Phe Ile Ala Gly Ser Lys Gln Tyr Ser Gln Ser Glu
            100                 105                 110

Ser Leu Asp Gln Ile Pro Asn Asn Val Ala His Ala Thr Glu Gly Lys
        115                 120                 125

Met Ala Arg Val Cys Trp Lys Gly Lys Arg Arg Ser Lys Ala Arg Lys
    130                 135                 140

Lys Arg Lys Lys Lys Ser Ser Lys Ser Leu Ala His Ala Gly Val Ala
145                 150                 155                 160

Leu Ala Lys Pro Leu Pro Arg Thr Pro Glu Gln Glu Ser Cys Thr Ile
                165                 170                 175
```

-continued

```
Pro Val Gln Glu Asp Glu Ser Pro Leu Gly Ala Pro Tyr Val Arg Asn
            180                 185                 190

Thr Pro Gln Phe Thr Lys Pro Leu Lys Glu Pro Gly Leu Gly Gln Leu
        195                 200                 205

Cys Phe Lys Gln Leu Gly Glu Gly Leu Arg Pro Ala Leu Pro Arg Ser
210                 215                 220

Glu Leu His Lys Leu Ile Ser Pro Leu Gln Cys Leu Asn His Val Trp
225                 230                 235                 240

Lys Leu His His Pro Gln Asp Gly Gly Pro Leu Pro Leu Pro Thr His
                245                 250                 255

Pro Phe Pro Tyr Ser Arg Leu Pro His Pro Phe Pro Phe His Pro Leu
            260                 265                 270

Gln Pro Trp Lys Pro His Pro Leu Glu Ser Phe Leu Gly Lys Leu Ala
        275                 280                 285

Cys Val Asp Ser Gln Lys Pro Leu Pro Asp Pro His Leu Ser Lys Leu
290                 295                 300

Ala Cys Val Asp Ser Pro Lys Pro Leu Pro Gly Pro His Leu Glu Pro
305                 310                 315                 320

Ser Cys Leu Ser Arg Gly Ala His Glu Lys Phe Ser Val Glu Glu Tyr
                325                 330                 335

Leu Val His Ala Leu Gln Gly Ser Val Ser Ser Gly Gln Ala His Ser
            340                 345                 350

Leu Thr Ser Leu Ala Lys Thr Trp Ala Ala Arg Gly Ser Arg Ser Arg
        355                 360                 365

Glu Pro Ser Pro Lys Thr Glu Asp Asn Glu Gly Val Leu Leu Thr Glu
370                 375                 380

Lys Leu Lys Pro Val Asp Tyr Glu Tyr Arg Glu Glu Val His Trp Ala
385                 390                 395                 400

Thr His Gln Leu Arg Leu Gly Arg Gly Ser Phe Gly Glu Val His Arg
                405                 410                 415

Met Glu Asp Lys Gln Thr Gly Phe Gln Cys Ala Val Lys Lys Val Arg
            420                 425                 430

Leu Glu Val Phe Arg Ala Glu Glu Leu Met Ala Cys Ala Gly Leu Thr
        435                 440                 445

Ser Pro Arg Ile Val Pro Leu Tyr Gly Ala Val Arg Glu Gly Pro Trp
450                 455                 460

Val Asn Ile Phe Met Glu Leu Leu Glu Gly Gly Ser Leu Gly Gln Leu
465                 470                 475                 480

Val Lys Glu Gln Gly Cys Leu Pro Glu Asp Arg Ala Leu Tyr Tyr Leu
                485                 490                 495

Gly Gln Ala Leu Glu Gly Leu Glu Tyr Leu His Ser Arg Arg Ile Leu
            500                 505                 510

His Gly Asp Val Lys Ala Asp Asn Val Leu Leu Ser Ser Asp Gly Ser
        515                 520                 525

His Ala Ala Leu Cys Asp Phe Gly His Ala Val Cys Leu Gln Pro Asp
530                 535                 540

Gly Leu Gly Lys Ser Leu Leu Thr Gly Asp Tyr Ile Pro Gly Thr Glu
545                 550                 555                 560

Thr His Met Ala Pro Glu Val Val Leu Gly Arg Ser Cys Asp Ala Lys
                565                 570                 575

Val Asp Val Trp Ser Ser Cys Cys Met Met Leu His Met Leu Asn Gly
            580                 585                 590
```

```
Cys His Pro Trp Thr Gln Phe Phe Arg Gly Pro Leu Cys Leu Lys Ile
            595                 600                 605

Ala Ser Glu Pro Pro Val Arg Glu Ile Pro Ser Cys Ala Pro
610                 615                 620

Leu Thr Ala Gln Ala Ile Gln Glu Gly Leu Arg Lys Glu Pro Ile His
625                 630                 635                 640

Arg Val Ser Ala Ala Glu Leu Gly Gly Lys Val Asn Arg Ala Leu Gln
                645                 650                 655

Gln Val Gly Gly Leu Lys Ser Pro Trp Arg Gly Glu Tyr Lys Glu Pro
            660                 665                 670

Arg His Pro Pro Pro Asn Gln Ala Asn Tyr His Gln Thr Leu His Ala
        675                 680                 685

Gln Pro Arg Glu Leu Ser Pro Arg Ala Pro Gly Pro Arg Pro Ala Glu
    690                 695                 700

Glu Thr Thr Gly Arg Ala Pro Lys Leu Gln Pro Pro Leu Pro Pro Glu
705                 710                 715                 720

Pro Pro Glu Pro Asn Lys Ser Pro Pro Leu Thr Leu Ser Lys Glu Glu
                725                 730                 735

Ser Gly Met Trp Glu Pro Leu Pro Leu Ser Ser Leu Glu Pro Ala Pro
            740                 745                 750

Ala Arg Asn Pro Ser Ser Pro Glu Arg Lys Ala Thr Val Pro Glu Gln
        755                 760                 765

Glu Leu Gln Gln Leu Glu Ile Glu Leu Phe Leu Asn Ser Leu Ser Gln
    770                 775                 780

Pro Phe Ser Leu Glu Glu Gln Glu Gln Ile Leu Ser Cys Leu Ser Ile
785                 790                 795                 800

Asp Ser Leu Ser Leu Ser Asp Asp Ser Glu Lys Asn Pro Ser Lys Ala
                805                 810                 815

Ser Gln Ser Ser Arg Asp Thr Leu Ser Ser Gly Val His Ser Trp Ser
            820                 825                 830

Ser Gln Ala Glu Ala Arg Ser Ser Trp Asn Met Val Leu Ala Arg
        835                 840                 845

Gly Arg Pro Thr Asp Thr Pro Ser Tyr Phe Asn Gly Val Lys Val Gln
850                 855                 860

Ile Gln Ser Leu Asn Gly Glu His Leu His Ile Arg Glu Phe His Arg
865                 870                 875                 880

Val Lys Val Gly Asp Ile Ala Thr Gly Ile Ser Ser Gln Ile Pro Ala
                885                 890                 895

Ala Ala Phe Ser Leu Val Thr Lys Asp Gly Gln Pro Val Arg Tyr Asp
            900                 905                 910

Met Glu Val Pro Asp Ser Gly Ile Asp Leu Gln Cys Thr Leu Ala Pro
        915                 920                 925

Asp Gly Ser Phe Ala Trp Ser Trp Arg Val Lys His Gly Gln Leu Glu
930                 935                 940

Asn Arg Pro
945

<210> SEQ ID NO 18
<211> LENGTH: 676
<212> TYPE: PRT
<213> ORGANISM: HUMAN
<300> PUBLICATION INFORMATION:
<301> AUTHORS: Li,W., Zhang,J., Bottaro,D.P. and Pierce,J.H.
<302> TITLE: Identification of serine 643 of protein kinase C-delta as
      an
<303> JOURNAL: J. Biol. Chem.
```

```
<304> VOLUME: 272
<305> ISSUE: 39
<306> PAGES: 24550-24555
<307> DATE: 1997
<308> DATABASE ACCESSION NUMBER: NP_997704
<309> DATABASE ENTRY DATE: 2014-02-01
<313> RELEVANT RESIDUES IN SEQ ID NO: (1)..(676)

<400> SEQUENCE: 18
```

Met Ala Pro Phe Leu Arg Ile Ala Phe Asn Ser Tyr Glu Leu Gly Ser
1               5                   10                  15

Leu Gln Ala Glu Asp Glu Ala Asn Gln Pro Phe Cys Ala Val Lys Met
            20                  25                  30

Lys Glu Ala Leu Ser Thr Glu Arg Gly Lys Thr Leu Val Gln Lys Lys
        35                  40                  45

Pro Thr Met Tyr Pro Glu Trp Lys Ser Thr Phe Asp Ala His Ile Tyr
    50                  55                  60

Glu Gly Arg Val Ile Gln Ile Val Leu Met Arg Ala Ala Glu Pro
65                  70                  75                  80

Val Ser Glu Val Thr Val Gly Val Ser Val Leu Ala Glu Arg Cys Lys
                85                  90                  95

Lys Asn Asn Gly Lys Ala Glu Phe Trp Leu Asp Leu Gln Pro Gln Ala
            100                 105                 110

Lys Val Leu Met Ser Val Gln Tyr Phe Leu Glu Asp Val Asp Cys Lys
        115                 120                 125

Gln Ser Met Arg Ser Glu Asp Glu Ala Lys Phe Pro Thr Met Asn Arg
    130                 135                 140

Arg Gly Ala Ile Lys Gln Ala Lys Ile His Tyr Ile Lys Asn His Glu
145                 150                 155                 160

Phe Ile Ala Thr Phe Phe Gly Gln Pro Thr Phe Cys Ser Val Cys Lys
                165                 170                 175

Asp Phe Val Trp Gly Leu Asn Lys Gln Gly Tyr Lys Cys Arg Gln Cys
            180                 185                 190

Asn Ala Ala Ile His Lys Lys Cys Ile Asp Lys Ile Ile Gly Arg Cys
        195                 200                 205

Thr Gly Thr Ala Ala Asn Ser Arg Asp Thr Ile Phe Gln Lys Glu Arg
    210                 215                 220

Phe Asn Ile Asp Met Pro His Arg Phe Lys Val His Asn Tyr Met Ser
225                 230                 235                 240

Pro Thr Phe Cys Asp His Cys Gly Ser Leu Leu Trp Gly Leu Val Lys
                245                 250                 255

Gln Gly Leu Lys Cys Glu Asp Cys Gly Met Asn Val His His Lys Cys
            260                 265                 270

Arg Glu Lys Val Ala Asn Leu Cys Gly Ile Asn Gln Lys Leu Leu Ala
        275                 280                 285

Glu Ala Leu Asn Gln Val Thr Gln Arg Ala Ser Arg Arg Ser Asp Ser
    290                 295                 300

Ala Ser Ser Glu Pro Val Gly Ile Tyr Gln Gly Phe Glu Lys Lys Thr
305                 310                 315                 320

Gly Val Ala Gly Glu Asp Met Gln Asp Asn Ser Gly Thr Tyr Gly Lys
                325                 330                 335

Ile Trp Glu Gly Ser Ser Lys Cys Asn Ile Asn Asn Phe Ile Phe His
            340                 345                 350

Lys Val Leu Gly Lys Gly Ser Phe Gly Lys Val Leu Leu Gly Glu Leu
        355                 360                 365

```
Lys Gly Arg Gly Glu Tyr Phe Ala Ile Lys Ala Leu Lys Lys Asp Val
    370                 375                 380
Val Leu Ile Asp Asp Val Glu Cys Thr Met Val Glu Lys Arg Val
385                 390                 395                 400
Leu Thr Leu Ala Ala Glu Asn Pro Phe Leu Thr His Leu Ile Cys Thr
                405                 410                 415
Phe Gln Thr Lys Asp His Leu Phe Phe Val Met Glu Phe Leu Asn Gly
            420                 425                 430
Gly Asp Leu Met Tyr His Ile Gln Asp Lys Gly Arg Phe Glu Leu Tyr
            435                 440                 445
Arg Ala Thr Phe Tyr Ala Ala Glu Ile Met Cys Gly Leu Gln Phe Leu
        450                 455                 460
His Ser Lys Gly Ile Ile Tyr Arg Asp Leu Lys Leu Asp Asn Val Leu
465                 470                 475                 480
Leu Asp Arg Asp Gly His Ile Lys Ile Ala Asp Phe Gly Met Cys Lys
                485                 490                 495
Glu Asn Ile Phe Gly Glu Ser Arg Ala Ser Thr Phe Cys Gly Thr Pro
            500                 505                 510
Asp Tyr Ile Ala Pro Glu Ile Leu Gln Gly Leu Lys Tyr Thr Phe Ser
            515                 520                 525
Val Asp Trp Trp Ser Phe Gly Val Leu Leu Tyr Glu Met Leu Ile Gly
        530                 535                 540
Gln Ser Pro Phe His Gly Asp Asp Glu Asp Glu Leu Phe Glu Ser Ile
545                 550                 555                 560
Arg Val Asp Thr Pro His Tyr Pro Arg Trp Ile Thr Lys Glu Ser Lys
                565                 570                 575
Asp Ile Leu Glu Lys Leu Phe Glu Arg Glu Pro Thr Lys Arg Leu Gly
            580                 585                 590
Val Thr Gly Asn Ile Lys Ile His Pro Phe Phe Lys Thr Ile Asn Trp
            595                 600                 605
Thr Leu Leu Glu Lys Arg Arg Leu Glu Pro Pro Phe Arg Pro Lys Val
        610                 615                 620
Lys Ser Pro Arg Asp Tyr Ser Asn Phe Asp Gln Glu Phe Leu Asn Glu
625                 630                 635                 640
Lys Ala Arg Leu Ser Tyr Ser Asp Lys Asn Leu Ile Asp Ser Met Asp
                645                 650                 655
Gln Ser Ala Phe Ala Gly Phe Ser Phe Val Asn Pro Lys Phe Glu His
            660                 665                 670
Leu Leu Glu Asp
        675
```

<210> SEQ ID NO 19
<211> LENGTH: 745
<212> TYPE: PRT
<213> ORGANISM: HUMAN
<300> PUBLICATION INFORMATION:
<301> AUTHORS: Dummler,B.A., Hauge,C., Silber,J., Yntema,H.G., Kruse,L.S.,
<302> TITLE: Functional characterization of human RSK4, a new 90-kDa ribosomal
<303> JOURNAL: J. Biol. Chem.
<304> VOLUME: 280
<305> ISSUE: 14
<306> PAGES: 13304-13314
<307> DATE: 2005
<308> DATABASE ACCESSION NUMBER: NP_055311
<309> DATABASE ENTRY DATE: 2014-02-03
<313> RELEVANT RESIDUES IN SEQ ID NO: (1)..(745)

<400> SEQUENCE: 19

```
Met Leu Pro Phe Ala Pro Gln Asp Glu Pro Trp Asp Arg Glu Met Glu
1               5                   10                  15

Val Phe Ser Gly Gly Ala Ser Gly Glu Val Asn Gly Leu Lys
            20                  25                  30

Met Val Asp Glu Pro Met Glu Gly Glu Ala Asp Ser Cys His Asp
        35                  40                  45

Glu Gly Val Val Lys Glu Ile Pro Ile Thr His His Val Lys Glu Gly
        50                  55                  60

Tyr Glu Lys Ala Asp Pro Ala Gln Phe Glu Leu Leu Lys Val Leu Gly
65                  70                  75                  80

Gln Gly Ser Phe Gly Lys Val Phe Leu Val Arg Lys Lys Thr Gly Pro
                85                  90                  95

Asp Ala Gly Gln Leu Tyr Ala Met Lys Val Leu Lys Lys Ala Ser Leu
            100                 105                 110

Lys Val Arg Asp Arg Val Arg Thr Lys Met Glu Arg Asp Ile Leu Val
        115                 120                 125

Glu Val Asn His Pro Phe Ile Val Lys Leu His Tyr Ala Phe Gln Thr
130                 135                 140

Glu Gly Lys Leu Tyr Leu Ile Leu Asp Phe Leu Arg Gly Gly Asp Val
145                 150                 155                 160

Phe Thr Arg Leu Ser Lys Glu Val Leu Phe Thr Glu Glu Asp Val Lys
                165                 170                 175

Phe Tyr Leu Ala Glu Leu Ala Leu Ala Leu Asp His Leu His Gln Leu
            180                 185                 190

Gly Ile Val Tyr Arg Asp Leu Lys Pro Glu Asn Ile Leu Leu Asp Glu
        195                 200                 205

Ile Gly His Ile Lys Leu Thr Asp Phe Gly Leu Ser Lys Glu Ser Val
210                 215                 220

Asp Gln Glu Lys Lys Ala Tyr Ser Phe Cys Gly Thr Val Glu Tyr Met
225                 230                 235                 240

Ala Pro Glu Val Val Asn Arg Arg Gly His Ser Gln Ser Ala Asp Trp
                245                 250                 255

Trp Ser Tyr Gly Val Leu Met Phe Glu Met Leu Thr Gly Thr Leu Pro
            260                 265                 270

Phe Gln Gly Lys Asp Arg Asn Glu Thr Met Asn Met Ile Leu Lys Ala
        275                 280                 285

Lys Leu Gly Met Pro Gln Phe Leu Ser Ala Glu Ala Gln Ser Leu Leu
290                 295                 300

Arg Met Leu Phe Lys Arg Asn Pro Ala Asn Arg Leu Gly Ser Glu Gly
305                 310                 315                 320

Val Glu Glu Ile Lys Arg His Leu Phe Phe Ala Asn Ile Asp Trp Asp
                325                 330                 335

Lys Leu Tyr Lys Arg Glu Val Gln Pro Pro Phe Lys Pro Ala Ser Gly
            340                 345                 350

Lys Pro Asp Asp Thr Phe Cys Phe Asp Pro Glu Phe Thr Ala Lys Thr
        355                 360                 365

Pro Lys Asp Ser Pro Gly Leu Pro Ala Ser Ala Asn Ala His Gln Leu
370                 375                 380

Phe Lys Gly Phe Ser Phe Val Ala Thr Ser Ile Ala Glu Glu Tyr Lys
385                 390                 395                 400

Ile Thr Pro Ile Thr Ser Ala Asn Val Leu Pro Ile Val Gln Ile Asn
                405                 410                 415
```

Gly Asn Ala Ala Gln Phe Gly Glu Val Tyr Glu Leu Lys Glu Asp Ile
            420                 425                 430

Gly Val Gly Ser Tyr Ser Val Cys Lys Arg Cys Ile His Ala Thr Thr
        435                 440                 445

Asn Met Glu Phe Ala Val Lys Ile Ile Asp Lys Ser Lys Arg Asp Pro
450                 455                 460

Ser Glu Glu Ile Glu Ile Leu Met Arg Tyr Gly Gln His Pro Asn Ile
465                 470                 475                 480

Ile Thr Leu Lys Asp Val Phe Asp Asp Gly Arg Tyr Val Tyr Leu Val
            485                 490                 495

Thr Asp Leu Met Lys Gly Gly Glu Leu Leu Asp Arg Ile Leu Lys Gln
        500                 505                 510

Lys Cys Phe Ser Glu Arg Glu Ala Ser Asp Ile Leu Tyr Val Ile Ser
    515                 520                 525

Lys Thr Val Asp Tyr Leu His Cys Gln Gly Val Val His Arg Asp Leu
530                 535                 540

Lys Pro Ser Asn Ile Leu Tyr Met Asp Glu Ser Ala Ser Ala Asp Ser
545                 550                 555                 560

Ile Arg Ile Cys Asp Phe Gly Phe Ala Lys Gln Leu Arg Gly Glu Asn
            565                 570                 575

Gly Leu Leu Leu Thr Pro Cys Tyr Thr Ala Asn Phe Val Ala Pro Glu
        580                 585                 590

Val Leu Met Gln Gln Gly Tyr Asp Ala Ala Cys Asp Ile Trp Ser Leu
    595                 600                 605

Gly Val Leu Phe Tyr Thr Met Leu Ala Gly Tyr Thr Pro Phe Ala Asn
610                 615                 620

Gly Pro Asn Asp Thr Pro Glu Glu Ile Leu Leu Arg Ile Gly Asn Gly
625                 630                 635                 640

Lys Phe Ser Leu Ser Gly Gly Asn Trp Asp Asn Ile Ser Asp Gly Ala
            645                 650                 655

Lys Asp Leu Leu Ser His Met Leu His Met Asp Pro His Gln Arg Tyr
        660                 665                 670

Thr Ala Glu Gln Ile Leu Lys His Ser Trp Ile Thr His Arg Asp Gln
    675                 680                 685

Leu Pro Asn Asp Gln Pro Lys Arg Asn Asp Val Ser His Val Val Lys
690                 695                 700

Gly Ala Met Val Ala Thr Tyr Ser Ala Leu Thr His Lys Thr Phe Gln
705                 710                 715                 720

Pro Val Leu Glu Pro Val Ala Ala Ser Ser Leu Ala Gln Arg Arg Ser
            725                 730                 735

Met Lys Lys Arg Thr Ser Thr Gly Leu
        740                 745

<210> SEQ ID NO 20
<211> LENGTH: 841
<212> TYPE: PRT
<213> ORGANISM: HUMAN
<300> PUBLICATION INFORMATION:
<301> AUTHORS: Levedakou EN, He M, Baptist EW, Craven RJ, Cance WG,
      Welcsh PL,
<302> TITLE: Two novel human serine/threonine kinases with homologies to
      the
<303> JOURNAL: ncogene
<304> VOLUME: 9
<305> ISSUE: 7
<306> PAGES: 1977-1988
<307> DATE: 1994

<308> DATABASE ACCESSION NUMBER: NP_003148
<309> DATABASE ENTRY DATE: 2014-02-03
<313> RELEVANT RESIDUES IN SEQ ID NO: (1)..(841)

<400> SEQUENCE: 20

```
Met Pro Leu Ala Ala Tyr Cys Tyr Leu Arg Val Gly Lys Gly Ser
1               5                   10                  15

Tyr Gly Glu Val Thr Leu Val Lys His Arg Arg Asp Gly Lys Gln Tyr
                20                  25                  30

Val Ile Lys Lys Leu Asn Leu Arg Asn Ala Ser Ser Arg Glu Arg Arg
            35                  40                  45

Ala Ala Glu Gln Glu Ala Gln Leu Leu Ser Gln Leu Lys His Pro Asn
        50                  55                  60

Ile Val Thr Tyr Lys Glu Ser Trp Glu Gly Gly Asp Gly Leu Leu Tyr
65                  70                  75                  80

Ile Val Met Gly Phe Cys Glu Gly Gly Asp Leu Tyr Arg Lys Leu Lys
                85                  90                  95

Glu Gln Lys Gly Gln Leu Leu Pro Glu Asn Gln Val Val Glu Trp Phe
            100                 105                 110

Val Gln Ile Ala Met Ala Leu Gln Tyr Leu His Glu Lys His Ile Leu
        115                 120                 125

His Arg Asp Leu Lys Thr Gln Asn Val Phe Leu Thr Arg Thr Asn Ile
    130                 135                 140

Ile Lys Val Gly Asp Leu Gly Ile Ala Arg Val Leu Glu Asn His Cys
145                 150                 155                 160

Asp Met Ala Ser Thr Leu Ile Gly Thr Pro Tyr Tyr Met Ser Pro Glu
                165                 170                 175

Leu Phe Ser Asn Lys Pro Tyr Asn Tyr Lys Ser Asp Val Trp Ala Leu
            180                 185                 190

Gly Cys Cys Val Tyr Glu Met Ala Thr Leu Lys His Ala Phe Asn Ala
        195                 200                 205

Lys Asp Met Asn Ser Leu Val Tyr Arg Ile Ile Glu Gly Lys Leu Pro
    210                 215                 220

Pro Met Pro Arg Asp Tyr Ser Pro Glu Leu Ala Glu Leu Ile Arg Thr
225                 230                 235                 240

Met Leu Ser Lys Arg Pro Glu Glu Arg Pro Ser Val Arg Ser Ile Leu
                245                 250                 255

Arg Gln Pro Tyr Ile Lys Arg Gln Ile Ser Phe Phe Leu Glu Ala Thr
            260                 265                 270

Lys Ile Lys Thr Ser Lys Asn Asn Ile Lys Asn Gly Asp Ser Gln Ser
        275                 280                 285

Lys Pro Phe Ala Thr Val Val Ser Gly Glu Ala Glu Ser Asn His Glu
    290                 295                 300

Val Ile His Pro Gln Pro Leu Ser Ser Glu Gly Ser Gln Thr Tyr Ile
305                 310                 315                 320

Met Gly Glu Gly Lys Cys Leu Ser Gln Gly Lys Pro Arg Ala Ser Gly
                325                 330                 335

Leu Leu Lys Ser Pro Ala Ser Leu Lys Ala His Thr Cys Lys Gln Asp
            340                 345                 350

Leu Ser Asn Thr Thr Glu Leu Ala Thr Ile Ser Ser Val Asn Ile Asp
        355                 360                 365

Ile Leu Pro Ala Lys Gly Arg Asp Ser Val Ser Asp Gly Phe Val Gln
    370                 375                 380

Glu Asn Gln Pro Arg Tyr Leu Asp Ala Ser Asn Glu Leu Gly Gly Ile
```

```
385                 390                 395                 400
Cys Ser Ile Ser Gln Val Glu Glu Met Leu Gln Asp Asn Thr Lys
                405                 410                 415
Ser Ser Ala Gln Pro Glu Asn Leu Ile Pro Met Trp Ser Ser Asp Ile
                420                 425                 430
Val Thr Gly Glu Lys Asn Glu Pro Val Lys Pro Leu Gln Pro Leu Ile
                435                 440                 445
Lys Glu Gln Lys Pro Lys Asp Gln Ser Leu Ala Leu Ser Pro Lys Leu
            450                 455                 460
Glu Cys Ser Gly Thr Ile Leu Ala His Ser Asn Leu Arg Leu Leu Gly
465                 470                 475                 480
Ser Ser Asp Ser Pro Ala Ser Ala Ser Arg Val Ala Gly Ile Thr Gly
                485                 490                 495
Val Cys His His Ala Gln Asp Gln Val Ala Gly Glu Cys Ile Ile Glu
                500                 505                 510
Lys Gln Gly Arg Ile His Pro Asp Leu Gln Pro His Asn Ser Gly Ser
            515                 520                 525
Glu Pro Ser Leu Ser Arg Gln Arg Arg Gln Lys Arg Glu Gln Thr
            530                 535                 540
Glu His Arg Gly Glu Lys Arg Gln Val Arg Arg Asp Leu Phe Ala Phe
545                 550                 555                 560
Gln Glu Ser Pro Pro Arg Phe Leu Pro Ser His Pro Ile Val Gly Lys
                565                 570                 575
Val Asp Val Thr Ser Thr Gln Lys Glu Ala Glu Asn Gln Arg Arg Val
                580                 585                 590
Val Thr Gly Ser Val Ser Ser Arg Ser Ser Glu Met Ser Ser Ser
            595                 600                 605
Lys Asp Arg Pro Leu Ser Ala Arg Glu Arg Arg Leu Lys Gln Ser
            610                 615                 620
Gln Glu Glu Met Ser Ser Ser Gly Pro Ser Val Arg Lys Ala Ser Leu
625                 630                 635                 640
Ser Val Ala Gly Pro Gly Lys Pro Gln Glu Glu Asp Gln Pro Leu Pro
                645                 650                 655
Ala Arg Arg Leu Ser Ser Asp Cys Ser Val Thr Gln Glu Arg Lys Gln
                660                 665                 670
Ile His Cys Leu Ser Glu Asp Glu Leu Ser Ser Thr Ser Ser Thr
            675                 680                 685
Asp Lys Ser Asp Gly Asp Tyr Gly Glu Gly Lys Gly Gln Thr Asn Glu
            690                 695                 700
Ile Asn Ala Leu Val Gln Leu Met Thr Gln Thr Leu Lys Leu Asp Ser
705                 710                 715                 720
Lys Glu Ser Cys Glu Asp Val Pro Val Ala Asn Pro Val Ser Glu Phe
                725                 730                 735
Lys Leu His Arg Lys Tyr Arg Asp Thr Leu Ile Leu His Gly Lys Val
                740                 745                 750
Ala Glu Glu Ala Glu Glu Ile His Phe Lys Glu Leu Pro Ser Ala Ile
            755                 760                 765
Met Pro Gly Ser Glu Lys Ile Arg Arg Leu Val Glu Val Leu Arg Thr
770                 775                 780
Asp Val Ile Arg Gly Leu Gly Val Gln Leu Leu Glu Gln Val Tyr Asp
785                 790                 795                 800
Leu Leu Glu Glu Glu Asp Glu Phe Asp Arg Glu Val Arg Leu Arg Glu
            805                 810                 815
```

```
His Met Gly Glu Lys Tyr Thr Thr Tyr Ser Val Lys Ala Arg Gln Leu
                820                 825                 830

Lys Phe Phe Glu Glu Asn Met Asn Phe
            835                 840

<210> SEQ ID NO 21
<211> LENGTH: 491
<212> TYPE: PRT
<213> ORGANISM: HUMAN
<300> PUBLICATION INFORMATION:
<301> AUTHORS: Creasy,C.L. and Chernoff,J.
<302> TITLE: Cloning and characterization of a human protein kinase with
<303> JOURNAL: J. Biol. Chem.
<304> VOLUME: 270
<305> ISSUE: 37
<306> PAGES: 21695-21700
<307> DATE: 1995
<308> DATABASE ACCESSION NUMBER: NP_006272
<309> DATABASE ENTRY DATE: 2014-01-11
<313> RELEVANT RESIDUES IN SEQ ID NO: (1)..(491)

<400> SEQUENCE: 21

Met Glu Gln Pro Pro Ala Pro Lys Ser Lys Leu Lys Lys Leu Ser Glu
1               5                   10                  15

Asp Ser Leu Thr Lys Gln Pro Glu Glu Val Phe Asp Val Leu Glu Lys
            20                  25                  30

Leu Gly Glu Gly Ser Tyr Gly Ser Val Phe Lys Ala Ile His Lys Glu
        35                  40                  45

Ser Gly Gln Val Val Ala Ile Lys Gln Val Pro Val Glu Ser Asp Leu
    50                  55                  60

Gln Glu Ile Ile Lys Glu Ile Ser Ile Met Gln Gln Cys Asp Ser Pro
65                  70                  75                  80

Tyr Val Val Lys Tyr Tyr Gly Ser Tyr Phe Lys Asn Thr Asp Leu Trp
                85                  90                  95

Ile Val Met Glu Tyr Cys Gly Ala Gly Ser Val Ser Asp Ile Ile Arg
            100                 105                 110

Leu Arg Asn Lys Thr Leu Ile Glu Asp Glu Ile Ala Thr Ile Leu Lys
        115                 120                 125

Ser Thr Leu Lys Gly Leu Glu Tyr Leu His Phe Met Arg Lys Ile His
    130                 135                 140

Arg Asp Ile Lys Ala Gly Asn Ile Leu Leu Asn Thr Glu Gly His Ala
145                 150                 155                 160

Lys Leu Ala Asp Phe Gly Val Ala Gly Gln Leu Thr Asp Thr Met Ala
                165                 170                 175

Lys Arg Asn Thr Val Ile Gly Thr Pro Phe Trp Met Ala Pro Glu Val
            180                 185                 190

Ile Gln Glu Ile Gly Tyr Asn Cys Val Ala Asp Ile Trp Ser Leu Gly
        195                 200                 205

Ile Thr Ser Ile Glu Met Ala Glu Gly Lys Pro Pro Tyr Ala Asp Ile
    210                 215                 220

His Pro Met Arg Ala Ile Phe Met Ile Pro Thr Asn Pro Pro Pro Thr
225                 230                 235                 240

Phe Arg Lys Pro Glu Leu Trp Ser Asp Asp Phe Thr Asp Phe Val Lys
                245                 250                 255

Lys Cys Leu Val Lys Asn Pro Glu Gln Arg Ala Thr Ala Thr Gln Leu
            260                 265                 270

Leu Gln His Pro Phe Ile Lys Asn Ala Lys Pro Val Ser Ile Leu Arg
        275                 280                 285
```

-continued

```
Asp Leu Ile Thr Glu Ala Met Glu Ile Lys Ala Lys Arg His Glu Glu
            290                 295                 300

Gln Gln Arg Glu Leu Glu Glu Glu Glu Asn Ser Asp Glu Asp Glu
305                 310                 315                 320

Leu Asp Ser His Thr Met Val Lys Thr Ser Val Glu Ser Val Gly Thr
                325                 330                 335

Met Arg Ala Thr Ser Thr Met Ser Glu Gly Ala Gln Thr Met Ile Glu
            340                 345                 350

His Asn Ser Thr Met Leu Glu Ser Asp Leu Gly Thr Met Val Ile Asn
        355                 360                 365

Ser Glu Asp Glu Glu Glu Asp Gly Thr Met Lys Arg Asn Ala Thr
370                 375                 380

Ser Pro Gln Val Gln Arg Pro Ser Phe Met Asp Tyr Phe Asp Lys Gln
385                 390                 395                 400

Asp Phe Lys Asn Lys Ser His Glu Asn Cys Asn Gln Asn Met His Glu
                405                 410                 415

Pro Phe Pro Met Ser Lys Asn Val Phe Pro Asp Asn Trp Lys Val Pro
            420                 425                 430

Gln Asp Gly Asp Phe Asp Phe Leu Lys Asn Leu Ser Leu Glu Glu Leu
        435                 440                 445

Gln Met Arg Leu Lys Ala Leu Asp Pro Met Met Glu Arg Glu Ile Glu
    450                 455                 460

Glu Leu Arg Gln Arg Tyr Thr Ala Lys Arg Gln Pro Ile Leu Asp Ala
465                 470                 475                 480

Met Asp Ala Lys Lys Arg Arg Gln Gln Asn Phe
                485                 490
```

<210> SEQ ID NO 22
<211> LENGTH: 487
<212> TYPE: PRT
<213> ORGANISM: HUMAN
<300> PUBLICATION INFORMATION:
<301> AUTHORS: Abdollahpour H, Appaswamy G, Kotlarz D, Diestelhorst J,
      Beier R,
<302> TITLE: The phenotype of human STK4 deficiency
<303> JOURNAL: Blood
<304> VOLUME: 119
<305> ISSUE: 15
<306> PAGES: 3450-3457
<307> DATE: 2012
<308> DATABASE ACCESSION NUMBER: NP_006273
<309> DATABASE ENTRY DATE: 2014-01-26
<313> RELEVANT RESIDUES IN SEQ ID NO: (1)..(487)

<400> SEQUENCE: 22

```
Met Glu Thr Val Gln Leu Arg Asn Pro Pro Arg Arg Gln Leu Lys Lys
1               5                   10                  15

Leu Asp Glu Asp Ser Leu Thr Lys Gln Pro Glu Glu Val Phe Asp Val
            20                  25                  30

Leu Glu Lys Leu Gly Glu Gly Ser Tyr Gly Ser Val Tyr Lys Ala Ile
        35                  40                  45

His Lys Glu Thr Gly Gln Ile Val Ala Ile Lys Gln Val Pro Val Glu
    50                  55                  60

Ser Asp Leu Gln Glu Ile Ile Lys Glu Ile Ser Ile Met Gln Gln Cys
65                  70                  75                  80

Asp Ser Pro His Val Val Lys Tyr Tyr Gly Ser Tyr Phe Lys Asn Thr
                85                  90                  95

Asp Leu Trp Ile Val Met Glu Tyr Cys Gly Ala Gly Ser Val Ser Asp
```

```
                100             105             110
Ile Ile Arg Leu Arg Asn Lys Thr Leu Thr Glu Asp Glu Ile Ala Thr
            115                 120                 125
Ile Leu Gln Ser Thr Leu Lys Gly Leu Glu Tyr Leu His Phe Met Arg
        130                 135                 140
Lys Ile His Arg Asp Ile Lys Ala Gly Asn Ile Leu Leu Asn Thr Glu
145                 150                 155                 160
Gly His Ala Lys Leu Ala Asp Phe Gly Val Ala Gly Gln Leu Thr Asp
                165                 170                 175
Thr Met Ala Lys Arg Asn Thr Val Ile Gly Thr Pro Phe Trp Met Ala
            180                 185                 190
Pro Glu Val Ile Gln Glu Ile Gly Tyr Asn Cys Val Ala Asp Ile Trp
        195                 200                 205
Ser Leu Gly Ile Thr Ala Ile Glu Met Ala Glu Gly Lys Pro Pro Tyr
        210                 215                 220
Ala Asp Ile His Pro Met Arg Ala Ile Phe Met Ile Pro Thr Asn Pro
225                 230                 235                 240
Pro Pro Thr Phe Arg Lys Pro Glu Leu Trp Ser Asp Asn Phe Thr Asp
                245                 250                 255
Phe Val Lys Gln Cys Leu Val Lys Ser Pro Glu Gln Arg Ala Thr Ala
            260                 265                 270
Thr Gln Leu Leu Gln His Pro Phe Val Arg Ser Ala Lys Gly Val Ser
        275                 280                 285
Ile Leu Arg Asp Leu Ile Asn Glu Ala Met Asp Val Lys Leu Lys Arg
        290                 295                 300
Gln Glu Ser Gln Gln Arg Glu Val Asp Gln Asp Glu Glu Asn Ser
305                 310                 315                 320
Glu Glu Asp Glu Met Asp Ser Gly Thr Met Val Arg Ala Val Gly Asp
                325                 330                 335
Glu Met Gly Thr Val Arg Val Ala Ser Thr Met Thr Asp Gly Ala Asn
            340                 345                 350
Thr Met Ile Glu His Asp Asp Thr Leu Pro Ser Gln Leu Gly Thr Met
        355                 360                 365
Val Ile Asn Ala Glu Asp Glu Glu Glu Gly Thr Met Lys Arg Arg
        370                 375                 380
Asp Glu Thr Met Gln Pro Ala Lys Pro Ser Phe Leu Glu Tyr Phe Glu
385                 390                 395                 400
Gln Lys Glu Lys Glu Asn Gln Ile Asn Ser Phe Gly Lys Ser Val Pro
                405                 410                 415
Gly Pro Leu Lys Asn Ser Ser Asp Trp Lys Ile Pro Gln Asp Gly Asp
            420                 425                 430
Tyr Glu Phe Leu Lys Ser Trp Thr Val Glu Asp Leu Gln Lys Arg Leu
        435                 440                 445
Leu Ala Leu Asp Pro Met Met Glu Gln Glu Ile Glu Glu Ile Arg Gln
        450                 455                 460
Lys Tyr Gln Ser Lys Arg Gln Pro Ile Leu Asp Ala Ile Glu Ala Lys
465                 470                 475                 480
Lys Arg Arg Gln Gln Asn Phe
                485
```

<210> SEQ ID NO 23
<211> LENGTH: 968
<212> TYPE: PRT
<213> ORGANISM: HUMAN

```
<300> PUBLICATION INFORMATION:
<301> AUTHORS: Walter SA, Cutler RE Jr, Martinez R, Gishizky M and Hill
      RJ.
<302> TITLE: Stk10, a new member of the polo-like kinase kinase family
      highly
<303> JOURNAL: J. Biol. Chem.
<304> VOLUME: 278
<305> ISSUE: 20
<306> PAGES: 18221-18228
<307> DATE: 2003
<308> DATABASE ACCESSION NUMBER: NP_005981
<309> DATABASE ENTRY DATE: 2014-02-01
<313> RELEVANT RESIDUES IN SEQ ID NO: (1)..(968)

<400> SEQUENCE: 23
```

| | | | | | | | | | | | | | | |
|---|---|---|---|---|---|---|---|---|---|---|---|---|---|---|
| Met | Ala | Phe | Ala | Asn | Phe | Arg | Arg | Ile | Leu | Arg | Leu | Ser | Thr | Phe | Glu |
| 1 | | | | 5 | | | | | 10 | | | | | 15 | |
| Lys | Arg | Lys | Ser | Arg | Glu | Tyr | Glu | His | Val | Arg | Arg | Asp | Leu | Asp | Pro |
| | | | 20 | | | | | 25 | | | | | 30 | | |
| Asn | Glu | Val | Trp | Glu | Ile | Val | Gly | Glu | Leu | Gly | Asp | Gly | Ala | Phe | Gly |
| | | | 35 | | | | | 40 | | | | | 45 | | |
| Lys | Val | Tyr | Lys | Ala | Lys | Asn | Lys | Glu | Thr | Gly | Ala | Leu | Ala | Ala | Ala |
| | 50 | | | | | 55 | | | | | 60 | | | | |
| Lys | Val | Ile | Glu | Thr | Lys | Ser | Glu | Glu | Leu | Glu | Asp | Tyr | Ile | Val | |
| 65 | | | | | 70 | | | | | 75 | | | | | 80 |
| Glu | Ile | Glu | Ile | Leu | Ala | Thr | Cys | Asp | His | Pro | Tyr | Ile | Val | Lys | Leu |
| | | | | 85 | | | | | 90 | | | | | 95 | |
| Leu | Gly | Ala | Tyr | Tyr | His | Asp | Gly | Lys | Leu | Trp | Ile | Met | Ile | Glu | Phe |
| | | | 100 | | | | | 105 | | | | | 110 | | |
| Cys | Pro | Gly | Gly | Ala | Val | Asp | Ala | Ile | Met | Leu | Glu | Leu | Asp | Arg | Gly |
| | | | 115 | | | | | 120 | | | | | 125 | | |
| Leu | Thr | Glu | Pro | Gln | Ile | Gln | Val | Val | Cys | Arg | Gln | Met | Leu | Glu | Ala |
| | 130 | | | | | 135 | | | | | 140 | | | | |
| Leu | Asn | Phe | Leu | His | Ser | Lys | Arg | Ile | Ile | His | Arg | Asp | Leu | Lys | Ala |
| 145 | | | | | 150 | | | | | 155 | | | | | 160 |
| Gly | Asn | Val | Leu | Met | Thr | Leu | Glu | Gly | Asp | Ile | Arg | Leu | Ala | Asp | Phe |
| | | | | 165 | | | | | 170 | | | | | 175 | |
| Gly | Val | Ser | Ala | Lys | Asn | Leu | Lys | Thr | Leu | Gln | Lys | Arg | Asp | Ser | Phe |
| | | | 180 | | | | | 185 | | | | | 190 | | |
| Ile | Gly | Thr | Pro | Tyr | Trp | Met | Ala | Pro | Glu | Val | Val | Met | Cys | Glu | Thr |
| | | | 195 | | | | | 200 | | | | | 205 | | |
| Met | Lys | Asp | Thr | Pro | Tyr | Asp | Tyr | Lys | Ala | Asp | Ile | Trp | Ser | Leu | Gly |
| | 210 | | | | | 215 | | | | | 220 | | | | |
| Ile | Thr | Leu | Ile | Glu | Met | Ala | Gln | Ile | Glu | Pro | Pro | His | His | Glu | Leu |
| 225 | | | | | 230 | | | | | 235 | | | | | 240 |
| Asn | Pro | Met | Arg | Val | Leu | Leu | Lys | Ile | Ala | Lys | Ser | Asp | Pro | Pro | Thr |
| | | | | 245 | | | | | 250 | | | | | 255 | |
| Leu | Leu | Thr | Pro | Ser | Lys | Trp | Ser | Val | Glu | Phe | Arg | Asp | Phe | Leu | Lys |
| | | | 260 | | | | | 265 | | | | | 270 | | |
| Ile | Ala | Leu | Asp | Lys | Asn | Pro | Glu | Thr | Arg | Pro | Ser | Ala | Ala | Gln | Leu |
| | | | 275 | | | | | 280 | | | | | 285 | | |
| Leu | Glu | His | Pro | Phe | Val | Ser | Ser | Ile | Thr | Ser | Asn | Lys | Ala | Leu | Arg |
| | 290 | | | | | 295 | | | | | 300 | | | | |
| Glu | Leu | Val | Ala | Glu | Ala | Lys | Ala | Glu | Val | Met | Glu | Glu | Ile | Glu | Asp |
| 305 | | | | | 310 | | | | | 315 | | | | | 320 |
| Gly | Arg | Asp | Glu | Gly | Glu | Glu | Glu | Asp | Ala | Val | Asp | Ala | Ala | Ser | Thr |
| | | | | 325 | | | | | 330 | | | | | 335 | |

```
Leu Glu Asn His Thr Gln Asn Ser Ser Glu Val Ser Pro Pro Ser Leu
                340                 345                 350

Asn Ala Asp Lys Pro Leu Glu Glu Ser Pro Ser Thr Pro Leu Ala Pro
            355                 360                 365

Ser Gln Ser Gln Asp Ser Val Asn Glu Pro Cys Ser Gln Pro Ser Gly
        370                 375                 380

Asp Arg Ser Leu Gln Thr Thr Ser Pro Pro Val Val Ala Pro Gly Asn
385                 390                 395                 400

Glu Asn Gly Leu Ala Val Pro Val Pro Leu Arg Lys Ser Arg Pro Val
                405                 410                 415

Ser Met Asp Ala Arg Ile Gln Val Ala Gln Glu Lys Gln Val Ala Glu
                420                 425                 430

Gln Gly Gly Asp Leu Ser Pro Ala Ala Asn Arg Ser Gln Lys Ala Ser
            435                 440                 445

Gln Ser Arg Pro Asn Ser Ser Ala Leu Glu Thr Leu Gly Gly Glu Lys
        450                 455                 460

Leu Ala Asn Gly Ser Leu Glu Pro Pro Ala Gln Ala Pro Gly Pro
465                 470                 475                 480

Ser Lys Arg Asp Ser Asp Cys Ser Ser Leu Cys Thr Ser Glu Ser Met
                485                 490                 495

Asp Tyr Gly Thr Asn Leu Ser Thr Asp Leu Ser Leu Asn Lys Glu Met
            500                 505                 510

Gly Ser Leu Ser Ile Lys Asp Pro Lys Leu Tyr Lys Lys Thr Leu Lys
        515                 520                 525

Arg Thr Arg Lys Phe Val Val Asp Gly Val Glu Val Ser Ile Thr Thr
530                 535                 540

Ser Lys Ile Ile Ser Glu Asp Glu Lys Lys Asp Glu Glu Met Arg Phe
545                 550                 555                 560

Leu Arg Arg Gln Glu Leu Arg Glu Leu Arg Leu Leu Gln Lys Glu Glu
                565                 570                 575

His Arg Asn Gln Thr Gln Leu Ser Asn Lys His Glu Leu Gln Leu Glu
            580                 585                 590

Gln Met His Lys Arg Phe Glu Gln Glu Ile Asn Ala Lys Lys Lys Phe
        595                 600                 605

Phe Asp Thr Glu Leu Glu Asn Leu Glu Arg Gln Gln Lys Gln Gln Val
610                 615                 620

Glu Lys Met Glu Gln Asp His Ala Val Arg Arg Arg Glu Glu Ala Arg
625                 630                 635                 640

Arg Ile Arg Leu Glu Gln Asp Arg Asp Tyr Thr Arg Phe Gln Glu Gln
                645                 650                 655

Leu Lys Leu Met Lys Lys Glu Val Lys Asn Glu Val Glu Lys Leu Pro
            660                 665                 670

Arg Gln Gln Arg Lys Glu Ser Met Lys Gln Lys Met Glu Glu His Thr
        675                 680                 685

Gln Lys Lys Gln Leu Leu Asp Arg Asp Phe Val Ala Lys Gln Lys Glu
690                 695                 700

Asp Leu Glu Leu Ala Met Lys Arg Leu Thr Thr Asp Asn Arg Arg Glu
705                 710                 715                 720

Ile Cys Asp Lys Glu Arg Glu Cys Leu Met Lys Lys Gln Glu Leu Leu
                725                 730                 735

Arg Asp Arg Glu Ala Ala Leu Trp Glu Met Glu Glu His Gln Leu Gln
            740                 745                 750

Glu Arg His Gln Leu Val Lys Gln Gln Leu Lys Asp Gln Tyr Phe Leu
```

-continued

```
                755                 760                 765
Gln Arg His Glu Leu Leu Arg Lys His Glu Lys Glu Arg Glu Gln Met
770                 775                 780

Gln Arg Tyr Asn Gln Arg Met Ile Glu Gln Leu Lys Val Arg Gln Gln
785                 790                 795                 800

Gln Glu Lys Ala Arg Leu Pro Lys Ile Gln Arg Ser Glu Gly Lys Thr
                805                 810                 815

Arg Met Ala Met Tyr Lys Lys Ser Leu His Ile Asn Gly Gly Gly Ser
                820                 825                 830

Ala Ala Glu Gln Arg Glu Lys Ile Lys Gln Phe Ser Gln Gln Glu Glu
                835                 840                 845

Lys Arg Gln Lys Ser Glu Arg Leu Gln Gln Gln Lys His Glu Asn
850                 855                 860

Gln Met Arg Asp Met Leu Ala Gln Cys Glu Ser Asn Met Ser Glu Leu
865                 870                 875                 880

Gln Gln Leu Gln Asn Glu Lys Cys His Leu Leu Val Glu His Glu Thr
                885                 890                 895

Gln Lys Leu Lys Ala Leu Asp Glu Ser His Asn Gln Asn Leu Lys Glu
                900                 905                 910

Trp Arg Asp Lys Leu Arg Pro Arg Lys Lys Ala Leu Glu Glu Asp Leu
                915                 920                 925

Asn Gln Lys Lys Arg Glu Gln Glu Met Phe Phe Lys Leu Ser Glu Glu
930                 935                 940

Ala Glu Cys Pro Asn Pro Ser Thr Pro Ser Lys Ala Ala Lys Phe Phe
945                 950                 955                 960

Pro Tyr Ser Ser Ala Asp Ala Ser
                965
```

<210> SEQ ID NO 24
<211> LENGTH: 1321
<212> TYPE: PRT
<213> ORGANISM: HUMAN
<300> PUBLICATION INFORMATION:
<301> AUTHORS: Walkinshaw,D.R., Weist,R., Kim,G.W., You,L., Xiao,L., Nie,J.,
<302> TITLE: The tumor suppressor kinase LKB1 activates the downstream kinases
<303> JOURNAL: J. Biol. Chem.
<304> VOLUME: 288
<305> ISSUE: 13
<306> PAGES: 9345-9362
<307> DATE: 2013
<308> DATABASE ACCESSION NUMBER: NP_079440
<309> DATABASE ENTRY DATE: 2014-01-11
<313> RELEVANT RESIDUES IN SEQ ID NO: (1)..(1321)

<400> SEQUENCE: 24

```
Met Ala Ala Ala Ala Ser Gly Ala Gly Gly Ala Gly Ala Gly
1               5                   10                  15

Thr Gly Gly Ala Gly Pro Ala Gly Arg Leu Leu Pro Pro Ala Pro
                20                  25                  30

Gly Ser Pro Ala Ala Pro Ala Ala Val Ser Pro Ala Ala Gly Gln Pro
                35                  40                  45

Arg Pro Pro Ala Pro Ala Ser Arg Gly Pro Met Pro Ala Arg Ile Gly
                50                  55                  60

Tyr Tyr Glu Ile Asp Arg Thr Ile Gly Lys Gly Asn Phe Ala Val Val
65                  70                  75                  80

Lys Arg Ala Thr His Leu Val Thr Lys Ala Lys Val Ala Ile Lys Ile
                85                  90                  95
```

```
Ile Asp Lys Thr Gln Leu Asp Glu Glu Asn Leu Lys Lys Ile Phe Arg
            100                 105                 110

Glu Val Gln Ile Met Lys Met Leu Cys His Pro His Ile Ile Arg Leu
            115                 120                 125

Tyr Gln Val Met Glu Thr Glu Arg Met Ile Tyr Leu Val Thr Glu Tyr
            130                 135                 140

Ala Ser Gly Gly Glu Ile Phe Asp His Leu Val Ala His Gly Arg Met
145                 150                 155                 160

Ala Glu Lys Glu Ala Arg Arg Lys Phe Lys Gln Ile Val Thr Ala Val
            165                 170                 175

Tyr Phe Cys His Cys Arg Asn Ile Val His Arg Asp Leu Lys Ala Glu
            180                 185                 190

Asn Leu Leu Leu Asp Ala Asn Leu Asn Ile Lys Ile Ala Asp Phe Gly
            195                 200                 205

Phe Ser Asn Leu Phe Thr Pro Gly Gln Leu Leu Lys Thr Trp Cys Gly
            210                 215                 220

Ser Pro Pro Tyr Ala Ala Pro Glu Leu Phe Glu Gly Lys Glu Tyr Asp
225                 230                 235                 240

Gly Pro Lys Val Asp Ile Trp Ser Leu Gly Val Val Leu Tyr Val Leu
            245                 250                 255

Val Cys Gly Ala Leu Pro Phe Asp Gly Ser Thr Leu Gln Asn Leu Arg
            260                 265                 270

Ala Arg Val Leu Ser Gly Lys Phe Arg Ile Pro Phe Phe Met Ser Thr
            275                 280                 285

Glu Cys Glu His Leu Ile Arg His Met Leu Val Leu Asp Pro Asn Lys
            290                 295                 300

Arg Leu Ser Met Glu Gln Ile Cys Lys His Lys Trp Met Lys Leu Gly
305                 310                 315                 320

Asp Ala Asp Pro Asn Phe Asp Arg Leu Ile Ala Glu Cys Gln Gln Leu
            325                 330                 335

Lys Glu Glu Arg Gln Val Asp Pro Leu Asn Glu Asp Val Leu Leu Ala
            340                 345                 350

Met Glu Asp Met Gly Leu Asp Lys Glu Gln Thr Leu Gln Ser Leu Arg
            355                 360                 365

Ser Asp Ala Tyr Asp His Tyr Ser Ala Ile Tyr Ser Leu Leu Cys Asp
            370                 375                 380

Arg His Lys Arg His Lys Thr Leu Arg Leu Gly Ala Leu Pro Ser Met
385                 390                 395                 400

Pro Arg Ala Leu Ala Phe Gln Ala Pro Val Asn Ile Gln Ala Glu Gln
            405                 410                 415

Ala Gly Thr Ala Met Asn Ile Ser Val Pro Gln Val Gln Leu Ile Asn
            420                 425                 430

Pro Glu Asn Gln Ile Val Glu Pro Asp Gly Thr Leu Asn Leu Asp Ser
            435                 440                 445

Asp Glu Gly Glu Glu Pro Ser Pro Glu Ala Leu Val Arg Tyr Leu Ser
            450                 455                 460

Met Arg Arg His Thr Val Gly Val Ala Asp Pro Arg Thr Glu Val Met
465                 470                 475                 480

Glu Asp Leu Gln Lys Leu Leu Pro Gly Phe Pro Gly Val Asn Pro Gln
            485                 490                 495

Ala Pro Phe Leu Gln Val Ala Pro Asn Val Asn Phe Met His Asn Leu
            500                 505                 510
```

-continued

| | | | | | | | | | | | |
|---|---|---|---|---|---|---|---|---|---|---|---|
|Leu|Pro|Met|Gln|Asn|Leu|Gln|Pro|Thr|Gly|Gln|Leu|Glu|Tyr|Lys|Glu|
| | |515| | | |520| | | |525| |

Gln Ser Leu Leu Gln Pro Pro Thr Leu Gln Leu Leu Asn Gly Met Gly
     530                535                540

Pro Leu Gly Arg Arg Ala Ser Asp Gly Gly Ala Asn Ile Gln Leu His
545           550                555                560

Ala Gln Gln Leu Leu Lys Arg Pro Arg Gly Pro Ser Pro Leu Val Thr
             565                570                575

Met Thr Pro Ala Val Pro Ala Val Thr Pro Val Asp Glu Glu Ser Ser
         580                585                590

Asp Gly Glu Pro Asp Gln Glu Ala Val Gln Ser Ser Thr Tyr Lys Asp
     595                600                605

Ser Asn Thr Leu His Leu Pro Thr Glu Arg Phe Ser Pro Val Arg Arg
     610                615                620

Phe Ser Asp Gly Ala Ala Ser Ile Gln Ala Phe Lys Ala His Leu Glu
625               630                635                640

Lys Met Gly Asn Asn Ser Ser Ile Lys Gln Leu Gln Gln Glu Cys Glu
                 645                650                655

Gln Leu Gln Lys Met Tyr Gly Gly Gln Ile Asp Glu Arg Thr Leu Glu
         660                665                670

Lys Thr Gln Gln Gln His Met Leu Tyr Gln Gln Glu Gln His His Gln
             675                680                685

Ile Leu Gln Gln Gln Ile Gln Asp Ser Ile Cys Pro Pro Gln Pro Ser
             690                695                700

Pro Pro Leu Gln Ala Ala Cys Glu Asn Gln Pro Ala Leu Leu Thr His
705               710                715                720

Gln Leu Gln Arg Leu Arg Ile Gln Pro Ser Ser Pro Pro Pro Asn His
                 725                730                735

Pro Asn Asn His Leu Phe Arg Gln Pro Ser Asn Ser Pro Pro Pro Met
             740                745                750

Ser Ser Ala Met Ile Gln Pro His Gly Ala Ala Ser Ser Ser Gln Phe
             755                760                765

Gln Gly Leu Pro Ser Arg Ser Ala Ile Phe Gln Gln Gln Pro Glu Asn
     770                775                780

Cys Ser Ser Pro Pro Asn Val Ala Leu Thr Cys Leu Gly Met Gln Gln
785               790                795                800

Pro Ala Gln Ser Gln Gln Val Thr Ile Gln Val Gln Glu Pro Val Asp
                 805                810                815

Met Leu Ser Asn Met Pro Gly Thr Ala Ala Gly Ser Ser Gly Arg Gly
             820                825                830

Ile Ser Ile Ser Pro Ser Ala Gly Gln Met Gln Met Gln His Arg Thr
             835                840                845

Asn Leu Met Ala Thr Leu Ser Tyr Gly His Arg Pro Leu Ser Lys Gln
     850                855                860

Leu Ser Ala Asp Ser Ala Glu Ala His Ser Leu Asn Val Asn Arg Phe
865               870                875                880

Ser Pro Ala Asn Tyr Asp Gln Ala His Leu His Pro His Leu Phe Ser
                 885                890                895

Asp Gln Ser Arg Gly Ser Pro Ser Ser Tyr Ser Pro Ser Thr Gly Val
             900                905                910

Gly Phe Ser Pro Thr Gln Ala Leu Lys Val Pro Pro Leu Asp Gln Phe
             915                920                925

Pro Thr Phe Pro Pro Ser Ala His Gln Gln Pro Pro His Tyr Thr Thr

-continued

```
                930             935             940
Ser Ala Leu Gln Gln Ala Leu Leu Ser Pro Thr Pro Pro Asp Tyr Thr
945                 950             955                 960

Arg His Gln Gln Val Pro His Ile Leu Gln Gly Leu Leu Ser Pro Arg
                965             970             975

His Ser Leu Thr Gly His Ser Asp Ile Arg Leu Pro Pro Thr Glu Phe
            980             985             990

Ala Gln Leu Ile Lys Arg Gln Gln Gln Arg Gln Gln Gln Gln Gln
        995             1000            1005

Gln Gln Gln Gln Gln Glu Tyr Gln Glu Leu Phe Arg His Met Asn
    1010            1015            1020

Gln Gly Asp Ala Gly Ser Leu Ala Pro Ser Leu Gly Gly Gln Ser
    1025            1030            1035

Met Thr Glu Arg Gln Ala Leu Ser Tyr Gln Asn Ala Asp Ser Tyr
    1040            1045            1050

His His His Thr Ser Pro Gln His Leu Leu Gln Ile Arg Ala Gln
    1055            1060            1065

Glu Cys Val Ser Gln Ala Ser Ser Pro Thr Pro Pro His Gly Tyr
    1070            1075            1080

Ala His Gln Pro Ala Leu Met His Ser Glu Ser Met Glu Glu Asp
    1085            1090            1095

Cys Ser Cys Glu Gly Ala Lys Asp Gly Phe Gln Asp Ser Lys Ser
    1100            1105            1110

Ser Ser Thr Leu Thr Lys Gly Cys His Asp Ser Pro Leu Leu Leu
    1115            1120            1125

Ser Thr Gly Gly Pro Gly Asp Pro Glu Ser Leu Leu Gly Thr Val
    1130            1135            1140

Ser His Ala Gln Glu Leu Gly Ile His Pro Tyr Gly His Gln Pro
    1145            1150            1155

Thr Ala Ala Phe Ser Lys Asn Lys Val Pro Ser Arg Glu Pro Val
    1160            1165            1170

Ile Gly Asn Cys Met Asp Arg Ser Ser Pro Gly Gln Ala Val Glu
    1175            1180            1185

Leu Pro Asp His Asn Gly Leu Gly Tyr Pro Ala Arg Pro Ser Val
    1190            1195            1200

His Glu His His Arg Pro Arg Ala Leu Gln Arg His His Thr Ile
    1205            1210            1215

Gln Asn Ser Asp Asp Ala Tyr Val Gln Leu Asp Asn Leu Pro Gly
    1220            1225            1230

Met Ser Leu Val Ala Gly Lys Ala Leu Ser Ser Ala Arg Met Ser
    1235            1240            1245

Asp Ala Val Leu Ser Gln Ser Ser Leu Met Gly Ser Gln Gln Phe
    1250            1255            1260

Gln Asp Gly Glu Asn Glu Glu Cys Gly Ala Ser Leu Gly Gly His
    1265            1270            1275

Glu His Pro Asp Leu Ser Asp Gly Ser Gln His Leu Asn Ser Ser
    1280            1285            1290

Cys Tyr Pro Ser Thr Cys Ile Thr Asp Ile Leu Leu Ser Tyr Lys
    1295            1300            1305

His Pro Glu Val Ser Phe Ser Met Glu Gln Ala Gly Val
    1310            1315            1320
```

<210> SEQ ID NO 25

```
<211> LENGTH: 745
<212> TYPE: PRT
<213> ORGANISM: HUMAN
<300> PUBLICATION INFORMATION:
<301> AUTHORS: Nishimura Y, Applegate K, Davidson MW, Danuser G and
      Waterman CM.
<302> TITLE: Automated screening of microtubule growth dynamics
      identifies MARK2
<303> JOURNAL: PLoS ONE
<304> VOLUME: 7
<305> ISSUE: 7
<306> PAGES: E41413
<307> DATE: 2012
<308> DATABASE ACCESSION NUMBER: NP_059672
<309> DATABASE ENTRY DATE: 2014-02-02
<313> RELEVANT RESIDUES IN SEQ ID NO: (1)..(745)

<400> SEQUENCE: 25
```

Met Ile Arg Gly Arg Asn Ser Ala Thr Ser Ala Asp Glu Gln Pro His
1               5                   10                  15

Ile Gly Asn Tyr Arg Leu Leu Lys Thr Ile Gly Lys Gly Asn Phe Ala
                20                  25                  30

Lys Val Lys Leu Ala Arg His Ile Leu Thr Gly Lys Glu Val Ala Val
            35                  40                  45

Lys Ile Ile Asp Lys Thr Gln Leu Asn Ser Ser Leu Gln Lys Leu
        50                  55                  60

Phe Arg Glu Val Arg Ile Met Lys Val Leu Asn His Pro Asn Ile Val
65                  70                  75                  80

Lys Leu Phe Glu Val Ile Glu Thr Glu Lys Thr Leu Tyr Leu Val Met
                85                  90                  95

Glu Tyr Ala Ser Gly Gly Glu Val Phe Asp Tyr Leu Val Ala His Gly
            100                 105                 110

Arg Met Lys Glu Lys Glu Ala Arg Ala Lys Phe Arg Gln Ile Val Ser
        115                 120                 125

Ala Val Gln Tyr Cys His Gln Lys Phe Ile Val His Arg Asp Leu Lys
130                 135                 140

Ala Glu Asn Leu Leu Leu Asp Ala Asp Met Asn Ile Lys Ile Ala Asp
145                 150                 155                 160

Phe Gly Phe Ser Asn Glu Phe Thr Phe Gly Asn Lys Leu Asp Thr Phe
                165                 170                 175

Cys Gly Ser Pro Pro Tyr Ala Ala Pro Glu Leu Phe Gln Gly Lys Lys
            180                 185                 190

Tyr Asp Gly Pro Glu Val Asp Val Trp Ser Leu Gly Val Ile Leu Tyr
        195                 200                 205

Thr Leu Val Ser Gly Ser Leu Pro Phe Asp Gly Gln Asn Leu Lys Glu
210                 215                 220

Leu Arg Glu Arg Val Leu Arg Gly Lys Tyr Arg Ile Pro Phe Tyr Met
225                 230                 235                 240

Ser Thr Asp Cys Glu Asn Leu Leu Lys Lys Phe Leu Ile Leu Asn Pro
                245                 250                 255

Ser Lys Arg Gly Thr Leu Glu Gln Ile Met Lys Asp Arg Trp Met Asn
            260                 265                 270

Val Gly His Glu Asp Asp Glu Leu Lys Pro Tyr Val Glu Pro Leu Pro
        275                 280                 285

Asp Tyr Lys Asp Pro Arg Arg Thr Glu Leu Met Val Ser Met Gly Tyr
290                 295                 300

Thr Arg Glu Glu Ile Gln Asp Ser Leu Val Gly Gln Arg Tyr Asn Glu
305                 310                 315                 320

```
Val Met Ala Thr Tyr Leu Leu Leu Gly Tyr Lys Ser Glu Leu Glu
                325                 330                 335

Gly Asp Thr Ile Thr Leu Lys Pro Arg Pro Ser Ala Asp Leu Thr Asn
                340                 345                 350

Ser Ser Ala Pro Ser Pro Ser His Lys Val Gln Arg Ser Val Ser Ala
                355                 360                 365

Asn Pro Lys Gln Arg Arg Phe Ser Asp Gln Ala Gly Pro Ala Ile Pro
370                 375                 380

Thr Ser Asn Ser Tyr Ser Lys Lys Thr Gln Ser Asn Asn Ala Glu Asn
385                 390                 395                 400

Lys Arg Pro Glu Glu Asp Arg Glu Ser Gly Arg Lys Ala Ser Ser Thr
                405                 410                 415

Ala Lys Val Pro Ala Ser Pro Leu Pro Gly Leu Glu Arg Lys Lys Thr
                420                 425                 430

Thr Pro Thr Pro Ser Thr Asn Ser Val Leu Ser Thr Ser Thr Asn Arg
                435                 440                 445

Ser Arg Asn Ser Pro Leu Leu Glu Arg Ala Ser Leu Gly Gln Ala Ser
                450                 455                 460

Ile Gln Asn Gly Lys Asp Ser Leu Thr Met Pro Gly Ser Arg Ala Ser
465                 470                 475                 480

Thr Ala Ser Ala Ser Ala Ala Val Ser Ala Ala Arg Pro Arg Gln His
                485                 490                 495

Gln Lys Ser Met Ser Ala Ser Val His Pro Asn Lys Ala Ser Gly Leu
                500                 505                 510

Pro Pro Thr Glu Ser Asn Cys Glu Val Pro Arg Pro Ser Thr Ala Pro
                515                 520                 525

Gln Arg Val Pro Val Ala Ser Pro Ser Ala His Asn Ile Ser Ser Ser
                530                 535                 540

Gly Gly Ala Pro Asp Arg Thr Asn Phe Pro Arg Gly Val Ser Ser Arg
545                 550                 555                 560

Ser Thr Phe His Ala Gly Gln Leu Arg Gln Val Arg Asp Gln Gln Asn
                565                 570                 575

Leu Pro Tyr Gly Val Thr Pro Ala Ser Pro Ser Gly His Ser Gln Gly
                580                 585                 590

Arg Arg Gly Ala Ser Gly Ser Ile Phe Ser Lys Phe Thr Ser Lys Phe
                595                 600                 605

Val Arg Arg Asn Leu Asn Glu Pro Glu Ser Lys Asp Arg Val Glu Thr
                610                 615                 620

Leu Arg Pro His Val Val Gly Ser Gly Gly Asn Asp Lys Glu Lys Glu
625                 630                 635                 640

Glu Phe Arg Glu Ala Lys Pro Arg Ser Leu Arg Phe Thr Trp Ser Met
                645                 650                 655

Lys Thr Thr Ser Ser Met Glu Pro Asn Glu Met Met Arg Glu Ile Arg
                660                 665                 670

Lys Val Leu Asp Ala Asn Ser Cys Gln Ser Glu Leu His Glu Lys Tyr
                675                 680                 685

Met Leu Leu Cys Met His Gly Thr Pro Gly His Glu Asp Phe Val Gln
                690                 695                 700

Trp Glu Met Glu Val Cys Lys Leu Pro Arg Leu Ser Leu Asn Gly Val
705                 710                 715                 720

Arg Phe Lys Arg Ile Ser Gly Thr Ser Met Ala Phe Lys Asn Ile Ala
                725                 730                 735

Ser Lys Ile Ala Asn Glu Leu Lys Leu
```

-continued

```
                740                 745

<210> SEQ ID NO 26
<211> LENGTH: 433
<212> TYPE: PRT
<213> ORGANISM: HUMAN
<300> PUBLICATION INFORMATION:
<301> AUTHORS: Zhuang Z, Wang K, Cheng X, Qu X, Jiang B, Li Z, Luo J,
      Shao Z and
<302> TITLE: LKB1 inhibits breast cancer partially through repressing
      the
<303> JOURNAL: PLoS ONE
<304> VOLUME: 8
<305> ISSUE: 7
<306> PAGES: E67431
<307> DATE: 2013
<308> DATABASE ACCESSION NUMBER: NP_000446
<309> DATABASE ENTRY DATE: 2014-02-09
<313> RELEVANT RESIDUES IN SEQ ID NO: (1)..(433)

<400> SEQUENCE: 26

Met Glu Val Val Asp Pro Gln Gln Leu Gly Met Phe Thr Glu Gly Glu
1               5                   10                  15

Leu Met Ser Val Gly Met Asp Thr Phe Ile His Arg Ile Asp Ser Thr
            20                  25                  30

Glu Val Ile Tyr Gln Pro Arg Arg Lys Arg Ala Lys Leu Ile Gly Lys
        35                  40                  45

Tyr Leu Met Gly Asp Leu Leu Gly Glu Gly Ser Tyr Gly Lys Val Lys
    50                  55                  60

Glu Val Leu Asp Ser Glu Thr Leu Cys Arg Arg Ala Val Lys Ile Leu
65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
        115                 120                 125

Met Glu Tyr Cys Val Cys Gly Met Gln Glu Met Leu Asp Ser Val Pro
    130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                165                 170                 175

Ile Lys Pro Gly Asn Leu Leu Leu Thr Thr Gly Gly Thr Leu Lys Ile
            180                 185                 190

Ser Asp Leu Gly Val Ala Glu Ala Leu His Pro Phe Ala Ala Asp Asp
        195                 200                 205

Thr Cys Arg Thr Ser Gln Gly Ser Pro Ala Phe Gln Pro Pro Glu Ile
    210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
                245                 250                 255

Gly Asp Asn Ile Tyr Lys Leu Phe Glu Asn Ile Gly Lys Gly Ser Tyr
            260                 265                 270

Ala Ile Pro Gly Asp Cys Gly Pro Pro Leu Ser Asp Leu Leu Lys Gly
        275                 280                 285

Met Leu Glu Tyr Glu Pro Ala Lys Arg Phe Ser Ile Arg Gln Ile Arg
    290                 295                 300
```

```
Gln His Ser Trp Phe Arg Lys His Pro Ala Glu Ala Pro Val
305                 310             315             320

Pro Ile Pro Pro Ser Pro Asp Thr Lys Asp Arg Trp Arg Ser Met Thr
            325             330             335

Val Val Pro Tyr Leu Glu Asp Leu His Gly Ala Asp Glu Asp
        340             345             350

Leu Phe Asp Ile Glu Asp Ile Ile Tyr Thr Gln Asp Phe Thr Val
        355             360             365

Pro Gly Gln Val Pro Glu Glu Glu Ala Ser His Asn Gly Gln Arg Arg
    370             375             380

Gly Leu Pro Lys Ala Val Cys Met Asn Gly Thr Glu Ala Ala Gln Leu
385             390             395             400

Ser Thr Lys Ser Arg Ala Glu Gly Arg Ala Pro Asn Pro Ala Arg Lys
            405             410             415

Ala Cys Ser Ala Ser Ser Lys Ile Arg Arg Leu Ser Ala Cys Lys Gln
            420             425             430

Gln

<210> SEQ ID NO 27
<211> LENGTH: 559
<212> TYPE: PRT
<213> ORGANISM: HUMAN
<300> PUBLICATION INFORMATION:
<301> AUTHORS: awley SA, Davison M, Woods A, Davies SP, Beri RK,
      Carling D and
<302> TITLE: Characterization of the AMP-activated protein kinase kinase
      from
<303> JOURNAL: J. Biol. Chem.
<304> VOLUME: 271
<305> ISSUE: 44
<306> PAGES: 27879-27887
<307> DATE: 1996
<308> DATABASE ACCESSION NUMBER: NP_006242
<309> DATABASE ENTRY DATE: 2014-02-09
<313> RELEVANT RESIDUES IN SEQ ID NO: (1)..(559)

<400> SEQUENCE: 27

Met Arg Arg Leu Ser Ser Trp Arg Lys Met Ala Thr Ala Glu Lys Gln
1               5                   10                  15

Lys His Asp Gly Arg Val Lys Ile Gly His Tyr Ile Leu Gly Asp Thr
            20                  25                  30

Leu Gly Val Gly Thr Phe Gly Lys Val Lys Val Gly Lys His Glu Leu
        35                  40                  45

Thr Gly His Lys Val Ala Val Lys Ile Leu Asn Arg Gln Lys Ile Arg
    50                  55                  60

Ser Leu Asp Val Val Gly Lys Ile Arg Arg Glu Ile Gln Asn Leu Lys
65                  70                  75                  80

Leu Phe Arg His Pro His Ile Ile Lys Leu Tyr Gln Val Ile Ser Thr
                85                  90                  95

Pro Ser Asp Ile Phe Met Val Met Glu Tyr Val Ser Gly Gly Glu Leu
            100                 105                 110

Phe Asp Tyr Ile Cys Lys Asn Gly Arg Leu Asp Glu Lys Glu Ser Arg
        115                 120                 125

Arg Leu Phe Gln Gln Ile Leu Ser Gly Val Asp Tyr Cys His Arg His
    130                 135                 140

Met Val Val His Arg Asp Leu Lys Pro Glu Asn Val Leu Leu Asp Ala
145                 150                 155                 160

His Met Asn Ala Lys Ile Ala Asp Phe Gly Leu Ser Asn Met Met Ser
```

```
                    165                 170                 175
Asp Gly Glu Phe Leu Arg Thr Ser Cys Gly Ser Pro Asn Tyr Ala Ala
                180                 185                 190

Pro Glu Val Ile Ser Gly Arg Leu Tyr Ala Gly Pro Glu Val Asp Ile
            195                 200                 205

Trp Ser Ser Gly Val Ile Leu Tyr Ala Leu Leu Cys Gly Thr Leu Pro
        210                 215                 220

Phe Asp Asp His Val Pro Thr Leu Phe Lys Lys Ile Cys Asp Gly
225                 230                 235                 240

Ile Phe Tyr Thr Pro Gln Tyr Leu Asn Pro Ser Val Ile Ser Leu Leu
                245                 250                 255

Lys His Met Leu Gln Val Asp Pro Met Lys Arg Ala Thr Ile Lys Asp
                260                 265                 270

Ile Arg Glu His Glu Trp Phe Lys Gln Asp Leu Pro Lys Tyr Leu Phe
                275                 280                 285

Pro Glu Asp Pro Ser Tyr Ser Ser Thr Met Ile Asp Asp Glu Ala Leu
            290                 295                 300

Lys Glu Val Cys Glu Lys Phe Glu Cys Ser Glu Glu Val Leu Ser
305                 310                 315                 320

Cys Leu Tyr Asn Arg Asn His Gln Asp Pro Leu Ala Val Ala Tyr His
                325                 330                 335

Leu Ile Ile Asp Asn Arg Arg Ile Met Asn Glu Ala Lys Asp Phe Tyr
                340                 345                 350

Leu Ala Thr Ser Pro Pro Asp Ser Phe Leu Asp Asp His His Leu Thr
            355                 360                 365

Arg Pro His Pro Glu Arg Val Pro Phe Leu Val Ala Glu Thr Pro Arg
    370                 375                 380

Ala Arg His Thr Leu Asp Glu Leu Asn Pro Gln Lys Ser Lys His Gln
385                 390                 395                 400

Gly Val Arg Lys Ala Lys Trp His Leu Gly Ile Arg Ser Gln Ser Arg
                405                 410                 415

Pro Asn Asp Ile Met Ala Glu Val Cys Arg Ala Ile Lys Gln Leu Asp
            420                 425                 430

Tyr Glu Trp Lys Val Val Asn Pro Tyr Tyr Leu Arg Val Arg Arg Lys
        435                 440                 445

Asn Pro Val Thr Ser Thr Tyr Ser Lys Met Ser Leu Gln Leu Tyr Gln
    450                 455                 460

Val Asp Ser Arg Thr Tyr Leu Leu Asp Phe Arg Ser Ile Asp Asp Glu
465                 470                 475                 480

Ile Thr Glu Ala Lys Ser Gly Thr Ala Thr Pro Gln Arg Ser Gly Ser
                485                 490                 495

Val Ser Asn Tyr Arg Ser Cys Gln Arg Ser Asp Ser Asp Ala Glu Ala
            500                 505                 510

Gln Gly Lys Ser Ser Glu Val Ser Leu Thr Ser Ser Val Thr Ser Leu
        515                 520                 525

Asp Ser Ser Pro Val Asp Leu Thr Pro Arg Pro Gly Ser His Thr Ile
    530                 535                 540

Glu Phe Phe Glu Met Cys Ala Asn Leu Ile Lys Ile Leu Ala Gln
545                 550                 555

<210> SEQ ID NO 28
<211> LENGTH: 1352
<212> TYPE: PRT
<213> ORGANISM: HUMAN
```

```
<300> PUBLICATION INFORMATION:
<301> AUTHORS: Luo, Y
<302> TITLE: TNIK, a novel member of the germinal center kinase family
      that
<303> JOURNAL: J. Biol. Chem.
<304> VOLUME: 274
<305> ISSUE: 43
<306> PAGES: 30729-30737
<307> DATE: 1999-03-15
<308> DATABASE ACCESSION NUMBER: NP_001155032
<309> DATABASE ENTRY DATE: 2015-03-15
<313> RELEVANT RESIDUES IN SEQ ID NO: (1)..(1352)

<400> SEQUENCE: 28
```

| | | | | | | | | | | | | | | |
|---|---|---|---|---|---|---|---|---|---|---|---|---|---|---|
| Met | Ala | Ser | Asp | Ser | Pro | Ala | Arg | Ser | Leu | Asp | Glu | Ile | Asp | Leu | Ser |
| 1 | | | | 5 | | | | | 10 | | | | | 15 | |

Ala Leu Arg Asp Pro Ala Gly Ile Phe Glu Leu Val Glu Leu Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Gly Asp Glu Glu Glu
        50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Asn Asp Ser Gly
                325                 330                 335

Glu Pro Ser Ser Ile Leu Asn Leu Pro Gly Glu Ser Thr Leu Arg Arg

```
                340                 345                 350
Asp Phe Leu Arg Leu Gln Leu Ala Asn Lys Glu Arg Ser Glu Ala Leu
            355                 360                 365

Arg Arg Gln Gln Leu Glu Gln Gln Arg Glu Asn Glu Glu His Lys
370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Glu Arg Arg Ala Glu His Glu Gln Glu Tyr Ile Arg
                435                 440                 445

Arg Gln Leu Glu Glu Gln Arg Gln Leu Glu Ile Leu Gln Gln Gln
            450                 455                 460

Leu Leu His Glu Gln Ala Leu Leu Glu Tyr Lys Arg Lys Gln Leu
465                 470                 475                 480

Glu Glu Gln Arg Gln Ala Glu Arg Leu Gln Arg Gln Leu Lys Gln Glu
                485                 490                 495

Arg Asp Tyr Leu Val Ser Leu Gln His Gln Arg Gln Glu Gln Arg Pro
                500                 505                 510

Val Glu Lys Lys Pro Leu Tyr His Tyr Lys Glu Gly Met Ser Pro Ser
            515                 520                 525

Glu Lys Pro Ala Trp Ala Lys Glu Val Glu Glu Arg Ser Arg Leu Asn
            530                 535                 540

Arg Gln Ser Ser Pro Ala Met Pro His Lys Val Ala Asn Arg Ile Ser
545                 550                 555                 560

Asp Pro Asn Leu Pro Pro Arg Ser Glu Ser Phe Ser Ile Ser Gly Val
                565                 570                 575

Gln Pro Ala Arg Thr Pro Pro Met Leu Arg Pro Val Asp Pro Gln Ile
            580                 585                 590

Pro His Leu Val Ala Val Lys Ser Gln Gly Pro Ala Leu Thr Ala Ser
            595                 600                 605

Gln Ser Val His Glu Gln Pro Thr Lys Gly Leu Ser Gly Phe Gln Glu
            610                 615                 620

Ala Leu Asn Val Thr Ser His Arg Val Glu Met Pro Arg Gln Asn Ser
625                 630                 635                 640

Asp Pro Thr Ser Glu Asn Pro Pro Leu Pro Thr Arg Ile Glu Lys Phe
                645                 650                 655

Asp Arg Ser Ser Trp Leu Arg Gln Glu Glu Asp Ile Pro Pro Lys Val
                660                 665                 670

Pro Gln Arg Thr Thr Ser Ile Ser Pro Ala Leu Ala Arg Lys Asn Ser
            675                 680                 685

Pro Gly Asn Gly Ser Ala Leu Gly Pro Arg Leu Gly Ser Gln Pro Ile
            690                 695                 700

Arg Ala Ser Asn Pro Asp Leu Arg Arg Thr Glu Pro Ile Leu Glu Ser
705                 710                 715                 720

Pro Leu Gln Arg Thr Ser Ser Gly Ser Ser Ser Ser Ser Ser Thr Pro
                725                 730                 735

Ser Ser Gln Pro Ser Ser Gln Gly Gly Ser Gln Pro Gly Ser Gln Ala
            740                 745                 750

Gly Ser Ser Glu Arg Thr Arg Val Arg Ala Asn Ser Lys Ser Glu Gly
            755                 760                 765
```

```
Ser Pro Val Leu Pro His Glu Pro Ala Lys Val Lys Pro Glu Glu Ser
        770                 775                 780

Arg Asp Ile Thr Arg Pro Ser Arg Pro Ala Asp Leu Thr Ala Leu Ala
785                 790                 795                 800

Lys Glu Leu Arg Glu Leu Arg Ile Glu Glu Thr Asn Arg Pro Met Lys
                805                 810                 815

Lys Val Thr Asp Tyr Ser Ser Ser Glu Glu Ser Glu Ser Ser Glu
                820                 825                 830

Glu Glu Glu Glu Asp Gly Glu Ser Gly Thr His Asp Gly Thr Val Ala
            835                 840                 845

Val Ser Asp Ile Pro Arg Leu Ile Pro Thr Gly Ala Pro Gly Ser Asn
    850                 855                 860

Glu Gln Tyr Asn Val Gly Met Val Gly Thr His Gly Leu Glu Thr Ser
865                 870                 875                 880

His Ala Asp Ser Phe Ser Gly Ser Ile Ser Arg Glu Gly Thr Leu Met
                885                 890                 895

Ile Arg Glu Thr Ser Gly Glu Lys Lys Arg Ser Gly His Ser Asp Ser
                900                 905                 910

Asn Gly Phe Ala Gly His Ile Asn Leu Pro Asp Leu Val Gln Gln Ser
            915                 920                 925

His Ser Pro Ala Gly Thr Pro Thr Glu Gly Leu Gly Arg Val Ser Thr
930                 935                 940

His Ser Gln Glu Met Asp Ser Gly Thr Glu Tyr Gly Met Gly Ser Ser
945                 950                 955                 960

Thr Lys Ala Ser Phe Thr Pro Phe Val Asp Pro Arg Val Tyr Gln Thr
                965                 970                 975

Ser Pro Thr Asp Glu Asp Glu Glu Asp Glu Glu Ser Ser Ala Ala Ala
            980                 985                 990

Leu Phe Thr Ser Glu Leu Leu Arg  Gln Glu Gln Ala Lys  Leu Asn Glu
            995                 1000                1005

Ala Arg  Lys Ile Ser Val Val  Asn Val Asn Pro Thr  Asn Ile Arg
    1010                1015                1020

Pro His  Ser Asp Thr Pro Glu  Ile Arg Lys Tyr  Lys Arg Phe
    1025                1030                1035

Asn Ser  Glu Ile Leu Cys Ala  Ala Leu Trp Gly Val  Asn Leu Leu
    1040                1045                1050

Val Gly  Thr Glu Asn Gly Leu  Met Leu Leu Asp Arg  Ser Gly Gln
    1055                1060                1065

Gly Lys  Val Tyr Asn Leu Ile  Asn Arg Arg Phe  Gln Gln Met
    1070                1075                1080

Asp Val  Leu Glu Gly Leu Asn  Val Leu Val Thr Ile  Ser Gly Lys
    1085                1090                1095

Lys Asn  Lys Leu Arg Val Tyr  Tyr Leu Ser Trp Leu  Arg Asn Arg
    1100                1105                1110

Ile Leu  His Asn Asp Pro Glu  Val Glu Lys Lys Gln  Gly Trp Ile
    1115                1120                1125

Thr Val  Gly Asp Leu Glu Gly  Cys Ile His Tyr Lys  Val Val Lys
    1130                1135                1140

Tyr Glu  Arg Ile Lys Phe Leu  Val Ile Ala Leu Lys  Asn Ala Val
    1145                1150                1155

Glu Ile  Tyr Ala Trp Ala Pro  Lys Pro Tyr His Lys  Phe Met Ala
    1160                1165                1170
```

```
Phe Lys Ser Phe Ala Asp Leu Gln His Lys Pro Leu Leu Val Asp
    1175            1180            1185

Leu Thr Val Glu Glu Gly Gln Arg Leu Lys Val Ile Phe Gly Ser
    1190            1195            1200

His Thr Gly Phe His Val Ile Asp Val Asp Ser Gly Asn Ser Tyr
    1205            1210            1215

Asp Ile Tyr Ile Pro Ser His Ile Gln Gly Asn Ile Thr Pro His
    1220            1225            1230

Ala Ile Val Ile Leu Pro Lys Thr Asp Gly Met Glu Met Leu Val
    1235            1240            1245

Cys Tyr Glu Asp Glu Gly Val Tyr Val Asn Thr Tyr Gly Arg Ile
    1250            1255            1260

Thr Lys Asp Val Val Leu Gln Trp Gly Glu Met Pro Thr Ser Val
    1265            1270            1275

Ala Tyr Ile His Ser Asn Gln Ile Met Gly Trp Gly Glu Lys Ala
    1280            1285            1290

Ile Glu Ile Arg Ser Val Glu Thr Gly His Leu Asp Gly Val Phe
    1295            1300            1305

Met His Lys Arg Ala Gln Arg Leu Lys Phe Leu Cys Glu Arg Asn
    1310            1315            1320

Asp Lys Val Phe Phe Ala Ser Val Arg Ser Gly Gly Ser Ser Gln
    1325            1330            1335

Val Phe Phe Met Thr Leu Asn Arg Asn Ser Met Met Asn Trp
    1340            1345            1350
```